(12) United States Patent
Kishore et al.

(10) Patent No.: US 10,392,644 B2
(45) Date of Patent: *Aug. 27, 2019

(54) PRODUCTION OF STEVIOL GLYCOSIDES IN MICROORGANISMS

(71) Applicant: EVOLVA SA, Reinach (CH)

(72) Inventors: Ganesh M. Kishore, Saint Louis, MO (US); Jorgen Hansen, Frederiksberg (DK); Jens Houghton-Larsen, Birkerod (DK); Esben Halkjaer Hansen, Frederiksberg (DK); Michael Dalgaard Mikkelsen, Vaerlose (DK); Sabina Tavares, San Francisco, CA (US); Charlotte Blom, San Francisco, CA (US)

(73) Assignee: EVOLVA SA, Reinach (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/382,354

(22) Filed: Dec. 16, 2016

(65) Prior Publication Data

US 2017/0218419 A1 Aug. 3, 2017
US 2019/0078128 A9 Mar. 14, 2019

Related U.S. Application Data

(62) Division of application No. 13/701,406, filed as application No. PCT/US2011/038967 on Jun. 2, 2011, now Pat. No. 9,562,251.

(60) Provisional application No. 61/350,553, filed on Jun. 2, 2010, provisional application No. 61/434,582, filed on Jan. 20, 2011, provisional application No. 61/741,622, filed on Apr. 4, 2011.

(51) Int. Cl.
| | | |
|---|---|---|
| *C12N 9/10* | (2006.01) |
| *C12N 9/88* | (2006.01) |
| *A23L 2/60* | (2006.01) |
| *C12P 19/56* | (2006.01) |
| *C12P 15/00* | (2006.01) |
| *C07H 15/256* | (2006.01) |
| *C12N 9/04* | (2006.01) |
| *C12N 9/90* | (2006.01) |
| *C12N 9/02* | (2006.01) |
| *A23L 27/30* | (2016.01) |

(52) U.S. Cl.
CPC .......... *C12P 19/56* (2013.01); *A23L 2/60* (2013.01); *A23L 27/36* (2016.08); *C07H 15/256* (2013.01); *C12N 9/0006* (2013.01); *C12N 9/0042* (2013.01); *C12N 9/0073* (2013.01); *C12N 9/1085* (2013.01); *C12N 9/88* (2013.01); *C12N 9/90* (2013.01); *C12P 15/00* (2013.01); *C12Y 101/01088* (2013.01); *C12Y 106/02004* (2013.01); *C12Y 114/13078* (2013.01); *C12Y 114/13079* (2013.01); *C12Y 205/01029* (2013.01); *C12Y 402/03019* (2013.01); *C12Y 505/01012* (2013.01)

(58) Field of Classification Search
CPC .... C12N 9/1051; C12N 9/1048; C12N 15/80; C12N 15/82; C12Y 204/00
See application file for complete search history.

(56) References Cited

U.S. PATENT DOCUMENTS

| | | | |
|---|---|---|---|
| 4,590,160 | A | 5/1986 | Nishihashi et al. |
| 5,204,253 | A | 4/1993 | Sanford et al. |
| 5,306,862 | A | 4/1994 | Chappell et al. |
| 5,460,949 | A | 10/1995 | Saunders et al. |
| 5,538,880 | A | 7/1996 | Lundquist et al. |
| 6,013,863 | A | 1/2000 | Lundquist et al. |
| 6,215,051 | B1 | 4/2001 | Yu et al. |
| 6,255,557 | B1 | 7/2001 | Brandle |
| 6,284,493 | B1 | 9/2001 | Roth |
| 6,284,506 | B1 | 9/2001 | Hoshino et al. |
| 6,329,571 | B1 | 12/2001 | Hiei |
| 6,586,202 | B2 | 7/2003 | Hoshino et al. |
| 6,660,507 | B2 | 12/2003 | Cheng et al. |
| 6,806,076 | B1 | 10/2004 | Miyake et al. |
| 6,969,595 | B2 | 11/2005 | Brzostowicz et al. |
| 7,034,140 | B2 | 4/2006 | Bramucci et al. |
| 7,056,717 | B2 | 6/2006 | Cheng et al. |
| 7,098,000 | B2 | 8/2006 | Cheng et al. |
| 7,129,392 | B2 | 10/2006 | Hahn et al. |
| 7,132,268 | B2 | 11/2006 | Miyake et al. |
| 7,172,886 | B2 | 2/2007 | Keasling et al. |

(Continued)

FOREIGN PATENT DOCUMENTS

| | | |
|---|---|---|
| CN | 101720910 | 6/2010 |
| CN | 102216313 | 10/2011 |

(Continued)

OTHER PUBLICATIONS

Morita, Yasumasa, et al. The Plant Journal 42.3 (2005): 353-363. (Year: 2005).*

(Continued)

*Primary Examiner* — Weihua Fan
(74) *Attorney, Agent, or Firm* — McDonnell Boehnen Hulbert & Berghoff LLP

(57) ABSTRACT

Recombinant microorganisms, plants, and plant cells are disclosed that have been engineered to express novel recombinant genes encoding steviol biosynthetic enzymes and UDP-glycosyltransferases (UGTs). Such microorganisms, plants, or plant cells can produce steviol or steviol glycosides, e.g., rubusoside or Rebaudioside A, which can be used as natural sweeteners in food products and dietary supplements.

22 Claims, 14 Drawing Sheets
Specification includes a Sequence Listing.

(56) References Cited

U.S. PATENT DOCUMENTS

| | | |
|---|---|---|
| 7,183,089 B2 | 2/2007 | Keasling et al. |
| 7,186,891 B1 | 3/2007 | Chappell et al. |
| 7,208,298 B2 | 4/2007 | Miyake et al. |
| 7,335,815 B2 | 2/2008 | Boronate et al. |
| 7,364,885 B2 | 4/2008 | Miyake et al. |
| 7,422,884 B2 | 9/2008 | Bai et al. |
| 7,514,597 B2 | 4/2009 | Nakamura et al. |
| 7,569,389 B2 | 9/2009 | Feldmann et al. |
| 7,692,065 B2 | 4/2010 | Harper et al. |
| 7,838,287 B2 | 11/2010 | Goldsmith et al. |
| 7,923,541 B2 | 4/2011 | Yang et al. |
| 7,927,851 B2 | 4/2011 | Brandle et al. |
| 9,562,251 B2 | 2/2017 | Kishore et al. |
| 2002/0142408 A1 | 10/2002 | DiCosimo et al. |
| 2003/0033626 A1 | 2/2003 | Hahn et al. |
| 2003/0148416 A1 | 8/2003 | Berry et al. |
| 2003/0148479 A1 | 8/2003 | Keasling et al. |
| 2003/0190734 A1 | 10/2003 | Hoshino et al. |
| 2003/0219798 A1 | 11/2003 | Gokarn et al. |
| 2004/0010815 A1 | 1/2004 | Lange et al. |
| 2004/0072311 A1 | 4/2004 | DiCosimo et al. |
| 2004/0078846 A1 | 4/2004 | DeSouza et al. |
| 2004/0176570 A1 | 9/2004 | Sadler et al. |
| 2004/0194162 A1 | 9/2004 | Hahn et al. |
| 2005/0003474 A1 | 1/2005 | DeSouza et al. |
| 2005/0032169 A1 | 2/2005 | Miyake et al. |
| 2006/0014264 A1 | 1/2006 | Sauer et al. |
| 2006/0079476 A1 | 4/2006 | Keasling et al. |
| 2006/0083838 A1 | 4/2006 | Jackson et al. |
| 2007/0004000 A1 | 1/2007 | Miyake et al. |
| 2007/0077616 A1 | 4/2007 | Keasling et al. |
| 2007/0099261 A1 | 5/2007 | Keasling et al. |
| 2007/0118916 A1 | 5/2007 | Puzio et al. |
| 2007/0128311 A1 | 6/2007 | Prakash et al. |
| 2007/0166782 A1 | 7/2007 | Keasling et al. |
| 2007/0202579 A1 | 8/2007 | Berry et al. |
| 2007/0238157 A1 | 10/2007 | Millis et al. |
| 2007/0238159 A1 | 10/2007 | Millis et al. |
| 2007/0238160 A1 | 10/2007 | Millis et al. |
| 2007/0254354 A1 | 11/2007 | Millis et al. |
| 2007/0269857 A1 | 11/2007 | Miyake et al. |
| 2007/0286850 A1 | 12/2007 | Bai et al. |
| 2008/0064063 A1* | 3/2008 | Brandle ............ C12N 9/0073 435/69.1 |
| 2008/0081358 A1 | 4/2008 | Vittanen et al. |
| 2008/0131926 A1 | 6/2008 | Miyake et al. |
| 2008/0261280 A1 | 10/2008 | Hahn et al. |
| 2008/0271205 A1 | 10/2008 | Yamaguchi et al. |
| 2008/0286870 A1 | 11/2008 | Vittanen et al. |
| 2008/0292775 A1 | 11/2008 | Prakash et al. |
| 2008/0318227 A1 | 12/2008 | Bacher et al. |
| 2009/0004724 A1 | 1/2009 | Keasling et al. |
| 2009/0047718 A1 | 2/2009 | Blaschek et al. |
| 2009/0055974 A1 | 2/2009 | Tanksley et al. |
| 2009/0074935 A1 | 3/2009 | Lee |
| 2009/0286262 A1 | 11/2009 | Slack |
| 2010/0112156 A1 | 5/2010 | Abelyan et al. |
| 2010/0120096 A1 | 5/2010 | Kitaoka et al. |
| 2010/0221801 A1 | 9/2010 | Van Dyk et al. |
| 2010/0297722 A1 | 11/2010 | Anterola et al. |
| 2010/0316782 A1 | 12/2010 | Shi et al. |
| 2011/0087011 A1 | 4/2011 | Chiang et al. |
| 2011/0092684 A1 | 4/2011 | Varuzhan et al. |
| 2011/0126318 A1 | 5/2011 | Allen et al. |
| 2011/0160311 A1 | 6/2011 | Prakash et al. |
| 2012/0021111 A1 | 1/2012 | Pfister et al. |
| 2012/0083593 A1 | 4/2012 | Liu et al. |
| 2012/0164678 A1 | 6/2012 | Stephanopoulos et al. |
| 2012/0178169 A1 | 7/2012 | Voytas et al. |
| 2013/0137138 A1 | 5/2013 | Hansen |
| 2014/0329281 A1 | 11/2014 | Houghton-Larsen et al. |
| 2015/0159188 A1 | 6/2015 | Ono et al. |
| 2015/0342234 A1 | 12/2015 | Hicks et al. |

FOREIGN PATENT DOCUMENTS

| | | |
|---|---|---|
| CN | 103397064 | 11/2013 |
| CN | 104845990 | 8/2015 |
| EP | 0955363 | 11/1999 |
| EP | 1072683 | 1/2001 |
| EP | 1171610 | 4/2007 |
| EP | 1198575 | 9/2007 |
| EP | 1383864 | 1/2008 |
| EP | 1897951 | 3/2008 |
| EP | 1947189 | 7/2008 |
| EP | 1392824 | 8/2008 |
| EP | 2902410 | 8/2015 |
| JP | 5910-001408 | 6/1984 |
| JP | 3-277275 | 12/1991 |
| JP | 05-115298 | 5/1993 |
| JP | 2009034080 | 2/2009 |
| KR | 20150000258 | 1/2015 |
| WO | 1999/018224 | 4/1999 |
| WO | 2000/036081 | 6/2000 |
| WO | 2000/037663 | 6/2000 |
| WO | 2000/063400 | 10/2000 |
| WO | 2001/012828 | 2/2001 |
| WO | 2001/083769 | 11/2001 |
| WO | 2001/094561 | 12/2001 |
| WO | 2002/020728 | 3/2002 |
| WO | 2002/020815 | 3/2002 |
| WO | WO 2002/024865 | 3/2002 |
| WO | 2002/055709 | 7/2002 |
| WO | 2003/008540 | 1/2003 |
| WO | 2004/029255 | 4/2004 |
| WO | 2005/079183 | 9/2005 |
| WO | 2006/016395 | 2/2006 |
| WO | 2006/096392 | 9/2006 |
| WO | WO 2006/093289 | 9/2006 |
| WO | 2007/136847 | 11/2007 |
| WO | 2008/008256 | 1/2008 |
| WO | 2008/034648 | 3/2008 |
| WO | 2008/039499 | 4/2008 |
| WO | 2008/051349 | 5/2008 |
| WO | WO 2008/091547 | 7/2008 |
| WO | 2009/005704 | 1/2009 |
| WO | 2009/071277 | 6/2009 |
| WO | 2009/086049 | 7/2009 |
| WO | WO 2009/105612 | 8/2009 |
| WO | 2009/108680 | 9/2009 |
| WO | 2009/140394 | 11/2009 |
| WO | 2010/021001 | 2/2010 |
| WO | 2010/038911 | 4/2010 |
| WO | 2010/146463 | 12/2010 |
| WO | WO 2010/142305 | 12/2010 |
| WO | 2011/028671 | 3/2011 |
| WO | 2011/037959 | 3/2011 |
| WO | 2011/046423 | 4/2011 |
| WO | 2011/056834 | 5/2011 |
| WO | 2011/153378 | 8/2011 |
| WO | WO 2011/140329 | 11/2011 |
| WO | 2011/151326 | 12/2011 |
| WO | 2011/153144 | 12/2011 |
| WO | 2012/075030 | 6/2012 |
| WO | 2013/019050 | 2/2013 |
| WO | 2013/022989 | 2/2013 |
| WO | WO 2013/076577 | 5/2013 |
| WO | 2013/096420 | 6/2013 |
| WO | 2013/102793 | 7/2013 |
| WO | 2013/110673 | 8/2013 |
| WO | 2013/176738 | 11/2013 |
| WO | 2014/086890 | 6/2014 |
| WO | 2014/122328 | 8/2014 |
| WO | WO2014/122323 | 8/2014 |
| WO | WO 2014/191580 | 12/2014 |
| WO | WO 2014/191581 | 12/2014 |
| WO | WO 2015/011209 | 1/2015 |
| WO | WO 2015007748 | 1/2015 |
| WO | WO 2015/014959 | 2/2015 |
| WO | WO 2015/014969 | 2/2015 |
| WO | WO 2015/016393 | 2/2015 |
| WO | WO 2015/028324 | 3/2015 |
| WO | WO 2015051454 | 4/2015 |

(56) References Cited

FOREIGN PATENT DOCUMENTS

| WO | WO 2015/132411 | 9/2015 |
|----|----------------|--------|
| WO | WO 2016/023844 | 2/2016 |
| WO | WO 2017/025362 | 2/2016 |
| WO | WO 2016/038095 | 3/2016 |
| WO | WO 2016/120486 | 8/2016 |

OTHER PUBLICATIONS

Gloster, Tracey M. "Advances in understanding glycosyltransferases from a structural perspective." Current opinion in structural biology 28 (2014): 131-141. (Year: 2014).*

Ünligil, Uluğ M., and James M. Rini. "Glycosyltransferase structure and mechanism." Current opinion in structural biology 10.5 (2000): 510-517. (Year: 2000).*

Brandle, J. E., and P. G. Telmer. "Steviol glycoside biosynthesis." Phytochemistry 68.14 (2007): 1855-1863 (Year: 2007).*

UDP-glucosyltransferase [Stevia rebaudiana ] GenBank: ACE87855. 1, retrieved from www.ncbi.nlm.nih.gov/protein/ACE87855.1?report=genbank&log$=protalign&blast_rank=1&RID=A4RE4U6301R (Year: 2008).*

Abraham & Bhat, "Permeabilization of baker's yeast with N-lauroyl sarcosine," J Ind Microbial Biotechnol. 35(8):799-804 (2008).

Ageitos et al., "Oily yeasts as oleaginous cell factories," Appl Microbiol Biotechnol. 90(4):1219-27 (May 2011).

Agrawal, "NMR spectroscopy in the structural elucidation of oligosaccharides and glycosides," Phytochemistry 31(10):3307-30 (1992).

Ajikumar et al., "Terpenoids: opportunities for biosynthsis of natural product drugs using engineered microorganisms," Molecular Pharmaceuticals 5(2):167-90 (2008).

Alakomi et al., "Lactic acid permeabilizes gram-negative bacteria by disrupting the outer membrane," Appl Environ Microbiol. 66(5):2001-5 (2000).

Ali et al., "Biochemical investigation during different stages of in vitro propagation of Stevia rebaudiana," Pak J Bot. 42(4):2827-37 (2010).

Bankar et al., "Environmental and industrial applications of Yarrowia lipolytica," Appl Microbiol Biotechnol. 84(5):847-65 (Oct. 2009).

Bateman et al., "Pfam 3.1: 1313 multiple alignments and profile HMMs match the majority of proteins," Nucl Acids Res. 27(1):260-2 (1999).

Bay & Turner, "Diversity and evolution of the small multidrug resistance protein family," BMC Evol. Biol. 9:140 (Jun. 2009).

Baykov et al., "A malachite green procedure for orthophosphate determination and its use in alkaline phosphatase-based enzyme immunoassay," Anal Biochem. 171(2):266-70 (Jun. 1988).

Beopoulos et al., "Yarrowia lipolytica: A model and a tool to understand the mechanisms implicated in lipid accumulation," Biochimie 91(6):692-6 (Jun. 2009).

Brandle et al., "Leaf ESTs from Stevia rebaudiana: A Resource for Gene Discovery in Diterpene Synthesis," Plant Mol Biol. 50(4-5):613-22 (2002).

Brachmann et al., "Designer deletion strains derived from Saccharomyces cerevisiae S288C: a useful set of strains and plasmids for PCR-mediated gene disruption and other applications," Yeast 14:115-32 (1998).

Brandle & Telmer, "Steviol glycoside biosynthesis," Phytochemistry 68(14):1855-63 (2007).

Brochado et al. "Improved vanillin production in baker's yeast through in silico design," Microb Cell Fact. 9:84-98 (2010).

Carretero-Paulet et al., " Expression and Molecular Analysis of the Arabidopsis DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).

Ceunen & Geuns, "Steviol glycosides: chemical diversity, metabolism, and function," J. Nat. Prod. 76(6):1201-28 (Jun. 2013).

Chemler et al., "Biosynthesis of isoprenoids, polyunsaturated fatty acids and flavonoids in Saccharomyces cerevisiae," Microb Cell Fact. 5:20 (2006).

Chen et al., "Transferring a biosynthetic cycle into a productive Escherichia coli strain: large-scale synthesis of galactosides," J Am Chem Soc. 123(36):8866-7 (2001).

Chen et al., "MolProbity: all-atom structure validation for macromolecular crystallography," Acta Crystallogr D Biol Crystallogr 66(Pt 1):12-21 (Jan. 2010).

Chenna et al., "Multiple sequence alignment with the Clustal series of programs," Nucleic Acids Res. 31(13):3497-500 (2003).

Chica et al., "Semi-rational approaches to engineering enzyme activity: combining the benefits of directed evolution and rational design," Curr Opin Biotechnol.16(4):378-84 (2005).

Chow & Palecek, "Enzyme encapsulation in permeabilized Saccharomyces cerevisiae cells," Biotechnol Prog. 20(2):449-56 (2004).

Correa et al., "Genetic mapping of 1,3-beta-glucanase-encoding genes in Saccharomyces cerevisiae," Current Genet. 22(4):283-8 (1992).

Darise et al., "Enzymic Transglucosylation of Rubusoside and the Structure-Sweetness Relationship of Steviol-Bisglycosides," Agric. Biol. Chem. 48(10):2483-8 (Jan. 1984).

Davis et al., "MolProbity: all-atom contacts and structure validation for proteins and nucleic acids," Nucleic Acids Res. 35:W375-83 (Apr. 2007).

Del Sorbo et al., "Fungal transporters involved in efflux of natural toxic compounds and fungicides," Fungal. Genet. Biol. 30(1):1-15 (Jun. 2000).

Diener et al., "Arabidopsis ALF5, a multidrug efflux transporter gene family member, confers resistance to toxins," Plant Cell 13(7):1625-38 (Jul. 2001).

Dodhia et al., "Engineering human cytochrome P450 enzymes into catalytically self-sufficient chimeras using molecular Lego," J Biol Inorg Chem. 11(7):903-16 (Oct. 2006).

Dubey, et al., An overview of the non-mevalonate pathway for terpenoid biosynthesis in plants, J. Biosci. 28(5):637-46 (2003).

Dubois & Stephenson, "Diterpenoid sweeteners. Synthesis and sensory evaluation of stevioside analogues with improved organoleptic properties," J. Med. Chem. 28(1):93-8 (Jan. 1985).

EFSA Panel on Food Additives and Nutrient Sources added to Food (ANS), "Scientific Opinion on the safety of steviol glycosides for the proposed uses as a food additive," EFSA Journal 8(4):1537 (2010).

Eisenreich et al., "Biosynthesis of isoprenoids via the non-mevalonate pathway," Cell Mol Life Sci. 61(12):1401-6 (2004).

Emmerstorfer et al., "Over-expression of ICE2 stabilizes cytochrome P450 reductase in Saccharomyces cerevisiae and Pichia pastoris," Biotechnol J. 10(4):623-35 (Apr. 2015).

Estrada De Martin et al., "Ice2p is important for the distribution and structure of the cortical ER network in Saccharomyces cerevisiae," J Cell Sci. 118(Pt 1):65-77 (Oct. 2006).

Fernandez et al., "Activation of chitin synthetase in permeabilized cells of a Saccharomyces cerevisiae mutant lacking proteinase B," J Bacteriol. 152(3):1255-64 (1982).

GenBank Accession No. DQ269454.4, dated May 28, 2008 (2 pages).

GenBank Accession No. DQ398871.3, dated May 28, 2008 (2 pages).

GenBank Accession No. EDY51667, dated Sep. 2, 2008 (2 pages).

GenBank Accession No. EU263989, dated Jun. 11, 2008 (2 pages).

GenBank Accession No. EU722415.1, dated Jun. 10, 2008 (2 pages).

GenBank Accession No. EU751291.1, dated Jun. 24, 2008 (2 pages).

GenBank Accession No. NM_116512, dated Jan. 22, 2014 (3 pages).

GenBank Accession No. NP_001105097, dated Aug. 4, 2015 (2 pages).

GenBank Accession No. NP_013636.1 (YML075C), dated Jul. 16, 2015 (3 pages).

GenBank Accession No. NP_194183, dated Jan. 22, 2014 (4 pages).

GenBank Accession No. NP_195399, dated Jan. 22, 2014 (3 pages).

(56) References Cited

OTHER PUBLICATIONS

GenBank Accession No. NP_197872.1, dated Jan. 22, 2014 (2 pages).
GenBank Accession No. Q9UVY5.1, dated Apr. 1, 2015 (3 pages).
GenBank Accession No. XM_001467423, dated Jul. 16, 2015 (2 pages).
GenBank Accession No. XP_002282091, dated Dec. 7, 2011 (1 page).
GenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
EBI Accession No. AAY05902, "Jerusalem artichoke in-chain hydroxylase CYP8161" (1 page).
EBI Accession No. ABM86477, "Rice abiotic stress responsive polypeptide SEQ ID No. 4723" (1 page).
UniProt Accession No. F2DG34, May 2011 (pp. 1-4).
UniProt Accession No. Q6VAA8, 2004 (pp. 1-6).
UniProt Accession No. Q7FPQ4, 2004 (pp. 1-6).
International Search Report issued by the International Searching Authority for International Application No. PCT/US2011/038967, dated Sep. 1, 2011 (10 pages).
Written Opinion of the International Searching Authority for International Application No. PCT/US2011/038967, dated Sep. 1, 2011 (12 pages).
International Preliminary Report on Patentability issued by the International Bureau for International Application No. PCT/US2011/038967, dated Dec. 4, 2012 (13 pages).
Third-Party Submission under 37 CFR 1.290 for U.S. Appl. No. 13/701,406, dated Mar. 22, 2013 (238 pages).
Patent Examination Report No. 1 issued by IP Australia for Australian Application No. 2011261394, dated Jan. 15, 2015.
Response to Patent Examination Report No. 1 issued by IP Australia for Australian Application No. 2011261394, dated Feb. 5, 2015.
Patent Examination Report No. 2 issued by IP Australia for Australian Application No. 2011261394, dated Feb. 23, 2015.
Notice of Acceptance issued by IP Australia for Australian Application No. 2011261394, dated Aug. 13, 2015 (pp. 1-3).
Office Action for Canadian Patent Application No. 2,802,627, dated Dec. 15, 2015 (pp. 1-5).
English Translation of First Office Action issued by the State Intellectual Property Office of People's Republic of China for CN Application No. 201180038475.4, dated Nov. 21, 2013.
English Translation on Response to First Office Action issued by the State Intellectual Property Office of People's Republic of China for CN Application No. 201180038475.4, dated Apr. 8, 2014.
English Translation of Second Office Action issued by the State Intellectual Property Office of People's Republic of China for Chinese Application No. 201180038475.4, dated Aug. 13, 2014.
English Translation of Response to Second Office Action issued by the State Intellectual Property Office of People's Republic of China for CN Application No. 201180038475.4, dated Oct. 28, 2014.
English Translation of Third Office Action issued by the State Intellectual Property Office of People's Republic of China for Chinese Application No. 201180038475.4, dated Mar. 3, 2015.
Notification of Grant of Patent Application issued by the State Intellectual Property Office of People's Republic of China for Chinese Application No. 201180038475.4, dated Dec. 1, 2015 (pp. 1-5). English translation included.
Extended European Search Report and Opinion issued by the European Patent Office for European Application No. 11790428.4, dated Dec. 20, 2013.
Response to Extended Search Report and Opinion issued by the European Patent Office for European Application No. 11790428.4, dated Jul. 16, 2014.
Communication pursuant to Rule 114(2) EPC for European Application No. 11790428.4, dated Nov. 28, 2014.

Examination Report issued by the European Patent Office for European Application No. 11790428.4, dated Dec. 1, 2014.
Response to Examination Report issued by the European Patent Office for European Application No. 11790428.4, dated Jun. 1, 2015 (16 pages).
English Translation of Notification of Reasons for Refusal of Japanese Application No. 2013-513355, dated Aug. 4, 2015 (pp. 1-10).
Examination Report issued by the Intellectual Property Corporation of Malaysia for Malaysian Application No. PI 2012005201, dated Jul. 31, 2014.
Response to Examination Report issued by the Intellectual Property Corporation of Malaysian for MY Application No. PI 2012005201, dated Sep. 18, 2014.
First Examination Report issued by the Intellectual Property Office of New Zealand for New Zealand Application No. 604915, dated Sep. 2, 2013.
Response to First Examination Report issued by the Intellectual Property Office of New Zealand for New Zealand Application No. 604915, dated Jan. 17, 2014.
Further Examination Report issued by the Intellectual Property Office of New Zealand for New Zealand Application No. 604915, dated Feb. 3, 2014.
Response to Further Examination Report issued by the Intellectual Property Office of New Zealand for New Zealand Application No. 604915, dated May 27, 2014.
Nelson et al., "P450 superfamily: update on new sequences, gene mapping, accession numbers and nomenclature," Pharmacogenetics 6:1-42 (1996).
Newman et al., "High-level production of amorpha-4,11-diene in a two-phase partitioning bioreactor of metabolically engineered *Escherichia coli*," Biotechnol Bioeng 95(4):684-91 (2006).
Nicaud, "Yarrowia lipolytica," Yeast 29(10):409-18 (Oct. 2012).
Nielsen et al., "Efficient PCR-based gene targeting with a recyclable marker for Aspergillus nidulans," Fungal Genet Biol. 43(1):54-64 (2006).
Nikaido & Takatsuk, "Mechanisms of RND multidrug efflux pumps," Biochim. Biophys. Acta. 1794(5):769-81 (May 2009).
Ohta et al., "Characterization of Novel Steviol Glycosides from Leaves of Stevia rebaudiana Morita," J. Applied Glycosides 57(3):199-209 (Mar. 2010).
Ohta et al., MassBank Accession No. FU000341 (May 2011).
Ohta et al., MassBank Accession No. FU000342 (May 2011).
Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka & Jigami, "Reconstruction of de novo pathway for synthesis of UDP-glucuronic acid and UDP-xylose from intrinsic UDP-glucose in *Saccharomyces cerevisiae*," FEBS J. 273(12):2645-57 (2006).
Orihara et al., "Biotransformation of steviol by cultured cells of eucalyptus perriniana and Coffea Arabica," Phytochemistry 30(12):3989-92 (1991).
Osmani et al., "Substrate specificity of plant UDP-dependent glycosyltransferases predicted from crystal structures and homology modeling," Phytochemistry 70(3):325-47 (2009).
Osmani et al., "Catalytic key amino acids and UDP-sugar donor specificity of a plant glucuronosyltransferase, UGT94B1: molecular modeling substantiated by site-specific mutagenesis and biochemical analyses," Plant Phys. 148(3):1295-1308 (2008).
Paradise et al., "Redirection of flux through the FPP branch-point in *Saccharomyces cerevisiae* by down-regulating squalene synthase," Biotechnol Bioeng. 100(2):371-8 (2008).
Pearson & Lipman, "Improved tools for biological sequence comparison," Proc Natl Acad Sci. 85(8):2444-8 (1998).
Piirainen et al., "Glycoengineering of yeasts from the perspective of glycosylation efficiency," N Biotechnol. 31(6):532-7 (Dec. 2014).
Pompon et al., "Yeast Expression of Animal and Plant P450s in Optimized Redox Environments," Methods Enzymol 272:51-64 (1996).
Prelich, "Gene overexpression: uses, mechanisms, and interpretation," Genetics 190(3):841-54 (Mar. 2012).

(56) References Cited

OTHER PUBLICATIONS

Presecki & Vasic-Racki, "Production of L-malic acid by permeabilized cells of commercial *Saccharomyces sp.* strains," Biotechnol Lett. 27(23-24):1835-9 (2005).
Richman et al., "Functional genomics uncovers three glucosyltransferases involved in the synthesis of the major sweet glucosides of Stevia rebaudiana," Plant J. 41(1):56-67 (2005).
Riesmeier et al., "Isolation and characterization of a sucrose carrier cDNA from spinach by functional expression in yeast," EMBO J 11(13):4705-13 (1992).
Ro et al., "Production of the antimalarial drug precursor artemisinic acid in engineered yeast," Nature 440(7086):940-3 (2006).
Rodriguez-Concepcion & Boronat, "Elucidation of the methylerythritol phosphate pathway for isoprenoid biosynthesis in bacteria and plastids. A metabolic milestone achieved through genomics," Plant Physiol. 130 (3):1079-89 (2002).
Saenge et al., "Potential use of oleaginous red yeast *Rhodotorula glutinis* for the bioconversion of crude glycerol from biodiesel plant to lipids and carotenoids," Process Biochemistry 46(1):210-8 (Jan. 2011).
Saier Jr et al., "The major facilitator superfamily," J. Mol. Microbiol. Biotechnol. 1(2):257-79 (Nov. 1999).
Saier et al., "The Transporter Classification Database: recent advances," Nucleic Acids Res. 37:D274-8 (Jan. 2009).
Sauer et al., "The soluble and membrane-bound transhydrogenases UdhA and PntAB have divergent functions in NADPH metabolism of *Escherichia coil*," J Biol Chem. 279(8):6613-9 (2004).
Sawada et al., "UDP-glucuronic acid:anthocyanin glucuronosyltransferase from red daisy (*Bellis perennis*) flowers. Enzymology and phylogenetics of a novel glucuronosyltransferase involved in flower pigment biosynthesis," J Biol Chem. 280(2):899-906 (2005).
Schwab et al., Poster, "Watchmaker?—Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol.143(3)212-23 (2007).
Senthilraja et al., "RNA secondary structure prediction: Analysis of *Saccharomyces cerevisiae* RNAs," Int. J. Pharm. Rev. Res. 25(2):287-91 (Mar.-Apr. 2014).
Shao et al., "Enhanced production of alpha-galactosyl epitopes by metabolically engineered Pichia pastoris," Appl Environ Microbiol. 69(9):5238-42 (2003).
Shao et al., "Crystal structures of a multifunctional triterpene/flavonoid glycosyltransferase from Medicago truncatula," Plant Cell 17(11):3141-54 (2005).
Singh et al., "Compendium of Transgenic Crop Plants: Transgenic Sugar, Tuber and Fiber," Ed. Kole & Hall, Blackwell Publishing Ltd. pp. 97-115 (2008).
Son et al., "Production of flavonoid o-glucoside using sucrose synthase and flavonoid o-glucosyltransferase fusion protein," J Microbiol Biotechnol. 19(7):709-12 (2009).
Sonnhammer et al., "Pfam: multiple sequence alignments and HMM-profiles of protein domains," Nucleic Acids Res. 26(1):320-2 (1998).
Sonnhammer et al., "Pfam: a comprehensive database of protein domain families based on seed alignments," Proteins 28(3):405-420 (1997).
U.S. Food and Drug Administration GRAS Notice 323, "GRAS Assessment of High Purity Steviol Glycosides; Food Usage Conditions for General Recognition of Safety for PureCircle USA, Inc.," pp. 1-262 (Feb. 2010).
U.S Food and Drug Administration GRAS Notice Notice 329, "Notice to the U.S. Food and Drug Administration that the use of RebpureTM (Rebaudioside A) derived from Stevia rebaudiana, as a Food Ingredient is Generally Recognized as Safe (GRAS)," pp. 1-275 (Mar. 2010).
Van Ooyen et al., "Heterologous protein production in the yeast *Kluyveromyces lactis*," FEMS Yeast Res. 6(3):381-92 (May 2006).
Vazquez De Aldana et al., "Nucleotide sequence of the exo-1,3-beta-glucanase-encoding gene, EXG1, of the yeast *Saccharomyces cerevisiae*," Gene 97(2):173-82 (1991).
Verwaal et al., "High-Level Production of Beta-Carotene in *Saccharomyces cerevisiae* by Successive Transformation with Carotenogenic Genes from Xanthophyllomyces dendrorhous," Appl Environ Microbiol. 73(13):4342-50 (2007).
Wallin, "Steviol Glycosides," Chem. Tech Assessment—63rd JECFA (2004).
Wallin, "Steviol Glycosides," Chem. Tech Assessment—69th JECFA (2007).
Wallner & Elofsson, "Can correct protein models be identified?," Protein Sci. 12(5):1073-86 (May 2003).
Wang, "Structure, mechanism and engineering of plant natural product glycosyltransferases," FEBS Letters 583(20)3303-9 (2009).
Yadav et al., "A review on the improvement of stevia [*Stevia rebaudiana* (Bertoni)]," Can J Plant Sci. 91:1-27 (2011).
Yao et al., "A genetic linkage map for Stevia rebaudiana," Genome 42:657-61 (1999).
Yazaki, "ABC transporters involved in the transport of plant secondary metabolites," FEBS Lett. 580(4):1183-91 (Feb. 2006).
Flores et al., "Permeabilization of yeast cells (*Kluyveromyces lactis*) with organic solvents," Enzyme Microb Technol. 16(4):340-6 (1994).
Fowler & Zabin, "Effects of Dimethylsulfoxide on the Lactose Operon in *Escherichia coli*," J Bacteriol. 92(2):353-7 (1966).
Freire, "Differential scanning calorimetry," Methods Mol Biol. 40:191-218 (1995).
Fukunaga et al., "Enzymatic transglucosylation products of stevioside: separation and sweetness-evaluation," Agric. Biol. Chem. 53(6):1603-7 (Jan. 1989).
Giaever & Nislow, "The yeast deletion collection: a decade of functional genomics," Genetics 197(2):451-65 (Jun. 2014).
Gietz & Schiestl, "High-efficiency yeast transformation using the LiAc/SS carrier DNA/PEG method," Nat Protoc. 2(1):31-4 (2007).
Girvan et al., "Flavocytochrome P450 BM3 mutant W1046A is a NADH-dependent fatty acid hydroxylase: implications for the mechanism of electron transfer in the P450 BM3 dimer," Arch Biochem Biophys. 507(1):75-85 (Mar. 2011).
Goralczyk, "Compounds from Stevia for Improving and Maintaining Mental Performance," Stevia World Forum, Feb. 24-25, 2010, 17 pages.
Gossen & Bujard, "Studying gene function in eukaryotes by conditional gene inactivation," Ann Rev Genet. 36:153-73 (2002).
Gritz & Davies, "Plasmid-encoded hygromycin B resistance: the sequence of hygromycin B phosphotransferase gene and its expression in *Escherichia coli* and *Saccharomyces cerevisiae*," Gene 25(2-3):179-88 (Nov. 1983).
Guleria & Yadav, "Insights into Steviol Glycoside Biosynthesis Pathway Enzymes Through Structural Homology Modeling," Am. J. Biochem. Molec. Biol. 3(1):1-19 (2013).
Gunel et al., "Metabolic Engineering for Production of Geranylgeranyl Pyrophosphate Synthase in Non-Carotenogenic Yeast *Schizosaccharomyces pombe*," Biotechnol. & Biotechnol. Eq. 20(3):76-82 (2006).
Hallstrom & Moye-Rowley, "Divergent transcriptional control of multidrug resistance genes in *Saccharomyces cerevisiae*," J. Biol. Chem. 273(4):2098-104 (Jan. 1998).
Hansen et al., "De novo biosynthesis of vanillin in fission yeast (*Schizosaccharomyces pombe*) and baker's yeast (*Saccharomyces cerevisiae*)," Appl Environ Microbiol. 75(9):2765-74 (2009).
Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9):3044-51 (2011).
Hellfritsch et al., "Human psychometric and taste receptor responses to steviol glycosides," J. Agric. Food Chem. 60(27):6782-93 (Jul. 2012).
Humphrey et al., "Spatial organisation of four enzymes from Stevia rebaudiana that are involved in steviol glycoside synthesis," Plant Mol Bio. 61(1-2):47-62 (2006).

(56) References Cited

OTHER PUBLICATIONS

Iandolino et al., "High-Quality RNA, cDNA, and Derived EST Libraries From Grapevine (*Vitis vinifera L.*)," Plant Mol Biol Reporter 22:269-78 (2004).
Irmler et al., "Indole alkaloid biosynthesis in Catharanthus roseus: new enzyme activities and identification of cytochrome P450 CYP72A1 as secologanin synthase," Plant J. 24(6):797-804 (2000).
Jennewein et al., "Taxol biosythesis: baxane 13 alpha-hydroxylase is a cytochrome P450-dependent monooxygenase," Proc Natl Acad Sci U S A 98(24):13595-600 (2001).
Jewett et al. "An integrated cell-free metabolic platform for protein production and synthetic biology," Mol Syst Biol. 4:220 (2008).
Johnstone et al., "Cloning an Aspergillus nidulans developmental gene by transformation," EMBO J. 4(5):1307-11 (1985).
Katzmann et al., "Expression of an ATP-binding cassette transporter-encoding gene (YOR1) is required for bligomycin resistance in *Saccharomyces cerevisiae*," Mol. Cell Biol. 15(12):6875-83 (Dec. 1995).
Khoury et al., "Computational design of Candida boidinii xylose reductase for altered cofactor specificity," Protein Sci. 18(10):2125-38 (Oct. 2009).
Kim et al., "Hydroxylation of ent-Kaurenoic Acid to Steviol in Stevia rebaudiana Bertoni-Purification and Partial Characterization of the Enzyme," Arch Biochem Biophys. 332(2):223-30 (1996).
Kim & Shibata, "Characterization of ent-kaurenoic acid 13-hydroxylase in steviol biosynthesis of Stevia rebaudiana Bertoni," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23-A (2003).
Kohda et al., "New Sweet Diterpene glucoside from Stevia Rebaudiana," Phytochemistry 15(6):981-3 (1976).
Kondo et al., "Preparation of high activity whole cell biocatalyst by permeabilization of recombinant flocculent yeast with alcohol," Enzyme Microb Technol. 27(10),806-11 (2000).
Kusama et al., "Transglucosylation into stevioside by the enzyme system from *Streptomyces* sp.," Agric. Biol. Chem. 50(10):2445-51 (Oct. 1986).
Li et al., "Phylogenetic analysis of the UDP-glycosyltransferase multigene family of *Arabidopsis thaliana*," J Biol Chem. 276(6):4338-43 (2001).
Li et al., "Crystal structure of Medicago truncatula UGT85H2—insights into the structural basis of a multifunctional (iso) flavonoid glycosyltransferase," J Mol Biol. 370(5):951-63 (2007).
Li et al., "Systematic Mutational Analysis of Peptide Inhibition of the p53-MDM2/MDMX," J Mol Biol. 398(2):200-13 (2010).
Li et al., "High-density cultivation of oleaginous yeast *Rhodosporidium toruloides* Y4 in fed-batch culture," Enzyme and Microbial Technology 41(3):312-7 (Aug. 2007).
Liu et al., "Preparation of high-activity whole cell biocatalysts by permeabilization of recombinant yeasts with alcohol," J Biosci Bioeng. 89(6):554-8 (2000).
Ma et al., "Molecular cloning and characterization of Stevia Rebaudiana UDP-glucosyltransferase," Acta Biologiae Experimentalis Sinica 36(2):123-9 (2003).
Madan et al., "Stevia rebaudiana (Bert.) Bertoni—A Review," Indian Journal of Natural Products and Resources 1(3)267-86 (2010).
Madhav et al., "Functional and structural variation of uridine diphosphate glycosyltransferase (UGT) gene of Stevia rebaudiana—UGTSr involved in the synthesis of rebaudioside A," Plant Physiol. Biochem. 63:245-53 (Feb. 2013).
MaLingBo, "1. Molecular Cloning and Functional Analysis of UDPG Glucosyltransferase Gene 2. Molecular Cloning, Sequence Analysis and Evolution of Actin and EF1a Genes in Stevia Rebaudiana," Chinese Doctor and Master Dissertations Full-Text Database, Agricultural Technology Part, vol. 2 (2004).
Malonek et al., "The NADPH-cytochrome P450 Reductase Gene from Gibberalla fujikuroi is Essential for Gibberellin Biosynthesis," J Bio Chem. 279(24):25075-84 (2004).
Mantovaneli et al., "The effect of temperature and flow rate on the clarification of the aqueous stevia-extract in a fixed-bed column with zeolites," Braz J Chem Eng. 21(3):449-58 (2004).
Masada et al., "An efficient chemoenzymatic production of small molecule glucosides with in situ UDP-glucose recycling," FEBS Lett. 581(13):2562-6 (2007).
Megeji et al., "Introducing Stevia rebaudiana, a natural zero-calorie sweetener," Current Science 88(5):801-4 (2005).
Morita et al., "Japanese morning glory dusky mutants displaying reddish-brown or purplish-gray flowers are deficient in a novel glycosylation enzyme for anthocyanin biosynthesis, UDP-glucose:anthocyanidin 3-O-glucoside-2"-O-glucosyltransferase, due to 4-bp insertions in the gene," Plant J. 42(3)353-63 (2005).
Mumberg et al., "Yeast vectors for the controlled expression of heterologous proteins in different genetic backgrounds," Gene 156(1):119-22 (1995).
Naesby et al., "Yeast artificial chromosomes employed for random assembly of biosynthetic pathways and production of diverse compounds in *Saccharomyces cerevisiae*," Microb Cell Fact. 8:45 (2009).
Naglak & Wang, " Rapid protein release from *Escherichia coli* by chemical permeabilization under fermentation conditions," Biotechnol Bioeng. 39(7):732-40 (1991).
Nagy et al., "Role of the yeast ABC transporter Yor1p in cadmium detoxification," Biochimie 88(11):1665-71 (Jun. 2006).
Nakagiri et al., "cDNA cloning, functional expression and characterization of ent-copalyl diphosphate synthase from *Scoparia dulcis* L.," Plant Sci. 169:760-7 (2005).
EMBOSS Needle results for Pairwise Sequence Alignment of UGT91D1 and UGT91D2; dated Apr. 4, 2016, 2 pages.
Kumar et al., "A comprehensive analysis of fifteen genes of steviol glycosides biosynthesis pathwayin Stevia rebaudiana (Bertoni)" Gene 492:276-84 (Epub Oct. 20, 2011).
Liu et al., "Functional and Biochemical Characteritzation of *Escherichia coli* Sugar Efflux Transporters," JBC, 274(33):22977-22984 (Aug. 1999).
Mohamed et al., "UDP-dependent glycosyltransferases involved in the biosynthesis of steviol glycosides" Journal of Plant Physiology 168(10):1136-1141 (Jul. 2011; Epub Apr. 7, 2011).
Shibata et al., "Glucosylation of Steviol and Steviol-Glucosides in Extracts from Stevia rebaudiana Bertoni" Plant Physiol. 95(1):152-56 (1991).
Sun et al., "Regulation and Function of *Escherichia coli* Sugar Efflux Transporter A (Set A) during Glucose-Phosphate Stress," J of Bacteriology, 193(1):143-153 (Jan. 2011)/.
Xu et al., "Generation of hepatitis B virus PreS2-S antigen in Hansenula polymorpha," Virol Sin. 29(6):403-9 (Dec. 2014).
Yadav et al ., "Steviol Glycosides from Stevia: Biosynthesis Pathway Review and their Application in Foods and Medicine.", CritRev. 52(11):988-998 (2012).
Third Party Observation in EP Application No. 13801569.8; dated Apr. 26, 2017. pp. 1-5.
International Search Report and Written Opinion of International Search Authority for International Application No. PCTEP2017/059028; dated Jun. 27, 2017, pp. 1-15.
Third Party Submission in U.S. Appl. No. 14/648,747; dated Mar. 28, 2016, pp. 1-231.
Starratt et al., "Rebaudioside F, a diterpene glycoside from Stevia redaudiana", Phytochemistry, 59(4):367-370. (Feb. 2002). Abstract.
International Search Report by the International Searching Authority for International Application No. PCT/EP2015/070620; dated Mar. 29, 2016, pp. 1-10.
Written Opinion of the International Searching Authority for International Application No. PCT/EP2015/070620; dated Mar. 29, 2016, pp. 1-24.
International Search Report and Written Opinion of the International Searching Authority for International Application No. PCT/EP2015/052007; dated Jul. 4, 2016, pp. 1-24.
International Search Report of the International Searching Authority for International Application No. PCT/EP2016/068259; dated Jan. 24, 2017 pp. 1-7.

(56) References Cited

OTHER PUBLICATIONS

Written Opinion of the International Searching Authority for International Application No. PCT/EP2016/068259; dated Jan. 24, 2017, pp. 1-10.
International Preliminary Report on Patentability from the International Bureau for International Application No. PCT/EP2015/068314; dated Jan. 24, 2017, pp. 1-10.
International Search Report and Written Opinion of the International Searching Authority for International Application No. PCT/EP2015/068314, dated Jan. 20, 2016 (pp. 1-7).
Written Opinion of the International Searching Authority for International Application No. PCT/EP2015/068314, dated Jan. 20, 2016 (pp. 1-9).
International Search Report and Written Opinion of International Search Authority for International Application No. PCT/EP2016/080516; dated Mar. 15, 2017, pp. 1-21.
Non-Final Office Action for U.S. Appl. No. 14/648,747, dated Mar. 23, 2017, pp. 1-20.
EMBOSS Needle results for Alignment of SEQ ID No. 5 of EP'432 and UGT91D1, dated Apr. 4, 2016 (2 pages).
Further Examination Report issued by the Intellectual Property Office of New Zealand for New Zealand Application No. 604915, dated Jun. 18, 2014.
Response to Further Examination Report issued by the Intellectual Property Office of New Zealand for New Zealand Application No. 604915, dated Sep. 15, 2014.
Notice of Acceptance issued by the Intellectual Property Office of New Zealand for New Zealand Application No. 604915, dated Oct. 7, 2014 (1 page).
First Examination Report issued by the Intellectual Property Office of New Zealand for New Zealand Application No. 700097, dated Oct. 6, 2014 (pp. 1-2).
Notice of Acceptance issued by the Intellectual Property Office of New Zealand for New Zealand Application No. 700097, dated Oct. 7, 2015 (1 page).
First Examination Report issued by the Intellectual Property Office of New Zealand for New Zealand Application No. 708078, dated May 28, 2015 (pp. 1-3).
Search Report issued by the Intellectual Property Office of Singapore for Singaporean Application No. 201208854-8, dated Nov. 3, 2014.
Written Opinion issued by the Intellectual Property Office of Singapore for Singaporean Application No. 201208854-8, dated Nov. 3, 2014.
International Search Report issued by the International Searching Authority for International Application No. PCT/US2012/050021, dated Apr. 12, 2013.
Written Opinion of the International Searching Authority for International Application No. PCT/US2012/050021, dated Apr. 12, 2013.
International Preliminary Report on Patentability issued by the International Bureau for International Application No. PCT/US2012/050021, dated Feb. 11, 2014.
English Translation of First Office Action and Search Report issued by the State Intellectual Property Office of People's Republic of China for Chinese Application No. 201280038853.3, dated Feb. 16, 2015.
English Translation of Second Office Action and Search Report issued by the State Intellectual Property Office of People's Republic of China for Chinese Application No. 201280038853.3, dated Jan. 11, 2016.
Communication pursuant to Rules 161(1) and 162 (EPC) issued by the European Patent Office for European Application No. 12750513.9, dated Mar. 14, 2014.
Response to Communication pursuant to Rules 161(1) and 162 (EPC) issued by the European Patent Office for European Application No. 12750513.9, dated Aug. 4, 2014.
Examination Report issued by the European Patent Office for European Application No. 12750513.9, dated Nov. 26, 2014.
Response to Examination Report issued by the European Patent Office for European Application No. 12750513.9, dated Mar. 25, 2015.
Non-Final Office Action for U.S. Appl. No. 14/237,540, dated Dec. 30, 2015 (pp. 1-19).
International Search Report from the International Searching Authority for International Application No. PCT/EP2014/052363, dated Sep. 22, 2014 (12 pages).
Written Opinion of the International Searching Authority for International Application No. PCT/EP2014/052363, dated Sep. 22, 2014 (10 pages).
International Preliminary Report on Patentability issued by the International Bureau for International Application No. PCT/EP2014/052363, dated Aug. 11, 2015. (11 pages).
Final Office Action issued in U.S. Appl. No. 14/237,540; dated Jul. 8, 2016, pp. 1-19.
International Search Report by the International Searching Authority for International Application No. PCT/EP2014/052675, dated Apr. 23, 2014 (5 pages).
Written Opinion of the International Searching Authority for International Application No. PCT/EP2014/052675, dated Apr. 23, 2014 (7 pages).
International Preliminary Report on Patentability issued by the International Bureau for International Application No. PCT/EP2014/052675, dated Aug. 11, 2015. (8 pages).
Communication pursuant to Rules 161(1) and 162 EPC for European Application No. 14704558.7, dated Sep. 18, 2015 (2 pages).
International Search Report of the International Searching Authority for International Application No. PCT/EP2013/075587, dated Feb. 20, 2014 (pp. 1-5).
Written Opinion of the International Searching Authority for International Application No. PCT/EP2013/075587, dated Feb. 20, 2014 (pp. 1-9).
International Preliminary Report on Patentability from the International Bureau for International Application No. PCT/EP2013/075587, dated Jun. 9, 2015 (pp. 1-10).
Extended European Search Report issued in EP 15193074.0; dated Feb. 12, 2016, pp. 1-9.
Response to Communication pursuant to Rules 161(1) and 162 EPC for European Application No. 14704558.7, dated Mar. 17, 2016 (pp. 1-24).
Mattanovich et al., "Recombinant protein production in yeasts," Methods Mol Biol. 824:329-58 (2012).
Nour-Eldin et al., "USER cloning and USER fusion: the ideal cloning techniques for small and big laboratories," Methods Mol Biol. 643:185-200 (2010).
Chen, "Summary on Study of Stevioside," China Pharmacist, vol. 10, No. 6, p. 598-599 (2007).
Chen et al., "Sugar transporters for intercellular exchange and nutrition of pathogens," Nature 468(7323):527-32 (2010).
Chen et al., "Fusion protein linkers: Property, design, and functionality", Advanced Drug Delivery reviews, 65(0):1257-69 (2013).
Daran et al., "Genetic and biochemical characterization of the UGP1 gene encoding the UDP-glucose pyrophosphorylase from *Saccharomyces cerevisiae*," Eur J Biochem. 233(2):520-30 (1995).
Garber et al., "Computational methods for transcriptome annotation and quantification using RNA-seq," Nat Methods 8(6):469-77 (2011).
Husar et al., Overexpression of the UGT73C6 alters brassinosteriod glucoside formation in *Arabidopsis thaliana*, BMC Plant Biology, 11:1-14 (2011).
Kawai et al., "Transformation of *Saccharomyces cerevisiae* and other fungi: methods and possible underlying mechanism," Bioeng Bugs. 1(6):395-403 (2010).
Khan et al., "Physical and chemical mutagenesis in Stevia rebaudiana: variant generation with higher UGT expression and glycosidic profile but with low photosynthetic capabilities," Acta Physiologiae Plantarum 38(1) (2016).
Lin et al., "Arrestin-related ubiquitin-ligase adaptors regulate endocytosis and protein turnover at the cell surface," Cell 135(4):714-25 (2008).
Liu et al., "Biosynthesis of Rebaudioside A by Whole Cell of Recombinant *Saccharomyces cerevisiae*," Food and Fermentation Industries, 38(7) : 6-10 (2012) (Abstract translation).

(56) References Cited

OTHER PUBLICATIONS

Mao et al., "Produce steviol glycosides in engineered yeast", 2015 Synthetic Biology: Engineering, Evolution & Design (SEED), Poster Abstract (Jun. 2015).
Nagalakshmi et al., "The transcriptional landscape of the yeast genome defined by RNA sequencing," Science 320 (5881 ): 1344-9 (2008).
Nagatoshi et al., "UGT75L6 and UGT94E5 mediate sequential glucosylation of crocetin to crocin in Gardenia asminoides", FEBS Letters, 586:1055-1061 (2012).
Nikko et al. "Arrestin-like proteins mediate ubiquitination and endocytosis of the yeast metal transporter Smf1," EMBO Rep. 9(12):1216-21 (2008).
Nikko & Pelham, "Arrestin-mediated endocytosis of yeast plasma membrane transporters," Traffic 10(12):1856-67 (2009).
Ohta et al., MassBank Accession No. FU000299 (May 2016).
Ohta et al., MassBank Accession No. FU000332 (May 2016).
Olsson et al., "Microbial production of next-generation stevia sweeteners," Microbial Cell Factories, 15:1-14 (2016).
Partow et al., "Characterization of different promoters for designing a new expression vector in *Saccharomyces cerevisiae*," Yeast 27:955-64 (2010).
Robinson & Oshlack et al., "A scaling normalization method for differential expression analysis of RNA-seq data," Genome Biol. 11(3):R25 (2010).
Saier Jr. et al., "The transporter classification database," Nucl. Acids Res., 42(1):D251-258 (2014).
Song et al., "The Aspergillus fumigatus 1-29 damage resistance protein family coordinately regulates ergosterol biosynthesis and azole susceptibility," MBIO, 7:1-13 (2016).
Tiwari et al., "Plant secondary metabolism linked glycosyltransferases: An update on expaning knowledge and scopes", Biotechnology Advances, 34:714-739 (May 2016).
Wang et al., "Pathway mining-based integration of critical enzyme parts for de novo biosynthesis of steviolglycoside sweetener in *Escherichia coli*", Cell Research, 26:258-261 (Sep. 2015).
Wang et al., "Efficient enzymatic production of rebaudioside A from stevioside", Bioscience, Biotechnology, and Biochemistry, 80:67-73 (Aug. 2015).
Wang et al., "RNA-Seq: a revolutionary tool for transcriptomics," Nat Rev Genet. 10(1):57-63 (2009).
Wang et al., "Design and construction of artificial biological systems for complex natural products biosynthesis," Chinese Journal of Biotechnology, 29(8):1146-60 (2013).
Warth et al., "Hydrophilic interaction liquid chromatography coupled with tandem mass spectrometry for the quantification of uridine diphosphate-glucose, uridine diphosphate-glucuronic acid, deoxynivalenol and its glucoside: In-house validation and application to wheat," Journal of Chromatography A, 1423, pp. 183-189 (2015).
Wilhelm et al., "Defining transcribed regions using RNA-seq," Nature Protocols 5:255-66 (2010).
Yang Quanhua et.al., "Analysis of the Chemical constituents of Stevia rebaudiana and its sweetness," Journal of Beijing University of Chemical Technology, vol. 39, No. 2., p. 28-32 (2012) (English Abstract).
Yang et al., Base substitution mutations in uridinediphosphate-dependent glycosyltransferase 76G1 gene of Stevia rebaudiana causes the low levels of rebaudioside A: mutations in UGT76G1, a key gene of steviol glycosides synthesis, Plant Physiol Biochem. 80:220-5 (2014).
Non-Final Office Action for U.S. Appl. No. 14/761,629, dated Mar. 21, 2017 (pp. 1-19).
Final Office Action for U.S. Appl. No. 14/761,629, dated Aug. 11, 2017 (pp. 1-16).
Non-Final Office Action for U.S. Appl. No. 14/764,898, dated Mar. 30, 2017 (pp. 1-17).
Final Office Action for U.S. Appl. No. 14/648,747, dated Sep. 6, 2017 (pp. 1-19).

Third Party Observation in EP Application No. 13801569.8; dated Oct. 23, 2017. pp. 1-6.
International Preliminary Report on Patentability from the International Bureau for International Application PCT/EP2015/070620; dated Mar. 14, 2017 (pp. 1-25).
Third Party Submission in U.S. Appl. No. 15/506,196; dated Mar. 9, 2018 pp. 1-68.
International Preliminary Report on Patentability from the International Bureau for International Application PCT/EP2015/052007; dated Aug. 1, 2017 (pp. 1-16).
International Preliminary Report on Patentability from the International Bureau for International Application PCT/EP2016/068259; dated Feb. 13, 2018 (pp. 1-11).
International Search Report and Written Opinion of International Search Authority for International Application No. PCT/EP2017/055589; dated May 12, 2017, pp. 1-18.
International Search Report of the International Searching Authority for International Application No. PCT/EP2017/061774; dated Aug. 30, 2017, pp. 1-20.
Written Opinion of the International Searching Authority for International Application No. PCT/EP2017/061774; dated Aug. 30, 2017, pp. 1-13.
International Search Report and Written Opinion of the International Searching Authority for International Application No. PCT/EP2017/061775; dated Sep. 6, 2017, pp. 1-17.
International Search Report and Written Opinion of the International Searching Authority for International Application No. PCT/EP2017/078473; dated Jan. 25, 2018, pp. 1-16.
Invitation to Pay Additional Fees and, Where Applicable, Protest Fee by the International Searching Authority for International Application No. PCT/EP2015/070620, dated Nov. 27, 2015 (pp. 1-14).
Yu et al., "Bioconversion of ethyl 4-chloro-3-oxobutanoate by permeabilized fresh brewer's yeast cells in the presence of allyl bromide," J Ind Microbiol Biotechnol. 34(2)151-6 (2007).
Yuan et al., "Kinetics and activation parameters for oxidations of styrene by Compounds I from the cytochrome P450 (BM-3) (CYP102A1) heme domain and from CYP119," Biochemistry 48(38):9140-6 (Sep. 2009).
Zheng et al. "An efficient one-step site-directed and site-saturation mutagenesis protocol," Nucleic Acids Res. 32(14):e115 (Aug. 2004).
Zhu et al., "A multi-omic map of the lipid-producing yeast *Rhodosporidium toruloides*," Nature Commun. 3:1112 (Oct. 2012).
GenBank Accession No. AAB62280, dated Jul. 2, 1997 (2 pages).
GenBank Accession No. AAB87091, dated Mar. 22, 2000 (2 pages).
GenBank Accession No. AAC28895.1, dated Aug. 6, 1998 (2 pages).
GenBank Accession No. AAC39505, dated Jul. 26, 1998 (1 page).
GenBank Accession No. AAD34294, dated Mar. 22, 2000 (2 pages).
GenBank Accession No. AAD34295, dated Mar. 22, 2000 (2 pages).
GenBank Accession No. AAD47596, dated Aug. 9, 1999 (2 pages).
GenBank Accession No. AAF61439.1, dated Sep. 25, 2000 (2 pages).
GenBank Accession No. AAH69913, dated Jul. 15, 2006 (2 pages).
GenBank Accession No. AAM53963.1, dated Jun. 17, 2002 (2 pages).
GenBank Accession No. AAR06912, dated Dec. 28, 2004 (2 pages).
GenBank Accession No. AAR06916.1, dated Dec. 28, 2004 (2 pages).
GenBank Accession No. AAR06918.1, dated Dec. 28, 2004 (2 pages).
GenBank Accession No. AAR06920.1, dated Dec. 28, 2004 (2 pages).
GenBank Accession No. AAT93110.1, dated Apr. 24, 2007 (2 pages).
GenBank Accession No. ABA42921, dated Jun. 21, 2006 (1 page).
GenBank Accession No. ABB88839, dated May 28, 2008 (2 pages).
GenBank Accession No. ABC59076, dated Jun. 6, 2007 (1 page).
GenBank Accession No. ABC98596, dated Jan. 31, 2014 (2 pages).
GenBank Accession No. ABD60225, dated May 28, 2008 (2 pages).
GenBank Accession No. ABD92926, dated Oct. 10, 2007 (2 pages).
GenBank Accession No. AC133334, dated Jan. 31, 2004 (44 pages).
GenBank Accession No. ACD93722, dated Jun. 10, 2008 (1 page).

(56) References Cited

OTHER PUBLICATIONS

GenBank Accession No. ACE87855.1, dated Jun. 24, 2008 (1 page).
GenBank Accession No. ACM47734.1, dated Feb. 7, 2009 (1 page).
GenBank Accession No. ACT33422.1, dated Jul. 17, 2009 (1 page).
GenBank Accession No. AEE36246, dated Oct. 6, 2014 (3 pages).
GenBank Accession No. AF034774, dated Apr. 17, 1998 (2 pages).
GenBank Accession No. AF515727.1, dated Jun. 17, 2002 (2 pages).
GenBank Accession No. AY345974.1, dated Dec. 28, 2004 (2 pages).
GenBank Accession No. AY345978.1, dated Dec. 28, 2004 (2 pages).
GenBank Accession No. AY345980.1, dated Dec. 28, 2004 (2 pages).
GenBank Accession No. AY345982.1, dated Dec. 28, 2004 (2 pages).
GenBank Accession No. AY562490, dated May 23, 2006 (3 pages).
GenBank Accession No. BAA43200, dated Mar. 13, 1999 (2 pages).
GenBank Accession No. BAB59027, dated Jan. 30, 2002 (1 page).
GenBank Accession No. BAF61135, dated May 9, 2007 (2 pages).
GenBank Accession No. BAG30962, dated Nov. 12, 2012 (2 pages).
GenBank Accession No. BC153262, dated Oct. 4, 2007 (3 pages).
GenBank Accession No. BG521726.1, dated May 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. CAA75568, dated Nov. 14, 2006 (2 pages).
GenBank Accession No. CAA76703, dated Nov. 14, 2006 (1 page).
GenBank Accession No. CAE09055, dated Nov. 14, 2006 (2 pages).
GenBank Accession No. CAG41604, dated Feb. 6, 2015 (2 pages).
Uniprot database entry Q75I83 version 31, updated Jul. 22, 2008 (pp. 1-4).
Uniprot database entry Q75I83 version 10, updated Jul. 5, 2004 (pp. 1-2).
Sequence alignment between the sequence of Uniprot database entry Q75I83 version 31, updated Jul. 22, 2008 and SEQ ID No. 152 (From European Pat. No. 2742142) as cited in Notice of Opposition against EP Application No. 12750513.9; dated Mar. 6, 2017; pp. 102.
Statement of Facts and Arguments in Support of Opposition for EP Application No. 12750513.9; dated Feb. 28, 2017, pp. 1-24.
Notice of Opposition against EP Application No. 12750513.9; dated Mar. 6, 2017, pp. 1-8.
Mahe et al., "The ATP Binding Cassette Transporters Pdr5 and Snq2 of *Saccharomyces cerevisiae* Can Mediate Transport of Steriods via in Vivo", JBC, 271(41):25167-25172 (Oct. 1996).
Communication pursuant to Rule 114(2) EPC for European Application No. 11790428.4, dated Apr. 25, 2016 (19 pages).
Examination Report issued by the European Patent Office for European Application No. 11790428.4, dated May 13, 2016 (12 pages).
Boer, "Strain and Process development for fermentative productive of Rebaudiosides", International Specialized Symposium of Yeasts, Abstract (Jun. 2017).
Geuns, "Stevioside," Phytochemistry 64(5):913-21 (2003).
Chen et al., "Progress in the Application of Affinity Tags for the Expression and Purification of Recombinant Proteins," China Biotechnology, vol. 32, No. 12, pp. 93-103, Dec. 15, 2012 (English Abstract Translation).
Guo et al., "Protein tolerance to random amino acid change", Proceedings of the National Academy of Sciences USA, vol. 101, No. 25, pp. 9205-9210 (2004).
Ni et al., "Outer membrane mutation effects on UDP-glucose permeability and whole-cell catalysis rate," Appl Microbiol Biotechnol. 73(2):384-93 (2006).
Prisic et al, "Synergistic substrate inhibition of ent-copalyl diphosphate synthase: a potential feed-forward inhibition mechanism limiting gibberellin metabolism," Plant Physiol. 144(1):445-54 (2007).
Ünligil et al., "Glycosyltransferase structure and mechanism," Curr Opin Struct Biol. 10(5):510-7 (2000).
Wanchao et al., "Advances on the Steviol Glycoside Biosynthesis and Its Key Enzymes," Biotechnology Bulletin, Feb. 2008 (English Abstract Translation).
GenBank Accession No. AAS07253.1, dated Jan. 31, 2004 (3 pages).

\* cited by examiner

Rubusoside
NMR-Data in d5-Pyridine

R$^1$  R$^2$
Glc  Glc

| No | Literature | | | Analyte | | HSQC |
|---|---|---|---|---|---|---|
| | 1H | | 13C | 1H | | |
| | δ [ppm] | M J[Hz] | | δ [ppm] | M J[Hz] | |
| 1 | | | 40.8 | | | 40.7 |
| 2 | | | 19.4 | | | 19.4 |
| 3 | | | 38.3 | | | 38.0 |
| 4 | | | 44.0 | | | - |
| 5 | | | 57.3 | | | 57.1 |
| 6 | | | 22.1 | | | 22.0 |
| 7 | | | 41.1 | | | 41.5 |
| 8 | | | 42.4 | | | - |
| 9 | | | 53.9 | | | 53.7 |
| 10 | | | 39.8 | | | - |
| 11 | | | 20.7 | | | 20.5 |
| 12 | | | 37.2 | | | 36.8 |
| 13 | | | 85.9 | | | - |
| 14 | | | 44.5 | | | 44.5 |
| 15 | | | 47.7 | | | 47.6 |
| 16 | | | 154.5 | | | - |
| 17 | 4.99 / 5.33 | br s / br s | 104.4 | 4.99 / 5.46 | br s / br s | 104.2 |
| 18 | 1.25 | s | 28.3 | 1.25 | s | 28.3 |
| 19 | | | 176.9 | | | - |
| 20 | 1.26 | s | 15.6 | 1.21 | s | 15.6 |
| 13-O-Glc | | | | | | |
| 1 | 5.13 | d 7.7 | 99.7 | 5.00 | d 8.4 | 99.0 |
| 2 | 4.07 | dd 7.7/9.0 | 75.2 | | | 74.8 |
| 2 | 4.22 | dd 9.0/8.9 | 78.8 | | | 78.2 |
| 4 | 4.32 | dd 8.9/8.8 | 72.3 | | | 71.8 |
| 5 | 4.00 | ddd 8.8/2.4/4.4 | 78.0 | | | 77.2 |
| 6 | 4.45 / 4.26 | dd 2.4/12.0 / dd 2.4/12.0 | 63.0 | 4.42 | dd 2.3/12.5 | 62.6 |
| 19-O-Glc | | | | | | |
| 1 | 6.14 | d 7.9 | 95.9 | 5.99 | d 8.1 | 95.2 |
| 2 | 4.20 | dd 7.9/9.0 | 74.0 | | | 73.5 |
| 2 | 4.22 | dd 9.0/9.0 | 79.1 | | | 78.4 |
| 4 | 4.09 | dd 9.0/8.8 | 71.1 | | | 70.7 |
| 5 | 3.98 | ddd 8.8/2.2/4.6 | 79.3 | | | 78.4 |
| 6 | 4.61 / 4.26 | dd 2.2/11.7 / dd 4.6/11.7 | 62.1 | 4.31 / 4.22 | dd 2.5/12.3 / dd 4.0/11.7 | 61.8 |

Multiple Sequence Alignment

```
SEQ ID NO:14    MYNTYHQMSKAMATSDSIVDDRKQLHVATPPWLAFGHILPFLQLSKLIA
SEQ ID NO:16    ------------MATSDSIVDDRKQLHVATPPWLAEGHILPFLQLSKLIA
SEQ ID NO:12    ------------MATSDSIVDDRKQLHVATPPWLAEGHILPFLQLSKLIA
SEQ ID NO: 5    ------------MATSDSIVDDRKQLHVATPPWLAFGHILPYLQLSKLIA
SEQ ID NO:10    ------------MATSDSIVDDRKQLHVATPPWLAFGHILPYLQLSKLIA
                            **********:*********.****:*******

SEQ ID NO:14    EKGHKVSFLSTTRNIQRLSSHISPLINVVQLTLPRVQELPEDAEATTDVH
SEQ ID NO:16    EKGHKVSFLSTTRNIQRLSSHISPLINVVQLTLPRVQELPEDAEATTDVH
SEQ ID NO:12    EKGHKVSFLSTTRNIQRLSSHISPLINVVQLTLPRVQELPEDAEATTDVH
SEQ ID NO: 5    EKGHKVSFLSTTRNIQRLSSHISPLINVVQLTLPRVQELPEDAEATTDVH
SEQ ID NO:10    EKGHKVSFLSTTRNIQRLSSHISPLINVVQLTLPRVQELPEDAEATTDVH
                *************************************************

SEQ ID NO:14    PEDIQYLKKAVDGLQPEVTRFLEQHSPDWIIYDFTHYWLPSIAASLGISR
SEQ ID NO:16    PEDIQYLKKAVDGLQPEVTRFLEQHSPDWIIYDFTHYWLPSIAASLGISR
SEQ ID NO:12    PEDIQYLKKAVDGLQPEVTRFLEQHSPDWIIYDFTHYWLPSIAASLGISR
SEQ ID NO: 5    PEDLPYLKKAEDGLQPEVTRFLEQHSPDWIIYDYTHYWLPSIAASLGISR
SEQ ID NO:10    PEDIPYLKKASDGLQPEVTRFLEQHSPDWIIYDYTHYWLPSIAASLGISR
                ***: *****  **********************:**************

SEQ ID NO:14    AYFCVITPWIIAYLAPSSDAMINDSDGRTTVEDLTTPKWFPFPTKVCWR
SEQ ID NO:16    AYFCVITPWIIAYLAPSSDAMINDSDGRTTVEDLTTPKWFPFPTKVCWR
SEQ ID NO:12    AYFCVITPWIIAYLAPSSDAMINDSDGRTTVEDLTTPKWFPFPTKVCWR
SEQ ID NO: 5    AHFSVTTPWAIAYMGPSADAMINGSDGRTTVEDLTTPKWFPFPTKVCWR
SEQ ID NO:10    AHFSVTTPWAIAYMGPSADAMINGSDGRTTVEDLTTPKWFPFPTKVCWR
                *:* **:** ***  **:****.********************

SEQ ID NO:14    KHDLARMEPYEAPGISDGYRMGMVFKGSDCLLFKCYHEFGTQWLPLLETL
SEQ ID NO:16    KHDLARMEPYEAPGISDGYRMGMVFKGSDCLLFKCYHEFGTQWLPLLETL
SEQ ID NO:12    KHDLARMEPYEAPGISDGYRMGMVFKGSDCLLFKCYHEFGTQWLPLLETL
SEQ ID NO: 5    KHDLARLVFKKAPGISDGYRMGLVLKGSDCLLSKCYHEFGTQWLPLLETL
SEQ ID NO:10    KHDLARLVPYKAPGISDGYRMGLVLKGSDCLLSKCYHEFGTQWLPLLETL
                ******:  :********** :*:****** *****************

SEQ ID NO:14    HQVPVPVGLLPPEIPGDEKDETWSLKKWLDGKQKGSVVVALGSSEALV
```

FIGURE 8

```
SEQ ID NO:16    HQVPVVPVGLLPPEIPGDEKDETWVSIKKWLDGKQKGSVVYVALGSEALV
SEQ ID NO:12    HQVPVVPVGLLPPEIPGDEKDETWVSIKKWLDGKQKGSVVYVALGSEALV
SEQ ID NO: 5    HQVPVVPVGLLPPEVPGDEKDETWVSIKKWLDGKQKGSVVYVALGSEVLV
SEQ ID NO:10    HQVPVVPVGLLPPEVPGDEKDETWVSIKKWLDGKQKGSVVYVALGSEVLV
                ************:*************************** ****:**

SEQ ID NO:14    SQTEVVELALGLELSGLPFVWAYRKPKGPAKSDSVELPDGFVERTRDRGL
SEQ ID NO:16    SQTEVVELALGLELSGLPFVWAYRKPKGPAKSDSVELPDGFVERTRDRGL
SEQ ID NO:12    SQTEVVELALGLELSGLPFVWAYRKPKGPAKSDSVELPDGFVERKRDRGL
SEQ ID NO: 5    SQTEVVELALGLELSGLPFVWAYRKPKGPAKSDSVELPDGFVERTRDRGL
SEQ ID NO:10    SQTEVVELALGLELSGLPFVWAYRKPKGPAKSDSVELPDGFVERTRDRGL
                ******************************************:*****

SEQ ID NO:14    VWTSWAPQLRILSHESVCGFLTHCGSGSIVEGLMFGHPLIMLPIFCDQPL
SEQ ID NO:16    VWTSWAPQLRILSHESVCGFLTHCGSGSIVEGLMFGHPLIMLPIFCDQPL
SEQ ID NO:12    VWTSWAPQLRILSHESVCGFLTHCGSGSIVEGLMFGHPLIMLPIFGDQPL
SEQ ID NO: 5    VWTSWAPQLRILSHESVCGFLTHCGSGSIVEGLMFGHPLIMLPLFGDQPL
SEQ ID NO:10    VWTSWAPQLRILSHESVCGFLTHCGSGSIVEGLMFGHPLIMLPIFGDQPL
                ******************************************:*.****

SEQ ID NO:14    NARLLEDKQVGIEIPRNEDGCLTKESVARSLRSVVENEGELYKANARA
SEQ ID NO:16    NARLLEDKQVGIEIPRNEDGCLTKESVARSLRSVVVENEGEIYKANARA
SEQ ID NO:12    NARLLEDKQVGIEIPRNEDGCLTKESVARSLRSVVEKEGEIYKANARE
SEQ ID NO: 5    NARLLEDKQVGIEIPRNEEDGCLTKESVARSLRSVVEKEGEIYKANARE
SEQ ID NO:10    NARLLEDKQVGIEIPRNEEDGCLTKESVARSLRSVVVEKEGEIYKANARE
                ******************:*****************::**:******:

SEQ ID NO:14    LSKIYNDTKVEKEYVSQFVDYLEKNARAVAIDHES
SEQ ID NO:16    LSKIYNDTKVEKEYVSQFVDYLEKNARAVAIDHES
SEQ ID NO:12    LSKIYNDTKVEKEYVSQFVDYLEKNARAVAIDHES
SEQ ID NO: 5    LSKIYNDTKVEKEYVSQFVDYLEKNARAVAIDHES
SEQ ID NO:10    LSKIYNDTKVEKEYVSQFVEYLEKNTRAVAIDHES
                *******************::****.********

CLUSTAL W (1.82) multiple sequence alignment
```

PRODUCTION OF STEVIOL GLYCOSIDES IN MICROORGANISMS

This application is a divisional of U.S. application Ser. No. 13/701,406, filed on Mar. 22, 2013, now U.S. Pat. No. 9,562,251, granted on Feb. 7, 2017, which is a U.S. national phase of International Application No. PCT/US2011/038967 filed on Jan. 2, 2011, which claims the benefit of U.S. Provisional Application No. 61/350,553, filed on Jun. 2, 2010, U.S. Provisional Application No. 61/434,582, filed on Jan. 20, 2011, and U.S. Provisional Application No. 61/471,622, filed on Apr. 4, 2011. The entire disclosure contents of these applications are herewith incorporated by reference in their entirety into the present application.

SEQUENCE LISTING

The instant application contains a Sequence Listing which has been submitted in ASCII format via EFS-Web and is hereby incorporated by reference in its entirety. Said ASCII copy, created on Jun. 2, 2011, is named 25933WO1.txt and is 483,406 bytes in size.

TECHNICAL FIELD

This disclosure relates to the recombinant production of steviol and steviol glycosides. In particular, this disclosure relates to the production of steviol and steviol glycosides such as rubusoside and/or rebaudioside A by recombinant hosts such as recombinant microorganisms, plants, or plant cells. This disclosure also provides compositions containing steviol glycosides.

BACKGROUND

Sweeteners are well known as ingredients used most commonly in the food, beverage, or confectionary industries. The sweetener can either be incorporated into a final food product during production or for stand-alone use, when appropriately diluted, as a tabletop sweetener or an at-home replacement for sugars in baking. Sweeteners include natural sweeteners such as sucrose, high fructose corn syrup, molasses, maple syrup, and honey and artificial sweeteners such as aspartame, saccharine and sucralose. *Stevia* extract is a natural sweetener that can be isolated and extracted from a perennial shrub, *Stevia rebaudiana*. *Stevia* is commonly grown in South America and Asia for commercial production of *stevia* extract. *Stevia* extract, purified to various degrees, is used commercially as a high intensity sweetener in foods and in blends or alone as a tabletop sweetener.

Extracts of the *Stevia* plant contain rebaudiosides and other steviol glycosides that contribute to the sweet flavor, although the amount of each glycoside often varies among different production batches. Existing commercial products are predominantly rebaudioside A with lesser amounts of other glycosides such as rebaudioside C, D, and F. *Stevia* extracts may also contain contaminants such as plant-derived compounds that contribute to off-flavors. These off-flavors can be more or less problematic depending on the food system or application of choice. Potential contaminants include pigments, lipids, proteins, phenolics, saccharides, spathulenol and other sesquiterpenes, labdane diterpenes, monoterpenes, decanoic acid, 8,11,14-eicosatrienoic acid, 2-methyloctadecane, pentacosane, octacosane, tetracosane, octadecanol, stigmasterol, β-sitosterol, α- and β-amyrin, lupeol, β-amryin acetate, pentacyclic triterpene, centaureidin, quercitin, epi-alpha-cadinol, carophyllenes and derivatives, beta-pinene, beta-sitosterol, and gibberellin.

SUMMARY

Provided herein is a recombinant host, such as a microorganism, comprising one or more biosynthesis genes whose expression results in production of steviol. Such genes include a gene encoding a copalyl diphosphate synthase, a gene encoding a kaurene synthase, a gene encoding a kaurene oxidase; and a gene encoding a steviol synthetase. The recombinant host can include a gene encoding a bifunctional copalyl diphosphate synthase and kaurene synthase, in place of the genes encoding copalyl diphosphate synthase and kaurene synthase. At least one of the genes is a recombinant gene. In some embodiments the recombinant host further comprises a gene encoding a geranylgeranyl diphosphate synthase. The recombinant host can further comprise a gene encoding a truncated HMG-CoA reductase and/or a gene encoding a CPR. The expression of one or more of the genes can be inducible.

In one aspect, this document features a recombinant host that includes a recombinant gene encoding a UGT91D2 polypeptide (e.g., a UGT91D2e or UGT91D2m polypeptide). The UGT91D2 polypeptide can have at least 90% identity (e.g., at least 95% or 99% identity) to the amino acid sequence set forth in SEQ ID NO:5. The UGT91D2 polypeptide can include at least one amino acid substitution at residues 1-19, 27-38, 44-87, 96-120, 125-141, 159-184, 199-202, 215-380, or 387-473 of SEQ ID NO:5. For example, the UGT91D2 polypeptide can include an amino acid substitution at one or more residues selected from the group consisting of residues 30, 93, 99, 122, 140, 142, 148, 153, 156, 195, 196, 199, 206, 207, 211, 221, 286, 343, 427, and 438 of SEQ ID NO:5. In one embodiment, the UGT91D2 polypeptide includes an arginine at residue 206, a cysteine at residue 207, and an arginine at residue 343 relative to SEQ ID NO:5. In one embodiment, the UGT91D2 polypeptide includes a phenylalanine at residue 30, a glutamine at residue 93, a valine at residue 99, a phenylalanine at residue 122, a tyrosine at residue 140, a cysteine at residue 142, a threonine at residue 148, an alanine at residue 153, a serine at residue 156, a methionine at residue 195, a glutamic acid at residue 196, a glutamic acid at residue 199, a methionine at residue 211, a phenylalanine at residue 221, an alanine at residue 286, an asparagine at residue 427, or an alanine at residue 438 relative to SEQ ID NO:5. The polypeptide can have the amino acid sequence of SEQ ID NO:5 or SEQ ID NO:95.

A host described herein further can include a recombinant gene encoding a UGT85C polypeptide having at least 90% identity to the amino acid sequence set forth in SEQ ID NO:3. For example, the UGT85C polypeptide can include one or more amino acid substitutions at residues 9, 10, 13, 15, 21, 27, 60, 65, 71, 87, 91, 220, 243, 270, 289, 298, 334, 336, 350, 368, 389, 394, 397, 418, 420, 440, 441, 444, and 471 of SEQ ID NO:3.

A host described herein further can include a recombinant gene encoding a UGT76G polypeptide having at least 90% identity to the amino acid sequence set forth in SEQ ID NO:7. For example, the UGT76G polypeptide can have one or more amino acid substitutions at residues 29, 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346 of SEQ ID NO:7.

This document also features a recombinant host that includes a recombinant gene encoding a UGT85C polypeptide having at least 90% identity to the amino acid sequence set forth in SEQ ID NO:3, and having one or more amino acid substitutions at residues 9, 10, 13, 15, 21, 27, 60, 65, 71, 87, 91, 220, 243, 270, 289, 298, 334, 336, 350, 368, 389, 394, 397, 418, 420, 440, 441, 444, and 471 of SEQ ID NO:3. For example, the UGT85C polypeptide can include substitutions at residues 13, 15, 60, 270, 289, and 418 of SEQ ID NO:3. For example, the UGT85C polypeptide can include a) substitutions at residues 13, 60, and 270 of SEQ ID NO:3; b) substitutions at residues 60 and 87 of SEQ ID NO:3; c) substitutions at residues 65, 71, 220, 243, and 270 of SEQ ID NO:3; d) substitutions at residues 65, 71, 220, 243, 270, and 441 of SEQ ID NO:3; e) substitutions at residues 65, 71, 220, 389, and 394 of SEQ ID NO:3; f) substitutions at residues 65, 71, 270, and 289 of SEQ ID NO:3; g) substitutions at residues 15 and 65 of SEQ ID NO:3; h) substitutions at residues 65 and 270 of SEQ ID NO:3; i) substitutions at residues 65 and 440 of SEQ ID NO:3; j) substitutions at residues 65 and 441 of SEQ ID NO:3; k) substitutions at residues 65 and 418 of SEQ ID NO:3; l) substitutions at residues 220, 243, 270, and 334 of SEQ ID NO:3; or m) substitutions at residues 270 and 289 of SEQ ID NO:3.

In another aspect, this document features a recombinant host that includes a recombinant gene encoding a UGT76G polypeptide having at least 90% identity to the amino acid sequence set forth in SEQ ID NO:7, and having one or more amino acid substitutions at residues 29, 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346. For example, the UGT76G polypeptide can have a) substitutions at amino acid residues 74, 87, 91, 116, 123, 125, 126, 130, 145, 192, 193, 194, 196, 198, 199, 200, 203, 204, 205, 206, 207, 208, and 291; b) substitutions at residues 74, 87, 91, 116, 123, 125, 126, 130, 145, 192, 193, 194, 196, 198, 199, 200, 203, 204, 205, 206, 207, 208, 266, 273, 274, 284, 285, and 291; or c) substitutions at residues 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346.

Any of the hosts described herein further can include a gene encoding a UGT74G1 polypeptide (e.g., a recombinant gene encoding a UGT74G1 polypeptide).

Any of the hosts described herein further can include one or more of: (i) a gene encoding a geranylgeranyl diphosphate synthase; (ii) a gene encoding a bifunctional copalyl diphosphate synthase and kaurene synthase, or a gene encoding a copalyl diphosphate synthase and a gene encoding a kaurene synthase; (iii) a gene encoding a kaurene oxidase; (iv) a gene encoding a steviol synthetase; (v) a gene encoding a truncated HMG-CoA; (vi) a gene encoding a CPR; (vii) a gene encoding a rhamnose synthetase; (viii) a gene encoding a UDP-glucose dehydrogenase; and (ix) a gene encoding a UDP-glucuronic acid decarboxylase. At least one of the genes of (i), (ii), (iii), (iv), (v), (vi), (vii), (viii), or (ix) can be a recombinant gene. In some so embodiments, each of the genes of (i), (ii), (iii), and (iv) is a recombinant gene.

This document also features an isolated nucleic acid encoding a polypeptide having at least 90% sequence identity (e.g., at least 95% or 99% sequence identity) to the amino acid sequence set forth in SEQ ID NO:5. The polypeptide can include at least one amino acid substitution at residues 1-19, 27-38, 44-87, 96-120, 125-141, 159-184, 199-202, 215-380, or 387-473 of SEQ ID NO:5. The polypeptide can include an amino acid substitution at one or more residues selected from the group consisting of residues 30, 93, 99, 122, 140, 142, 148, 153, 156, 195, 196, 199, 206, 207, 211, 221, 286, 343, 427, and 438 of SEQ ID NO:5. The polypeptide can include an arginine at residue 206, a cysteine at residue 207, and an arginine at residue 343 of SEQ ID NO:5. In some embodiments, the polypeptide includes a phenylalanine at residue 30, a glutamine at residue 93, a valine at residue 99, a phenylalanine at residue 122, a tyrosine at residue 140, a cysteine at residue 142, a threonine at residue 148, an alanine at residue 153, a serine at residue 156, a methionine at residue 195, a glutamic acid at residue 196, a glutamic acid at residue 199, a methionine at residue 211, a phenylalanine at residue 221, an alanine at residue 286, an asparagine at residue 427, or an alanine at residue 438 of SEQ ID NO:5.

In another aspect, this document features an isolated polypeptide having an amino acid sequence with at least 90% identity to the amino acid sequence of SEQ ID NO:5.

This document also features a recombinant host that includes (i) a gene encoding a geranylgeranyl diphosphate synthase; (ii) a gene encoding a bifunctional copalyl diphosphate synthase and kaurene synthase, or a gene encoding a copalyl diphosphate synthase and a gene encoding a kaurene synthase; (iii) a gene encoding a kaurene oxidase; and (iv) a gene encoding a steviol synthetase; wherein at least one of said genes. The host can produce steviol when cultured under conditions in which each of the genes is expressed, and can accumulate to at least 1 mg/L in the culture medium. The geranylgeranyl diphosphate synthase can have greater than 90% sequence identity to one of the amino acid sequences set forth in SEQ ID NOs: 121-128. The copalyl diphosphate synthase can have greater than 90% sequence identity to one of the amino acid sequences set forth in SEQ ID NOs:129-131. The kaurene synthase can have greater than 90% sequence identity to one of the amino acid sequences set forth in 132-135. The kaurene oxidase can have greater than 90% sequence identity to one of the amino acid sequences set forth in 138-141. The steviol synthetase can have greater than 90% sequence identity to one of the amino acid sequences set forth in SEQ ID NOs:142-146. The host further can include a gene encoding a truncated HMG-CoA and/or a gene encoding a CPR.

Any of the recombinant hosts further can include one or more of a gene encoding a UGT74GI polypeptide, a UGT85C2 polypeptide, a UGT76G1 polypeptide, or a UGT91D2 polypeptide.

Any of the recombinant hosts can produce at least one steviol glycoside when cultured under conditions in which each of the genes is expressed. The steviol glycoside can be selected from the group consisting of steviol-13-O-glucoside, steviol-19-O-glucoside, rubusoside, rebaudioside A, rebaudioside B, rebaudioside C, rebaudioside D, rebaudioside E, rebaudioside F, and dulcoside A. The steviol glycoside can accumulate to at least 1 mg/liter (e.g., at least 10 mg/liter or 20 mg/liter) of culture medium when cultured under said conditions.

Any of the recombinant hosts further can include one or more of i) a gene encoding a deoxyxylulose 5-phosphate synthase (DXS); ii) a gene encoding a D-1-deoxyxylulose 5-phosphate reductoisomerase (DXR); iii) a gene encoding a 4-diphosphocytidyl-2-C-methyl-D-erythritol synthase (CMS); iv) a gene encoding a 4-diphosphocytidyl-2-C-methyl-D-erythritol kinase (CMK); v) a gene encoding a 4-diphosphocytidyl-2-C-methyl-D-erythritol 2,4-cyclodiphosphate synthase (MCS); vi) a gene encoding a 1-hydroxy-2-methyl-2(E)-butenyl 4-diphosphate synthase (HDS); or vii) a gene encoding a 1-hydroxy-2-methyl-2(E)-butenyl 4-diphosphate reductase (HDR).

Any of the recombinant hosts further can include one or more of ix) a gene encoding a acetoacetyl-CoA thiolase; x) a gene encoding a truncated HMG-CoA reductase; xi) a gene encoding a mevalonate kinase; xii) a gene encoding a phosphomevalonate kinase; or xiii) a gene encoding a mevalonate pyrophosphate decarboxylase.

In any of the hosts described herein, expression of one or more of the genes can be inducible.

Any of the hosts described herein can be a microorganism (e.g., a *Saccharomycete* such as *Saccharomyces cerevisiae*, or *Escherichia coli*), or a plant or plant cell (e.g., a *Stevia* such as a *Stevia rebaudiana, Physcomitrella*, or tobacco plant or plant cell).

In another aspect, this document features a method of producing steviol or a steviol glycoside. The method includes growing a host described herein in a culture medium, under conditions in which the genes are expressed; and recovering the steviol or steviol glycoside produced by the host. The growing step can include inducing expression of one or more of the genes. The steviol or steviol glycoside is selected from the group consisting of steviol-13-O-glucoside, steviol-19-O-glucoside, rubusoside, rebaudioside A, rebaudioside B, rebaudioside C, rebaudioside D, rebaudioside E, rebaudioside F, and dulcoside A.

Also provided herein is a method of producing steviol or a steviol glycoside. The method includes growing a microorganism in a culture medium, under conditions in which a geranylgeranyl diphosphate synthase, copalyl diphosphate synthase, kaurene synthase, kaurene oxidase, kaurenoic acid 13-hydroxylase gene and optionally a UGT74G1 and/or a UGT85C2 gene are expressed, and recovering the steviol or steviol glycoside produced by the microorganism. The microorganism can be a *Saccharomyces* spp. In some embodiments, the growing step comprises inducing expression of one or more of the geranylgeranyl diphosphate synthase, copalyl diphosphate synthase, kaurene synthase, kaurene oxidase, kaurenoic acid 13-hydroxylase, UGT74G1 and UGT85C2 genes. In some embodiments, the recovering step comprises purifying the steviol or steviol glycoside from the culture medium by HPLC. The steviol or steviol glycoside can be steviol, rubusoside, rebaudioside C, rebaudioside F, or dulcoside A.

Also provided herein is a recombinant *Saccharomyces* strain, comprising one or more biosynthesis genes whose expression results in production of ent-kaurene. The biosynthesis genes include a gene encoding a bifunctional copalyl diphosphate synthase and kaurene synthase, or a gene encoding a copalyl diphosphate synthase and a gene encoding a kaurene synthase. The strain produces ent-kaurene upon expression of the copalyl diphosphate synthase and the kaurene synthase.

In another aspect, this document features an isolated nucleic acid having greater than 90% sequence identity (e.g., greater than 95% or 99% sequence identity) to one of the nucleotide sequences set forth in SEQ ID NOs: 18-25, 34-36, 4-43, 48, 49, 52-55, 60-64, 70-72, 77, or 79.

This document also features a recombinant host that includes (i) a gene encoding a UGT74G1; (ii) a gene encoding a UGT85C2; (iii) a gene encoding a UGT76G1; and (iv) a gene encoding a UGT91D2, wherein at least one of said genes is a recombinant gene. In some embodiments, each of the genes is a recombinant gene. The host can produce at least one steviol glycoside when cultured under conditions in which each of the genes is expressed. The host further can include (a) a gene encoding a bifunctional copalyl diphosphate synthase and kaurene synthase, or a gene encoding a copalyl diphosphate synthase and a gene encoding a kaurene synthase; (b) a gene encoding a kaurene oxidase; (c) a gene encoding a steviol synthetase; and (d) a gene encoding a geranylgeranyl diphosphate synthase. The steviol glycoside can be rebaudioside A, rebaudioside D or rebaudioside E. This document also features a steviol glycoside composition produced by such a host. The composition can have greater than 4% rebaudioside D by weight of total steviol glycosides and a reduced level of *stevia* plant-derived contaminants relative to a *stevia* extract. The composition can have greater than 4% rebaudioside E by weight of total steviol glycosides and a reduced level of *stevia* plant-derived contaminants relative to a *stevia* extract.

Also featured herein is an isolated nucleic acid encoding a polypeptide having greater than 90% sequence identity to the amino acid sequences of UGT91D2e and UGT91D2m, excluding the amino acid sequence of UGT91D2m, as well as the isolated polypeptides having greater than 90% sequence identity to the amino acid sequence of UGT91D2e or UGT91D2m, excluding the amino acid sequence of UGT91D2m.

This document also features steviol glycoside composition produced by the host described herein. The composition having reduced levels of *stevia* plant-derived contaminants relative to a *stevia* extract.

In another aspect, this document features a recombinant host. The host includes (i) a recombinant gene encoding a UGT91D2; (ii) a recombinant gene encoding a UGT74G1; (iii) a recombinant gene encoding a UGT85C2; (iv) a recombinant gene encoding a UGT76G1; and (v) a gene encoding a rhamnose synthetase, wherein the host produces at least one steviol glycoside when cultured under conditions in which each of the genes is expressed. The host further can include (a) a gene encoding a bifunctional copalyl diphosphate synthase and kaurene synthase, or a gene encoding a copalyl diphosphate synthase and a gene encoding a kaurene synthase; (b) a gene encoding a kaurene oxidase; (c) a gene encoding a steviol synthetase; and (d) a gene encoding a geranylgeranyl diphosphate synthase. The steviol glycoside can be rebaudioside C or dulcoside A. This document also features a steviol glycoside composition produced by such a host. The composition has greater than 15% rebaudioside C by weight of total steviol glycosides and a reduced level of *stevia* plant-derived contaminants relative to a *stevia* extract. A steviol glycoside composition produced by such a host also is featured. The composition can have greater than 15% dulcoside A by weight of total steviol glycosides and a reduced level of *stevia* plant-derived contaminants relative to a *stevia* extract.

This document also features a recombinant host. The host includes (i) a recombinant gene encoding a UGT91D2; (ii) a recombinant gene encoding a UGT74G1; (iii) a recombinant gene encoding a UGT85C2; (iv) a recombinant gene encoding a UGT76G1; (v) a gene encoding a UDP-glucose dehydrogenase; and (vi) a gene encoding a UDP-glucuronic acid decarboxylase, wherein the host produces at least one steviol glycoside when cultured under conditions in which each of the genes is expressed. The host further can include (a) a gene encoding a bifunctional copalyl diphosphate synthase and kaurene synthase, or a gene encoding a copalyl diphosphate synthase and a gene encoding a kaurene synthase; (b) a gene encoding a kaurene oxidase; (c) a gene encoding a steviol synthetase; and (d) a gene encoding a geranylgeranyl diphosphate synthase. The steviol glycoside can be rebaudioside F. This document also features a steviol glycoside composition produced by such hosts. The composition can have greater than 4% rebaudioside F by weight of total steviol glycosides and a reduced level of *stevia* plant-derived contaminants relative to a *stevia* extract.

In another aspect, this document features a method of producing a steviol glycoside composition. The method includes growing a host described herein in a culture medium, under conditions in which each of the genes is expressed; and recovering the steviol glycoside composition produced by the host, wherein the recovered composition is enriched for rebaudioside A, rebaudioside C, rebaudioside D, rebaudioside E, rebaudioside F or dulcoside A relative to the steviol glycoside composition of a wild-type *Stevia* plant. The steviol glycoside composition produced by the host (e.g., microorganism) can have a reduced level of *stevia* plant-derived contaminants relative to a *stevia* extract.

This document also features a food product that includes a steviol glycoside composition enriched for rebaudioside A, rebaudioside C, rebaudioside D, rebaudioside E, rebaudioside F or dulcoside A relative to the steviol glycoside composition of a wild-type *Stevia* plant.

In another aspect, this document features a method of identifying whether a polymorphism is associated with variation in a trait. The method includes determining whether one or more genetic polymorphisms in a population of plants is associated with the locus for a polypeptide set forth in SEQ ID NO:5 and functional homologs thereof; and measuring the correlation between variation in the trait in plants of the population and the presence of the one or more genetic polymorphisms in plants of the population, thereby identifying whether or not the one or more genetic polymorphisms are associated with variation in the trait.

In yet another aspect, this document features a method of making a plant line. The method includes determining whether one or more genetic polymorphisms in a population of plants is associated with the locus for a polypeptide set forth in SEQ ID NO:5 and functional homologs thereof; identifying one or more plants in the population in which the presence of at least one of the genetic polymorphisms is associated with variation in a trait; crossing one or more of the identified plants with itself or a different plant to produce seed; crossing at least one progeny plant grown from the seed with itself or a different plant; and repeating the crossing steps for an additional 0-5 generations to make said plant line, wherein at least one of the genetic polymorphisms is present in the plant line.

This document also features a method for transferring a second sugar moiety to the C-2' of a glucose in a steviol glycoside. The method includes contacting the steviol glycoside with a UGT91D2 polypeptide and a UDP-sugar under suitable reaction conditions for the transfer of the second sugar moiety to the steviol glycoside. The UGT9ID2 polypeptide can have at least 90% sequence identity (e.g., at least 95% or 99%) to the amino acid sequence set forth in SEQ ID NO:5. The UGT91D2 polypeptide can include at least one amino acid substitution at residues 1-19, 27-38, 44-87, 96-120, 125-141, 159-184, 199-202, 215-380, or 387-473 of SEQ ID NO:5. The UGT91D2 polypeptide can include an amino acid substitution at one or more residues selected from the group consisting of residues 30, 93, 99, 122, 140, 142, 148, 153, 156, 195, 196, 199, 206, 207, 211, 221, 286, 343, 427, and 438 of SEQ ID NO:5. The steviol glycoside can be selected from the group consisting of steviol-13-O-glucoside, rubusoside, stevioside, and Rebaudioside A. The steviol glycoside can be rubusoside and the second sugar moiety is glucose, and stevioside is produced upon transfer of the second glucose moiety. The steviol glycoside can be stevioside and the second sugar moiety can be glucose, and Rebaudioside E is produced upon transfer of the second glucose moiety. The steviol glycoside can be stevioside, wherein stevioside is contacted with the UGT91D2 polypeptide and a UGT76G1 polypeptide under suitable reaction conditions to produce Rebaudioside D. The steviol glycoside can be steviol-13-O-glucoside and steviol-1,2 bioside is produced upon transfer of said second glucose moiety. The steviol glycoside can be steviol-13-O-glucoside and steviol-1,2-xylobioside is produced upon transfer of the second sugar moiety. The steviol glycoside can be steviol-13-O-glucoside and steviol-1,2-rhamnobioside can be produced upon transfer of the second sugar moiety. The steviol glycoside can be Rebaudioside A, and Rebaudioside D is produced upon transfer of a second glucose moiety.

In another aspect, this document features a method of determining the presence of a polynucleotide in a *Stevia* plant. The method includes contacting at least one probe or primer pair with nucleic acid from the *Stevia* plant, wherein the probe or primer pair is specific for a polynucleotide that encodes a UGT polypeptide, wherein the UGT polypeptide has at least 90% sequence identity to SEQ ID NO: 5, SEQ ID NO: 1, SEQ ID NO: 3 or SEQ ID NO:7 and determining whether or not the polynucleotide is present in said *Stevia* plant.

This document also features a kit for genotyping a *Stevia* biological sample. The kit includes a primer pair that specifically amplifies, or a probe that specifically hybridizes to, a polynucleotide that encodes a UGT polypeptide having at least 90% sequence identity to SEQ ID NO: 5, SEQ ID NO: 1, SEQ ID NO: 3 or SEQ ID NO:7.

Also provided herein is a recombinant microorganism, comprising one or more biosynthesis genes whose expression results in production of one or more steviol glycosides. The biosynthesis genes include a gene encoding a geranylgeranyl diphosphate synthase, a gene encoding a copalyl diphosphate synthase and a gene encoding a kaurene synthase, a gene encoding a kaurene oxidase, a gene encoding a steviol synthetase, and a gene encoding a UGT74G1 and/or a UGT85C2. At least one of the genes is a recombinant gene. The microorganism can comprise a gene encoding a bifunctional copalyl diphosphate synthase and kaurene synthase in place of the genes encoding copalyl diphosphate synthase and kaurene synthase.

The recombinant microorganism produces at least one steviol glycoside when cultured under conditions in which each of the genes is expressed. The steviol glycoside can be rubusoside, rebaudioside C, rebaudioside F, dulcoside B, or dulcoside A.

The recombinant microorganism can be a *Saccharomycete*, e.g., *Saccharomyces cerevisiae*, and can have one or more genetic modifications that reduce EXG1 and EXG2 glycoside hydrolase activity relative to a control microorganism that lacks such genetic modifications, and can have one or more genetic modifications that reduce ergosterol biosynthesis relative to a control microorganism that lacks such genetic modifications. The *Saccharomycete* produces rubusoside when cultured under conditions in which each of the genes is expressed. The rubusoside can accumulate to at least 10 mg/liter of culture medium. The *Saccharomycete* can be a *Saccharomyces cerevisiae* strain designated CEY171, CEY191, or CEY213.

The recombinant microorganism can further comprise a gene encoding an SM12UGT and a gene encoding a UGT76G1, and produce a steviol glycoside when cultured under conditions in which each of the genes is expressed. The steviol glycoside can be rebaudioside A.

Also provided herein is a recombinant microorganism, comprising one or more biosynthesis genes whose expression results in production of at least one steviol glycoside. The biosynthesis genes include a gene encoding an SM12UGT, a gene encoding a UGT74G1, a gene encoding a UGT76G1 and a gene encoding a UGT85C2. The recombinant microorganism produces rebaudioside A or rebaudioside B when cultured under conditions in which each of the genes is expressed. The rebaudioside A or rebaudioside B can accumulate to at least 1 mg/L in the culture medium.

Also featured herein is a recombinant microorganism, comprising a gene encoding a UGT91D2 polypeptide, e.g., a recombinant UGT91D2 gene.

Also featured herein is a recombinant microorganism, comprising a gene encoding a geranylgeranyl diphosphate synthase, a gene encoding a bifunctional copalyl diphosphate synthase and kaurene synthase (or a gene encoding a copalyl diphosphate synthase and a gene encoding a kaurene synthase), a gene encoding a kaurene oxidase, a gene encoding a steviol synthetase, a gene encoding a UGT74G1, a gene encoding a UGT85C2, a gene encoding a UGT76G1, and a gene encoding a UGT91D2. At least one of the genes is a recombinant gene. The recombinant microorganism can produce at least one steviol glycoside, e.g., rebaudioside A, rebaudioside B, and/or rebaudioside F, when cultured under conditions in which each of the genes is expressed. The recombinant microorganism can accumulate at least 20 mg of steviol glycoside per liter of culture medium when cultured under such conditions. The recombinant microorganism can be a Saccharomycete, e.g., Saccharomyces cerevisiae, and can have one or more genetic modifications that reduce EXG1 and EXG2 glycoside hydrolase activity relative to a control microorganism that lacks such genetic modifications, and can have one or more genetic modifications that reduce ergosterol biosynthesis relative to a control microorganism that lacks such genetic modifications.

Also featured herein is a recombinant microorganism, comprising a gene encoding a UGT74G1, a gene encoding a UGT85C2, a gene encoding a UGT76G1, and a gene encoding a UGT91D2. At least one of the genes is a recombinant gene. The recombinant microorganism can produce a steviol glycoside, e.g., rebaudioside A or rebaudioside B, when cultured under conditions in which each of the genes is expressed. The rebaudioside A or rebaudioside B can accumulate to at least 15 mg/L in the culture medium.

The recombinant microorganisms described above can further comprise a gene encoding a deoxyxylulose 5-phosphate synthase (DXS), and/or a gene encoding a D-1-deoxyxylulose 5-phosphate reductoisomerase (DXR), and/or a gene encoding a 4-diphosphocytidyl-2-C-methyl-D-erythritol synthase (CMS), and/or a gene encoding a 4-diphosphocytidyl-2-C-methyl-D-erythritol kinase (CMK), and/or a gene encoding a 4-diphosphocytidyl-2-C-methyl-D-erythritol 2,4-cyclodiphosphate synthase (MCS), and/or a gene encoding a 1-hydroxy-2-methyl-2(E)-butenyl 4-diphosphate synthase (HDS), and/or a gene encoding a 1-hydroxy-2-methyl-2(E)-butenyl 4-diphosphate reductase (HDR).

The recombinant microorganisms described above can further comprise a gene encoding a acetoacetyl-CoA thiolase, and/or a gene encoding a truncated HMG-CoA reductase, and/or a gene encoding a mevalonate kinase, and/or a gene encoding a phosphomevalonate kinase, and/or a gene encoding a mevalonate pyrophosphate decarboxylase.

Unless otherwise defined, all technical and scientific terms used herein have the same meaning as commonly understood by one of ordinary skill in the art to which the invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and are not intended to be limiting. Other features and advantages of the invention will be apparent from the following detailed description. Applicants reserve the right to alternatively claim any disclosed invention using the transitional phrase "comprising," "consisting essentially of," or "consisting of," according to standard practice in patent law.

DESCRIPTION OF DRAWINGS

FIG. 8 is an alignment of UGT91D1 and UGT91D2 amino acid sequences (SEQ ID NOs:14, 16, 12, 5, and 10, respectively).

Like reference symbols in the various drawings indicate like elements.

DETAILED DESCRIPTION

Figure 1:
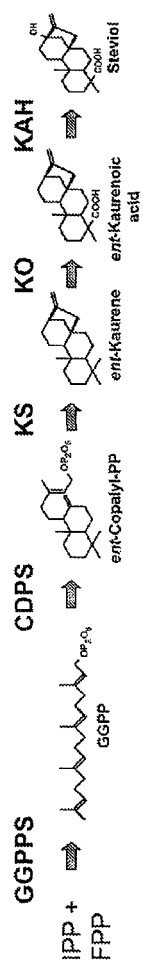
FIG. 1 is a scheme illustrating the biosynthesis of steviol from geranylgeranyl diphosphate.

Two glycosides, stevioside and rebaudioside A, are the primary compounds in commercially-produced stevia extracts. Stevioside is reported to have a more bitter and less sweet taste than rebaudioside A and, therefore, a higher proportion of rebaudioside A in an extract preparation is preferred. However, the composition of stevia extract can vary from lot to lot depending on the soil and climate in which the plants are grown. Depending upon the sourced plant, the climate conditions, and the extraction process, the amount of rebaudioside A in commercial preparations is reported to vary from 20 to 97% of the total steviol glycoside content, typically >50-80% and sometimes as high as >95-

97% of the total steviol glycosides. Moreover, other steviol glycosides are present in varying amounts in *stevia* extracts, which further complicates the ability to produce a sweetener with a consistent taste profile by extraction and purification from *Stevia* plants. For example, Rebaudioside B is typically present at less than 1-2%, whereas Rebaudioside C can be present at levels as high as 7-15%. Rebaudioside D is typically present in levels of 2% or less, and Rebaudioside F is typically present in compositions at 3.5% or less of the total steviol glycosides. Even trace amounts of the minor steviol glycosides are reported to affect the flavor profile of a *Stevia* extract. Additionally, it is thought that some of the contaminants from the *Stevia* plant, even at very low concentrations, may also provide off-flavors to some of the commercially available plant extracts.

This document is based on the discovery that recombinant hosts such as plant cells, plants, or microorganisms can be developed that express polypeptides useful for the biosynthesis of steviol. Further, such hosts can express Uridine 5'-diphospho (UDP) glycosyl transferases suitable for producing steviol glycosides such as rubusoside and rebaudioside A. Recombinant microorganisms are particularly useful hosts. Expression of these biosynthetic polypeptides in various microbial chassis allows steviol and its glycosides to be produced in a consistent, reproducible manner from energy and carbon sources such as sugars, glycerol, $CO_2$, $H_2$, and sunlight. The proportion of each steviol glycoside produced by a recombinant host can be tailored by incorporating preselected biosynthetic enzymes into the hosts and expressing them at appropriate levels, to produce a sweetener composition with a consistent taste profile. Furthermore, the concentrations of steviol glycosides produced by recombinant hosts are expected to be higher than the levels of steviol glycosides produced in the *Stevia* plant, which improves the efficiency of the downstream purification. Such sweetener compositions contain little or no plant based contaminants, relative to the amount of contaminants present in *Stevia* extracts.

At least one of the genes is a recombinant gene, the particular recombinant gene(s) depending on the species or strain selected for use. Additional genes or biosynthetic modules can be included in order to increase steviol and glycoside yield, improve efficiency with which energy and carbon sources are converted to steviol and its glycosides, and/or to enhance productivity from the cell culture or plant. Such additional biosynthetic modules include genes involved in the synthesis of the terpenoid precursors, isopentenyl diphosphate and dimethylallyl diphosphate. Additional biosynthetic modules include terpene synthase and terpene cyclase genes, such as genes encoding geranylgeranyl diphosphate synthase and copalyl diphosphate synthase; these genes may be endogenous genes or recombinant genes.

I. Steviol and Steviol Glycoside Biosynthesis Polypeptides

A. Steviol Biosynthesis Polypeptides

Figure 3:
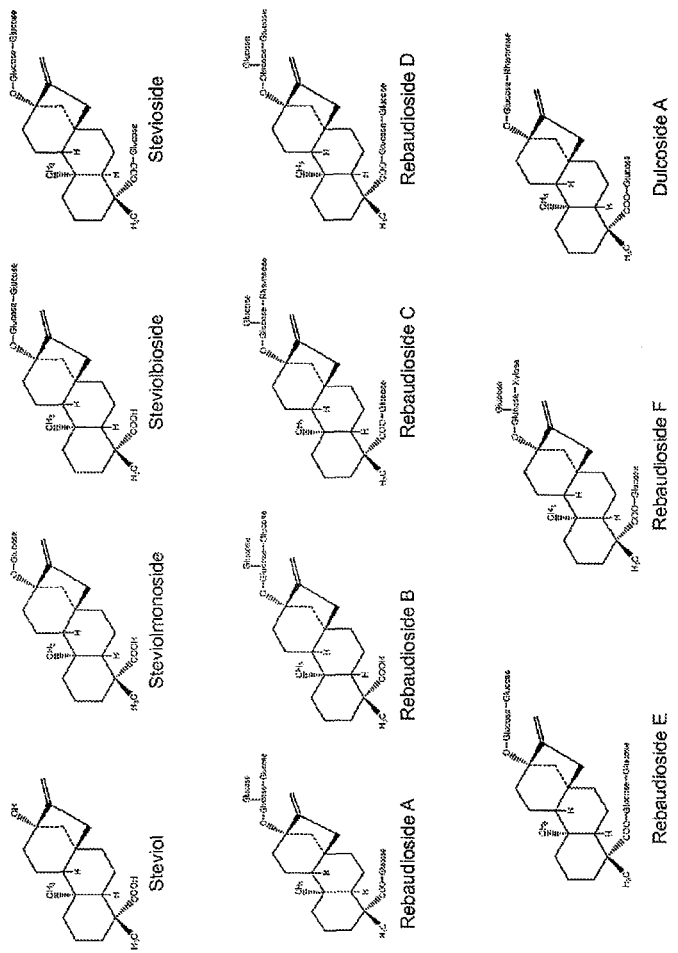
FIG. 3 shows chemical structures for various steviol glycosides.
Figure 4:
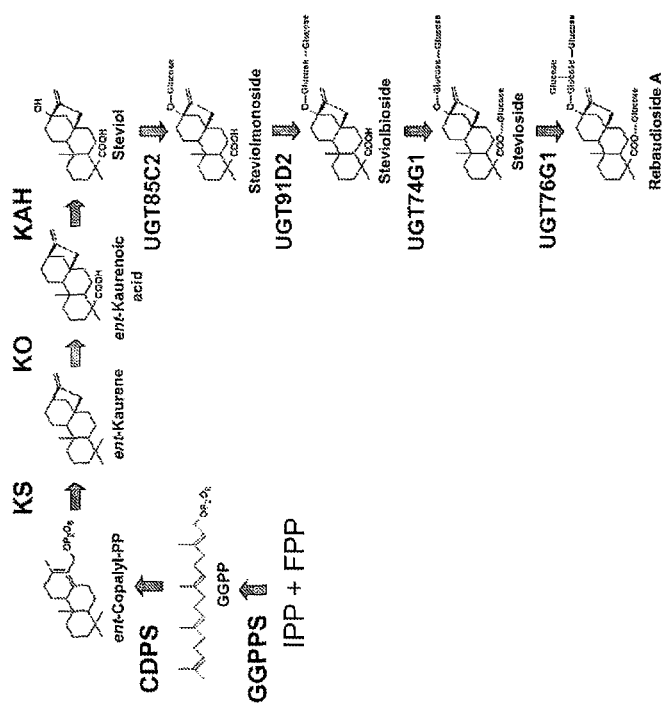
FIG. 4 is a schematic representation of rebA production in Saccharomyces cerevisiae.

Chemical structures for several of the compounds found in *Stevia* extracts are shown in FIG. 3, including the diterpene steviol and various steviol glycosides. CAS numbers are shown in Table A below. See also, *Steviol Glycosides Chemical and Technical Assessment 69th JECFA*, prepared by Harriet Wallin, Food Agric. Org. (2007).

TABLE A

| COMPOUND | CAS # |
|---|---|
| Steviol | 471-80-7 |
| Rebaudioside A | 58543-16-1 |
| Steviolbioside | 41093-60-1 |
| Stevioside | 57817-89-7 |
| Rebaudioside B | 58543-17-2 |
| Rebaudioside C | 63550-99-2 |
| Rebaudioside D | 63279-13-0 |
| Rebaudioside E | 63279-14-1 |
| Rebaudioside F | 438045-89-7 |
| Rubusoside | 63849-39-4 |
| Dulcoside A | 64432-06-0 |

It has been discovered that expression of certain genes in a host such as a microorganism confers the ability to synthesize steviol upon that host. As discussed in more detail below, one or more of such genes may be present naturally in a host. Typically, however, one or more of such genes are recombinant genes that have been transformed into a host that does not naturally possess them.

The biochemical pathway to produce steviol involves formation of geranylgeranyl diphosphate, cyclization to (−) copalyl diphosphate, followed by oxidation and hydroxylation to form steviol. See FIG. 1. Thus, conversion of geranylgeranyl diphosphate to steviol in a recombinant microorganism involves the expression of a gene encoding a kaurene synthase (KS), a gene encoding a kaurene oxidase (KO), and a gene encoding a steviol synthetase (KAH). Steviol synthetase also is known as kaurenoic acid 13-hydroxylase.

Suitable KS polypeptides are known. For example, suitable KS enzymes include those made by *Stevia rebaudiana*, *Zea mays* and *Populus trichocarpa*. See, SEQ ID NOs: 132-135. Nucleotide sequences encoding these polypeptides are described in more detail below. See, for example, Table 3 and SEQ ID NOs: 40-47.

Suitable KO polypeptides are known. For example, suitable KO enzymes include those made by *Stevia rebaudiana*, *Arabidopsis thaliana*, *Gibberella fujikoroi* and *Trametes versicolor*. See, SEQ ID NOs: 138-141. Nucleotide sequences encoding these polypeptides are described in more detail below. See, for example, Table 5 and SEQ ID NOs: 52-59.

Suitable KAH polypeptides are known. For example, suitable KAH enzymes include those made by *Stevia rebaudiana*, *Arabidopsis thaliana*, *Vitis vinifera* and *Medicago trunculata*. See, e.g., SEQ ID NOs: 142-146; U.S. Patent Publication No. 2008-0271205; U.S. Patent Publication No. 2008-0064063 and Genbank Accession No. gi 189098312. The steviol synthetase from *Arabidopsis thaliana* is classified as a CYP714A2. Nucleotide sequences encoding these polypeptides are described in more detail below. See, for example, Table 6 and SEQ ID NOs: 60-69.

In some embodiments, a recombinant microorganism contains a recombinant gene encoding a KO and/or a KAH polypeptide. Such microorganisms also typically contain a recombinant gene encoding a cytochrome P450 reductase (CPR) polypeptide, since certain combinations of KO and/or KAH polypeptides require expression of an exogenous CPR polypeptide. In particular, the activity of a KO and/or a KAH polypeptide of plant origin can be significantly increased by the inclusion of a recombinant gene encoding an exogenous CPR polypeptide. Suitable CPR polypeptides are known. For example, suitable CPR enzymes include those made by *Stevia rebaudiana*, *Arabidopsis thaliana*, and *Giberella fujikuroi*. See, e.g., SEQ ID NOs: 147-149. Nucleotide sequences encoding these polypeptides are described in more detail below. See, for example, Table 7 and SEQ ID NOs: 70-75.

Expression in a recombinant microorganism of these genes results in the conversion of geranylgeranyl diphosphate to steviol.

B. Steviol Glycoside Biosynthesis Polypeptides

In some embodiments, a recombinant host described herein can convert steviol to a steviol glycoside. Such a host (e.g., microorganism) contains genes encoding one or more UDP Glycosyl Transferases, also known as UGTs. UGTs transfer a monosaccharide unit from an activated nucleotide sugar to an acceptor moiety, in this case, an —OH or —COOH moiety on steviol or steviol derivative. UGTs have been classified into families and subfamilies based on sequence homology. Li et al. *J. Biol. Chem.* 276:4338-4343 (2001).

B.1 Rubusoside Biosynthesis Polypeptides

Figure 2A:
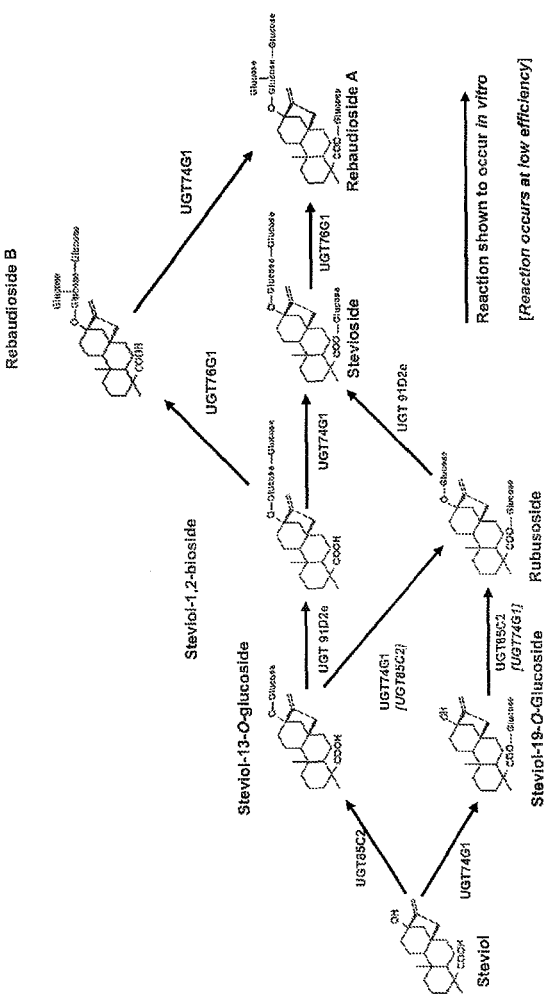
FIGS. 2A-D show representative pathways for the biosynthesis of steviol glycosides from steviol.
Figure 2B:
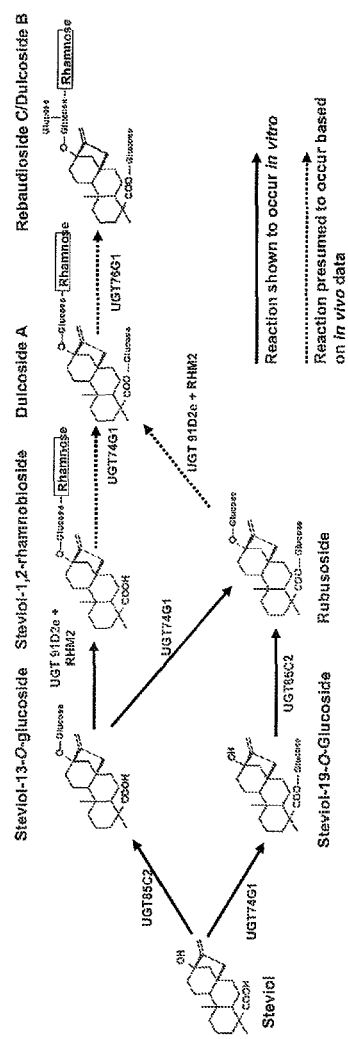
Figure 2C:
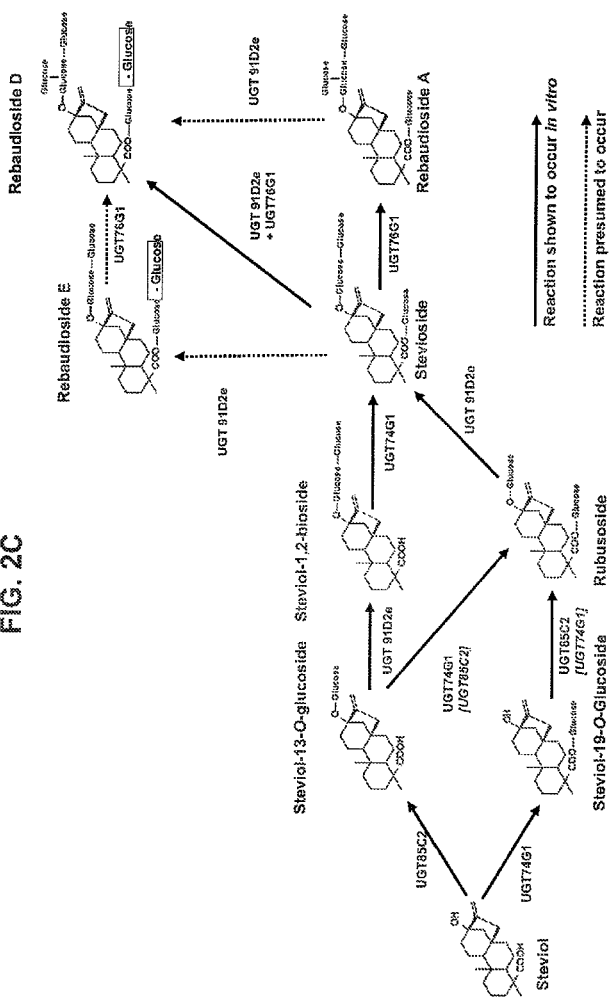
Figure 2D:
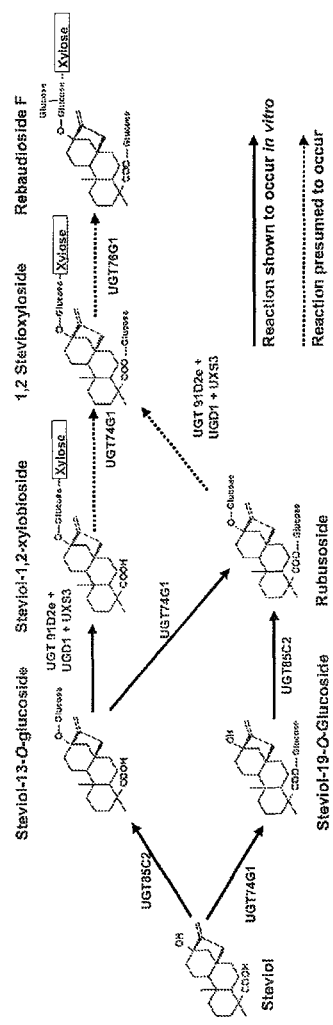

The biosynthesis of rubusoside involves glycosylation of the 13-OH and the 19-COOH of steviol. See FIG. 2A. It has been discovered that conversion of steviol to rubusoside in a recombinant host such as a microorganism can be accomplished by the expression of gene(s) encoding UGTs 85C2 and 74G1, which transfer a glucose unit to the 13-OH or the 19-COOH, respectively, of steviol.

Thus, a suitable UGT85C2 functions as a uridine 5'-diphospho glucosyl: steviol 13-OH transferase, and a uridine 5'-diphospho glucosyl: steviol-19-O-glucoside 13-OH transferase. Functional UGT85C2 polypeptides also may catalyze glucosyl transferase reactions that utilize steviol glycoside substrates other than steviol and steviol-19-O-glucoside.

A suitable UGT74G1 polypeptide functions as a uridine 5'-diphospho glucosyl: steviol 19-COOH transferase and a uridine 5'-diphospho glucosyl: steviol-13-O-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose.

A recombinant microorganism expressing a functional UGT74G1 and a functional UGT85C2 can make rubusoside and both steviol monosides (i.e., Steviol 13-O-monoglucoside and Steviol 19-O-monoglucoside) when fed steviol in the medium. One or more of such genes may be present naturally in the host. Typically, however, such genes are recombinant genes that have been transformed into a host (e.g., microorganism) that does not naturally possess them.

As used herein, the term recombinant host is intended to refer to a host, the genome of which has been augmented by at least one incorporated DNA sequence. Such DNA sequences include but are not limited to genes that are not naturally present, DNA sequences that are not normally transcribed into RNA or translated into a protein ("expressed"), and other genes or DNA sequences which one desires to introduce into the non-recombinant host. It will be appreciated that typically the genome of a recombinant host described herein is augmented through the stable introduction of one or more recombinant genes. Generally, the introduced DNA is not originally resident in the host that is the recipient of the DNA, but it is within the scope of the invention to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms, plant cells, and plants.

The term "recombinant gene" refers to a gene or DNA sequence that is introduced into a recipient host, regardless of whether the same or a similar gene or DNA sequence may already be present in such a host. "Introduced," or "augmented" in this context, is known in the art to mean introduced or augmented by the hand of man. Thus, a recombinant gene may be a DNA sequence from another species, or may be a DNA sequence that originated from or is present in the same species, but has been incorporated into a host by genetic engineering methods to form a recombinant host. It will be appreciated that a recombinant gene that is introduced into a host can be identical to a DNA sequence that is normally present in the host being transformed, and is introduced to provide one or more additional copies of the DNA to thereby permit overexpression or modified expression of the gene product of that DNA.

Suitable UGT74G1 and UGT85C2 polypeptides include those made by *Stevia rebaudiana*. Genes encoding functional UGT74G1 and UGT85C2 polypeptides from *Stevia* are reported in Richman, et al. *Plant J.* 41: 56-67 (2005). Amino acid sequences of *S. rebaudiana* UGT74G1 and UGT85C2 polypeptides are set forth in SEQ ID NOs: 1 and 3, respectively. Nucleotide sequences encoding UGT74G1 and UGT85C2 that have been optimized for expression in yeast are set forth in SEQ ID NOs: 2 and 4, respectively. See also the UGT85C2 and UGT74G1 variants described in Examples 17 and 18, respectively.

In some embodiments, the recombinant host is a microorganism. The recombinant microorganism can be grown on media containing steviol in order to produce rubusoside. In other embodiments, however, the recombinant microorganism expresses one or more recombinant genes involved in steviol biosynthesis, e.g., a CDPS gene, a KS gene, a KO gene and/or a KAH gene. Thus, a microorganism containing a CDPS gene, a KS gene, a KO gene and a KAH gene in addition to a UGT74G1 and a UGT85C2 gene is capable of producing both steviol monosides and rubusoside without the necessity for including steviol in the culture media.

In some embodiments, the recombinant microorganism further expresses a recombinant gene encoding a geranylgeranyl diphosphate synthase (GGPPS). Suitable GGPPS polypeptides are known. For example, suitable GGPPS enzymes include those made by *Stevia rebaudiana, Gibberella fujikuroi, Mus musculus, Thalassiosira pseudonana, Streptomyces clavuligerus, Sulfulobus acidocaldarius, Synechococcus* sp. and *Arabidopsis thaliana*. See, SEQ ID NOs: 121-128. Nucleotide sequences encoding these polypeptides are described in more detail below. See Table 1 and SEQ ID NOs:18-33. In some embodiments, the recombinant microorganism further expresses recombinant genes involved in diterpene biosynthesis or production of terpenoid precursors, e.g., genes in the methylerythritol 4-phosphate (MEP) pathway or genes in the mevalonate (MEV) pathway discussed below.

B.2 Rebaudioside A Biosynthesis Polypeptides

The biosynthesis of rebaudioside A involves glucosylation of the aglycone steviol. Specifically, rebaudioside A can be formed by glucosylation of the 13-OH of steviol which forms the 13-O-steviolmonoside, glucosylation of the C-2' of the 13-O-glucose of steviolmonoside which forms steviol-1,2-bioside, glucosylation of the C-19 carboxyl of steviol-1,2-bioside which forms stevioside, and glucosylation of the C-3' of the C-13-O-glucose of stevioside. The order in which each glucosylation reaction occurs can vary. See FIG. 2A.

It has been discovered that conversion of steviol to rebaudioside A in a recombinant host can be accomplished by the expression of gene(s) encoding the following functional UGTs: 74G1, 85C2, 76G1 and 91D2. Thus, a recombinant microorganism expressing these four UGTs can make rebaudioside A when fed steviol in the medium. Typically, one or more of these genes are recombinant genes that have been transformed into a microorganism that does not naturally possess them. It has also been discovered that UGTs designated herein as SM12UGT can be substituted for UGT91D2.

Suitable UGT74G1 and UGT85C2 polypeptides include those discussed above. A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-O-1,2 glucoside C-3' glucosyl transferase and a uridine 5'-diphospho glucosyl: steviol-19-O-glucose, 13-O-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. See, FIGS. 2A, 2B, 2C and 2D. Suitable UGT76G1 polypeptides include those made by *S. rebaudiana* and reported in Richman, et al. *Plant J.* 41: 56-67 (2005). The amino acid sequence of a *S. rebaudiana* UGT76G1 polypeptide is set forth in SEQ ID NO:7. The nucleotide sequence encoding the UGT76G1 polypeptide of SEQ ID NO:7 has been optimized for expression in yeast and is set forth in SEQ ID NO:8. See also the UGT76G1 variants set forth in Example 18.

A suitable UGT91D2 polypeptide functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside. Typically, a suitable UGT91D2 polypeptide also functions as a uridine 5'-diphospho glucosyl: rubusoside transferase transferring a glucose moiety to the C-2' of the 13-O-glucose of the acceptor molecule, rubusoside.

Functional UGT91D2 polypeptides may also catalyze reactions that utilize steviol glycoside substrates other than steviol-13-O-glucoside and rubusoside, e.g., functional UGT91D2 polypeptides may utilize stevioside as a substrate, transferring a glucose moiety to the C-2' of the 19-O-glucose residue to produce Rebaudioside E. Functional UGT91D2 polypeptides may also utilize Rebaudioside A as a substrate, transferring a glucose moiety to the C-2' of the 19-O-glucose residue to produce Rebaudioside D. However, a functional UGT91D2 polypeptide typically does not transfer a glucose moiety to steviol compounds having a 1,3-bound glucose at the C-13 position, i.e., transfer of a glucose moiety to steviol 1,3-bioside and 1,3-stevioside does not occur.

Functional UGT91D2 polypeptides can transfer sugar moieties from donors other than uridine diphosphate glucose. For example, a functional UGT91D2 polypeptide can act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a functional UGT91D2 polypeptide can act as a uridine 5'-diphospho L-rhamnosyl: steviol-13-O-glucoside transferase, transferring a rhamnose moiety to the C-2' of the 13-O-glucose of the acceptor molecule, steviol-13-O-glucoside Suitable functional UGT91D2 polypeptides include those disclosed herein, e.g., the polypeptides designated UGT91D2e and UGT91D2m. The amino acid sequence of an exemplary UGT91D2e polypeptide from *Stevia rebaudiana* is set forth in SEQ ID NO: 5. SEQ ID NO:6 is a nucleotide sequence encoding the polypeptide of SEQ ID NO:5 that has been codon optimized for expression in yeast. The *S. rebaudiana* nucleotide sequence encoding the polypeptide of SEQ ID NO:5 is set forth in SEQ ID NO:9. The amino acid sequences of exemplary UGT91D2m polypeptides from *S. rebaudiana* are set forth in SEQ ID NOs: 10 and 12, and are encoded by the nucleic acid sequences set forth in SEQ ID NOs: 11 and 13, respectively. See also the UGT91D2 variants of Example 16, e.g., a variant containing a substitution at amino acid residues 206, 207, and 343.

As indicated above, UGTs designated herein as SM12UGT can be substituted for UGT91D2. Suitable functional SM12UGT polypeptides include those made by *Ipomoea purpurea* (Japanese morning glory) and described in Morita et al. *Plant J.* 42, 353-363 (2005). The amino acid sequence encoding the *I. purpurea* IP3GGT polypeptide is set forth in SEQ ID NO:76. SEQ ID NO:77 is a nucleotide sequence encoding the polypeptide of SEQ ID NO:76 that has been codon optimized for expression in yeast. Another suitable SM12UGT polypeptide is a Bp94B1 polypeptide having an R25S mutation. See Osmani et al. *Plant Phys.* 148: 1295-1308 (2008) and Sawada et al. *J. Biol. Chem.* 280:899-906 (2005). The amino acid sequence encoding the *Bellis perennis* (red daisy) UGT94B1 polypeptide is set forth in SEQ ID NO:78. SEQ ID NO:79 is the nucleotide sequence encoding the polypeptide of SEQ ID NO:78 that has been codon optimized for expression in yeast.

In some embodiments, the recombinant microorganism is grown on media containing steviol-13-O-glucoside or steviol-19-O-glucoside in order to produce rebaudioside A. In such embodiments, the microorganism contains and expresses genes encoding a functional UGT91D2, a functional UGT74G1 and a functional UGT76G1, and is capable of producing rebaudioside A when it is fed steviol, one or both of the steviolmonosides, or rubusoside in the culture media.

In other embodiments, the recombinant microorganism is grown on media containing rubusoside in order to produce rebaudioside A. In such embodiments, the microorganism contains and expresses genes encoding a functional UGT91D2 and a functional UGT76G1, and is capable of producing rebaudioside A when it is fed rubusoside in the culture media.

In other embodiments the recombinant microorganism expresses one or more genes involved in steviol biosynthesis, e.g., a CDPS gene, a KS gene, a KO gene and/or a KAH gene. Thus, for example, a microorganism containing a CDPS gene, a KS gene, a KO gene and a KAH gene, in addition to a UGT74G1, a UGT85C2, a UGT91D2 gene and a UGT76G1 gene, is capable of producing rebaudioside A without the necessity for including steviol in the culture media.

In some embodiments, the recombinant microorganism further contains and expresses a recombinant GGPPS gene in order to provide increased levels of the diterpene precursor geranylgeranyl diphosphate, for increased flux through the rebaudioside A biosynthetic pathway. In some embodiments, the recombinant microorganism further contains and expresses recombinant genes involved in diterpene biosynthesis or production of terpenoid precursors, e.g., genes in the MEP or MEV pathway discussed below.

B.3 Dulcoside a and Rebaudioside C Biosynthesis Polypeptides

The biosynthesis of rebaudioside C and/or dulcoside A involves glucosylation and rhamnosylation of the aglycone steviol. Specifically, dulcoside A can be formed by glucosylation of the 13-OH of steviol which forms steviol-13-O-glucoside, rhamnosylation of the C-2' of the 13-O-glucose of steviol-13-O-glucoside which forms the 1,2 rhamnobioside, and glucosylation of the C-19 carboxyl of the 1,2 rhamnobioside. Rebaudioside C can be formed by glucosylation of the C-3' of the C-13-O-glucose of dulcoside A. The order in which each glycosylation reaction occurs can vary. See FIG. 2B.

It has been discovered that conversion of steviol to dulcoside A in a recombinant host can be accomplished by the expression of gene(s) encoding the following functional UGTs: 85C2, 91D2, and 74G1. Thus, a recombinant microorganism expressing these three UGTs and a rhamnose synthetase can make dulcoside A when fed steviol in the medium. Alternatively, a recombinant microorganism expressing two UGTs, 91D2 and 74G1, and rhamnose synthetase can make dulcoside A when fed the monoside, steviol-13-O-glucoside or steviol-19-O-glucoside, in the medium. Similarly, conversion of steviol to rebaudioside C in a recombinant microorganism can be accomplished by the expression of gene(s) encoding UGTs 85C2, 91D2, 74G1, and 76G1 and rhamnose synthetase when fed steviol, by the expression of genes encoding UGTs 91D2, 74G1 and 76G1, and rhamnose synthetase when fed steviol-13-O-glucoside, by the expression of genes encoding UGTs 85C2, 91D2 and 76G1, and rhamnose synthetase when fed steviol-19-O-glucoside, or by the expression of genes encoding UGTs 91D2 and 76G1 and rhamnose synthetase when fed rubusoside. Typically, one or more of these genes are recombinant genes that have been transformed into a microorganism that does not naturally possess them.

Suitable UGT91D2, UGT74G1, UGT76G1 and UGT85C2 polypeptides include the functional UGT polypeptides discussed herein. Rhamnose synthetase provides increased amounts of the UDP-rhamnose donor for rhamnosylation of the steviol compound acceptor. Suitable rhamnose synthetases include those made by *Arabidopsis thaliana*, such as the product of the *A. thaliana* RHM2 gene.

In some embodiments, a UGT79B3 polypeptide is substituted for a UGT91D2 polypeptide. Suitable UGT79B3 polypeptides include those made by *Arabidopsis thaliana*, which are capable of rhamnosylation of steviol 13-O-monoside in vitro. *A. thaliana* UGT79B3 can rhamnosylate glucosylated compounds to form 1,2-rhamnosides. The amino acid sequence of an *Arabidopsis thaliana* UGT79B3 is set forth in SEQ ID NO:150. The nucleotide sequence encoding the amino acid sequence of SEQ ID NO:150 is set forth in SEQ ID NO:151.

In some embodiments rebaudioside C can be produced using in vitro methods while supplying the appropriate UDP-sugar or a cell-free system for regeneration of UDP-sugars. See, for example, "An integrated cell-free metabolic platform for protein production and synthetic biology" by Jewett M C, Calhoun K A, Voloshin A, Wuu J J and Swartz J R in Molecular Systems Biology, 4, article 220 (2008). Reactions may be carried out together, or stepwise. For instance, rebaudioside C may be produced from rubusoside with the addition of stoichiometric amounts of UDP-rhamnose and UGT91d2e, followed by addition of UGT76G1 and an excess or stoichiometric supply of UDP-glucose. In some embodiments phosphatases are used to remove secondary products and improve the reaction yields.

In other embodiments, the recombinant host expresses one or more genes involved in steviol biosynthesis, e.g., a CDPS gene, a KS gene, a KO gene and/or a KAH gene. Thus, for example, a microorganism containing a CDPS gene, a KS gene, a KO gene and a KAH gene, in addition to a UGT85C2, a UGT74G1, a UGT91D2 gene and a UGT76G1 gene, is capable of producing rebaudioside C without the necessity for including steviol in the culture media. In addition, the recombinant host typically expresses an endogenous or a recombinant gene encoding a rhamnose synthetase. Such a gene is useful in order to provide increased amounts of the UDP-rhamnose donor for rhamnosylation of the steviol compound acceptor. Suitable rhamnose synthetases include those made by *Arabidopsis thaliana*, such as the product of the *A. thaliana* RHM2 gene.

One with skill in the art will recognize that by modulating relative expression levels of different UGT genes as well as modulating the availability of UDP-rhamnose, a recombinant host can be tailored to specifically produce steviol and steviol glycoside products in a desired proportion. Transcriptional regulation of steviol biosynthesis genes, and steviol glycoside biosynthesis genes can be achieved by a combination of transcriptional activation and repression using techniques known to those in the art. For in vitro reactions, one with skill in the art will recognize that addition of different levels of UGT enzymes in combination or under conditions which impact the relative activities of the different UGTS in combination will direct synthesis towards a desired proportion of each steviol glycoside.

In some embodiments, the recombinant host further contains and expresses a recombinant GGPPS gene in order to provide increased levels of the diterpene precursor geranylgeranyl diphosphate, for increased flux through the rebaudioside A biosynthetic pathway. In some embodiments, the recombinant host further contains a genetic construct to silence or reduce the expression of non-steviol pathways consuming geranylgeranyl diphosphate, ent-Kaurenoic acid or farnesyl pyrophosphate, thereby providing increased flux through the steviol and steviol glycosides biosynthetic pathways. For example, flux to sterol production pathways such as ergosterol may be reduced by downregulation of the ERGS gene. In cells that produce gibberellins, gibberellin synthesis may be downregulated to increase flux of ent-kaurenoic acid to steviol. In carotenoid-producing organisms, flux to steviol may be increased by downregulation of one or more carotenoid biosynthetic genes.

In some embodiments, the recombinant host further contains and expresses recombinant genes involved in diterpene biosynthesis or production of terpenoid precursors, e.g., genes in the MEP or MEV pathway discussed below.

In some embodiments, a recombinant host such as a microorganism produces steviol glycoside compositions that have greater than at least 15% rebaudioside C of the total steviol glycosides, e.g., at least 20% rebaudioside C, 30-40% rebaudioside C, 40-50% rebaudioside C, 50-60% rebaudioside C, 60-70% rebaudioside C, 70-80% rebaudioside C, 80-90% rebaudioside C. In some embodiments, a recombinant host such as a microorganism produces steviol glycoside compositions that have at least 90% rebaudioside C, e.g., 90-99% rebaudioside C. Other steviol glycosides present may include those depicted in FIGS. 2A and B such as steviol monosides, steviol glucobiosides, steviol rhamnobiosides, rebaudioside A, and Dulcoside A. In some embodiments, the rebaudioside C-enriched composition produced by the host can be further purified and the rebaudioside C or Dulcoside A so purified may then be mixed with other steviol glycosides, flavors, or sweeteners to obtain a desired flavor system or sweetening composition. For instance, a rebaudioside C-enriched composition produced by a recombinant microorganism can be combined with a rebaudioside A, F, or D-enriched composition produced by a different recombinant microorganism, with rebaudioside A, F, or D purified from a *Stevia* extract, or with rebaudioside A, F, or D produced in vitro.

B.4 Rebaudioside E and Rebaudioside D Biosynthesis Polypeptides

The biosynthesis of rebaudioside E and/or rebaudioside D involves glucosylation of the aglycone steviol. Specifically, rebaudioside E can be formed by glucosylation of the 13-OH of steviol which forms steviol-13-O-glucoside, glucosylation of the C-2' of the 13-O-glucose of steviol-13-O-glucoside which forms the steviol-1,2-bioside, glucosylation of the C-19 carboxyl of the 1,2-bioside to form 1,2-stevioside, and glucosylation of the C-2' of the 19-O-glucose of the 1,2-stevioside to form rebaudioside E. Rebaudioside D can be formed by glucosylation of the C-3' of the C-13-O-glucose of rebaudioside E. The order in which each glycosylation reaction occurs can vary. For example, the glucosylation of the C-2' of the 19-O-glucose may be the last step in the pathway, wherein Rebaudioside A is an intermediate in the pathway. See FIG. 2C.

It has been discovered that conversion of steviol to rebaudioside D in a recombinant host can be accomplished by the expression of gene(s) encoding the following functional UGTs: 85C2, 91D2, 74G1 and 76G1. Thus, a recombinant microorganism expressing these four UGTs can make rebaudioside D when fed steviol in the medium. Alternatively, a recombinant microorganism expressing two functional UGTs, 91D2 and 76G1, can make rebaudioside D when fed rubusoside or 1,2-stevioside in the medium. As another alternative, a recombinant microorganism expressing three functional UGTs, 74G1, 91D2 and 76G1, can make rebaudioside D when fed the monoside, steviol-13-O-glucoside, in the medium. Similarly, conversion of steviol-19-O-glucoside to rebaudioside D in a recombinant microorganism can be accomplished by the expression of genes encoding UGTs 85C2, 91D2 and 76G1 when fed steviol-19-O-glucoside. Typically, one or more of these genes are recombinant genes that have been transformed into a host that does not naturally possess them.

Suitable UGT91D2, UGT74G1, UGT76G1 and UGT85C2 polypeptides include the functional UGT polypeptides discussed herein. In some embodiments, a UGT79B3 polypeptide is substituted for a UGT91, as discussed above.

In some embodiments, rebaudioside D or rebaudioside E can be produced using in vitro methods while supplying the appropriate UDP-sugar or a cell-free system for regeneration of UDP-sugars. See, for example, Jewett M C, et al. Molecular Systems Biology, Vol. 4, article 220 (2008). Conversions requiring multiple reactions may be carried out together, or stepwise. Rebaudioside D may be produced from Rebaudioside A that is commercially available enriched extract or produced via biosynthesis, with the addition of stoichiometric or excess amounts of UDP-glucose and UGT91D2e. In some embodiments phosphatases are used to remove secondary products and improve the reaction yields.

One with skill in the art will recognize that by modulating relative expression levels of different UGT genes, a recombinant host can be tailored to specifically produce steviol and steviol glycoside products in a desired proportion. Transcriptional regulation of steviol biosynthesis genes and steviol glycoside biosynthesis genes can be achieved by a combination of transcriptional activation and repression using techniques known to those in the art. For in vitro reactions, one with skill in the art will recognize that addition of different levels of UGT enzymes in combination or under conditions which impact the relative activities of the different UGTS in combination will direct synthesis towards a desired proportion of each steviol glycoside. One with skill in the art will recognize that a higher proportion of rebaudioside D or E or more efficient conversion to rebaudioside D or E can be obtained with a diglycosylation enzyme that has a higher activity for the 19-O-glucoside reaction as compared to the 13-O-glucoside reaction (substrates rebaudioside A and stevioside).

In other embodiments, the recombinant host expresses one or more genes involved in steviol biosynthesis, e.g., a CDPS gene, a KS gene, a KO gene and/or a KAH gene. Thus, for example, a microorganism containing a CDPS gene, a KS gene, a KO gene and a KAH gene, in addition to a UGT85C2, a UGT74G1, a UGT91D2 gene and a UGT76G1 gene, is capable of producing rebaudiosides E and D without the necessity for including steviol in the culture media.

In some embodiments, the recombinant host further contains and expresses a recombinant GGPPS gene in order to provide increased levels of the diterpene precursor geranylgeranyl diphosphate, for increased flux through the steviol biosynthetic pathway. In some embodiments, the recombinant host further contains a genetic construct to silence the expression of non-steviol pathways consuming geranylgeranyl diphosphate, ent-Kaurenoic acid or farnesyl pyrophosphate, thereby providing increased flux through the steviol and steviol glycosides biosynthetic pathways. For example, flux to sterol production pathways such as ergosterol may be reduced by downregulation of the ERG9 gene. hi cells that produce gibberellins, gibberellin synthesis may be downregulated to increase flux of ent-kaurenoic acid to steviol. In carotenoid-producing organisms, flux to steviol may be increased by downregulation of one or more carotenoid biosynthetic genes. In some embodiments, the recombinant host further contains and expresses recombinant genes involved in diterpene biosynthesis or production of terpenoid precursors, e.g., genes in the MEP or MEV pathways discussed below.

In some embodiments, a recombinant host such as a microorganism produces rebaudioside D-enriched steviol glycoside compositions that have greater than at least 3% rebaudioside D by weight total steviol glycosides, e.g., at least 4% rebaudioside D at least 5% rebaudioside D, 10-20% rebaudioside D, 20-30% rebaudioside D, 30-40% rebaudioside D, 40-50% rebaudioside D, 50-60% rebaudioside D, 60-70% rebaudioside D, 70-80% rebaudioside D. In some embodiments, a recombinant host such as a microorganism produces steviol glycoside compositions that have at least 90% rebaudioside D, e.g., 90-99% rebaudioside D. Other steviol glycosides present may include those depicted in FIG. 2C such as steviol monosides, steviol glucobiosides, rebaudioside A, rebaudioside E, and stevioside. In some embodiments, the rebaudioside D-enriched composition produced by the host (e.g., microorganism) can be further purified and the rebaudioside D or rebaudioside E so purified can then be mixed with other steviol glycosides, flavors, or sweeteners to obtain a desired flavor system or sweetening composition. For instance, a rebaudioside D-enriched composition produced by a recombinant host can be combined with a rebaudioside A, C, or F-enriched composition produced by a different recombinant host, with rebaudioside A, F, or C purified from a *Stevia* extract, or with rebaudioside A, F, or C produced in vitro.

B.5 Rebaudioside F Biosynthesis Polypeptides

The biosynthesis of rebaudioside F involves glucosylation and xylosylation of the aglycone steviol. Specifically, rebaudioside F can be formed by glucosylation of the 13-OH of steviol which forms steviol-13-O-glucoside, xylosylation of the C-2' of the 13-O-glucose of steviol-13-O-glucoside which forms steviol-1,2-xylobioside, glucosylation of the C-19 carboxyl of the 1,2-xylobioside to form 1,2-stevioxyloside, and glucosylation of the C-3' of the C-13-O-glucose of 1,2-stevioxyloside to form rebaudioside F. The order in which each glycosylation reaction occurs can vary. See FIG. 2D.

It has been discovered that conversion of steviol to rebaudioside F in a recombinant host can be accomplished by the expression of genes encoding the following functional UGTs: 85C2, 91D2, 74G1 and 76G1, along with endogenous or recombinantly expressed UDP-glucose dehydrogenase and UDP-glucuronic acid decarboxylase. Thus, a recombinant microorganism expressing these four UGTs along with endogenous or recombinant UDP-glucose dehydrogenase and UDP-glucuronic acid decarboxylase can make rebaudioside F when fed steviol in the medium. Alternatively, a recombinant microorganism expressing two functional UGTs, 91D2 and 76G1, can make rebaudioside F when fed rubusoside in the medium. As another alternative, a recombinant microorganism expressing a functional UGT 76G1 can make rebaudioside F when fed 1,2 steviorhamnoside. As another alternative, a recombinant microorganism expressing three functional UGTs, 74G1, 91D2 and 76G1, can make rebaudioside F when fed the monoside, steviol-13-O-glucoside, in the medium. Similarly, conversion of steviol-19-O-glucoside to rebaudioside F in a recombinant microorganism can be accomplished by the expression of genes encoding UGTs 85C2, 91D2 and 76G1 when fed steviol-19-O-glucoside. Typically, one or more of these genes are recombinant genes that have been transformed into a host that does not naturally possess them.

Suitable UGT91D2, UGT74G1, UGT76G1 and UGT85C2 polypeptides include the functional UGT polypeptides discussed herein. In some embodiments, a UGT79B3 polypeptide is substituted for a UGT91, as discussed above. UDP-glucose dehydrogenase and UDP-glucuronic acid decarboxylase provide increased amounts of the UDP-xylose donor for xylosylation of the steviol compound acceptor. Suitable UDP-glucose dehydrogenases and UDP-glucuronic acid decarboxylases include those made by *Arabidopsis thaliana* or *Cryptococcus neoformans*. For example, suitable UDP-glucose dehydrogenase and UDP-glucuronic acid decarboxylases polypeptides can be encoded by the *A. thaliana* UGD1 gene and UXS3 gene, respectively. See, Oka and Jigami, *FEBS J.* 273:2645-2657 (2006).

In some embodiments rebaudioside F can be produced using in vitro methods while supplying the appropriate UDP-sugar or a cell-free system for regeneration of UDP-sugars. See, for example, Jewett M C, et al. Molecular Systems Biology, Vol. 4, article 220 (2008). Reactions may be carried out together, or stepwise. For instance, rebaudioside F may be produced from rubusoside with the addition of stoichiometric amounts of UDP-xylose and UGT91D2e, followed by addition of UGT76G1 and an excess or stoichiometric supply of UDP-glucose. In some embodiments phosphatases are used to remove secondary products and improve the reaction yields.

In other embodiments, the recombinant host expresses one or more genes involved in steviol biosynthesis, e.g., a CDPS gene, a KS gene, a KO gene and/or a KAH gene. Thus, for example, a microorganism containing a CDPS gene, a KS gene, a KO gene and a KAH gene, in addition to a UGT85C2, a UGT74G1, a UGT91D2 gene and a UGT76G1 gene, is capable of producing rebaudioside F without the necessity for including steviol in the culture media. In addition, the recombinant host typically expresses an endogenous or a recombinant gene encoding a UDP-glucose dehydrogenase and a UDP-glucuronic acid decarboxylase. Such genes are useful in order to provide increased amounts of the UDP-xylose donor for xylosylation of the steviol compound acceptor. Suitable UDP-glucose dehydrogenases and UDP-glucuronic acid decarboxylases include those made by *Arabidopsis thaliana* or *Cryptococcus neoformans*. For example, suitable UDP-glucose dehydrogenase and UDP-glucuronic acid decarboxylases polypeptides can be encoded by the *A. thaliana* UGD1 gene and UXS3 gene, respectively. See, Oka and Jigami, *FEBS J.* 273:2645-2657 (2006).

One with skill in the art will recognize that by modulating relative expression levels of different UGT genes as well as modulating the availability of UDP-xylose, a recombinant microorganism can be tailored to specifically produce steviol and steviol glycoside products in a desired proportion. Transcriptional regulation of steviol biosynthesis genes can be achieved by a combination of transcriptional activation and repression using techniques known to those in the art. For in vitro reactions, one with skill in the art will recognize that addition of different levels of UGT enzymes in combination or under conditions which impact the relative activities of the different UGTS in combination will direct synthesis towards a desired proportion of each steviol glycosides.

In some embodiments, the recombinant host further contains and expresses a recombinant GGPPS gene in order to provide increased levels of the diterpene precursor geranylgeranyl diphosphate, for increased flux through the steviol biosynthetic pathway. In some embodiments, the recombinant host further contains a genetic construct to silence the expression of non-steviol pathways consuming geranylgeranyl diphosphate, ent-Kaurenoic acid or farnesyl pyrophosphate, thereby providing increased flux through the steviol and steviol glycosides biosynthetic pathways. For example, flux to sterol production pathways such as ergosterol may be reduced by downregulation of the ERG9 gene. In cells that produce gibberellins, gibberellin synthesis may be downregulated to increase flux of ent-kaurenoic acid to steviol. In carotenoid-producing organisms, flux to steviol may be increased by downregulation of one or more carotenoid biosynthetic genes. In some embodiments, the recombinant host further contains and expresses recombinant genes involved in diterpene biosynthesis, e.g., genes in the MEP pathway discussed below.

In some embodiments, a recombinant host such as a microorganism produces rebaudioside F-enriched steviol glycoside compositions that have greater than at least 4% rebaudioside F by weight total steviol glycosides, e.g., at least 5% rebaudioside F, at least 6% of rebaudioside F, 10-20% rebaudioside F, 20-30% rebaudioside F, 30-40% rebaudioside F, 40-50% rebaudioside F, 50-60% rebaudioside F, 60-70% rebaudioside F, 70-80% rebaudioside F. In some embodiments, a recombinant host such as a microorganism produces steviol glycoside compositions that have at least 90% rebaudioside F, e.g., 90-99% rebaudioside F. Other steviol glycosides present may include those depicted in FIGS. 2A and D such as steviol monosides, steviol glucobiosides, steviol xylobiosides, rebaudioside A, stevioxyloside, rubusoside and stevioside. In some embodiments, the rebaudioside F-enriched composition produced by the host can be mixed with other steviol glycosides, flavors, or sweeteners to obtain a desired flavor system or sweetening composition. For instance, a rebaudioside F-enriched composition produced by a recombinant microorganism can be combined with a rebaudioside A, C, or D-enriched composition produced by a different recombinant microorganism, with rebaudioside A, C, or D purified from a Stevia extract, or with rebaudioside A, C, or D produced in vitro.

C. Other Polypeptides

Genes for additional polypeptides whose expression facilitates more efficient or larger scale production of steviol or a steviol glycoside can also be introduced into a recombinant host. For example, a recombinant microorganism, plant, or plant cell can also contain one or more genes encoding a geranylgeranyl diphosphate synthase (GGPPS, also referred to as GGDPS). As another example, the recombinant host can contain one or more genes encoding a rhamnose synthetase, or one or more genes encoding a UDP-glucose dehydrogenase and/or a UDP-glucuronic acid decarboxylase. As another example, a recombinant host can also contain one or more genes encoding a cytochrome P450 reductase (CPR). Expression of a recombinant CPR facilitates the cycling of NADP+ to regenerate NADPH, which is utilized as a cofactor for terpenoid biosynthesis. Other methods can be used to regenerate NADHP levels as well. In circumstances where NADPH becomes limiting; strains can be further modified to include exogenous transhydrogenase genes. See, e.g., Sauer et al., *J. Biol. Chem.* 279: 6613-6619 (2004). Other methods are known to those with skill in the art to reduce or otherwise modify the ratio of NADH/NADPH such that the desired cofactor level is increased.

As another example, the recombinant host can contain one or more genes encoding one or more enzymes in the MEP pathway or the mevalonate pathway. Such genes are useful because they can increase the flux of carbon into the diterpene biosynthesis pathway, producing geranylgeranyl diphosphate from isopentenyl diphosphate and dimethylallyl diphosphate generated by the pathway. The geranylgeranyl diphosphate so produced can be directed towards steviol and steviol glycoside biosynthesis due to expression of steviol biosynthesis polypeptides and steviol glycoside biosynthesis polypeptides.

C.1 MEP Biosynthesis Polypeptides

In some embodiments, a recombinant host contains one or more genes encoding enzymes involved in the methylerythritol 4-phosphate (MEP) pathway for isoprenoid biosynthesis. Enzymes in the MEP pathway include deoxyxylulose 5-phosphate synthase (DXS), D-1-deoxyxylulose 5-phosphate reductoisomerase (DXR), 4-diphosphocytidyl-2-C-methyl-D-erythritol synthase (CMS), 4-diphosphocytidyl-2-C-methyl-D-erythritol kinase (CMK), 4-diphosphocytidyl-2-C-methyl-D-erythritol 2,4-cyclodiphosphate synthase (MCS), 1-hydroxy-2-methyl-2(E)-butenyl 4-diphosphate synthase (HDS) and 1-hydroxy-2-methyl-2(E)-butenyl 4-diphosphate reductase (HDR). One or more DXS genes, DXR genes, CMS genes, CMK genes, MCS genes, HDS genes and/or HDR genes can be incorporated into a recombinant microorganism. See, Rodriguez-Concepción and Boronat *Plant Phys.* 130: 1079-1089 (2002).

Suitable genes encoding DXS, DXR, CMS, CMK, MCS, HDS and/or HDR polypeptides include those made by *E. coli, Arabidopsis thaliana* and *Synechococcus leopoliensis.* Nucleotide sequences encoding DXR polypeptides are described, for example, in U.S. Pat. No. 7,335,815.

C.2 Mevalonate Biosynthesis Polypeptides

In some embodiments, a recombinant host contains one or more genes encoding enzymes involved in the mevalonate pathway for isoprenoid biosynthesis. Genes suitable for transformation into a host encode enzymes in the mevalonate pathway such as a truncated 3-hydroxy-3-methyl-glutaryl (HMG)-CoA reductase (tHMG), and/or a gene encoding a mevalonate kinase (MK), and/or a gene encoding a phosphomevalonate kinase (PMK), and/or a gene encoding a mevalonate pyrophosphate decarboxylase (MPPD). Thus, one or more HMG-CoA reductase genes, MK genes, PMK genes, and/or MPPD genes can be incorporated into a recombinant host such as a microorganism.

Suitable genes encoding mevalonate pathway polypeptides are known. For example, suitable polypeptides include those made by *E. coli, Paracoccus denitrificans, Saccharomyces cerevisiae, Arabidopsis thaliana, Kitasatospora griseola, Homo sapiens, Drosophila melanogaster, Gallus gallus, Streptomyces* sp. KO-3988, *Nicotiana attenuata, Kitasatospora griseola, Hevea brasiliensis, Enterococcus faecium* and *Haematococcus pluvialis.* See, e.g., U.S. Pat. Nos. 7,183,089, 5,460,949, and 5,306,862.

D. Functional Homologs

Functional homologs of the polypeptides described above are also suitable for use in producing steviol or steviol glycosides in a recombinant host. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Techniques for modifying genes encoding functional UGT polypeptides described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide:polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of steviol or steviol glycoside biosynthesis polypeptides. Sequence analysis can involve BLAST, Reciprocal BLAST, or PSI-BLAST analysis of nonredundant databases using a GGPPS, a CDPS, a KS, a KO or a KAH amino acid sequence as the reference sequence. Amino acid sequence is, in some instances, deduced from the nucleotide sequence. Those polypeptides in the database that have greater than 40% sequence identity are candidates for further evaluation for suitability as a steviol or steviol glycoside biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in steviol biosynthesis polypeptides, e.g., conserved functional domains.

Conserved regions can be identified by locating a region within the primary amino acid sequence of a steviol or a steviol glycoside biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. The information included at the Pfam database is described in Sonnhammer et al., *Nucl. Acids Res.,* 26:320-322 (1998); Sonnhammer et al., *Proteins* 28:405-420 (1997); and Bateman et al. *Nucl. Acids Res.,* 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

For example, polypeptides suitable for producing steviol glycosides in a recombinant host include functional homologs of UGT91D2e, UGT91D2m, UGT85C, and UGT76G. Such homologs have greater than 90% (e.g., at least 95% or 99%) sequence identity to the amino acid sequence of UGT91D2e (SEQ ID NO:5), UGT91D2m (SEQ ID NO:10), UGT85C (SEQ ID NO:3), or UGT76G (SEQ ID NO:7). Variants of UGT91D2, UGT85C, and UGT76G polypeptides typically have 10 or fewer amino acid substitutions within the primary amino acid sequence, e.g., 7 or fewer amino acid substitutions, 5 or conservative amino acid substitutions, or between 1 and 5 substitutions. However, in some embodiments, variants of UGT91D2, UGT85C, and UGT76G polypeptides can have 10 or more amino acid substitutions (e.g., 10, 15, 20, 25, 30, 35, 10-20, 10-35, 20-30, or 25-35 amino acid substitutions). The substitutions may be conservative, or in some embodiments, non-conservative. Non-limiting examples of non-conservative changes in UGT9ID2e polypeptides include glycine to arginine and tryptophan to arginine. Non-limiting examples of non-conservative substitutions in UGT76G polypeptides include valine to glutamic acid, glycine to glutamic acid, glutamine to alanine, and serine to proline. Non-limiting examples of changes to UGT85C polypeptides include histidine to aspartic acid, proline to serine, lysine to threonine, and threonine to arginine.

In some embodiments, a useful UGT91D2 homolog can have amino acid substitutions (e.g., conservative amino acid substitutions) in regions of the polypeptide that are outside of predicted loops, e.g., residues 20-26, 39-43, 88-95, 121-124, 142-158, 185-198, and 203-214 are predicted loops in the N-terminal domain and residues 381-386 are predicted loops in the C-terminal domain of SEQ ID NO:5. For example, a useful UGT91D2 homolog can include at least one amino acid substitution at residues 1-19, 27-38, 44-87, 96-120, 125-141, 159-184, 199-202, 215-380, or 387-473 of SEQ ID NO:5. In some embodiments, a UGT91D2 homolog can have an amino acid substitution at one or more residues selected from the group consisting of residues 30, 93, 99, 122, 140, 142, 148, 153, 156, 195, 196, 199, 206, 207, 211, 221, 286, 343, 427, and 438 of SEQ ID NO:5. For example, a UGT91D2 functional homolog can have an amino acid substitution at one or more of residues 206, 207, and 343, such as an arginine at residue 206, a cysteine at residue 207, and an arginine at residue 343 of SEQ ID NO:5. See, SEQ ID NO:95. Other functional homologs of UGT91D2 can have one or more of the following: a tyrosine or phenylalanine at residue 30, a proline or glutamine at residue 93, a serine or valine at residue 99, a tyrosine or a phenylalanine at residue 122, a histidine or tyrosine at residue 140, a serine or cysteine at residue 142, an alanine or threonine at residue 148, a methionine at residue 152, an alanine at residue 153, an alanine or serine at residue 156, a glycine at residue 162, a leucine or methionine at residue 195, a glutamic acid at residue 196, a lysine or glutamic acid at residue 199, a leucine or methionine at residue 211, a leucine at residue 213, a serine or phenylalanine at residue 221, a valine or isoleucine at residue 253, a valine or alanine at residue 286, a lysine or asparagine at residue 427, an alanine at residue 438, and either an alanine or threonine at residue 462 of SEQ ID NO:5. See, Examples 11 and 16, and Tables 12 and 14. A useful variant UGT91D2 polypeptide also can be constructed based on the alignment set forth in FIG. 8.

In some embodiments, a useful UGT85C homolog can have one or more amino acid substitutions at residues 9, 10, 13, 15, 21, 27, 60, 65, 71, 87, 91, 220, 243, 270, 289, 298, 334, 336, 350, 368, 389, 394, 397, 418, 420, 440, 441, 444, and 471 of SEQ ID NO:3. Non-limiting examples of useful UGT85C homologs include polypeptides having substitutions (with respect to SEQ ID NO:3) at residue 65; at residue 65 in combination with residue 15, 270, 418, 440, or 441; residues 13, 15, 60, 270, 289, and 418; substitutions at residues 13, 60, and 270; substitutions at residues 60 and 87; substitutions at residues 65, 71, 220, 243, and 270; substitutions at residues 65, 71, 220, 243, 270, and 441; substitutions at residues 65, 71, 220, 389, and 394; substitutions at residues 65, 71, 270, and 289; substitutions at residues 220, 243, 270, and 334; or substitutions at residues 270 and 289. See, Example 17 and Table 15.

In some embodiments, a useful UGT76G homolog can have one or more amino acid substitutions at residues 29, 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346 of SEQ ID NO:7. Non-limiting examples of useful UGT76G homologs include polypeptides having substitutions (with respect to SEQ ID NO:7) at residues 74, 87, 91, 116, 123, 125, 126, 130, 145, 192, 193, 194, 196, 198, 199, 200, 203, 204, 205, 206, 207, 208, and 291; residues 74, 87, 91, 116, 123, 125, 126, 130, 145, 192, 193, 194, 196, 198, 199, 200, 203, 204, 205, 206, 207, 208, 266, 273, 274, 284, 285, and 291; or residues 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346. See, Example 18 and Table 16.

Methods to modify the substrate specificity of, for example UGT91D2c, are known to those skilled in the art, and include without limitation site-directed/rational mutagenesis approaches, random directed evolution approaches and combinations in which random mutagenesis/saturation techniques are performed near the active site of the enzyme. For example see Sarah A. Osmani, et al. *Phytochemistry* 70 (2009) 325-347.

A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., *Nucleic. Acids Res.,* 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

It will be appreciated that a functional UGT91D2 polypeptide can include additional amino acids that are not involved in glucosylation or other enzymatic activities carried out by UGT91D2, and thus such a polypeptide can be longer than would otherwise be the case. For example, a UGT91D2 polypeptide can include a purification tag, a chloroplast transit peptide, a mitochondrial transit peptide, an amyloplast peptide, signal peptide, or a secretion tag added to the amino or carboxy terminus. In some embodiments, a UGT91D2 polypeptide includes an amino acid sequence that functions as a reporter, e.g., a green fluorescent protein or yellow fluorescent protein.

II. Steviol and Steviol Glycoside Biosynthesis Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

One or more genes can be combined in a recombinant nucleic acid construct in "modules" useful for a discrete aspect of steviol and/or steviol glycoside production. Combining a plurality of genes in a module, particularly a polycistronic module, facilitates the use of the module in a variety of species. For example, a steviol biosynthesis gene cluster, or a UGT gene cluster, can be combined in a polycistronic module such that, after insertion of a suitable regulatory region, the module can be introduced into a wide variety of species. As another example, a UGT gene cluster can be combined such that each UGT coding sequence is operably linked to a separate regulatory region, to form a UGT module. Such a module can be used in those species for which monocistronic expression is necessary or desirable. In addition to genes useful for steviol or steviol glycoside production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). SEQ ID NOs:18-25, 34-36, 40-43, 48-49, 52-55, 60-64, and 70-72 set forth nucleotide sequences encoding certain enzymes for steviol and steviol glycoside biosynthesis, modified for increased expression in yeast. As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards steviol or steviol glycoside biosynthesis. For example, it may be desirable to downregulate synthesis of sterols in a yeast strain in order to further increase steviol or steviol glycoside production, e.g., by downregulating squalene epoxidase. As another example, it may be desirable to inhibit degradative functions of certain endogenous gene products, e.g., glycohydrolases that remove glucose moieties from secondary metabolites. As another example, expression of membrane transporters involved in transport of steviol glycosides can be inhibited, such that secretion of glycosylated steviosides is inhibited. Such regulation can be beneficial in that secretion of steviol glycosides can be inhibited for a desired period of time during culture of the microorganism, thereby increasing the yield of glycoside product(s) at harvest. In such cases, a nucleic acid that inhibits expression of the polypeptide or gene product may be included in a recombinant construct that is transformed into the strain. Alternatively, mutagenesis can be used to generate mutants in genes for which it is desired to inhibit function.

III. Hosts

A. Microorganisms

A number of prokaryotes and eukaryotes are suitable for use in constructing the recombinant microorganisms described herein, e.g., gram-negative bacteria, yeast and fungi. A species and strain selected for use as a steviol or steviol glycoside production strain is first analyzed to determine which production genes are endogenous to the strain and which genes are not present. Genes for which an endogenous counterpart is not present in the strain are assembled in one or more recombinant constructs, which are then transformed into the strain in order to supply the missing function(s).

Exemplary prokaryotic and eukaryotic species are described in more detail below. However, it will be appreciated that other species may be suitable. For example, suitable species may be in a genus selected from the group consisting of *Agaricus*, *Aspergillus*, *Bacillus*, *Candida*, *Corynebacterium*, *Escherichia*, *Fusarium/Gibberella*, *Kluyveromyces*, *Laetiporus*, *Lentinus*, *Phaffia*, *Phanerochaete*, *Pichia*, *Physcontitrella*, *Rhodoturula*, *Saccharomyces*, *Schizosaccharomyces*, *Sphaceloma*, *Xanthophyllomyces* and *Yarrowia*. Exemplary species from such genera include *Lentinus tigrinus*, *Laetiporus sulphureus*, *Phanerochaete chrysosporium*, *Pichia pastoris*, *Physcomitrella patens*, *Rhodoturula glutinis* 32, *Rhodoturula mucilaginosa*, *Phaffia rhodozyma* UBV-AX, *Xanthophyllomyces dendrorhous*, *Fusarium fujikuroi/Gibberella fujikurol*, *Candida utilis* and *Yarrowia lipolytica*. In some embodiments, a microorganism can be an *Ascomycete* such as *Gibberella fujikuroi*, *Kluyveromyces lactis*, *Schizosaccharomyces pombe*, *Aspergillus niger*, or *Saccharomyces cerevisiae*. In some embodiments, a microorganism can be a prokaryote such as *Escherichia coli*, *Rhodobacter sphaeroides*, or *Rhodobacter capsulatus*. It will be appreciated that certain microorganisms can be used to screen and test genes of interest in a high throughput manner, while other microorganisms with desired productivity or growth characteristics can be used for large-scale production of steviol glycosides.

*Saccharomyces cerevisiae*

*Saccharomyces cerevisiae* is a widely used chassis organism in synthetic biology, and can be used as the recombinant microorganism platform. There are libraries of mutants, plasmids, detailed computer models of metabolism and other information available for *S. cerevisiae*, allowing for rational design of various modules to enhance product yield. Methods are known for making recombinant microorganisms.

A steviol biosynthesis gene cluster can be expressed in yeast using any of a number of known promoters. Strains that overproduce terpenes are known and can be used to increase the amount of geranylgeranyl diphosphate available for steviol and steviol glycoside production.

*Aspergillus* spp.

*Aspergillus* species such as *A. oryzae*, *A. niger* and *A. sojae* are widely used microorganisms in food production, and can also be used as the recombinant microorganism platform. Nucleotide sequences are available for genomes of *A. nidulans*, *A. fumigatus*, *A. oryzae*, *A. clavatus*, *A. flavus*, *A. niger*, and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for the production of food ingredients such as steviol and steviol glycosides. Example 23 describes cloning methodology for production of steviol glycosides in *Aspergillus nidulans*.

*Escherichia coli*

*Escherichia coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus, Gibberella*, and *Phanerochaete* spp.

*Agaricus, Gibberella*, and *Phanerochaete* spp. can be useful because they are known to produce large amounts of gibberellin in culture. Thus, the terpene precursors for producing large amounts of steviol and steviol glycosides are already produced by endogenous genes. Thus, modules containing recombinant genes for steviol or steviol glycoside biosynthesis polypeptides can be introduced into species from such genera without the necessity of introducing mevalonate or MEP pathway genes.

*Rhodobacter* spp.

*Rhodobacter* can be use as the recombinant microorganism platform. Similar to *E. coli*, there are libraries of mutants available as well as suitable plasmid vectors, allowing for rational design of various modules to enhance product yield. Isoprenoid pathways have been engineered in membraneous bacterial species of *Rhodobacter* for increased production of carotenoid and CoQ10. See, U.S. Patent Publication Nos. 20050003474 and 20040078846. Methods similar to those described above for *E. coli* can be used to make recombinant *Rhodobacter* microorganisms.

*Physcomitrella* spp.

*Physcomitrella* mosses, when grown in suspension culture, have characteristics similar to yeast or other fungal cultures. This genera is becoming an important type of cell for production of plant secondary metabolites, which can be difficult to produce in other types of cells. Example 22 describes production of active UGT enzymes in the steviol glycoside pathway in *P. patens*.

B. Plant Cells or Plants

In some embodiments, the nucleic acids and polypeptides described herein are introduced into plants or plant cells to increase overall steviol glycoside production or enrich for the production of specific steviol glycosides in proportion to others. Thus, a host can be a plant or a plant cell that includes at least one recombinant gene described herein. A plant or plant cell can be transformed by having a recombinant gene integrated into its genome, i.e., can be stably transformed. Stably transformed cells typically retain the introduced nucleic acid with each cell division. A plant or plant cell can also be transiently transformed such that the recombinant gene is not integrated into its genome. Transiently transformed cells typically lose all or some portion of the introduced nucleic acid with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques.

As used herein, a transgenic plant also refers to progeny of an initial transgenic plant provided the progeny inherits the transgene. Seeds produced by a so transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, U.S. Pat. Nos. 5,538,880; 5,204,253; 6,329,571; and 6,013,863. If a cell or cultured tissue is used as the recipient tissue for transformation, plants can be regenerated from transformed cultures if desired, by techniques known to those skilled in the art.

A population of transgenic plants can be screened and/or selected for those members of the population that have a trait or phenotype conferred by expression of the transgene. For example, a population of progeny of a single transformation event can be screened for those plants having a desired level of expression of a steviol or steviol glycoside biosynthesis polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or nucleic acids. Methods for performing all of the referenced techniques are known. As an alternative, a population of plants comprising independent transformation events can be screened for those plants having a desired trait, such as production of a steviol glycoside or modulated biosynthesis of a steviol glycoside. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a steviol glycoside level relative to a control plant that lacks the transgene.

The nucleic acids, recombinant genes, and constructs described herein can be used to transform a number of monocotyledonous and dicotyledonous plants and plant cell systems. Non-limiting examples of suitable monocots include, for example, cereal crops such as rice, rye, sorghum, millet, wheat, maize, and barley. The plant may be a non-cereal monocot such as asparagus, banana, or onion. The plant also may be a dicot such as stevia (Stevia rebaudiana), soybean, cotton, sunflower, pea, geranium, spinach, or tobacco. In some cases, the plant may contain the precursor pathways for phenyl phosphate production such as the mevalonate pathway, typically found in the cytoplasm and mitochondria. The non-mevalonate pathway is more often found in plant plastids [Dubey, et al., 2003 J. Biosci. 28 637-646]. One with skill in the art may target expression of steviol glycoside biosynthesis polypeptides to the appropriate organelle through the use of leader sequences, such that steviol glycoside biosynthesis occurs in the desired location of the plant cell. One with skill in the art will use appropriate promoters to direct synthesis, e.g., to the leaf of a plant, if so desired. Expression may also occur in tissue cultures such as callus culture or hairy root culture, if so desired.

In one embodiment, one or more nucleic acid or polypeptides described herein are introduced into Stevia (e.g., Stevia rebaudiana) such that overall steviol glycoside biosynthesis is increased or that the the overall steviol glycoside composition is selectively enriched for one or more specific steviol glycosides. For example, one or more recombinant genes can be introduced into Stevia such that one or more of the following are expressed: a UGT91D enzyme such as UGT91D2e (e.g., SEQ ID NO:5 or a functional homolog thereof), UGT91D2m (e.g., SEQ ID NO:10); a UGT85C enzyme such as a variant set forth in Table 15, or a UGT76G1 enzyme such as a variant set forth in Example 18. Nucleic acid constructs typically include a suitable promoter (e.g., 35S, e35S, or ssRUBISCO promoters) operably linked to a nucleic acid encoding the UGT polypeptide. Nucleic acids can be introduced into Stevia by Agrobacterium-mediated transformation; electroporation-mediated gene transfer to protoplasts; or by particle bombardment. See, e.g., Singh, et al., Compendium of Transgenic Crop Plants: Transgenic Sugar, Tuber and Fiber, Edited by Chittaranjan Kole and Timothy C. Hall, Blackwell Publishing Ltd. (2008), pp. 97-115. For particle bombardment of stevia leaf derived callus, the parameters can be as follows: 6 cm distance, 1100 psi He pressure, gold particles, and one bombardment.

Stevia plants can be regenerated by somatic embryogenesis as described by Singh et al., 2008, supra. In particular, leaf segments (approximately 1-2 cm long) can be removed from 5 to 6-week-old in vitro raised plants and incubated (adaxial side down) on MS medium supplemented with B5 vitamins, 30 g sucrose and 3 g Gelrite. 2,4-dichlorophenoxyacetic acid (2,4-D) can be used in combination with 6-benzyl adenine (BA), kinetin (KN), or zeatin. Proembryogenic masses appear after 8 weeks of subculture. Within 2-3 weeks of subcultures, somatic embryos will appear on the surface of cultures. Embryos can be matured in medium containing BA in combination with 2,4-D, a-naphthaleneacetic acid (NAA), or indolbutyric acid (IBA). Mature somatic embryos that germinate and form plantlets can be excised from calli. After plantlets reach 3-4 weeks, the plantlets can be transferred to pots with vermiculite and grown for 6-8 weeks in growth chambers for acclimatization and transferred to greenhouses.

In one embodiment, steviol glycosides are produced in rice. Rice and maize are readily transformable using techniques such as Agrobacterium-mediated transformation. Binary vector systems are commonly utilized for Agrobacterium exogenous gene introduction to monocots. See, for example, U.S. Pat. Nos. 6,215,051 and 6,329,571. In a binary vector system, one vector contains the T-DNA region, which includes a gene of interest (e.g., a UGT described herein) and the other vector is a disarmed Ti plasmid containing the vir region. Co-integrated vectors and mobilizable vectors also can be used. The types and pretreatment of tissues to be transformed, the strain of Agrobacterium used, the duration of the inoculation, the prevention of overgrowth and necrosis by the Agrobacterium, can be readily adjusted by one of skill in the art. Immature embryo cells of rice can be prepared for transformation with Agrobacterium using binary vectors. The culture medium used is supplemented with phenolic compounds. Alternatively, the transformation can be done in planta using vacuum infiltration. See, for example, WO 2000037663, WO 2000063400, and WO 2001012828.

IV. Methods of Producing Steviol and Steviol Glycosides

Recombinant hosts described herein can be used in methods to produce steviol or steviol glycosides. For example, if the recombinant host is a microorganism, the method can include growing the recombinant microorganism in a culture medium under conditions in which steviol and/or steviol glycoside biosynthesis genes are expressed. The recombinant microorganism may be grown in a fed batch or continuous process. Typically, the recombinant microorganism is grown in a fermentor at a defined temperature(s) for a desired period of time. Depending on the particular microorganism used in the method, other recombinant genes such as isopentenyl biosynthesis genes and terpene synthase and cyclase genes may also be present and expressed. Levels of substrates and intermediates, e.g., isopentenyl diphosphate, dimethylallyl diphosphate, geranylgeranyl diphosphate, kaurene and kaurenoic acid, can be determined by extracting samples from culture media for analysis according to published methods.

After the recombinant microorganism has been grown in culture for the desired period of time, steviol and/or one or more steviol glycosides can then be recovered from the culture using various techniques known in the art. If the recombinant host is a plant or plant cells, steviol or steviol glycosides can be extracted from the plant tissue using various techniques known in the art. For example, a crude lysate of the cultured microorganism or plant tissue can be centrifuged to obtain a supernatant. The resulting supernatant can then be applied to a chromatography column, e.g., a C-18 column, and washed with water to remove hydrophilic compounds, followed by elution of the compound(s) of interest with a solvent such as methanol. The compound (s) can then be further purified by preparative HPLC. See also WO 2009/140394.

The amount of steviol or steviol glycoside produced can be from about 1 mg/l to about 1,500 mg/l, e.g., about 1 to about 10 mg/l, about 3 to about 10 mg/l, about 5 to about 20 mg/l, about 10 to about 50 mg/l, about 10 to about 100 mg/l, about 25 to about 500 mg/l, about 100 to about 1,500 mg/l, or about 200 to about 1,000 mg/l. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce steviol and/or steviol glycosides. For example, a first microorganism can comprise one or more biosynthesis genes for producing steviol while a second microorganism comprises steviol glycoside biosynthesis genes. Alternatively, the two or more microorganisms each can be grown in a separate culture medium and the product of the first culture medium, e.g., steviol, can be introduced into second culture medium to be converted into a subsequent intermediate, or into an end product such as rebaudioside A. The product produced by the second, or final microorganism is then recovered. It will also be appreciated that in some embodiments, a recombinant microorganism is grown using nutrient sources other than a culture medium and utilizing a system other than a fermentor.

Steviol glycosides do not necessarily have equivalent performance in different food systems. It is therefore desirable to have the ability to direct the synthesis to steviol glycoside compositions of choice. Recombinant hosts described herein can produce compositions that are selectively enriched for specific steviol glycosides and have a consistent taste profile. Thus, the recombinant microorganisms, plants, and plant cells described herein can facilitate the production of compositions that are tailored to meet the sweetening profile desired for a given food product and that have a proportion of each steviol glycoside that is consistent from batch to batch. Microorganisms described herein do not produce the undesired plant byproducts found in *Stevia* extracts. Thus, steviol glycoside compositions produced by the recombinant microorganisms described herein are distinguishable from compositions derived from *Stevia* plants.

V. Food Products

The steviol and steviol glycosides obtained by the methods disclosed herein can be used to make food products, dietary supplements and sweetener compositions. For example, substantially pure steviol or steviol glycoside such as rebaudioside A can be included in food products such as ice cream, carbonated beverages, fruit juices, yogurts, baked goods, chewing gums, hard and soft candies, and sauces. Substantially pure steviol or steviol glycoside can also be included in non-food products such as pharmaceutical products, medicinal products, dietary supplements and nutritional supplements. Substantially pure steviol or steviol glycosides may also be included in animal feed products for both the agriculture industry and the companion animal industry. Alternatively, a mixture of steviol and/or steviol glycosides can be made by culturing recombinant microorganisms separately or growing different plants/plant cells, each producing a specific steviol or steviol glycoside, recovering the steviol or steviol glycoside in substantially pure form from each microorganism or plant/plant cells and then combining the compounds to obtain a mixture containing each compound in the desired proportion. The recombinant microorganisms, plants, and plant cells described herein permit more precise and consistent mixtures to be obtained compared to current *Stevia* products. In another alternative, a substantially pure steviol or steviol glycoside can be incorporated into a food product along with other sweeteners, e.g. saccharin, dextrose, sucrose, fructose, erythritol, aspartame, sucralose, monatin, or acesulfame potassium. The weight ratio of steviol or steviol glycoside relative to other sweeteners can be varied as desired to achieve a satisfactory taste in the final food product. See, e.g., U.S. Patent Publication No. 2007/0128311. In some embodiments, the steviol or steviol glycoside may be provided with a flavor (e.g., citrus) as a flavor modulator. For example, Rebaudioside C can be used as a sweetness enhancer or sweetness modulator, in particular for carbohydrate based sweeteners, such that the amount of sugar can be reduced in the food product.

Compositions produced by a recombinant microorganism, plant, or plant cell described herein can be incorporated into food products. For example, a steviol glycoside composition produced by a recombinant microorganism, plant, or plant cell can be incorporated into a food product in an amount ranging from about 20 mg steviol glycoside/kg food product to about 1800 mg steviol glycoside/kg food product on a dry weight basis, depending on the type of steviol glycoside and food product. For example, a steviol glycoside composition produced by a recombinant microorganism, plant, or plant cell can be incorporated into a dessert, cold confectionary (e.g., ice cream), dairy product (e.g., yogurt), or beverage (e.g., a carbonated beverage) such that the food product has a maximum of 500 mg steviol glycoside/kg food on a dry weight basis. A steviol glycoside composition produced by a recombinant microorganism, plant, or plant cell can be incorporated into a baked good (e.g., a biscuit) such that the food product has a maximum of 300 mg steviol glycoside/kg food on a dry weight basis. A steviol glycoside composition produced by a recombinant microorganism, plant, or plant cell can be incorporated into a sauce (e.g., chocolate syrup) or vegetable product (e.g., pickles) such that the food product has a maximum of 1000 mg steviol glycoside/kg food on a dry weight basis. A steviol glycoside composition produced by a recombinant microorganism, plant, or plant cell can be incorporated into a bread such that the food product has a maximum of 160 mg steviol glycoside/kg food on a dry weight basis. A steviol glycoside composition produced by a recombinant microorganism, plant, or plant cell can be incorporated into a hard or soft candy such that the food product has a maximum of 1600 mg steviol glycoside/kg food on a dry weight basis. A steviol glycoside composition produced by a recombinant microorganism, plant, or plant cell can be incorporated into a processed fruit product (e.g., fruit juices, fruit filling, jams, and jellies) such that the food product has a maximum of 1000 mg steviol glycoside/kg food on a dry weight basis.

For example, such a steviol glycoside composition can have from 90-99% rebaudioside A and an undetectable amount of *stevia* plant-derived contaminants, and be incorporated into a food product at from 25-1600 mg/kg, e.g., 100-500 mg/kg, 25-100 mg/kg, 250-1000 mg/kg, 50-500 mg/kg or 500-1000 mg/kg on a dry weight basis.

Such a steviol glycoside composition can be a rebaudioside B-enriched composition having greater than 3% rebaudioside B and be incorporated into the food product such that the amount of rebaudioside B in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the rebaudioside B-enriched composition has an undetectable amount of *stevia* plant-derived contaminants.

Such a steviol glycoside composition can be a rebaudioside C-enriched composition having greater than 15% rebaudioside C and be incorporated into the food product such that the amount of rebaudioside C in the product is from 20-600 mg/kg, e.g., 100-600 mg/kg, 20-100 mg/kg, 20-95 mg/kg, 20-250 mg/kg, 50-75 mg/kg or 50-95 mg/kg on a dry weight basis. Typically, the rebaudioside C-enriched composition has an undetectable amount of *stevia* plant-derived contaminants.

Such a steviol glycoside composition can be a rebaudioside D-enriched composition having greater than 3% rebaudioside D and be incorporated into the food product such that the amount of rebaudioside D in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the rebaudioside D-enriched composition has an undetectable amount of *stevia* plant-derived contaminants.

Such a steviol glycoside composition can be a rebaudioside E-enriched composition having greater than 3% rebaudioside E and be incorporated into the food product such that the amount of rebaudioside E in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the rebaudioside E-enriched composition has an undetectable amount of *stevia* plant-derived contaminants.

Such a steviol glycoside composition can be a rebaudioside F-enriched composition having greater than 4% rebaudioside F and be incorporated into the food product such that the amount of rebaudioside F in the product is from 25-1000 mg/kg, e.g., 100-600 mg/kg, 25-100 mg/kg, 25-95 mg/kg, 50-75 mg/kg or 50-95 mg/kg on a dry weight basis. Typically, the rebaudioside F-enriched composition has an undetectable amount of *stevia* plant-derived contaminants.

Such a steviol glycoside composition can be a dulcoside A-enriched composition having greater than 4% dulcoside A and be incorporated into the food product such that the amount of dulcoside A in the product is from 25-1000 mg/kg, e.g., 100-600 mg/kg, 25-100 mg/kg, 25-95 mg/kg, 50-75 mg/kg or 50-95 mg/kg on a dry weight basis. Typically, the dulcoside A-enriched composition has an undetectable amount of *stevia* plant-derived contaminants.

In some embodiments, a substantially pure steviol or steviol glycoside is incorporated into a tabletop sweetener or "cup-for-cup" product. Such products typically are diluted to the appropriate sweetness level with one or more bulking agents, e.g., maltodextrins, known to those skilled in the art. Steviol glycoside compositions enriched for rebaudioside A, rebaudioside C, rebaudioside D, rebaudioside E, rebaudioside F, or dulcoside A can be package in a sachet, for example, at from 10,000 to 30,000 mg steviol glycoside/kg product on a dry weight basis, for tabletop use.

VI. Plant Breeding

A. Polymorphisms

Polymorphisms among the nucleic acids described herein (e.g., UGT91D2 nucleic acids) can be used as markers in plant genetic mapping and plant breeding programs in *Stevia*. See, e.g., Yao et al., *Genome*, 1999, 42:657-661. Thus, the polymorphisms described herein can be used in a method of identifying whether that polymorphism is associated with variation in a trait. The method involves measuring the correlation between variation in the trait in plants of a *Stevia* line or population and the presence of one or more genetic polymorphisms in those plants, thereby identifying whether or not the genetic polymorphisms are associated with variation in the trait. Typically, the trait is the total amount of steviol glycosides present in leaves of the plant, although the trait also can be the amount of a particular steviol glycoside, e.g., rebaudioside A, rebaudioside B, rebaudioside C, rebaudioside D, rebaudioside E, rebaudioside F, or dulcoside A. In some embodiments, the trait is the amount of steviol, or the amount of an isoprenoid precursor. A statistically significant correlation between the trait and the presence of the polymorphic marker is determined using an appropriate parametric or non-parametric statistic, e.g., Chi-square test, Student's t-test, Mann-Whitney test, or F-test. A statistically significant correlation between, for example, the amount of rebaudioside A in a plant and presence of a polymorphic marker indicates that the marker may be useful in a marker-assisted breeding program for selection of altered rebaudioside A levels.

Polymorphisms may be detected by means known in the art, including without limitation, restriction fragment length polymorphism (RFLP), random amplified polymorphic DNA detection (RAPD), amplified fragment length polymorphism (AFLP), simple sequence repeat (SSR) or microsatellites. Discovery, detection, and genotyping of polymorphisms have been described in the literature. See, e.g., Henry, ed. (2001) Plant Genotyping. The DNA Fingerprinting of Plants Wallingford: CABI Publishing; and Phillips and Vasil, eds. (2001) DNA-based Markers in Plants Dordrecht: Kluwer Academic Publishers. For example, a primer or probe derived from the nucleic acid sequences set forth in SEQ ID NO:6, SEQ ID NO:9, or SEQ ID NO:96, or the complements thereof, can be used to identify one or more individual plants that possess the polymorphic allele that is correlated with a desired steviol glycoside composition. Those plants then can be used in a breeding program to combine the polymorphic allele with a plurality of other alleles at other loci that are correlated with the desired steviol glycoside composition. As will be evident to one of skill, the number and type of markers required can differ, depending on the trait(s) to be selected for and the degree of correlation for each marker. The methods, therefore, involve detecting a plurality of polymorphisms in the genome of the plant in certain embodiments. It will be appreciated that the method may further comprise storing the results of the step of detecting the plurality of polymorphisms on a computer readable medium.

Thus, in some embodiments, a method for identifying *Stevia* plant lines or populations comprises supplying a nucleic acid sample for a *Stevia* plant, providing amplification primers for amplifying a region of a *Stevia* plant corresponding to a UGT gene having 90% or greater sequence identity to a nucleic acid encoding the polypeptides set forth in SEQ ID NOs: 1, 3, 5, or 7, present in the sample, applying the amplification primers to the nucleic acid sample such that amplification of the region occurs, and identifying plants having a desired trait based on the presence of one or more polymorphisms in the amplified nucleic acid sample that correlate with the trait.

In some embodiments, a method of determining the presence of a polynucleotide in a *Stevia* plant involves contacting at least one probe or primer pair with nucleic acid from the plant. The probe or primer pair is specific for a polynucleotide that encodes a UGT polypeptide having at least 90% sequence identity to SEQ ID NOs: 1, 3, 5, or 7. The presence or absence of the polynucleotide is then determined.

In addition to methods for detecting polymorphisms and determining the genotype of a *Stevia* plant, kits suitable for carrying out the methods are also described, as well as a computer readable medium produced by such methods that contains data generated by the methods. A kit for genotyping a *Stevia* biological sample includes a primer pair that specifically amplifies, or a probe that specifically hybridizes to, a polynucleotide that encodes a UGT polypeptide having at least 90% sequence identity to SEQ ID NOs: 1, 3, 5, or 7. Such kits typically have the primer or probe contained within suitable packaging material.

In some embodiments of the methods and kits described herein, one or more sets of oligonucleotides, each capable of recognizing the presence or absence of a specific and defined genomic position, is used. For polyploid *Stevia* lines or populations, more oligonucleotides are desirable. The lower limit is one oligonucleotide pair and the upper limit is set by the desired resolution capacity of the method and the test kit. Hybridization of the oligonucleotides to DNA from the *Stevia* plant is preferably recorded in situ by any conventional labelling system, applying for instance terminal transferase and conventional recordable labels. As an alternative to in situ labelling the hybridized sample DNA may be released from the solid support and subsequently hybridized with labelled polynucleotide sequences corresponding to each of the original oligonucleotide sequences attached to the solid support. Hybridization is optionally reversible and the solid support can be returned to its original state for reuse. A labelled dideoxynucleotide can be incorporated at the end of the oligonucleotide provided that the oligonucleotide is hybridized to genomic DNA as template. The nucleotide sequence at the genomic position adjacent to the region matching the oligonucleotide is known and therefore the particular nucleotide which will be incorporated (A, C, G, T or U) is known. Co-dominant scoring is achieved using paired, i.e. two or parallel, i.e. three, flanking oligonucleotide sequences. The results obtained are recorded as full, empty, failure or null alleles and can be used to distinguish between heterozygous and/or homozygous genotypes. Optional post-hybridization treatments, including washing and digestion, are provided in order to remove sample DNA not fully hybridized to the solid support-attached oligonucleotide sequences, for example before and after labelling. The presence or absence of hybridization is recorded using a method allowing the recording of the hybridization state, typically on a computer readable medium.

B. Breeding Programs

*Stevia* is typically an outcrossing species, although self-polination is occasionally observed. Thus, a *Stevia* plant breeding program typically involves the use of one or more of: recurrent selection mass selection, bulk selection, and intercrossing. These techniques can be used alone or in combination with one or more other techniques in a breeding program. See, Yadav et al. *Can. J. Plant Sci.* 91: 1-27 (2011). Each identified plant can be crossed to a different plant to produce seed, which is then germinated to form progeny plants. Seed from one or more progeny plants possessing the desired phenotype(s) and desired polymorphism(s) is composited and then randomly mated to form a subsequent progeny generation. The breeding program can repeat these steps for an additional 0 to 5 generations as appropriate in order to achieve the desired stability in the resulting plant population, which retains the polymorphic allele(s). In most breeding programs, analysis for the particular polymorphic allele will be carried out in each generation, although analysis can be carried out in alternate generations if desired. Selfing of progeny plants may be carried out for those *stevia* lines and populations in which selfing is feasible.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny and selfed progeny. The selected progeny are self pollinated or cross pollinated with each other to form progeny for another population. This population is planted and again superior plants are selected to self pollinate or cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties. The number of parental plant varieties, populations, wild accessions, ecotypes, etc., that are used to generate a synthetic can vary from as little as 10 to as much as 500. Typically, about 100 to 300 varieties, populations, etc., are used a parents for the synthetic variety. Seed from the parental seed production plot of a synthetic variety can be sold to the farmer. Alternatively, seed from the parental seed production plot can subsequently undergo one or two generations of multiplication, depending on the amount of seed produced in the parental plot and the demand for seed.

Mass selection is a useful technique when used in conjunction with molecular marker-assisted selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Also, instead of self pollination, directed pollination could be used as part of the breeding program.

Thus, in some embodiments, a method of making a *Stevia* plant line or population involves identifying one or more plants in the line or population in which the presence of a polymorphism at a locus having nucleotide sequence encoding a polypeptide that is at least 90% identical to SEQ ID NOs: 1, 3, 5, or 7 is associated with variation in a trait of interest. The identified plant(s) is then crossed with itself or a different *stevia* plant to produce seed, and at least one progeny plant grown from the seed is again crossed with itself or a different *stevia* plant for an additional 0-5 generations to make a line or population that possesses the polymorphism.

In some cases, selection for other useful traits is also carried out, e.g., selection for disease resistance. Selection for such other traits can be carried out before, during or after identification of individual plants that possess the desired polymorphic allele.

Marker-assisted breeding techniques may be used in addition to, or as an alternative to, other sorts of identification techniques.

The invention will be further described in the following examples, which do not limit the scope of the invention described in the claims.

VI. Examples

Example 1—Construction of Kaurene Biosynthesis Pathway Genes

A nucleotide sequence encoding a truncated baker's yeast HMG CoA reductase was cloned into a yeast high copy episomal plasmid vector such that the coding sequence was operably linked to and under the transcriptional control of a promoter which can be repressed by the amino acid methionine. See, U.S. Pat. Nos. 5,460,949 and 5,306,862.

Nucleotide sequences encoding the GGPPS enzymes shown in Table 1 were modified for expression in yeast (see SEQ ID NOs:18-25) and cloned into an *E. coli* vector such that the coding sequence was operably linked to and under the transcriptional control of a yeast promoter which can be repressed by the amino acid methionine. The name for each expression cassette-containing plasmid ("entry vector") is also shown in Table 1. The nucleotide sequences from the source organisms from which the polypeptides were originally identified are set forth in SEQ ID NOs: 26-33. Other entry vectors were constructed using GGPPS enzymes expressed by an unmodified nucleotide sequence from *Catharanthus roseus* designated EV270, an unmodified nucleotide sequence from *Aspergillus nidulans* designated C301 and an unmodified nucleotide sequence from *Xanthophyllomyces dendrorhous* designated C413.

TABLE 1

GGPPS Clones

| Enzyme Source Organism | gi Number | Accession Number | Plasmid Name | Construct Name | Length (nts) | SEQ ID (DNA) | SEQ ID (protein) |
|---|---|---|---|---|---|---|---|
| *Stevia rebaudiana* | 90289577 | ABD92926 | pMUS14 | MM-1 | 1086 | 18 | 121 |
| *Gibberella fujikuroi* | 3549881 | CAA75568 | pMUS15 | MM-2 | 1029 | 19 | 122 |
| *Mus musculus* | 47124116 | AAH69913 | pMUS16 | MM-3 | 903 | 20 | 123 |
| *Thalassiosira pseudonana* | 223997332 | XP_002288339 | pMUS17 | MM-4 | 1020 | 21 | 124 |
| *Streptomyces clavuligerus* | 254389342 | ZP_05004570 | pMUS18 | MM-5 | 1068 | 22 | 125 |
| *Sulfulobus acidocaldarius* | 506371 | BAA43200 | pMUS19 | MM-6 | 993 | 23 | 126 |
| *Synechococcus* sp. | 86553638 | ABC98596 | pMUS20 | MM-7 | 894 | 24 | 127 |
| *Arabidopsis thaliana* | 15234534 | NP_195399 | pMUS21 | MM-8 | 1113 | 25 | 128 |

Nucleotide sequences encoding the CDPS enzymes shown in Table 2 were modified for expression in yeast (see SEQ ID NOs: 34-36) and cloned into yeast entry vectors. The nucleotide sequences from the source organisms from which the polypeptides were originally identified are set forth in SEQ ID NOs: 37-39. Other entry vectors were constructed using CDPS enzymes expressed by an unmodified nucleotide sequence from *Arabidopsis thaliana* designated EV64, an unmodified nucleotide sequence from *Zea mays* designated EV65 and an unmodified nucleotide sequence from *Lycopersicon esculentum* designated EV66.

TABLE 2

CDPS Clones

| Enzyme Source Organism | gi Number | Accession Number | Plasmid Name | Construct Name | Length (nts) | SEQ ID: (DNA) | SEQ ID (protein) |
|---|---|---|---|---|---|---|---|
| *Stevia rebaudiana* | 2642661 | AAB87091 | pMUS22 | MM-9 | 2364 | 34 | 129 |
| *Streptomyces clavuligerus* | 197705855 | EDY51667 | pMUS23 | MM-10 | 1584 | 35 | 130 |
| *Bradyrhizobium japonicum* | 529968 | AAC28895.1 | pMUS24 | MM-11 | 1551 | 36 | 131 |

Nucleotide sequences encoding the KS enzymes shown in Table 3 were modified for expression in yeast (see SEQ ID NOs: 40-43) and cloned into yeast entry vectors. The nucleotide sequences from the source organisms from which the polypeptides were originally identified are set forth in SEQ ID NOs:44-47. Other entry vectors were constructed using KS enzymes expressed by an unmodified nucleotide sequence from *Arabidopsis thaliana* designated EV70, an unmodified nucleotide sequence from *Cucurbita maxima* designated EV71 and an unmodified nucleotide sequence from *Cucumis sativus* designated EV72.

TABLE 3

KS Clones

| Enzyme Source Organism | gi Number | Accession Number | Plasmid Name | Construct Name | Length (nts) | SEQ ID (DNA) | SEQ ID (protein) |
|---|---|---|---|---|---|---|---|
| Stevia rebaudiana | 4959241 | AAD34295 | pMUS25 | MM-12 | 2355 | 40 | 132 |
| Stevia rebaudiana | 4959239 | AAD34294 | pMUS26 | MM-13 | 2355 | 41 | 133 |
| Zea mays | 162458963 | NP_001105097 | pMUS27 | MM-14 | 1773 | 42 | 134 |
| Populus trichocarpa | 224098838 | XP_002311286 | pMUS28 | MM-15 | 2232 | 43 | 135 |

Nucleotide sequences encoding the CDPS-KS fusion enzymes shown in Table 4 were modified for expression in yeast (see SEQ ID NOs: 48 and 49) and cloned into yeast entry vectors. The nucleotide sequences from the source organisms from which the polypeptides were originally identified are set forth in SEQ ID NOs: 50 and 51.

TABLE 4

CDPS-KS Clones

| Enzyme Source Organism | gi Number | Accession Number | Plasmid Name | Construct Name | Length (nts) | SEQ ID (DNA) | SEQ ID (protein) |
|---|---|---|---|---|---|---|---|
| Phomopsis amygdali | 186704306 | BAG30962 | pMUS29 | MM-16 | 2952 | 48 | 136 |
| Physcomitrella patens | 146325986 | BAF61135 | pMUS30 | MM-17 | 2646 | 49 | 137 |

Nucleotide sequences encoding the KO enzymes shown in Table 5 were modified for expression in yeast (see SEQ ID NOs: 52-55) and cloned into yeast entry vectors. The nucleotide sequences from the source organisms from which the polypeptides were originally identified are set forth in SEQ ID NOs: 56-59.

TABLE 5

KO Clones

| Enzyme Source Organism | gi Number | Accession Number | Plasmid Name | Construct Name | Length (nts) | SEQ ID (DNA) | SEQ ID (protein) |
|---|---|---|---|---|---|---|---|
| Stevia rebaudiana | 76446107 | ABA42921 | pMUS31 | MM-18 | 1542 | 52 | 138 |
| Arabidopsis thaliana | 3342249 | AAC39505 | pMUS32 | MM-19 | 1530 | 53 | 139 |
| Gibberella fujikoroi | 4127832 | CAA76703 | pMUS33 | MM-20 | 1578 | 54 | 140 |
| Trametes versicolor | 14278967 | BAB59027 | pMUS34 | MM-21 | 1500 | 55 | 141 |

Nucleotide sequences encoding the KAH enzymes shown in Table 6 were modified for expression in yeast (see SEQ ID NOs: 60-64) and cloned into yeast entry vectors. The nucleotide sequences from the source organisms from which the polypeptides were originally identified are set forth in SEQ ID NOs: 65-69.

TABLE 6

KAH Clones

| Enzyme Source Organism | gi Number | Accession Number | Plasmid Name | Construct Name | Length (nts) | SEQ ID (DNA) | SEQ ID (protein) |
|---|---|---|---|---|---|---|---|
| Stevia rebaudiana | | —* | pMUS35 | MM-22 | 1578 | 60 | 142 |
| Stevie rebaudiana | 189418962 | ACD93722 | pMUS36 | MM-23 | 1431 | 61 | 143 |
| Arabidopsis thaliana | 15238644 | NP_197872 | pMUS37 | MM-24 | 1578 | 62 | 144 |
| Vitis vinifera | 225458454 | XP_002282091 | pMUS38 | MM-25 | 1590 | 63 | 145 |
| Medicago trunculata | 84514135 | ABC59076 | pMUS39 | MM-26 | 1440 | 64 | 146 |

*= Sequence is shown in U.S. Patent Publication No. 2008-0064063.

Nucleotide sequences encoding the CPR enzymes shown in Table 7 were modified for expression in yeast (see SEQ ID NOs: 70-72) and cloned into yeast entry vectors. The nucleotide sequences from the source organisms from which the polypeptides were originally identified are set forth in SEQ ID NOs:73-75.

TABLE 7

CPR Clones

| Enzyme Source Organism | gi Number | Accession Number | Plasmid Name | Construct Name | Length (nts) | SEQ ID (DNA) | SEQ ID (protein) |
|---|---|---|---|---|---|---|---|
| Stevia rebaudiana | 93211213 | ABB88839 | pMUS40 | MM-27 | 2133 | 70 | 147 |
| Arabidopsis thaliana | 15233853 | NP_194183 | pMUS41 | MM-28 | 2079 | 71 | 148 |
| Giberella fujikuroi | 32562989 | CAE09055 | pMUS42 | MM-29 | 2142 | 72 | 149 |

Example 2—Construction of Steviol Glycoside Pathway Genes

Integration vectors containing nucleotide sequences encoding the UGT85C2 and UGT74G1 enzymes listed in Table 8 were transformed into yeast. Transformants were obtained that contained UGT85C2, or UGT85C2 and UGT74G1, integrated into the genome.

TABLE 8

UGT Clones

| Source Organism | UGT No. | gi Number | Accession Number | Type | Plasmid Name | Length (nucleotides) | SEQ ID |
|---|---|---|---|---|---|---|---|
| Stevia rebaudiana | UGT85C2 | 37993660 | AY345978.1 | Integration vector | pMUS11 | 1446 | 4 |
| Stevia rebaudiana | UGT74G1 | 37993668 | AY345982 | Integration vector | pMUS12 | 1383 | 2 |
| Stevia rebaudiana | UGT76G1 | 37993652 | AY345974 | Integration vector | pMUS13 | 1377 | 8 |
| Ipomoea purpurea | IP3GGT | 62857205 | AB192315.1 | High copy vector | pMUS10 | 1380 | 77 |
| Bellis perennis | UGT94B1 R25S mutant | 56550538 (wild type) | AB190262.1 (wild type) | High copy vector | pEF1156 | 1317 (wild type) | 79 |
| Arabidopsis thaliana | UGT79B3 | 28951020 | BT005370.1 | High copy vector | pEF1153 | 1362 | 151 |

Nucleotide sequences encoding the IP3GGT and UGT94B1 R25S enzymes were modified for expression in yeast (see SEQ ID NOs: 77 and 79) and cloned into yeast entry vectors. Amino acid sequences for IP3GGT and UGT94B1 R25S are set forth in SEQ ID NOs: 76 and 78, respectively. The high copy episomal vector containing a modified IP3GGT nucleotide sequence was designated pEF1155. The high copy episomal vector containing a modified UGT94B1 R25S nucleotide sequence was designated pEF1156.

Example 3—Construction of Yeast Strains

A yeast strain designated EFSC301 was modified by replacing the endogenous ERG9 promoter with the copper inducible CUP1 promoter. Strain EFSC301 is a derivative of EUROSCARF collection yeast strain BY4742. See, the world wide web at uni-frankfurtde/fb15/mikro/euroscarf/data/by.html. In standard yeast growth medium, the ERG9 gene is transcribed at very low levels, since the concentration of copper in such medium is low. The decrease in ergosterol production in this strain results in increased amounts of isoprene units available for steviol biosynthesis. The yeast strain was also modified by genomically integrating the *Stevia* UGT85C2 and UGT74G1 genes, each under the transcriptional control of the strong constitutive GPD1 promoter. See Table 8. The strain has one copy of each of the *Stevia* UGT85C2 and UGT74G1 genes integrated in the MUS1241 strain genome.

Example 4—Analysis of Steviol Glycoside Pathway Gene Expression in Yeast

Figure 5:
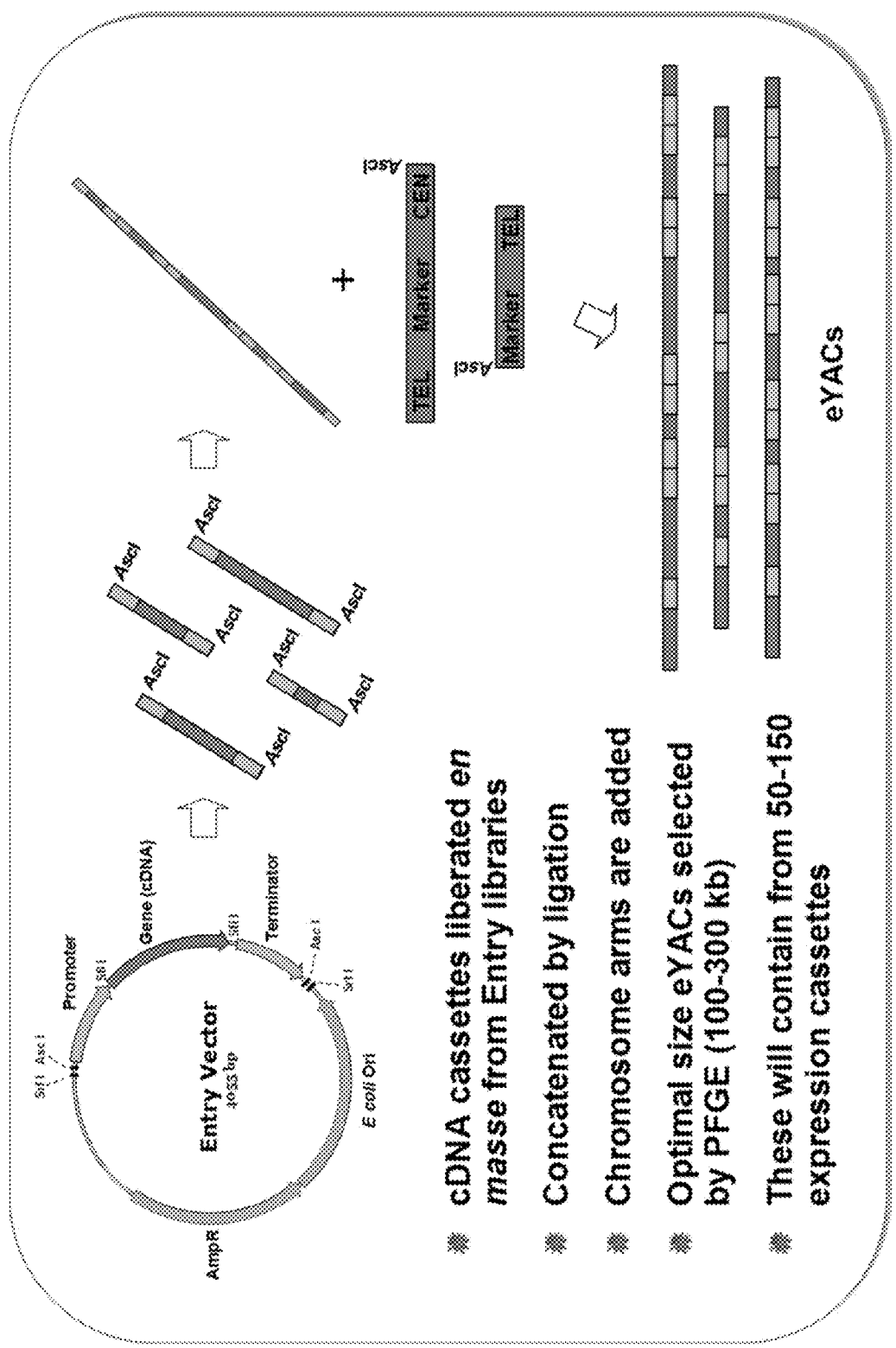
FIG. 5 is a schematic representation of the concatenation of genes to form eYACs.

To examine steviol glycoside biosynthesis in yeast, the expression cassettes of the 36 entry vectors of Tables 1-7 and Example 1 were randomly concatenated in ligation reactions to create artificial yeast chromosomes ("eYACs"). The process is shown schematically in FIG. 5.

Two different sets of ligations were carried out. Ligation set A included all genes listed in Tables 1-7, except that no bi-functional CDPS-KS genes (Table 4) were included. Ligation set B included all genes listed in Tables 1-7 except that no mono-functional CDPS and KS genes (Tables 2-3) were included.

From 30 to 200 μg of DNA was prepared from each of the cassette-containing entry vectors. The gene expression cassettes were released from each vector by digestion with the restriction enzyme AscI. The cassettes were then randomly concatenated into eYACs by ligation with T4 ligase in a 3 hour reaction. The success of the concatenation reaction was assessed by the viscosity of the reaction mixture, since concatenated DNA is highly viscous. DNA fragments ("arms") containing a centromere, two telomeres and the LEU2 and TRP1 selection markers were added to the end of the concatenated expression cassettes, thereby creating functional eYACs.

The eYACs were transformed into spheroplasts of the competent yeast strain MUS1243 by zymolyase digestion of the yeast cell wall, followed by treatment with a $CaCl_2$/PEG buffer, making the spheroplasts permeable to large molecules such as eYACs.

After transformation, the yeast spheroplasts were embedded in a noble agar based solid growth medium, in which regeneration of the cell wall can take place. Colonies appeared from 4-8 days after inoculation. The regeneration medium lacked the amino acids leucine and tryptophan, thus selecting for the presence of double-armed eYACs in the yeast cells.

About 3,000 transformants were obtained for each set. Each transformant was re-streaked and tested for yeast strain markers and the genetic presence of both arms of the eYAC, i.e., the LEU2 and TRP1 markers. More than 97% of the transformants had the comet genotype. Each transformant was given a CEY designation number.

Initially, 24 CEYs from each set were grown for 24 hours in 2 ml of Synthetic Complete medium (SC), without methionine, so as to induce gene expression from the eYACs. After 24 hours, the supernatant from each culture was collected and subjected to LC-MS (Liquid Chromatography-coupled Mass Spectrometry (Triple Quadropole)) analysis for the presence of rubusoside. Since the *Stevia* UGT74G1 and UGT85C2 genes are co-expressed in each CEY transformant, the expected end product when steviol is produced is rubusoside (steviol-(13-β-D-glucopyranosyloxy)-β-D-glueopyranosyl ester).

None of the CEYs from set B produced detectable levels of rubusoside, whereas 7 of the CEYs from set A did. Strain CEY19 was the top producer. CEY19 produced a compound with a mass of 665.2, which could correspond to a sodium adduct of rubusoside. A compound with a mass of 643.2 also was seen, and probably corresponds to protonated rubusoside. MS-MS-based molecular fractionation of the 665.2 mass compound resulted in a break down mass of 503.2, which corresponds to steviol monoside as a sodium adduct. Since the mass, the fractionation pattern, the HPLC spectrum, and the retention standard of this compound corresponded exactly to that of a rubusoside standard produced in vitro by the glucosylation of steviol using *Stevia* enzymes 85C2 and 74G1, the compound produced by CEY was determined to be rubusoside.

Additional Screening for Rubusoside Production

An additional 95 clones from set A and 95 clones from set B were grown in 96 deep-well trays in 1 ml SC medium without methionine. Supernatants from each of these cultures were combined in pools of two clones, analyzed by LC-MS, and the MS signal/noise ratio determined. The MS s/n ratio is an approximate measure of the relative rubusoside content. When a pool of 2 CEYs was found to produce rubusoside, each clone in that pool was analyzed separately. The results showed that no set B CEYs produced rubusoside, while at least 28 CEYs from set A produced detectable levels of rubusoside.

Identification of Genes Present in Rubusoside Producing CEY Clones

To correlate the gene content of eYACs to rubusoside production, a PCR protocol was developed in which similar sized fragments (0.5 kb) of all the possible eYAC-borne genes could be amplified. Internal primers of 20-25 nt were placed so that a similar annealing temperature could be used to amplify all genes. Genomic DNA, which includes eYAC DNA, was prepared from 4 CEYs with no rubusoside production, 4 with low rubusoside production and 6 with high to very high rubusoside production. Using equimolar amounts of these 14 DNA preparations, analytical PCR was performed for all 37 genes for these 14 CEYs, as well as positive and negative controls. All genes were amplified except one, apparently due to primer failure.

The genes present in the six high rubusoside-producing CEY strains are shown in Table 9. The genes present in the eight low or no rubusoside-producing CEY strains are shown in Table 10.

TABLE 9

Genes Present in High Rubusoside-Producing CEY Strains

| | HIGH production | | | VERY high production | | |
|---|---|---|---|---|---|---|
| Gene | CEY50 | CEY176 | CEY19 | CEY173 | CEY191 | CEY213 |
| tHMG1 | + | + | + | + | − | + |
| MM-1 | − | + | + | + | + | − |
| MM-2 | − | + | + | + | + | − |
| MM-3 | + | + | + | + | + | + |
| MM-4 | + | + | + | − | + | + |
| MM-5 | + | + | + | + | + | + |
| MM-6 | + | + | + | + | + | + |
| MM-7 | − | + | − | + | + | − |
| MM-8 | + | + | + | + | − | + |
| EV270 | + | + | − | + | + | + |
| C301 | + | + | + | + | + | + |
| C413 | + | + | − | + | + | + |
| MM-9 | + | + | + | + | + | + |
| MM-10 | + | − | − | + | + | + |
| MM-11 | + | + | − | + | + | + |
| EV64 | + | + | + | + | + | + |
| EV65 | − | − | + | + | + | + |
| EV66 | + | + | + | + | + | + |
| MM-12 | + | − | − | + | + | + |
| MM-13 | + | + | + | + | + | + |
| MM-14 | + | + | + | + | + | + |
| MM-15 | − | − | − | − | + | − |
| EV70 | − | + | + | + | − | − |
| EV71 | | | Primers failed | | | |
| EV72 | + | + | + | + | + | + |
| MM-18 | + | + | + | + | + | − |
| MM-19 | + | − | + | − | + | + |
| MM-20 | + | + | + | + | + | + |
| MM-21 | − | − | + | + | − | + |
| MM-22 | + | + | + | + | + | + |
| MM-23 | + | − | + | + | − | + |
| MM-24 | + | + | + | + | + | + |
| MM-25 | + | + | + | + | + | + |
| MM-26 | + | + | + | + | + | + |
| MM-27 | + | + | + | + | + | + |
| MM-28 | − | − | − | − | − | − |
| MM-29 | + | + | + | + | + | + |

TABLE 10

Genes Present in CEY Strains Producing Low or No Rubusoside

| | NO rubusoside production | | | | LOW production | | | |
|---|---|---|---|---|---|---|---|---|
| Gene | CEY162 | CEY169 | CEY171 | CEY188 | CEY75 | CEY147 | CEY214 | CEY87 |
| tHMG1 | − | − | − | − | − | − | + | + |
| MM-1 | + | + | + | + | − | + | − | − |
| MM-2 | + | − | + | + | + | + | + | + |
| MM-3 | + | + | + | + | + | + | + | + |
| MM-4 | − | − | + | − | − | + | − | + |
| MM-5 | + | + | + | + | + | + | + | + |
| MM-6 | + | + | + | − | + | + | + | + |
| MM-7 | + | − | + | + | + | + | + | + |
| MM-8 | + | + | + | + | + | + | + | + |
| EV270 | + | + | + | + | + | + | + | + |
| C301 | + | + | + | + | + | + | + | + |
| C413 | + | + | + | + | + | + | + | + |
| MM-9 | + | + | + | + | − | + | + | + |
| MM-10 | + | + | + | + | − | + | + | + |
| MM-11 | + | + | + | + | + | + | + | − |
| EV64 | + | + | + | + | − | + | + | + |
| EV65 | + | − | − | − | + | − | + | − |
| EV66 | + | + | + | + | + | + | + | + |
| MM-12 | + | + | + | + | + | + | + | + |
| MM-13 | + | + | + | + | + | + | + | + |
| MM-14 | + | + | + | + | + | + | + | + |
| MM-15 | + | − | + | − | + | + | − | + |
| EV70 | + | + | + | + | + | + | + | + |

TABLE 10-continued

Genes Present in CEY Strains Producing Low or No Rubusoside

| | NO rubusoside production | | | | LOW production | | | |
|---|---|---|---|---|---|---|---|---|
| Gene | CEY162 | CEY169 | CEY171 | CEY188 | CEY75 | CEY147 | CEY214 | CEY87 |
| EV71 | | | | Primers failed | | | | |
| EV72 | + | + | + | + | + | + | + | + |
| MM-18 | + | + | + | + | + | + | + | + |
| MM-19 | + | + | + | + | + | + | + | + |
| MM-20 | + | + | + | + | + | + | + | + |
| MM-21 | − | + | − | − | − | + | − | + |
| MM-22 | + | + | + | + | + | − | + | + |
| MM-23 | + | − | + | − | + | + | − | + |
| MM-24 | + | − | + | + | + | + | + | + |
| MM-25 | + | − | + | + | + | + | + | + |
| MM-26 | + | + | + | + | + | − | + | + |
| MM-27 | + | + | + | + | + | + | + | + |
| MM-28 | − | − | + | − | − | − | − | + |
| MM-29 | + | + | + | + | − | + | + | + |

Example 5—Modification of Yeast Culture Conditions

Experiments were carried out with strain CEY213 in order to determine culture conditions conducive to maximum rubusoside production. The starting material was a glycerol freezer stock (−80° C.) of CEY213. Frozen cells originally came from an agar plate containing SC yeast medium without tryptophan, leucine and histidine (SC-TLH), and containing 2 mM methionine. Five ml of liquid SC-TLH medium containing 2 mM methionine was inoculated with a loop-full of freeze stock CEY213 yeast cells. eYAC expression in CEY213 is repressed under these conditions. The cells were grown overnight at 30° C. with slow shaking (170 rpm) and were designated as "pre-cultures."

The CEY 213 pre-cultures were used to inoculate 25-50 ml of SC media without methionine, in which the parameters indicated below were varied. Rubusoside production under each of the growth conditions was measured by centrifuging 500 µl of each culture medium, transferring 250 µl of the supernatant to a new tube, adding 250 µl methanol, shaking thoroughly and centrifuging for 10 minutes at maximum speed. An aliquot of the supernatant was analyzed for rubusoside production by LC-MS.

Cooper Levels

CEY213 precultures were grown in SC medium to which 50 µM bathocuproinedisulfonic acid was added. Bathocuproinedisulfonic acid chelates copper in the growth medium. The ERG9 gene in CEY213 has been modified so that expression is controlled by the CUP1 promoter. A decrease in copper levels in the medium will further decrease ERG9 activity and thereby increase the amount of isoprene units available for steviol biosynthesis.

Chelation of copper ions in the growth medium had a detrimental effect on growth of the yeast culture and rubusoside production was decreased proportionally. These results suggested that even without copper chelation, strain CEY213 is at its minimum rate of ergosterol biosynthesis, and no more isoprene units can be diverted from ergosterol biosynthesis towards steviol glycoside production.

Glucose

Doubling the available glucose from 2 to 4% had a marginal effect on rubusoside production, about a 5-10% increase in rubusoside production.

Limiting Available Nitrogen

CEY213 pre-cultures were grown under conditions of limited available nitrogen. Limiting nitrogen during growth of yeast in culture is known to increase production of ergosterol. When the concentration of $NH_4SO_4$ was decreased from 4 g/l to 2, 1 or 0.4 g/l, the growth rate of CEY213 decreased in proportion to the amount of nitrogen. Rubusoside production decreased proportionally with the decrease in growth.

Aeration of Cultures

CEY213 was grown in Ehrlenmeyer flasks with or without baffles. The results indicated that there was at best a marginal effect of increased aeration via the use of baffles. If anything, the lack of aeration via the lack of baffles increased production.

Optical Density at Initiation, Fermentation Time and Growth Temperature

Cultures were initiated at two different optical densities, $OD_{600}=0.1$ or $OD_{600}=1.0$ of pre-cultured CEY213. Fermentation was then carried out for 24, 48, 72 or 144 hours at a temperature of 20, 25 or 30° C.

Figure 6:
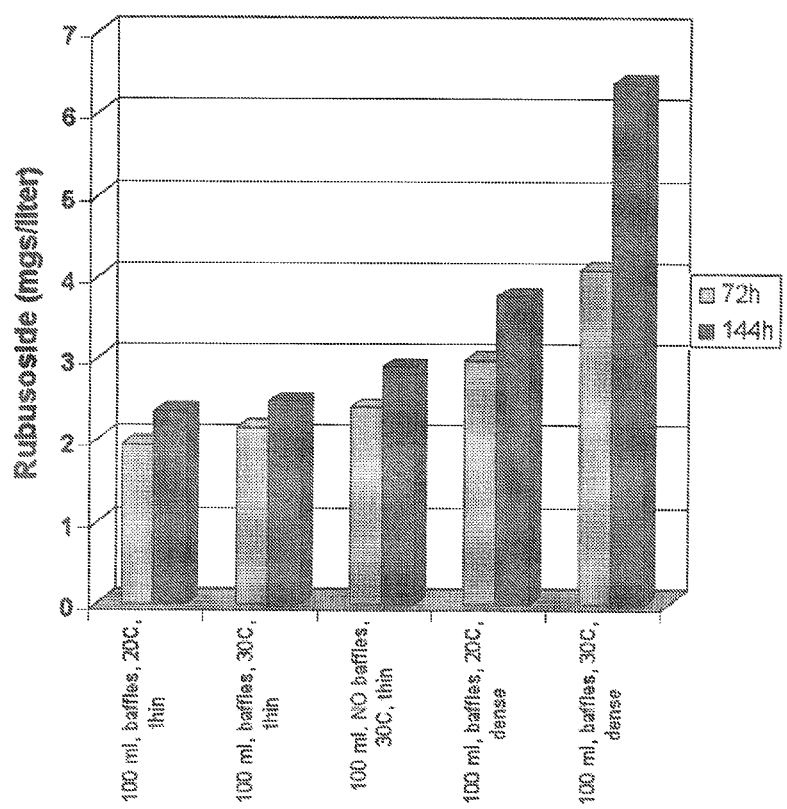
FIG. 6 shows rubusoside production by yeast strain CEY13 under various culture conditions.

As shown in FIG. 6, the density of the batch culture at fermentation start, the culture temperature and the length of time in fermentation, in combination, had a significant effect on the amount of rubusoside produced by CEY213. Thus, 144 hours growth of a culture with a starting density of $OD_{600}=1.0$, at 30° C., resulted in the production of no less than 8.5 mgs/liter of rubusoside.

Example 6—Large Scale Production of Rubusoside

A series of fermentation experiments with CEY213 were performed using 3 kinds of yeast medium (rich medium and two types of synthetic medium), varying inoculation density, and changing timing of eYAC gene cassette expression.

Batch Fermentation Conditions

Batch fermentation was carried out by centrifuging a CEY213 pre-culture, discarding the supernatant and re-suspending the cells in 6 liters of SC-TLH medium containing 100 µM methionine and 4% glucose. The $OD_{600}$ was adjusted to 1.0 in a 100 ml Ehrlenmeyer flask without baffles and the cells were allowed to grow for 144 hours at 30° C. with slow shaking.

Recovery of Rubusoside

After fermentation, the culture was centrifuged and the supernatant was mixed with an equal volume of methanol, shaken thoroughly, and centrifuged to remove precipitated material. The resulting supernatant was purified by flash C18-silica column chromatography with methanol as the eluent, followed by preparative HPLC to obtain one major compound, with one additional minor compound detected.

Figure 7:
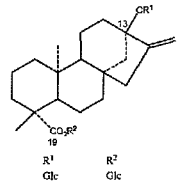
FIG. 7 shows data obtained from $^1$H and $^{13}$C NMR analysis of the compound produced by yeast strain CEY213, compared to literature values for rubusoside.

The purified compound was analyzed by $^1$H and $^{13}$C NMR, and the data are shown in FIG. 7. The compound was confirmed to be rubusoside based on comparison to $^1$H and $^{13}$C NMR literature values for rubusoside. Quantitative analysis indicated that CEY213 fermentation produced 12.8 mgs/liter of rubusoside.

Example 7—IP3GGT Activity

1. Enzymatic Activity of *Ipomoea purpurea* 3GGT glycosyltransferase in Vitro

The enzymatic activity of *Ipomoea purpurea* 3GGT glycosyltransferase (IP3GGT) using steviol as a substrate was determined in vitro. Genes for *Stevia rebaudiana* UGT85C2 and IP3GGT glycosyltransferase were each expressed in *E. coli* and each enzyme was purified.

The enzymatic reaction was performed in two steps. First, 0.5 mM steviol (9.55 mgs total) was incubated with ca. 0.5 ng UGT85C2 enzyme for 16 hours at 30° C. in a reaction buffer (containing 1 mM UDP-glucose, 100 mM Tris-HCl (pH 8.0), 5 mM MgCl$_2$, 1 mM KCl, 0.1 U/ul calf intestine phosphatase). Then ca. 0.5 µg IP3GGT enzyme was added and the reaction mixture incubated for an additional 20 hours at 30° C.

Analysis of the reaction products indicated about 100% conversion of steviol to steviol-13-O-monoside, 25% of which was further glycosylated into stevio-13-O-1,2-bioside. The theoretical steviol-13-O-1,2-bioside yield was about 4.8 mg. The reaction mixture was then subjected to preparative HPLC, which yielded 2.5 mg steviol-13-O-1,2-bioside (52% purification yield). Using LC-MS, the mass of the purified compound had a different retention time than rubusoside and steviol-13-O-1,3-bioside. The purified compound was subjected to $^1$H NMR, heteronuclear single quantum coherence (HSQC)-NMR and heteronuclear multiple bond correlation (HMBC)-NMR analysis, which confirmed that the compound was steviol-13-O-1,2-bioside.

2. In Vivo Expression of IP3GGT in Steviol- or Steviol Monoside-Fed Yeast

To determine whether the IP3GGT was active in yeast, the 2µ high copy (episomal) plasmid, pMUS10, containing an unmodified IP3GGT coding sequence operably linked to a strong GPD1 promoter was transformed into the yeast strain MUS1245. MUS1245 contains a genomically integrated UGT85C2 expression cassette. The resulting yeast strain was grown in SC medium without histidine to select for the continued presence of the IP3GGT expression plasmid, at a starting density of OD$_{600}$=0.2. Steviol or steviol monoside was added to the medium at 3 mM. After growth for 72 hours at 30° C., culture supernatants were assayed for the presence of steviol and steviol glucosides by HPLC.

LC-MS analysis indicated that no 1,2-glucosylated steviol-13-O-glucoside was detected after feeding with steviol, although steviol-13-O-monoside could be detected. In contrast, low but detectable amounts of the steviol 1,2-bioside were produced by MUS1245 carrying pMUS10 after feeding with steviol-13-O-monoside. These results show that the native *Ipomoea purpurea* 3GGT coding sequence is expressed in yeast at levels sufficient to obtain detectable in vivo conversion of steviol monoside to steviol 1,2-bioside.

Example 8—Modification of Yeast Strains

EXG1 and EXG2

*S. cerevisiae* may contain enzymes that degrade the 1,2 or 1,3 sugar bonds in steviol 1,2- and steviol 1,3-biosides. To test this possibility, yeast strain CEY213 was grown for 3 days at 30° C. on media containing 0.1 mM of each of the two biosides. LC-MS analysis of the culture showed the level of 1,2-bioside to be stable, whereas the 1,3-bond in the 1,3-bioside appeared to completely hydrolyse within the limits of detection of the assay.

Twenty-five *S. cerevisiae* mutants, each disrupted in one known or putative glycoside hydrolase gene, were examined for their ability to degrade steviol biosides. A culture of each yeast mutant was grown as described above on media containing steviol 1,3-bioside and analyzed by LC-MS. The yeast strain carrying a mutation in the EXG1 (exo-1,3-β-glucanase) gene was found to have lost most of the 1,3-bioside hydrolysing activity. The nucleotide sequence of the yeast EXG1 gene is reported in Vazquez de Aldana et al. *Gene* 97:173-182 (1991). The yeast strain carrying a mutation in the EXG2 gene (another exo-1,3-β-glucanase) showed a small decrease in hydrolysing activity. Correa, et al., *Current Genetics* 22:283-288 (1992).

A double mutant yeast strain (exg1 exg2) was made. When the double mutant strain was grown on media containing steviol 1,3-bioside, no hydrolysis of the bioside was detected.

Example 9—Increased Titer of Steviol Biosynthesis

Individual clones of enzymes from each of the different enzyme classes tested in Example 4 (and Table 11) were examined using eYAC technology to identify particular clones that exhibited the greatest production of steviol from isopentenyl pyrophoshate and farnesyl pyrophosphate. The GGPPS, KO and KAH enzymes have been tested on eYACs, individually or in the case of GGPPS enzymes individually or in pools of two (e.g., *Synechococcus* sp.+*S. acidocaldarius* GGPPS or *Aspergillus nidulans* GGPPS alone), in a *S. cerevisiae* strain expressing all remaining enzymatic steps in the steviol pathway. The results indicated that the *Synechococcus* spp. GGPPS clone MM-7 (encoded by SEQ ID NO:24) was the most efficient. GGPPS clones from *Aspergillus nidulans* and *Sulfulobus acidocaldarius* also were quite active. The results also indicated that among the KO and KAH clones, the *Stevia* KO clone MM-18 (encoded by SEQ ID NO:52) and the *A. thaliana* KAH clone MM-24 (encoded by SEQ ID NO:62) resulted in the greatest steviol production.

TABLE 11

| Source Organism | Enzyme | gi Number | Accession Number | Coding Sequence | Coding Sequence Length (nucleotides) |
|---|---|---|---|---|---|
| *Stevia rebaudiana* | GGPPS-1 | 158104429 | AED92926 | MM-1 | 1086 |
| *Gibberella fujikoroi* | GGPPS-2 | 3549881 | CAA75568 | MM-2 | 1029 |
| *Mus musculus* | GGPPS-3 | | BC069913.1 | MM-3 | 903 |

TABLE 11-continued

| Source Organism | Enzyme | gi Number | Accession Number | Coding Sequence | Coding Sequence Length (nucleotides) |
|---|---|---|---|---|---|
| Thalassiosira pseudonana | GGPPS-4 | 223997332 | XP_002288339 | MM-4 | 1020 |
| Sulfulobus acidocaldarius | GGPPS-6 | 506371 | BAA43200 | MM-6 | 993 |
| Synechococcus sp. | GGPPS-7 | 86553638 | ABC98596 | MM-7 | 894 |
| Cantharanthus roseus | GGPPS-9 | 1063275 | X92893 | EV270 | 1074 |
| Aspergillus nidulans | GGPPS-10 | 29468175 | AF479566 | C301 | 1191 |
| Xanthophyllomyces dendrorhous | GGPPS11 | 63145970 | DQ016502 | C413 | 1131 |
| Stevia rebaudiana | CDPS-1 | 2642661 | AAB87091 | MM-9 | 2364 |
| Streptomyces clavuligerus | CDPS-2 | 197705855 | EDY51667 | MM-10 | 1584 |
| Bradyrhizobium japonicum | CDPS-3 | 529968 | AAC28895.1 | MM-11 | 1551 |
| Arabidopsis thaliana | CDPS-4 | 18412041 | NM_116512 | EV-64 | 2409 |
| Zea mays | CDPS-5 | 50082774 | AY562490 | EV-65 | 2484 |
| Lycopersicon esculentum | CDPS-6 | 6009477 | A13015675 | EV-66 | 2403 |
| Stevia rebaudiana | KS-1 | 4959241 | AAD34295 | MM-12 | 2355 |
| Stevia rebaudiana | KS-2 | 4959239 | AAD34294 | MM-13 | 2355 |
| Zea mays | KS-3 | 162458963 | NP_001105097 | MM-14 | 1773 |
| Populus trichocarpa | KS-4 | 224098838 | XP_002311286 | MM-15 | 2232 |
| Arabidopsis thaliana | KS-5 | 3056724 | AF034774 | EV-70 | 2358 |
| Cucurbita maxima | KS-6 | 1431869 | U43904 | EV-71 | 2370 |
| Cucumis sativus | KS-7 | 21326756 | AB045310 | EV-72 | 2358 |
| Stevia rebaudiana | KO-1 | 76446107 | ABA42921 | MM-18 | 1542 |
| Arabidopsis thaliana | KO-2 | 3342249 | AAC39505 | MM-19 | 1530 |
| Gibberella fujikoroi | KO-3 | 74676162 | 094142 | MM-20 | 1578 |
| Trametes versicolor | KO-4 | 14278966 | AB057426 | MM-21 | 1500 |
| Stevia rebaudiana | KAH-1 | * | | MM-22 | 1578 |
| Stevia rebaudiana | KAH-2 | 189418962 | ACD93722 | MM-23 | 1431 |
| Arabidopsis thaliana | KAH-3 | 15238644 | NM_122399 | MM-24 | 1578 |
| Vitis vinifera | KAH4 | 225458453 | XM_002282055 | MM-25 | 1590 |
| Medicago truncatula | KAH5 | 84514134 | DQ335781 | MM-26 | 1440 |
| Stevia rebaudiana | CPR-1 | 189098311 | DQ269454.4 | MM-27 | 2133 |
| Arabidopis thaliana | CPR-2 | 145343899 | NM_118585 | MM-28 | 2079 |
| Gibberella fujikoroi | CPR-3 | 32562988 | AJ576025.1 | MM-29 | 2142 |

* U.S. Patent Publication No. 20080064063

S. cerevisiae strain CEY213, described in Example 4, was transformed with high copy plasmids carrying one of the CDPS or KS genes shown in Table 11, operably linked to the strong GPD1 promoter. Preliminary experiments indicated that overexpression of the Stevia rebaudiana CDPS (CDPS-1, encoded by SEQ ID NO:34) in CEY213 gave an increase in rubusoside production relative to CEY213 that lacked the high copy CDPS-1 overexpressing plasmid. The experiments also indicated that the Stevia rebaudiana KO (KO-1, encoded by SEQ ID NO:52) was the most active KO of the two tested.

To construct a yeast strain with consistently high levels of steviol glycoside production, expression cassettes containing the GGPPS-10 clone, the KO-1 clone (SEQ ID NO:52) and the KAH-3 clone (SEQ TD NO:62) were stably integrated into the genome of the S. cerevisiae strain CEN.PK 111-61A. Expression of these cassettes was driven by the constitutive GPD1 and TPI1 promoters. In addition, expression cassettes containing KS-1 (SEQ ID NO:40), CDPS-1 (SEQ ID NO:34) and UGT74G1 (SEQ ID NO:2) were stably integrated into the gnome. The resulting yeast strain, EFSC1751, however, did not produce any steviol-19-O-monoside when grown at laboratory scale under the conditions described in Example 6.

To determine the basis for the lack of steviol glycoside production in EFSC1751, CDPS-3, CDPS-4, CDPS-5 and CPR-1 genes, alone or in combination, were expressed in strain EFSC1751. CPR-1 is from Stevia rebaudiana and its sequence can be found at Genbank Accession DQ269454.4. The results showed that CPR-1, when expressed with either CDPS-3, CDPS-4 or CDPS-5, resulted in production of steviol-19-O-monoside in EFSC1751. None of these genes alone in the same strain resulted in any production. These results indicate that the genomically integrated copy of CDPS-1, Stevia enzyme, is non-functional in this yeast construct, whereas the Bradyrhizobium, Arabidopsis or Zea CDPS clones were functional in this construct. In addition, the plant-derived KAH and/or KO genes integrated into the chromosome for this construct appear to require an exogenous CPR for activity. The CPR from Giberella fujikuroi (MM-29) also appears to be able to work with plant-derived KAH and/or KO polypeptides.

The two leading GGPPS candidates, GGPPS-6 (encoded by SEQ ID NO:23) and GGPPS-7 (encoded by SEQ ID NO:24), were further expressed individually in a *S. cerevisiae* strain that has a functional steviol glycoside pathway (including UGT74G1) but no GGPPS genes. Transformants then were analyzed for the production of 19-SMG by LC-MS analysis of culture samples that had been boiled in 50% DMSO for 5 minutes and centrifuged at 16000 relative centrifugal force (RCF) for 5 minutes. It was found that many transformants containing the GGPPS-6-expressing plasmid did not produce 19-SMG.

Very few transformants were obtained containing GGPPS-7, indicating that GGPPS-7 (*Synechococcus* sp.) may be the more active of the two enzymes, and that the activity could be high enough to confer toxicity. For example, a dramatic increase in GGPP production could result in a drain on a downstream pathway such as ergosterol production. To test this hypothesis, a UPC2-1 gene was co-expressed with GGPPS-7, and ergosterol feeding of the cells was attempted to see if this would rescue growth of cells. However, cell growth was not rescued.

Cell toxicity also may be due to an accumulation of GGPP or a metabolite of GGPP. To test this hypothesis, CDPS-5 was further overexpressed in the GGPPS-7-expressing yeast strain to see if the toxicity could be alleviated by increased GGPP usage. CDPS5 over-expression did appear to rescue growth to some extent since transformants with a plasmid overexpressing this enzyme along with the GGPPS-7 gave rise to a few colonies. The number of transformants was still low. Over-expression of CDPS-5 in a similar strain but with GGPPS-10 instead of GGPPS-7 resulted in a doubling of steviol glycoside production, and these results together could suggest that CDPS is a limiting bottleneck in the introduced steviol glycoside biosynthesis pathway.

In summary, based upon production of 19-SMG or rubusoside in test tube cell cultures at 30° C. with yeast medium+ 2% glucose, for 24-72 hours, the following conclusions were made with the eYAC constructs: KS-1 (*Stevia rebaudiana*, encoded by SEQ ID NO:40), KO-1 (*S. rebaudiana*, encoded by SEQ ID NO:52) and KAH-1 (*S. rebaudiana*) or KAH-3 (*Arabidopsis thaliana*, encoded by SEQ ID NO:62) appear to be the best combinations for the steviol pathway. GGPPS-7 (*Synechococcus* sp.) appears to show the highest amount of activity for this step, but if downstream bottlenecks occur overexpression also could lead to toxicity and overall lower levels of steviol glycosides. All combinations of CDPS and CPR gene analogs were tested and it was found that all 3 CPRs in Table 11 were active, and that combinations of CPR-1 (*S. rebaudiana*, encoded by SEQ ID NO:70) or CPR-3 (*Gibberella fujikuroi*, encoded by SEQ ID NO:72) with either CDPS-5 (*Zea mays*) or CDPS-4 (*A. thaliana*) were particularly useful. CDPS-5 appears to be the optimal CDPS in the pathway. Combinations can be further tested in a reporter strain with reduced flux to sterol pathways.

To investigate the potential for even higher activity of the CDPS from *Zea mays* (CDPS-5), this gene was expressed from a 2 micron multicopy plasmid using the GPD promoter, with and without a plastid signal peptide, to determine if activity is higher in the cytoplasm when targeting sequences are removed. The nucleotide sequence and amino acid sequence of the CDPS-5 from *Zea mays* and containing the chloroplast signal peptide are set forth in SEQ ID NOs:80 and 81, respectively. The chloroplast signal peptide is encoded by nucleotides 1-150 of SEQ ID NO:80, and corresponds to amino acids 1 to 50 of SEQ ID NO:81. The plasmid was transformed into the stable rubusoside producer strain (EFSC1859) that has GGPPS-10, CDPS-5, KS-1, KO-1, KAH-3, CPR-1 and UGT74G1 (SEQ ID NO:2) integrated into the genome and expressed from the strong constitutive GPD and TPI promoters. Furthermore, in strain EFSC1859, expression of squalene synthase, which is encoded by ERGS, was downregulated by displacement of the endogenous promoter with the CUP1 inducible promoter. In addition to these genes, strain EFSC1859 also expresses UGT85C2 (SEQ ID NO:3) from a 2 micron multicopy vector using a GPD1 promoter. Rubusoside and 19-SMG production were measured by LC-MS to estimate the production level. The removal of the plastid leader sequence did not appear to increase steviol glycoside production as compared to the wild-type sequence. However, this work demonstrates that the leader sequences can be removed without causing a loss of steviol pathway function.

Similarly, plasmids were constructed for CPR-3, KAH-3 and KO-1 without membrane anchoring sequences (i.e., nucleotides 4-63 of SEQ ID NO:72; nucleotides 4-87 of SEQ ID NO:62; and nucleotides 1-117 of SEQ ID NO:52) and were transformed into strain EFSC1859 with the UGT85C2 integrated on the chromosome rather than on a plasmid. It is expected that these enzymes will be functional without the anchoring sequence.

Example 10—Identification of Steviol-1,3-O-Monoducoside 1,2-Glucosyltransferase Sequences

*Stevia* EST Analysis

A tBLASTN search of a *Stevia* (*Stevia rebaudiana*) leaf EST (Expressed Sequence Tags) database (Brandle et al., *Plant Mol. Biol.* 50:613-622, 2002) was carried out using complete *Ipomoea* (*Ipomoea purpurea*) UGT79 type UGT (IP3GGT), *Bellis* (*Bellis perennis*) UGT94B1, *Stevia* UGT79A2, *Stevia* UGT76G1 and *Stevia* UGT91D1 amino acid sequences as queries, thus representing UGTs from all Family 1 glycosyltransferase sub-families known to primarily contain diglycosyltransferases. Partial sequences for 9 previously undescribed UGT genes were identified. One of the partial sequences was from the UGT 79 sub-family ("79-EV1"), one from the UGT 76 sub-family ("76-EV1") and two from the UGT 91 sub-family ("91-EV-1" and "91-EV2"), as well as members of the UGT 71, 72, 78, 84 and 88 sub-families. Seven of the partial sequences were isolated using *Stevia* cDNA or cDNA libraries as the PCR template for isolation. In addition, two *Stevia* members of the UGT 76 sub-family were isolated, GenBank accession ACT33422.1 which is a member of the 76G1 sub-family (Mohankumar), and GenBank accession ACM47734.1 which is a member of the 76G2 (Yang) sub-family.

Pyrosequencing

Additional UGT clones were identified and isolated by performing pyrosequencing with *Stevia* cDNA as follows. *Stevia* mRNA was prepared from *Stevia* leaves, using the Ambion® Micro Poly Purist™ mRNA preparation kit. As a quality control, reverse transcribed mRNA was tested for the presence of the *Stevia* Rebaudioside A pathway UGT genes 85C2, 74G1 and 76G1, by employing analytical PCR with oligonucleotide primers identical to 21 nucleotides at the 5'- and 3'-termini of each sequence. The amplified full length mRNA was then used for pyrosequencing and contig assembly (MOgene, St. Louis, Mo. USA). About 3.4 million reads of an average length of 393 nucleotides were performed, and the resulting raw sequences used to obtain 25907 sequence contigs. A database was constructed, containing publicly available amino acid sequences of a total of ca. 1,500 UGTs. About 150 of the sequenced UGTs were fully annotated UGTs from a wide variety of sub-families. The remaining sequenced UGTs were partially annotated homologs of these. A BLASTX search was performed (CLC Genomics, Muehltal, Germany), using the 25907 Stevia EST contigs as query, to the fabricated UGT database (Genetic code=1, Low complexity=Yes, Expect value=10.0, Word size=3, No of processors=2, Matrix=BLOSUM62, Gap cost (open)=11, Gap cost (extension)=1). The results suggested that sequences for more than 90 previously unknown UGTs from Stevia were present in the pyrosequencing database.

No additional members of the UGT 79 sub-family or the UGT 94 sub-family were identified in the pyrosequencing database. However, the analysis showed new members of the UGT 76 and 91 sub-families. For a few of the genes, full length sequence data was immediately available from the pyrosequencing EST data. A previously constructed Stevia plasmid cDNA library was used to obtain full-length sequences for those members for which partial sequence data was obtained. An oligonucleotide primer identical to each specific, partial UGT sequence was combined with an oligonucleotide primer identical to the library plasmid vector sequence. These primers were employed in PCR to obtain the full length product, which was subsequently sequenced. Based on the full length sequence, a second PCR was performed using a proof-reading PCR polymerase enzyme for amplification of the full length UGT gene from a Stevia cDNA library as the template for the reaction. Using this strategy, five members of the UGT 76 sub-family, six members of the UGT 91 sub-family, as well as ten members of other UGT sub-families were isolated.

Each of the 7 UGTs identified from the Stevia EST database, the 2 publicly available Stevia UGT 76 sequences, and the 21 UGTs identified from pyrosequencing was cloned into the E. coli expression vectors pET30A+ or pETDuet (making use of the HIS-tag for purification purposes) and expressed in the autolysis-prone E. coli strains XjA and XjB. For a large number of these UGTs, expression of the UGT protein resulted in the formation of inclusion bodies. In order to overcome formation of those inclusion bodies, some of these UGTs were expressed in the low temperature expression strain "Arctic Express" (Agilent Technologies). For those which failed to express in this system, coupled in vitro transcription-translation of PCR products (TNT®T7 Quick for PCR DNA kit, Promega) was attempted, allowing successful expression of the remaining UGTs. Efficiency of the reaction was ensured by labeling with $^{35}$S-methionine, separation on SDS-PAGE and phosphorimaging detection of a protein band of the expected size for the UGT protein in question.

UGT polypeptides from each clone, expressed as described above, were tested for 1,2-glycosylation activity, using steviol-13-O-monoglucoside as substrate. In vitro transcribed/translated protein, corresponding to approximately one fifth of the total protein formed in a 25 μL reaction, was used in an in vitro reaction, using 0.5 mM steviol-13-O-monoglucoside (SMG) as substrate, in a reaction buffer (containing 1 mM UDP-glucose, 100 mM Tris-HCl (pH 8.0), 5 mM MgCl$_2$, 1 mM KCl, 0.1 U/μl calf intestine phosphatase). The reaction mixture was incubated at 30° C. for 20 hours. The reaction mixture was then analyzed by LC-MS analysis for the presence of Steviol-1,2-bioside. LC-MS analyses were performed using an Agilent 1100 Series HPLC system (Agilent Technologies) fitted with a Phenomenex® Synergy Hydro-RP column (250×3 mm, 3 nm particles, 80 Å pore size) and hyphenated to a TSQ Quantum (ThermoFisher Scientific) triple quadropole mass spectrometer with electrospray ionization. Elution was carried out using a mobile phase (30° C.) containing MeCN (0.01%, Formic acid) and H$_2$O (0.01% Formic acid) by applying a gradient composed of 0.6→0.4 ml/min, 5% MeCN for 4 min; 0.4 ml/min, 5→40% MeCN for 2 min; 0.4 ml/min, 40→55% MeCN for 11 min; 0.4→1.0 ml/min, 55→100% MeCN for 3 mM. Steviol biosides were detected using SIM (Single Ion Monitoring) on Mw 665.2 [M+Na$^+$]. None of the 30 UGT enzymes tested exhibited detectable steviol-13-O-monoglucoside glycosylation activity.

The nucleotide sequences of the six UGT91 members identified by pyrosequencing were compared to the sequence of Stevia UGT91D1 in Genbank Accession No. AY345980. It appeared that the GenBank sequence encoded 12 additional amino acids at the N-terminus, relative to the six sequences identified by pyrosequencing. To re-test UGT91D1 family members for activity, UGT91D1 sequences were re-isolated by PCR amplification of Stevia leaf cDNA. The resulting PCR products were cloned into a plasmid vector and enzymatic activity for each product was measured as described above by: GST-tagged expression in E. coli, coupled in vitro transcription-translation, and/or in vivo expression in yeast. Steviol 1,2-glucosylation activity was detected from one clone by all three methods. This clone was designated UGT91D2c. The amino acid sequence of UGT91D2e is set forth in SEQ ID NO:5. In contrast, no 1,2-glucosylation activity was detected from a clone having the same sequence as described by Accession No. AY345980 (Protein Accession number AAR06918), but lacking the 12 amino acids of the amino terminus.

Example 11—Analysis of UGT91D2e Sequences

Sequence Variants of UGT91D2e

As evidenced in FIG. 8, a small number of amino acid modifications exist between the active (91D2e) variants and the closest inactive homologs (91D1). The 91D1 genes cloned by Ma et al., Shi Yan Sheng Wu Xue Baa. 2003 36(2):123-9 (Protein Accession number AAM53963, GI:21435782) and Brandle et al., supra (Protein Accession number AAR06918, GI:37993665) did not exhibit the 1,2-glycosylating activity required for RebA biosynthesis. To ascertain which amino acids are required for activity, 21 single site-directed mutants were created such that the amino acid in UGT91D2e (SEQ ID NO:5) was changed to the corresponding amino acid in an inactive homolog. See Table 12. In addition, a site-directed mutation was made such that position 364 (S→P) also was changed. The mutants were made using the QuikChange® II Site-Directed Mutagenesis kit according to manufacturer's protocols (Agilent Technologies, Santa Clara, Calif.), and the pGEX-4T1 vectors were transformed into a XJb Autolysis E. coli strain (ZymoResearch, Orange, Calif.). A mutant was not made to change residue 162 from a glycine to an aspartic acid.

In order to assess the activity of the mutant enzymes, a substrate-feeding experiment was performed in vitro using protein produced in E. coli. Initially, E. coli cells were grown overnight at 30° C., followed by induction with 3 mM arabinose and 0.1 mM IPTG, and further incubation at 20° C. For the in vitro assay, cells were induced overnight at 20° C., lysed by a freeze/thaw cycle, and the crude cell extract used for an enzymatic reaction in which the substrates were 0.5 mM steviol-13-O-glucoside and 0.5 mM rubusoside.

The results are shown in Table 12 for the steviol monoglucoside (SMG) and Rubusoside (Rub) substrates. A "+" indicates that diglycosylation activity was detected, a "−"

indicates activity was not detected, and "NA" indicates the assay was not performed. The noted mutations are based on the numbering of the 91D2e sequence (SEQ ID NO:5).

As some of the genes have a tendency to express in inclusion bodies in *E. coli*, the coding sequences that did not show activity in the *E. coli* experiments also were produced by coupled in vitro transcription-translation of PCR products (TNT®T7 Quick for PCR DNA kit, Promega) as above in Example 10. Briefly, 2 µL of DNA from the PCR amplification of the five single mutants and the wild type enzyme were incubated for 90 minutes at 30° C. with the kit master mix and 1 µL L-[$^{35}$S]-Methionine, in a total of 25 µL reaction. For each sample, a volume of 2 µL final reaction was run on a SDS-PAGE gel. All six proteins showed similar levels of soluble recombinant protein as judged by visual observation of the SDS-PAGE gel. The results for the in vitro-translated proteins are shown on the right side of Table 12. The percentages in this table indicate the approximate amount of conversion of substrate to product based on relative peak areas of substrate and product.

TABLE 12

| Mutation | E. coli protein SMG | E. coli protein Rub | in vitro protein SMG | in vitro protein Rub |
|---|---|---|---|---|
| Y30→F | + | + | NA | NA |
| P93→Q | + | + | NA | NA |
| S99→V | + | + | NA | NA |
| Y122→F | + | + | NA | NA |
| H→140Y | + | + | NA | NA |
| S142→C | + | + | NA | NA |
| T144→I | − | − | 5.9% | 0.05% |
| A148→T | + | + | NA | NA |
| M152→L | − | − | 25.1% | 0.85% |
| G153→A | + | + | NA | NA |
| A156→S | + | + | NA | NA |
| L195→M | + | + | NA | NA |
| V196→E | + | + | NA | NA |
| K199→E | + | + | NA | NA |
| L211→M | + | + | NA | NA |
| L213→F | − | − | 29.4% | 1.59% |
| S221→F | + | + | NA | NA |
| V286→A | + | + | NA | NA |
| S364→P | − | − | 4.1% | 0.4% |
| G384→C | − | − | 14.1% | 1.28% |
| K427→N | + | + | NA | NA |
| E438→A | + | + | NA | NA |

The approximate amount of diglycosylation activity as compared to UGT91D2e (SEQ ID NO:5) was found to be: 6.1% for T144S, 26.2% for M152L, 30.7% for L213F, 4.3% for S364P, and 14.7% for G384C using 13-SMG as substrate. For rubusoside, the approximate amount of diglycosylation activity as compared to UGT91D2e was 1.4%, 23.4%, 43.7%, 10.9% and 35.2% for T144S, M152L, L213F, S364P, and G384C, respectively.

These results indicate that 5 of the 22 amino acid mutations were noticeably deleterious for activity when done in isolation. It is also possible that combinations of the other 17 mutations also could result in inactivity or loss of activity.

By aligning the 91D2e sequences and the variants described above with proteins termed At72B1, Mt85H2, VvGT1 and Mt71G1 (Osmani et al (2009) *Phytochemistry* 70, 325-347), and analyzing predicted tertiary structures (alpha helices, beta-sheets, and coil regions), regions can be identified where mutations are likely to result in loss of diglycosylation activity. The first three mutations that are deleterious are found in the N-terminal domain, in regions that are thought to be loops. The N-terminal domain (amino acid residues 1-240), in particular the predicted loop regions of the N-terminal domain (amino acids 20-26, 39-43, 88-95, 121-124, 142-158, 185-198, and 203-214), are thought to be primarily responsible for binding of the glucose acceptor molecule substrate. The fourth mutation that appears to be deleterious for activity is found in the C-terminal domain, in a region that is believed to be the C5 loop (corresponding to amino acids 381-386). This loop is also thought to be important for glucose acceptor substrate specificity. Nineteen of the twenty-two mutations that separate the inactive versus the active rubusoside diglycosylase enzymes are located within five amino acids of the predicted acceptor substrate binding regions of 91D2e. Therefore it is likely that the published 91D1 enzymes catalyze a glycosyl transferase reaction between UDP-glucose and an alternative acceptor substrate.

Example 12—Production of Rebaudioside a in Yeast

Production of Rebaudioside a in Steviol-Fed Yeast

The yeast strain EFSC1580, which contains a genomically integrated UGT74G1 expression cassette, was transformed with three different 2µ high copy (episomal) plasmids for co-expression of *Stevia* UGTs 91D2e (SEQ ID NO:5), 85C2 (SEQ ID NO:3), and 76G1 (SEQ ID NO:7). The three plasmids, designated pMUS44, pMUS7 and pMUS9, contain coding sequences for UGT91D2e, UGT85C2 and UGT76G1, respectively, operably linked to the strong GPD1 promoter. The resulting yeast strain was grown in SC medium without uracil, histidine, and leucine to select for the continued presence of the pMUS44, pMUS7 and pMUS9 expression plasmids. Steviol was added to the medium to a final concentration of 250 µM, and the strain was cultured at 30° C. At 18 hours and 72 hours of culture, aliquots of the supernatants and cell pellets were analyzed for the presence of Rebaudioside A by LC-MS. LC-MS analyses were performed using an Agilent 1100 Series HPLC system (Agilent Technologies, Wilmington, Del., USA) fitted with a Phenomenex® Synergy Hydro-RP column (250×3 mm, 3 µm particles, 80 Å pore size) and hyphenated to a TSQ Quantum (ThermoFisher Scientific) triple quadropole mass spectrometer with electrospray ionization. Elution was carried out using a mobile phase (30° C.) containing MeCN (0.01% Formic acid) and H$_2$O (0.01% Formic acid) by applying a gradient composed of 0.6→0.4 ml/min, 5% MeCN for 4 min; 0.4 ml/min, 5→40% MeCN for 2 min; 0.4 ml/min, 40→55% MeCN for 11 min; 0.4→1.0 ml/min, 55→100% MeCN for 3 min. Steviol biosides were detected using SIM (Single Ion Monitoring).

LC-MS results showed that detectable amounts of Rebaudioside A were found in the supernatant at 18 and 72 hours of culture when strain EFSC1580 containing pMUS44, pMUS7 and pMUS9 was grown in the presence of steviol. The product co-eluted with a Rebaudioside A standard and the expected mass was confirmed as the [M+Na]$^+$=989. By comparing the absorbance of the product to the absorbance of a 10 µM Rebaudioside A standard, the accumulation in the supernatant of the cell culture was estimated to be more than 6 mg/L at 18 hours, and more than 15 mg/L at 72 hours.

Production of Rebaudioside a and Rebaudioside D in Glucose-Fed Yeast

Yeast strain CEY213, described in Example 4, contains steviol biosynthetic pathway genes expressed from eYACs as well as genomically integrated UGT74G1 and UGT85C2 expression cassettes. Strain CEY213 produces rubusoside, as described in Example 6.

Strain CEY213 was transformed with a 24 high copy (episomal) dual expression plasmid, pMUS47, for simultaneous expression of UGT91D2e (SEQ ID NO:5) and UGT76G1 (SEQ ID NO:7). The pMUS47 plasmid contains two expression cassettes, one having the coding sequence of UGT91D2e and the other having the coding sequence of UGT76G1. Both coding sequences are operably linked to the strong constitutive GPD1 promoter. The resulting yeast strain was pre-cultured overnight at 30° C. in SC medium without histidine, leucine and tryptophan in order to maintain selection for the presence of eYACs, without uracil in order to maintain selection for the presence pMUS47, and finally with methionine (2 mM) in order to suppress promoters present on the eYACs. The next day, the cells were washed and transferred to an identical medium, but without methionine, for induction of the eYAC promoters. Samples were collected after 24 hours and 99 hours of incubation, and supernatants and cell pellets analyzed for the presence of Rebaudioside A and Rebaudioside D, using LC-MS as described above.

Figure 9:
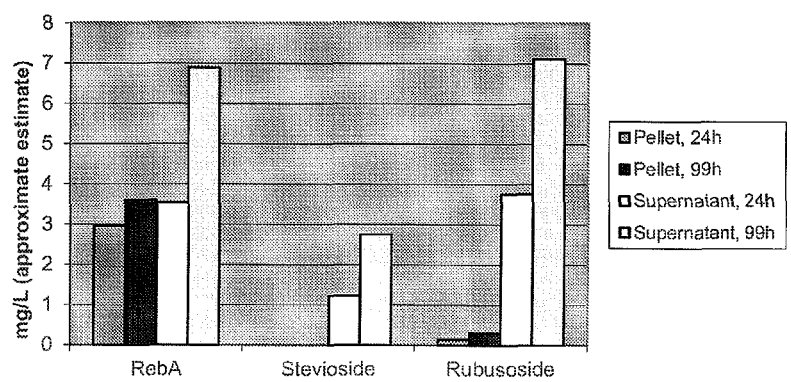
FIG. 9 shows Rebaudioside A, stevioside, and rubusoside production by yeast CEY213 containing plasmid pMUS47 after 24 and 99 hours of culture.

The results showed that detectable amounts of Rebaudioside A were found in the supernatants at both 24 and 99 hours. The product co-eluted with a Rebaudioside A standard and the expected mass was confirmed as the $[M+Na]^+$ =989. By comparing the absorbance of the product to a 10 µM Rebaudioside A standard, the accumulation of Rebaudioside A in the supernatant was estimated to be more than 3 mg/L at 24 hours and more than 6 mg/L at 99 hours. See FIG. 9. The results also indicated that small amounts of stevioside and rubusoside were present in the yeast cell pellet and that detectable amounts of stevioside and rubusoside were present in the culture supernatant. See FIG. 9.

The results also showed that small but detectable amounts of Rebaudioside D were produced, suggesting that UGT91D2e is capable of conjugating an additional glucose to the 19-O glucose of either stevioside producing Rebaudioside E or directly to the 19-O glucose of Rebaudioside A. These results also suggest that UGT76G1 may be capable of accepting Rebaudioside E as a substrate to produce Rebaudioside D. See FIG. 2C.

Example 13—Production of Rebaudioside A with Codon Optimized Sequences for UGT Sequences Optimal coding sequences for UGT 91d2e, 74G1, 76G1, and 85C2 were designed and synthesized for yeast expression using two methodologies, supplied by GeneArt (Regensburg, Germany) (SEQ ID NOs: 6, 2, 8, and 4, respectively) or DNA 2.0 (Menlo Park, Calif.) (SEQ ID NOs: 84, 83, 85, and 82, respectively). The amino acid sequences of UGT 91d2e, 74G1, 76G1, and 85C2 (SEQ ID NOs: 5, 1, 7, and 3, respectively) were not changed.

High copy number plasmids containing expression cassettes with all four optimized UGTs were constructed and expressed, and their activity compared to expression products of similar constructs containing wild-type sequences. The plasmids were transformed into the universal Watchmaker strain, EFSC301 (described in Example 3). UGTs were inserted in high copy (2µ) vectors and expressed from a strong constitutive promoter (GPD1) (vectors P423-GPD, P424-GPD, P425-GPD, and P426-GPD). After overnight growth and re-inoculation in fresh media at an $OD_{600}$ of 0.25, the culture medium (SC-leu-trp-ura-his) was supplemented with 25 µM steviol (final concentration), and production of Rubusoside (Rub), 19-SMG (19SMG) and RebA (RebA) was measured in the media after 24 h. The experiment was repeated, in part due to the fact that 19-SMG was undetectable in one of the first samples.

The results from the two separate studies, shown in Table 13 below, indicate that all eight of the codon-optimized UGTs were active. However, enzyme expression for at least one of the codon-optimized UGTs in each strategy was reduced by the new codon optimization algorithm used to make the constructs. It appears that in the GeneArt modified constructs (SEQ ID NOs: 6, 2, 8, and 4), a bottleneck was potentially created between rubusoside and RebA. It is expected that individual enzyme activity assays and expression analyses of these coding sequences expressed in the yeast strains will allow for the optimal combination of UGT genes in the pathway.

TABLE 13

|  | RebA (µM) | 19SMG (µM) | Rub (µM) |
| --- | --- | --- | --- |
| Wild-type | 3.2 | 17.2 | 4.9 |
|  | 1.7 | 14.0 | 3.2 |
| DNA2.0 | 4.4 | 12.4 | 4.6 |
|  | 1.7 | 10.8 | 3.1 |
| GeneArt | 1.2 | nd | 4.6 |
|  | 0.8 | 11.1 | 4.5 | nd = below detection limit

Example 14—Production of Rebaudioside A Using UGTs with Sequence Tags

Fusions of small peptides or protein binding domains with the UGT proteins 85C2, 91D2e, 74G1, and 76G1 can promote interactions between the UGTs (channeling) or aid in targeting/anchoring the UGTs to specific components of the yeast cells.

To assess if scaffolding of the UGTs in the RebA pathway could result in active pathway enzymes, the DNA 2.0 codon-optimized UGTs 85C2 and 74G1 were fused in-frame to a string of 4 high-affinity, short (also known as PMI) peptides that resemble the p53 protein motif. The p53 protein motif interacts with the MDM2 protein in humans (see Li et al. *J Mol Biol.* 2010, 398(2):200-13). DNA 2.0 codon-optimized UGTs 85C2, 91D2e, 74G1 and 76G1 (SEQ ID NOs: 82, 84, 83, and 85, respectively) were fused in-frame to the first 158 amino acids of the human protein MDM2 (gene accession number ABT17086). A small GS-rich linker region also was fused just prior to the N-terminal methionine of the UGTs. Unfused, the affinity of PMI/MDM2 binding is in the low nM range representing a high-affinity binding. Yeast cells transformed with the above constructs are expected to produce a UGT scaffold around the 4x PMI (P53-like) peptide repeat fused N-terminally to the 85C2 protein (designated 85C2_P53) scaffold.

Figure 10A:
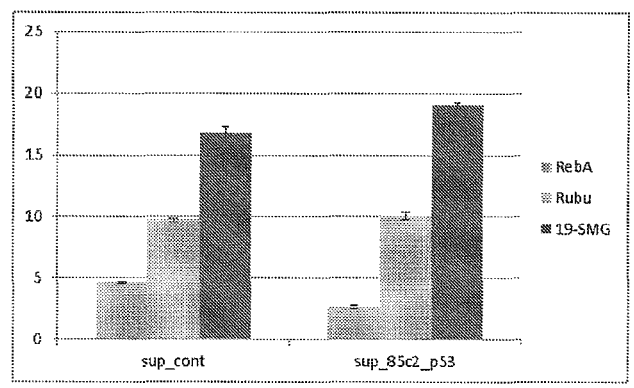
FIG. 10A is a graph illustrating the concentrations of RebA, rubusoside and 19-SMG in supernatants.
Figure 10B:
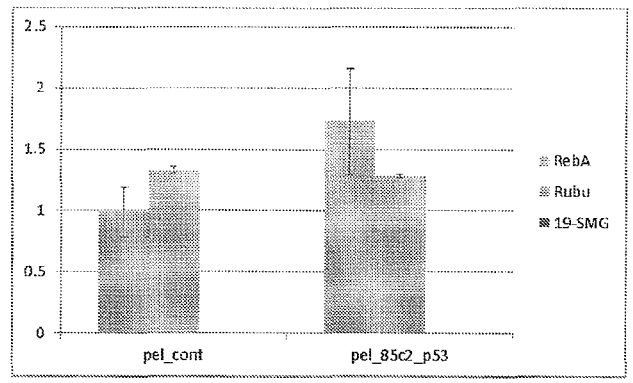
FIG. 10B is a graph of the concentrations of RebA, rubusoside and 19-SMG measured in cell pellets, for experiments where yeast cells were fed with 100 μM steviol. In both graphs, the first set of bars represents the untagged control strains; the second set of bars represents the strain containing the UGT74G1, UGT76G1, and UGT91D2e fusion proteins in which the N-terminal 158 amino acids of the MDM2 protein are fused to each UGT, and a UGT85C2 fusion protein in which four repeats of the synthetic PMI peptide is fused in-frame to the N-terminus of 85C2. The y-axis is concentration in micromolar units.

The laboratory yeast strain BY4741, deleted for TRP1, was transformed with expression plasmids p423-426 GPD (Mumberg et al, *Gene,* 156 (1995), 119-122) expressing *Stevia rebaudiana* UGTs 74G1,76G1 and 91D2e with N-terminal, in-frame fusions of the first 158 amino acids of human MDM2 protein, and expressing *Stevia rebaudiana* UGT85C2 with an N-terminal in-frame fusion of 4 repeats of the synthetic PMI peptide (4x TSFAEYWNLLSP, SEQ ID NO:86). See SEQ ID NOs: 88, 90, 92, and 94 for the amino acid sequences of the 85C2, 74G1, 91D2e, and 76G1 fusion proteins, respectively; see SEQ ID NOs: 89, 92, 93, and 95 for the nucleotide sequences encoding the fusion proteins. This yeast strain and a control strain (expressing the four UGT's without any fusions) were grown overnight in synthetic yeast medium selecting for the presence of plasmids and then transferred the next day to a 96 deep-well tray containing synthetic yeast medium to a cell density giving an $OD_{600}$ of 1. A final concentration of 100 µM steviol was added. After 72 hours, samples were taken and analysed by LC-MS, as described in Example 12. As indicated in FIGS. 10A and 10B, the UGTs are active in yeast when expressed with the various fusion tags.

Example 15—UGT91D2e Activity

Additional sub-family 91 UGTs were cloned using cDNA/library preparations made from 3 Stevia sources of different genetic backgrounds. Oligonucleotide primers identical to UGT91D1/91D2e were used for PCR amplification of the cDNA preparations, and the resulting PCR products of correct size were cloned into appropriate plasmid vectors. Numerous clones from each experiment were sequenced, and the sequencing results showed that UGT91D nucleic acids with slight variations in sequence could be amplified. The twenty UGT91D variants with the greatest differences in sequence relative to UGT91D2e were expressed by in vitro transcription-translation followed by enzymatic testing for steviol-13-O-monoglucoside-1,2-glucosylating activity. One of the variants showed weak 1,2-bioside glucosylation activity, while the reminder showed no detectable glucosylation activity. It therefore appears that UGT91D2 polypeptides are the primary steviol-13-O-monoglucoside-1,2-glucosylating enzymes in Stevia.

Enzymatic Activity of UGT91D2e

UGT91D2e (SEQ ID NO:5), made by coupled in vitro transcription-translation, was tested for the ability to xylosylate and rhamnosylate steviol-13-O-monoglucoside in an in vitro enzyme assay, using UDP-xylose or UDP-rhamnose as the sugar donors rather than UDP-glucose.

The xylosylation assay was performed as follows: 3 mM UDP-glucuronic acid was mixed with ca. 1 µg *Arabidopsis thaliana*-encoded UDP-glucuronic acid decarboxylase UXS3 (produced in *E. coli* and then purified), 100 mM Tris-HCl (pH 8.0), 1 mM DTT, 6 µg BSA, 1 mM $MgCl_2$, and 1% calf intestine phosphatase. The reaction mixture was incubated for 30 minutes at 30° C., in order for UDP-glucuronic acid to be turned into UDP-xylose. Then 1.5 mM steviol-13-O-monoglucoside substrate and ca. 0.5 µg UGT91D2e enzyme made as described in Example 9 was added to the mixture, which was allowed to incubate at 30° C. for an additional 20 hours.

The rhamnosylation assay was performed in the following way: 3 mM UDP-glucose was mixed with 0.6 µg of each of the N-terminal and C-terminal parts of *Arabidopsis thaliana*-encoded RHM2 rhamnose synthetase (produced in *E. coli* and then purified), 100 mM Tris-HCl (pH 8.0), 1 mM DTT, 1.5 mM NADPH, 1.5 mM NAD+, 6 µg BSA, 1 mM $MgCl_2$, and 1% calf intestine phosphatase. The reaction mixture was incubated for 30 minutes at 30° C., in order for UDP-glucose to be turned into UDP-rhamnose. Then 1.5 mM steviol-13-O-monoglucoside substrate and ca. 0.5 µg UGT91D2e enzyme was added to the mixture, which was allowed to incubate at 30° C. for an additional 20 hours.

The results indicated that UGT91D2e was capable of carrying out xylosylation of the steviol-13-O-monoglucoside substrate at about one half to one third the rate observed with UDP-glucose, forming 1,2-xylosylated steviol-13-O-monoside, which is a precursor to Rebaudioside F. UGT91D2e was capable of carrying out rhamnosylation of the steviol-13-O-monoglucoside substrate at about the same rate as the rate observed with UDP-glucose, forming 1,2-rhamnosylated steviol-13-O-monoside, which is a precursor for Rebaudioside C (Dulcoside B). These results indicate that synthesis of appropriate precursor molecules and expression of appropriate UGTs in vivo should result in the production of Rebaudioside F and C in vivo. See FIGS. 2B and 2D.

UGT91D2e also was tested for its ability to 1,2-glucosylate substrates other than steviol-13-O-monoglucoside in vitro, i.e., rubusoside, steviol-1,3-bioside and 1,3-stevioside. The results indicated that UGT 91D2e was not active when a 1,3-bound glucose was present (e.g., steviol 1,3-bioside and 1,3-stevioside), while UGT 91D2e was active regardless of primary glucosylation at the 19-O position. These results suggest that steviol 1,3-bioside and 1,3-stevioside are likely not present in the in vivo Stevia pathway for rebA formation. See FIG. 2A and FIG. 3.

Example 16—UGT91D Homologs

Different ecotypes of *S. rebaudiana* are genetically diverse. Investigation of 96 clones of 91Ds from different Stevia RNA accessions revealed many amino acid changes between six investigated ecotypes (e.g., at nucleotide 74 (resulting in an amino acid change of G to D), 89 (Y to F), 131 (V to A), 137 (F to S), 278 (P to Q), 295 (S to V or P), 331 (E to Q), 365 (Y to F), 395 (A to V), 418 (H to Y), 425 (S to G), 431 (T to I), 442 (A to T), 454 (M to L), 458 (G to A), 466 (A to S), 485 (G to D), 583 (L to M), 587 (V to E), 595 (K to E), 614 (D to G), 616 (G to R), 631 (L to M), 637 (L to F), 662 (S to F), 664 (K to E), 671 (Y to C), 857 (V to A), 867 (S to R), 919 (F to L), 989 (V to A), 1000 (R to C), 1090 (S to P), 1150 (G to C), 1232 (L to S), 1281 (K to N), 1313 (E to A), 1354 (Q to R), and 1369 (V to I)), as numbered with respect to the nucleotide sequence of 91D2e set forth in SEQ ID NO:9. Some additional variation from these polymorphisms was noted, which is likely due to sequencing or PCR errors, particularly if the polymorphisms were found only once. Twenty coding regions were chosen for further analysis. See Table 14 for descriptions of clones that were isolated. The numbering of the amino acids in Table 14 is based on the amino acid sequence of UGT91D2e set forth in SEQ ID NO:5.

TABLE 14

Clone Mutations as compared to UGT91D2e (SEQ ID NO: 5)

1   +1 frameshift between residues 119-145 in the nucleotide sequence, G165V, I367V, L388P
2   27 bp deletion starting at nucleotide 728, K214R
3   D205G, V286A, Y443C
4   L28P, Y30F, P93Q, S99V, E111Q, I118V, Y122F, H140Y, S142C, T144I, A148T, M152L, G153A, A156S, G162D, L195M, V196E, K199E, L211M, L213F, S221F, L411S, V425A
5   G206R, Y207C, W343R
6   Q13R, F46S, S99P, D395G
7   Y30F, S364G, G384C, K427N, E438A
8   Y94C, A132V, Y224C, G384C, K427N, E438A, Q455R
9   K222E, T341M, G384C
10  Y94C, A132V, Y224C, K313N, R334C, G384C
11  Y30F, K222E, V286A, G384C, K427N, E438A
12  Y30F, P93Q, S99V, Y122F, H140Y, S142C, T144I, T145N, A148T, M152L, G153A, A156S, G162D, L195M, V196E, K199E, L211M, L213F, S221F, V286A S289R, R334C, G384C, K427N, E438A
13  V44A, I136V, G374D, V457I, N463S
14  I60S, K97R, Q103R, F181S, L411S
15  V244A, F307L TABLE 14-continued Clone Mutations as compared to UGT91D2e (SEQ ID NO: 5)

| | |
|---|---|
| 16 | H140Y, S142C, T144I, A148T, M152L, G153A, A156S |
| 17 | L195M, V196E, K199E, L211M, L213F, S221F, V286A, R334C, G384C, K427N, E438A |
| 18 | V169A, R334C, G384C, K427N, E438A |
| 19 | G25D, Y30F, P93Q, S99V, Y122F, H140Y, S142C, T144I, A148T, M152L, G153A, A156S, G162D, L195M, V196E, K199E, L211M, L213F, S221F, V286A, G384C |
| 20 | I64T, V323A, V330A, G384C, K427N, E438A |

All of the clones in Table 14 were tested for activity using 13-SMG as a substrate. Clone 5 had weak 1,2-glycosylating activity whereas the remaining nineteen did not appear to have activity under the conditions tested. The sequence of clone 5 is set forth in SEQ ID NO:95 and has the following mutations with respect to wild-type UGT92D2e (SEQ ID NO:5): G206R, Y207C, and W343R.

Example 17—UGT85C Homologs

The genetic diversity of UGT85Cs from six different *S. rebaudiana* ecotypes was examined to identify homologs that have the same or enhanced activity in pathways for steviol glycoside production. PCR primers were designed that were specific for UGT85C genes, and PCR reactions were carried out on cDNA (some were done on cDNA libraries, some were done on cDNA preparations). The resulting PCR products were cloned and 96 clones were sequenced. Amino acid polymorphisms were mapped and 16 UGT 85C clones were chosen with varying common polymorphism representation. See Table 15. Additional modifications were also noted for some clones, but could be due to PCR errors or were not common polymorphisms. Polymorphisms are described with respect to the nucleotide and amino acid numbering of the wild-type *S. rebaudiana* UGT85C nucleotide sequence set forth in Accession No. AY345978.1 (see Table 8).

TABLE 15

| | Allele | | | | | | | | | | | | | | | | | |
|---|---|---|---|---|---|---|---|---|---|---|---|---|---|---|---|---|---|---|
| | 38 | 44 | 179 | 194 | 212 | 260 | 659 | 728 | 809 | 866 | 1001 | 1007 | 1116 | 1181 | 1190 | 1253 | 1319 | 1322 |
| | Amino Acid # | | | | | | | | | | | | | | | | | |
| Clone | 13 | 15 | 60 | 65 | 71 | 87 | 220 | 243 | 270 | 289 | 334 | 336 | 389 | 394 | 397 | 418 | 440 | 441 |
| 1 | V-F | F-L | H-D | | | | | | T-M | Q-H | | | | | | E-V | | |
| 2 | V-F | | | | | | | | T-M | | | | | | | | | |
| 3 | | | H-D | | | | | | | | | | | | | E-V | | |
| 4 | | | H-D | | I-F | | | | | | | | | | | | | |
| 6 | | | H-D | | | | | | | | | | | | P-S | | | |
| 7 | | | H-D | | | | | | | | | | | | | | | |
| 8 | | | H-D | | | | | | T-M | | | | | A-V | I-V | | | |
| 13 | | | | A-S | | | | | T-M | | | | | | | | | |
| 16 | | | | A-S | E-Q | | K-T | R-W | T-R | | | | | | | | | H-N |
| 17 | | | | A-S | E-Q | | K-T | R-W | T-R | | | | | A-V | I-V | | | |
| 19 | | | | A-S | E-Q | | K-T | | | | | | | | | | | |
| 20 | | | | A-S | E-Q | | | | T-M | Q-H | | | | | | | | |
| 21 | | F-L | | A-S | | | | | | | | | | | | | | |
| 22 | | | | A-S | | I-F | | | | | | | | | | | G-D | |
| 23 | | | | A-S | | | | | T-A | | | | | | | | | |
| 24 | | | | A-S | | | | | T-M | Q-H | | | | | | | | |
| 26 | | | | A-S | | | | | T-M | | | | | | | | | |
| 27 | | | | A-S | | | | | | | | | I-T | | | | | |
| 28 | | | | A-S | | | | | | | | | | | | | | |
| 29 | | | | | A-S | | | | | | | | | | | | G-D | |
| 30 | | | | | A-S | | | | | | | | | | | | | H-N |
| 31 | | | | | A-S | | | | | | | | | | | E-V | | |
| 32 | | | | | A-S | | | | | | | | | | P-S | | | |
| 33 | | | | | | | K-T | R-W | T-R | | | L-S | | | | | | |
| 36 | | | | | | | | | T-M | | | | | | | | | |
| 37 | | | | | | | | | T-M | Q-H | | | | | | | | |
| 38 | | | | | | | | | T-M | | | | I-T | | | | | |
| 39 | | | H-D | | | | | | T-M | | | | | | | | | |
| 41 | | | | | | | | | | | | L-S | | | | | | |

The clones were expressed through coupled in vitro transcription-translation of PCR products (TNT®T7 Quick for PCR DNA kit, Promega) and assayed for glycosylation activity on the substrates steviol and steviol-19-O-glucoside (0.5 mM), as described in previous examples. The UGT85Cs produced from clones 1, 4, 16, 17, 19, 20, 21, 26, 29, 30, 31, 37, and 39 were soluble and were able to convert 19-SMG to rubusoside in a 90 min assay. The UGT85C produced from clone 27 was considered insoluble. Although UGT85Cs produced from clones 2 and 33 were considered insoluble, trace amounts of rubusoside were produced despite the protein band not being visible. These experiments were independently performed three times. The experiments showed that the following amino acid mutations did not result in a loss of activity: V13F, F15L, H60D, A65S, E71Q, I87F, K220T, R243W, T270M, T270R, Q289H, L334S, A389V, I394V, P397S, E418V, G440D, and H441N. Additional mutations that were seen in active clones include K9E in clone 37, K10R in clone 26, Q211I in clone 2, M27V in clone 30, L91P in clone 4, Y298C in clone 31, K350T in clone 37, H368R in clone 1, G420R in clone 19, L431P in clone 4, R444G in clone 16, and M471T in clone 30.

The only common polymorphisms that were not tested were T270A and I336T, which are both fairly conservative substitutions. Clone 17 had the most changes incorporated as compared to UGT85C, 6/480 amino acids. The 17-20 amino acids that appear to be changeable represent approximately a 4% difference at the amino acid level.

Generally, there is low genetic diversity among the 85Cs and it is likely that all of the 85C homologs with the common polymorphisms set forth in Table 15 will be active.

Example 18—UGT76G Homologs

The genetic diversity of UGT76Gs from six different *S. rebaudiana* ecotypes was examined to identify homologs that have the same or enhanced activity in pathways for steviol glycoside production. PCR primers were designed that were specific for UGT76G, and PCR reactions were carried out on preparations of cDNA (cDNA libraries or cDNA preparations). The resulting PCR fragments were cloned and 96 clones were sequenced. Common amino acid polymorphisms were mapped and sixteen UGT76G clones chosen, with varying polymorphism representation, including (amino acid numbering): R10S, I16L, F22V, M29I, K52S, V74K/E, P80S, L85A, V87S/G, L91P, I92F, I93F, H96Y, G97R, L108V, E113D, G116E, A123T, Q125A, I126L, Y128H, T130A, L142I, V145M, S147N, N151T, F152I, H153L, H155Y, V156D, Q160L, E163D, L167F, P169L, K188N, K191Q, C192S/F, S193G/A, F194Y, M196N, K198Q, K199(I, V, Q), Y200(L, A, G), Y203I, F204L, E205G, N206K, I207M, T208I, V217I/F, E226Q, S228P, L230V, V233I, I234T, E236D, I237F, S253P, P266Q, S273P, R274S, G284T/A, T285S, 287-3 bp deletion, R298H, P326A, L330V, G331A, P341L, L346I, S376L, D377A, G379A, L380F, S438P, and K441N. Generally, there was very high diversity among the 76Gs.

The clones were expressed through in vitro translation and assayed for glycosylation activity using 0.5 mM steviol-13-O-glucoside and 0.5 mM stevioside as substrates, as described in previous examples. Reactions were carried out for 90 min at 30° C. The native 76G1 activity was found in thee new 76Gs designated 76G_C4, 76G_G7 and 76G_H12, by formation of 1,3-bioside when steviol-13-O-glucoside was used as substrate. Activity in this case was determined comparatively to the positive control, the functional 76G1. Clones 76G_G7 and 76G_H12 produced slightly higher levels of Reb A than the control but 76G_C4 had slightly less Reb A than the control. The number of changes in these clones represents a difference of about 7% at the amino acid level, from the control enzyme. SEQ ID NOs: 98, 100, and 102 set forth the amino acid sequence of 76G_C4, 76G_G7, and 76G_H12, respectively. SEQ ID NOs: 97, 99, and 101 set forth the nucleotide sequences encoding 76G_C4, 76G_G7, and 76G_H12, respectively. SEQ ID NOs: 98, 100, and 102 set forth the amino acid sequence of 76G_C4, 76G_G7, and 76G_H12, respectively. SEQ ID NOs: 97, 99, and 101 set forth the nucleotide sequences encoding 76G_C4, 76G_G7, and 76G_H12, respectively.

Table 16 summarizes the amino acid changes of the 76G clones that had activity, as compared to the wildtype enzyme. There are a large number of overlapping polymorphisms in the active clones, thus it is expected that these polymorphisms do not cause a loss of activity for the enzyme. It appears that certain mutations are frequent in inactive clones, such as the P→S mutation at position 80 or the F→V mutation at position 22.

TABLE 16

| Clone | Mutations |
| --- | --- |
| 76G_G7 | M29I, V74E, V87G, L91P, GI16E, A123T, Q125A, I126L, T130A, V145M, C192S, S193A, F194Y, M196N, K198Q, K199I, Y200L, Y203I, F204L, E205G, N206K, I207M, T208I, P266Q, S273P, R274S, G284T, T285S, 287-3 bp deletion, L330V, G331A, L346I |
| 76G_H12 | M29I, V74E, V87G, L91P, G116E, A123T, Q125A, I126L, T130A, V145M, C192S, S193A, F194Y, M196N, K198Q, K199I, Y200L, Y203I, F204L, E205G, N206K, I207M, T208I, P266Q, S273P, R274S, G284T, T285S, 287-3 bp deletion |
| 76G_C4 | M29I, V74E, V87G, L91P, G116E, A123T, Q125A, I126L, T130A, V145M, C192S, S193A, F194Y, M196N, K198Q, K199I, Y200L, Y203I, F204L, E205G, N206K, I207M, T208I |

Example 19—Expression of Truncated Yeast HMG-CoA Reductase and Other HMG-CoA Reductases In *S. cerevisiae*, the mevalonate pathway is heavily regulated, for example, at the level of the enzyme 3-Hydroxy-3-methylglutaryl-coenzyme A (HMG-CoA) reductase. Expressing a truncated HMG-CoA reductase (tHMG1, encoding an enzyme stabilized from degradation) is one method in which flux towards PPP production can be increased in yeast. For example, expression of tHMG1 in yeast has led to dramatic overproduction of β-carotene. See, Verwaal et al., 2007 *Appl. Environ. Microbiol.* 73:4342. Interestingly, such yeast did not show a darker orange coloration on solid growth medium as was expected, but rather a stronger yellow color, likely due to even higher overproduction of the intermediate phytoene.

To determine if expression of HMG-CoA reductase could be used to improve flux to the steviol and steviol glycoside pathways, a yeast reporter strain for testing isoprenoid flux was prepared by substituting the inherent promoter of the ERG9 gene with a CUP1 promoter. See, U.S. Patent Application No. 61/346,853, filed May 20, 2010.

The genes used to produce the yeast strain are shown in Table 17. The genes from the source organisms were codon optimized according to DNA 2.0 Inc™. For the purpose of monitoring the cellular prenyl phosphate availability, a construct was produced which had a high copy number plasmid containing gene expression cassettes (methionine-repressible promoters) with the genes for the three enzymes needed to turn prenyl phosphates into β-carotene (GGPP synthase from *Xanthophyllomyces dendrorhous*, phytoene synthase and beta carotene synthase from *X. dendrorhous*, and zeta carotene synthase and delta carotene synthase from *Neurospora crassa*). See, Verwaal et al., 2007 supra; and U.S. Patent Application No. 61/346,853.

TABLE 17

Sources of HMG CoA Reductases and other Mevalonate Genes

| Accession# | Organism | Enzyme | Size (nt) | Gene name | SEQ ID (codon optimized) | SEQ ID (protein) |
|---|---|---|---|---|---|---|
| XM_001467423 | Leishmania infantum | Acetyl-CoA C-acetyltransferase | 1323 | MEV-4 | 103 | 104 |
| YML075C | Saccharomyces cerevisiae | Truncated HMG (tHMG1) | 1584 | tHMG1 | 105 | 106 |
| EU263989 | Ganoderma lucidum | 3-HMG-CoA reductase | 3681 | MEV-11 | 107 | 108 |
| BC153262 | Bos taurus | 3-HMG-CoA reductase | 2667 | MEV-12 | 109 | 110 |
| AAD47596 | Artemisia annua | 3-HMG-CoA reductase | 1704 | MEV-13 | 111 | 112 |
| AAB62280 | Trypanosoma cruzi | 3-HMG-CoA reductase | 1308 | MEV-14 | 113 | 114 |
| CAG41604 | Staph aureus | 3-HMG-CoA reductase | 1281 | MEV-15 | 115 | 116 |
| DNA2.0 sequence | Archaeoglobus fulgidus | 3-HMG-CoA reductase | 1311 | HMG reductase | 117 | 118 |
| DNA2.0 sequence | Pseudomonas mevalonii | 3-HMG-CoA reductase | 1287 | HMG reductase | 119 | 120 |

The yeast tHMG1 was expressed in the CEN.PK-based yeast strain that produces β-carotene, resulting in a color change from orange to light yellow. Interestingly, expression of the full length HMGs from *Artemisia annua, Trypanosoma cruzi* and *Staphylococcus aureus*, as well as the NADH-dependent HMG's from *Pseudomonas mevalonii* and *Archeoglobus fulgidus* produced a similar result, indicating these genes also improve the flux through the mevalonate pathway in yeast (similar overexpression of *Bos taurus* HMG had no such effect). Finally, the same color change was seen after over-expression of *Leishmania infantum* acetyl-CoA C-acetyltransferase (first enzyme of mevalonate pathway, described in Tabe 17) or native *S. cerevisiae* (CAB1, YDR531W) or *B. subtilis*, (acc. No. YP004204141) pantothenate kinases (known to result in increased acetyl-CoA production).

To test if the color change in these experiments were indeed due to higher GGPP availability, the yeast tHMG1, *P. mevalonii* or *S. aureus* HMGs, or *B. subtilis* pantothenate kinase were expressed in a stable 19-SMG producer strain. None of these constructs appeared to produce an increase in 19-SMG or rubusoside production (UGT85C2 co-expressed) under the conditions tested. Mevalonate feeding to the yeast reporter strain also did not result in increased rubusoside production. The rubusoside reporter strain, however, has not been genetically modified to reduce the ERG9-encoded flux towards ergosterol biosynthesis. It is expected that control of flux to ergosterol production would result in increased steviol glycoside production using the HMG reductase genes and other mevalonate pathway genes found to be beneficial to beta-carotene production.

Example 20—Production of RebC In Vivo

The synthesis of a precursor molecule to Rebaudioside C, steviol-13-O-glucopyranosyl-1,2-rhamnoside, was shown in vitro in Example 15. In that example steviol-13-O-monoglucoside was used as a substrate, along with UDP-glucose and the *Arabidopsis thaliana* RHM2 enzyme (locus tag AT1G53500) and UGT91D2c. To further demonstrate the pathway shown in FIG. 2B, production of Rebaudioside C from steviol was accomplished in vivo.

A yeast strain capable of producing Rebaudioside C was constructed, and production of rebaudioside C and rebaudioside A was assayed by LC-MS. A modified *Saccharomyces cerevisiae* strain BY4742 was constructed and designated EYS583-7A. The use of BY4742 has been described by Naesby et al., *Microb Cell Fact.* 8:45 (2009) All four UGTs (91D2d, 76G1, 74G1, and 85C2) were constitutively expressed iin plasmids with GPD promoters. This type of strain has been described by Naesby et. al, *Microb Cell Fact.* 8:45 (2009). UGT85C2 was inserted in plasmid P423 GPD (ATCC#87355), UGT74G1 was cloned into P424 GPD (ATCC#87357) and both UGT91D2e and UGT76G1 were cloned into P425-GPD (ATCC#87359) with 91D2e in the original multiple cloning site (MCS), and 76G1 inserted with an additional GPD promoter and a CYC terminator. The resulting strain was transformed with plasmid P426 GPD (ATCC#87361) containing the RHM2 gene expressed from the GPD promoter. The strain was grown on SC medium lacking histidine, leucine, tryptophan and uracil for 24 hours. The culture was then re-inoculated to an $OD_{600}$ of 0.4 in fresh media containing 25 μM steviol, and the yeast was allowed to grow for 72 more hours before detecting if Rebaudioside C was present in the supernatant and the cell pellets. Rebaudioside C was quantified using an authentic Rebaudioside C standard (Chromadex, Irvine Calif.). A total of 1.27 μM±0.36 μM of RebC was detected in the supernatant. Similarly, 3.17 μM±1.09 μM RebA was detected in the cell pellet One of skill in the art will recognize that different ratios of of RebC to RebA can be obtained by modulation of the activity of the RHM2 enzyme and/or by usage of UGT91D2e or UGT76G1-like enzymes with higher activity for the UDP-rhamnose reactions. The alternative UGTs can be mutagenized versions of the wildtype enzymes or unique enzymes that are obtained through discovery initiatives.

One of skill in the art will recognize that a yeast strain capable of production of Rebaudioside A from glucose, such as strain CEY213 transformed with a plasmid containing UGT91D2e and UGT76G1 in Example 12 would produce Rebaudioside C with the addition of the RHM2 gene either via a vector or integrated into the chromosome.

Example 21—Production of Steviol Glycosides Using UGTs Expressed in *Escherichia coli*

Activity of UGT Enzymes in Gram Negative Bacteria

The wildtype genes for UGTs 91D2e, 74G1, 76G1, and 85C2 were cloned individually into *E. coli* XjB-autolysis BL21(DE3) cells using the pET30 vector system from Novagen (EMD4 Biosciences, Madison, Wis.), except for UGT91D2e, which was cloned into a pGEX 4T-1 (GE Healthcare, Uppsala, Sweden) vector. Similar cloning was described in Examples 7 and 10. All vectors use an IPTG-inducible promoter. Plasmid DNA was transformed into chemically competent cells as described by the vendor.

Transformants displaying the desired antibiotic resistance were grown overnight at 30° C. in 2 mL cultures using NZCYM-media and antibiotic. For in vivo feedings, 5 cultures were grown: UGT 91d2e, 74G1, 76G1, and 85C2 individually, and a mix of all 4 clones. The following day, the cultures were induced to a final concentration of 0.3 mM IPTG and 3 mM arabinose, and grown 2 days at 20° C. in the presence of 50 μM steviol (UGT74G1, UGT85C2 and the quadruple mix) or 50 μM rubusoside (UGT91D2e and UGT76G1). The temperature was raised to 30° C. and the cells were grown for one more day. The cells were then harvested by centrifugation at 4000 rpm for 5 min., and the supernatants were removed for LC-MS analysis. The cells were resuspended in 50% DMSO, lysed at 80° C. for 5 min and the lysates were analyzed by LC-MS.

For in vitro assays, transformants displaying the desired antibiotic resistance were grown overnight at 30° C. in 2 mL cultures using NZCYM-media and antibiotic. The following day, the cultures were induced to a final concentration of 0.3 mM IPTG and 3 mM arabinose, and grown for 24 h at 20° C. The cells were then harvested by centrifugation at 4000 rpm for 5 min and resuspended in 2004 μL GT-buffer (RBC Bioscience) and 3 tablets/100 ml of Complete mini, protease inhibitor (Roche), transferred to Eppendorf tubes, vortexed and frozen at −80° C. for 1.5 hour. Cells were thawed on ice, and left at room temperature for 3 minutes. When approximately half-way thawed, 15 μl of 0.14 mg/ml H$_2$O DNase solution+30 μl 0.05M MgCl$_2$ was added to each tube and the samples were incubated for approximately 5 minutes at room temperature. The cells were centrifuged at maximum speed for 5 minutes. One-hundred μL of supernatant (lysate) was transferred to fresh microfuge tubes, and 100 μL of glycerol was added.

Enzyme assays were performed by adding 15.15 μL H$_2$O, 7.5 μL 4× Buffer (400 mM Tris, 20 mM MgCl2, 4 mM KCl), 0.3 μL FastAP™ (1 u/μL) from Fermentas, 0.45 μL of a 100 mM stock of UDP-glucose, 0.6 μL of substrate (steviol or rubusoside) and 6 μL of the crude enzyme preparations described above. UGT74G1, UGT85C2, as well as all four UGTs mixed were incubated with steviol. UGT 76G1 and 85C2 were incubated with rubusoside. The enzyme assays were incubated overnight at 37° C. Following centrifugation at 4000 rpm for 5 minutes, 30 μL samples were transferred to a fresh 96 well plate and 30 μL of DMSO was added. The samples were then subjected to LC-MS analysis. Similar in vitro experiments were also done using steviol 1,2-bioside (for UGT76G1 and UGT74G1) or Rebaudioside B (for UGT74G1) as substrates.

No activity was detected in the in vivo feedings. Table 18 illustrates the results for the in vitro assays.

TABLE 18

| Tube | UGT Clone(s) | Substrate fed | Product detected |
|---|---|---|---|
| 1 | 74G1 | Steviol | 19-SMG, low levels of rubusoside |
| 2 | 85G1 | Steviol | 13-SMG, low levels of rubusoside |
| 3 | 76G1 | Rubusoside | 1,3-stevioside, an unknown tetra-glycoside |
| 4 | 91D2e | Rubusoside | stevioside |
| 5 | Mix of 4 crude UGT preparations | Steviol | Rubusoside, 1,3-stevioside, trace RebA (no monosides) |
| 6 | 76G1 | Steviol 1,2-bioside | RebaudiosideB |
| 7 | 74G1 | Steviol 1,2-bioside | Stevioside |
| 8 | 74G1 | Rebaudioside B | Rebaudioside A |

These results indicate that the UGT enzymes are all active in *E. coli* cells. However, the substrates may not be readily imported into the cytoplasm. It is expected that if the steviol were produced in *E. coli* from precursor pathways, the production of the various steviol glycoside products would be feasible from glucose. It is unexpected that the 74G1 and 85G1 UGTs, which have slightly overlapping substrate specificities, can produce rubusoside from steviol singly. The mix of the four crude enzyme preparations gave very low levels of the monosides, which indicates that the conversion to di- and tri-glycosides was efficient. With respect to UGT91D2e, the preparation that was used had lost some of its original activity after long-term storage. It is expected that a fresh preparation of the enzyme would have yielded higher levels of Rebaudioside A.

Example 22—Production of Steviol Glycosides in *Physcomitrella Patens*

Feeding Experiments in Moss Cells

The genes for UGT 91d2e, 74G1, 76G1, and 85C2 were cloned into *Physcomitrella patens* using the pTHUbi:Gateway vector system described in U.S. Patent Publication No. 20100297722. This vector uses a strong maize Ubiquitin promoter. PCR primers were designed to amplify the coding regions in previous examples (native sequences) with the addition of "CACC" upstream of the start codon. Plasmid DNA was digested with SwaI and used for transformation into protoplasts (generally around 0.5×10$^6$ protoplasts). Transformants displaying the desired resistance were grown 1 day in 10 ml. cultures and then fed either steviol, rubusoside, or buffer+DMSO as indicated by Table 19. One-half mL of buffer containing substrate was added per 10 mL of culture, and final concentrations of 0.1% DMSO, 50 μM steviol or rubusoside, and 0.125 mM phosphate buffer were added to the cultures. A positive control was done where the YFP (yellow fluorescent protein) was expressed in the presence of steviol or just buffer and DMSO. Cultures were grown 2 more days prior to separation of cells and freezing in liquid nitrogen until further analysis. In some cases multiple UGT-containing plasmids were transformed into the same protoplast cells, to illustrate conversion of multiple steps within the moss cells.

TABLE 19

| Tube | UGT Gene(s) | Substrate fed |
|---|---|---|
| 1 | YFP (control) | none |
| 2 | YFP | Steviol (50 μM) |

TABLE 19-continued

| Tube | UGT Gene(s) | Substrate fed |
|---|---|---|
| 3 | 74G1 | none |
| 4 | 76G1 | none |
| 5 | 85C2 | none |
| 6 | 91D2E | none |
| 7 | 74G1 | Steviol (50 μM) |
| 8 | 76G1 | Steviol (50 μM) |
| 9 | 85C2 | Steviol (50 μM) |
| 10 | 91D2E | Steviol (50 μM) |
| 11 | 74G1/85C2 | none |
| 12 | 74G1/85C2 | Steviol (50 μM) |
| 13 | 74G1/85C2/91D2E | none |
| 14 | 74G1/85C2/91D2E | Steviol (50 μM) |
| 15 | 76G1 | Rubusoside (50 μM) |
| 16 | 91D2E | Rubusoside (50 μM) |
| 17 | 76G1/91D2E | none |
| 18 | 76G1/91D2E | Rubusoside (50 μM) |

Expression was positive in the controls (tubes 1 and 2) as measured by fluorescent signal observation. The supernatants from the experiments were analyzed by LC-MS; 200 μL of each supernatant sample was mixed with an equal volume of 50 percent DMSO. The samples were spun (15,700 relative centrifugal force, 10 minutes) and 100 microliters of the resulting supernatant was analyzed by LC-MS.

Protoplast pellets were thawed on ice and 10 mM Tris-HCl pH 8 containing 3 tablets/100 ml of Complete Mini Protease Inhibitor (Roche) was added to reach a final volume of 150 μL. The solutions were divided in two: 75 μL was transferred to a new tube and protoplasts were pelleted (15,700 relative centrifugal force, 1 minute). Pellets were washed with 75 μL Milli-Q water before resuspenion in 150 μL DMSO (50 percent). Samples were then heated (80 degrees Celsius, 10 minutes), vortexed and centrifuged (15,700 relative centrifugal force, 10 minutes). Fifty μL of the resulting supernatant was analyzed by LC-MS.

No steviol glycoside production was detectable in supernatants or pellets. It is unknown if the steviol and rubusoside can be transported into moss cells.

In Vitro Feeding of Pellet Extracts

In vitro feeding experiments were conducted with samples 1, 3, 4, 5, 6, 11, 13 and 17). Glass beads (425-600 microns) were added to the remaining 75 μL of the original resuspensions and protoplasts were mechanically lysed by vortexing 3 times, 2 minutes each time, at 4 degrees Celsius and storage on ice in between vortexing. The samples were spun (15,700 relative centrifugal force, 10 minutes, 4 degrees Celsius) and 6 μL of resulting supernatants was used in in vitro enzyme reactions. For the enzyme reactions FastAP™ phosphatase (Fermentas) was used (0.3 U/reaction) and the UDP-glucose:substrate ratio was 5. The samples were fed either steviol or rubusoside according to Table 20.

TABLE 20

| Cell extract from tube | UGT Gene(s) | Substrate fed |
|---|---|---|
| 1 | YFP | None |
| 1 | YFP | 0.5 mM steviol |
| 1 | YFP | 0.5 mM rubusoside |
| 3 | 74G1 | 0.5 mM steviol |
| 4 | 76G1 | 0.5 mM rubusoside |
| 5 | 85C2 | 0.5 mM steviol |
| 6 | 91D2E | 0.5 mM rubusoside |
| 11 | 74G1/85C2 | 0.5 mM steviol |
| 13 | 74G1/85C2/91D2E | 0.5 mM steviol |
| 17 | 76G1/91D2E | 0.5 mM rubusoside |

Reactions were incubated at 30° C. overnight. After incubation, an equal amount of DMSO (100 percent) was added to the samples and mixed, then the sample was spun (15,700 relative centrifugal force, 10 minutes) and 30 μL of the resulting supernatant was analyzed by LC-MS.

LC-MS analysis showed conversion of rubusoside to 1,3-stevioside by UGT76G1. None of the other steviol glycosides were detectable. It is unknown if soluble expression of the UGTs occurred in *Physcomitrella*. It is expected if one UGT is active in the moss cells, the others would also be active if expression occurred. In addition, the cloning was done in a transient manner. Stable integration of the genes is expected to produce additional clones that are active for UGT activity when tested.

Methods are known to those with skill in the art for increasing soluble expression of recombinant proteins. Alternative promoters, ribosome binding sites, codon usage, co-expression with chaperones, and change in temperature are non-limiting examples of methods for increasing soluble expression of recombinant proteins.

Example 23—Production of Steviol Glycosides in *Aspergillus nidulans*

Activity of UGT Enzymes in Fungal Cells

The native genes for UGT 91D2e, 74G1, 76G1, and 85C2 were cloned into *Aspergillus nidulans* using a PCR-fabricated expression cassette and the USER vector system. Cloning methods are described in Hansen et al., *Appl. Environ. Microbiol.* 77: 3044-3051 (2011). Briefly, a nucleotide sequence encoding each UGT was inserted between the constitutive PgpdA promoter and the TtrpC terminator, in a vector containing additionally two targeting sequences for genomic integration and argB as selection marker. Plasmid DNA was transformed into *A. nidulans* protoplasts according to Nielsen et al., *Fungal Genet. Biol.* 43:54-64 (2006) and Johnstone et al., *EMBO J.* 4:1307-1311 (1985). Transformants displaying the desired resistance were grown for 48 hours in 150 mL cultures using minimal media (1% Glucose; 10 mM NaNO$_3$; mineral mix).

Cell lysates prepared by disruption of the mycelia with glass beads were used to determine the activities of the individual UGTs in in vitro. The cell lysates of strains expressing 74G1 and 85C2 were incubated with 0.5 mM steviol and the strains expressing 76G1 and 91D2c were incubated with 0.5 mM steviol-13-O-glucoside for 24 hours, and the supernatants further analyzed using LC/MS. No steviol glycosides were detected.

It is unknown whether soluble expression of the UGT enzymes was achieved as these products are not typically visible on SDS-PAGE. Since *Aspergillus* and *Saccharomyces* are both fungi, it is expected that additional experimentation would result in active clones. Methods are known to those with skill in the art for increasing soluble expression of recombinant proteins. Alternative promoters, inducer levels, ribosome binding sites, codon usage, co-expression with chaperones, and change in temperature are non-limiting examples of methods for increasing soluble expression of recombinant proteins.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A recombinant host cell capable of producing steviol, a target steviol glycoside or a target steviol glycoside composition, comprising:
   (a) a gene encoding a polypeptide capable of beta 1,2 glycosylation of the C2' of the 13-O-glucose, 19-O-glucose, or both 13-O-glucose and 19-O-glucose of a precursor steviol glycoside and having at least 95% sequence identity to the amino acid sequence set forth in SEQ ID NO:5;
      wherein the polypeptide is capable of transferring a sugar moiety to the C2' of a glucose in the precursor steviol glycoside;
   and one or more of:
   (b) a gene encoding a polypeptide capable of glycosylating steviol or the precursor steviol glycoside at its C-13 hydroxyl group; and/or
   (c) a gene encoding a polypeptide capable of beta 1,3 glycosylation of the C3' of the 13-O-glucose of the precursor steviol glycoside; and/or
   (d) a gene encoding a polypeptide capable of glycosylating steviol or the precursor steviol glycoside at its C-19 carboxyl group;
   wherein at least one of the genes is a recombinant gene.

2. The recombinant host cell of claim 1, wherein:
   (a) the precursor steviol glycoside is rubusoside, wherein the sugar moiety is glucose, and stevioside is produced upon transfer of the glucose moiety;
   (b) the precursor steviol glycoside is stevioside, the sugar moiety is glucose, and rebaudioside E is produced upon transfer of the glucose moiety;
   (c) the precursor steviol glycoside is stevioside, the sugar moiety is glucose, the stevioside is contacted with the polypeptide capable of beta 1,2 glycosylation of the C2' of the 13-O-glucose, 19-O-glucose, or both 13-O-glucose and 19-O-glucose of the precursor steviol glycoside and a polypeptide capable of beta 1,3 glycosylation of the C3' of the 13-O-glucose of the precursor steviol glycoside, and rebaudioside D is produced upon transfer of the glucose moiety;
   (d) the precursor steviol glycoside is steviol-13-O-glucoside, the sugar moiety is glucose, and steviol-1,2 bioside is produced upon transfer of the glucose moiety;
   (e) the precursor steviol glycoside is steviol-13-O-glucoside, the sugar moiety is xylose, and steviol-1,2-xylobioside is produced upon transfer of the sugar moiety;
   (f) the precursor steviol glycoside is steviol-13-O-glucoside, the sugar moiety is rhamnose, and steviol-1,2-rhamnobioside is produced upon transfer of the sugar moiety;
   (g) the precursor steviol glycoside is rebaudioside A, the sugar moiety is glucose, and rebaudioside D is produced upon transfer of the glucose moiety; or
   (h) the precursor steviol glycoside is rubusoside, wherein the I sugar moiety is xylose, and 1,2-stevioxyloside is produced upon transfer of the sugar moiety.

3. The recombinant host cell of claim 1, wherein:
   (a) the polypeptide capable of beta 1,2 glycosylation of the C2' of the 13-O-glucose, 19-O-glucose, or both 13-O-glucose and 19-O-glucose of the precursor steviol glycoside comprises:
      (i) a polypeptide having at least 95% sequence identity to the amino acid sequence set forth in SEQ ID NO:5 and having one or more amino acid substitutions of residues 1-19, 27-38, 44-87, 96-120, 125-141, 159-184, 199-202, 215-380, or 387-473 of SEQ ID NO:5;
      (ii) a polypeptide having at least 95% sequence identity to the amino acid sequence set forth in SEQ ID NO:5 and having one or more amino acid substitutions of residues 30, 93, 99, 122, 140, 142, 144, 148, 152, 153, 156, 195, 196, 199, 206, 207, 211, 213, 221, 286, 343, 364, 384, 427, and 438 of SEQ ID NO:5;
      (iii) a polypeptide having at least 95% sequence identity to the amino acid sequence set forth in SEQ ID NO:5 and having an arginine at residue 206, a cysteine at residue 207, and an arginine at residue 343 relative to SEQ ID NO:5; or
      (iv) a polypeptide having at least 95% sequence identity to the amino acid sequence set forth in SEQ ID NO:5 and having a tyrosine or phenylalanine at residue 30, a proline or glutamine at residue 93, a serine or valine at residue 99, a tyrosine or phenylalanine at residue 122, a histidine or tyrosine at residue 140, a serine or cysteine at residue 142, an alanine or threonine at residue 148, a methionine at residue 152, an alanine at residue 153, an alanine or serine at residue 156, a glycine at residue 162, a leucine or methionine at residue 195, a glutamic acid at residue 196, a lysine or glutamic acid at residue 199, a leucine or methionine at residue 211, a leucine at residue 213, a serine or phenylalanine at residue 221, a valine or isoleucine at residue 253, a valine or alanine at residue 286, an asparagine or lysine at residue 427, or an alanine at residue 438 and an alanine or threonine at residue 462 relative to SEQ ID NO:5;
   (b) the polypeptide capable of glycosylating steviol or the precursor steviol glycoside at its C-13 hydroxyl group comprises
      a polypeptide having at least 95% sequence identity to the amino acid sequence set forth in SEQ ID NO:3; or
      (II) a polypeptide and having one or more amino acid substitutions of residues 9, 10, 13, 15, 21, 27, 60, 65, 71, 87, 91, 220, 243, 270, 289, 298, 334, 336, 350, 368, 389, 394, 397, 418, 420, 440, 441, 444, and 471 of SEQ ID NO:3;
   (c) the polypeptide capable of beta 1,3 glycosylation of the C3' of the 13-O-glucose of the precursor steviol glycoside comprises;
      a polypeptide having at least 95% sequence identity to the amino acid sequence set forth in SEQ ID NO:7 and having one or more amino acid substitutions of residues 29, 74, 87, 91, 116, 123, 125, 126, 130, 145, 192, 193, 194, 196, 198, 199, 200, 203, 204, 205, 206, 207, 208, 266, 273, 274, 284, 285, 291, 330, 331, and 346 of SEQ ID NO:7;
   and
   (d) the polypeptide capable of glycosylating steviol or the precursor steviol glycoside at its C-19 carboxyl group comprises a polypeptide having at least 95% sequence identity to the amino acid sequence set forth in SEQ ID NO:1.

4. The recombinant host cell of claim 1, further comprising:
   (a) a gene encoding a polypeptide capable of synthesizing geranylgeranyl pyrophosphate (GGPP) from farnesyl diphosphate (FPP) and isopentenyl diphosphate (IPP);
      wherein the polypeptide comprises a polypeptide having at least 95% sequence identity to one of the amino acid sequences set forth in SEQ ID NOs:121-128;

(b) a gene encoding a polypeptide capable of synthesizing ent-copalyl diphosphate from GGPP;
   wherein the polypeptide comprises a polypeptide having at least 90% sequence identity to one of the amino acid sequences set forth in SEQ ID NOs:129-131;
(c) a gene encoding a polypeptide capable of synthesizing ent-kaurene from ent-copalyl pyrophosphate;
   wherein the polypeptide comprises a polypeptide having at least 95% sequence identity to one of the amino acid sequences set forth in SEQ ID NOs:132-135;
(d) a gene encoding a polypeptide capable of synthesizing ent-kaurenoic acid from ent-kaurene;
   wherein the polypeptide comprises a polypeptide having at least 95% sequence identity to one of the amino acid sequences set forth in SEQ ID NOs:138-141;
(e) a gene encoding a polypeptide capable of synthesizing steviol from ent-kaurenoic acid;
   wherein the polypeptide comprises a polypeptide having at least 95% sequence identity to one of the amino acid sequences set forth in SEQ ID NOs:142-146; and
(f) a gene encoding a polypeptide polypeptide capable of reducing cytochrome P450 complex;
   wherein the polypeptide comprises a polypeptide having at least 95% sequence identity to one of the amino acid sequences set forth in SEQ ID NOs: 147-149;
wherein at least one of the genes is a recombinant gene.

5. The recombinant host cell of claim 1, wherein the host cell is in a cell culture that comprises:
   (a) glucose, fructose, sucrose, xylose, rhamnose, uridine diphosphate (UDP)-glucose, UDP-rhamnose, UDP-xylose, and/or N-acetyl-glucosamine; and/or
   (b) supplemental nutrients comprising trace metals, vitamins, salts, yeast nitrogen base (YNB) and/or amino acids.

6. The recombinant host cell of claim 1, wherein the host cell comprises a plant cell, a mammalian cell, an insect cell, a fungal cell from *Aspergillus* genus or a yeast cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous,* or *Candida albicans* species, an algal cell or a bacterial cell from *Escherichia coli* species or *Bacillus* genus.

7. A method of producing steviol, a target steviol glycoside or a target steviol glycoside composition in a cell culture, comprising growing the recombinant host cell of claim 1 under conditions in which one or more of the genes are expressed;
   wherein steviol, the target steviol glycoside, or the target steviol glycoside composition is produced by the recombinant host cell;
   wherein the target steviol glycoside is, or the target steviol glycoside composition comprises, stevioside, rebaudioside E, rebaudioside D, steviol-1,2-bioside, steviol-1,2-xylobioside, steviol-1,2-rhamnobioside, 1,2-stevioxyloside, and/or an isomer thereof.

8. The method of claim 7, wherein the growing includes inducing expression of one or more of the genes or constitutively, expressing one or more of the genes.

9. The method of claim 7, wherein the recombinant host cell is grown in a fermentor at a temperature for a period of time, wherein the temperature and period of time facilitate the production of steviol, the target steviol glycoside or the target steviol glycoside composition.

10. The method of claim 7, wherein steviol, the target steviol glycoside or the target steviol glycoside composition is produced in a permeabilized recombinant host cell which has been transformed with:
   (a) a gene encoding a polypeptide capable of beta 1,2 glycosylation of the C2' of the 13-O-glucose, 19-O-glucose, or both 13-O-glucose and 19-O-glucose of the precursor steviol glycoside;
   (b) a gene encoding a polypeptide capable of glycosylating steviol or the precursor steviol glycoside at its C-13 hydroxyl group;
   (c) a gene encoding a polypeptide capable of beta 1,3 glycosylation of the C3' of the 13-O-glucose of the precursor steviol glycoside; and/or
   (d) a gene encoding a polypeptide capable of glycosylating steviol or the precursor steviol glycoside at its C-19 carboxyl group.

11. The method of claim 10, wherein the target steviol glycoside is rebaudioside D, wherein rebaudioside D is produced upon transfer of a glucose moiety to rebaudioside A.

12. The method of claim 7, further comprising isolating the rebaudioside D, alone or together with at least one other steviol glycoside from the cell culture.

13. The method of claim 12, wherein the isolating step comprises:
   (a) providing the cell culture comprising Rebaudioside D, alone or together with at least one other steviol glycoside;
   (b) separating a liquid phase of the cell culture from a solid phase of the cell culture to obtain a supernatant comprising Rebaudioside D, alone or together with at least one other steviol glycoside;
   (c) providing one or more adsorbent resins, comprising providing the adsorbent resins in a packed column; and
   (d) contacting the supernatant of step (b) with the one or more adsorbent resins in order to obtain at least a portion of Rebaudioside D, alone or together with at least one other steviol glycoside, thereby isolating Rebaudioside D, alone or together with at least one other steviol glycoside;
or
   (a) providing the cell culture comprising Rebaudioside D, alone or together with at least one other steviol glycoside;
   (b) separating a liquid phase of the cell culture from a solid phase of the cell culture to obtain a supernatant comprising Rebaudioside D, alone or together with at least one other steviol glycoside;
   (c) providing one or more ion exchange or ion exchange or reversed-phase chromatography columns; and
   (d) contacting the supernatant of step (b) with the one or more ion exchange or ion exchange or reversed-phase chromatography columns in order to obtain at least a portion of Rebaudioside D, alone or together with at least one other steviol glycoside, thereby isolating Rebaudioside D, alone or together with at least one other steviol glycoside;
or
   (a) providing the cell culture comprising Rebaudioside D, alone or together with at least one other steviol glycoside;
   (b) separating a liquid phase of the cell culture from a solid phase of the cell culture to obtain a supernatant comprising Rebaudioside D, alone or together with at least one other steviol glycoside;

(c) crystallizing or extracting Rebaudioside D, alone or together with at least one other steviol glycoside, thereby isolating Rebaudioside D, alone or together with at least one other steviol glycoside.

14. The method of claim 7, further comprising recovering Rebaudioside D, alone or together with at least one other steviol glycoside, or the target steviol glycoside composition from the cell culture;

wherein the recovered target steviol glycoside composition is enriched for Rebaudioside D relative to a steviol glycoside composition from a *Stevia* plant and has a reduced level of *Stevia* plant-derived components relative to a plant-derived *Stevia* extract.

15. The method of claim 7, wherein the cell culture comprises:

(a) glucose, fructose, sucrose, xylose, rhamnose, uridine diphosphate (UDP)-glucose, UDP-rhamnose, UDP-xylose, and/or N-acetyl-glucosamine; and/or (b) supplemental nutrients comprising trace metals, vitamins, salts, yeast nitrogen base (YNB) and/or amino acids.

16. The method of claim 7, wherein the recombinant host cell comprises a plant cell, a mammalian cell, an insect cell, a fungal cell from *Aspergillus* genus or a yeast cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous,* or *Candida albicans* species, an algal cell or a bacterial cell from *Escherichia coli* species or *Bacillus* genus.

17. A cell culture, comprising the host cell of claim 1, the cell culture further comprising:

(a) the target steviol glycoside or the target steviol glycoside composition produced by the recombinant host cell;

(b) glucose, fructose, sucrose, xylose, rhamnose, uridine diphosphate (UDP)-glucose, UDP-rhamnose, UDP-xylose, and/or N-acetyl-glucosamine; and (c) supplemental nutrients comprising trace metals, vitamins, salts, YNB, and/or amino acids;

wherein the target steviol glycoside or the target steviol glycoside composition is present at a concentration of at least 1 mg/liter of the cell culture;

wherein the cell culture is enriched for the target steviol glycoside or the target steviol glycoside composition relative to a steviol glycoside composition from a *Stevia* plant and has a reduced level of *Stevia* plant-derived components relative to a plant-derived *Stevia* extract.

18. A cell lysate from the host cell of claim 1 grown in the cell culture, comprising:

(a) steviol, the target steviol glycoside or the target steviol glycoside composition produced by the recombinant host cell;

(b) glucose, fructose, sucrose, xylose, rhamnose, uridine diphosphate (UDP)-glucose, UDP-rhamnose, UDP-xylose, and/or N-acetyl-glucosamine; and/or (c) supplemental nutrients comprising trace metals, vitamins, salts, yeast nitrogen base, YNB, and/or amino acids;

wherein steviol, the target steviol glycoside or the target steviol glycoside composition produced by the recombinant host cell is present at a concentration of at least 1 mg/liter of the cell culture.

19. A reaction mixture, comprising:

(a) one or more of stevioside, rebaudioside E, rebaudioside D, steviol-1,2-bioside, steviol-1,2-xylobioside, steviol-1,2-rhamnobioside, 1,2-stevioxyloside, and/or an isomer thereof produced by the host cell of claim 1;

(b) a polypeptide capable of beta 1,2 glycosylation of the C2' of the 13-O-glucose, 19-O-glucose, or both 13-O-glucose and 19-O-glucose of a steviol glycoside;

(c) a polypeptide capable of glycosylating steviol or a steviol glycoside at its C-13 hydroxyl group;

(d) a polypeptide capable of beta 1,3 glycosylation of the C3' of the 13-O-glucose, 19-O-glucose, or both 13-O-glucose and 19-O-glucose of a steviol glycoside;

(e) a polypeptide capable of glycosylating steviol or a steviol glycoside at its C-19 carboxyl group;

(f) glucose, fructose, sucrose, xylose, rhamnose, uridine diphosphate (UDP)-glucose, UDP-rhamnose, UDP-xylose, and/or N-acetyl-glucosamine; and (g) reaction buffer and/or salts.

20. The target steviol glycoside or the target steviol glycoside composition produced by the host cell of claim 1.

21. The recombinant host cell of claim 1, wherein the host cell is a *Yarrowia lipolytica* cell.

22. The recombinant host cell of claim 1, wherein the target steviol glycoside is, or the target steviol glycoside composition comprises, stevioside, rebaudioside E, rebaudioside D, steviol-1,2-bioside, steviol-1,2-xylobioside, steviol-1,2-rhamnobioside, 1,2-stevioxyloside, and/or an isomer thereof.

* * * * *

SEQUENCE LISTING

<160> NUMBER OF SEQ ID NOS: 151

<210> SEQ ID NO 1
<211> LENGTH: 460
<212> TYPE: PRT
<213> ORGANISM: Stevia rebaudiana

<400> SEQUENCE: 1

Met Ala Glu Gln Gln Lys Ile Lys Lys Ser Pro His Val Leu Leu Ile
1               5                   10                  15

Pro Phe Pro Leu Gln Gly His Ile Asn Pro Phe Ile Gln Phe Gly Lys
            20                  25                  30

Arg Leu Ile Ser Lys Gly Val Lys Thr Thr Leu Val Thr Thr Ile His
        35                  40                  45

Thr Leu Asn Ser Thr Leu Asn His Ser Asn Thr Thr Thr Ser Ile
    50                  55                  60

Glu Ile Gln Ala Ile Ser Asp Gly Cys Asp Glu Gly Gly Phe Met Ser
65                  70                  75                  80

Ala Gly Glu Ser Tyr Leu Glu Thr Phe Lys Gln Val Gly Ser Lys Ser
                85                  90                  95

Leu Ala Asp Leu Ile Lys Lys Leu Gln Ser Glu Gly Thr Thr Ile Asp
            100                 105                 110

Ala Ile Ile Tyr Asp Ser Met Thr Glu Trp Val Leu Asp Val Ala Ile
        115                 120                 125

Glu Phe Gly Ile Asp Gly Gly Ser Phe Phe Thr Gln Ala Cys Val Val
    130                 135                 140

Asn Ser Leu Tyr Tyr His Val His Lys Gly Leu Ile Ser Leu Pro Leu
145                 150                 155                 160

Gly Glu Thr Val Ser Val Pro Gly Phe Pro Val Leu Gln Arg Trp Glu
                165                 170                 175

Thr Pro Leu Ile Leu Gln Asn His Glu Gln Ile Gln Ser Pro Trp Ser
            180                 185                 190

Gln Met Leu Phe Gly Gln Phe Ala Asn Ile Asp Gln Ala Arg Trp Val
        195                 200                 205

Phe Thr Asn Ser Phe Tyr Lys Leu Glu Glu Glu Val Ile Glu Trp Thr
    210                 215                 220

Arg Lys Ile Trp Asn Leu Lys Val Ile Gly Pro Thr Leu Pro Ser Met
225                 230                 235                 240

Tyr Leu Asp Lys Arg Leu Asp Asp Asp Lys Asp Asn Gly Phe Asn Leu
                245                 250                 255

Tyr Lys Ala Asn His His Glu Cys Met Asn Trp Leu Asp Asp Lys Pro
            260                 265                 270

Lys Glu Ser Val Val Tyr Val Ala Phe Gly Ser Leu Val Lys His Gly
        275                 280                 285

Pro Glu Gln Val Glu Glu Ile Thr Arg Ala Leu Ile Asp Ser Asp Val
    290                 295                 300

Asn Phe Leu Trp Val Ile Lys His Lys Glu Glu Gly Lys Leu Pro Glu
305                 310                 315                 320

Asn Leu Ser Glu Val Ile Lys Thr Gly Lys Gly Leu Ile Val Ala Trp
                325                 330                 335

Cys Lys Gln Leu Asp Val Leu Ala His Glu Ser Val Gly Cys Phe Val
            340                 345                 350

Thr His Cys Gly Phe Asn Ser Thr Leu Glu Ala Ile Ser Leu Gly Val
        355                 360                 365

```
Pro Val Val Ala Met Pro Gln Phe Ser Asp Gln Thr Thr Asn Ala Lys
    370             375                 380

Leu Leu Asp Glu Ile Leu Gly Val Gly Val Arg Val Lys Ala Asp Glu
385                 390                 395                 400

Asn Gly Ile Val Arg Arg Gly Asn Leu Ala Ser Cys Ile Lys Met Ile
                405                 410                 415

Met Glu Glu Glu Arg Gly Val Ile Ile Arg Lys Asn Ala Val Lys Trp
            420                 425                 430

Lys Asp Leu Ala Lys Val Ala Val His Glu Gly Gly Ser Ser Asp Asn
            435                 440                 445

Asp Ile Val Glu Phe Val Ser Glu Leu Ile Lys Ala
    450                 455                 460

<210> SEQ ID NO 2
<211> LENGTH: 1383
<212> TYPE: DNA
<213> ORGANISM: Stevia rebaudiana

<400> SEQUENCE: 2
atggcagagc aacaaaagat caaaaagtca cctcacgtct tacttattcc atttcctctg      60
caaggacata tcaacccatt catacaattt gggaaaagat tgattagtaa gggtgtaaag     120
acaacactgg taaccactat ccacactttg aattctactc tgaaccactc aaatactact     180
actacaagta tagaaattca agctatatca gacggatgcg atgagggtgg ctttatgtct     240
gccggtgaat cttacttgga acattcaag caagtgggat ccaagtctct ggccgatcta     300
atcaaaaagt tacagagtga aggcaccaca attgacgcca taatctacga ttctatgaca     360
gagtgggttt tagacgttgc tatcgaattt ggtattgatg aggttccctt tttcacacaa     420
gcatgtgttg tgaattctct atactaccat gtgcataaag ggttaatctc tttaccattg     480
ggtgaaactg tttcagttcc aggttttcca gtgttacaac gttgggaaac cccattgatc     540
ttacaaaatc atgaacaaat acaatcacct tggtcccaga tgttgtttgg tcaattcgct     600
aacatcgatc aagcaagatg ggtctttact aattcattct ataagttaga ggaagaggta     660
attgaatgga ctaggaagat ctggaatttg aaagtcattg gtccaacatt gccatcaatg     720
tatttggaca aaagacttga tgatgataaa gataatggtt tcaatttgta caaggctaat     780
catcacgaat gtatgaattg gctggatgac aaaccaaagg aatcagttgt atatgttgct     840
ttcggctctc ttgttaaaca tggtccagaa caagttgagg agattacaag agcacttata     900
gactctgacg taaacttttt gtgggtcatt aagcacaaag aggagggaa actgccagaa     960 aacctttctg aagtgataaa gaccggaaaa ggtctaatcg ttgcttggtg taaacaattg    1020
gatgttttag ctcatgaatc tgtaggctgt tttgtaacac attgcggatt caactctaca    1080
ctagaagcca tttccttagg cgtacctgtc gttgcaatgc ctcagttctc cgatcagaca    1140
accaacgcta aacttttgga cgaaatacta ggggtgggtg tcagagttaa agcagacgag    1200
aatggtatcg tcagaagagg gaacctagct tcatgtatca aaatgatcat ggaagaggaa    1260
agaggagtta tcataaggaa aaacgcagtt aagtggaagg atcttgcaaa ggttgccgtc    1320
catgaaggcg gctcttcaga taatgatatt gttgaatttg tgtccgaact aatcaaagcc    1380
taa                                                                  1383

<210> SEQ ID NO 3
<211> LENGTH: 481
<212> TYPE: PRT
<213> ORGANISM: Stevia rebaudiana
```

<400> SEQUENCE: 3

Met Asp Ala Met Ala Thr Thr Glu Lys Lys Pro His Val Ile Phe Ile
1               5                   10                  15

Pro Phe Pro Ala Gln Ser His Ile Lys Ala Met Leu Lys Leu Ala Gln
            20                  25                  30

Leu Leu His His Lys Gly Leu Gln Ile Thr Phe Val Asn Thr Asp Phe
        35                  40                  45

Ile His Asn Gln Phe Leu Glu Ser Ser Gly Pro His Cys Leu Asp Gly
    50                  55                  60

Ala Pro Gly Phe Arg Phe Glu Thr Ile Pro Asp Gly Val Ser His Ser
65              70                  75                  80

Pro Glu Ala Ser Ile Pro Ile Arg Glu Ser Leu Leu Arg Ser Ile Glu
            85                  90                  95

Thr Asn Phe Leu Asp Arg Phe Ile Asp Leu Val Thr Lys Leu Pro Asp
            100                 105                 110

Pro Pro Thr Cys Ile Ile Ser Asp Gly Phe Leu Ser Val Phe Thr Ile
            115                 120                 125

Asp Ala Ala Lys Lys Leu Gly Ile Pro Val Met Met Tyr Trp Thr Leu
130                 135                 140

Ala Ala Cys Gly Phe Met Gly Phe Tyr His Ile His Ser Leu Ile Glu
145                 150                 155                 160

Lys Gly Phe Ala Pro Leu Lys Asp Ala Ser Tyr Leu Thr Asn Gly Tyr
            165                 170                 175

Leu Asp Thr Val Ile Asp Trp Val Pro Gly Met Glu Gly Ile Arg Leu
            180                 185                 190

Lys Asp Phe Pro Leu Asp Trp Ser Thr Asp Leu Asn Asp Lys Val Leu
            195                 200                 205

Met Phe Thr Thr Glu Ala Pro Gln Arg Ser His Lys Val Ser His His
            210                 215                 220

Ile Phe His Thr Phe Asp Glu Leu Glu Pro Ser Ile Ile Lys Thr Leu
225                 230                 235                 240

Ser Leu Arg Tyr Asn His Ile Tyr Thr Ile Gly Pro Leu Gln Leu Leu
            245                 250                 255

Leu Asp Gln Ile Pro Glu Glu Lys Lys Gln Thr Gly Ile Thr Ser Leu
            260                 265                 270

His Gly Tyr Ser Leu Val Lys Glu Glu Pro Glu Cys Phe Gln Trp Leu
            275                 280                 285

Gln Ser Lys Glu Pro Asn Ser Val Val Tyr Val Asn Phe Gly Ser Thr
            290                 295                 300

Thr Val Met Ser Leu Glu Asp Met Thr Glu Phe Gly Trp Gly Leu Ala
305                 310                 315                 320

Asn Ser Asn His Tyr Phe Leu Trp Ile Ile Arg Ser Asn Leu Val Ile
            325                 330                 335

Gly Glu Asn Ala Val Leu Pro Pro Glu Leu Glu His Ile Lys Lys
            340                 345                 350

Arg Gly Phe Ile Ala Ser Trp Cys Ser Gln Glu Lys Val Leu Lys His
            355                 360                 365

Pro Ser Val Gly Gly Phe Leu Thr His Cys Gly Trp Gly Ser Thr Ile
            370                 375                 380

Glu Ser Leu Ser Ala Gly Val Pro Met Ile Cys Trp Pro Tyr Ser Trp
385                 390                 395                 400

Asp Gln Leu Thr Asn Cys Arg Tyr Ile Cys Lys Glu Trp Glu Val Gly 405                 410                 415
Leu Glu Met Gly Thr Lys Val Lys Arg Asp Glu Val Lys Arg Leu Val
        420                 425                 430

Gln Glu Leu Met Gly Glu Gly Gly His Lys Met Arg Asn Lys Ala Lys
        435                 440                 445

Asp Trp Lys Glu Lys Ala Arg Ile Ala Ile Ala Pro Asn Gly Ser Ser
        450                 455                 460

Ser Leu Asn Ile Asp Lys Met Val Lys Glu Ile Thr Val Leu Ala Arg
465                 470                 475                 480

Asn

<210> SEQ ID NO 4
<211> LENGTH: 1446
<212> TYPE: DNA
<213> ORGANISM: Stevia rebaudiana

<400> SEQUENCE: 4

| | |
|---|---|
| atggatgcaa tggcaactac tgagaaaaag cctcatgtga tcttcattcc atttcctgca | 60 |
| caatctcaca taaaggcaat gctaaagtta gcacaactat tacaccataa gggattacag | 120 |
| ataactttcg tgaataccga cttcatccat aatcaatttc tggaatctag tggccctcat | 180 |
| tgtttggacg gagccccagg gtttagattc gaaacaattc ctgacggtgt ttcacattcc | 240 |
| ccagaggcct ccatcccaat aagagagagt ttactgaggt caatagaaac caactttttg | 300 |
| gatcgtttca ttgacttggt cacaaaactt ccagacccac caacttgcat aatctctgat | 360 |
| ggctttctgt cagtgtttac tatcgacgct gccaaaaagt tgggtatccc agttatgatg | 420 |
| tactggactc ttgctgcatg cggtttcatg ggtttctatc acatccattc tcttatcgaa | 480 |
| aagggttttg ctccactgaa agatgcatca tacttaacca acggctacct ggatactgtt | 540 |
| attgactggg taccaggtat ggaaggtata agacttaaag attttccttt ggattggtct | 600 |
| acagacctta tgataaagt attgatgttt actacagaag ctccacaaag atctcataag | 660 |
| gtttcacatc atatctttca cactttgat gaattggaac atcaatcat caaaaccttg | 720 |
| tctctaagat acaatcatat ctacactatt ggtccattac aattacttct agatcaaatt | 780 |
| cctgaagaga aaaagcaaac tggtattaca tccttacacg gctactcttt agtgaaagag | 840 |
| gaaccagaat gttttcaatg gctacaaagt aaagagccta attctgtggt ctacgtcaac | 900 |
| ttcggaagta acagtcat gtccttggaa gatatgactg aatttggttg gggccttgct | 960 |
| aattcaaatc attactttct atggattatc aggtccaatt tggtaatagg gaaaacgcc | 1020 |
| gtattacctc cagaattgga ggaacacatc aaaaagagag gtttcattgc ttcctggtgt | 1080 |
| tctcaggaaa aggtattgaa acatccttct gttggtggtt tccttactca ttgcggttgg | 1140 |
| ggctctacaa tcgaatcact aagtgcagga gttccaatga tttgttggcc atattcatgg | 1200 |
| gaccaactta caaattgtag gtatatctgt aaagagtggg aagttggatt agaaatggga | 1260 |
| acaaaggtta acgtgatga agtgaaaaga ttggttcagg agttgatggg ggaaggtggc | 1320 |
| cacaagatga gaaacaaggc caaagattgg aaggaaaaag ccagaattgc tattgctcct | 1380 |
| aacgggtcat cctctctaaa cattgataag atggtcaaag agattacagt cttagccaga | 1440 |
| aactaa | 1446 |

<210> SEQ ID NO 5
<211> LENGTH: 473
<212> TYPE: PRT
<213> ORGANISM: Stevia rebaudiana

<400> SEQUENCE: 5

```
Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Val Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
```

405                 410                 415
Ala Arg Ser Leu Arg Ser Val Val Glu Lys Glu Gly Glu Ile Tyr
            420                 425                 430

Lys Ala Asn Ala Arg Glu Leu Ser Lys Ile Tyr Asn Asp Thr Lys Val
        435                 440                 445

Glu Lys Glu Tyr Val Ser Gln Phe Val Asp Tyr Leu Glu Lys Asn Ala
    450                 455                 460

Arg Ala Val Ala Ile Asp His Glu Ser
465                 470

<210> SEQ ID NO 6
<211> LENGTH: 1422
<212> TYPE: DNA
<213> ORGANISM: Stevia rebaudiana

<400> SEQUENCE: 6
atggctacat ctgattctat tgttgatgac aggaagcagt tgcatgtggc tactttccct      60
tggcttgctt tcggtcatat actgccttac ctacaactat caaaactgat agctgaaaaa     120
ggacataaag tgtcattcct ttcaacaact agaaacattc aaagattatc ttcccacata     180
tcaccattga ttaacgtcgt tcaattgaca cttccaagag tacaggaatt accagaagat     240
gctgaagcta acagatgt gcatcctgaa gatatccctt acttgaaaaa ggcatccgat       300
ggattacagc ctgaggtcac tagattcctt gagcaacaca gtccagattg gatcatatac     360
gactacactc actattggtt gccttcaatt gcagcatcac taggcatttc tagggcacat     420
ttcagtgtaa ccacaccttg gccattgct tacatgggtc catccgctga tgctatgatt      480
aacggcagtg atggtagaac taccgttgaa gatttgacaa ccccaccaaa gtggtttcca     540
tttccaacta aagtctgttg gagaaaaacac gacttagcaa gactggttcc atacaaggca   600
ccaggaatct cagacggcta tagaatgggt ttagtcctta agggtctga ctgcctattg      660 tctaagtgtt accatgagtt tgggacacaa tggctaccac ttttggaaac attcaccaa     720 gttcctgtcg taccagttgg tctattacct ccagaaatcc ctggtgatga aaggacgag     780 acttgggttt caatcaaaaa gtggttagac gggaagcaaa aaggctcagt ggtatatgtg     840
gcactgggtt ccgaagtttt agtatctcaa acagaagttg tggaacttgc cttaggtttg     900
gaactatctg gattgccatt tgtctgggcc tacagaaaac caaaaggccc tgcaaagtcc     960
gattcagttg aattgccaga cggctttgtc gagagaacta gagatagagg ttggtatgg    1020 acttcatggg ctccacaatt gagaatcctg agtcacgaat ctgtgtgcgg tttcctaaca    1080
cattgtggtt ctggttctat agttgaagga ctgatgtttg gtcatccact tatcatgttg    1140
ccaatctttg gtgaccagcc tttgaatgca cgtctgttag aagataaaca agttggaatt    1200
gaaatcccac gtaatgagga agatggatgt ttaaccaagg agtctgtggc cagatcatta    1260
cgttccgttg tcgttgaaaa ggaaggcgaa atctacaagg ccaatgcccg tgaactttca    1320
aagatctaca atgacacaaa agtagagaag gaatatgttt ctcaatttgt agattaccta    1380
gagaaaaacg ctagagccgt agctattgat catgaatcct aa                      1422

<210> SEQ ID NO 7
<211> LENGTH: 458
<212> TYPE: PRT
<213> ORGANISM: Stevia rebaudiana

<400> SEQUENCE: 7

Met Glu Asn Lys Thr Glu Thr Thr Val Arg Arg Arg Arg Arg Ile Ile

```
1               5                   10                  15
Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
                35                  40                  45

Asn Phe Asn Lys Pro Lys Thr Ser Asn Tyr Pro His Phe Thr Phe Arg
            50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
                100                 105                 110

Glu Glu Asp Glu Glu Val Ser Cys Leu Ile Thr Asp Ala Leu Trp Tyr
                115                 120                 125

Phe Ala Gln Ser Val Ala Asp Ser Leu Asn Leu Arg Arg Leu Val Leu
            130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
                180                 185                 190

Ala Tyr Ser Asn Trp Gln Ile Leu Lys Glu Ile Leu Gly Lys Met Ile
            195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
                260                 265                 270

Pro Ser Ser Val Leu Tyr Val Ser Phe Gly Ser Thr Ser Glu Val Asp
    275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
                340                 345                 350

Phe Trp Thr His Ser Gly Trp Asn Ser Thr Leu Glu Ser Val Cys Glu
            355                 360                 365

Gly Val Pro Met Ile Phe Ser Asp Phe Gly Leu Asp Gln Pro Leu Asn
            370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
                420                 425                 430
```

Lys Ala Asp Val Ser Leu Met Lys Gly Gly Ser Ser Tyr Glu Ser Leu
        435                 440                 445

Glu Ser Leu Val Ser Tyr Ile Ser Ser Leu
        450                 455

<210> SEQ ID NO 8
<211> LENGTH: 1377
<212> TYPE: DNA
<213> ORGANISM: Stevia rebaudiana

<400> SEQUENCE: 8

| | | |
|---|---|---|
| atggaaaaca agaccgaaac aacagttaga cgtaggcgta gaatcattct gtttccagta | 60 |
| cctttcaag ggcacatcaa tccaatacta caactagcca acgttttgta ctctaaaggt | 120 |
| ttttctatta caatctttca caccaatttc aacaaaccaa aaacatccaa ttacccacat | 180 |
| ttcacattca gattcatact tgataatgat ccacaagatg aacgtatttc aaacttacct | 240 |
| acccacggtc cttagctgg aatgagaatt ccaatcatca tgaacatgg tgccgatgag | 300 |
| cttagaagag aattagagtt acttatgttg gcatccgaag aggacgagga agtctcttgt | 360 |
| ctgattactg acgctctatg gtactttgcc caatctgtgg ctgatagttt gaatttgagg | 420 |
| agattggtac taatgacatc cagtctgttt aactttcacg ctcatgttag tttaccacaa | 480 |
| tttgacgaat tgggatactt ggaccctgat gacaagacta ggttagagga acaggcctct | 540 |
| ggttttccta tgttgaaagt caaagatatc aagtctgcct attctaattg gcaaatcttg | 600 |
| aaagagatct taggaaagat gatcaaacag acaaaggctt catctggagt gatttggaac | 660 |
| agtttcaaag agttagaaga gtctgaattg gagactgtaa tcagagaaat tccagcacct | 720 |
| tcattcctga taccattacc aaaacatttg actgcttcct cttcctcttt gttggatcat | 780 |
| gacagaacag ttttcaatg gttggaccaa caaccaccta gttctgtttt gtacgtgtca | 840 |
| tttggtagta cttctgaagt cgatgaaaag gacttccttg aaatcgcaag aggcttagtc | 900 |
| gatagtaagc agtcattcct ttgggtcgtg cgtccaggtt tcgtgaaagg ctcaacatgg | 960 |
| gtcgaaccac ttccagatgg ttttctaggc gaaagaggta gaatagtcaa atgggttcct | 1020 |
| caacaggaag tttagctca tggcgctatt ggggcattct ggactcattc cggatggaat | 1080 |
| tcaactttag aatcagtatg cgaagggta cctatgatct tttcagattt tggtcttgat | 1140 |
| caaccactga acgcaagata catgtctgat gttttgaaag tgggtgtata tctagaaaat | 1200 |
| ggctgggaaa ggggtgaaat agctaatgca ataagacgtg ttatggttga tgaagagggg | 1260 |
| gagtatatca gacaaaacgc aagagtgctg aagcaaaagg ccgacgtttc tctaatgaag | 1320 |
| ggaggctctt catacgaatc cttagaatct cttgtttcct acatttcatc actgtaa | 1377 |

<210> SEQ ID NO 9
<211> LENGTH: 1422
<212> TYPE: DNA
<213> ORGANISM: Stevia rebaudiana

<400> SEQUENCE: 9

| | | |
|---|---|---|
| atggctacca gtgactccat agttgacgac cgtaagcagc ttcatgttgc gacgttccca | 60 |
| tggcttgctt tcggtcacat cctcccttac cttcagcttt cgaaattgat agctgaaaag | 120 |
| ggtcacaaag tctcgtttct ttctaccacc agaaacattc aacgtctctc ttctcatatc | 180 |
| tcgccactca taaatgttgt tcaactcaca cttccacgtg tccaagagct gccggaggat | 240 |
| gcagaggcga ccactgacgt ccaccctgaa gatattccat atctcaagaa ggcttctgat | 300 |

```
ggtcttcaac cggaggtcac ccggtttcta gaacaacact ctccggactg gattatttat    360
gattatactc actactggtt gccatccatc gcggctagcc tcggtatctc acgagcccac    420
ttctccgtca ccactccatg ggccattgct tatatgggac cctcagctga cgccatgata    480
aatggttcag atggtcgaac cacgguugag atctcacga caccgcccaa gtggtttccc    540
tttccgacca agtatgctg gcggaagcat gatcttgccc gactggtgcc ttacaaagct    600
ccggggatat ctgatggata ccgtatgggg ctggttctta agggatctga ttgtttgctt    660
tccaaatgtt accatgagtt tggaactcaa tggctacctc ttttggagac actacaccaa    720
gtaccggtgg ttccggtggg attactgcca ccggaaatac ccggagacga gaaagatgaa    780
acatgggtgt caatcaagaa atggctcgat ggtaaacaaa aaggcagtgt ggtgtacgtt    840
gcattaggaa gcgaggtttt ggtgagccaa accgaggttg ttgagttagc attgggtctc    900
gagctttctg ggttgccatt tgtttgggct tatagaaaac caaaaggtcc cgcgaagtca    960
gactcggtgg agttgccaga cgggttcgtg gaacgaactc gtgaccgtgg gttggtctgg   1020
acgagttggg cacctcagtt acgaatactg agccatgagt cggtttgtgg tttcttgact   1080
cattgtggtt ctggatcaat tgtggaaggg ctaatgtttg gtcaccctct aatcatgcta   1140
ccgatttttg gggaccaacc tctgaatgct cgattactgg aggacaaaca ggtgggaatc   1200
gagataccaa gaaatgagga agatggttgc ttgaccaagg agtcggttgc tagatcactg   1260
aggtccgttg ttgtggaaaa agaaggggag atctacaagg cgaacgcgag ggagctgagt   1320
aaaatctata cgacactaa ggttgaaaaa gaatatgtaa gccaattcgt agactatttg   1380
gaaaagaatg cgcgtgcggt tgccatcgat catgagagtt aa                       1422

<210> SEQ ID NO 10
<211> LENGTH: 473
<212> TYPE: PRT
<213> ORGANISM: Stevia rebaudiana

<400> SEQUENCE: 10

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Pro Tyr Leu Lys
                85                  90                  95

Lys Ala Ser Asp Gly Leu Gln Pro Glu Val Thr Arg Phe Leu Glu Gln
            100                 105                 110

His Ser Pro Asp Trp Ile Ile Tyr Asp Tyr Thr His Tyr Trp Leu Pro
        115                 120                 125

Ser Ile Ala Ala Ser Leu Gly Ile Ser Arg Ala His Phe Ser Val Thr
    130                 135                 140

Thr Pro Trp Ala Ile Ala Tyr Met Gly Pro Ser Ala Asp Ala Met Ile
145                 150                 155                 160

Asn Gly Ser Asp Gly Arg Thr Thr Val Glu Asp Leu Thr Thr Pro Pro
                165                 170                 175
```

Lys Trp Phe Pro Phe Pro Thr Lys Val Cys Trp Arg Lys His Asp Leu
            180                 185                 190

Ala Arg Leu Val Pro Tyr Lys Ala Pro Gly Ile Ser Asp Gly Tyr Arg
        195                 200                 205

Met Gly Leu Val Leu Lys Gly Ser Asp Cys Leu Leu Ser Lys Cys Tyr
    210                 215                 220

His Glu Phe Gly Thr Gln Trp Leu Pro Leu Leu Glu Thr Leu His Gln
225                 230                 235                 240

Val Pro Val Val Pro Val Gly Leu Leu Pro Pro Glu Val Pro Gly Asp
                245                 250                 255

Glu Lys Asp Glu Thr Trp Val Ser Ile Lys Lys Trp Leu Asp Gly Lys
            260                 265                 270

Gln Lys Gly Ser Val Val Tyr Val Ala Leu Gly Ser Glu Val Leu Val
        275                 280                 285

Ser Gln Thr Glu Val Val Glu Leu Ala Leu Gly Leu Glu Leu Ser Gly
    290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
            340                 345                 350

Glu Ser Val Cys Gly Phe Leu Thr His Cys Gly Ser Gly Ser Ile Val
        355                 360                 365

Glu Gly Leu Met Phe Gly His Pro Leu Ile Met Leu Pro Ile Phe Gly
    370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Glu Lys Glu Gly Glu Ile Tyr
            420                 425                 430

Lys Ala Asn Ala Arg Glu Leu Ser Lys Ile Tyr Asn Asp Thr Lys Val
        435                 440                 445

Glu Lys Glu Tyr Val Ser Gln Phe Val Asp Tyr Leu Glu Lys Asn Thr
    450                 455                 460

Arg Ala Val Ala Ile Asp His Glu Ser
465                 470

<210> SEQ ID NO 11
<211> LENGTH: 1422
<212> TYPE: DNA
<213> ORGANISM: Stevia rebaudiana

<400> SEQUENCE: 11

```
atggctacca gtgactccat agttgacgac cgtaagcagc ttcatgttgc gacgttccca      60
tggcttgctt tcggtcacat cctcccttac cttcagcttt cgaaattgat agctgaaaag     120
ggtcacaaag tctcgtttct ttctaccacc agaaacattc aacgtctctc ttctcatatc     180
tcgccactca taaatgttgt tcaactcaca cttccacgtg tccaagagct gccggaggat     240
gcagaggcga ccactgacgt ccaccctgaa gatattccat atctcaagaa ggcttctgat     300
ggtcttcaac ggaggtcac ccggtttcta aacaacact ctccggactg gattatttat     360
gattatactc actactggtt gccatccatc gcggctagcc tcggtatctc acgagcccac     420
```

```
ttctccgtca ccactccatg ggccattgct tatatgggac cctcagctga cgccatgata    480
aatggttcag atggtcgaac cacgcgttgag atctcacga caccgcccaa gtggtttccc    540
tttccgacca agtatgctg gcggaagcat gatcttgccc gactggtgcc ttacaaagct    600
ccggggatat ctgatggata ccgtatgggg ctggttctta agggatctga ttgtttgctt    660
tccaaatgtt accatgagtt tggaactcaa tggctacctc ttttggagac actacaccaa    720
gtaccggtgg ttccggtggg attactgcca ccggaagtac ccggagacga gaaagatgaa    780
acatgggtgt caatcaagaa atggctcgat ggtaaacaaa aaggcagtgt ggtgtacgtt    840
gcattaggaa gcgaggtttt ggtgagccaa accgaggttg ttgagttagc attgggtctc    900
gagctttctg ggttgccatt tgtttgggct tatagaaaac caaaaggtcc cgcgaagtca    960
gactcggtgg agttgccaga cgggttcgtg aacgaactc gtgaccgtgg gttggtctgg   1020
acgagttggg cacctcagtt acgaatactg agccatgagt cggtttgtgg tttcttgact   1080
cattgtggtt ctggatcaat tgtggaaggg ctaatgtttg gtcaccctct aatcatgcta   1140 ccgattttg gggaccaacc tctgaatgct cgattactgg aggacaaaca ggtgggaatc   1200
gagataccaa gaaatgagga agatggttgc ttgaccaagg agtcggttgc tagatcactg   1260
aggtccgttg ttgtggaaaa agaagggag atctacaagg cgaacgcgag ggagctgagt   1320
aaaatctata cgacactaa ggttgaaaaa gaatatgtaa gccaattcgt agactatttg   1380
gaaaagaata cgcgtgcggt tgccatcgat catgagagtt aa                       1422
```

<210> SEQ ID NO 12
<211> LENGTH: 473
<212> TYPE: PRT
<213> ORGANISM: Stevia rebaudiana

<400> SEQUENCE: 12

```
Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Phe Leu Gln
            20                  25                  30

Leu Ser Lys Leu Ile Ala Glu Lys Gly His Lys Val Ser Phe Leu Ser
        35                  40                  45

Thr Thr Arg Asn Ile Gln Arg Leu Ser Ser His Ile Ser Pro Leu Ile
    50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Gln Tyr Leu Lys
                85                  90                  95

Lys Ala Val Asp Gly Leu Gln Pro Glu Val Thr Arg Phe Leu Glu Gln
            100                 105                 110

His Ser Pro Asp Trp Ile Ile Tyr Asp Phe Thr His Tyr Trp Leu Pro
        115                 120                 125

Ser Ile Ala Ala Ser Leu Gly Ile Ser Arg Ala Tyr Phe Cys Val Ile
    130                 135                 140

Thr Pro Trp Thr Ile Ala Tyr Leu Ala Pro Ser Ser Asp Ala Met Ile
145                 150                 155                 160

Asn Asp Ser Asp Gly Arg Thr Thr Val Glu Asp Leu Thr Pro Pro
                165                 170                 175

Lys Trp Phe Pro Phe Pro Thr Lys Val Cys Trp Arg Lys His Asp Leu
            180                 185                 190

Ala Arg Met Glu Pro Tyr Glu Ala Pro Gly Ile Ser Asp Gly Tyr Arg
```

```
                195                 200                 205
Met Gly Met Val Phe Lys Gly Ser Asp Cys Leu Leu Phe Lys Cys Tyr
    210                 215                 220
His Glu Phe Gly Thr Gln Trp Leu Pro Leu Leu Glu Thr Leu His Gln
225                 230                 235                 240
Val Pro Val Val Pro Val Gly Leu Leu Pro Pro Glu Ile Pro Gly Asp
                245                 250                 255
Glu Lys Asp Glu Thr Trp Val Ser Ile Lys Lys Trp Leu Asp Gly Lys
            260                 265                 270
Gln Lys Gly Ser Val Val Tyr Val Ala Leu Gly Ser Glu Ala Leu Val
        275                 280                 285
Ser Gln Thr Glu Val Val Glu Leu Ala Leu Gly Leu Glu Leu Ser Gly
    290                 295                 300
Leu Pro Phe Val Trp Ala Tyr Arg Lys Pro Lys Gly Pro Ala Lys Ser
305                 310                 315                 320
Asp Ser Val Glu Leu Pro Asp Gly Phe Val Glu Arg Thr Arg Asp Arg
                325                 330                 335
Gly Leu Val Trp Thr Ser Trp Ala Pro Gln Leu Arg Ile Leu Ser His
            340                 345                 350
Glu Ser Val Cys Gly Phe Leu Thr His Cys Gly Ser Gly Ser Ile Val
        355                 360                 365
Glu Gly Leu Met Phe Gly His Pro Leu Ile Met Leu Pro Leu Phe Gly
    370                 375                 380
Asp Gln Pro Leu Asn Ala Arg Leu Leu Glu Asp Lys Gln Val Gly Ile
385                 390                 395                 400
Glu Ile Pro Arg Asn Glu Glu Asp Gly Cys Leu Thr Lys Glu Ser Val
                405                 410                 415
Ala Arg Ser Leu Arg Ser Val Val Glu Asn Glu Gly Glu Ile Tyr
            420                 425                 430
Lys Ala Asn Ala Arg Glu Leu Ser Lys Ile Tyr Asn Asp Thr Lys Val
        435                 440                 445
Glu Lys Glu Tyr Val Ser Gln Phe Val Asp Tyr Leu Glu Lys Asn Ala
    450                 455                 460
Arg Ala Val Ala Ile Asp His Glu Ser
465                 470

<210> SEQ ID NO 13
<211> LENGTH: 1422
<212> TYPE: DNA
<213> ORGANISM: Stevia rebaudiana

<400> SEQUENCE: 13
atggctacca gtgactccat agttgacgac cgtaagcagc ttcatgttgc gacgttccca      60
tggcttgctt tcggtcacat cctcccttc cttcagcttt cgaaattgat agctgaaaag     120
ggtcacaaag tctcgtttct ttctaccacc agaaacattc aacgtctctc ttctcatatc     180
tcgccactca taaatgttgt tcaactcaca cttccacgtg tccaagagct gccggaggat     240
gcagaggcga ccactgacgt ccaccctgaa gatattcaat atctcaagaa ggctgttgat     300
ggtcttcaac cggaggtcac ccggtttcta gaacaacact ctccggactg gattatttat     360
gattttactc actactggtt gccatccatc gcggctagcc tcggtatctc acgagcctac     420
ttctgcgtca tcactccatg gaccattgct tatttggcac cctcatctga cgccatgata     480
aatgattcag atggtcgaac cacggttgag gatctcacga caccgcccaa gtggtttccc     540
```

```
tttccgacca aagtatgctg gcggaagcat gatcttgccc gaatggagcc ttacgaagct    600
ccagggatat ctgatggata ccgtatgggg atggttttta agggatctga ttgtttgctt    660
ttcaaatgtt accatgagtt tggaactcaa tggctacctc ttttggagac actacaccaa    720
gtaccggtgg ttccggtggg attactgccg ccggaaatac ccggagacga gaaagatgaa    780
acatgggtgt caatcaagaa atggctcgat ggtaaacaaa aaggcagtgt ggtgtacgtt    840
gcattaggaa gcgaggcttt ggtgagccaa accgaggttg ttgagttagc attgggtctc    900
gagctttctg ggttgccatt tgtttgggct tatagaaaac caaaggtcc cgcgaagtca    960 gactcggtgg agttgccaga cgggttcgtg gaacgaactc gtgaccgtgg gttggtctgg    1020
acgagttggg cacctcagtt acgaatactg agccatgagt cggtttgtgg tttcttgact    1080
cattgtggtt ctggatcaat tgtggaaggg ctaatgtttg gtcaccctct aatcatgcta    1140 ccgcttttg gggaccaacc tctgaatgct cgattactgg aggacaaaca ggtgggaatc    1200
gagataccaa gaaatgagga agatggttgc ttgaccaagg agtcggttgc tagatcactg    1260
aggtccgttg ttgtggaaaa cgaagggag atctacaagg cgaacgcgag ggagctgagt    1320
aaaatctata acgacactaa ggtggaaaaa gaatatgtaa gccaattcgt agactatttg    1380
gaaaagaatg cgcgtgcggt tgccatcgat catgagagtt aa                      1422

<210> SEQ ID NO 14
<211> LENGTH: 485
<212> TYPE: PRT
<213> ORGANISM: Stevia rebaudiana

<400> SEQUENCE: 14

Met Tyr Asn Val Thr Tyr His Gln Asn Ser Lys Ala Met Ala Thr Ser
1               5                   10                  15

Asp Ser Ile Val Asp Asp Arg Lys Gln Leu His Val Ala Thr Phe Pro
            20                  25                  30

Trp Leu Ala Phe Gly His Ile Leu Pro Phe Leu Gln Leu Ser Lys Leu
        35                  40                  45

Ile Ala Glu Lys Gly His Lys Val Ser Phe Leu Ser Thr Thr Arg Asn
    50                  55                  60

Ile Gln Arg Leu Ser Ser His Ile Ser Pro Leu Ile Asn Val Val Gln
65                  70                  75                  80

Leu Thr Leu Pro Arg Val Gln Glu Leu Pro Glu Asp Ala Glu Ala Thr
                85                  90                  95

Thr Asp Val His Pro Glu Asp Ile Gln Tyr Leu Lys Lys Ala Val Asp
            100                 105                 110

Gly Leu Gln Pro Glu Val Thr Arg Phe Leu Glu Gln His Ser Pro Asp
        115                 120                 125

Trp Ile Ile Tyr Asp Phe Thr His Tyr Trp Leu Pro Ser Ile Ala Ala
    130                 135                 140

Ser Leu Gly Ile Ser Arg Ala Tyr Phe Cys Val Ile Thr Pro Trp Thr
145                 150                 155                 160

Ile Ala Tyr Leu Ala Pro Ser Ser Asp Ala Met Ile Asn Asp Ser Asp
                165                 170                 175

Gly Arg Thr Thr Val Glu Asp Leu Thr Thr Pro Pro Lys Trp Phe Pro
            180                 185                 190

Phe Pro Thr Lys Val Cys Trp Arg Lys His Asp Leu Ala Arg Met Glu
        195                 200                 205

Pro Tyr Glu Ala Pro Gly Ile Ser Asp Gly Tyr Arg Met Gly Met Val
    210                 215                 220
```

```
Phe Lys Gly Ser Asp Cys Leu Leu Phe Lys Cys Tyr His Glu Phe Gly
225                 230                 235                 240

Thr Gln Trp Leu Pro Leu Leu Glu Thr Leu His Gln Val Pro Val Val
            245                 250                 255

Pro Val Gly Leu Leu Pro Pro Glu Ile Pro Gly Asp Glu Lys Asp Glu
        260                 265                 270

Thr Trp Val Ser Ile Lys Lys Trp Leu Asp Gly Lys Gln Lys Gly Ser
    275                 280                 285

Val Val Tyr Val Ala Leu Gly Ser Glu Ala Leu Val Ser Gln Thr Glu
290                 295                 300

Val Val Glu Leu Ala Leu Gly Leu Glu Leu Ser Gly Leu Pro Phe Val
305                 310                 315                 320

Trp Ala Tyr Arg Lys Pro Lys Gly Pro Ala Lys Ser Asp Ser Val Glu
            325                 330                 335

Leu Pro Asp Gly Phe Val Glu Arg Thr Arg Asp Arg Gly Leu Val Trp
        340                 345                 350

Thr Ser Trp Ala Pro Gln Leu Arg Ile Leu Ser His Glu Ser Val Cys
    355                 360                 365

Gly Phe Leu Thr His Cys Gly Ser Gly Ser Ile Val Glu Gly Leu Met
370                 375                 380

Phe Gly His Pro Leu Ile Met Leu Pro Ile Phe Cys Asp Gln Pro Leu
385                 390                 395                 400

Asn Ala Arg Leu Leu Glu Asp Lys Gln Val Gly Ile Glu Ile Pro Arg
            405                 410                 415

Asn Glu Glu Asp Gly Cys Leu Thr Lys Glu Ser Val Ala Arg Ser Leu
        420                 425                 430

Arg Ser Val Val Val Glu Asn Glu Gly Glu Ile Tyr Lys Ala Asn Ala
    435                 440                 445

Arg Ala Leu Ser Lys Ile Tyr Asn Asp Thr Lys Val Glu Lys Glu Tyr
450                 455                 460

Val Ser Gln Phe Val Asp Tyr Leu Glu Lys Asn Ala Arg Ala Val Ala
465                 470                 475                 480

Ile Asp His Glu Ser
            485

<210> SEQ ID NO 15
<211> LENGTH: 1458
<212> TYPE: DNA
<213> ORGANISM: Stevia rebaudiana

<400> SEQUENCE: 15
atgtacaacg ttacttatca tcaaaattca aaagcaatgg ctaccagtga ctccatagtt      60
gacgaccgta agcagcttca tgttgcgacg ttcccatggc ttgctttcgg tcacatcctc     120
cctttccttc agctttcgaa attgatagct gaaaagggtc acaaagtctc gtttctttct     180
accaccagaa acattcaacg tctctcttct catatctcgc cactcataaa tgttgttcaa     240
ctcacacttc acgtgtccca agagctgccg gaggatgcag aggcgaccac tgacgtccac     300
cctgaagata ttcaatatct caagaaggct gttgatggtc ttcaaccgga ggtcaccccgg   360 tttctagaac aacactctcc ggactggatt atttatgatt ttactcacta ctggttgcca     420
tccatcgcgg ctagcctcgg tatctcacga gcctacttct gcgtcatcac tccatggacc     480
attgcttatt tggcaccctc atctgacgcc atgataaatg attcagatgg tcgaaccacg     540
gttgaggatc tcacgacacc gcccaagtgg tttcccttc cgaccaaagt atgctggcgg      600
```

```
aagcatgatc ttgcccgaat ggagccttac gaagctccgg ggatatctga tggataccgt    660
atggggatgg ttttaaggg atctgattgt ttgcttttca aatgttacca tgagtttgga    720
actcaatggc tacctctttt ggagacacta caccaagtac cggtggttcc ggtgggatta    780
ctgccgccgg aaatacccgg agacgagaaa gatgaaacat gggtgtcaat caagaaatgg    840
ctcgatggta aacaaaaagg cagtgtggtg tacgttgcat taggaagcga ggctttggtg    900
agccaaaccg aggttgttga gttagcattg ggtctcgagc tttctgggtt gccatttgtt    960
tgggcttata gaaaaccaaa aggtcccgcg aagtcagact cggtggagtt gccagacggg   1020
ttcgtggaac gaactcgtga ccgtgggttg gtctggacga gttgggcacc tcagttacga   1080
atactgagcc acgagtcagt ttgtggtttc ttgactcatt gtggttctgg atcaattgtg   1140
gaagggctaa tgtttggtca ccctctaatc atgctaccga ttttttgtga ccaacctctg   1200
aatgctcgat tactggagga caaacaggtg ggaatcgaga taccaagaaa tgaggaagat   1260
ggttgcttga ccaaggagtc ggttgctaga tcactgaggt ccgttgttgt ggaaaacgaa   1320
ggggagatct acaaggcgaa cgcgagggcg ctgagtaaaa tctataacga cactaaggtg   1380
gaaaaagaat atgtaagcca attcgtagac tatttggaaa agaatgcgcg tgcggttgcc   1440
atcgatcatg agagttaa                                                 1458
```

<210> SEQ ID NO 16
<211> LENGTH: 473
<212> TYPE: PRT
<213> ORGANISM: Stevia rebaudiana

<400> SEQUENCE: 16

```
Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Phe Leu Gln
                20                  25                  30

Leu Ser Lys Leu Ile Ala Glu Lys Gly His Lys Val Ser Phe Leu Ser
            35                  40                  45

Thr Thr Arg Asn Ile Gln Arg Leu Ser Ser His Ile Ser Pro Leu Ile
        50                  55                  60

Asn Val Val Gln Leu Thr Leu Pro Arg Val Gln Glu Leu Pro Glu Asp
65                  70                  75                  80

Ala Glu Ala Thr Thr Asp Val His Pro Glu Asp Ile Gln Tyr Leu Lys
                85                  90                  95

Lys Ala Val Asp Gly Leu Gln Pro Glu Val Thr Arg Phe Leu Glu Gln
            100                 105                 110

His Ser Pro Asp Trp Ile Ile Tyr Asp Phe Thr His Tyr Trp Leu Pro
        115                 120                 125

Ser Ile Ala Ala Ser Leu Gly Ile Ser Arg Ala Tyr Phe Cys Val Ile
    130                 135                 140

Thr Pro Trp Thr Ile Ala Tyr Leu Ala Pro Ser Ser Asp Ala Met Ile
145                 150                 155                 160

Asn Asp Ser Asp Gly Arg Thr Thr Val Glu Asp Leu Thr Thr Pro Pro
                165                 170                 175

Lys Trp Phe Pro Phe Pro Thr Lys Val Cys Trp Arg Lys His Asp Leu
            180                 185                 190

Ala Arg Met Glu Pro Tyr Glu Ala Pro Gly Ile Ser Asp Gly Tyr Arg
        195                 200                 205

Met Gly Met Val Phe Lys Gly Ser Asp Cys Leu Leu Phe Lys Cys Tyr
```

```
                210                 215                 220
His Glu Phe Gly Thr Gln Trp Leu Pro Leu Leu Glu Thr Leu His Gln
225                 230                 235                 240

Val Pro Val Pro Val Gly Leu Leu Pro Pro Glu Ile Pro Gly Asp
                245                 250                 255

Glu Lys Asp Glu Thr Trp Val Ser Ile Lys Lys Trp Leu Asp Gly Lys
                260                 265                 270

Gln Lys Gly Ser Val Val Tyr Val Ala Leu Gly Ser Glu Ala Leu Val
            275                 280                 285

Ser Gln Thr Glu Val Val Glu Leu Ala Leu Gly Leu Glu Leu Ser Gly
        290                 295                 300

Leu Pro Phe Val Trp Ala Tyr Arg Lys Pro Lys Gly Pro Ala Lys Ser
305                 310                 315                 320

Asp Ser Val Glu Leu Pro Asp Gly Phe Val Glu Arg Thr Arg Asp Arg
                325                 330                 335

Gly Leu Val Trp Thr Ser Trp Ala Pro Gln Leu Arg Ile Leu Ser His
                340                 345                 350

Glu Ser Val Cys Gly Phe Leu Thr His Cys Gly Ser Gly Ser Ile Val
            355                 360                 365

Glu Gly Leu Met Phe Gly His Pro Leu Ile Met Leu Pro Ile Phe Cys
        370                 375                 380

Asp Gln Pro Leu Asn Ala Arg Leu Leu Glu Asp Lys Gln Val Gly Ile
385                 390                 395                 400

Glu Ile Pro Arg Asn Glu Glu Asp Gly Cys Leu Thr Lys Glu Ser Val
                405                 410                 415

Ala Arg Ser Leu Arg Ser Val Val Glu Asn Glu Gly Glu Ile Tyr
                420                 425                 430

Lys Ala Asn Ala Arg Ala Leu Ser Lys Ile Tyr Asn Asp Thr Lys Val
            435                 440                 445

Glu Lys Glu Tyr Val Ser Gln Phe Val Asp Tyr Leu Glu Lys Asn Ala
        450                 455                 460

Arg Ala Val Ala Ile Asp His Glu Ser
465                 470

<210> SEQ ID NO 17
<211> LENGTH: 1422
<212> TYPE: DNA
<213> ORGANISM: Stevia rebaudiana

<400> SEQUENCE: 17
atggctacca gtgactccat agttgacgac cgtaagcagc ttcatgttgc gacgttccca        60
tggcttgctt tcggtcacat cctccctttc cttcagcttt cgaaattgat agctgaaaag       120
ggtcacaaag tctcgtttct ttctaccacc agaaacattc aacgtctctc ttctcatatc       180
tcgccactca taaatgttgt tcaactcaca cttccacgtg tccaagagct gccggaggat       240
gcagaggcga ccactgacgt ccaccctgaa gatattcaat atctcaagaa ggctgttgat       300
ggtcttcaac cggaggtcac ccggtttcta gaacaacact ctccggactg gattatttat       360
gattttactc actactggtt gccatccatc gcggctagcc tcggtatctc acgagcctac       420
ttctgcgtca tcactccatg gaccattgct tatttggcac cctcatctga cgccatgata       480
aatgattcag atggtcgaac cacggttgag gatctcacga caccgcccaa gtggtttccc       540
tttccgacca agtatgctgg cggaagcat gatcttgccc gaatgagcc ttacgaagct       600 ccggggatat ctgatggata ccgtatgggg atggttttta aggatctga ttgtttgctt       660
```

```
ttcaaatgtt accatgagtt tggaactcaa tggctacctc ttttggagac actacaccaa    720
gtaccggtgg ttccggtggg attactgccg ccggaaatac ccggagacga gaaagatgaa    780
acatgggtgt caatcaagaa atggctcgat ggtaaacaaa aaggcagtgt ggtgtacgtt    840
gcattaggaa gcgaggcttt ggtgagccaa accgaggttg ttgagttagc attgggtctc    900
gagctttctg ggttgccatt tgtttgggct tatagaaaac caaaaggtcc cgcgaagtca    960
gactcggtga gttgccaga cgggttcgtg aacgaactc gtgaccgtgg gttggtctgg      1020
acgagttggg cacctcagtt acgaatactg agccacgagt cagtttgtgg tttcttgact    1080
cattgtggtt ctggatcaat tgtggaaggg ctaatgtttg gtcaccctct aatcatgcta    1140
ccgatttttt gtgaccaacc tctgaatgct cgattactgg aggacaaaca ggtgggaatc    1200
gagataccaa gaaatgagga agatggttgc ttgaccaagg agtcggttgc tagatcactg    1260
aggtccgttg ttgtggaaaa cgaaggggag atctacaagg cgaacgcgag ggcgctgagt    1320
aaaatctata acgacactaa ggtggaaaaa gaatatgtaa gccaattcgt agactatttg    1380
gaaaagaatg cgcgtgcggt tgccatcgat catgagagtt aa                       1422
```

<210> SEQ ID NO 18
<211> LENGTH: 1086
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atggctttgg taaacccaac cgctctttc tatggtacct ctatcagaac aagacctaca      60
aacttactaa atccaactca aaagctaaga ccagtttcat catcttcctt accttctttc    120
tcatcagtta gtgcgattct tactgaaaaa catcaatcta atccttctga gaacaacaat    180
ttgcaaactc atctagaaac tcctttcaac tttgatagtt atatgttgga aaaagtcaac    240
atggttaacg aggcgcttga tgcatctgtc ccactaaaag acccaatcaa atccatgaa     300 tccatgagat actctttatt ggcaggcggt aagagaatca gaccaatgat gtgtattgca    360
gcctgcgaaa tagtcggagg taatatcctt aacgccatgc cagccgcatg tgccgtggaa    420
atgattcata ctatgtcttt ggtgcatgac gatcttccat gtatggataa tgatgacttc    480
agaagaggta aacctatttc acacaaggtc tacggggagg aaatggcagt attgaccggc    540
gatgctttac taagtttatc tttcgaacat atagctactg ctacaaaggg tgtatcaaag    600
gatagaatcg tcagagctat aggggagttg gcccgttcag ttggctccga aggtttagtg    660
gctggacaag ttgtagatat cttgtcagag ggtgctgatg ttggattaga tcacctagaa    720
tacattcaca tccacaaaac agcaatgttg cttgagtcct cagtagttat tggcgctatc    780
atgggaggag gatctgatca gcagatcgaa aagttgagaa aattcgctag atctattggt    840
ctactattcc aagttgtgga tgacattttg gatgttacaa aatctaccga agagttgggg    900
aaaacagctg gtaaggattt gttgacagat aagacaactt acccaaagtt gttaggtata    960
gaaagtccaa gagaattgcc cgaaaaactt aacaaggaag cacaagagca attaagtggc   1020
tttgatagac gtaaggcagc tcctttgatc gcgttagcca actacaatgc gtaccgtcaa   1080
aattga                                                               1086
```

<210> SEQ ID NO 19
<211> LENGTH: 1029

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

| | |
|---|---:|
| atggctgagc aacaaatatc taacttgctg tctatgtttg atgcttcaca tgctagtcag | 60 |
| aaattagaaa ttactgtcca aatgatggac ataccatt acagagaaac gcctccagat | 120 |
| tcctcatctt ctgaaggcgg ttcattgtct agatacgacg agagaagagt ctctttgcct | 180 |
| ctcagtcata atgctgcctc tccagatatt gtatcacaac tatgttttc cactgcaatg | 240 |
| tcttcagagt tgaatcacag atggaaatct caaagattaa aggtggccga ttctccttac | 300 |
| aactatatcc taacattacc atcaaaagga attagaggtg cctttatcga ttccctgaac | 360 |
| gtatggttgg aggttccaga ggatgaaaca tcagtcatca aggaagttat tggtatgctc | 420 |
| cacaactctt cattaatcat tgatgacttc caagataatt ctccacttag aagaggaaag | 480 |
| ccatctaccc atacagtctt cggccctgcc caggctatca atactgctac ttacgttata | 540 |
| gttaaagcaa tcgaaaagat acaagacata gtgggacacg atgcattggc agatgttacg | 600 |
| ggtactatta caactatttt ccaaggtcag gccatggact tgtggtggac agcaaatgca | 660 |
| atcgttccat caatacagga atacttactt atggtaaacg ataaaaccgg tgctctcttt | 720 |
| agactgagtt tggagttgtt agctctgaat tccgaagcca gtatttctga ctctgcttta | 780 |
| gaaagtttat ctagtgctgt ttccttgcta ggtcaatact tccaaatcag agacgactat | 840 |
| atgaacttga tcgataacaa gtatacagat cagaaaggct ctgcgaaga tcttgatgaa | 900 |
| ggcaagtact cactaacact tattcatgcc ctccaaactg attcatccga tctactgacc | 960 |
| aacatccttt caatgagaag agtgcaagga aagttaacgg cacaaaagag atgttggttc | 1020 |
| tggaaatga | 1029 |

<210> SEQ ID NO 20
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

| | |
|---|---:|
| atggaaaaga ctaaggagaa agcagaacgt atcttgctgg agccatacag atacttatta | 60 |
| caactaccag gaaagcaagt ccgttctaaa ctatcacaag cgttcaatca ctggttaaaa | 120 |
| gttcctgaag ataagttaca aatcattatt gaagtcacag aaatgctaca caatgcttct | 180 |
| ttactgatcg atgatataga ggattcttcc aaactgagaa gaggttttcc tgtcgctcat | 240 |
| tccatatacg gggtaccaag tgtaatcaac tcagctaatt acgtctactt cttgggattg | 300 |
| gaaaaagtat tgacattaga tcatccgac gctgtaaagc tattccacag caacttctt | 360 |
| gaattgcatc aaggtcaagg tttggatatc tattggagag acacttatac ttgcccaaca | 420 |
| gaagaggagt acaaagcaat ggttctacaa aagactggcg gtttgttcgg acttgccgtt | 480 |
| ggtctgatgc aacttttctc tgattacaag gaggacttaa gcctctgtt ggataccttg | 540 |
| ggcttgtttt tccagattag agatgactac gctaacttac attcaaagga atattcagaa | 600 |
| aacaaatcat tctgtgaaga tttgactgaa gggaagttta gttttccaac aatccacgcc | 660 |
| atttggtcaa gaccagaatc tactcaagtg caaaacattc tgcgtcagag aacagagaat | 720 |

| | |
|---|---|
| attgacatca aaaagtattg tgttcagtac ttggaagatg ttggttcttt tgcttacaca | 780 |
| agacatacac ttagagaatt agaggcaaaa gcatacaagc aaatagaagc ctgtggaggc | 840 |
| aatccttctc tagtggcatt ggttaaacat ttgtccaaaa tgttcaccga ggaaaacaag | 900 |
| taa | 903 |

<210> SEQ ID NO 21
<211> LENGTH: 1020
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 21

| | |
|---|---|
| atggcaagat tctattttct taacgcacta ttgatggtta tctcattaca atcaactaca | 60 |
| gccttcactc cagctaaact tgcttatcca acaacaacaa cagctctaaa tgtcgcctcc | 120 |
| gccgaaactt ctttcagtct agatgaatac ttggcctcta agataggacc tatagagtct | 180 |
| gccttggaag catcagtcaa atccagaatt ccacagaccg ataagatctg cgaatctatg | 240 |
| gcctactctt tgatggcagg aggcaagaga attagaccag tgttgtgtat cgctgcatgt | 300 |
| gagatgttcg gtggatccca agatgtcgct atgcctactg ctgtggcatt agaaatgata | 360 |
| cacacaatgt ctttgattca tgatgatttg ccatccatgg ataacgatga cttgagaaga | 420 |
| ggtaaaccaa caaaccatgt cgttttcggc gaagatgtag ctattcttgc aggtgactct | 480 |
| ttattgtcaa cttccttcga gcacgtcgct agagaaacaa aaggagtgtc agcagaaaag | 540 |
| atcgtggatg ttatcgctag attaggcaaa tctgttggtg ccgagggcct tgctggcggt | 600 |
| caagttatgg acttagaatg tgaagctaaa ccaggtacca cattagacga cttgaaatgg | 660 |
| attcatatcc ataaaaccgc tacattgtta caagttgctg tagcttctgg tgcagttcta | 720 |
| ggtggtgcaa ctcctgaaga ggttgctgca tgcgagttgt ttgctatgaa tataggtctt | 780 |
| gcctttcaag ttgccgacga tatccttgat gtaaccgctt catcagaaga tttgggtaaa | 840 |
| actgcaggca agatgaagc tactgataag acaacttacc caaagttatt aggattagaa | 900 |
| gagagtaagg catacgcaag acaactaatc gatgaagcca aggaaagttt ggctcctttt | 960 |
| ggagatagag ctgcccctt attggccatt gcagatttca ttattgatag aaagaattga | 1020 |

<210> SEQ ID NO 22
<211> LENGTH: 1068
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 22

| | |
|---|---|
| atgcacttag caccacgtag agtccctaga ggtagaagat caccacctga cagagttcct | 60 |
| gaaagacaag gtgccttggg tagaagacgt ggagctggct ctactggctg tgcccgtgct | 120 |
| gctgctggtg ttcaccgtag aagaggagga ggcgaggctg atccatcagc tgctgtgcat | 180 |
| agaggctggc aagccggtgg tggcaccggt ttgcctgatg aggtggtgtc taccgcagcc | 240 |
| gccttagaaa tgtttcatgc ttttgcttta atccatgatg atatcatgga tgatagtgca | 300 |
| actagaagag gctccccaac tgttcacaga gccctagctg atcgtttagg cgctgctctg | 360 |
| gacccagatc aggccggtca actaggagtt tctactgcta tcttggttgg agatctggct | 420 |
| ttgacatggt ccgatgaatt gttatacgct ccattgactc cacatagact ggcagcagta | 480 |

```
ctaccattgg taacagctat gagagctgaa accgttcatg gccaatatct tgatataact    540
agtgctagaa gacctgggac cgatacttct cttgcattga gaatagccag atataagaca    600
gcagcttaca caatggaacg tccactgcac attggtgcag ccctggctgg ggcaagacca    660
gaactattag cagggctttc agcatacgcc ttgccagctg gagaagcctt ccaattggca    720
gatgacctgc taggcgtctt cggtgatcca agacgtacag ggaaacctga cctagatgat    780
cttagaggtg gaaagcatac tgtcttagtc gccttggcaa gagaacatgc cactccagaa    840
cagagacaca cattggatac attattgggt acaccaggtc ttgatagaca aggcgcttca    900
agactaagat gcgtattggt agcaactggt gcaagagccg aagccgaaag acttattaca    960
gagagaagag atcaagcatt aactgcattg aacgcattaa cactgccacc tcctttagct   1020
gaggcattag caagattgac attagggtct acagctcatc ctgcctaa                1068
```

<210> SEQ ID NO 23
<211> LENGTH: 993
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
atgtcatatt tcgataacta cttcaatgag atagttaatt ccgtgaacga catcattaag     60
tcttacatct ctggcgacgt accaaaacta tacgaagcct cctaccattt gtttacatca    120
ggaggaaaga gactaagacc attgatcctt acaatttctt ctgatctttt cggtggacag    180
agagaaagag catactatgc tggcgcagca atcgaagttt tgcacacatt cactttggtt    240
cacgatgata tcatggatca agataacatt cgtagaggtc ttcctactgt acatgtcaag    300
tatggcctac ctttggccat tttagctggt gacttattgc atgcaaaagc ctttcaattg    360
ttgactcagg cattgagagg tctaccatct gaaactatca tcaaggcgtt tgatatcttt    420
acaagatcta tcattatcat atcagaaggt caagctgtcg atatggaatt cgaagataga    480
attgatatca aggaacaaga gtatttggat atgatatctc gtaaaaccgc tgccttattc    540
tcagcttctt cttccattgg ggcgttgata gctggagcta atgataacga tgtgagatta    600
atgtccgatt tcggtacaaa tcttgggatc gcatttcaaa ttgtagatga tatacttggt    660
ttaacagctg atgaaaaaga gctaggaaaa cctgttttca gtgatatcag agaaggtaaa    720
aagaccatat tagtcattaa gactttagaa ttgtgtaagg aagacgagaa aaagattgtg    780
ttaaaagcgc taggcaacaa gtcagcatca aaggaagagt tgatgagttc tgctgacata    840
atcaaaaagt actcattgga ttacgcctac aacttagctg agaaatacta caaaaacgcc    900
atcgattctc taaatcaagt ttcaagtaaa agtgatattc cagggaaggc attgaaatat    960
cttgctgaat tcaccatcag aagacgtaag taa                                 993
```

<210> SEQ ID NO 24
<211> LENGTH: 894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
atggtcgcac aaactttcaa cctggatacc tacttatccc aaagacaaca acaagttgaa     60
```

```
gaggccctaa gtgctgctct tgtgccagct tatcctgaga gaatatacga agctatgaga      120
tactccctcc tggcaggtgg caaaagatta agacctatct tatgtttagc tgcttgcgaa      180
ttggcaggtg gttctgttga acaagccatg ccaactgcgt gtgcacttga aatgatccat      240
acaatgtcac taattcatga tgacctgcca gccatggata cgatgatttt cagaagagga      300
aagccaacta atcacaaggt gttcggggaa gatatagcca tcttagcggg tgatgcgctt      360
ttagcttacg cttttgaaca tattgcttct caaacaagag gagtaccacc tcaattggtg      420
ctacaagtta ttgctagaat cggacacgcc gttgctgcaa caggcctcgt tggaggccaa      480
gtcgtagacc ttgaatctga aggtaaagct atttccttag aaacattgga gtatattcac      540
tcacataaga ctggagcctt gctggaagca tcagttgtct caggcggtat tctcgcaggg      600
gcagatgaag agcttttggc cagattgtct cattacgcta gagatatagg cttggctttt      660
caaatcgtcg atgatatcct ggatgttact gctacatctg aacagttggg gaaaaccgct      720
ggtaaagacc aggcagccgc aaaggcaact tatccaagtc tattgggttt agaagcctct      780
agacagaaag cggaagagtt gattcaatct gctaaggaag ccttaagacc ttacggttca      840
caagcagagc cactcctagc gctggcagac ttcatcacac gtcgtcagca ttaa            894

<210> SEQ ID NO 25
<211> LENGTH: 1116
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atggcctctg ttactttggg ttcctggatc gtcgtccacc accataacca tcaccatcca       60
tcatctatcc taactaaatc tcgttcaaga tcctgtccta ttacactaac caaaccaatc      120
tcttttcgtt caaagagaac agtttcctct agtagttcta tcgtgtcctc tagtgtcgtc      180
actaaggaag acaatctgag acagtctgaa ccttcttcct ttgatttcat gtcatatatc      240
attactaagg cagaactagt gaataaggct cttgattcag cagttccatt aagagagcca      300
ttgaaaatcc atgaagcaat gagatactct cttctagctg gcgggaagag agtcagacct      360
gtactctgca tagcagcgtg cgaattagtt ggtggcgagg aatcaaccgc tatgcctgcc      420
gcttgtgctg tagaaatgat tcatacaatg tcactgatac acgatgattt gccatgtatg      480
gataacgatg atctgagaag gggtaagcca actaaccata aggttttcgg cgaagatgtt      540
gccgtcttag ctggtgatgc tttgttatct ttcgcgttcg aacatttggc atccgcaaca      600
tcaagtgatg ttgtgtcacc agtaagagta gttagagcag ttggagaact ggctaaagct      660
attggaactg agggtttagt tgcaggtcaa gtcgtcgata tctcttccga aggtcttgat      720
ttgaatgatg taggtcttga acatctcgaa ttcatccatc ttcacaagac agctgcactt      780
ttagaagcca gtgcggttct cggcgcaatt gttggcggag ggagtgatga cgaaattgag      840
agattgagga agtttgctag atgtatagga ttactgttcc aagtagtaga cgatatacta      900
gatgtgacaa agtcttccaa agagttggga aaaacagctg gtaaagattt gattgccgac      960
aaattgacct accctaagat tatggggcta gaaaaatcaa gagaatttgc cgagaaactc     1020
aatagagagg cgcgtgatca actgttgggt ttcgattctg ataaagttgc accactctta     1080
gccttagcca actacatcgc ttacagacaa aactaa                              1116

<210> SEQ ID NO 26
```

```
<211> LENGTH: 1086
<212> TYPE: DNA
<213> ORGANISM: Stevia rebaudiana

<400> SEQUENCE: 26
atggctcttg taaatcccac agctttgttc tatggaacct ccataagaac cagacccaca      60
aacttgctca acccgaccca aaacttcga cccgtttcct cgtcttcttt gccttccttc     120
tcttcagttt ctgcaatctt gacggaaaaa caccaatcaa acccatcaga aacaataac     180 ttgcaaaccc atctcgaaac accattcaat ttcgactctt acatgctgga gaaagtaaac     240
atggtgaatg aagctctgga cgcctcggtt ccactcaaag acccgataaa gatccatgaa     300
tccatgcggt actcccttct agctggcggg aaacgcatcc gaccgatgat gtgcatcgcc     360
gcttgcgaaa tagtcggagg caacatatta acgccatgc cagctgcatg cgcggtcgag      420
atgattcaca ccatgtcact agttcatgac gaccttccat gcatggataa cgacgacttc     480
cgacgtggaa aaccaataag ccacaaggtg tacggtgaag aaatggcggt tctaaccggg     540
gacgcgttac tctcattatc cttcgaacat atcgcgaccg cgacaaaagg cgtatccaaa     600
gacaggatcg tccgagccat tggtgaactc gcaaggtccg ttggctcgga gggtttggtc     660
gccggtcagg tggttgatat tttatccgaa ggggctgatg ttgggttaga ccacttggag     720
tatattcata tacacaagac tgcaatgttg cttgagagct cggtcgtgat cggcgcgatc     780
atgggcggtg ggtctgacca acagatcgaa aagttgcgaa agtttgcgag atcgattggt     840
ttgttgtttc aggtggtaga tgatattctt gatgtcacaa agtcgactga ggaattgggg     900
aaaacggcgg gaaaagattt gctgacggac aagacaacgt atccgaagtt gttgggatc     960 gaaaaatcga gagaatttgc ggagaaatta acaaggaag cgcaagaaca attgtcgggg    1020
tttgatcgcc gcaaggcggc tccgttaatt gcccttgcta attacaatgc ttataggcaa    1080
aactga                                                               1086

<210> SEQ ID NO 27
<211> LENGTH: 1029
<212> TYPE: DNA
<213> ORGANISM: Gibberella fujikuroi

<400> SEQUENCE: 27
atggctgaac aacagatctc caaccttctt tcaatgtttg atgcttctca cgcaagccag      60
aagttggaga ttacggttca gatgatggat acctaccatt acagagaaac tcctccagac     120
tcttcctctt cagaaggcgg ttccttatct cgctatgatg agcgacgggt ctcccttccg     180
ctctctcaca atgcagcctc cccagacata gtctcccagt tatgcttctc aacagctatg     240
agctcggagc tcaatcacag gtggaagtca cagcgcctca aggttgctga ctctcctac      300 aactacatcc tgactcttcc atctaaaggt attcgtgggg ctttcattga ctcactgaat     360
gtctggctcg aggtccccga agacgagacc tcggtgatca agaggtgat tggcatgctc      420 cacaactcgt ctctcataat cgatgacttc aagacaact ccccacttcg gcggggcaag      480
ccatctacac atactgtctt cggtccagca aagcaatca acacagcaac atatgtcatc     540
gtcaaggcca tcgagaaaat acaggatatc gtcggtcacg atgcattggc agatgtaact     600
ggcactataa ccacaatctt ccagggtcag gcaatggatc tgtggtggac tgctaatgcc     660
attgttccgt ctatccaaga atatctcctg atggtcaatg acaagactgg tgccctgttc     720
aggttatcgc ttgaactact ggcgctgaac tctgaagcat ccatcagtga cagcgcgctt     780
gaatctctca gcagcgctgt ctcactgctc gggcagtatt ccagataag agatgattac     840
```

```
atgaatctca ttgacaacaa gtatactgat cagaaaggat tttgcgagga tctggacgag    900
gggaaatact cgttgactct aatccatgct ctgcagaccg actccagcga ccttctcacc    960
aacatcttat cgatgagaag agtccaagga aaacttacgg cgcagaaaag atgctggttt   1020
tggaagtga                                                           1029
```

<210> SEQ ID NO 28
<211> LENGTH: 903
<212> TYPE: DNA
<213> ORGANISM: Mus musculus

<400> SEQUENCE: 28

```
atggagaaaa ctaaagagaa agctgagagg attcttctag agccctatag gtacttactt     60
cagttaccag gtaaacaggt gagaagcaaa cttcacagg catttaatca ctggctgaaa    120
gttccagaag acaagctaca gattatcatt gaagtgactg aaatgttgca taatgccagt    180
ttactcattg atgatattga agacagttca aagctccgac gtggtttccc agtggctcac    240
agcatctatg gtgtcccatc tgtcattaat tctgccaatt acgtctactt ccttggactg    300
gaaaaagtct taacccttga tcacccggat gcggtgaagc ttttcacacg ccagcttctg    360
gaacttcatc agggacaagg cctcgatatt tactggaggg acacctacac ttgtccaact    420
gaagaagaat ataaagccat ggtgttgcag aagacaggtg gtttgtttgg attagcagta    480
ggtcttatgc agctgttctc tgattacaaa gaagatctaa agccactgct tgacacactt    540
gggctctttt tccagattag agatgattat gccaatctac actccaaaga atacagtgaa    600
aacaaaagtt tctgtgaaga cttgacagaa gggaagttct cattccccac tatccatgcc    660
atttggtcaa ggccagaaag cacccaggta cagaacatcc tgcgccagag aacagagaat    720
atagatatta aaaagtattg tgtgcagtac ctggaggatg taggttcttt tgcatacact    780
cgacacactc ttagagagct tgaagctaaa gcctacaaac aaattgaggc ctgtggtggg    840
aacccttcac tagtggcttt agtcaagcac ttaagtaaga tgttcacaga agaaaataaa    900
taa                                                                 903
```

<210> SEQ ID NO 29
<211> LENGTH: 1020
<212> TYPE: DNA
<213> ORGANISM: Thalassiosira pseudonana

<400> SEQUENCE: 29

```
atggctcgtt tctacttcct gaacgctctc ctcatggtga tttctttaca aagcaccacg     60
gcattcaccc cggcaaaact cgcctaccca acaaccacca ctgcattaaa cgttgcctct    120
gccgaaacat catttagcct cgatgaatac ctagcctcca aaatcggacc cattgaatca    180
gctctcgagg catctgtcaa atctcgcatt cctcaaactg acaagatatg cgagtctatg    240
gcatactcac tcatggctgg aggaaagcgt atccgtcccg ttttgtgcat gctgcttgt     300
gaaatgtttg ggggaagtca agatgtggct atgccgacgg ctgtggcttt ggagatgatt    360
catactatga gtcttattca tgacgatttg ccttcaatgg acaacgatga tctccgacga    420
ggaaagccaa ctaatcatgt tgtctttgga gaggatgttg ctattcttgc tggggattct    480
cttctcagta cgtcttttga acatgttgcc cgtgaaacca aaggagtgtc agctgaaaag    540
attgtagatg ttatcgctcg cctcgggaag tctgtgggtg cagagggtct tgctggtgga    600
caggttatgg atcttgagtg tgaggcgaag ccaggaacta ccctcgacga tctcaagtgg    660
```

| | |
|---|---|
| attcacattc acaaaactgc cactcttctt caagtggcag tggcatcagg tgctgttctt | 720 |
| ggaggggcca caccagagga ggttgctgct tgtgaactgt tcgcaatgaa tattggactt | 780 |
| gccttccagg tcgctgatga tattttggac gtgacggcat cgagtgagga tcttggcaaa | 840 |
| actgctggaa aggatgaagc cacagataag acaacttatc ctaagctttt gggattggag | 900 |
| gagagtaagg catacgctcg acaactcata gacgaagcaa aggaatcttt ggctcctttc | 960 |
| ggtgatcgtg ctgctccatt gttggcaatt gccgacttta tcattgatcg aaagaactag | 1020 |

<210> SEQ ID NO 30
<211> LENGTH: 1068
<212> TYPE: DNA
<213> ORGANISM: Streptomyces clavuligerus

<400> SEQUENCE: 30

| | |
|---|---|
| atgcacctgg ctccccgccg agtaccgcgc ggccgtcgaa gcccacctga ccgcgttcct | 60 |
| gaacgccaag gagcgctcgg ccgccgccgg ggggccggtt ccacaggatg tgcccgcgct | 120 |
| gctgcgggag ttcatcggcg ccggggggggg ggggaagcgg atccgtccgc tgctgtgcat | 180 |
| cgcggctggc aggccggcgg cggaacagga ctgccggacg aggtggtgtc cacagcggcg | 240 |
| gcgctggaga tgttccacgc gttcgcgctg atccacgacg acatcatgga tgactccgcg | 300 |
| accaggcgcg gcagcccgac ggtgcaccgg gcactcgccg accggctcgg cgccgctctc | 360 |
| gaccccgacc aagccggaca actggggtg agcacgcgca tcctcgtcgg ggacctcgcc | 420 |
| ctgacctggt cggacgaact gctgtacgct ccctgaccc ccaccggct ggccgcggta | 480 |
| ctgccctgg tcacggccat gcgcgcgaa acggtccacg ccagtacct ggacatcacc | 540 |
| tccgcccgcc ggcccggcac ggacacctca ctggcgctgc gaatcgcgcg ctacaaaacc | 600 |
| gctgcttaca ccatggaacg ccccctgcac atcggagcag cgctcgccgg cgcacgaccg | 660 |
| gaactcctgg cagggctcag cgcctacgcg ctgccggcgg gcgaggcatt ccagctcgcc | 720 |
| gacgacctcc tgggagtgtt cggcgatcca cggagaaccg gcaaacccga cctcgacgac | 780 |
| ctccgcggcg gcaagcacac cgtcctcgtg gccctcgccc gggaacacgc cacacctgaa | 840 |
| cagcggcaca ccctggacac cctgctcggc acaccaggcc tcgaccggca gggcgcgtcc | 900 |
| cggctgcgct gcgtcctcgt cgccaccggg gcccggcgg aagccgaacg cctgatcacc | 960 |
| gaacggcgcg accaggccct caccgcgctc aacgccctga cactgccccc accgctcgcc | 1020 |
| gaggcactcg cccgcctcac cctcgggagt accgcacacc cggcctga | 1068 |

<210> SEQ ID NO 31
<211> LENGTH: 993
<212> TYPE: DNA
<213> ORGANISM: Sulfulobus acidicaldarius

<400> SEQUENCE: 31

| | |
|---|---|
| atgagttact tgacaactac ttttaatgag attgttaatt ctgtaaacga cattattaag | 60 |
| agctatatat ctggagatgt tcctaaaacta tatgaagcct catatcattt gtttacatct | 120 |
| ggaggtaaga ggttaagacc attaatctta actatatcat cagatttatt cggaggacag | 180 |
| agagaaagag cttattatgc aggtgcagct ttgaagttc ttcatacttt tacgcttgtg | 240 |
| catgatgata ttatggatca agataatatc agaagagggt tacccacagt ccacgtgaaa | 300 |
| tacggcttac ccttagcaat attagctggg gatttactac atgcaaaggc ttttcagctc | 360 |
| ttaacccagg ctcttagagg tttgccaagt gaaaccataa ttaaggcttt cgatattttc | 420 |
| actcgttcaa taataattat atccgaagga caggcagtag atatggaatt tgaggacaga | 480 |

| | |
|---|---|
| attgatataa aggagcagga ataccttgac atgatctcac gtaagacagc tgcattattc | 540 |
| tcggcatcct caagtatagg cgcacttatt gctggtgcta atgataatga tgtaagactg | 600 |
| atgtctgatt tcggtacgaa tctaggtatt gcatttcaga ttgttgacga tatcttaggt | 660 |
| ctaacagcag acgaaaagga acttggaaag cctgttttta gtgatattag ggagggtaaa | 720 |
| aagactatac ttgtaataaa aacactggag ctttgtaaag aggacgagaa gaagattgtc | 780 |
| ctaaaggcgt taggtaataa gtcagcctca aagaagaat taatgagctc agcagatata | 840 |
| attaagaaat actctttaga ttatgcatac aatttagcag agaaatatta taaaaatgct | 900 |
| atagactctt taaatcaagt ctcctctaag agtgatatac ctggaaaggc tttaaaatat | 960 |
| ctagctgaat ttacgataag aaggagaaaa taa | 993 |

<210> SEQ ID NO 32
<211> LENGTH: 894
<212> TYPE: DNA
<213> ORGANISM: Synechococcus sp.

<400> SEQUENCE: 32

| | |
|---|---|
| ttggttgccc aaaccttcaa cctggacacc tacttgagcc aacgccagca acaggtggaa | 60 |
| gaggcgcttt ctgcggcatt ggttcccgcc tatccggagc gcatttacga ggcgatgcgc | 120 |
| tacagcctgc tggcggggg gaaacgcctg aggccgatcc tctgtctggc ggcctgtgag | 180 |
| ttggccggcg gctctgtgga gcaggccatg cccaccgcct gcgccctgga gatgatccac | 240 |
| accatgtcgc tgatccacga cgatctgccg gcgatggaca cgacgatttt cgccgcggc | 300 |
| aagcccacca atcacaaggt attcggcgag gatatcgcca ttttggcagg gatgccctg | 360 |
| ttggcctatg cctttgagca tatcgccagc caaacgcggg gggtgccgcc gcagttggtg | 420 |
| ctgcaagtca ttgcccgcat tggccatgct gtggcggcaa ccggcttggt aggggccag | 480 |
| gtggtggatc tggagtccga aggcaaagcc atttccctag aaactttgga gtacatccac | 540 |
| agtcacaaga cgggtgctct gctggaggcc tcggtggttt cgggagggat cctggcaggg | 600 |
| gccgatgagg agctgctggc gcggctgagc cactacgctc gggacatcgg cctggctttt | 660 |
| cagatcgtgg acgacatttt ggatgttact gccaccagcg agcaactggg caaaacggca | 720 |
| ggcaaggatc aagctgccgc caaagccacc taccccagct tgttgggcct agaggcttcc | 780 |
| cggcagaaag ctgaggaact gatccaatcg gccaaggagg cgttgcgccc ctacggatcc | 840 |
| caggccgagc ccctgttggc tctggccgat tcatcaccc gccgccagca ttga | 894 |

<210> SEQ ID NO 33
<211> LENGTH: 1116
<212> TYPE: DNA
<213> ORGANISM: Arabidopsis thaliana

<400> SEQUENCE: 33

| | |
|---|---|
| atggcttcag tgactctagg ttcatggatt gttgttcacc accacaatca tcatcatcca | 60 |
| tcttcaatcc ttaccaaatc cagatccaga tcttgtccta aactcttac taaacccatc | 120 |
| tcctttcgat caaaacgcac cgtttcatca tcttcttcaa tcgtttcttc ttccgttgtt | 180 |
| acaaaagaag acaatctacg ccaatctgaa ccatcctctt tcgatttcat gtcgtacatc | 240 |
| atcaccaaag ccgaattagt caacaaagct ttagattcag ctgttcctct ccgtgagcca | 300 |
| ctcaagatcc acgaagcgat gcgttactct cttctcgccg gtggcaaaag agttagacca | 360 |
| gttctctgca tcgctgcttg tgaactcgtc ggaggtgaag aatcaaccgc tatgccagca | 420 |

| | |
|---|---:|
| gcttgcgccg tcgagatgat tcacaccatg tcgttgatcc acgacgatct cccttgtatg | 480 |
| gataacgacg atctccgccg tggaaaaccg accaaccaca aagtgtttgg tgaagacgtc | 540 |
| gctgttttag ccggagacgc gcttctctct ttcgctttcg agcatttagc ttcggcgacg | 600 |
| agttctgatg ttgtttctcc ggtgagagtg gttcgagccg ttggagaatt ggctaaagcg | 660 |
| ataggaacag aagggttagt ggcgggtcaa gtcgtggata ttagtagtga agggttagat | 720 |
| ttaaacgacg tcggtttaga gcatttggag tttatccatt tgcataaaac ggcggcgttg | 780 |
| cttgaagctt ctgctgtttt gggagctatt gttggtggag aagtgatga tgagattgag | 840 |
| aggttaagaa agtttgcgag atgtattggt ttgttgtttc agtggttga tgatatcttg | 900 |
| gatgtgacga atcgtcgaa agagttaggg aaaactgctg ggaaagattt gattgctgat | 960 |
| aagttgacgt atcctaagat tatgggtttg gagaaatcga gagagtttgc tgagaaattg | 1020 |
| aatagagagg ctcgtgatca gctttaggg tttgattctg ataaggttgc tcctttgttg | 1080 |
| gctttggcta attacattgc ctatagacag aactga | 1116 |

<210> SEQ ID NO 34
<211> LENGTH: 2364
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 34

| | |
|---|---:|
| atgaaaaccg ggtttatctc accagcaaca gtatttcatc acagaatctc accagcgacc | 60 |
| actttcagac atcacttatc acctgctact acaaactcta caggcattgt cgccttaaga | 120 |
| gacatcaact tcagatgtaa agcagtttct aaagagtact ctgatctgtt gcagaaagat | 180 |
| gaggcttctt tcacaaaatg ggacgatgac aaggtgaaag atcatcttga taccaacaaa | 240 |
| aacttatacc caaatgatga gattaaggaa tttgttgaat cagtaaaggc tatgttcggt | 300 |
| agtatgaatg acggggagat aaacgtctct gcatacgata ctgcatgggt tgctttggtt | 360 |
| caagatgtcg atggatcagg tagtcctcag ttcccttctt ctttagaatg gattgccaac | 420 |
| aatcaattgt cagatggatc atggggagat catttgctgt tctcagctca cgatagaatc | 480 |
| atcaacacat tagcatgcgt tattgcactt acaagttgga atgttcatcc ttctaagtgt | 540 |
| gaaaaggtt tgaattttct gagagaaaac atttgcaaat tagaagatga aaacgcagaa | 600 |
| catatgccaa ttggttttga agtaacattc ccatcactaa ttgatatcgc gaaaagttg | 660 |
| aacattgaag tacctgagga tactccagca cttaaagaga tctacgcacg tagagatatc | 720 |
| aagttaacta agatcccaat ggaagttctt cacaaggtac ctactacttt gttacattct | 780 |
| ttggaaggaa tgcctgattt ggagtgggaa aaactgttaa agctacaatg taaagatggt | 840 |
| agtttcttgt ttcccccatc tagtaccgca ttcgccctaa tgcaaacaaa agatgagaaa | 900 |
| tgcttacagt atctaacaaa tatcgtcact aagttcaacg tggcgtgcc taatgtgtac | 960 |
| ccagtcgatt tgtttgaaca tatttgggtt gttgatagac tgcagagatt ggggattgcc | 1020 |
| agatacttca atcagagat aaaagattgt gtagagtata tcaataagta ctggaccaaa | 1080 |
| aatggaattt gttgggctag aaatactcac gttcaagata tcgatgatac agccatggga | 1140 |
| ttcagagtgt tgagagcgca cggttatgac gtcactccag atgttttag acaatttgaa | 1200 |
| aaagatggta aattcgtttg ctttgcaggg caatcaacac aagccgtgac aggaatgttt | 1260 |
| aacgtttaca gagcctctca aatgttgttc ccaggggaga gaattttgga agatgccaaa | 1320 |

```
aagttctctt acaattactt aaaggaaaag caaagtacca acgaattgct ggataaatgg    1380
ataatcgcta aagatctacc tggtgaagtt ggttatgctc tggatatccc atggtatgct    1440
tccttaccaa gattggaaac tcgttattac cttgaacaat acggcggtga agatgatgtc    1500
tggataggca agacattata cagaatgggt tacgtgtcca ataacacata tctagaaatg    1560
gcaaagctgg attacaataa ctatgttgca gtccttcaat tagaatggta cacaatacaa    1620
caatggtacg tcgatattgg tatagagaag ttcgaatctg acaacatcaa gtcagtcctg    1680
gtttcttact acttggctgc ggcttcaata ttcgaacctg agagatctaa ggagagaatc    1740
gcttgggcaa agacaacaat cttagtcgat aagatcacat caattttcga ttcctctcag    1800
tcaagtaagg aagatattac tgcctttatt gacaagtttc gtaacaagtc ctcctctaaa    1860
aagcactcta tcaacggtga accatggcat gaagttatgg tagctttgaa aaagacctta    1920
cacggctttg ctctggatgc tcttatgact cattctcaag atatacatcc acagttacat    1980
caagcctggg aaatgtggtt gactaaacta caagacggcg tagatgttac tgctgagcta    2040
atggtccaaa tgatcaacat gactgctggc agatgggtat caaaggaatt acttactcat    2100
ccacaatatc aaagattgtc tactgtgaca aattctgtgt gtcacgatat taccaaactt    2160
cacaatttca aggagaattc caccacagtg gattcaaagg ttcaggaact agtccagttg    2220
gtttttagtg acacaccaga tgatttggat caagatatga aacaaacatt cctgacagtg    2280
atgaagacat tctactacaa ggcgtggtgt gatccaaaca ctataaacga tcatatatct    2340
aaagttttcg aaatcgtaat ttga                                            2364
```

<210> SEQ ID NO 35
<211> LENGTH: 1584
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 35

```
atgcctgatg cacacgatgc tccacctcca caaataagac agagaacact agtagatgag      60
gctacccaac tgctaactga gtccgcagaa gatgcatggg gtgaagtcag tgtgtcagaa    120
tacgaaacag caaggctagt tgcccatgct acatggttag gtggacacgc cacaagagtg    180
gccttccttc tggagagaca acacgaagac gggtcatggg gtccaccagg tggatatagg    240
ttagtcccta cattatctgc tgttcacgca ttattgacat gtcttgcctc tcctgctcag    300
gatcatggcg ttccacatga tagactttta agagctgttg acgcaggctt gactgccttg    360
agaagattgg ggacatctga ctccccacct gatactatag cagttgagct ggttatccca    420
tctttgctag agggcattca acacttactg gaccctgctc atcctcatag tagaccagcc    480
ttctctcaac atagaggctc tcttgtttgt cctggtggac tagatgggag aactctagga    540
gctttgagat cacacgccgc agcaggtaca ccagtaccag aaaagtctg gcacgcttcc    600 gagactttgg gcttgagtac cgaagctgct tctcacttgc aaccagccca aggtataatc    660
ggtggctctg ctgctgccac agcaacatgg ctaaccaggg ttgcaccatc tcaacagtca    720
gattctgcca agatacctc tgaggaatta caacacagat actctggccc agttccttcc    780
attaccccta tcacatactt cgaaagagca tggttattga caatttttgc agcagccggt    840
gttccttgtg aggctccagc tgctttgttg gattccttag aagcagcact acaccacaa    900 ggtgctcctg ctggagcagg attgcctcca gatgctgatg atacagccgc tgtgttgctt    960
```

```
gcattggcaa cacatgggag aggtagaaga ccagaagtac tgatggatta caggactgac    1020
gggtatttcc aatgctttat tggggaaagg actccatcaa tttcaacaaa cgctcacgta    1080
ttggaaacat tagggcatca tgtggcccaa catccacaag atagagccag atacggatca    1140
gccatggata ccgcatcagc ttggctgctg gcagctcaaa agcaagatgg ctcttggtta    1200
gataaatggc atgcctcacc atactacgct actgtttgtt gcacacaagc cctagccgct    1260
catgcaagtc ctgcaactgc accagctaga cagagagctg tcagatgggt tttagccaca    1320
caaagatccg atggcggttg gggtctatgg cattcaactg ttgaagagac tgcttatgcc    1380
ttacagatct tggccccacc ttctggtggt ggcaatatcc cagtccaaca agcacttact    1440
agaggcagag caagattgtg tggagccttg ccactgactc ctttatggca tgataaggat    1500
ttgtatactc cagtaagagt agtcagagct gccagagctg ctgctctgta cactaccaga    1560
gatctattgt taccaccatt gtaa                                           1584

<210> SEQ ID NO 36
<211> LENGTH: 1551
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 36
atgaacgccc tatccgaaca cattttgtct gaattgagaa gattattgtc tgaaatgagt      60
gatggcggat ctgttggtcc atctgtgtat gatacggccc aggccctaag attccacggt     120
aacgtaacag gtagacaaga tgcatatgct tggttgatcg cccagcaaca agcagatgga     180
ggttggggct ctgccgactt tccactcttt agacatgctc caacatgggc tgcacttctc     240
gcattacaaa gagctgatcc acttcctggc gcagcagacg cagttcagac cgcaacaaga     300
ttcttgcaaa gacaaccaga tccatacgct catgccgttc ctgaggatgc ccctattggt     360
gctgaactga tcttgcctca gttttgtgga gaggctgctt ggttgttggg aggtgtggcc     420
ttccctagac acccagccct attaccatta agacaggctt gtttagtcaa actgggtgca     480
gtcgccatgt tgccttcagg acacccattg ctccactcct gggaggcatg gggtacttct     540
ccaacaacag cctgtccaga cgatgatggt tctataggta tctcaccagc agctacagcc     600
gcctggagag cccaggctgt gaccagaggc tcaactcctc aagtgggcag agctgacgca     660
tacttacaaa tggcttcaag agcaacgaga tcaggcatag aaggagtctt ccctaatgtt     720
tggcctataa acgtattcga accatgctgg tcactgtaca ctctccatct tgccggtctg     780
ttcgcccatc cagcactggc tgaggctgta agagttatcg ttgctcaact tgaagcaaga     840
ttgggagtgc atggcctcgg accagcttta cattttgctg ccgacgctga tgatactgca     900
gttgccttat gcgttctgca tttggctggc agagatcctg cagttgacgc attgagacat     960
tttgaaattg gtgagctctt tgttacattc caggagagaa gaatgctagt gtctctacg     1020 aacattcacg ctcttcatgc tttgagattg ttaggtaaac cagctgccgg agcaagtgca     1080
tacgtcgaag caaatagaaa tccacatggt ttgtgggaca cgaaaaatg gcacgtttca     1140 tggctttatc caactgcaca cgccgttgca gctctagctc aaggcaagcc tcaatggaga     1200
gatgaaagag cactagccgc tctactacaa gctcaaagag atgatggtgg ttggggagct     1260
ggtagaggat ccactttcga ggaaaccgcc tacgctctttt cgctttaca cgttatggac     1320 ggatctgagg aagccacagg cagaagaaga atcgctcaag tcgtcgcaag agccttagaa     1380
```

```
tggatgctag ctagacatgc cgcacatgga ttaccacaaa caccactctg gattggtaag    1440
gaattgtact gtcctactag agtcgtaaga gtagctgagc tagctggcct gtggttagca    1500
ttaagatggg gtagaagagt attagctgaa ggtgctggtg ctgcacctta a             1551

<210> SEQ ID NO 37
<211> LENGTH: 2364
<212> TYPE: DNA
<213> ORGANISM: Stevia rebaudiana

<400> SEQUENCE: 37
atgaagaccg gcttcatctc tcccgccacc gtcttccacc accgtatttc tccggcaacc      60
accttccgcc accacctttc tccggcgacc accaactcca ctggaattgt agctcttaga     120
gacatcaact tccggtgtaa agcggtatcc aaagagtact ctgatttact acaaaaagat     180
gaggcttcat ttaccaagtg ggacgatgac aaagtgaagg accatttgga cacaaataag     240
aatttgtatc caaacgatga gatcaaggag tttgttgaga gcgtgaaagc aatgtttggt     300
tctatgaatg acggagaaat aaatgtgtca gcgtatgata cggcttgggt tgcactcgtg     360
caagatgttg atggaagtgg ttcccctcaa tttccatcaa gtttggagtg gatcgcgaac     420
aatcaactct cagatgggtc ttggggcgat catttgttat tttcggctca tgataggatc     480
attaacacgt tggcatgtgt tatagcgctt acttcttgga acgtccatcc aagtaaatgt     540 gaaaaggac tgaattttct tagagaaaac atatgtaaac tcgaagacga aacgcggaa      600 catatgccaa ttggttttga agtcacgttc ccgtcgctaa tagatatcgc aaagaagcta     660
aatattgaag ttcctgagga tactcctgcc ttaaaagaaa tttatgcaag aagagacata     720
aaactcacaa agataccaat ggaagtattg cacaaagtgc ccacaacttt acttcatagt     780
ttggaaggaa tgccagattt tggaatggga aaacttctga aattgcaatg caaagatgga     840
tcatttctgt tttctccatc atctactgct tttgcactca tgcaaacaaa agatgaaaag     900
tgtcttcagt atttgacaaa tattgttacc aaattcaatg gtggagttcc gaatgtgtac     960
ccggtggatc tattcgaaca tatttgggta gttgatcgac ttcaacgact tgggattgct    1020
cgttatttca atcagagatt caaagattgc gttgaatata ttaacaagta ttggacaaag    1080
aatgggattt gttgggcaag aaacacgcac gtacaagata ttgatgatac cgcaatggga    1140
tttagggttt taagagcaca tggttatgat gttactccag atgtatttcg acaatttgag    1200
aaggatggta aattcgtatg tttcgctgga cagtcaacac aagccgtcac cggaatgttc    1260
aatgtgtata gagcgtcaca aatgctcttt cccggagaaa gaattcttga agatgcaaag    1320
aaattttcat ataattattt gaaagaaaaa caatcgacaa atgagcttct tgataaatgg    1380
atcatcgcca aagacttacc tggagaggtt ggatatgcgc tagacatacc atggtatgca    1440
agcttaccgc gactcgagac aagatattac ttagagcaat acggggcga ggatgatgtt    1500 tggattggaa aaactctata caggatggga tatgtgagca ataatacgta ccttgaaatg    1560
gccaaattgg actacaataa ctatgtggcc gtgcttcaac tcgaatggta cactatccag    1620
caatggtatg ttgatatcgg tatcgaaaag tttgaaagtg acaatatcaa agcgtatta     1680 gtgtcgtatt acttggctgc agccagcata ttcgagccgg aaaggtccaa ggaacgaatc    1740
gcgtgggcta aaccaccat attagttgac aagatcacct caatttttga ttcatcacaa    1800
tcctcaaaag aggacataac agcctttata gacaaattta ggaacaaatc gtcttctaag    1860
aagcattcaa taaatggaga accatggcac gaggtgatgg ttgcactgaa aaagaccccta    1920 cacggcttcg ctttggatgc actcatgact catagtcaag acatccaccc gcaactccat    1980
```

```
caagcttggg agatgtggtt gacgaaattg caagatggag tagatgtgac agcggaatta    2040
atggtacaaa tgataaatat gacagctggt cgttgggtat ccaaagaact tttaactcat    2100
cctcaatacc aacgcctctc aaccgtcaca aatagtgtgt gtcacgatat aactaagctc    2160
cataacttca aggagaattc cacgacggta gactcgaaag ttcaagaact agtgcaactt    2220
gtgtttagcg acacgcccga tgatcttgat caggatatga aacagacgtt tctaaccgtc    2280
atgaaaacct tctactacaa ggcgtggtgt gatccgaaca cgataaatga ccatatctcc    2340
aaggtgttcg agattgtaat atga                                          2364

<210> SEQ ID NO 38
<211> LENGTH: 1584
<212> TYPE: DNA
<213> ORGANISM: Streptomyces clavuligerus

<400> SEQUENCE: 38
ttgcccgacg cgcatgatgc ccctccgcct cagatacgac agcggaccct tgtcgatgag      60
gcgacgcaac tcctcacgga gtcggccgag gacgcctggg gtgaggtgtc cgtgtccgag     120
tacgaaacgg cgcggctggt ggcccacgcc acctggctcg gcggtcacgc cacacgggtg     180
gccttcctgc tggagcggca gcatgaggac ggctcgtggg gcccgcccgg cgggtaccgt     240
ctcgtaccca cgctgagtgc cgtacacgcc ctgctcacct gtctggcgtc tcccgcgcag     300
gaccacggag tgcctcatga ccggctcctg cgcgcagttg acgcgggcct gacggcactg     360
cgtcgtcttg ggacgagcga cagcccgccg gacaccattg cggtcgaact ggtcatacc     420 tcgctccttg agggcatcca gcacctcctg gacccggcgc accgcattc ccgacccgct     480 ttttcgcaac accgcggcag cctcgtctgc cccggggggcc tcgacggccg cacgctgggg    540
gccttgcgct cccacgccgc agccggcaca cctgtcccgg gcaaggtgtg gcacgcctcg    600
gaaaccttgg ggctatcgac cgaggcagcc tcccaccttc aacccgccca gggcatcatc    660
ggtggctccg ccgccgcgac agcaacatgg ctcaccaggg tcgccccgtc gcaacagagc    720
gacagcgcac ggcgctacct ggaagaactc cagcaccgat acagcggccc ggtgccctcc    780
atcaccccga tcacctattt cgaacgggcc tggctgctca caacttcgc tgccgcgggg    840 gttccatgcg aggctccggc agccttctc gacagcctgg aggcagcgct cacaccacag    900
ggcgctccag cgggtgcggg actgccgccg gacgcggatg acaccgccgc cgttctgctg    960
gcgcttgcca cgcacggccg cgggcgccgt cccgaggtcc tcatggacta ccgcacggac   1020
ggctacttcc agtgcttcat cggcgaacgc acccccttcca tcagcaccaa tgcccatgtc    1080
ctggagacgc tcggtcacca cgtcgcccaa caccctcagg acagggcccg atacggctca   1140
gccatggaca ccgcatcagc gtggctcctc gcggctcaga agcaggatgg cagctggctc   1200
gacaagtggc acgcctcccc ctactacgcc accgtctgct gcacccaggc actggcagcc   1260
cacgcttccc ctgccaccgc ccccgcacgg cagcgtgctg tgcggtgggt gctggcaaca    1320
caacgctcgg acgcggctg gggcctgtgg cactccacgg tcgaggagac cgcctacgcc    1380
ctgcagatcc tcgcccccacc ttccggcggc gggaacatcc ccgtgcaaca ggcgctcacc    1440 aggggggcgcg cccgcctctg cggcgctttg ccgctgactc cctatggca tgacaaggac    1500 ctgtacacgc cggtacgtgt cgtccgcgcc gcccgtgccg ccgccctgta caccacccgt   1560
gacctgcttc tgccgcccct gtga                                         1584

<210> SEQ ID NO 39
```

<211> LENGTH: 1551
<212> TYPE: DNA
<213> ORGANISM: Bradyrhizobium japonicum

<400> SEQUENCE: 39

```
gtgaacgcgc tgtccgaaca tatcctttcc gaattgcgcc gcctgctgag cgaaatgagc      60
gatggcggca gcgtcggtcc gtccgtctac gacacggcgc aggcgctgcg cttccacggc     120
aacgtcaccg gtcggcagga cgcatacgcg tggctcatcg cgcagcaaca ggccgacggc     180
ggatggggaa gcgcggactt cccgctgttc cgccatgcgc ccacgtgggc ggcgttactg     240
gcattgcagc gtgccgatcc tcttcccgga gctgcggacg cagtccagac tgcaacgagg     300
ttcctccagc gccagcccga tccctacgca catgcggtgc cagaagacgc gccgatcggc     360
gcggagctga tcctgccgca gttttgcggt gaggccgcat ggttgctggg tggcgtagcg     420
tttccgcgcc atcctgcgct gttgccattg cggcaagcgt gcctggtcaa gctggggggcg     480
gtggcgatgt tgccgagcgg ccatccgttg ctacactcct gggaagcctg ggggacgtcg     540
ccgaccaccg catgcccgga tgacgacggc agcatcggga tcagtccggc ggccaccgcc     600
gcgtggcgtg cccaggccgt gacacggggg agcacgccgc aggtcgggcg cgccgatgcg     660
tatctgcaga tggcatcgcg ggcgacgcgc agcggcatcg aaggtgtctt tcccaacgtc     720
tggccgatca atgtgttcga gccatgctgg tcgctgtaca ccctgcatct ggccgggctt     780
ttcgcgcatc ccgcgctcgc ggaggcggtt cgcgtgatcg tcgcgcagct cgaggcccgt     840
ctgggcgtgc acggtctggg cccggccttg cacttcgcgg ctgatgcgga cgacaccgcc     900
gttgcgttgt gcgtcctgca ccttgcaggc cgtgacccgg cggtcgatgc gttgcgccat     960
ttcgaaatcg gcgagctgtt cgtcaccttc cccggcgaac gcaatgcctc ggtgtcgacc    1020
aacattcatg ccctgcatgc gttgcgactg ttgggaaagc ccgccgcggg cgccagcgcg    1080
tacgtcgagg ccaatcgcaa cccgcacggt ctatgggaca acgaaaaatg cacgtttcg    1140
tggctgtatc ccaccgcgca tgcggtcgct gcgctggcgc aaggcaagcc ccagtggcga    1200
gatgagcgcg cgctggcggc gctgctgcag gcgcagcgcg acgacggtgg ctggggcgcg    1260
ggtcgcgggt ccacgttcga ggaaaccgcc tatgcgctgt ttgcgttgca cgtgatggat    1320
gggagcgaag aggcgacagg gcgccggcgc atcgcgcagg tggtggcgcg tgcgctggag    1380
tggatgctcg cccgccatgc ggcgcatgga ttgccgcaga cgccgctgtg atcggcaag    1440
gaactgtatt gccccactcg ggtcgtgcgc gtggccgaac tcgccgggtt gtggctggcg    1500
cttcgttggg ggcggcgcgt cctggccgag ggggcaggag cggcgccatg a             1551
```

<210> SEQ ID NO 40
<211> LENGTH: 2355
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 40

```
atgaatttga gtttgtgtat agcatctcca ctattgacca aatctaatag accagctgct      60
ttatcagcaa ttcatacagc tagtacatcc catggtggcc aaaccaaccc tacgaatctg     120
ataatcgata cgaccaagga gagaatacaa aaacaattca aaaatgttga atttcagtt      180
tcttcttatg atactgcgtg ggttgccatg gttccatcac ctaattctcc aaagtctcca     240
tgtttcccag aatgtttgaa ttggctgatt aacaaccagt tgaatgatgg atcttggggt     300
```

```
ttagtcaatc acacgcacaa tcacaaccat ccacttttga aagattcttt atcctcaact    360
ttggcttgca tcgtggccct aaagagatgg aacgtaggtg aggatcagat taacaagggg    420
cttagtttca ttgaatctaa cttggcttcc gcgactgaaa aatctcaacc atctccaata    480
ggattcgata tcatctttcc aggtctgtta gagtacgcca aaaatctaga tatcaactta    540
ctgtctaagc aaactgattt ctcactaatg ttacacaaga gagaattaga acaaaagaga    600
tgtcattcaa acgaaatgga tggttaccta gcttatatct ctgaaggtct tggtaatctt    660
tacgattgga atatggtgaa aaagtaccag atgaaaaatg gctcagtttt caattcccct    720
tctgcaactg cggcagcatt cattaaccat caaaatccag gatgcctgaa ctatttgaat    780
tcactactag acaaattcgg caacgcagtt ccaactgtat accctcacga tttgtttatc    840
agattgagta tggtggatac aattgaaaga cttggtatat cccaccactt tagagtcgag    900
atcaaaaatg ttttggatga gacataccgt tgttgggtgg agagagatga acaaatcttt    960
atggatgttg tgacgtgcgc gttggccttt agattgttgc gtattaacgg ttacgaagtt   1020
agtccagatc cacttgccga aattacaaac gaattagctt taaaggatga atacgccgct   1080
cttgaaacat atcatgcgtc acatatcctt taccaagagg acttatcatc tggaaaacaa   1140
attcttaaat ctgctgattt cctgaaggaa atcatatcca ctgatagtaa tagactgtcc   1200
aaactgatcc ataaagaggt tgaaaatgca cttaagttcc ctattaacac cggcttagaa   1260
cgtattaaca caagacgtaa catccagctt tacaacgtag acaatactag aatcttgaaa   1320
accacttacc attcttccaa catatcaaac actgattacc taagattagc tgttgaagat   1380
ttctacacat gtcagtctat ctatagagaa gagctgaaag gattagagag atgggtcgtt   1440
gagaataagc tagatcaatt gaaatttgcc agacaaaaga cagcttattg ttacttctca   1500
gttgccgcca ctttatcaag tccagaattg tcagatgcac gtatttcttg ggctaaaaac   1560
ggaattttga caactgttgt tgatgatttc tttgatattg gcgggacaat cgacgaattg   1620
acaaacctga ttcaatgcgt tgaaaagtgg aatgtcgatg tcgataaaga ctgttgctca   1680
gaacatgtta gaatactgtt cttggctctg aaagatgcta tctgttggat cggggatgag   1740
gctttcaaat ggcaagctag agatgtgacg tctcacgtca ttcaaacctg gctagaactg   1800
atgaactcta tgttgagaga agcaatttgg actagagatg catacgttcc tacattaaac   1860
gagtatatgg aaaacgctta tgtctccttt gctttgggtc ctatcgttaa gcctgccata   1920
tactttgtag gaccaaagct atccgaggaa atcgtcgaat catcagaata ccataacttg   1980
ttcaagttaa tgtccacaca aggcagatta cttaatgata ttcattcttt caaaagagag   2040
tttaaggaag gaaagttaaa tgctgttgct ctgcatcttt ctaatggcga aagtggtaaa   2100
gtcgaagagg aagtagttga ggaaatgatg atgatgatca aaacaagag aaaggagttg   2160
atgaaactaa tcttcgaaga gaacggttca attgttccta gagcatgtaa ggatgcattt   2220
tggaacatgt gtcatgtgct aaactttttc tacgcaaacg acgatggttt tactgggaac   2280
acaatactag atacagtaaa agacatcata tacaacccct tggtcttagt aaacgaaaac   2340
gaggagcaaa gataa                                                    2355
```

<210> SEQ ID NO 41
<211> LENGTH: 2355
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 41
atgaatctgt cccttttgtat agctagtcca ctgttgacaa atcttctag accaactgct      60
cttctgcaa ttcatactgc cagtactagt catggaggtc aaacaaaccc aacaaatttg     120
ataatcgata ctactaagga gagaatccaa aagctattca aaaatgttga aatctcagta     180
tcatcttatg acaccgcatg ggttgcaatg gtgccatcac ctaattcccc aaaaagtcca     240
tgttttccag agtgcttgaa ttggttaatc aataatcagt taaacgatgg ttcttggggt     300
ttagtcaacc acactcataa ccacaatcat ccattattga aggactcttt atcatcaaca     360
ttagcctgta ttgttgcatt gaaaagatgg aatgtaggtg aagatcaaat caacaagggt     420
ttatcattca tagaatccaa tctagcttct gctaccgaca atcacaacc atctccaatc     480
gggttcgaca taatcttccc tggttttgctg gagtatgcca aaaaccttga tatcaactta     540
ctgtctaaac aaacagattt ctctttgatg ctacacaaaa gagagttaga gcagaaaaga     600
tgccattcta acgaaattga cgggtactta gcatatatct cagaaggttt gggtaatttg     660
tatgactgga acatggtcaa aaagtatcag atgaaaaatg gatccgtatt caattctcct     720
tctgcaactg ccgcagcatt cattaatcat caaaaccctg ggtgtcttaa ctacttgaac     780
tcactattag ataagtttgg aaatgcagtt ccaacagtct atcctttgga cttgtacatc     840
agattatcta tggttgacac tatagagaga ttaggtatt ctcatcattt cagagttgag     900
atcaaaaatg ttttggacga acatacaga tgttgggtcg aaagagatga gcaaatcttt     960
atggatgtcg tgacctgcgc tctggcttt agattgctaa ggatacacgg atacaaagta    1020
tctcctgatc aactggctga gattacaaac gaactggctt tcaaagacga atacgccgca    1080
ttagaaacat accatgcatc ccaaatactt taccaggaag acctaagttc aggaaaacaa    1140
atcttgaagt ctgcagattt cctgaaaggc attctgtcta cagatagtaa taggttgtct    1200
aaattgatac acaaggaagt agaaaacgca ctaaagtttc ctattaacac tggtttagag    1260
agaatcaata ctaggagaaa cattcagctg tacaacgtag ataatacaag gattcttaag    1320
accacctacc atagttcaaa catttccaac acctattact taagattagc tgtcgaagac    1380
ttttacactt gtcaatcaat ctacagagag gagttaaagg gcctagaaag atgggtagtt    1440
caaaacaagt tggatcaact gaagtttgct agacagaaga cagcatactg ttatttctct    1500
gttgctgcta cccttttcatc cccagaattg tctgatgcca gaataagttg ggccaaaaat    1560
ggtattctta caactgtagt cgatgatttc tttgatattg gaggtactat tgatgaactg    1620
acaaatctta ttcaatgtgt tgaaaagtgg aacgtggatg tagataagga ttgctgcagt    1680
gaacatgtga gaatactttt cctggctcta aaagatgcaa tatgttggat tggcgacgag    1740
gccttcaagt ggcaagctag agatgttaca tctcatgtca tccaaacttg gcttgaactg    1800
atgaactcaa tgctaagaga agcaatctgg acaagagatg catacgttcc aacattgaac    1860
gaatacatgg aaaacgctta cgtctcattt gccttgggtc ctattgttaa gccagccata    1920
tactttgttg ggccaaagtt atccgaagag attgttgagt cttccgaata tcataaccta    1980
ttcaagttaa tgtcaacaca aggcagactt ctgaacgata ccactccctt caaaagagaa    2040
ttcaaggaag taagctaaa cgctgttgct ttgcacttgt ctaatggtga atctggcaaa    2100
gtggaagagg aagtcgttga ggaaatgatg atgatgatca aaaacaagag aaaggaattg    2160
atgaaattga ttttcgagga aaatggttca atcgtaccta gagcttgtaa agatgctttt    2220
tggaatatgt gccatgttct taacttcttt tacgctaatg atgatggctt cactggaaat    2280
acaatattgg atacagttaa agatatcatc tacaacccac ttgttttggt caatgagaac    2340
```

<210> SEQ ID NO 42
<211> LENGTH: 1773
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 42

```
atggctatgc cagtgaagct aacacctgcg tcattatcct taaaagctgt gtgctgcaga      60
ttctcatccg gtggccatgc tttgagattc gggagtagtc tgccatgttg gagaaggacc     120
cctacccaaa gatctacttc ttcctctact actagaccag ctgccgaagt gtcatcaggt     180
aagagtaaac aacatgatca ggaagctagt gaagcgacta tcagacaaca attcaacttt    240
gtggatgtcc tggagaatat gggaatatcc agacattttg ctgcagagat aaagtgcata     300
ctagacagaa cttacagatc ttggttacaa agacacgagg aaatcatgct ggacactatg     360
acatgtgcta tggcttttag aatcctaaga ttgaacggat acaacgtttc atcagatgaa     420
ctataccacg ttgtagaggc atctggtctg cataattctt gggtgggta tcttaacgat      480
accagaacac tacttgaatt acacaaggct tcaacagtta gtatctctga ggatgaatct     540
atcttagatt caattggctc tagatccaga acattgctta gagaacaatt ggagtctggt     600
ggcgcactga gaaagccttc tttattcaaa gaggttgaac atgcactgga tggacctttt     660
tacaccacac ttgatagact tcatcatagg tggaatattg aaaacttcaa cattattgag     720
caacacatgt tggagactcc atacttatct aaccagcata catcaaggga tatcctagca     780
ttgtcaatta gagatttttc ctcctcacaa ttcacttatc aacaagagct acagcatctg     840
gagagttggg ttaaggaatg tagattagat caactacagt tcgcaagaca gaaattagcg     900
tactttacc tatcagccgc aggcaccatg ttttctcctg agctttctga tgcgagaaca      960
ttatgggcca aaacgggt gttgacaact attgttgatg atttctttga tgttgccggt      1020
tctaaagagg aattggaaaa cttagtcatg ctggtcgaaa tgtgggatga acatcacaaa    1080
gttgaattct attctgagca ggtcgaaatc atcttctctt ccatctacga ttctgtcaac    1140
caattgggtg agaaggcctc tttggttcaa gacagatcaa ttacaaaaca ccttgttgaa    1200
atatggttag acttgttaaa gtccatgatg acggaagttg aatggagact gtcaaaatac    1260
gtgcctacag aaaaggaata catgattaat gcctctctta tcttcggcct aggtccaatc    1320
gttttaccag ctttgtattt cgttggtcca agatttcag aaagtatagt aaaggaccca     1380
gaatatgatg aattgttcaa actaatgtca acatgtggta gattgttgaa tgacgtgcaa    1440
acgttcgaaa gagaatacaa tgagggtaaa ctgaattctg tcagtctatt ggttcttcac    1500
ggaggcccaa tgtctatttc agacgcaaag aggaaattac aaaagcctat tgatacgtgt    1560
agaagagatc ttctttcttt ggtccttaga gaagagtctg tagtaccaag accatgtaag   1620
gaactattct ggaaaatgtg taaagtgtgc tatttctttt actcaacaac tgatgggttt    1680
tctagtcaag tcgaaagagc aaaagaggta gacgctgtca taatgagcc actgaagttg    1740
caaggttctc atacactggt atctgatgtt taa                                 1773
```

<210> SEQ ID NO 43
<211> LENGTH: 2232
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 43

| | | | | | |
|---|---|---|---|---|---|
| atgcagaact | tccatggtac | aaaggaaagg | atcaaaaaga | tgtttgacaa | gattgaattg | 60 |
| tccgtttctt | cttatgatac | agcctgggtt | gcaatggtcc | catcccctga | ttgcccagaa | 120 |
| acaccttgtt | ttccagaatg | tactaaatgg | atcctagaaa | atcagttggg | tgatggtagt | 180 |
| tggtcacttc | ctcatggcaa | tccacttcta | gttaaagatg | cattatcttc | cactcttgct | 240 |
| tgtattctgg | ctcttaaaag | atggggaatc | ggtgaggaac | agattaacaa | aggactgaga | 300 |
| ttcatagaac | tcaactctgc | tagtgtaacc | gataacgaac | aacacaaacc | aattggattt | 360 |
| gacattatct | ttccaggtat | gattgaatac | gctatagact | tagacctgaa | tctaccacta | 420 |
| aaaccaactg | acattaactc | catgttgcat | cgtagagccc | ttgaattgac | atcaggtgga | 480 |
| ggcaaaaatc | tagaaggtag | aagagcttac | ttggcctacg | tctctgaagg | aatcggtaag | 540 |
| ctgcaagatt | gggaaatggc | tatgaaatac | aacgtaaaa | acggatctct | gttcaatagt | 600 |
| ccatcaacaa | ctgcagctgc | attcatccat | atacaagatg | ctgaatgcct | ccactatatt | 660 |
| cgttctcttc | tccagaaatt | tggaaacgca | gtccctacaa | tataccctct | cgatatctat | 720 |
| gccagacttt | caatggtaga | tgccctggaa | cgtcttggta | ttgatagaca | tttcagaaag | 780 |
| gagagaaagt | tcgttctgga | tgaaacatac | agattttggt | tgcaaggaga | gaggagatt | 840 |
| ttctccgata | acgcaacctg | tgctttggcc | ttcagaatat | tgagacttaa | tggttacgat | 900 |
| gtctctcttg | aagatcactt | ctctaactct | ctgggcggtt | acttaaagga | ctcaggagca | 960 |
| gctttagaac | tgtacagagc | cctccaattg | tcttacccag | acgagtccct | cctggaaaag | 1020 |
| caaaattcta | gaacttctta | cttcttaaaa | caaggtttat | ccaatgtctc | cctctgtggt | 1080 |
| gacagattgc | gtaaaaacat | aattggagag | gtgcatgatg | ctttaaactt | tccgaccac | 1140 |
| gctaacttac | aaagattagc | tattcgtaga | aggattaagc | attacgctac | tgacgataca | 1200 |
| aggattctaa | aaacttccta | cagatgctca | acaatcggta | accaagattt | tctaaaactt | 1260 |
| gcagtggaag | atttcaatat | ctgtcaatca | atacaaagag | aggaattcaa | gcatattgaa | 1320 |
| agatgggtcg | ttgaaagacg | tctagacaag | ttaaagttcg | ctagacaaaa | agaggcctat | 1380 |
| tgctatttct | cagccgcagc | aacattgttt | gcccctgaat | tgtctgatgc | tagaatgtct | 1440 |
| tgggccaaaa | atggtgtatt | gacaactgtg | gttgatgatt | tcttcgatgt | cggaggctct | 1500 |
| gaagaggaat | tagttaactt | gatagaattg | atcgagcgtt | gggatgtgaa | tggcagtgca | 1560 |
| gattttgta | gtgaggaagt | tgagattatc | tattctgcta | tccactcaac | tatctctgaa | 1620 |
| ataggtgata | agtcatttgg | ctggcaaggt | agagatgtaa | agtctcaagt | tatcaagatc | 1680 |
| tggctggact | tattgaaatc | aatgttaact | gaagctcaat | ggtcttcaaa | caagtctgtt | 1740 |
| cctaccctag | atgagtatat | gacaaccgcc | catgtttcat | tcgcacttgg | tccaattgta | 1800 |
| cttccagcct | tatacttcgt | tggcccaaag | ttgtcagaag | aggttgcagg | tcatcctgaa | 1860 |
| ctactaaaacc | tctacaaagt | cacatctact | tgtggcagac | tactgaatga | ttggagaagt | 1920 |
| tttaagagag | aatccgagga | aggtaagctc | aacgctatta | gtttatacat | gatccactcc | 1980 |
| ggtggtgctt | ctacagaaga | ggaaacaatc | gaacatttca | aaggtttgat | tgattctcag | 2040 |
| agaaggcaac | tgttacaatt | ggtgttgcaa | gagaaggata | gtatcatacc | tagaccatgt | 2100 |
| aaagatctat | tttggaatat | gattaagtta | ttacacactt | tctacatgaa | agatgatggc | 2160 |
| ttcacctcaa | atgagatgag | gaatgtagtt | aaggcaatca | ttaacgaacc | aatctcactg | 2220 |

```
gatgaattat ga                                                          2232

<210> SEQ ID NO 44
<211> LENGTH: 2355
<212> TYPE: DNA
<213> ORGANISM: Stevia rebaudiana

<400> SEQUENCE: 44
atgaatcttt cactatgcat cgcgtcccct tgttaacca aatcaaatcg acccgcggct         60
ctgtcagcta ttcatacagc atcaacttca catggtggac aaactaatcc cactaatctg       120
atcattgata caaccaaaga acggatccaa aaacagttta aaaatgtaga aatttctgtt       180
tcttcatatg acacagcatg ggtagccatg gtcccttctc caaactcacc caaatcgcct       240
tgtttccctg agtgtctcaa ttggttaatt aataatcagc ttaatgatgg ttcatggggt       300
cttgttaatc acactcataa tcataatcac ccgttgctta agattctct atcttcaaca       360 ttagcatgta ttgttgcatt aaaaagatgg aatgttgggg aagatcaaat aaataaaggt       420
ctaagtttta ttgagtcaaa tcttgcttca gctactgaaa aagtcaacc atctcccatt       480 ggttttgaca tcatatttcc tggtttgctt gagtatgcga aaaacttgga cataaacctc       540
ctttcaaaac aaacagattt tagtttgatg ctacataaga gggaattgga gcaaaaaga       600 tgccattcaa atgagatgga tggatacttg gcgtatatct ctgaaggact cggtaattta       660
tatgattgga atatggtgaa gaaatatcag atgaaaaatg gttctgtttt caactcacca       720
tcagcaacag ctgctgcttt cattaatcat caaaatcctg gttgtcttaa ttatttaaat       780
tcacttttgg acaagtttgg taatgcagtc ccaacagttt atcctcatga tttatttatc       840
cgactttcta tggttgacac aattgaaaga ttaggaattt cacaccattt cagagtggaa       900
attaaaaatg ttttagatga aacatacaga tgttgggtgg aacgagatga gcaaatattc       960
atggatgttg taacatgtgc tttagccttt cggttattaa ggatcaatgg gtatgaagtt      1020
tccccagatc cattggctga aattactaat gaattagctt tgaaagacga atatgcagct      1080
cttgaaacat atcatgcgtc acatatatta taccaagagg atttatcttc tggaaaacaa      1140
atcttgaagt cagctgattt cctcaaagag ataaatatcca ctgattcaaa caggctttct      1200
aaattaattc acaagagggt ggaaaatgct cttaagttcc ctatcaatac cggtttagaa      1260
cgcataaaca ctagacgaaa tatacagctt tacaatgtag acaatacaag aattctgaaa      1320
actacatatc actcatcaaa tattagtaac actgattacc taaggttggc tgttgaagat      1380
ttctacacct gccaatctat ttatcgtgaa gaattaaaag tcttgaaag gtgggtggta      1440 gagaataagt tggaccagct caagtttgct aggcaaaaga ccgcctactg ttatttctct      1500
gttgctgcaa cactttcgtc tcccgaatta tcagatgcgc gtatttcatg gccaaaaat      1560 ggcatattaa ctacagtagt tgatgacttt tttgatatcg gtggtacaat cgatgaattg      1620
accaacctga ttcaatgtgt tgaaaaatgg aatgtagatg tcgacaagga ttgttgttca      1680
gagcatgttc ggatttttatt tttagcatta aaagatgcaa tctgttggat tggagatgaa      1740
gcttttaaat ggcaagcgcg cgatgtaact agccatgtta ttcaaacttg gttggaacta      1800
atgaatagta tgttgagaga agctatatgg acaagagatc ttatgtgcc aacattaaat      1860 gaatatatgg aaaacgctta cgtgtcattt gcattaggcc cgattgtcaa gccggctatt      1920
tactttgtgg ggcccaaatt atcagaggag attgttgaaa gctctgaata tcataatcta      1980
tttaagctaa tgagcacgca gggtcgactt ctaaacgata tccatagctt caagagggaa      2040
```

```
tttaaggaag gcaaattaaa cgcggtagca ttgcatttga gtaacggaga aagtgggaaa   2100
gtggaagaag aggttgtgga ggagatgatg atgatgatta aaaacaagag gaaagaatta   2160
atgaaattaa tttttgaaga aaatggtagc attgttccta gagcttgtaa agatgcattt   2220
tggaacatgt gtcacgtgtt gaattttttt tacgcaaacg atgacgggtt tactggaaac   2280
acgattcttg atactgtgaa ggacatcatt tacaacccgt tggtgcttgt gaatgaaaat   2340
gaagaacaaa ggtaa                                                    2355

<210> SEQ ID NO 45
<211> LENGTH: 2355
<212> TYPE: DNA
<213> ORGANISM: Stevia rebaudiana

<400> SEQUENCE: 45
atgaatcttt cactatgcat tgcgtcccct ttgttaacca aatcaagtcg acccacggct     60
ctgtcagcta ttcatacagc atcaacttca catggtggac aaactaatcc cactaatctg    120
atcattgata caaccaaaga acggatccaa aaactgttta aaaatgtaga aatttctgtt    180
tcttcatatg acacagcatg ggtagccatg gtcccttctc caaactcacc caaatcgcct    240
tgtttccctg agtgtctcaa ttggttaatt aataatcagc ttaatgatgg ttcatggggt    300
cttgttaatc acactcataa tcataatcac ccgttgctta aagattctct atcttcaaca    360
ttagcatgta ttgttgcatt aaaaagatgg aatgttgggg aagatcaaat aaataaaggt    420
ctaagtttta ttgagtcaaa tcttgcttca gcaactgaca aaagtcaacc atctcccatt    480
ggttttgata tcatatttcc tggtttgctt gagtatgcga aaaacttgga cataaacctc    540
ctttcaaaac aaacagattt tagtttgatg ctacataaga gggaattgga gcaaaaaaga    600
tgccattcaa atgagattga tggatacttg gcgtatatct ctgaaggact cggtaattta    660
tatgattgga atatggtgaa gaaatatcag atgaaaaatg gttctgtttt caactcacca    720
tcagcaacag cagctgcttt cattaatcat caaaatcccg gttgtcttaa ttatttaaat    780
tcacttttgg acaagtttgg taatgcagtc ccaacagttt atcctcttga tttatatatc    840
cggctttcta tggttgacac aattgaaaga ttaggaattt cacaccattt cagagtggaa    900
attaaaaatg ttttagatga aacatacaga tgttgggtgg aacgagatga gcaaatattc    960
atggatgttg taacatgtgc tttagccttt cggttattaa ggatccacgg gtataaagtc   1020
tccccagatc aattggctga aattactaat gaattagctt tcaaagacga atacgcagct   1080
cttgaaacat atcatgcatc acagatatta taccaagagg atttatcttc tggaaaacaa   1140
atcttgaagt cagctgattt cctcaaaggg atattatcca ctgattcaaa caggctttct   1200
aaattaattc acaaagaggt ggaaaatgct cttaagttcc ctatcaatac cggtttagaa   1260
cgcataaaca ctagacgaaa tatacagctt tacaatgtag acaatacaag aattctgaaa   1320
actacatatc actcatcaaa tattagtaac acttattacc taaggttggc tgttgaagat   1380
ttctacacct gccaatctat ttatcgtgaa gaattaaaag gtcttgaaag gtgggtggta   1440
cagaataagt tggaccagct caagtttgct aggcaaaaga ccgcctactg ttatttctct   1500
gttgctgcaa cactttcgtc tcccgaatta tcagatgcgc gtatttcatg ggccaaaaat   1560
ggcatattaa ctacagtagt tgatgacttt tttgatatcg gtggtacaat cgatgaattg   1620
accaacctga ttcaatgtgt tgaaaaatgg aatgtagatg tcgacaagga ttgttgttca   1680
gagcatgttc ggattttatt tttagcatta aaagatgcaa tctgttggat tggagatgaa   1740
gcttttaaat ggcaagcgcg cgatgtaact agccatgtta ttcaaacttg gttggaacta   1800
```

```
atgaatagta tgttgagaga agctatatgg acaagagatg cttatgtgcc aacattaaat    1860
gaatatatgg aaaacgctta cgtgtcattt gcattaggcc cgattgtcaa gccggctatt    1920
tactttgtgg ggcccaaatt atcagaggag attgttgaaa gctctgaata tcataatcta    1980
tttaagctaa tgagcacgca gggtcgactt ctaaacgata tccatagctt caagagggaa    2040
tttaaggaag gcaaattaaa cgcggtagca ttgcatttga gtaacggaga agtgggaaa     2100 gtggaagaag aggttgtgga ggagatgatg atgatgatta aaaacaagag aaagaattaa    2160
atgaaattaa ttttttgaaga aaatggtagc attgttccta gagcttgtaa agatgcattt   2220
tggaacatgt gtcacgtgtt gaattttttt tacgcaaacg atgacgggtt tactggaaac    2280
acgattcttg atactgtgaa ggacatcatt tacaacccgt tggtgcttgt gaatgaaaat    2340
gaagaacaaa ggtaa                                                      2355
```

<210> SEQ ID NO 46
<211> LENGTH: 1773
<212> TYPE: DNA
<213> ORGANISM: Zea mays

<400> SEQUENCE: 46

```
atggccatgc cagtgaagct gactcctgcc tccctctcgc tgaaggcggt ctgctgccgc     60
ttcagctccg gagggcatgc gctgcgcttc ggctcgtcgc taccgtgctg gaggaggacg    120
ccgacgcaac ggagcacgtc gtcgtctacg acgcgccctg cggctgaggt tagctctggc    180
aaaagcaagc agcacgatca agaagcatcg gaggctacga taagacagca gctccagcta    240
gtcgatgtgc ttgagaacat ggggatttct cggcattttg ctgctgaaat caaatgcatc    300
cttgacagga catacagaag ttggttacag agacatgagg aaattatgct ggacacaatg    360
acctgtgcga tggcatttcg tattctaagg ttgaatggat acaatgtctc ttctgatgag    420
ttgtatcatg ttgttgaagc ttccggactc cataattcac ttggaggata tctcaatgat    480
acaagaacct tgttagaatt acacaaggcc tcgacagtta gtatctctga agatgagtct    540
atcctggata gcataggctc aaggtcacgt accttactga gggaacaact agagtctggt    600
ggtgctctac gaaaaccttc actctttaaa gaggtggaac atgctctgga cggtcccttc    660
tacaccacat tggaccgtct acaccatagg tggaacatcg aaaatttcaa tattatagag    720
cagcacatgc tagagacacc atacttgtca aatcaacata ccagtagaga tattctagcg    780
ttgagtatta gagacttcag ttcctctcag tttacttacc agcaagaact tcaacatctt    840
gaaagctggg tgaaagagtg caggttagac cagctacaat ttgcgcgaca gaagttggca    900
tacttctact tgtctgctgc tggcaccatg ttctctcctg agctgtctga tgctcgaact    960
ttgtgggcca aaaatggtgt gctcacaact attgttgacg acttctttga tgttgcggga   1020
tcaaaagaag aacttgaaaa ccttgtcatg ttggttgaga tgtgggacga gcatcacaaa   1080
gttgagttct actcagaaca agtagagatt atatttcttt caatttatga ctcagttaac    1140
caacttggtg aaaaggcttc tttggtacaa gaccgcagta ttaccaaaca cctagtagaa    1200
atatggttgg atttgctaaa gtctatgatg acagaggtag agtggcgttt gagcaaatat    1260
gtgccaacag agaaggaata catgataaat gcatctttaa tatttggact aggccccatt   1320
gtattgccag cattatattt tgttgggcca aagatctcag agtctattgt taaagatcca    1380
gaatatgatg aattgttcaa actgatgagc acatgtggtc gcctcttgaa tgatgttcag    1440
acttttgaga gggagtacaa cgagggcaag ttgaatagtg tttctctcct cgttcttcat    1500
```

| | |
|---|---|
| ggtggcccca tgtccatatc agacgccaaa aggaaattac agaagcccat agacacatgc | 1560 |
| agaagagacc tcctaagttt agttcttcgt gaagaaagtg ttgttcctag gccctgcaag | 1620 |
| gaattatttt ggaaaatgtg caaggtgtgc tacttcttct actcgacgac ggatgggttt | 1680 |
| agctcacaag tggagagggc taagaagtg atgcggtga tcaatgagcc actaaagcta | 1740 |
| caaggaagtc atacgctggt gtctgatgtg tga | 1773 |

<210> SEQ ID NO 47
<211> LENGTH: 2232
<212> TYPE: DNA
<213> ORGANISM: Populus trichocarpa

<400> SEQUENCE: 47

| | |
|---|---|
| atgcagaact tcatggaac taaggaaagg atcaagaaga tgtttgataa gattgaattg | 60 |
| tcagtgtctt catatgacac tgcttgggtg gcaatggtcc catctccaga ttgtccggaa | 120 |
| actccttgtt ttccagagtg cacaaaatgg attttggaaa atcaacttgg tgatggctcc | 180 |
| tggagtcttc ctcatggcaa tccattatta gttaaggatg ctctttcatc tacattagcg | 240 |
| tgcatccttg cattgaagcg atggggtatc ggtgaagaac aaataaataa aggccttcga | 300 |
| tttattgagt tgaattccgc ttcagttacg ataacgagc aacataaacc aattggattt | 360 |
| gatataatat ttcctggcat gattgaatat gccatagatt tggatttgaa cctcccttg | 420 |
| aagccgacag atataaattc catgctccac aggagggctt tggagcttac aagtggcggt | 480 |
| ggcaagaact tggagggaag aagagcctac ttagcatatg tttcggaagg aattggaaaa | 540 |
| ttacaggatt gggaaatggc catgaaatat caaagaaaga atggatcact gttcaattca | 600 |
| ccatccacca cagcagctgc ctttattcat attcaagatg ctgagtgtct ccattatatt | 660 |
| cgttcactct tacagaagtt tgggaatgca gttccaacca tttatccttt ggatatatat | 720 |
| gctcgtcttt ctatggttga tgctcttgaa aggttgggaa tcgatcggca ttttaggaag | 780 |
| gaaagaaaat ttgttttgga cgaaacatac cgattttggt tgcagggga ggaagagata | 840 |
| ttttctgata atgccacttg tgctttggca tttaggatat tacgtttgaa cggatatgat | 900 |
| gtctctctag aagatcattt ctctaattca ctgggaggat atttgaagga ttcgggagct | 960 |
| gccttagagt tgtacagagc tctgcagcta agttatccag atgaatcact tctggaaaaa | 1020 |
| caaaattctc ggacaagcta tttcctgaaa cagggattat ccaacgtttc acttgtgga | 1080 |
| gataggcttc gtaaaaatat tatcggagag gtgcatgatg ctctcaattt ttctgaccat | 1140 |
| gcaaatttgc aacgcttagc tatcagaaga gaattaaac attatgctac agatgatacg | 1200 |
| aggatttga aaacttcgta tcgttgttcg actattggta accaggattt tctcaaattg | 1260 |
| gctgtagaag acttcaatat ctgtcaatca atacagcgtg aagaatttaa acatatcgag | 1320 |
| aggtgggttg tagagaggag actggacaag ctaaagtttg ctaggcagaa ggaggcctac | 1380 |
| tgttacttct ctgctgcagc aactctcttc gctccagaac tatctgatgc acgcatgtca | 1440 |
| tgggcaaaaa atggtgtgct tactactgtt gttgatgact ctttgatgt tggtggttct | 1500 |
| gaagaagaac tggtaaacct tattgaattg attgagaggt gggatgtcaa tggcagtgct | 1560 |
| gatttttgtt ctgaggaagt tgagatcata tattcggcaa ttcacagcac ataagtgag | 1620 |
| ataggagaca aatctttcgg atggcaagga cgcgatgtga aaagtcaggt tatcaagatt | 1680 |
| tggttggatt tgctcaaatc catgttgaca gaagcacaat ggtcaagtaa caaatcagtg | 1740 |
| ccgacccttg atgaatatat gacaactgca catgtatcgt tcgctctagg gcctattgtt | 1800 |
| cttccagctc tgtattttgt ggggcctaag cttcagagg aggttgctgg acatcctgaa | 1860 |

```
ttgcttaatc tatacaaggt tacgagcact tgcgggcgtc tgctcaatga ctggagaagc    1920
tttaagagag aatctgaaga agggaaattg aatgccatct cattgtacat gattcacagc    1980
ggtggtgctt caactgaaga agagaccatc gaacatttta aaggattgat cgacagccag    2040
agaagacaat tgcttcaatt agtttttgcag gaaaaggata gtataattcc tagaccctgc    2100
aaggatttgt tttggaacat gataaaatta ttgcacacgt tctacatgaa ggatgatgga    2160
ttcacttcaa acgagatgag aaatgttgtc aaggcaataa taaatgaacc catctctcta    2220
gatgaattat aa                                                        2232
```

<210> SEQ ID NO 48
<211> LENGTH: 2952
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 48

```
atggaatttg atgaaccatt ggttgacgaa gcaagatctt tagtgcagcg tactttacaa      60
gattatgatg acagatacgg cttcggtact atgtcatgtg ctgcttatga tacagcctgg     120
gtgtctttag ttacaaaaac agtcgatggg agaaaacaat ggcttttccc agagtgtttt     180
gaatttctac tagaaacaca atctgatgcc ggaggatggg aaatcgggaa ttcagcacca     240
atcgacggta tattgaatac agctgcatcc ttacttgctc taaaacgtca cgttcaaact     300
gagcaaatca tccaacctca acatgaccat aaggatctag caggtagagc tgaacgtgcc     360
gctgcatctt tgagagcaca attggctgca ttggatgtgt ctacaactga acacgtcggt     420
tttgagataa ttgttcctgc aatgctagac ccattagaag ccgaagatcc atctctagtt     480
ttcgattttc cagctaggaa acctttgatg aagattcatg atgctaagat gagtagattc     540
aggccagaat acttgtatgg caaacaacca atgaccgcct acattcatt agaggctttc      600 ataggcaaaa tcgacttcga taaggtaaga caccaccgta cccatgggtc tatgatgggt     660
tctccttcat ctaccgcagc ctacttaatg cacgcttcac aatgggatgg tgactcagag     720 gcttaccta gacacgtgat taaacacgca gcagggcagg gaactggtgc tgtaccatct      780
gctttcccat caaacatttt tgagtcatct tggattctta ccacattgtt tagagctgga    840
ttttcagctt ctcatcttgc ctgtgatgag ttgaacaagt tggtcgagat acttgagggc    900
tcattcgaga aggaaggtgg ggcaatcggt tacgctccag ggtttcaagc agatgttgat    960
gatactgcta aaacaataag tacattagca gtccttggaa gagatgctac accaagacaa   1020
atgatcaagg tatttgaagc taatacacat tttagaacat accctggtga aagagatcct   1080
tctttgacag ctaattgtaa tgctctatca gccttactac accaaccaga tgcagcaatg   1140
tatggatctc aaattcaaaa gattaccaaa tttgtctgtg actattggtg gaagtctgat   1200
ggtaagatta agataagtg gaacacttgc tacttgtacc catctgtctt attagttgag   1260
gttttggttg atcttgttag tttattggag cagggtaaat tgcctgatgt tttggatcaa   1320
gagcttcaat acagagtcgc catcacattg ttccaagcat gtttaaggcc attactagac   1380
caagatgccg aaggatcatg gaacaagtct atcgaagcca cagcctacgg catccttatc   1440
ctaactgaag ctaggagagt tgtttcttc gacagattgt ctgagccatt gaatgaggca    1500
atccgtagag gtatcgcttt cgccgactct atgtctggaa ctgaagctca gttgaactac   1560
atttggatcg aaaaggttag ttacgcacct gcattattga ctaaatccta tttgttagca   1620
```

-continued

```
gcaagatggg ctgctaagtc tcctttaggc gcttccgtag gctcttcttt gtggactcca       1680
ccaagagaag gattggataa gcatgtcaga ttattccatc aagctgagtt attcagatcc       1740
cttccagaat gggaattaag agcctccatg attgaagcag ctttgttcac accacttcta       1800
agagcacata gactagacgt tttccctaga caagatgtag gtgaagacaa atatcttgat       1860
gtagttccat tcttttggac tgccgctaac aacagagata gaacttacgc ttccactcta       1920
ttcctttacg atatgtgttt tatcgcaatg ttaaacttcc agttagacga attcatggag       1980
gccacagccg gtatcttatt cagagatcat atggatgatt tgaggcaatt gattcatgat       2040
cttttggcag agaaaacttc cccaaagagt tctggtagaa gtagtcaggg cacaaaagat       2100
gctgactcag gtatagagga agacgtgtca atgtccgatt cagcttcaga ttcccaggat       2160
agaagtccag aatacgactt ggttttcagt gcattgagta cctttacaaa acatgtcttg       2220
caacacccat ctatacaaag tgcctctgta tgggatagaa aactacttgc tagagagatg       2280
aaggcttact tacttgctca tatccaacaa gcagaagatt caactccatt gtctgaattg       2340
aaagatgtgc ctcaaaagac tgatgtaaca agagtttcta catctactac taccttcttt       2400
aactgggtta gaacaacttc cgcagaccat atatcctgcc catactcctt ccactttgta       2460
gcatgccatc taggcgcagc attgtcacct aaagggtcta acggtgattg ctatccttca       2520
gctggtgaga agttcttggc agctgcagtc tgcagacatt tggccaccat gtgtagaatg       2580
tacaacgatc ttggatcagc tgaacgtgat tctgatgaag gtaatttgaa ctccttggac       2640
ttccctgaat tcgccgattc cgcaggaaac ggagggatag aaattcagaa ggccgctcta       2700
ttaaggttag ctgagtttga gagagattca tacttagagg ccttccgtcg tttacaagat       2760
gaatccaata gagttcacgg tccagccggt ggtgatgaag ccagattgtc cagaaggaga       2820
atggcaatcc ttgaattctt cgcccagcag gtagatttgt acggtcaagt atacgtcatt       2880
agggatattt ccgctcgtat tcctaaaaac gaggttgaga aaagagaaaa attggatgat       2940
gctttcaatt ga                                                          2952
```

<210> SEQ ID NO 49
<211> LENGTH: 2646
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49

```
atggcttcta gtacacttat ccaaaacaga tcatgtggcg tcacatcatc tatgtcaagt        60
tttcaaatct tcagaggtca accactaaga tttcctggca ctagaacccc agctgcagtt       120
caatgcttga aaagaggag atgccttagg ccaaccgaat ccgtactaga atcatctcct       180
ggctctggtt catatagaat agtaactggc ccttctggaa ttaaccctag ttctaacggg       240
cacttgcaag agggttcctt gactcacagg ttaccaatac caatggaaaa atctatcgat       300
aacttccaat ctactctata tgtgtcagat atttggtctg aaacactaca gagaactgaa       360
tgtttgctac aagtaactga aaacgtccag atgaatgagt ggattgagga aattagaatg       420
tactttagaa atatgacttt aggtgaaatt tccatgtccc cttacgacac tgcttgggtg       480
gctagagttc cagcgttgga cggttctcat gggcctcaat tccacagatc tttgcaatgg       540
attatcgaca accaattacc agatggggac tggggcgaac cttctctttt cttgggttac       600
gatagagttt gtaatacttt agcctgtgtg attgcgttga aaacatgggg tgttggggca       660
```

```
caaaacgttg aaagaggaat tcagttccta caatctaaca tatacaagat ggaggaagat      720
gacgctaatc atatgccaat aggattcgaa atcgtattcc ctgctatgat ggaagatgcc      780
aaagcattag gtttggattt gccatacgat gctactattt tgcaacagat ttcagccgaa      840
agagagaaaa agatgaaaaa gatcccaatg gcaatggtgt acaaataccc aaccacttta      900
cttcactcct tagaaggctt gcatagagaa gttgattgga ataagttgtt acaattacaa      960
tctgaaaatg gtagttttct ttattcacct gcttcaaccg catgcgcctt aatgtacact     1020
aaggacgtta aatgttttga ttacttaaac cagttgttga tcaagttcga ccacgcatgc     1080
ccaaatgtat atccagtcga tctattcgaa agattatgga tggttgacag attgcagaga     1140
ttagggatct ccagatactt tgaaagagag attagagatt gtttacaata cgtctacaga     1200
tattggaaag attgtggaat cggatgggct tctaactctt ccgtacaaga tgttgatgat     1260
acagccatgg cgtttagact tttaaggact catggtttcg acgtaaagga agattgcttt     1320
agacagtttt tcaaggacgg agaattcttc tgcttcgcag gccaatcatc tcaagcagtt     1380
acaggcatgt ttaatctttc aagagccagt caaacattgt ttccaggaga atctttattg     1440
aaaaaggcta gaaccttctc tagaaacttc ttgagaacaa agcatgagaa caacgaatgt     1500
ttcgataaat ggatcattac taaagatttg gctggtgaag tcgagtataa cttgaccttc     1560
ccatggtatg cctctttgcc tagattagaa cataggacat acttagatca atatggaatc     1620
gatgatatct ggataggcaa atctttatac aaaatgcctg ctgttaccaa cgaagttttc     1680
ctaaagttgg caaaggcaga ctttaacatg tgtcaagctc tacacaaaaa ggaattggaa     1740
caagtgataa agtggaacgc gtcctgtcaa ttcagagatc ttgaattcgc cagacaaaaa     1800
tcagtagaat gctattttgc tggtgcagcc acaatgttcg aaccagaaat ggttcaagct     1860
agattagtct gggcaagatg ttgtgtattg acaactgtct tagacgatta ctttgaccac     1920
gggacacctg ttgaggaact tagagtgttt gttcaagctg tcagaacatg gaatccagag     1980
ttgatcaacg gtttgccaga gcaagctaaa atcttgttta tgggcttata caaaacagtt     2040
aacacaattg cagaggaagc attcatggca cagaaaagag acgtccatca tcatttgaaa     2100
cactattggg acaagttgat aacaagtgcc ctaaaggagg ccgaatgggc agagtcaggt     2160
tacgtcccaa catttgatga atacatggaa gtagctgaaa tttctgttgc tctagaacca     2220
attgtctgta gtaccttgtt ctttgcgggt catagactag atgaggatgt tctagatagt     2280
tacgattacc atctagttat gcatttggta aacagagtcg gtagaatctt gaatgatata     2340
caaggcatga gagggaggc ttcacaaggt aagatctcat cagttcaaat ctacatggag     2400
gaacatccat ctgttccatc tgaggccatg gcgatcgctc atcttcaaga gttagttgat     2460
aattcaatgc agcaattgac atacgaagtt cttaggttca ctgcggttcc aaaaagttgt     2520
aagagaatcc acttgaatat ggctaaaatc atgcatgcct tctacaagga tactgatgga     2580
ttctcatccc ttactgcaat gacaggattc gtcaaaaagg ttcttttcga acctgtgcct     2640
gagtaa                                                                2646
```

<210> SEQ ID NO 50
<211> LENGTH: 2952
<212> TYPE: DNA
<213> ORGANISM: Phomopsis amygdali

<400> SEQUENCE: 50

```
atggagttcg atgaaccact tgtggacgag gcgaggtcct tggtccaaag aaccctgcaa       60
```

```
gattatgacg accgctatgg cttttggcact atgagctgtg cggcctatga cacagcatgg    120
gtatcgctgg tgactaaaac agtcgatggg cgtaaacaat ggttgttccc tgagtgcttc    180
gaatttctcc tagaaacgca gtccgatgct ggcggctggg aaatcggcaa cagcgcaccc    240
atcgatggga tccttaacac tgctgcttca ctgctggcat tgaagcgcca cgtccaaaca    300
gagcagatta ttcagccgca acacgaccat aaagacctgg ccgggcgtgc ggaaagagcg    360
gcggcgtctt tgcgagcaca gttggcggct ctggatgtgt cgacaacgga gcatgtgggc    420
ttcgaaatca tcgtcccggc catgctcgac cctctcgagg ccgaagaccc gtctttggtg    480
ttcgactttc cagcacgcaa accactgatg aagatccacg acgctaagat gtcgcgattc    540
cgaccagagt acctctacgg taaacagccg atgacggcat tgcattcgct cgaggccttt    600
atcgggaaaa tagacttcga caaagtacgg catcacagga cacacggttc gatgatgggg    660
tcgccctcgt cgacggctgc atacctgatg catgcttctc agtgggacgg cgactctgag    720
gcctatctac gccatgtcat caagcacgca gctggccagg gcaccggagc tgttccgagt    780
gcatttcctt cgacgcattt cgagtcttct tggattttga acacattgtt tcgagctggg    840
ttctcagcct ctcatctagc atgcgacgaa ttaaacaagc tggtagagat cctcgaaggc    900
tcatttgaga agaaggggg agccatcggt tatgctcctg ggtttcaagc agatgtggat    960
gataccgcaa agaccatctc cactttggct gtgcttggga gagatgccac tccccggcaa   1020
atgatcaagg ttttgaagc caatacacac tttcggactt accctggtga agagatcca   1080 agcttgactg ccaattgcaa cgcgctctcg gctcttcttc accagccaga cgcagcaatg   1140
tacggcagcc agatccagaa gatcacaaag tttgtttgtg actactggtg aaaagtgac   1200 ggcaaaatca aggacaagtg gaatacctgc tacttgtatc catcggtcct cctcgtcgag   1260
gtgttagtag accttgtgtc cctgttggag caaggaaagc tacccgacgt gctggatcag   1320
gagctgcaat acagggtcgc cattacgtta ttccaggcct gcttgcgacc gctacttgat   1380
caagatgctg aaggttcatg gaacaaatcc attgaagcca cagcctacgg cattctaatc   1440
cttacggagg cgcggcgagt atgcttttt gaccgtctga gtgagcctct gaatgaggct   1500
attcgacgcg ggattgcgtt tgcagattcg atgagcggta ctgaagctca gctgaattat   1560
atatggatcg agaaagtgag ctacgcacct gctcttctga ccaaatcata cctcctcgca   1620
gctcggtggg cggcaaagtc cccgcttggc gcttccgttg gatccagcct ttggacgcct   1680
ccaagagaag gcttggataa gcacgtccgt ctattccacc aggcagagct cttcaggtcg   1740
ttgccggagt gggagctgcg cgcgtccatg atcgaggcag ccctgttcac tcctttgctg   1800
cgtgcgcata ggctggatgt atttccacgc caagacgtcg gcgaggacaa gtacctggac   1860
gttgtgccgt tcttctggac ggccgccaat aaccgcgatc gcacgtacgc atccactctg   1920
tttctgtatg acatgtgctt tatcgccatg cttaacttcc agctggatga gttcatggag   1980
gctacagcgg gaatcctctt ccgggaccat atggatgatt tgcgccaact catccacgac   2040
ctgcttgccg aaaagacgag ccccaagtca tcgggcagaa gtagccaagg aaccaaagac   2100
gcggactcgg gcatcgaaga agacgtttct atgagcgact cagcgtcaga ctcccaggac   2160
cgcagccctg aatacgacct ggtcttctct gcgctctcta ccttcaccaa acatgtcctg   2220
cagcaccctt caatccagtc agccagtgtc tgggatagga aactactcgc tcgcgagatg   2280
aaagcatacc tcctagctca tattcaacag gctgaggaca gcacgccctt gagtgagctc   2340
aaggacgtcc ctcaaaaaac tgacgtgaca cgcgtctcaa cgtccacaac gactttcttc   2400
aactgggtac gcacaacatc cgcagaccac atatcctgcc catattcatt ccatttcgtg   2460
```

```
gcgtgtcacc tcggcgccgc gctgagcccc aagggcagca acggcgactg ttacccgtca    2520
gccggtgaaa agttcctcgc ggccgccgta tgccgccatt tggccacgat gtgccgcatg    2580
tacaatgact tgggatcggc ggagcgcgac agtgacgagg gaaatttgaa ttcactcgac    2640
tttcccgagt tcgccgactc agcggggaat ggtgggattg agatccagaa agctgccttg    2700
ctcaggctgg ccgagttcga acgcgactcg tatctcgagg ctttccggcg acttcaggat    2760
gaaagcaacc gcgttcacgg accggctggt ggggatgaag ccagactcag caggcggcgc    2820
atggccatcc ttgagttctt tgcccagcag gtggacttgt atggccaggt ctacgttatt    2880
cgcgatatct cggccaggat tccaaagaac gaggttgaga agaaaaggaa actagatgat    2940
gctttcaatt ag                                                        2952

<210> SEQ ID NO 51
<211> LENGTH: 2646
<212> TYPE: DNA
<213> ORGANISM: Physcomitrella patens

<400> SEQUENCE: 51
atggcttcca gcaccttgat acagaatcgc tcttgtggcg ttacgtcaag catgtcttcc      60
tttcagattt ttcgagggca acctctacgt tttccaggca ctagaactcc tgctgcagtt     120
caatgcctaa agaagcgtcg atgtttgcga cctactgaat cagtcctcga gctctcct      180 ggtagcggat cttacaggat gtaactgga ccctccggca tcaatccttc ttcaaacggc      240
cacttgcaag aggggtccct tactcacaga cttccgatac ccatggaaaa atccattgat     300
aacttccagt ctactttgta cgtatcagac atatggtcag aaaccttgca agaacggaa      360 tgtttgttgc aggtgactga gaatgtacag atgaacgagt ggattgagga aatcagaatg     420
tacttccgaa atatgacact gggggaaata tccatgtctc catacgacac agcttgggta     480
gcgcgagtgc cagcgctgga tggctcacat ggccctcagt tccatcggtc tttgcagtgg     540
attattgata atcagctccc ggatggcgat tggggtgaac cgtctctttt ccttggatac     600
gatcgcgttt gcaacactct cgcctgtgta attgccctga aaacttgggg tgttggggct     660
cagaacgtag agcgtggaat ccagtttctg caatctaaca tctacaaaat ggaggaagat     720
gacgccaatc atatgccgat tggatttgag attgtcttcc cagcgatgat ggaagatgcc     780
aaggcactgg gactggattt accatacgat gccactatct tgcaacaaat ctcggctgaa     840
agagagaaga aaatgaaaaa gattcctatg gcgatggtgt acaagtaccc cactactttg     900
ctgcattctc tggaaggcct gcaccgggaa gtggactgga caagctcct ccagctacag      960 tccgagaatg gctcctttct gtattcaccc gcatccactg catgcgcact tatgtacaca    1020
aaagatgtga agtgcttcga ctacttgaac cagctcctca tcaagttcga ccacgcttgt    1080
ccaaacgtgt accccgttga tctcttcgag cgtttgtgga tggtagaccg cctacaaagg    1140 ctggaatat cccgctactt cgagcgagaa atcagagact gtctacaata tgtataccga     1200
tactggaagg attgtggtat tggctggca agcaattcgt ccgtgcagga cgtggacgac     1260
acggccatgg ccttccgcct ctccgcaca cacggattcg acgtcaagga ggactgcttc     1320
agacagtttt tcaaagatgg tgagttcttc tgcttcgccg ccagtccag ccaagccgtc      1380 acgggaatgt tcaacctcag cagagcatcg caaacgctct cccaggggga atcactccta    1440
aaaaaggcca gaacctttc cagaaacttt tgagaaacca agcatgaaaa caatgaatgc     1500
ttcgacaagt ggataatcac gaaggatcta gcgggcgagg tggaatacaa tctcacattc    1560
```

```
ccctggtatg ctagccttcc tcgtcttgag catcgcacct acttggacca atatgggatt    1620
gatgatatct ggattggcaa gtcgctctac aaaatgccgg ccgtcaccaa cgaagtgttt    1680
ctcaaattgg ccaaagccga cttcaacatg tgccaagctc ttcacaagaa ggaactcgag    1740
caggtcatca aatggaatgc cagctgccaa tttagagacc tcgagtttgc tagacagaaa    1800
tccgtggagt gctacttcgc aggcgctgca accatgtttg agcccgaaat ggtgcaggcg    1860
aggctcgttt gggcacgctg ttgcgtgctc accaccgttc tagacgatta cttcgatcac    1920
ggtacacctg tggaagagct tcgggttttt gtgcaggccg taaggacttg gaatcccgag    1980
ctcatcaacg gactacctga gcaagccaag attctcttta tgggactgta caagactgtg    2040
aacactatcg ccgaggaggc attcatggca cagaaacgag acgtacatca tcatctcaag    2100
cattactggg acaaattgat cacttcagct ttgaaagaag ccgaatgggc agagtccggc    2160
tacgtcccca ccttcgacga gtatatggaa gtcgctgaaa tctccgtcgc actagagccc    2220
attgtatgta gcactctctt cttcgccggc cataggctcg atgaggatgt gcttgacagt    2280
tatgactacc atcttgtcat gcatctcgtc aaccgcgtag gtcgcatcct caacgacatc    2340
caaggaatga agagggaagc cagccaaggg aagatatcga gcgtgcagat ctacatggag    2400
gagcatccaa gtgtgccttc agaggccatg gccatcgctc atctgcagga attggtcgac    2460
aactccatgc aacagctgac atacgaagtg ctgcgcttca ctgcagtccc gaagtcctgt    2520
aagagaatcc atttaaacat ggcgaagatc atgcacgctt tctacaagga cactgatggg    2580
ttttcgtcac tgacagccat gacagggttt gtgaagaagg tgctcttcga gccagtacct    2640
gaatag                                                                2646
```

<210> SEQ ID NO 52
<211> LENGTH: 1542
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
atggatgctg tgacgggttt gttaactgtc ccagcaaccg ctataactat tggtggaact      60
gctgtagcat ggcggtagc gctaatcttt tggtacctga atcctacac atcagctaga     120
agatcccaat caaatcatct tccaagagtg cctgaagtcc caggtgttcc attgttagga     180
aatctgttac aattgaagga gaaaaagcca tacatgactt ttacgagatg ggcagcgaca     240
tatgaccta tctatagtat caaaactggg gctacagta tggttgtggt atcatctaat     300
gagatagcca aggaggcatt ggtgaccaga ttccaatcca tatctacaag gaacttatct     360
aaagccctga agtacttac agcagataag acaatggtcg caatgtcaga ttatgatgat     420
tatcataaaa cagttaagag acacatactg accgccgtct ggtgtcctaa tgcacagaaa     480
aagcatagaa ttcacagaga tatcatgatg gataacatat ctactcaact tcatgaattc     540
gtgaaaaaca acccagaaca ggaagaggta gaccttagaa aaatctttca atctgagtta     600
ttcggcttag ctatgagaca agccttagga aaggatgttg aaagtttgta cgttgaagac     660
ctgaaaatca ctatgaatag agacgaaatc tttcaagtcc ttgttgttga tccaatgatg     720
ggagcaatcg atgttgattg gagagacttc tttccatacc taaagtgggt cccaaacaaa     780
aagttcgaaa atactattca acaaatgtac atcagaagaa aagctgttat gaaatctta     840
atcaaagagc acaaaaagag aatagcgtca ggcgaaaagc taaatagtta tatcgattac     900
```

```
cttttatctg aagctcaaac tttaaccgat cagcaactat tgatgtcctt gtgggaacca    960
atcattgaat cttcagatac aacaatggtc acaacagaat gggcaatgta cgaattagct   1020
aaaaacccta aattgcaaga taggttgtac agagacatta agtccgtctg tggatctgaa   1080
aagataaccg aagagcatct atcacagctg ccttacatta cagctatttt ccacgaaaca   1140
ctgagaagac actcaccagt tcctatcatt cctctaagac atgtacatga agataccgtt   1200
ctaggcggct accatgttcc tgctggcaca gaacttgccg ttaacatcta cggttgcaac   1260
atggacaaaa acgtttggga aaatccagag gaatggaacc cagaaagatt catgaaagag   1320
aatgagacaa ttgattttca aaagacgatg gccttcggtg gtggtaagag agtttgtgct   1380
ggttccttgc aagccctttt aactgcatct attgggattg ggagaatggt tcaagagttc   1440
gaatggaaac tgaaggatat gactcaagag gaagtgaaca cgataggcct aactacacaa   1500
atgttaagac cattgagagc tattatcaaa cctaggatct aa                      1542
```

<210> SEQ ID NO 53
<211> LENGTH: 1530
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53

```
atggcatttt tctctatgat ttcaattttg ttgggatttg ttatttcttc tttcatcttc     60 atcttttct tcaaaaagtt acttagtttt agtaggaaaa acatgtcaga agtttctact    120
ttgccaagtg ttccagtagt gcctggtttt ccagttattg ggaatttgtt gcaactaaag    180
gagaaaaagc tcataaaac tttcactaga tggtcagaga tatatggacc tatctactct    240
ataaagatgg gttcttcatc tcttattgta ttgaacagta cagaaactgc taaggaagca    300
atggtcacta gattttcatc aatatctacc agaaaattgt caaacgccct aacagttcta    360
acctgcgata agtctatggt cgccacttct gattatgatg acttccacaa attagttaag    420
agatgtttgc taaatggact tcttggtgct aatgctcaaa agagaaaaag acactacaga    480
gatgctttga ttgaaaatgt gagttccaag ctacatgcac acgctagaga tcatccacaa    540
gagccagtta actttagagc aattttcgaa cacgaattgt ttggtgtagc attaaagcaa    600
gccttcggta aagacgtaga atccatatac gtcaaggagt taggcgtaac attatcaaaa    660
gatgaaatct ttaaggtgct tgtacatgat atgatggagg gtgcaattga tgtagattgg    720
agagatttct tcccatattt gaatggatc cctaataagt cttttgaagc taggatacaa    780
caaaagcaca agagaagact agctgttatg aacgcactta acaggacag attgaagcaa    840 aatgggtctg aatcagatga tgattgttac cttaacttct taatgtctga ggctaaaaca    900
ttgactaagg aacagatcgc aatccttgtc tgggaaacaa tcattgaaac agcagatact    960
accttagtca caactgaatg ggccatatac gagctagcca acatccatc tgtgcaagat   1020 aggttgtgta aggagatcca gaacgtgtgt ggtggagaga attcaagga agagcagttg   1080 tcacaagttc cttaccttaa cggcgttttc catgaaacct tgagaaaata ctcacctgca   1140
ccattagttc ctattagata cgcccacgaa gatacacaaa tcggtggcta ccatgttcca   1200
gctgggtccg aaattgctat aaacatctac gggtgcaaca tggacaaaaa gagatgggaa   1260
agaccagaag attggtggcc agaaagattc ttagatgatg caaatatga acatctgat   1320 ttgcataaaa caatggcttt cggagctggc aaaagagtgt gtgccggtgc tctacaagcc   1380
```

```
tccctaatgg ctggtatcgc tattggtaga ttggtccaag agttcgaatg gaaacttaga    1440
gatggtgaag aggaaaatgt cgatacttat gggttaacat ctcaaaagtt atacccacta    1500
atggcaatca tcaatcctag aagatcctaa                                    1530
```

<210> SEQ ID NO 54
<211> LENGTH: 1578
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
atgagtaagt ctaatagtat gaattctaca tcacacgaaa cccttttta acaattggtc      60 ttgggtttgg accgtatgcc attgatggat gttcactggt tgatctacgt tgctttcggc    120
gcatggttat gttcttatgt gatacatgtt ttatcatctt cctctacagt aaaagtgcca    180
gttgttggat acaggtctgt attcgaacct acatggttgc ttagactag attcgtctgg     240 gaaggtggct ctatcatagg tcaagggtac aataagttta aagactctat tttccaagtt    300
aggaaattgg gaactgatat tgtcattata ccacctaact atattgatga agtgagaaaa    360
ttgtcacagg acaagactag atcagttgaa cctttcatta atgattttgc aggtcaatac    420
acaagaggca tggttttctt gcaatctgac ttacaaaacc gtgttataca acaaagacta    480
actccaaaat tggtttcctt gaccaaggtc atgaaggaag agttggatta tgctttaaca    540
aaagagatgc ctgatatgaa aaatgacgaa tgggtagaag tagatatcag tagtataatg    600
gtgagattga tttccaggat ctccgccaga gtctttctag ggcctgaaca ctgtcgtaac    660
caggaatggt tgactactac agcagaatat tcagaatcac ttttcattac agggtttatc    720
ttaagagttg tacctcatat cttaagacca ttcatcgccc ctctattacc ttcatacagg    780
actctactta gaaacgtttc aagtggtaga agagtcatcg tgacatcat aagatctcag     840 caagggatg gtaacgaaga tatactttcc tggatgagag atgctgccac aggagaggaa     900
aagcaaatcg ataacattgc tcagagaatg ttaattcttt ctttagcatc aatccacact    960
actgcgatga ccatgacaca tgccatgtac gatctatgtg cttgccctga gtacattgaa   1020
ccattaagag atgaagttaa atctgttgtt ggggcttctg gctgggacaa gacagcgtta   1080
aacagatttc ataagttgga ctccttccta aagagtcac aaagattcaa cccagtattc    1140
ttattgacat tcaatagaat ctaccatcaa tctatgacct tatcagatgg cactaacatt   1200
ccatctggaa cacgtattgc tgttccatca cacgcaatgt gcaagattc tgcacatgtc    1260 ccaggtccaa ccccacctac tgaatttgat ggattcagat atagtaagat acgttctgat   1320
agtaactacg cacaaaagta cctattctcc atgaccgatt cttcaaacat ggctttcgga   1380
tacggcaagt atgcttgtcc aggtagattt tacgcgtcta atgagatgaa actaacatta   1440 gccatttgt tgctacaatt tgagttcaaa ctaccagatg gtaaaggtcg tcctagaaat    1500
atcactatcg attctgatat gattccagac ccaagagcta gactttgcgt cagaaaaga    1560 tcacttagag atgaatga                                                 1578
```

<210> SEQ ID NO 55
<211> LENGTH: 1500
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 55

```
atggaagatc ctactgtctt atatgcttgt cttgccattg cagttgcaac tttcgttgtt      60
agatggtaca gagatccatt gagatccatc ccaacagttg gtggttccga tttgcctatt     120
ctatcttaca tcggcgcact aagatggaca agacgtggca gagagatact tcaagaggga     180
tatgatggct acagaggatc tacattcaaa atcgcgatgt tagaccgttg gatcgtgatc     240
gcaaatggtc ctaaactagc tgatgaagtc agacgtagac cagatgaaga gttaaacttt     300
atggacggat taggagcatt cgtccaaact aagtacacct taggtgaagc tattcataac     360
gatccatacc atgtcgatat cataagagaa aaactaacaa gaggccttcc agccgtgctt     420
cctgatgtca ttgaagagtt gacacttgcg gttagacagt acattccaac agaaggtgat     480
gaatgggtgt ccgtaaactg ttcaaaggcc gcaagagata ttgttgctag agcttctaat     540
agagtctttg taggtttgcc tgcttgcaga aaccaaggtt acttagattt ggcaatagac     600
tttacattgt ctgttgtcaa ggatagagcc atcatcaata tgtttccaga attgttgaag     660
ccaatagttg gcagagttgt aggtaacgcc accagaaatg ttcgtagagc tgttcctttt     720
gttgctccat tggtggagga agacgtaga cttatggaag agtacggtga agactggtct      780
gaaaaaccta atgatatgtt acagtggata atggatgaag ctgcatccag agatagttca     840
gtgaaggcaa tcgcagagag attgttaatg gtgaacttcg cggctattca tacctcatca     900
aacactatca ctcatgcttt gtaccacctt gccgaaatgc ctgaaacttt gcaaccactt     960
agagaagaga tcgaaccatt agtcaaagag gagggctgga ccaaggctgc tatgggaaaa    1020
atgtggtggt tagattcatt tctaagagaa tctcaaagat acaatggcat taacatcgta    1080
tctttaacta gaatggctga caaagatatt acattgagtg atggcacatt tttgccaaaa    1140
ggtactctag tggccgttcc agcgtattct actcatagag atgatgctgt ctacgctgat    1200
gccttagtat tcgatccttt cagattctca cgtatgagag cgagagaagg tgaaggtaca    1260
aagcaccagt tcgttaatac ttcagtcgag tacgttccat ttggtcacgg aaagcatgct    1320
tgtccaggaa gattcttcgc cgcaaacgaa ttgaaagcaa tgttggctta cattgttcta    1380
aactatgatg taaagttgcc tggtgacggt aaacgtccat tgaacatgta ttggggtcca    1440
acagttttgc ctgcaccagc aggccaagta ttgttcagaa agagacaagt tagtctataa    1500
```

<210> SEQ ID NO 56
<211> LENGTH: 1542
<212> TYPE: DNA
<213> ORGANISM: Stevia rebaudiana

<400> SEQUENCE: 56

```
atggatgccg tcaccggttt gctgacagtt ccggcaaccg caataaccat cggcggtacg      60
gccgtcgcac tcgccgtcgc tctgatattc tggtacctca aaagctacac atctgcacgc     120
aggagccaat caaccatctc ccctcgggtt cccgaggtac ctggtgtgcc attattgggg     180
aatttattgc agttgaagga gaagaaacct tacatgactt ttacaagatg gcggcaact      240
tatggtccga tttattcgat taaaaccgga gcaacttcta tggtggtcgt cagttcaaat     300
gaaattgcaa aggaggcatt ggttaccaga tttcaatcta tctcaaccag aaacctatca     360
aaggcattaa aggttctcac agcagataaa accatggtgg cgatgagtga ttatgatgat     420
tatcataaga ctgtcaaacg ccatatactg accgctgttt tgggaccaaa tgctcagaag     480
aaacaccgca tccataggga catcatgatg gataatatat caacccaact tcatgaattt     540
```

| | |
|---|---|
| gttaaaaata atcctgaaca agaggaagtg gatctaagga aaatattcca atccgaactt | 600 |
| tttggattag ctatgagaca agcattggga aaggatgtgg agagcttata tgttgaggat | 660 |
| cttaaaatca ccatgaaccg agacgagata tttcaggtat tggttgttga cccgatgatg | 720 |
| ggtgcaattg acgtcgactg gagagatttc ttcccgtatc taaagtgggt cccgaataaa | 780 |
| aagtttgaaa acacgatcca acaaatgtat atccggagag aagctgtgat gaagtctctt | 840 |
| attaaagaac ataaaaaacg tattgcatcc ggagagaaat aaacagcta cattgattac | 900 |
| ttgctatcgg aagcacaaac gttaaccgat caacaactac ttatgtctct atgggaacct | 960 |
| attattgaat catcagacac cactatggtt acaactgaat gggctatgta tgaacttgca | 1020 |
| aaaaacccca aacttcagga tcgtttgtat cgggatatca aaagtgtttg cgggtcagag | 1080 |
| aagattacag aagaacactt gtctcaactg ccatacataa ctgccatttt tcatgaaacc | 1140 |
| ttgagaaggc atagtccagt tcctataatt ccattaagac acgtgcatga agacacagtg | 1200 |
| ttaggagggt accatgtgcc agctggaacc gagctagcgg taaacattta tggatgtaac | 1260 |
| atggataaga atgtgtggga gaatcctgaa gaatggaatc cagagagatt catgaaggaa | 1320 |
| aatgaaacga tagatttcca gaaaacaatg gcgtttggag gtggaaagcg cgtatgtgct | 1380 |
| ggttcgcttc aagcattgtt gactgcttcc attggaattg gaagaatggt gcaagagttt | 1440 |
| gagtggaaac tgaaagayat gacccaagaa gaagttaata cgattgggct tacgacccag | 1500 |
| atgcttcgtc cactgcgggc cataataaag cccaggatat ga | 1542 |

<210> SEQ ID NO 57
<211> LENGTH: 1530
<212> TYPE: DNA
<213> ORGANISM: Arabidopsis thaliana

<400> SEQUENCE: 57

| | |
|---|---|
| atggccttct ctccatgat ctccattctc cttggctttg ttatctcctc cttcatcttc | 60 |
| atcttcttct tcaagaaact tctctccttc tccagaaaga acatgtctga agtctccact | 120 |
| ctccccctctg ttccagtggt accagggttt cctgttattg ggaacttgct gcaactaaaa | 180 |
| gagaagaaac ctcacaagac tttcactaga tggtcagaga tttatggtcc tatttactct | 240 |
| ataaagatgg gttcttcttc tcttattgtc ctcaattcta ctgagactgc caaagaggcc | 300 |
| atggtgacgc ggttttcgtc tatctcaacg aggaagttgt caaatgcgtt gacagtcctt | 360 |
| acttgtgaca aatctatggt tgctactagt gattatgatg atttccacaa gttggtgaaa | 420 |
| cggtgtctct tgaacggtct tttgggtgct aatgcacaga acgaaaaag acattacaga | 480 |
| gatgcactca ttgaaaatgt gtcttccaag ttgcatgccc atgctaggga ccatccacaa | 540 |
| gaacctgtaa acttcagagc tatatttgag catgagcttt tcggtgtagc attgaagcaa | 600 |
| gcttttggga aagatgtgga atccatttat gttaaagaac tcggtgtgac tttgtcgaaa | 660 |
| gacgagatct tcaaggtttt agtacatgac atgatggaag gtgcaattga tgttgattgg | 720 |
| agagacttct tcccatactt gaaatggatt ccaaataaaa gttttgaagc aagaatccag | 780 |
| caaaagcata aacgtagact cgcggtgatg aatgctctga ttcaagatcg actgaagcag | 840 |
| aatggttcag aatcggatga tgattgctat ctcaacttct tgatgtcgga agcgaaaaca | 900 |
| ctaaccaagg agcaaattgc tatcttggtt tgggagcga ttatcgagac agctgacact | 960 |
| actttggtta caactgaatg ggccatctat gagctcgcta agcatccaag tgtccaagat | 1020 |
| cgtctgtgta agaaaatcca aaatgtctgc ggagagaaa gttcaaaga agagcaattg | 1080 |
| tctcaagttc cttatctcaa tggagtattc catgaaacgc ttaggaaata cagtcctgct | 1140 |

```
cctctagtcc ccattcgcta tgcccacgaa gatacgcaaa tcggaggcta tcatgtccct    1200
gcaggaagtg agattgcaat aaacatctat ggatgcaaca tggataagaa gcgttgggag    1260
agaccagagg actggtggcc ggagcggttt cttgatgatg gcaaatacga acgtcggat    1320 cttcacaaga caatggcgtt tggagcggga aagaggGTTT tgctggtgc cttcaagca    1380 tctctcatgg caggcattgc cattgggagg ttagtgcaag aattcgagtg gaagcttaga    1440
gacggtgaag aagagaatgt ggatacatat ggcttgacct ctcagaagct ttatcctctt    1500
atggctatta tcaatccaag gcgttcttaa                                    1530
```

<210> SEQ ID NO 58
<211> LENGTH: 1578
<212> TYPE: DNA
<213> ORGANISM: Gibberella fujikoroi

<400> SEQUENCE: 58

```
atgagtaagt ccaacagcat gaacagtacc agccatgaaa cgttattcca gcagctcgtc     60
ttaggtcttg acagaatgcc gctaatggac gttcactggc tgatctacgt ggcctttggc    120
gcttggttat gctcttatgt catccatgtc ctatcgtcct cttctacagt caaagtgccc    180
gtcgtaggct accgcagcgt cttttgagcct acatggcttc tccgtttgcg ctttgtttgg    240
gaagggggat ctatcatcgg ccaaggctac aacaaattta agactctat cttccaggtg    300 cgaaagcttg gtaccgatat cgtcatcatc ccgccaaact acatcgatga ggtcagaaag    360
ctgtcccaag acaagactcg ctcggtcgag cccttcatca atgactttgc gggacagtat    420
acacggggca tggtctttct gcaaagtgat ttgcagaacc gtgtgattca gcagcggttg    480
acgccaaaac tcgtatcgtt gacaaaggta atgaaggagg agcttgacta tgccttgacc    540
aaagagatgc ctgacatgaa gaatgatgaa tgggttgaag tcgacatttc ttccatcatg    600
gtcaggctca tatcacgcat ctcagccaga gtgtttctcg gtccagagca ctgccgcaac    660
caagaatggt tgacgaccac tgcagagtac agcgagagcc tgttcataac tggctttatt    720
ctccgcgttg tcccccatat tctaagacca ttcatagccc cgctgctacc ctcctacaga    780
acactacttc gcaacgtctc gtcaggtcga agagttattg gagacatcat tcgctcccag    840
caaggtgatg gcaacgagga catcctgtca tggatgaggg atgctgcgac aggggaagaa    900
aagcaaattg caacattgc ccagcggatg cttatcctga gtctcgcgtc tattcacact    960
acggcaatga cgatgacgca tgctatgtat gacttatgtg cttgccctga gtacatagag    1020
cctcttagag atgaggtcaa aagtgtcgtt ggcgctagtg gttgggacaa gacggcgttg    1080
aatcgattcc acaaactcga cagctttctc aaagagtcac aacgcttcaa ccccgtgttc    1140
ctcttaacgt tcaatcgcat ttatcaccaa tccatgacac tctcagatgg caccaacatc    1200
ccatcaggca ctcgcatcgc ggttccctct cacgcgatgc ttcaggactc agcgcatgtc    1260
ccaggcccga cgccaccaac cgagtttgat ggattagat actcaaagat cgctcagac    1320 tcaaactatg cacagaaata tctcttctcc atgactgatt ctagtaacat ggcgtttggg    1380
tatgggaaat acgcctgccc agggcggttc tatgcatcta atgagatgaa gctgactttg    1440
gcgatactcc ttttacaatt tgagttcaag ttgccagatg ggaaaggaag accacgaaat    1500
atcactattg atagtgacat gataccTGAT ccgagagcta ggctgtgcgt taggaagcga    1560
tcactgagag atgaatga                                                1578
```

<210> SEQ ID NO 59

<211> LENGTH: 1500
<212> TYPE: DNA
<213> ORGANISM: Trametes versicolor

<400> SEQUENCE: 59

```
atggaggatc ccaccgtact ctacgcttgc ctcgccatcg ctgtcgctac tttcgttgtc    60
agatggtaca gagacccgct tcggtccatt cctacggttg ggggctctga ccttcccatc   120
ctctcataca tcggggcgct caggtggacc cgccgcggaa gagagatact gcaagaaggt   180
tatgatgggt atcgcggatc cacgttcaag atcgcgatgc tcgaccggtg gatcgtcatc   240
gccaacggcc caaagctcgc cgacgaggtg aggaggcgtc ctgacgaaga gctaaacttc   300
atggacggac tgggagcgtt cgtgcagacg aagtataccc ttggggaagc aatccacaat   360
gacccgtacc acgtggacat tattcgtgag aagctgacgc gaggcctccc ggcagtcctg   420
ccggacgtca tcgaggaact cacgctagcc gttcgccagt acatcccgac ggaaggagat   480
gaatgggtca gcgtgaactg ctccaaagca gcgcggaca tcgtcgcccg ggcaagcaac   540
cgcgtctttg tcgggttgcc cgcttgccgc aaccaggggtt atctcgacct cgccattgac   600
ttcaccctga gcgttgtcaa agacagggcg atcatcaata tgttcccgga gttgctgaaa   660
cctatcgtcg gacgcgtggt tggaaatgcc actaggaacg tgcgccgcgc ggtcccattc   720
gtagcgccgt tggtggagga acgtcgccgc ctcatggagg agtacggtga ggattggtcg   780
gagaaaccga acgacatgct ccagtggatc atggacgagg cagcctcgcg ggactcctcc   840
gtcaaagcga tcgctgagcg tcttctcatg gtcaactttg ccgcaattca cacgtcgtcg   900
aacaccatca cccacgctct ttaccacctc gccgagatgc cggagaccct acagccgctg   960
cgggaagaga tcgagccgct cgtcaaggaa gaaggctgga cgaaggccgc catgggcaag  1020
atgtggtggc tcgacagctt cctgcgggag tcacagcgct acaatggcat caacatcgtc  1080
tccctgacgc gcatggccga caaggacata acgctcagcg acggcacgtt cctcccgaag  1140
ggcacgctcg tcgcggtccc cgcgtactcg acgcaccgcg acgacgcggt gtacgcggac  1200
gcgctggtct tcgacccgtt ccgcttctcc cgcatgcgcg cccgcgaggg cgagggcacg  1260
aagcaccagt tcgtcaacac ctccgtggag tacgtgccct tcggccacgg gaagcacgcc  1320
tgccccgggc ggttcttcgc ggccaacgag ctgaaggcga tgctcgcgta catcgtgctc  1380
aactacgacg tgaagctgcc cggcgatggc aagcgccccc tgaacatgta ctggggcccg  1440
acggtcttgc ctgctccggc tgggcaggtg ctcttccgca agaggcaggt gtcgctgtag  1500
```

<210> SEQ ID NO 60
<211> LENGTH: 1578
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 60

```
atgggtttgt tcccattaga ggattcctac gcgctggtct ttgaaggact agcaataaca    60
ctggctttgt actatctact gtctttcatc tacaaaacat ctaaaaagac atgtacacct   120
cctaaagcat ctggtgaaat cattccaatt acaggaatca tattgaatct gctatctggc   180
tcaagtggtc tacctattat cttagcactt gcctctttag cagacagatg tggtcctatt   240
ttcaccatta ggctgggtat taggagagtg ctagtagtat caaattggga aatcgctaag   300
gagattttca ctacccacga tttgatagtt tctaatagac caaaatactt agccgctaag   360
```

```
attcttggtt tcaattatgt ttcattctct ttcgctccat acggcccata ttgggtcgga    420
atcagaaaga ttattgctac aaaactaatg tcttcttcca gacttcagaa gttgcaattt    480
gtaagagttt ttgaactaga aaactctatg aaatctatca gagaatcatg aaggagaaa     540
aaggatgaag agggaaaggt attagttgag atgaaaaagt ggttctggga actgaatatg    600
aacatagtgt taaggacagt tgctggtaaa caatacactg gtacagttga tgatgccgat    660
gcaaagcgta tctccgagtt attcagaaaa tggtttcact acactggcag atttgtcgtt    720
ggagacgctt ttccttttct aggttggttg gacctgggcg atacaaaaa gacaatggaa     780
ttagttgcta gtagattgga ctcaatggtc agtaaatggt tagatgagca tcgtaaaaag    840
caagctaacg atgacaaaaa ggaggatatg gatttcatgg atatcatgat ctccatgaca    900
gaagcaaatt caccacttga aggatacggc actgatacta ttatcaagac acatgtatg    960
actttgattg tttcaggagt tgatacaacc tcaatcgtac ttacttgggc cttatcactt   1020
ttgttaaaca acagagatac tttgaaaaag gcacaagagg aattagatat gtgcgtaggt   1080
aaaggaagac aagtcaacga gtctgatctt gttaacttga tatacttgga agcagtgctt   1140
aaagaggctt taagacttta cccagcagcg ttcttaggcg gaccaagagc attcttggaa   1200
gattgtactg ttgctggtta tagaattcca aagggcacct gcttgttgat taacatgtgg   1260
aaactgcata gagatccaaa catttggagt gatccttgcg aattcaagcc agaaagattt   1320
ttgcaccta atcaaaagga tgttgatgtg atcggtatgg atttcgaatt gataccattt   1380
ggtgccggca agagatattg tccaggtact agattggctt acagatgtt gcatatcgta    1440
ttagcgacat tgctgcaaaa cttcgaaatg tcaacaccaa acgatgcgcc agtcgatatg   1500
actgcttctg ttggcatgac aaatgccaaa gcatcacctt tagaagtctt gctatcacct   1560
cgtgttaaat ggtcctaa                                                  1578

<210> SEQ ID NO 61
<211> LENGTH: 1431
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
atgatacaag ttttaactcc aattctactc ttcctcatct tcttcgtttt ctggaaagtc      60
tacaaacatc aaaagactaa aatcaatcta ccaccaggtt ccttcggctg ccattttg      120
ggtgaaacct tagccttact tagagcaggc tgggattctg agccagaaag attcgtaaga    180
gagcgtatca aaaagcatgg atctccactt gttttcaaga catcactatt tggagacaga    240
ttcgctgttc tttgcggtcc agctggtaat aagttttgt tctgcaacga aaacaaatta    300
gtggcatctt ggtggccagt ccctgtaagg aagttgttcg gtaaaagttt actcacaata    360
agaggagatg aagcaaaatg gatgagaaaa atgctattgt cttacttggg tccagatgca    420
tttgccacac attatgccgt tactatggat gttgtaacac gtagacatat tgatgtccat    480
tggaggggca aggaggaagt taatgtattt caaacagtta agttgtacgc attcgaatta    540
gcttgtagat tattcatgaa cctagatgac ccaaaccaca tcgcgaaact cggtagtctt    600
ttcaacattt tcctcaaagg gatcatcgag cttcctatag acgttcctgg aactagattt    660
tactccagta aaaaggccgc agctgccatt agaattgaat tgaaaaagct cattaaagct    720
agaaaactcg aattgaagga gggtaaggcg tcttcttcac aggacttgct ttctcatcta    780
```

```
ttaacatcac ctgatgagaa tgggatgttc ttgacagaag aggaaatagt cgataacatt      840 ctactttgt tattcgctgg tcacgatacc tctgcactat caataacact tttgatgaaa       900
accttaggtg aacacagtga tgtgtacgac aaggttttga aggaacaatt agaaatttcc     960
aaaacaaagg aggcttggga atcactaaag tgggaagata tccagaagat gaagtactca     1020
tggtcagtaa tctgtgaagt catgagattg aatcctcctg tcatagggac atacagagag    1080
gcgttggttg atatcgacta tgctggttac actatcccaa aaggatggaa gttgcattgg    1140
tcagctgttt ctactcaaag agacgaagcc aatttcgaag atgtaactag attcgatcca    1200
tccagatttg aaggggcagg ccctactcca ttcacatttg tgcctttcgg tggaggtcct   1260
agaatgtgtt taggcaaaga gtttgccagg ttagaagtgt tagcatttct ccacaacatt   1320
gttaccaact ttaagtggga tcttctaatc cctgatgaga agatcgaata tgatccaatg   1380
gctactccag ctaagggctt gccaattaga cttcatccac accaagtcta a            1431

<210> SEQ ID NO 62
<211> LENGTH: 1578
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
atggagtctt tagtggttca tacagtaaat gctatctggt gtattgtaat cgtcgggatt     60
ttctcagttg gttatcacgt ttacggtaga gctgtggtcg aacaatggag aatgagaaga    120
tcactgaagc tacaaggtgt taaaggccca ccaccatcca tcttcaatgg taacgtctca    180
gaaatgcaac gtatccaatc cgaagctaaa cactgctctg gcgataacat tatctcacat    240
gattattctt cttcattatt cccacacttc gatcactgga gaaaacagta cggcagaatc    300
tacacatact ctactggatt aaagcaacac ttgtacatca atcatccaga aatggtgaag    360
gagctatctc agactaacac attgaacttg ggtagaatca cccatataac caaaagattg    420
aatcctatct taggtaacgg aatcataacc tctaatggtc tcattgggc ccatcagcgt     480 agaattatcg cctacgagtt tactcatgat aagatcaagg gtatggttgg tttgatggtt    540
gagtctgcta tgcctatgtt gaataagtgg gaggagatgg taaagagagg cggagaaatg    600
ggatgcgaca taagagttga tgaggacttg aaagatgttt cagcagatgt gattgcaaaa    660
gcctgtttcg gatcctcatt ttctaaaggt aaggctattt tctctatgat aagagatttg   720
cttacagcta tcacaaagag aagtgttcta ttcagattca acggattcac tgatatggtc   780
tttgggagta aaaagcatgg tgacgttgat atagacgctt tagaaatgga attggaatca    840
tccatttggg aaactgtcaa ggaacgtgaa atagaatgta aagatactca caaaaaggat    900
ctgatgcaat tgattttgga aggggcaatg cgttcatgtg acggtaaccct ttgggataaa   960 tcagcatata aagatttgt tgtagataat tgtaaatcta tctacttcgc agggcatgat    1020
agtacagctg tctcagtgtc atggtgtttg atgttactgg ccctaaaccc atcatggcaa   1080
gttaagatcc gtgatgaaat tctgtcttct tgcaaaaatg gtattccaga tgccgaaagt   1140
atcccaaacc ttaaaacagt gactatggtt attcaagaga caatgagatt ataccctcca   1200
gcaccaatcg tcgggagaga agcctctaaa gatatcagat tgggcgatct agttgttcct   1260
aaaggcgtct gtatatggac actaatacca gctttacaca gagatcctga gatttgggga   1320
ccagatgcaa acgattcaa accagaaaga ttttctgaag gaatttcaaa ggcttgtaag    1380
```

```
tatcctcaaa gttacattcc atttggtctg ggtcctagaa catgcgttgg taaaaacttt    1440
ggcatgatgg aagtaaaggt tcttgtttcc ctgattgtct ccaagttctc tttcactcta    1500
tctcctacct accaacatag tcctagtcac aaacttttag tagaaccaca acatggggtg    1560
gtaattagag tggtttaa                                                  1578

<210> SEQ ID NO 63
<211> LENGTH: 1590
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63
atgtacttcc tactacaata cctcaacatc acaaccgttg gtgtctttgc cacattgttt      60
ctctcttatt gtttacttct ctggagaagt agagcgggta acaaaaagat tgccccagaa     120
gctgccgctg catggcctat tatcggccac ctccacttac ttgcaggtgg atcccatcaa     180
ctaccacata ttacattggg taacatggca gataagtacg gtcctgtatt cacaatcaga     240
ataggcttgc atagagctgt agttgtctca tcttgggaaa tggcaaagga atgttcaaca     300
gctaatgatc aagtgtcttc ttcaagacct gaactattag cttctaagtt gttgggttat     360
aactacgcca tgtttggttt ttcaccatac ggttcatact ggagagaaat gagaaagatc     420
atctctctcg aattactatc taattccaga ttggaactat tgaaagatgt tagagcctca     480
gaagttgtca catctattaa ggaactatac aaattgtggg cggaaaagaa gaatgagtca     540
ggattggttt ctgtcgagat gaaacaatgg ttcggagatt tgactttaaa cgtgatcttg     600
agaatggtgg ctggtaaaag atacttctcc gcgagtgacg cttcagaaaa caaacaggcc     660
cagcgttgta gaagagtctt cagagaattc ttccatctct ccggcttgtt tgtggttgct     720
gatgctatac ctttcttgg atggctcgat tggggaagac acgagaagac cttgaaaaag     780
accgccatag aaatggattc catcgcccag gagtggcttg aggaacatag acgtagaaaa     840
gattctggag atgataattc tacccaagat ttcatggacg ttatgcaatc tgtgctagat     900
ggcaaaaatc taggcggata cgatgctgat acgattaaca aggctacatg cttaactctt     960
atatcaggtg gcagtgatac tactgtagtt tctttgacat gggctcttag tcttgtgtta    1020
aacaatagag atactttgaa aaaggcacag gaagagttag acatccaagt cggtaaggaa    1080
agattggtta cgagcaaga catcagtaag ttagtttact tgcaagcaat agtaaaagag    1140
acactcagac tttatccacc aggtcctttg ggtggtttga caattcac tgaagattgt    1200 acactaggtg gctatcacgt ttcaaaagga actagattaa tcatgaactt atccaagatt    1260
caaaaagatc cacgtatttg gtctgatcct actgaattcc aaccagagag attccttacg    1320
actcataaag atgtcgatcc acgtggtaaa cactttgaat tcattccatt cggtgcagga    1380
agacgtgcat gtcctggtat cacattcgga ttacaagtac tacatctaac attggcatct    1440
ttcttgcatg cgtttgaatt ttcaacacca tcaaatgagc aggttaacat gagagaatca    1500
ttaggtctta cgaatatgaa atctacccca ttagaagttt tgatttctcc aagactatcc    1560
cttaattgct tcaaccttat gaaaatttga                                    1590

<210> SEQ ID NO 64
<211> LENGTH: 1440
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 64

```
atggaaccta actttttactt gtcattacta ttgttgttcg tgaccttcat ttctttaagt      60
ctgttttttca tcttttacaa acaaaagtcc ccattgaatt tgccaccagg gaaaatgggt    120
tacccctatca taggtgaaag tttagaattc ctatccacag gctggaaggg acatcctgaa    180
aagttcatat ttgatagaat gcgtaagtac agtagtgagt tattcaagac ttctattgta    240
ggcgaatcca cagttgtttg ctgtggggca gctagtaaca aattcctatt ctctaacgaa    300
aacaaactgg taactgcctg gtggccagat tctgttaaca aaatcttccc aacaacttca    360
ctggattcta atttgaagga ggaatctata aagatgagaa agttgctgcc acagttcttc    420
aaaccagaag cacttcaaag atacgtcggc gttatggatg taatcgcaca agacattttt    480
gtcactcact gggacaacaa aaatgagatc acagtttatc cacttgctaa agatacact    540
ttcttgcttg cgtgtagact gttcatgtct gttgaggatg aaaatcatgt ggcgaaattc    600
tcagacccat tccaactaat cgctgcaggc atcatttcac ttcctatcga tcttcctggt    660
actccattca acaaggccat aaaggcttca aatttcatta gaaaagagct gataaagatt    720
atcaaacaaa gacgtgttga tctggcagag ggtacagcat ctccaaccca ggatatcttg    780
tcacatatgc tattaacatc tgatgaaaac ggtaaatcta tgaacgagtt gaacattgcc    840
gacaagattc ttggactatt gataggaggc cacgatacag cttcagtagc ttgcacattt    900
ctagtgaagt acttaggaga attaccacat atctacgata agtctacca agagcaaatg    960
gaaattgcca agtccaaacc tgctggggaa ttgttgaatt gggatgactt gaaaaagatg   1020
aagtattcat ggaatgtggc atgtgaggta atgagattgt caccaccttt acaaggtggt   1080
tttagagagg ctataactga ctttatgttt aacggtttct ctattccaaa agggtggaag   1140
ttatactggt ccgccaactc tacacacaaa aatgcagaat gtttcccaat gcctgagaaa   1200
ttcgatccta ccagatttga aggtaatggt ccagcgcctt atacatttgt accattcggt   1260
ggaggcccta gaatgtgtcc tggaaaggaa tacgctagat tagaaatctt ggttttcatg   1320
cataatctgg tcaaacgttt taagtgggaa aaggttattc cagacgaaaa gattattgtc   1380
gatccattcc caatcccagc taaagatctt ccaatccgtt tgtatcctca caaagcttaa   1440
```

<210> SEQ ID NO 65
<211> LENGTH: 1572
<212> TYPE: DNA
<213> ORGANISM: Stevia rebaudiana

<400> SEQUENCE: 65

```
atgggtctct tcccttttgga agatagttac gcactcgtct ttgaaggttt agcaataact     60
actctagctc tctactactt attatccttc atctataaaa cctctaaaaa gacttgtact    120
ccacctaaag caagcggtga gcacccctata acaggccact aaaaccttct tagtggttca    180
tccggtcttc cccatctagc cttagcatct ttggctgacc gatgtgggcc catattcacc    240
atccgacttg gcatacgtag agttttggtg gttagtaatt gggaaattgc taaggagatc    300
ttcactaccc atgatttgat tgtttcaaac cgtcccaaat acctcgctgc aaagattttg    360
ggattcaact atgtgtcctt ttcgtttgct ccatatggcc cctattgggt tggaatccgt    420
aagatcatcg ccacaaaaact gatgtcaagt agcaggctcc agaagcttca gtttgtccga    480
gttttcgaac tagaaaactc catgaaaagc atacgcgagt cttggaaaga gaaaaagac    540
```

```
gaagaaggta aagtgttggt ggagatgaaa aaatggtttt gggaattgaa tatgaatata      600
gttcttagaa ctgttgctgg taaacagtac actggaactg ttgatgatgc ggatgcgaag      660
aggattagtg aattgtttag agaatggttt cattacacag gaaggtttgt tgtgggagat      720
gcttttcctt ttcttgggtg gttggatttg ggtggatata agaagaccat ggaactagtg      780
gcttccagac tagattccat ggtctcaaaa tggttagacg agcatcgcaa aaagcaggct      840
aacgacgaca aaaagagga catgggattc atggacatca tgatatcgat gactgaagcc      900
aattcccctt tggagggtta tggtacggat acaataatta aaccacttg catgactctt       960
attgtcagtg gtgtagatac aacctccatc gtgctaactt gggcactctc gttactactg     1020
aacaaccgtg acactcttaa gaaagctcaa gaagagctag acatgtgtgt gggaaaaggt     1080
cgacaagtaa acgaatcaga tctagtaaac ctaatctacc ttgaagccgt attaaaagaa     1140
gcattgcgac tatcccagc agcattcctt ggaggtccta gagcctttt agaagactgc       1200
accgtggcag ggtaccgtat cccaaaaggc acatgtctac ttattaacat gtggaaactt     1260
catcgtgatc caaacatatg gtcagaccca tgtgagttta aaccagagag gttcttaacc     1320
ccaaaccaaa aggacgtaga tgttattgga atggattttg agttaatccc atttggtgcg     1380
ggaagaaggt attgtccagg gacacgtttg gcattacaaa tgttacacat agttctggcc     1440
actctactac aaaactttga gatgtcaact ccaaatgatg cacccgttga tatgaccgcg     1500
agtgttggaa tgacaaatgc gaaggcaagt ccacttgaag ttctactttc gccacgtgtt     1560
aagtggtcat ag                                                         1572

<210> SEQ ID NO 66
<211> LENGTH: 1431
<212> TYPE: DNA
<213> ORGANISM: Stevia rebaudiana

<400> SEQUENCE: 66
atgattcaag ttctaacacc gatcttctc ttcctcattt tcttcgtttt ctggaaggtt        60
tacaagcacc agaaaaccaa aatcaatctt ccaccgggaa gcttcggatg ccatttctg      120
ggcgaaactc tggcactcct acgtgcaggt tgggactcag agccggagag atttgttcgt     180
gaacggatca agaaacacgg aagtcctcta gtgtttaaga cgtcgttgtt tggcgaccgt     240
tttgcggtgt tgtgtggacc tgccggaaac aagttcctgt tctgcaacga gaacaagctg     300
gtggcgtcgt ggtggccggt tccggtgagg aagctttcg gcaagtctct gctcacgatt      360
cgtggtgatg aagctaagtg gatgaggaag atgttgttat cgtatctcgg tcctgatgct     420
ttcgcaactc attatgccgt caccatggac gtcgtcaccc gtcggcatat cgacgttcat     480
tggcgaggga aggaagaggt gaacgtattc caaaccgtta agttatatgc ctttgagctt     540
gcatgtcgtt tattcatgaa cctagacgac ccaaaccaca ttgcaaaact cggttccttg     600
ttcaacattt tcttgaaagg catcattgag cttccaatcg acgtcccagg acacgatttt    660
tatagctcca aaaagcagc agcagctatc aggattgaac taaaaaaatt gattaaagca     720
agaaaactgg aactgaaaga agggaaggca tcatcttcac aagacctctt atcacatttg    780
cttacatctc cagatgaaaa tggtatgttt ctaaccgaag aagagattgt agacaacatc    840
ttgttactac tctttgcggg tcatgatacc tcggctcttt caatcacttt gctcatgaag    900
actcttggcg aacattctga tgtttatgac aaggtgttaa agagcaact agagatatcg    960
aagacgaaag aagcatggga gtccctgaaa tgggaggaca tacaaaagat gaaatactcc   1020
tggagtgtta tatgtgaagt catgagacta aatccacctg ttataggaac ctatagagag   1080
```

```
gcccttgtgg atattgatta tgcgggttat accatcccca aaggatggaa gctgcactgg    1140
agtgctgtat cgacacaaag ggacgaggct aactttgaag acgtaacacg ttttgaccca    1200
tcacggtttg aaggcgcagg accgactcca ttcacctttg ttccgtttgg aggggggcct    1260
agaatgtgtt tagggaaaga atttgctcga ttggaagtac ttgcgtttct tcacaatatt    1320
gtcaccaatt tcaaatggga cctgttgata cctgatgaga aaatagaata tgatcccatg    1380
gctaccccag caaaggggct tccaattcgt cttcatcccc atcaagtttg a            1431
```

<210> SEQ ID NO 67
<211> LENGTH: 1578
<212> TYPE: DNA
<213> ORGANISM: Arabidopsis thaliana

<400> SEQUENCE: 67

```
atggagagtt tggttgttca tacggtaaat gcaatttggt gcatagttat tgtcggaatc     60
ttcagcgtag gttatcatgt gtatggaaga gcggtggtgg agcagtggag gatgcggagg    120
agtttaaagt tgcaaggcgt gaagggtcct ccaccgtcga tctttaacgg caatgtgtcg    180
gagatgcaac ggattcagtc ggaggctaaa cactgttccg gcgataacat catttctcat    240
gactattctt cttctctatt tcctcatttc gatcactggc gaaaacaata cggaaggatt    300
tacacatact caacgggggtt aaagcagcac ctttacataa accacccgga atggtgaag    360 gagcttagcc aaaccaacac acttaacctt ggtagaatca ctcacatcac caaacgcctt    420
aaccccattc tcggcaatgg catcatcacc tctaatgggc tcattgggcc catcaacgt    480 cgtatcattg cctatgagtt tacccacgac aaaatcaagg gaatggttgg tttaatggtg    540
gaatctgcca tgccaatgtt gaacaaatgg aagagatgg tgaaaagagg aggaaatg    600 ggttgtgaca taagagtgga cgaagacctt aaggatgtct cagctgatgt catcgctaag    660
gcttgctttg ggagctcttt ttcaaaaggc aaagcaatat tctctatgat tagggatctt    720
ttaaccgcca ttactaaacg aagcgtcctc ttcagattca atggcttcac tgatatggtg    780
tttggaagta agaagcatgg tgatgtggat attgatgcgc ttgagatgga attagaatct    840
tctatatggg aaacggttaa ggagagggaa attgaatgta aggatactca caagaaggat    900
ctaatgcagt tgatactcga gggagcgatg cgaagctgcg atggtaactt gtgggacaag    960
tcagcctata gacggtttgt ggtggacaat tgcaagagca tctatttcgc cggacatgat   1020
tcaaccgcag tctcagtgtc ttggtgcctt atgctcctcg ctctcaatcc tagttggcag   1080
gttaaaattc gcgatgaaat cttgagttct tgcaagaatg gcattcccga cgcagaatca   1140
attcctaatc tcaaaacggt gacaatggta atacaagaaa caatgagact atacccacca   1200
gcaccaatcg tgggaagaga agcatccaaa gacataagac ttggagacct tgtggtgcca   1260
aaaggagtgt gcatttggac actcattcct gccttacacc gagaccccga gatctgggga   1320
ccagacgcaa acgacttcaa gccagagagg tttagtgagg aatctctaa ggcttgcaaa   1380 taccctcagt catacatccc atttggcctt ggaccaagaa catgcgtagg caaaaacttt   1440
ggtatgatgg aagtgaaagt gcttgtttca cttattgtct caaagttcag ttttactctt   1500
tccccgactt atcagcactc tccaagccat aaactccttg tagagcctca acatggtgtt   1560
gtcattaggg ttgtttga                                                 1578
```

<210> SEQ ID NO 68
<211> LENGTH: 1590
<212> TYPE: DNA

<213> ORGANISM: Vitis vinifera

<400> SEQUENCE: 68

| | | |
|---|---|---|
| atgtatttcc ttctccaata cctaaacatc accacggtcg gagtctttgc cacacttttc | 60 |
| ctttcctact gtctattatt atggaggtct agagctggta acaaaaaaat agcacctgaa | 120 |
| gctgctgctg catggcccat aatcggtcac ctacacctgt tagctggtgg ttctcatcag | 180 |
| cttccccaca taaccttggg aaacatggcc gacaaatatg gaccggtctt cacaattcgg | 240 |
| attgggttgc atcgagctgt ggtggtaagt tcttgggaga tggctaaaga atgctcgacc | 300 |
| gccaatgacc aggtttcatc ctcgcgtccc gaacttttag cctcaaaact tttgggctac | 360 |
| aactacgcca tgtttggttt ctctccatac ggttcttact ggcgtgaaat gcgcaagata | 420 |
| atcagcctag agctactctc taacagccgc ttagagctgc tgaaggacgt ccgagcttca | 480 |
| gaagtggtga catccataaa agagctatac aagctctggg cagagaaaaa aaatgaatcg | 540 |
| ggccttgtct cggtggagat gaagcagtgg tttggagact tgactctgaa cgtaattctt | 600 |
| aggatggtgg cagggaagcg ttatttcagt gcttcagatg caagtgaaaa taaacaggcg | 660 |
| cagaggtgcc ggagagtgtt cagggaattc tttcatttgt cagggctctt tgtggtggcg | 720 |
| gacgctattc catttcttgg atggctcgac tgggggagac atgagaaaac cctaaagaag | 780 |
| acagcaatag aaatggacag tattgctcaa gaatggttag aggagcaccg tcggaggaaa | 840 |
| gactccggta tgataatag tacgcaagac ttcatggatg tgatgcagtc agttcttgat | 900 |
| ggcaaaaacc ttggtggtta cgacgctgat accatcaata agccacatg cctgactcta | 960 |
| atctccggag gtagcgacac aactgttgtc tctctaacat gggcactctc tcttgtacta | 1020 |
| aacaaccgtg acaccttaaa aaaagctcaa gaagaattag acatccaagt tggtaaggaa | 1080 |
| agattagtga atgaacaaga tataagtaag ttggtctatc tccaagccat tgttaaagag | 1140 |
| acattacggt tatatccacc aggaccactt ggaggactac gccaatttac cgaggattgc | 1200 |
| accttgggtg gataccatgt ctctaaaggc acccgtttaa taatgaacct ttcgaagatc | 1260 |
| caaaaggatc caagaatttg gtcagatccg acagaattcc aaccagagag gtttctcacc | 1320 |
| acccataaag atgttgatcc tcggggaaaa cattttgagt ttataccatt tggagctggt | 1380 |
| cgaagagcat gtccaggaat aacttttggt cttcaagtat tacatttaac attggctagt | 1440 |
| ttcttacatg cgtttgaatt ttcaactcca tcaaatgaac aggtcaatat gcgcgagagc | 1500 |
| cttggactta caaatatgaa atctaccca cttgaagttc tcatttctcc acgcttatca | 1560 |
| ttgaattgtt ttaacctaat gaagatataa | 1590 |

<210> SEQ ID NO 69
<211> LENGTH: 1440
<212> TYPE: DNA
<213> ORGANISM: Medicago trunculata

<400> SEQUENCE: 69

| | | |
|---|---|---|
| atggagccta atttctatct ctcccttctc cttctctttg tcactttcat atctctctct | 60 |
| cttttttca tattctacaa acagaaatct ccattaaatt tgccacctgg taaaatgggt | 120 |
| tacccaatca taggtgaaag ccttgagttc ttatcaacag gatggaaagg acatcctgaa | 180 |
| aaattcattt tcgaccgtat gcgtaaatat tcctcagaac tctttaaaac atcaatcgta | 240 |
| ggagaatcta cggtggtttg ttgcggagca gcaagtaaca agttttgtt ttcaaacgag | 300 |
| aataaacttg tgactgcatg gtggccagat agtgtaaaca aaatcttccc tactacttct | 360 |
| cttgactcta acttgaagga agaatccatc aagatgagaa aattgcttcc acaattctt | 420 |

```
aaacccgaag ctctacaacg ttatgttggt gtcatggatg ttattgctca aagacatttt      480
gttactcatt gggataataa aaatgaaatc accgtctacc ccttggccaa gaggtacacc      540
tttttgttag cttgtcggtt gttcatgagc gttgaagacg agaatcatgt agcaaaattt      600
agtgatccat ttcagttaat tgcggccgga atcatatctc taccaattga tttgccagga      660
acaccattca acaaagctat aaaggcctca aactttataa gaaggagtt gattaagatc        720 ataaagcaaa ggagggtaga tttggcagaa gggacagcat caccaacaca agatatattg      780
tctcacatgt tgttgacaag tgatgaaaat ggaaagagta tgaatgaact taatattgct      840
gataagattc ttggcctttt gatcggagga catgacactc tagcgtcgc atgcactttc       900 cttgtcaaat atctcggcga gttacctcac atttatgata aagtctatca agagcaaatg      960
gaaattgcaa aatcgaaacc agcaggagaa ttgttgaatt gggatgacct gaagaaaatg     1020
aaatactctt ggaacgtagc ttgtgaagta atgagacttt cccctccact ccaaggaggt      1080 ttcaggaag ccatcactga ctttatgttc aatggattct caattcctaa gggatggaag       1140
ctttattgga gtgcaaattc aacacataag aacgcagaat gttttcccat gccagagaaa     1200
tttgacccaa caagatttga aggaaatgga ccagctcctt atactttgt tcccttggt       1260 ggaggaccaa ggatgtgtcc tggaaaagag tatgcaagat tagaaatact tgttttcatg     1320
cacaatttgg tgaaaaggtt taagtgggaa aaggtgattc cagatgagaa gattattgtt     1380
gatccattcc ccatccctgc aaaggatctt ccaattcgcc tttatccaca caaagcttaa      1440

<210> SEQ ID NO 70
<211> LENGTH: 2133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
atgcaatcag attcagtcaa agtctctcca tttgatttgg tttccgctgc tatgaatggc       60
aaggcaatgg aaaagttgaa cgctagtgaa tctgaagatc caacaacatt gcctgcacta      120
aagatgctag ttgaaaatag agaattgttg acactgttca caacttcctt cgcagttctt      180
attgggtgtc ttgtatttct aatgtggaga cgttcatcct ctaaaaagct ggtacaagat      240
ccagttccac aagttatcgt tgtaaagaag aaagagaagg agtcagaggt tgatgacggg      300
aaaaagaaag tttctatttt ctacggcaca caaacaggaa ctgccgaagg ttttgctaaa      360
gcattagtcg aggaagcaaa agtgagatat gaaaagacct ctttcaaggt tatcgatcta      420
gatgactacg ctgcagatga tgatgaatat gaggaaaaac tgaaaaagga atccttagcc      480
ttcttcttct tggccacata cggtgatggt gaacctactg ataatgctgc taacttctac      540
aagtggttca cagaaggcga cgataaaggt gaatggctga aaaagttaca atacggagta      600
tttggtttag gtaacagaca atatgaacat ttcaacaaga tcgctattgt agttgatgat      660
aaacttactg aaatgggagc caaaagatta gtaccagtag gattagggga tgatgatcag      720
tgtatagaag atgacttcac cgcctggaag gaattggtat ggccagaatt ggatcaactt      780 ttaaggggacg aagatgatac ttctgtgact acccccataca ctgcagccgt attggagtac     840
agagtggttt accatgataa accagcagac tcatatgctg aagatcaaac ccatacaaac      900
ggtcatgttg ttcatgatgc acagcatcct tcagatgtca atgtggcttt caaaaaggaa      960
ctacacacct ctcaatcaga taggtcttgt actcacttag aattcgatat ttctcacaca     1020
```

```
ggactgtctt acgaaactgg cgatcacgtt ggcgtttatt ccgagaactt gtccgaagtt    1080
gtcgatgaag cactaaaact gttagggtta tcaccagaca catacttctc agtccatgct    1140
gataaggagg atgggacacc tatcggtggt gcttcactac caccacctt tcctccttgc     1200 acattgagag acgctctaac cagatacgca gatgtcttat cctcacctaa aaaggtagct    1260
ttgctggcat tggctgctca tgctagtgat cctagtgaag ccgataggtt aaagttcctg    1320
gcttcaccag ccgaaaaga tgaatatgca caatggatcg tcgccaacca acgttctttg     1380
ctagaagtga tgcaaagttt tccatctgcc aagcctccat taggtgtgtt cttcgcagca    1440
gtagctccac gtttacaacc aagatactac tctatcagtt catctcctaa gatgtctcct    1500
aacagaatac atgttacatg tgctttggtg tacgagacta ctccagcagg cagaattcac    1560
agaggattgt gttcaacctg gatgaaaaat gctgtcccctt aacagagtc acctgattgc    1620 tctcaagcat ccattttcgt tagaacatca aatttcagac ttccagtgga tccaaaagtt    1680
ccagtcatta tgataggacc aggcactggt cttgccccat tcaggggctt tcttcaagag    1740
agattggcct tgaaggaatc tggtacagaa ttgggttctt ctatcttttt ctttggttgc    1800
cgtaatagaa aagttgactt tatctacgag gacgagctta acaattttgt tgagacagga    1860
gcattgtcag aattgatcgt cgcattttca agagaaggga ctgccaaaga gtacgttcag    1920
cacaagatga gtcaaaaagc ctccgatata tggaaacttc taagtgaagg tgcctatctt    1980
tatgtctgtg gcgatgcaaa gggcatggcc aaggatgtcc atagaactct gcatacaatt    2040
gttcaggaac aagggagtct ggattcttcc aaggctgaat tgtacgtcaa aaacttacag    2100
atgtctggaa gatacttaag agatgtttgg taa                                 2133
```

<210> SEQ ID NO 71
<211> LENGTH: 2079
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
atgacttctg cactttatgc ctccgatctt ttcaaacaat tgaaaagtat catgggaacg     60
gattctttgt ccgatgatgt tgtattagtt attgctacaa cttctctggc actggttgct    120
ggtttcgttg tcttattgtg gaaaaagacc acggcagatc gttccggcga gctaaagcca    180
ctaatgatcc ctaagtctct gatggcgaaa gatgaggatg atgacttaga tctaggttct    240
ggaaaaacga gagtctctat cttcttcggc acacaaaccg gaacagccga aggattcgct    300
aaagcacttt cagaagagat caaagcaaga tacgaaaagg cggctgtaaa agtaatcgat    360
ttggatgatt acgctgccga tgatgaccaa tatgaggaaa agttgaaaaa ggaaacattg    420
gctttctttt gtgtagccac gtatggtgat ggtgaaccaa ccgataacgc cgcaagattc    480
tacaagtggt ttactgaaga aacgaaaga gatatcaagt tgcagcaact tgcttacggc     540 gttttttgcct taggtaacag acaatacgag cactttaaca agataggtat tgtcttagat    600
gaagagttat gcaaaagggg tgcgaagaga ttgattgaag tcggtttagg agatgatgat    660
caatctatcg aggatgactt taatgcatgg aaggaatctt gtggtctga attagataag    720 ttacttaagg acgaagatga taaatccgtt gccactccat acacagccgt cattccagaa    780
tatagagtag ttactcatga tccaagattc acaacacaga aatcaatgga agtaatgtgg    840
gctaatggta atactaccat cgatattcat catccatgta gagtagacgt tgcagttcaa    900
```

```
aaggaattgc acactcatga atcagacaga tcttgcatac atcttgaatt tgatatatca      960
cgtactggta tcacttacga aacaggtgat cacgtgggtg tctacgctga aaaccatgtt     1020
gaaattgtag aggaagctgg aaagttgttg ggccatagtt tagatcttgt tttctcaatt     1080
catgccgata agaggatgg ctcaccacta gaaagtgcag tgcctccacc atttccagga      1140
ccatgcaccc taggtaccgg tttagctcgt tacgcggatc tgttaaatcc tccacgtaaa     1200
tcagctctag tggccttggc tgcgtacgcc acagaacctt ctgaggcaga aaaactgaaa     1260
catctaactt caccagatgg taaggatgaa tactcacaat ggatagtagc tagtcaacgt     1320
tctttactag aagttatggc tgcttttccca tccgctaaac ctcctttggg tgttttcttc    1380
gccgcaatag cgcctagact gcaaccaaga tactattcaa tttcatcctc acctagactg     1440
gcaccatcaa gagttcatgt cacatccgct ttagtgtacg gtccaactcc tactggtaga    1500
atccataagg gcgtttgttc aacatggatg aaaaacgcgg ttccagcaga gaagtctcac    1560
gaatgttctg gtgctccaat ctttatcaga gcctccaact tcaaactgcc ttccaatcct    1620
tctactccta ttgtcatggt cggtcctggt acaggtcttg ctccattcag aggtttctta    1680
caagagagaa tggccttaaa ggaggatggt gaagagttgg gatcttcttt gttgttttc     1740 ggctgtagaa acagacaaat ggatttcatc tacgaagatg aactgaataa ctttgtagat    1800
caaggagtta tttcagagtt gataatggct ttttctagag aaggtgctca gaaggagtac    1860
gtccaacaca aaatgatgga aaaggccgca caagtttggg acttaatcaa agaggaaggc    1920
tatctatatg tctgtggtga tgcaaagggt atggcaagag atgttcacag aacacttcat    1980
actatagtcc aggaacagga aggcgttagt tcttctgaag cggaagcaat tgtgaaaaag    2040
ttacaaacag agggaagata cttgagagat gtgtggtaa                            2079
```

<210> SEQ ID NO 72
<211> LENGTH: 2142
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 72

```
atggcagaat tagatacact tgatatagta gtattaggtg ttatcttttt gggtactgtg       60
gcatacttta ctaagggtaa attgtggggt gttaccaagg atccatacgc taacggattc     120
gctgcaggtg gtgcttccaa gcctggcaga actagaaaca tcgtcgaagc tatggaggaa     180
tcaggtaaaa actgtgttgt tttctacggc agtcaaacag gtacagcgga ggattacgca     240
tcaagacttg caaggaagg aaagtccaga ttcggtttga acactatgat cgccgatcta      300
gaagattatg acttcgataa cttagacact gttccatctg ataacatcgt tatgtttgta     360
ttggctactt acggtgaagg cgaaccaaca gataacgccg tggatttcta tgagttcatt     420
actggcgaag atgcctcttt caatgagggc aacgatcctc cactaggtaa cttgaattac     480
gttgcgttcg gtctgggcaa caataccctac gaacactaca actcaatggt caggaacgtt     540
aacaaggctc tagaaaagtt aggagctcat agaattggag aagcaggtga gggtgacgac    600
ggagctggaa ctatggaaga ggactttta gcttggaaag atccaatgtg gaagccttg      660 gctaaaaaga tgggcttgga ggaaagagaa gctgtatatg aacctatttt cgctatcaat     720
gagagagatg atttgacccc tgaagcgaat gaggtatact ggggagaacc taataagcta    780
cacttggaag gtacagcgaa aggtccattc aactcccaca acccatatat cgcaccaatt     840
```

```
gcagaatcat acgaactttt ctcagctaag gatagaaatt gtctgcatat ggaaattgat      900
atttctggta gtaatctaaa gtatgaaaca ggcgaccata tcgcgatctg gcctaccaac      960
ccaggtgaag aggtcaacaa atttcttgac attctagatc tgtctggtaa gcaacattcc     1020
gtcgtaacag tgaaagcctt agaacctaca gccaaagttc cttttccaaa tccaactacc     1080
tacgatgcta tattgagata ccatctggaa atatgcgctc cagtttctag acagtttgtc     1140
tcaactttag cagcattcgc ccctaatgat gatatcaaag ctgagatgaa ccgtttggga     1200
tcagacaaag attacttcca cgaaaagaca ggaccacatt actacaatat cgctagattt     1260
ttggcctcag tctctaaagg tgaaaaatgg acaaagatac cattttctgc tttcatagaa     1320
ggccttacaa aactacaacc aagatactat tctatctctt cctctagttt agttcagcct     1380
aaaaagatta gtattactgc tgttgtcgaa tctcagcaaa ttccaggtag agatgaccca     1440
ttcagaggtg tagcgactaa ctacttgttc gctttgaagc agaaacaaaa cggtgatcca     1500
aatccagctc cttttggcca atcatacgag ttgacaggac caaggaataa gtatgatggt     1560
atacatgttc cagtccatgt aagacattct aactttaagc taccatctga tccaggcaaa     1620
cctattatca tgatcggtcc aggtaccggt gttgccccct ttagaggctt cgtccaagag     1680
agggcaaaac aagccagaga tggtgtagaa gttggtaaaa cactgctgtt ctttggatgt     1740
agaaagagta cagaagattt catgtatcaa aaagagtggc aagagtacaa ggaagctctt     1800
ggcgacaaat tcgaaatgat tacagctttt tcaagagaag gatctaaaaa ggtttatgtt     1860
caacacagac tgaaggaaag atcaaaggaa gtttctgatc ttctatccca aaaagcatac     1920
ttctacgttt gcggagacgc cgcacatatg gcacgtgaag tgaacactgt gttagcacag     1980
atcatagcag aaggccgtgg tgtatcagaa gccaagggtg aggaaattgt caaaaacatg     2040
agatcagcaa atcaatacca agtgtgttct gatttcgtaa ctttacactg taaagagaca     2100
acatacgcga attcagaatt gcaagaggat gtctggagtt aa                       2142

<210> SEQ ID NO 73
<211> LENGTH: 2133
<212> TYPE: DNA
<213> ORGANISM: Stevia rebaudiana

<400> SEQUENCE: 73
atgcaatcag attccgtaaa agtgtcgccg ttcgatctcg tatctgcagc tatgaacgga       60
aaagcaatgg agaaattgaa cgcatcggaa tcggaagatc cgacgacgct accggcgttg      120
aagatgctgg tggagaatcg cgagctgctg acactgttta cgacgtcgtt tgctgtattg      180
atcggatgtc tcgtgttttt gatgtggcgg agatcgtcct cgaagaaact ggttcaggat      240
ccggtgccgc aggtaatcgt tgttaagaag aaagagaagg agtctgaggt tgatgatggc      300
aagaagaaag tttcgatatt ctacggaact caaacaggaa ccgctgaagg ttttgccaag      360
gcacttgtag aggaagctaa agttcgatat gaaaagacat cctttaaagt tattgatctg      420
gatgattatg ctgctgatga cgatgagtat gaggagaagc ttaagaaaga atctttggcg      480
tttttctttt tggcaacgta tggagatggt gaaccaacag ataatgcagc caatttttac      540 aaaatggttta cagagggaga tgacaaaggc gaatggctga agaaacttca atatggcgtg      600
tttggcctcg gtaacagaca atatgagcat tcaataagga ttgcaatagt ggttgatgac      660
aaactcacag aaatgggcgc aaaacgcctt gttcctgtgg gtcttggaga tgacgatcaa      720
tgtatagaag atgactttac agcatggaaa gagttagtgt ggcccgagtt ggatcaattg      780
```

```
ttgcgtgatg aggatgacac gagtgttacg actccttaca ctgctgcggt tttggaatac      840
cgagttgtat atcatgataa acctgcagac tcgtatgcag aagatcaaac tcatacaaat      900
ggtcatgttg ttcatgatgc tcaacatcca tctagatcca atgtggcatt taaaaaggaa      960
ttgcacacct ctcaatctga ccggtcttgc actcatttgg aatttgatat ctctcacacc     1020
gggctatcat acgagacggg ggatcatgtt ggtgtctaca gtgagaatct aagtgaagtt     1080
gtagatgaag ctttaaaatt actcggtttg tcacccgaca cttatttctc agtccatgct     1140
gacaaggaag acgaacacc tattggcggc gcctccttgc cgccacctt ccctccatgc       1200 actttaagag atgcattaac gcgctacgca gatgttttga gttctcctaa aaaggttgct     1260
ttgcttgctc tggctgctca tgcttctgat cctagcgaag ccgatcgatt aaaatttcta     1320
gcatctccgg ctgcaagga tgaatatgct caatggatag ttgcaaacca agaagtctt      1380 cttgaagtta tgcagtcatt tccgtcagct aaaccgccac ttggtgtttt cttcgcagct     1440
gtcgccccac gtttacaacc tcgatattac tcgatttctt cttctccaaa gatgtcacca     1500
aacagaattc atgtgacttg tgcattagtt tatgagacaa cacctgcagg acgtattcac     1560
agaggattgt gttcaacatg gatgaagaat gctgtgcctt tgaccgaaag tccagattgt     1620
agtcaggcgt cgattttgt tagaacgtct aacttccgac ttccggttga cccgaaagtc       1680
ccggtcatca tgatcggtcc cgggactggg ttagccccct tcagaggttt tcttcaagaa     1740
cggttagctt tgaaggaatc tggaaccgaa ctcgggtcat ctattttctt tttcggatgc     1800
agaaaccgca agtggatttt tatatacgaa gacgaactaa acaactttgt ggagaccggt     1860
gctttatcgg agcttattgt tgcattctcc cgtgaaggaa ccgcaaagga gtatgtgcaa     1920
cataaaatga gccagaaggc ttcagatatc tggaagttgc tttcagaggg agcatattta     1980
tatgtatgtg gtgatgctaa aggcatggct aaagatgtac acagaaccct tcacacaatt     2040
gtacaagaac agggatctct agattcttcc aaggcagaat tgtatgtaaa gaacctacaa     2100
atgtcgggaa gatatcttcg tgatgtttgg taa                                  2133
```

<210> SEQ ID NO 74
<211> LENGTH: 2079
<212> TYPE: DNA
<213> ORGANISM: Arabidopsis thaliana

<400> SEQUENCE: 74

```
atgacttctg ctttgtatgc ttccgatttg tttaagcagc tcaagtcaat tatggggaca       60
gattcgttat ccgacgatgt tgtacttgtg attgcaacga cgtctttggc actagtagct      120
ggatttgtgg tgttgttatg aagaaaacg acggcggatc ggagcgggga gctgaagcct      180
ttgatgatcc ctaagtctct tatggctaag gacgaggatg atgatttgga tttgggatcc     240
gggaagacta gagtctctat cttcttcggt acgcagactg gaacagctga gggatttgct     300
aaggcattat ccgaagaaat caaagcgaga tatgaaaaag cagcagtcaa agtcattgac     360
ttggatgact atgctgccga tgatgaccag tatgaagaga aattgaagaa ggaaactttg     420
gcatttttct gtgttgctac ttatggagat ggagagccta ctgacaatgc tgccagattt     480
tacaaatggt ttacggagga aaatgaacgg gatataaagc ttcaacaact agcatatggt     540
gtgtttgctc ttggtaatcg ccaatatgaa catttttaata agatcgggat agttcttgat    600
gaagagttat gtaagaaagg tgcaaagcgt cttattgaag tcggtctagg agatgatgat    660
cagagcattg aggatgattt taatgcctgg aaagaatcac tatggtctga gctagacaag    720
ctcctcaaag acgaggatga taaaagtgtg gcaactcctt atacagctgt tattcctgaa     780
```

```
taccgggtgg tgactcatga tcctcggttt acaactcaaa atcaatgga atcaaatgtg      840
gccaatggaa atactactat tgacattcat catccctgca gagttgatgt tgctgtgcag     900
aaggagcttc acacacatga atctgatcgg tcttgcattc atctcgagtt cgacatatcc     960
aggacgggta ttacatatga aacaggtgac catgtaggtg tatatgctga aaatcatgtt    1020
gaaatagttg aagaagctgg aaaattgctt ggccactctt tagatttagt attttccata    1080
catgctgaca aggaagatgg ctccccattg aaaagcgcag tgccgcctcc tttccctggt    1140
ccatgcacac ttgggactgg tttggcaaga tacgcagacc ttttgaaccc tcctcgaaag    1200
tctgcgttag ttgccttggc ggcctatgcc actgaaccaa gtgaagccga aaacttaag    1260
cacctgacat cacctgatgg aaaggatgag tactcacaat ggattgttgc aagtcagaga    1320
agtcttttag aggtgatggc tgcttttcca tctgcaaaac ccccactagg tgtattttt    1380
gctgcaatag ctcctcgtct acaacctcgt tactactcca tctcatcctc gccaagattg    1440
gcgccaagta gagttcatgt tacatccgca ctagtatatg gtccaactcc tactggtaga    1500
atccacaagg gtgtgtgttc tacgtggatg aagaatgcag ttcctgcgga gaaaagtcat    1560
gaatgtagtg gagccccaat ctttattcga gcatctaatt tcaagttacc atccaaccct    1620
tcaactccaa tcgttatggt gggacctggg actgggctgg cacctttag aggttttctg     1680
caggaaagga tggcactaaa agaagatgga gaagaactag gttcatcttt gctcttcttt    1740
gggtgtagaa atcgacagat ggactttata tacgaggatg agctcaataa ttttgttgat    1800
caaggcgtaa tatctgagct catcatggca ttctcccgtg aaggagctca gaaggagtat    1860
gttcaacata gatgatgga gaaggcagca caagtttggg atctaataaa ggaagaagga     1920
tatctctatg tatgcggtga tgctaagggc atggcgaggg acgtccaccg aactctacac    1980
accattgttc aggagcagga aggtgtgagt tcgtcagagg cagaggctat agttaagaaa    2040
cttcaaaccg aaggaagata cctcagagat gtctggtga                           2079
```

<210> SEQ ID NO 75
<211> LENGTH: 2142
<212> TYPE: DNA
<213> ORGANISM: Giberella fujikuroi
<400> SEQUENCE: 75

```
atggctgaac tcgacactct ggacatcgtc gtcctcggcg ttatcttcct cggaacggtt      60
gcatacttta caagggcaa gctatgggt gttaccaagg atccctacgc gaatggcttc       120
gctgccggcg gcgcttctaa gccgggtcgc acgaggaaca tcgtcgaggc aatggaagaa     180
tccggcaaga actgtgttgt cttctatggt tctcagaccg gtactgctga agattatgct     240
tctcgcctcg ccaaggaggg taagagtcga ttcggactaa acaccatgat tgccgatctt    300
gaggactacg atttcgacaa cctggatacc gttcccagtg acaacattgt catgttcgtt    360
ctcgcaactt atggtgaagg tgagcctacc gataacgcgg tcgacttcta tgaattcatt    420
accggcgagg atgccagctt caatgagggc aatgatcctc cgctgggcaa cctcaactac    480
gttgctttcg gtctcggaaa caacacgtac gagcactaca actctatggt ccgcaatgtt    540
aacaaggctc tcgagaagct tggcgctcac cgcatcggtg aagctggtga gggtgatgat    600
ggtgctggta ccatggaaga ggacttcttg gcctggaagg atcccatgtg gaagccctc     660
gctaagaaaa tgggactgga agagcgtgaa gcagtctacg agcctatttt tgccattaac    720
gaacgcgacg acctgactcc tgaagccaat gaagtgtatc tcggtgagcc caacaagctg    780
```

```
catctcgaag gcaccgccaa gggaccattc aactctcaca acccctacat tgcccctatc      840
gctgaatctt atgagttgtt ctccgccaag gacagaaact gcctccacat ggaaattgac      900
atcagcggtt ctaacctcaa gtacgaaact ggagaccata ttgctatctg gcctaccaac      960
cctggtgagg aggtcaacaa attcctggat attctcgacc tctctggaaa gcagcacagc     1020
gttgtcactg tcaaggctct cgagcctacc gccaaggttc ctttccccaa ccctacaacc     1080
tacgatgcca ttctgcgata ccacctcgag atctgcgctc ctgtttcacg tcaattcgtc     1140
tctactctcg ccgcatttgc tcccaacgat gatatcaagg ctgagatgaa ccgccttggc     1200
agcgataagg attatttcca cgagaagact ggcccgcatt actacaacat tgcccgtttc     1260
cttgccagcg tcagcaaggg cgagaagtgg accaaaatcc cgttctctgc cttcatcgag     1320
ggtctcacca agctccagcc ccgttactac tccatttctt cctcgtctct ggttcagccc     1380
aagaaaatct cgatcactgc cgtcgttgaa tcccagcaga ttcctggccg ggatgatcct     1440
ttccgtggtg ttgctacaaa ctatcttttt gccctaaagc aaaagcagaa cggtgacccc     1500
aaccctgcac ttttggtca gagctacgag cttacaggcc cccgcaataa gtatgatggc     1560
atccacgttc ctgtccatgt tcgtcactcc aacttcaagc tcccctcgga ccccggtaag     1620
cccatcatca tgattggtcc tggtactggt gtcgctccct tccgcggttt cgtgcaggag     1680
cgtgctaagc aagcccgtga tggtgttgag gttggaaaga cactcttgtt ctttggttgc     1740
cgaaagtcaa ccgaggattt catgtaccaa aggagtggc aggaatacaa ggaggctctt     1800
ggcgataagt ttgaaatgat caccgccttt tctcgagagg gctccaagaa ggtttatgtt     1860
cagcaccgac ttaaggagcg atctaaggag gtcagcgatc tgctctccca gaaggcttat     1920
ttctatgtct gcggtgatgc agcccacatg gcccgcgagg tcaataccgt cttggcacaa     1980
atcattgccg agggacgtgg ggtgtctgag gccaagggcg aggagatcgt gaagaacatg     2040
agatcagcga accaatacca ggtatgtagt gactttgtta ctcttcactg caaagaaacc     2100
acatatgcta actcagaatt acaggaggat gtttggtcat ag                         2142
```

<210> SEQ ID NO 76
<211> LENGTH: 459
<212> TYPE: PRT
<213> ORGANISM: Ipomoea purpurea

<400> SEQUENCE: 76

```
Met Gly Ser Gln Ala Thr Thr Tyr His Met Ala Met Tyr Pro Trp Phe
1               5                   10                  15

Gly Val Gly His Leu Thr Gly Phe Phe Arg Leu Ala Asn Lys Leu Ala
            20                  25                  30

Gly Lys Gly His Arg Ile Ser Phe Leu Ile Pro Lys Asn Thr Gln Ser
        35                  40                  45

Lys Leu Glu Ser Phe Asn Leu His Pro His Leu Ile Ser Phe Val Pro
    50                  55                  60

Ile Val Val Pro Ser Ile Pro Gly Leu Pro Pro Gly Ala Glu Thr Thr
65                  70                  75                  80

Ser Asp Val Pro Phe Pro Ser Thr His Leu Leu Met Glu Ala Met Asp
                85                  90                  95

Lys Thr Gln Asn Asp Ile Glu Ile Ile Leu Lys Asp Leu Lys Val Asp
            100                 105                 110

Val Val Phe Tyr Asp Phe Thr His Trp Leu Pro Ser Leu Ala Arg Lys
        115                 120                 125

Ile Gly Ile Lys Ser Val Phe Tyr Ser Thr Ile Ser Pro Leu Met His
```

```
                130                 135                 140
Gly Tyr Ala Leu Ser Pro Glu Arg Arg Val Val Gly Lys Gln Leu Thr
145                 150                 155                 160

Glu Ala Asp Met Met Lys Ala Pro Ala Ser Phe Pro Asp Pro Ser Ile
                165                 170                 175

Lys Leu His Ala His Glu Ala Arg Gly Phe Thr Ala Arg Thr Val Met
                180                 185                 190

Lys Phe Gly Gly Asp Ile Thr Phe Phe Asp Arg Ile Phe Thr Ala Val
                195                 200                 205

Ser Glu Ser Asp Gly Leu Ala Tyr Ser Thr Cys Arg Glu Ile Glu Gly
            210                 215                 220

Gln Phe Cys Asp Tyr Ile Glu Thr Gln Phe Gln Lys Pro Val Leu Leu
225                 230                 235                 240

Ala Gly Pro Ala Leu Pro Val Pro Ser Lys Ser Thr Met Glu Gln Lys
                245                 250                 255

Trp Ser Asp Trp Leu Gly Lys Phe Lys Glu Gly Ser Val Ile Tyr Cys
                260                 265                 270

Ala Phe Gly Ser Glu Cys Thr Leu Arg Lys Asp Lys Phe Gln Glu Leu
                275                 280                 285

Leu Trp Gly Leu Glu Leu Thr Gly Met Pro Phe Phe Ala Ala Leu Lys
            290                 295                 300

Pro Pro Phe Glu Thr Glu Ser Val Glu Ala Ala Ile Pro Glu Glu Leu
305                 310                 315                 320

Lys Glu Lys Ile Gln Gly Arg Gly Ile Val His Gly Glu Trp Val Gln
                325                 330                 335

Gln Gln Leu Phe Leu Gln His Pro Ser Val Gly Cys Phe Val Ser His
                340                 345                 350

Cys Gly Trp Ala Ser Leu Ser Glu Ala Leu Val Asn Asp Cys Gln Ile
            355                 360                 365

Val Leu Leu Pro Gln Val Gly Asp Gln Ile Ile Asn Ala Arg Ile Met
            370                 375                 380

Ser Val Ser Leu Lys Val Gly Val Glu Val Glu Lys Gly Glu Glu Asp
385                 390                 395                 400

Gly Val Phe Ser Arg Glu Ser Val Cys Lys Ala Val Lys Ala Val Met
                405                 410                 415

Asp Glu Lys Ser Glu Ile Gly Arg Glu Val Arg Gly Asn His Asp Lys
                420                 425                 430

Leu Arg Gly Phe Leu Met Asn Ala Asp Leu Asp Ser Lys Tyr Met Asp
            435                 440                 445

Ser Phe Asn Gln Lys Leu Gln Asp Leu Leu Gly
450                 455

<210> SEQ ID NO 77
<211> LENGTH: 1380
<212> TYPE: DNA
<213> ORGANISM: Ipomoea purpurea

<400> SEQUENCE: 77
atgggttctc aagctacaac ttaccatatg gccatgtatc catggtttgg ggttggacat      60
ttgactggtt tcttccgttt ggcaaacaaa ttagctggca aaggacatag aatctcattt     120
ctaattccta aaaacactca atctaagtta gaatctttca accttcatcc acacttaatc     180
tcttttgtgc ctatcgttgt cccaagtata ccaggcctgc cacctggtgc agagactaca     240
tcagatgttc ctttcccaag tacacatttg ctaatggaag caatggacaa gactcaaaac     300
```

```
gatatagaga ttatcctgaa ggatcttaaa gtagatgttg ttttctatga ttttactcac    360
tggttgcctt ctctggccag aaagattggc attaagagtg tcttttactc caccatttct    420
cctttaatgc atggatatgc tttatcacca gaaagacgtg tagttggtaa gcaattgaca    480
gaggcagata tgatgaaggc cccagcttct ttcccagacc catccattaa gctacatgca    540
catgaagcta ggggttttac agccagaacc gttatgaaat cggtggtga catcaccttt     600
ttcgatagaa tattcacagc agtttccgaa agtgatggcc tggcctactc tacttgtaga    660
gagatcgagg gacaattctg tgattacatt gaaacacaat tccagaagcc agtcttgtta    720
gccggtccag ctttgccagt cccatccaaa tccactatgg aacaaaagtg gtcagattgg    780
ttggggaaat tcaaggaagg ctccgtcatc tactgtgctt cgggtctga atgtacattg     840
agaaaggaca aatttcagga actttatgg ggtttggaat tgacaggaat gcctttcttc     900
gctgctctga agccacctt tgagactgag tctgttgagg ctgctatccc tgaggaacta     960
aaggaaaaga ttcagggaag aggtatagta catggagaat gggtacaaca acaattgttt   1020
cttcaacacc catctgtcgg gtgcttcgtt tctcactgcg gctgggcaag tttatctgaa   1080
gcccttgtta atgattgtca atcgtgtta cttccacaag ttggcgatca gattatcaac    1140
gccagaataa tgtcagtatc acttaaagtg ggcgtggaag ttgaaaaggg tgaggaggac   1200
ggtgtctttt caagagaatc tgtgtgcaag gctgttaaag cagtaatgga tgaaaaatct   1260
gaaatcggta gagaagtcag aggtaatcat gataaactga ggggtttctt gatgaatgca   1320
gacttagatt caaagtacat ggattcattc aatcaaaagc tacaagattt gctaggttaa   1380
```

<210> SEQ ID NO 78
<211> LENGTH: 438
<212> TYPE: PRT
<213> ORGANISM: Bellis perennis

<400> SEQUENCE: 78

Met Asp Ser Lys Ile Asp Ser Lys Thr Phe Arg Val Val Met Leu Pro
1               5                   10                  15

Trp Leu Ala Tyr Ser His Ile Ser Ser Phe Leu Val Phe Ala Lys Arg
            20                  25                  30

Leu Thr Asn His Asn Phe His Ile Tyr Ile Cys Ser Ser Gln Thr Asn
        35                  40                  45

Met Gln Tyr Leu Lys Asn Asn Leu Thr Ser Gln Tyr Ser Lys Ser Ile
    50                  55                  60

Gln Leu Ile Glu Leu Asn Leu Pro Ser Ser Glu Leu Pro Leu Gln
65                  70                  75                  80

Tyr His Thr Thr His Gly Leu Pro Pro His Leu Thr Lys Thr Leu Ser
                85                  90                  95

Asp Asp Tyr Gln Lys Ser Gly Pro Asp Phe Glu Thr Ile Leu Ile Lys
            100                 105                 110

Leu Asn Pro His Leu Val Ile Tyr Asp Phe Asn Gln Leu Trp Ala Pro
        115                 120                 125

Glu Val Ala Ser Thr Leu His Ile Pro Ser Ile Gln Leu Leu Ser Gly
    130                 135                 140

Cys Val Ala Leu Tyr Ala Leu Asp Ala His Leu Tyr Thr Lys Pro Leu
145                 150                 155                 160

Asp Glu Asn Leu Ala Lys Phe Pro Phe Pro Glu Ile Tyr Pro Lys Asn
                165                 170                 175

Arg Asp Ile Pro Lys Gly Gly Ser Lys Tyr Ile Glu Arg Phe Val Asp

```
                    180                 185                 190
Cys Met Arg Arg Ser Cys Glu Ile Ile Leu Val Arg Ser Thr Met Glu
            195                 200                 205
Leu Glu Gly Lys Tyr Ile Asp Tyr Leu Ser Lys Thr Leu Gly Lys Lys
        210                 215                 220
Val Leu Pro Val Gly Pro Leu Val Gln Glu Ala Ser Leu Leu Gln Asp
225                 230                 235                 240
Asp His Ile Trp Ile Met Lys Trp Leu Asp Lys Lys Glu Glu Ser Ser
                245                 250                 255
Val Val Phe Val Cys Phe Gly Ser Glu Tyr Ile Leu Ser Asp Asn Glu
            260                 265                 270
Ile Glu Asp Ile Ala Tyr Gly Leu Glu Leu Ser Gln Val Ser Phe Val
        275                 280                 285
Trp Ala Ile Arg Ala Lys Thr Ser Ala Leu Asn Gly Phe Ile Asp Arg
        290                 295                 300
Val Gly Asp Lys Gly Leu Val Ile Asp Lys Trp Val Pro Gln Ala Asn
305                 310                 315                 320
Ile Leu Ser His Ser Ser Thr Gly Gly Phe Ile Ser His Cys Gly Trp
                325                 330                 335
Ser Ser Thr Met Glu Ser Ile Arg Tyr Gly Val Pro Ile Ile Ala Met
            340                 345                 350
Pro Met Gln Phe Asp Gln Pro Tyr Asn Ala Arg Leu Met Glu Thr Val
        355                 360                 365
Gly Ala Gly Ile Glu Val Gly Arg Asp Gly Glu Gly Arg Leu Lys Arg
        370                 375                 380
Glu Glu Ile Ala Ala Val Val Arg Lys Val Val Val Glu Asp Ser Gly
385                 390                 395                 400
Glu Ser Ile Arg Glu Lys Ala Lys Glu Leu Gly Glu Ile Met Lys Lys
                405                 410                 415
Asn Met Glu Ala Glu Val Asp Gly Ile Val Ile Glu Asn Leu Val Lys
            420                 425                 430
Leu Cys Glu Met Asn Asn
        435

<210> SEQ ID NO 79
<211> LENGTH: 1317
<212> TYPE: DNA
<213> ORGANISM: Bellis perennis

<400> SEQUENCE: 79
atggattcta aaatcgattc aaagacattc agagtcgtta tgttgccttg gcttgcatac      60
tcacacattt catcattcct agtgtttgcc aagagactaa caaatcataa cttccacatc     120
tacatttgtt cctctcaaac aaatatgcaa tacctgaaaa acaacttgac gtctcagtat     180
tcaaaatcta caactgat tgagttgaat cttccatcta gttccgaatt gcctctgcag       240
tatcatacta ctcacggact accaccacac cttacgaaaa cattgtctga tgattatcaa     300
aagtccggac ctgactttga aaccattttg atcaaattga acccacatct ggtaatctac     360
gactttaatc aactttgggc tccagaggtt gctagtacac ttcatattcc atccatacag     420
ttactgtctg gttgcgtcgc cttatatgcc ttagacgccc atctgtacac aaagccacta     480
gacgaaaact tggctaagtt tccttttccca gaaatctatc ctaaaaacag agatattcct     540
aagggaggta gtaaatacat cgaaaggttc gtagactgta tgagaagatc ttgtgaaatc     600
atattagtca gaagtaccat ggaacttgaa ggaaaataca ttgattactt gtctaagaca     660
```

```
ttagggaaaa aggtgttgcc agtagggcct ctggtgcaag aggcttcttt gttgcaagat      720
gatcatatat ggattatgaa gtggttagac aaaaaggagg agtcatccgt cgtgtttgtt      780
tgttttggtt ctgagtacat cttatcagac aacgaaatag aagatattgc ttatggccta      840
gagttgtccc aagtaagttt cgtttgggca ataagagcta agacttctgc cttaaatggc      900
ttcattgata gagtgggtga taaaggctta gtcatcgata aatgggttcc acaggctaac      960
atcttatctc actcttctac tggtggattc attagtcatt gcggttggtc atcaacaatg     1020
gaatctatta gatatggggt tcctattatc gccatgccaa tgcaattcga tcaaccttac     1080
aatgctaggt tgatggaaac tgttggtgca ggtatcgaag ttggcagaga tggcgaaggt     1140
agattgaaaa gagaagagat tgctgccgtg gttagaaagg tcgttgttga agattctggg     1200
gaatccataa gggagaaggc aaaggaattg ggagaaatca tgaaaaaaaa catggaggcc     1260
gaagtagatg gtatagtgat tgaaaatcta gttaagctat gtgagatgaa caattaa       1317
```

<210> SEQ ID NO 80
<211> LENGTH: 2490
<212> TYPE: DNA
<213> ORGANISM: Zea mays

<400> SEQUENCE: 80

```
atggttttgt cttcttcttg tactacagta ccacacttat cttcattagc tgtcgtgcaa       60
cttggtcctt ggagcagtag gattaaaaag aaaaccgata ctgttgcagt accagccgct      120
gcaggaaggt ggagaagggc cttggctaga gcacagcaca catcagaatc cgcagctgtc      180
gcaaagggca gcagtttgac ccctatagtg agaactgacg ctgagtcaag gagaacaaga      240
tggccaaccg atgacgatga cgccgaacct ttagtggatg agatcagggc aatgcttact      300
tccatgtctg atggtgacat ttccgtgagc gcatacgata cagcctgggt cggattggtt      360
ccaagattag acggcggtga aggtcctcaa tttccagcag ctgtgagatg gataagaaat      420
aaccagttgc ctgacggaag ttggggcgat gccgcattat tctctgccta tgacaggctt      480
atcaataccc ttgcctgcgt tgtaactttg acaaggtggt ccctagaacc agagatgaga      540
ggtagaggac tatcttttt gggtaggaac atgtggaaat tagcaactga agatgaagag      600
tcaatgccta ttggcttcga attagcattt ccatctttga tagagcttgc taagagccta      660
ggtgtccatg acttccctta tgatcaccag gccctacaag aatctactc ttcaagagag      720 atcaaaatga agaggattcc aaaagaagtg atgcataccg ttccaacatc aatattgcac      780
agtttggagg gtatgcctgg cctagattgg gctaaactac ttaaactaca gagcagcgac      840
ggaagttttt tgttctcacc agctgccact gcatatgctt taatgaatac cggagatgac      900
aggtgtttta gctacatcga tagaacagta aagaaattca acggcggcgt ccctaatgtt      960
tatccagtgg atctatttga acatatttgg gccgttgata gacttgaaag attaggaatc     1020
tccaggtact tccaaaagga gatcgaacaa tgcatggatt atgtaaacag gcattggact     1080
gaggacggta tttgttgggc aaggaactct gatgtcaaag aggtggacga cacagctatg     1140
gcctttagac ttcttaggtt gcacggctac agcgtcagtc ctgatgtgtt taaaaacttc     1200
gaaaaggacg tgaatttttt cgcatttgtc ggacagtcta atcaagctgt taccggtatg     1260
tacaacttaa acagagcaag ccagatatcc ttcccaggcg aggatgtgct tcatagagct     1320
ggtgccttct catatgagtt cttgaggaga aagaagcag gggagcttt gagggacaag     1380 tggatcattt ctaaagatct acctggtgaa gttgtgtata ctttggattt tccatggtac     1440
```

```
ggcaacttac ctagagtcga ggccagagac tacctagagc aatacggagg tggtgatgac    1500
gtttggattg gcaagacatt gtataggatg ccacttgtaa acaatgatgt atatttggaa    1560
ttggcaagaa tggatttcaa ccactgccag gctttgcatc agttagagtg gcaaggacta    1620
aaaagatggt atactgaaaa taggttgatg gactttggtg tcgcccaaga agatgccctt    1680
agagcttatt ttcttgcagc cgcatctgtt tacgagcctt gtagagctgc cgagaggctt    1740
gcatgggcta gagccgcaat actagctaac gccgtgagca cccacttaag aaatagccca    1800
tcattcagag aaaggttaga gcattctctt aggtgtagac ctagtgaaga gacagatggc    1860
tcctggttta actcctcaag tggctctgat gcagttttag taaaggctgt cttaagactt    1920
actgattcat tagccaggga agcacagcca atccatggag gtgacccaga agatattata    1980
cacaagttgt taagatctgc ttgggccgag tgggttaggg aaaaggcaga cgctgccgat    2040
agcgtgtgca atggtagttc tgcagtagaa caagagggat caagaatggt ccatgataaa    2100
cagacctgtc tattattggc tagaatgatc gaaatttctg ccggtagggc agctggtgaa    2160
gcagccagtg aggacggcga tagaagaata attcaattaa caggctccat ctgcgacagt    2220
cttaagcaaa aaatgctagt ttcacaggac cctgaaaaaa atgaagagat gatgtctcac    2280
gtggatgacg aattgaagtt gaggattaga gagttcgttc aatatttgct tagactaggt    2340
gaaaaaaaga ctggatctag cgaaaccagg caaacatttt taagtatagt gaaatcatgt    2400
tactatgctg ctcattgccc acctcatgtc gttgatagac acattagtag agtgattttc    2460
gagccagtaa gtgccgcaaa gtaaccgcgg                                    2490
```

<210> SEQ ID NO 81
<211> LENGTH: 827
<212> TYPE: PRT
<213> ORGANISM: Zea mays

<400> SEQUENCE: 81

```
Met Val Leu Ser Ser Cys Thr Thr Val Pro His Leu Ser Ser Leu
1               5                   10                  15

Ala Val Val Gln Leu Gly Pro Trp Ser Ser Arg Ile Lys Lys Lys Thr
                20                  25                  30

Asp Thr Val Ala Val Pro Ala Ala Ala Gly Arg Trp Arg Arg Ala Leu
            35                  40                  45

Ala Arg Ala Gln His Thr Ser Glu Ser Ala Ala Val Ala Lys Gly Ser
        50                  55                  60

Ser Leu Thr Pro Ile Val Arg Thr Asp Ala Glu Ser Arg Arg Thr Arg
65                  70                  75                  80

Trp Pro Thr Asp Asp Asp Ala Glu Pro Leu Val Asp Glu Ile Arg
                85                  90                  95

Ala Met Leu Thr Ser Met Ser Asp Gly Asp Ile Ser Val Ser Ala Tyr
                100                 105                 110

Asp Thr Ala Trp Val Gly Leu Val Pro Arg Leu Asp Gly Gly Glu Gly
            115                 120                 125

Pro Gln Phe Pro Ala Ala Val Arg Trp Ile Arg Asn Asn Gln Leu Pro
        130                 135                 140

Asp Gly Ser Trp Gly Asp Ala Ala Leu Phe Ser Ala Tyr Asp Arg Leu
145                 150                 155                 160

Ile Asn Thr Leu Ala Cys Val Val Thr Leu Thr Arg Trp Ser Leu Glu
                165                 170                 175

Pro Glu Met Arg Gly Arg Gly Leu Ser Phe Leu Gly Arg Asn Met Trp
                180                 185                 190
```

Lys Leu Ala Thr Glu Asp Glu Ser Met Pro Ile Gly Phe Glu Leu
    195                 200                 205

Ala Phe Pro Ser Leu Ile Glu Leu Ala Lys Ser Leu Gly Val His Asp
    210                 215                 220

Phe Pro Tyr Asp His Gln Ala Leu Gln Gly Ile Tyr Ser Ser Arg Glu
225                 230                 235                 240

Ile Lys Met Lys Arg Ile Pro Lys Glu Val Met His Thr Val Pro Thr
                245                 250                 255

Ser Ile Leu His Ser Leu Glu Gly Met Pro Gly Leu Asp Trp Ala Lys
                260                 265                 270

Leu Leu Lys Leu Gln Ser Ser Asp Gly Ser Phe Leu Phe Ser Pro Ala
                275                 280                 285

Ala Thr Ala Tyr Ala Leu Met Asn Thr Gly Asp Asp Arg Cys Phe Ser
    290                 295                 300

Tyr Ile Asp Arg Thr Val Lys Lys Phe Asn Gly Gly Val Pro Asn Val
305                 310                 315                 320

Tyr Pro Val Asp Leu Phe Glu His Ile Trp Ala Val Asp Arg Leu Glu
                325                 330                 335

Arg Leu Gly Ile Ser Arg Tyr Phe Gln Lys Glu Ile Glu Gln Cys Met
                340                 345                 350

Asp Tyr Val Asn Arg His Trp Thr Glu Asp Gly Ile Cys Trp Ala Arg
                355                 360                 365

Asn Ser Asp Val Lys Glu Val Asp Asp Thr Ala Met Ala Phe Arg Leu
    370                 375                 380

Leu Arg Leu His Gly Tyr Ser Val Ser Pro Asp Val Phe Lys Asn Phe
385                 390                 395                 400

Glu Lys Asp Gly Glu Phe Phe Ala Phe Val Gly Gln Ser Asn Gln Ala
                405                 410                 415

Val Thr Gly Met Tyr Asn Leu Asn Arg Ala Ser Gln Ile Ser Phe Pro
                420                 425                 430

Gly Glu Asp Val Leu His Arg Ala Gly Ala Phe Ser Tyr Glu Phe Leu
    435                 440                 445

Arg Arg Lys Glu Ala Glu Gly Ala Leu Arg Asp Lys Trp Ile Ile Ser
    450                 455                 460

Lys Asp Leu Pro Gly Glu Val Val Tyr Thr Leu Asp Phe Pro Trp Tyr
465                 470                 475                 480

Gly Asn Leu Pro Arg Val Glu Ala Arg Asp Tyr Leu Glu Gln Tyr Gly
                485                 490                 495

Gly Gly Asp Asp Val Trp Ile Gly Lys Thr Leu Tyr Arg Met Pro Leu
                500                 505                 510

Val Asn Asn Asp Val Tyr Leu Glu Leu Ala Arg Met Asp Phe Asn His
    515                 520                 525

Cys Gln Ala Leu His Gln Leu Glu Trp Gln Gly Leu Lys Arg Trp Tyr
    530                 535                 540

Thr Glu Asn Arg Leu Met Asp Phe Gly Val Ala Gln Glu Asp Ala Leu
545                 550                 555                 560

Arg Ala Tyr Phe Leu Ala Ala Ala Ser Val Tyr Glu Pro Cys Arg Ala
                565                 570                 575

Ala Glu Arg Leu Ala Trp Ala Arg Ala Ala Ile Leu Ala Asn Ala Val
                580                 585                 590

Ser Thr His Leu Arg Asn Ser Pro Ser Phe Arg Glu Arg Leu Glu His
                595                 600                 605

| | | | | | | | | | | | |
|---|---|---|---|---|---|---|---|---|---|---|---|
|Ser|Leu|Arg|Cys|Arg|Pro|Ser|Glu|Glu|Thr|Asp|Gly|Ser|Trp|Phe|Asn|
| |610| | | | |615| | | | |620| | | | |

Ser Ser Ser Gly Ser Asp Ala Val Leu Val Lys Ala Val Leu Arg Leu
625             630             635             640

Thr Asp Ser Leu Ala Arg Glu Ala Gln Pro Ile His Gly Gly Asp Pro
            645             650             655

Glu Asp Ile Ile His Lys Leu Leu Arg Ser Ala Trp Ala Glu Trp Val
            660             665             670

Arg Glu Lys Ala Asp Ala Ala Asp Ser Val Cys Asn Gly Ser Ser Ala
            675             680             685

Val Glu Gln Gly Ser Arg Met Val His Asp Lys Gln Thr Cys Leu
690             695             700

Leu Leu Ala Arg Met Ile Glu Ile Ser Ala Gly Arg Ala Ala Gly Glu
705             710             715             720

Ala Ala Ser Glu Asp Gly Asp Arg Arg Ile Ile Gln Leu Thr Gly Ser
            725             730             735

Ile Cys Asp Ser Leu Lys Gln Lys Met Leu Val Ser Gln Asp Pro Glu
            740             745             750

Lys Asn Glu Glu Met Met Ser His Val Asp Asp Glu Leu Lys Leu Arg
            755             760             765

Ile Arg Glu Phe Val Gln Tyr Leu Leu Arg Leu Gly Glu Lys Lys Thr
770             775             780

Gly Ser Ser Glu Thr Arg Gln Thr Phe Leu Ser Ile Val Lys Ser Cys
785             790             795             800

Tyr Tyr Ala Ala His Cys Pro Pro His Val Val Asp Arg His Ile Ser
            805             810             815

Arg Val Ile Phe Glu Pro Val Ser Ala Ala Lys
            820             825

<210> SEQ ID NO 82
<211> LENGTH: 1461
<212> TYPE: DNA
<213> ORGANISM: Artificial Sequence
<220> FEATURE:
<223> OTHER INFORMATION: Description of Artificial Sequence: Synthetic
       polynucleotide

<400> SEQUENCE: 82

```
actagtaaaa tggatgcaat ggcaactact gagaaaaagc tcatgtgat cttcattcca      60
tttcctgcac aatctcacat aaaggcaatg ctaaagttag cacaactatt acaccataag     120
ggattacaga taactttcgt gaataccgac ttcatccata tcaatttcct ggaatctagt     180
ggccctcatt gtttggacgg agccccaggg tttagattcg aaacaattcc tgacggtgtt     240
tcacattccc cagaggcctc catcccaata agagagagtt tactgaggtc aatagaaacc     300
aactttttgg atcgtttcat tgacttggtc acaaaacttc cagacccacc aacttgcata     360
atctctgatg ctttctgtc agtgtttact atcgacgctg ccaaaaagtt gggtatccca     420
gttatgatgt actggactct tgctgcatgc ggtttcatgg gtttctatca catccattct     480
cttatcgaaa agggttttgc tccactgaaa gatgcatcat acttaaccaa cggctacctg     540
gatactgtta ttgactgggt accaggtatg gaaggtataa gacttaaaga tttttccttt     600
gattggtcta cagaccttaa tgataaagta ttgatgttta ctacagaagc tccacaaaga     660
tctcataagg tttcacatca tatctttcac acctttgatg aattggaacc atcaatcatc     720
aaaaccttgt ctctaagata caatcatatc tacactattg gtccattaca attacttcta     780
```

```
gatcaaattc ctgaagagaa aaagcaaact ggtattacat ccttacacgg ctactcttta      840
gtgaaagagg aaccagaatg ttttcaatgg ctacaaagta aagagcctaa ttctgtggtc      900
tacgtcaact tcggaagtac aacagtcatg tccttggaag atatgactga atttggttgg      960
ggccttgcta attcaaatca ttactttcta tggattatca ggtccaattt ggtaataggg     1020
gaaaacgccg tattacctcc agaattggag gaacacatca aaagagagg tttcattgct      1080 tcctggtgtt ctcaggaaaa ggtattgaaa catccttctg ttggtggttt ccttactcat     1140
tgcggttggg gctctacaat cgaatcacta agtgcaggag ttccaatgat tgttggcca      1200 tattcatggg accaacttac aaattgtagg tatatctgta aagagtggga agttggatta     1260
gaaatgggaa caaggttaa acgtgatgaa gtgaaaagat tggttcagga gttgatgggg     1320
gaaggtggcc acaagatgag aaacaaggcc aaagattgga aggaaaaagc cagaattgct     1380
attgctccta acgggtcatc ctctctaaac attgataaga tggtcaaaga gattacagtc     1440
ttagccagaa actaagtcga c                                               1461
```

```
<210> SEQ ID NO 83
<211> LENGTH: 1398
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 83
```

```
actagtaaaa tggcagagca acaaaagatc aaaaagtcac ctcacgtctt acttattcca       60
tttcctctgc aaggacatat caacccattc atacaatttg ggaaaagatt gattagtaag      120
ggtgtaaaga caacactggt aaccactatc cacactttga attctactct gaaccactca      180
aatactacta ctacaagtat agaaattcaa gctatatcag acggatgcga tgagggtggc      240
tttatgtctg ccggtgaatc ttacttggaa acattcaagc aagtgggatc caagtctctg      300
gccgatctaa tcaaaaagtt acagagtgaa ggcaccacaa ttgacgccat aatctacgat      360
tctatgacag agtgggtttt agacgttgct atcgaatttg gtattgatgg aggttccttt      420
ttcacacaag catgtgttgt gaattctcta tactaccatg tgcataaagg gttaatctct      480
ttaccattgg gtgaaactgt ttcagttcca ggttttccag tgttacaacg ttgggaaacc      540
ccattgatct tacaaaatca tgaacaaata caatcacctt ggtcccagat gttgtttggt      600
caattcgcta acatcgatca agcaagatgg gtctttacta attcattcta taagttagag      660
gaagaggtaa ttgaatggac taggaagatc tggaatttga agtcattgg tccaacattg      720 ccatcaatgt atttggacaa aagacttgat gatgataaag ataatggttt caatttgtac      780
aaggctaatc atcacgaatg tatgaattgg ctggatgaca aaccaaagga atcagttgta      840
tatgttgctt tcggctctct tgttaaacat ggtccagaac aagttgagga gattacaaga      900
gcacttatag actctgacgt aaacttttg tgggtcatta gcacaaaga ggagggggaaa      960 ctgccagaaa acctttctga agtgataaag accggaaaag gtctaatcgt tgcttggtgt     1020
aaacaattgg atgtttttagc tcatgaatct gtaggctgtt ttgtaacaca ttgcggattc     1080
aactctacac tagaagccat ttccttaggc gtacctgtcg ttgcaatgcc tcagttctcc     1140
gatcagacaa ccaacgctaa acttttggac gaaatactag gggtgggtgt cagagttaaa     1200
gcagacgaga atggtatcgt cagaagaggg aacctagctt catgtatcaa aatgatcatg     1260
gaagaggaaa gaggagttat cataaggaaa aacgcagtta agtggaagga tcttgcaaag     1320
```

```
gttgccgtcc atgaaggcgg ctcttcagat aatgatattg ttgaatttgt gtccgaacta   1380
atcaaagcct aagtcgac                                                1398
```

<210> SEQ ID NO 84
<211> LENGTH: 1437
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

```
actagtaaaa tggctacatc tgattctatt gttgatgaca ggaagcagtt gcatgtggct     60
actttccctt ggcttgcttt cggtcatata ctgccttacc tacaactatc aaaactgata   120
gctgaaaaag gacataaagt gtcattcctt caacaacta gaaacattca agattatct    180
tcccacatat caccattgat taacgtcgtt caattgacac ttccaagagt acaggaatta   240
ccagaagatg ctgaagctac aacagatgtg catcctgaag atatcccta cttgaaaaag   300
gcatccgatg gattacagcc tgaggtcact agattccttg agcaacacag tccagattgg   360
atcatatacg actacactca ctattggttg ccttcaattg cagcatcact aggcatttct   420
agggcacatt tcagtgtaac cacaccttgg gccattgctt acatgggtcc atccgctgat   480
gctatgatta acggcagtga tggtagaact accgttgaag atttgacaac cccaccaaag   540
tggtttccat ttccaactaa agtctgttgg agaaaacacg acttagcaag actggttcca   600
tacaaggcac caggaatctc agacggctat agaatgggtt tagtccttaa agggtctgac   660
tgcctattgt ctaagtgtta ccatgagttt gggacacaat ggctaccact tttggaaaca   720
ttacaccaag ttcctgtcgt accagttggt ctattacctc cagaaatccc tggtgatgag   780
aaggacgaga cttgggtttc aatcaaaaag tggttagacg ggaagcaaaa aggctcagtg   840
gtatatgtgg cactgggttc cgaagtttta gtatctcaaa cagaagttgt ggaacttgcc   900
ttaggttttgg aactatctgg attgccattt gtctgggcct acagaaaacc aaaaggccct   960
gcaaagtccg attcagttga attgccagac ggctttgtcg agagaactag agatagaggg   1020
ttggtatgga cttcatgggc tccacaattg agaatcctga gtcacgaatc tgtgtgcggt   1080
ttcctaacac attgtggttc tggttctata gttgaaggac tgatgtttgg tcatccactt   1140
atcatgttgc caatctttgg tgaccagcct ttgaatgcac gtctgttaga agataaacaa   1200
gttggaattg aaatcccacg taatgaggaa gatggatgtt taaccaagga gtctgtggcc   1260
agatcattac gttccgttgt cgttgaaaag gaaggcgaaa tctacaaggc caatgcccgt   1320
gaactttcaa agatctacaa tgacacaaaa gtagagaagg aatatgtttc tcaatttgta   1380
gattacctag agaaaaacgc tagagccgta gctattgatc atgaatccta agtcgac      1437
```

<210> SEQ ID NO 85
<211> LENGTH: 1392
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 85

```
actagtaaaa tggaaaacaa gaccgaaaca acagttagac gtaggcgtag aatcattctg    60
tttccagtac cttttcaagg gcacatcaat ccaatactaa aactagccaa cgttttgtac   120
tctaaaggtt tttctattac aatctttcac accaatttca caaaccaaa aacatccaat   180
```

```
tacccacatt tcacattcag attcatactt gataatgatc cacaagatga acgtatttca    240
aacttaccta cccacggtcc tttagctgga atgagaattc caatcatcaa tgaacatggt    300
gccgatgagc ttagaagaga attagagtta cttatgttgg catccgaaga ggacgaggaa    360
gtctcttgtc tgattactga cgctctatgg tactttgccc aatctgtggc tgatagtttg    420
aatttgagga gattggtact aatgacatcc agtctgttta actttcacgc tcatgttagt    480
ttaccacaat ttgacgaatt gggatacttg daccctgatg acaagactag gttagaggaa    540
caggcctctg gttttcctat gttgaaagtc aaagatatca agtctgccta ttctaattgg    600
caaatcttga agagatcttt aggaaagatg atcaaacaga caaaggcttc atctggagtg    660
atttggaaca gtttcaaaga gttagaagag tctgaattgg agactgtaat cagagaaatt    720
ccagcacctt cattcctgat accattacca aaacatttga ctgcttcctc ttcctctttg    780
ttggatcatg acagaacagt ttttcaatgg ttggaccaac aaccacctag ttctgttttg    840
tacgtgtcat ttggtagtac ttctgaagtc gatgaaaagg acttccttga aatcgcaaga    900
ggcttagtcg atagtaagca gtcattcctt tgggtcgtgc gtccaggttt cgtgaaaggc    960
tcaacatggg tcgaaccact tccagatggt tttctaggcg aaagaggtag aatagtcaaa    1020
tgggttcctc aacaggaagt tttagctcat ggcgctattg gggcattctg gactcattcc    1080
ggatggaatt caactttaga atcagtatgc gaaggggtac ctatgatctt ttcagatttt    1140
ggtcttgatc aaccactgaa cgcaagatac atgtctgatg ttttgaaagt gggtgtatat    1200
ctagaaaatg gctgggaaag gggtgaaata gctaatgcaa taagacgtgt tatggttgat    1260
gaagaggggg agtatatcag acaaaacgca agagtgctga agcaaaaggc cgacgtttct    1320
ctaatgaagg gaggctcttc atacgaatcc ttagaatctc ttgtttccta catttcatca    1380
ctgtaagtcg ac                                                        1392
```

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Thr Ser Phe Ala Glu Tyr Trp Asn Leu Leu Ser Pro
1               5                   10

<210> SEQ ID NO 87
<211> LENGTH: 1602
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 87

```
atgaccagct ttgccgagta ttggaatctg ttaagtccca cttcttttgc agaatattgg    60
aaccttctat caccgacgag tttcgcggag tactggaatt tgttttctcc aacatcgttc    120
gctgaatact ggaacttact cagccctgct agtaaaatgg atgcaatggc aactactgag    180
aaaaagcctc atgtgatctt cattccattt cctgcacaat ctcacataaa ggcaatgcta    240
aagttagcac aactattaca ccataaggga ttacagataa ctttcgtgaa taccgacttc    300
atccataatc aatttctgga atctagtggc cctcattgtt tggacggagc cccagggttt    360
```

```
agattcgaaa caattcctga cggtgtttca cattccccag aggcctccat cccaataaga      420
gagagtttac tgaggtcaat agaaaccaac tttttggatc gtttcattga cttggtcaca      480
aaacttccag acccaccaac ttgcataatc tctgatggct ttctgtcagt gtttactatc      540
gacgctgcca aaaagttggg tatcccagtt atgatgtact ggactcttgc tgcatgcggt      600
ttcatgggtt tctatcacat ccattctctt atcgaaaagg gttttgctcc actgaaagat      660
gcatcatact taaccaacgg ctacctggat actgttattg actgggtacc aggtatggaa      720
ggtataagac ttaaagattt tcctttggat tggtctacag accttaatga taaagtattg      780
atgtttacta cagaagctcc acaaagatct cataaggttt cacatcatat ctttcacacc      840
tttgatgaat tggaaccatc aatcatcaaa accttgtctc taagatacaa tcatatctac      900
actattggtc cattacaatt acttctagat caaattcctg aagagaaaaa gcaaactggt      960
attacatcct tacacggcta ctctttagtg aaagaggaac cagaatgttt tcaatggcta     1020
caaagtaaag agcctaattc tgtggtctac gtcaacttcg aagtacaaca agtcatgtcc     1080
ttggaagata tgactgaatt tggttggggc cttgctaatt caaatcatta ctttctatgg     1140
attatcaggt ccaatttggt aatagggaaa acgccgtat acctccaga attggaggaa      1200
cacatcaaaa agagaggttt cattgcttcc tggtgttctc aggaaaaggt attgaaacat     1260
ccttctgttg gtggtttcct tactcattgc ggttggggct ctacaatcga atcactaagt     1320
gcaggagttc caatgatttg ttggccatat tcatgggacc aacttacaaa ttgtaggtat     1380
atctgtaaag agtgggaagt tggattagaa atgggaacaa aggttaaacg tgatgaagtg     1440
aaaagattgg ttcaggagtt gatgggggaa ggtggccaca agatgagaaa caaggccaaa     1500
gattggaagg aaaaagccag aattgctatt gctcctaacg ggtcatcctc tctaaacatt     1560
gataagatgg tcaaagagat tacagtctta gccagaaact aa                         1602
```

<210> SEQ ID NO 88
<211> LENGTH: 533
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Met Thr Ser Phe Ala Glu Tyr Trp Asn Leu Leu Ser Pro Thr Ser Phe
1               5                   10                  15

Ala Glu Tyr Trp Asn Leu Leu Ser Pro Thr Ser Phe Ala Glu Tyr Trp
            20                  25                  30

Asn Leu Phe Ser Pro Thr Ser Phe Ala Glu Tyr Trp Asn Leu Leu Ser
        35                  40                  45

Pro Ala Ser Lys Met Asp Ala Met Ala Thr Thr Glu Lys Lys Pro His
    50                  55                  60

Val Ile Phe Ile Pro Phe Pro Ala Gln Ser His Ile Lys Ala Met Leu
65                  70                  75                  80

Lys Leu Ala Gln Leu Leu His His Lys Gly Leu Gln Ile Thr Phe Val
                85                  90                  95

Asn Thr Asp Phe Ile His Asn Gln Phe Leu Glu Ser Ser Gly Pro His
                100                 105                 110

Cys Leu Asp Gly Ala Pro Gly Phe Arg Phe Glu Thr Ile Pro Asp Gly
            115                 120                 125

Val Ser His Ser Pro Glu Ala Ser Ile Pro Ile Arg Glu Ser Leu Leu
```

```
            130                 135                 140
Arg Ser Ile Glu Thr Asn Phe Leu Asp Arg Phe Ile Asp Leu Val Thr
145                 150                 155                 160

Lys Leu Pro Asp Pro Thr Cys Ile Ile Ser Asp Gly Phe Leu Ser
                165                 170                 175

Val Phe Thr Ile Asp Ala Ala Lys Lys Leu Gly Ile Pro Val Met Met
            180                 185                 190

Tyr Trp Thr Leu Ala Ala Cys Gly Phe Met Gly Phe Tyr His Ile His
                195                 200                 205

Ser Leu Ile Glu Lys Gly Phe Ala Pro Leu Lys Asp Ala Ser Tyr Leu
            210                 215                 220

Thr Asn Gly Tyr Leu Asp Thr Val Ile Asp Trp Val Pro Gly Met Glu
225                 230                 235                 240

Gly Ile Arg Leu Lys Asp Phe Pro Leu Asp Trp Ser Thr Asp Leu Asn
                245                 250                 255

Asp Lys Val Leu Met Phe Thr Thr Glu Ala Pro Gln Arg Ser His Lys
            260                 265                 270

Val Ser His His Ile Phe His Thr Phe Asp Glu Leu Glu Pro Ser Ile
            275                 280                 285

Ile Lys Thr Leu Ser Leu Arg Tyr Asn His Ile Tyr Thr Ile Gly Pro
            290                 295                 300

Leu Gln Leu Leu Leu Asp Gln Ile Pro Glu Glu Lys Lys Gln Thr Gly
305                 310                 315                 320

Ile Thr Ser Leu His Gly Tyr Ser Leu Val Lys Glu Glu Pro Glu Cys
                325                 330                 335

Phe Gln Trp Leu Gln Ser Lys Glu Pro Asn Ser Val Val Tyr Val Asn
            340                 345                 350

Phe Gly Ser Thr Thr Val Met Ser Leu Glu Asp Met Thr Glu Phe Gly
                355                 360                 365

Trp Gly Leu Ala Asn Ser Asn His Tyr Phe Leu Trp Ile Ile Arg Ser
            370                 375                 380

Asn Leu Val Ile Gly Glu Asn Ala Val Leu Pro Pro Glu Leu Glu Glu
385                 390                 395                 400

His Ile Lys Lys Arg Gly Phe Ile Ala Ser Trp Cys Ser Gln Glu Lys
                405                 410                 415

Val Leu Lys His Pro Ser Val Gly Gly Phe Leu Thr His Cys Gly Trp
            420                 425                 430

Gly Ser Thr Ile Glu Ser Leu Ser Ala Gly Val Pro Met Ile Cys Trp
            435                 440                 445

Pro Tyr Ser Trp Asp Gln Leu Thr Asn Cys Arg Tyr Ile Cys Lys Glu
450                 455                 460

Trp Glu Val Gly Leu Glu Met Gly Thr Lys Val Lys Arg Asp Glu Val
465                 470                 475                 480

Lys Arg Leu Val Gln Glu Leu Met Gly Glu Gly Gly His Lys Met Arg
                485                 490                 495

Asn Lys Ala Lys Asp Trp Lys Glu Lys Ala Arg Ile Ala Ile Ala Pro
            500                 505                 510

Asn Gly Ser Ser Ser Leu Asn Ile Asp Lys Met Val Lys Glu Ile Thr
            515                 520                 525

Val Leu Ala Arg Asn
            530

<210> SEQ ID NO 89
```

<211> LENGTH: 1893
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

| | |
|---|---:|
| atgtgcaata ccaacatgtc tgtacctact gatggtgctg taaccacctc acagattcca | 60 |
| gcttcggaac aagagaccct ggttagacca aagccattgc ttttgaagtt attaaagtct | 120 |
| gttggtgcac aaaaagacac ttatactatg aaagaggttc ttttttatct tggccagtat | 180 |
| attatgacta acgattata tgatgagaag caacaacata ttgtatattg ttcaaatgat | 240 |
| cttctaggag atttgtttgg cgtgccaagc ttctctgtga agagcacag gaaaatatat | 300 |
| accatgatct acaggaactt ggtagtagtc aatcagcagg aatcatcgga ctcaggtaca | 360 |
| tctgtgagtg agaacaggtg tcaccttgaa ggtgggagtg atcaaaagga ccttgtacaa | 420 |
| gagcttcagg aagagaaacc ttcatcttca catttggttt ctagaccatc taccggtggt | 480 |
| agcggatcct ctggaggcag tgctagtaaa atggcagagc aacaaaagat caaaaagtca | 540 |
| cctcacgtct tacttattcc atttcctctg caaggacata tcaacccatt catacaattt | 600 |
| gggaaaagat tgattagtaa gggtgtaaag acaacactgg taaccactat ccacactttg | 660 |
| aattctactc tgaaccactc aaatactact actacaagta tagaaattca agctatatca | 720 |
| gacggatgcg atgagggtgg ctttatgtct gccggtgaat cttacttgga aacattcaag | 780 |
| caagtgggat ccaagtctct ggccgatcta atcaaaaagt tacagagtga aggcaccaca | 840 |
| attgacgcca taatctacga ttctatgaca gagtgggttt tagacgttgc tatcgaattt | 900 |
| ggtattgatg gaggttcctt tttcacacaa gcatgtgttg tgaattctct atactaccat | 960 |
| gtgcataaag ggttaatctc tttaccattg ggtgaaactg tttcagttcc aggttttcca | 1020 |
| gtgttacaac gttgggaaac cccattgatc ttacaaaatc atgaacaaat acaatcacct | 1080 |
| tggtcccaga tgttgtttgg tcaattcgct aacatcgatc aagcaagatg ggtctttact | 1140 |
| aattcattct ataagttaga ggaagaggta attgaatgga ctaggaagat ctggaatttg | 1200 |
| aaagtcattg gtccaacatt gccatcaatg tatttggaca aaagacttga tgatgataaa | 1260 |
| gataatggtt tcaatttgta caaggctaat catcacgaat gtatgaattg ctggatgac | 1320 |
| aaaccaaagg aatcagttgt atatgttgct ttcggctctc ttgttaaaca tggtccagaa | 1380 |
| caagttgagg agattacaag agcacttata gactctgacg taaacttttt gtgggtcatt | 1440 |
| aagcacaaag aggagggaa actgccagaa aacctttctg aagtgataaa gaccggaaaa | 1500 |
| ggtctaatcg ttgcttggtg taaacaattg gatgtttag ctcatgaatc tgtaggctgt | 1560 |
| tttgtaacac attgcggatt caactctaca ctagaagcca tttccttagg cgtacctgtc | 1620 |
| gttgcaatgc ctcagttctc cgatcagaca accaacgcta aacttttgga cgaaatacta | 1680 |
| ggggtgggtg tcagagttaa agcagacgag aatggtatcg tcagaagagg gaacctagct | 1740 |
| tcatgtatca aaatgatcat ggaagaggaa agaggagtta tcataaggaa aaacgcagtt | 1800 |
| aagtggaagg atcttgcaaa ggttgccgtc catgaaggcg gctcttcaga taatgatatt | 1860 |
| gttgaatttg tgtccgaact aatcaaagcc taa | 1893 |

<210> SEQ ID NO 90
<211> LENGTH: 630
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 90

| | | | | | | | | | | | | | | |
|---|---|---|---|---|---|---|---|---|---|---|---|---|---|---|
| Met | Cys | Asn | Thr | Asn | Met | Ser | Val | Pro | Thr | Asp | Gly | Ala | Val | Thr | Thr |
| 1 | | | | 5 | | | | | 10 | | | | | 15 | |
| Ser | Gln | Ile | Pro | Ala | Ser | Glu | Gln | Glu | Thr | Leu | Val | Arg | Pro | Lys | Pro |
| | | | 20 | | | | | 25 | | | | | 30 | | |
| Leu | Leu | Leu | Lys | Leu | Leu | Lys | Ser | Val | Gly | Ala | Gln | Lys | Asp | Thr | Tyr |
| | | 35 | | | | | 40 | | | | | 45 | | | |
| Thr | Met | Lys | Glu | Val | Leu | Phe | Tyr | Leu | Gly | Gln | Tyr | Ile | Met | Thr | Lys |
| | 50 | | | | | 55 | | | | | 60 | | | | |
| Arg | Leu | Tyr | Asp | Glu | Lys | Gln | Gln | His | Ile | Val | Tyr | Cys | Ser | Asn | Asp |
| 65 | | | | | 70 | | | | | 75 | | | | | 80 |
| Leu | Leu | Gly | Asp | Leu | Phe | Gly | Val | Pro | Ser | Phe | Ser | Val | Lys | Glu | His |
| | | | | 85 | | | | | 90 | | | | | 95 | |
| Arg | Lys | Ile | Tyr | Thr | Met | Ile | Tyr | Arg | Asn | Leu | Val | Val | Val | Asn | Gln |
| | | | 100 | | | | | 105 | | | | | 110 | | |
| Gln | Glu | Ser | Ser | Asp | Ser | Gly | Thr | Ser | Val | Ser | Glu | Asn | Arg | Cys | His |
| | | 115 | | | | | 120 | | | | | 125 | | | |
| Leu | Glu | Gly | Gly | Ser | Asp | Gln | Lys | Asp | Leu | Val | Gln | Glu | Leu | Gln | Glu |
| | 130 | | | | | 135 | | | | | 140 | | | | |
| Glu | Lys | Pro | Ser | Ser | His | Leu | Val | Ser | Arg | Pro | Ser | Thr | Gly | Gly | |
| 145 | | | | | 150 | | | | | 155 | | | | | 160 |
| Ser | Gly | Ser | Ser | Gly | Gly | Ser | Ala | Ser | Lys | Met | Ala | Glu | Gln | Gln | Lys |
| | | | | 165 | | | | | 170 | | | | | 175 | |
| Ile | Lys | Lys | Ser | Pro | His | Val | Leu | Leu | Ile | Pro | Phe | Pro | Leu | Gln | Gly |
| | | | 180 | | | | | 185 | | | | | 190 | | |
| His | Ile | Asn | Pro | Phe | Ile | Gln | Phe | Gly | Lys | Arg | Leu | Ile | Ser | Lys | Gly |
| | | | 195 | | | | | 200 | | | | | 205 | | |
| Val | Lys | Thr | Thr | Leu | Val | Thr | Thr | Ile | His | Thr | Leu | Asn | Ser | Thr | Leu |
| | 210 | | | | | 215 | | | | | 220 | | | | |
| Asn | His | Ser | Asn | Thr | Thr | Thr | Ser | Ile | Glu | Ile | Gln | Ala | Ile | Ser | |
| 225 | | | | | 230 | | | | | 235 | | | | | 240 |
| Asp | Gly | Cys | Asp | Glu | Gly | Gly | Phe | Met | Ser | Ala | Gly | Glu | Ser | Tyr | Leu |
| | | | | 245 | | | | | 250 | | | | | 255 | |
| Glu | Thr | Phe | Lys | Gln | Val | Gly | Ser | Lys | Ser | Leu | Ala | Asp | Leu | Ile | Lys |
| | | | 260 | | | | | 265 | | | | | 270 | | |
| Lys | Leu | Gln | Ser | Glu | Gly | Thr | Thr | Ile | Asp | Ala | Ile | Ile | Tyr | Asp | Ser |
| | | 275 | | | | | 280 | | | | | 285 | | | |
| Met | Thr | Glu | Trp | Val | Leu | Asp | Val | Ala | Ile | Glu | Phe | Gly | Ile | Asp | Gly |
| | 290 | | | | | 295 | | | | | 300 | | | | |
| Gly | Ser | Phe | Phe | Thr | Gln | Ala | Cys | Val | Val | Asn | Ser | Leu | Tyr | Tyr | His |
| 305 | | | | | 310 | | | | | 315 | | | | | 320 |
| Val | His | Lys | Gly | Leu | Ile | Ser | Leu | Pro | Leu | Gly | Glu | Thr | Val | Ser | Val |
| | | | | 325 | | | | | 330 | | | | | 335 | |
| Pro | Gly | Phe | Pro | Val | Leu | Gln | Arg | Trp | Glu | Thr | Pro | Leu | Ile | Leu | Gln |
| | | | 340 | | | | | 345 | | | | | 350 | | |
| Asn | His | Glu | Gln | Ile | Gln | Ser | Pro | Trp | Ser | Gln | Met | Leu | Phe | Gly | Gln |
| | | 355 | | | | | 360 | | | | | 365 | | | |
| Phe | Ala | Asn | Ile | Asp | Gln | Ala | Arg | Trp | Val | Phe | Thr | Asn | Ser | Phe | Tyr |
| | 370 | | | | | 375 | | | | | 380 | | | | |
| Lys | Leu | Glu | Glu | Glu | Val | Ile | Glu | Trp | Thr | Arg | Lys | Ile | Trp | Asn | Leu |
| 385 | | | | | 390 | | | | | 395 | | | | | 400 |

Lys Val Ile Gly Pro Thr Leu Pro Ser Met Tyr Leu Asp Lys Arg Leu
                405                 410                 415
Asp Asp Asp Lys Asp Asn Gly Phe Asn Leu Tyr Lys Ala Asn His His
            420                 425                 430
Glu Cys Met Asn Trp Leu Asp Asp Lys Pro Lys Glu Ser Val Val Tyr
        435                 440                 445
Val Ala Phe Gly Ser Leu Val Lys His Gly Pro Glu Gln Val Glu Glu
    450                 455                 460
Ile Thr Arg Ala Leu Ile Asp Ser Asp Val Asn Phe Leu Trp Val Ile
465                 470                 475                 480
Lys His Lys Glu Glu Gly Lys Leu Pro Glu Asn Leu Ser Glu Val Ile
                485                 490                 495
Lys Thr Gly Lys Gly Leu Ile Val Ala Trp Cys Lys Gln Leu Asp Val
            500                 505                 510
Leu Ala His Glu Ser Val Gly Cys Phe Val Thr His Cys Gly Phe Asn
        515                 520                 525
Ser Thr Leu Glu Ala Ile Ser Leu Gly Val Pro Val Val Ala Met Pro
    530                 535                 540
Gln Phe Ser Asp Gln Thr Thr Asn Ala Lys Leu Leu Asp Glu Ile Leu
545                 550                 555                 560
Gly Val Gly Val Arg Val Lys Ala Asp Glu Asn Gly Ile Val Arg Arg
                565                 570                 575
Gly Asn Leu Ala Ser Cys Ile Lys Met Ile Met Glu Glu Arg Gly
            580                 585                 590
Val Ile Ile Arg Lys Asn Ala Val Lys Trp Lys Asp Leu Ala Lys Val
        595                 600                 605
Ala Val His Glu Gly Gly Ser Ser Asp Asn Asp Ile Val Glu Phe Val
    610                 615                 620
Ser Glu Leu Ile Lys Ala
625                 630

<210> SEQ ID NO 91
<211> LENGTH: 1932
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91
atgtgcaata ccaacatgtc tgtacctact gatggtgctg taaccacctc acagattcca      60
gcttcggaac aagagaccct ggttagacca aagccattgc ttttgaagtt attaaagtct     120
gttggtgcac aaaaagacac ttatactatg aaagaggttc ttttttatct tggccagtat     180
attatgacta acgattata tgatgagaag caacaacata ttgtatattg ttcaaatgat     240
cttctaggag atttgtttgg cgtgccaagc ttctctgtga agagcacag gaaaatatat     300 accatgatct acaggaactt ggtagtagtc aatcagcagg aatcatcgga ctcaggtaca     360
tctgtgagtg agaacaggtg tcaccttgaa ggtgggagtg atcaaaagga ccttgtacaa     420
gagcttcagg aagagaaacc ttcatcttca catttggttt ctagaccatc taccggtggt     480
agcggatcct ctggaggcag tgctagtaaa atggctacat ctgattctat tgttgatgac     540
aggaagcagt tgcatgtggc tactttccct tggcttgctt tcggtcatat actgccttac     600
ctacaactat caaaactgat agctgaaaaa ggacataaag tgtcattcct ttcaacaact     660

```
agaaacattc aaagattatc ttcccacata tcaccattga ttaacgtcgt tcaattgaca    720
cttccaagag tacaggaatt accagaagat gctgaagcta aacagatgt gcatcctgaa    780
gatatcccctt acttgaaaaa ggcatccgat ggattacagc ctgaggtcac tagattcctt    840
gagcaacaca gtccagattg gatcatatac gactacactc actattggtt gccttcaatt    900
gcagcatcac taggcatttc tagggcacat tcagtgtaa ccacaccttg ggccattgct    960
tacatgggtc catccgctga tgctatgatt aacggcagtg atggtagaac taccgttgaa   1020
gatttgacaa ccccaccaaa gtggtttcca tttccaacta aagtctgttg agaaaacac    1080
gacttagcaa gactggttcc atacaaggca ccaggaatct cagacggcta tagaatgggt   1140
ttagtcctta aagggtctga ctgcctattg tctaagtgtt accatgagtt tgggacacaa   1200
tggctaccac tttttggaaac attacaccaa gttcctgtcg taccagttgg tctattacct   1260
ccagaaatcc ctggtgatga aaggacgag acttgggttt caatcaaaaa gtggttagac   1320
gggaagcaaa aaggctcagt ggtatatgtg gcactgggtt ccgaagtttt agtatctcaa   1380
acagaagttg tggaacttgc cttaggtttg aactatctg gattgccatt tgtctgggcc   1440
tacagaaaac caaaaggccc tgcaaagtcc gattcagttg aattgccaga cggctttgtc   1500
gagagaacta gagatagagg gttggtatgg acttcatggg ctccacaatt gagaatcctg   1560
agtcacgaat ctgtgtgcgg tttcctaaca cattgtggtt ctggttctat agttgaagga   1620
ctgatgtttg gtcatccact tatcatgttg ccaatctttg gtgaccagcc tttgaatgca   1680
cgtctgttag aagataaaca agttggaatt gaaatcccac gtaatgagga agatggatgt   1740
ttaaccaagg agtctgtggc cagatcatta cgttccgttg tcgttgaaaa ggaaggcgaa   1800
atctacaagg ccaatgcccg tgaactttca aagatctaca atgacacaaa agtagagaag   1860
gaatatgttt ctcaatttgt agattaccta gagaaaaacg ctagagccgt agctattgat   1920
catgaatcct aa                                                       1932
```

<210> SEQ ID NO 92
<211> LENGTH: 643
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

```
Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Val Leu Phe Tyr Leu Gly Gln Tyr Ile Met Thr Lys
    50                  55                  60

Arg Leu Tyr Asp Glu Lys Gln Gln His Ile Val Tyr Cys Ser Asn Asp
65                  70                  75                  80

Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
        115                 120                 125
```

```
Leu Glu Gly Gly Ser Asp Gln Lys Asp Leu Val Gln Glu Leu Gln Glu
    130                 135                 140

Glu Lys Pro Ser Ser His Leu Val Ser Arg Pro Ser Thr Gly Gly
145                 150                 155                 160

Ser Gly Ser Ser Gly Gly Ser Ala Ser Lys Met Ala Thr Ser Asp Ser
                165                 170                 175

Ile Val Asp Asp Arg Lys Gln Leu His Val Ala Thr Phe Pro Trp Leu
                180                 185                 190

Ala Phe Gly His Ile Leu Pro Tyr Leu Gln Leu Ser Lys Leu Ile Ala
                195                 200                 205

Glu Lys Gly His Lys Val Ser Phe Leu Ser Thr Thr Arg Asn Ile Gln
    210                 215                 220

Arg Leu Ser Ser His Ile Ser Pro Leu Ile Asn Val Val Gln Leu Thr
225                 230                 235                 240

Leu Pro Arg Val Gln Glu Leu Pro Glu Asp Ala Glu Ala Thr Thr Asp
                245                 250                 255

Val His Pro Glu Asp Ile Pro Tyr Leu Lys Lys Ala Ser Asp Gly Leu
                260                 265                 270

Gln Pro Glu Val Thr Arg Phe Leu Glu Gln His Ser Pro Asp Trp Ile
    275                 280                 285

Ile Tyr Asp Tyr Thr His Tyr Trp Leu Pro Ser Ile Ala Ala Ser Leu
    290                 295                 300

Gly Ile Ser Arg Ala His Phe Ser Val Thr Thr Pro Trp Ala Ile Ala
305                 310                 315                 320

Tyr Met Gly Pro Ser Ala Asp Ala Met Ile Asn Gly Ser Asp Gly Arg
                325                 330                 335

Thr Thr Val Glu Asp Leu Thr Thr Pro Pro Lys Trp Phe Pro Phe Pro
                340                 345                 350

Thr Lys Val Cys Trp Arg Lys His Asp Leu Ala Arg Leu Val Pro Tyr
                355                 360                 365

Lys Ala Pro Gly Ile Ser Asp Gly Tyr Arg Met Gly Leu Val Leu Lys
    370                 375                 380

Gly Ser Asp Cys Leu Leu Ser Lys Cys Tyr His Glu Phe Gly Thr Gln
385                 390                 395                 400

Trp Leu Pro Leu Leu Glu Thr Leu His Gln Val Pro Val Val Pro Val
                405                 410                 415

Gly Leu Leu Pro Pro Glu Ile Pro Gly Asp Glu Lys Asp Glu Thr Trp
                420                 425                 430

Val Ser Ile Lys Lys Trp Leu Asp Gly Lys Gln Lys Gly Ser Val Val
                435                 440                 445

Tyr Val Ala Leu Gly Ser Glu Val Leu Val Ser Gln Thr Glu Val Val
    450                 455                 460

Glu Leu Ala Leu Gly Leu Glu Leu Ser Gly Leu Pro Phe Val Trp Ala
465                 470                 475                 480

Tyr Arg Lys Pro Lys Gly Pro Ala Lys Ser Asp Ser Val Glu Leu Pro
                485                 490                 495

Asp Gly Phe Val Glu Arg Thr Arg Asp Arg Gly Leu Val Trp Thr Ser
                500                 505                 510

Trp Ala Pro Gln Leu Arg Ile Leu Ser His Glu Ser Val Cys Gly Phe
    515                 520                 525

Leu Thr His Cys Gly Ser Gly Ser Ile Val Glu Gly Leu Met Phe Gly
    530                 535                 540

His Pro Leu Ile Met Leu Pro Ile Phe Gly Asp Gln Pro Leu Asn Ala
```

```
                545                  550                  555                  560
Arg Leu Leu Glu Asp Lys Gln Val Gly Ile Glu Ile Pro Arg Asn Glu
                    565                  570                  575

Glu Asp Gly Cys Leu Thr Lys Glu Ser Val Ala Arg Ser Leu Arg Ser
                580                  585                  590

Val Val Val Glu Lys Glu Gly Glu Ile Tyr Lys Ala Asn Ala Arg Glu
            595                  600                  605

Leu Ser Lys Ile Tyr Asn Asp Thr Lys Val Glu Lys Glu Tyr Val Ser
        610                  615                  620

Gln Phe Val Asp Tyr Leu Glu Lys Asn Ala Arg Ala Val Ala Ile Asp
625                  630                  635                  640

His Glu Ser

<210> SEQ ID NO 93
<211> LENGTH: 1887
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93
atgtgcaata ccaacatgtc tgtacctact gatggtgctg taaccacctc acagattcca      60
gcttcggaac aagagaccct ggttagacca agccattgc ttttgaagtt attaaagtct      120
gttggtgcac aaaaagacac ttatactatg aaagaggttc ttttttatct tggccagtat      180
attatgacta acgattata tgatgagaag caacaacata ttgtatattg ttcaaatgat      240
cttctaggag atttgtttgg cgtgccaagc ttctctgtga agagcacag gaaaatatat      300 accatgatct acaggaactt ggtagtagtc aatcagcagg aatcatcgga ctcaggtaca      360
tctgtgagtg agaacaggtg tcaccttgaa ggtgggagtg atcaaaagga ccttgtacaa      420
gagcttcagg aagagaaacc ttcatcttca catttggttt ctagaccatc taccggtggt      480
agcggatcct ctggaggcag tgctagtaaa atggaaaaca agaccgaaac aacagttaga      540
cgtaggcgta gaatcattct gtttccagta ccttttcaag ggcacatcaa tccaatacta      600
caactagcca acgttttgta ctctaaaggt ttttctatta caatctttca caccaatttc      660
aacaaaccaa aaacatccaa ttacccacat ttcacattca gattcatact tgataatgat      720
ccacaagatg aacgtatttc aaacttacct acccacggtc ctttagctgg aatgagaatt      780
ccaatcatca tgaacatgg tgccgatgag cttagaagag aattagagtt acttatgttg      840
gcatccgaag aggacgagga agtctcttgt ctgattactg acgctctatg gtactttgcc      900
caatctgtgg ctgatagttt gaatttgagg agattggtac taatgacatc cagtctgttt      960
aactttcacg ctcatgttag tttaccacaa tttgacgaat gggatactt ggaccctgat     1020 gacaagacta ggttagagga acaggcctct ggttttccta tgttgaaagt caaagatatc     1080
aagtctgcct attctaattg gcaaatcttg aaagagatct taggaaagat gatcaaacag     1140
acaaaggctt catctggagt gatttggaac agtttcaaag agttagaaga gtctgaattg     1200
gagactgtaa tcagagaaat tccagcacct tcattcctga taccattacc aaaacatttg     1260
actgcttcct cttcctcttt gttggatcat gacagaacag ttttcaatg gttggaccaa     1320 caaccaccta gttctgtttt gtacgtgtca tttggtagta cttctgaagt cgatgaaaag     1380
gacttccttg aaatcgcaag aggcttagtc gatagtaagc agtcattcct ttgggtcgtg     1440
cgtccaggtt tcgtgaaagg ctcaacatgg gtcgaaccac ttccagatgg ttttctaggc     1500
```

```
gaaagaggta gaatagtcaa atgggttcct caacaggaag ttttagctca tggcgctatt    1560
ggggcattct ggactcattc cggatggaat tcaactttag aatcagtatg cgaaggggta    1620
cctatgatct tttcagattt tggtcttgat caaccactga acgcaagata catgtctgat    1680
gttttgaaag tgggtgtata tctagaaaat ggctgggaaa ggggtgaaat agctaatgca    1740
ataagacgtg ttatggttga tgaagagggg gagtatatca gacaaaacgc aagagtgctg    1800
aagcaaaagg ccgacgtttc tctaatgaag ggaggctctt catacgaatc cttagaatct    1860
cttgtttcct acatttcatc actgtaa                                        1887
```

<210> SEQ ID NO 94
<211> LENGTH: 628
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

```
Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Val Leu Phe Tyr Leu Gly Gln Tyr Ile Met Thr Lys
    50                  55                  60

Arg Leu Tyr Asp Glu Lys Gln Gln His Ile Val Tyr Cys Ser Asn Asp
65                  70                  75                  80

Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
        115                 120                 125

Leu Glu Gly Gly Ser Asp Gln Lys Asp Leu Val Gln Glu Leu Gln Glu
    130                 135                 140

Glu Lys Pro Ser Ser Ser His Leu Val Ser Arg Pro Ser Thr Gly Gly
145                 150                 155                 160

Ser Gly Ser Ser Gly Gly Ser Ala Ser Lys Met Glu Asn Lys Thr Glu
                165                 170                 175

Thr Thr Val Arg Arg Arg Arg Ile Ile Leu Phe Pro Val Pro Phe
            180                 185                 190

Gln Gly His Ile Asn Pro Ile Leu Gln Leu Ala Asn Val Leu Tyr Ser
        195                 200                 205

Lys Gly Phe Ser Ile Thr Ile Phe His Thr Asn Phe Asn Lys Pro Lys
    210                 215                 220

Thr Ser Asn Tyr Pro His Phe Thr Phe Arg Phe Ile Leu Asp Asn Asp
225                 230                 235                 240

Pro Gln Asp Glu Arg Ile Ser Asn Leu Pro Thr His Gly Pro Leu Ala
                245                 250                 255

Gly Met Arg Ile Pro Ile Ile Asn Glu His Gly Ala Asp Glu Leu Arg
            260                 265                 270

Arg Glu Leu Glu Leu Leu Met Leu Ala Ser Glu Glu Asp Glu Glu Val
        275                 280                 285
```

Ser Cys Leu Ile Thr Asp Ala Leu Trp Tyr Phe Ala Gln Ser Val Ala
    290                 295                 300

Asp Ser Leu Asn Leu Arg Arg Leu Val Leu Met Thr Ser Ser Leu Phe
305                 310                 315                 320

Asn Phe His Ala His Val Ser Leu Pro Gln Phe Asp Glu Leu Gly Tyr
                325                 330                 335

Leu Asp Pro Asp Asp Lys Thr Arg Leu Glu Glu Gln Ala Ser Gly Phe
            340                 345                 350

Pro Met Leu Lys Val Lys Asp Ile Lys Ser Ala Tyr Ser Asn Trp Gln
        355                 360                 365

Ile Leu Lys Glu Ile Leu Gly Lys Met Ile Lys Gln Thr Lys Ala Ser
    370                 375                 380

Ser Gly Val Ile Trp Asn Ser Phe Lys Glu Leu Glu Glu Ser Glu Leu
385                 390                 395                 400

Glu Thr Val Ile Arg Glu Ile Pro Ala Pro Ser Phe Leu Ile Pro Leu
                405                 410                 415

Pro Lys His Leu Thr Ala Ser Ser Ser Leu Leu Asp His Asp Arg
            420                 425                 430

Thr Val Phe Gln Trp Leu Asp Gln Gln Pro Pro Ser Ser Val Leu Tyr
        435                 440                 445

Val Ser Phe Gly Ser Thr Ser Glu Val Asp Glu Lys Asp Phe Leu Glu
    450                 455                 460

Ile Ala Arg Gly Leu Val Asp Ser Lys Gln Ser Phe Leu Trp Val Val
465                 470                 475                 480

Arg Pro Gly Phe Val Lys Gly Ser Thr Trp Val Glu Pro Leu Pro Asp
                485                 490                 495

Gly Phe Leu Gly Glu Arg Gly Arg Ile Val Lys Trp Val Pro Gln Gln
            500                 505                 510

Glu Val Leu Ala His Gly Ala Ile Gly Ala Phe Trp Thr His Ser Gly
        515                 520                 525

Trp Asn Ser Thr Leu Glu Ser Val Cys Glu Gly Val Pro Met Ile Phe
    530                 535                 540

Ser Asp Phe Gly Leu Asp Gln Pro Leu Asn Ala Arg Tyr Met Ser Asp
545                 550                 555                 560

Val Leu Lys Val Gly Val Tyr Leu Glu Asn Gly Trp Glu Arg Gly Glu
                565                 570                 575

Ile Ala Asn Ala Ile Arg Arg Val Met Val Asp Glu Glu Gly Glu Tyr
            580                 585                 590

Ile Arg Gln Asn Ala Arg Val Leu Lys Gln Lys Ala Asp Val Ser Leu
        595                 600                 605

Met Lys Gly Gly Ser Ser Tyr Glu Ser Leu Glu Ser Leu Val Ser Tyr
    610                 615                 620

Ile Ser Ser Leu
625

<210> SEQ ID NO 95
<211> LENGTH: 473
<212> TYPE: PRT
<213> ORGANISM: Stevia rebaudiana

<400> SEQUENCE: 95

Met Ala Thr Ser Asp Ser Ile Val Asp Asp Arg Lys Gln Leu His Val
1               5                   10                  15

Ala Thr Phe Pro Trp Leu Ala Phe Gly His Ile Leu Pro Tyr Leu Gln

```
                20                  25                  30
Leu Ser Lys Leu Ile Ala Glu Lys Gly His Lys Val Ser Phe Leu Ser
            35                  40                  45
Thr Thr Arg Asn Ile Gln Arg Leu Ser Ser His Ile Ser Pro Leu Ile
        50                  55                  60
Asn Val Val Gln Leu Thr Leu Pro Arg Val Gln Glu Leu Pro Glu Asp
65                  70                  75                  80
Ala Glu Ala Thr Thr Asp Val His Pro Glu Asp Ile Pro Tyr Leu Lys
                85                  90                  95
Lys Ala Ser Asp Gly Leu Gln Pro Glu Val Thr Arg Phe Leu Glu Gln
            100                 105                 110
His Ser Pro Asp Trp Ile Ile Tyr Asp Tyr Thr His Tyr Trp Leu Pro
        115                 120                 125
Ser Ile Ala Ala Ser Leu Gly Ile Ser Arg Ala His Phe Ser Val Thr
    130                 135                 140
Thr Pro Trp Ala Ile Ala Tyr Met Gly Pro Ser Ala Asp Ala Met Ile
145                 150                 155                 160
Asn Gly Ser Asp Gly Arg Thr Thr Val Glu Asp Leu Thr Thr Pro Pro
                165                 170                 175
Lys Trp Phe Pro Phe Pro Thr Lys Val Cys Trp Arg Lys His Asp Leu
            180                 185                 190
Ala Arg Leu Val Pro Tyr Lys Ala Pro Gly Ile Ser Asp Arg Cys Arg
        195                 200                 205
Met Gly Leu Val Leu Lys Gly Ser Asp Cys Leu Leu Ser Lys Cys Tyr
    210                 215                 220
His Glu Phe Gly Thr Gln Trp Leu Pro Leu Leu Glu Thr Leu His Gln
225                 230                 235                 240
Val Pro Val Val Pro Val Gly Leu Leu Pro Pro Glu Ile Pro Gly Asp
                245                 250                 255
Glu Lys Asp Glu Thr Trp Val Ser Ile Lys Lys Trp Leu Asp Gly Lys
            260                 265                 270
Gln Lys Gly Ser Val Val Tyr Val Ala Leu Gly Ser Glu Val Leu Val
        275                 280                 285
Ser Gln Thr Glu Val Val Glu Leu Ala Leu Gly Leu Glu Leu Ser Gly
    290                 295                 300
Leu Pro Phe Val Trp Ala Tyr Arg Lys Pro Lys Gly Pro Ala Lys Ser
305                 310                 315                 320
Asp Ser Val Glu Leu Pro Asp Gly Phe Val Glu Arg Thr Arg Asp Arg
                325                 330                 335
Gly Leu Val Trp Thr Ser Arg Ala Pro Gln Leu Arg Ile Leu Ser His
            340                 345                 350
Glu Ser Val Cys Gly Phe Leu Thr His Cys Gly Ser Gly Ser Ile Val
        355                 360                 365
Glu Gly Leu Met Phe Gly His Pro Leu Ile Met Leu Pro Ile Phe Gly
    370                 375                 380
Asp Gln Pro Leu Asn Ala Arg Leu Leu Glu Asp Lys Gln Val Gly Ile
385                 390                 395                 400
Glu Ile Pro Arg Asn Glu Glu Asp Gly Cys Leu Thr Lys Glu Ser Val
                405                 410                 415
Ala Arg Ser Leu Arg Ser Val Val Glu Lys Glu Gly Glu Ile Tyr
            420                 425                 430
Lys Ala Asn Ala Arg Glu Leu Ser Lys Ile Tyr Asn Asp Thr Lys Val
        435                 440                 445
```

```
Glu Lys Glu Tyr Val Ser Gln Phe Val Asp Tyr Leu Glu Lys Asn Ala
    450                 455                 460

Arg Ala Val Ala Ile Asp His Glu Ser
465                 470
```

<210> SEQ ID NO 96
<211> LENGTH: 1422
<212> TYPE: DNA
<213> ORGANISM: Stevia rebaudiana

<400> SEQUENCE: 96

| | | | | | |
|---|---|---|---|---|---|
| atggctacca | gtgactccat | agttgacgac | cgtaagcagc | ttcatgttgc | gacgttccca | 60 |
| tggcttgctt | tcggtcacat | cctcccttac | cttcagcttt | cgaaattgat | agctgaaaag | 120 |
| ggtcacaaag | tctcgtttct | ttctaccacc | agaaacattc | aacgtctctc | ttctcatatc | 180 |
| tcgccactca | taaatgttgt | tcaactcaca | cttccacgtg | tccaagagct | gccggaggat | 240 |
| gcagaggcga | ccactgacgt | ccaccctgaa | gatattccat | atctcaagaa | ggcttctgat | 300 |
| ggtcttcaac | cggaggtcac | ccggtttcta | gaacaacact | ctccggactg | gattatttat | 360 |
| gattatactc | actactggtt | gccatccatc | gcggctagcc | tcggtatctc | acgagcccac | 420 |
| ttctccgtca | ccactccatg | ggccattgct | tatatgggac | cctcagctga | cgccatgata | 480 |
| aatggttcag | atggtcgaac | cacgttgag | gatctcacga | caccgcccaa | gtggtttccc | 540 |
| tttccgacca | agtatgctg | gcggaagcat | gatcttgccc | gactggtgcc | ttacaaagct | 600 |
| ccggggatat | ctgatcgatg | ccgtatgggg | ctggttctta | agggatctga | ttgtttgctc | 660 |
| tccaaatgtt | accatgagtt | tggaactcaa | tggctacctc | ttttggagac | actacaccaa | 720 |
| gtaccggtgg | ttccggtggg | attactgcca | ccggaaatac | ccggagacga | gaaagatgaa | 780 |
| acatgggtgt | caatcaagaa | atggctcgat | ggtaaacaaa | aaggcagtgt | ggtgtacgtt | 840 |
| gcattaggaa | gcgaggtttt | ggtgagccaa | accgaggttg | ttgagttagc | attgggtctc | 900 |
| gagctttctg | ggttgccatt | tgtttgggct | tatagaaaac | caaaaggtcc | cgcgaagtca | 960 |
| gactcggtgg | agttgccaga | cgggttcgtg | gaacgaactc | gtgaccgtgg | gttggtctgg | 1020 |
| acgagtcggg | cacctcagtt | acgaatactg | agccatgagt | cggtttgtgg | gttcttgacg | 1080 |
| cattgtggtt | ctggatcaat | tgtggaaggg | ctaatgtttg | gtcaccctct | aatcatgcta | 1140 |
| ccgattttg | gggaccaacc | tctgaatgct | cgattactgg | aggacaaaca | ggtgggaatc | 1200 |
| gagataccaa | gaaatgagga | agatggttgc | ttgaccaagg | agtcggttgc | tagatcactg | 1260 |
| aggtccgttg | ttgtggaaaa | agaaggggag | atctacaagg | cgaacgcgag | ggagctgagt | 1320 |
| aaaatctata | cgacactaa | ggttgaaaaa | gaatatgtaa | gccaattcgt | agactatttg | 1380 |
| gaaaagaatg | cgcgtgcggt | tgccatcgat | catgagagtt | aa | | 1422 |

<210> SEQ ID NO 97
<211> LENGTH: 1380
<212> TYPE: DNA
<213> ORGANISM: Stevia rebaudiana

<400> SEQUENCE: 97

| | | | | | |
|---|---|---|---|---|---|
| atggaaaata | aaacggagac | caccgttcgc | cggcgccgga | gaataatatt | attcccggta | 60 |
| ccatttcaag | gccacattaa | cccaattctt | cagctagcca | atgtgttgta | ctctaaagga | 120 |
| ttcagtatca | ccatctttca | caccaacttc | aacaaaccca | aaacatctaa | ttaccctcac | 180 |
| ttcactttca | gattcatcct | cgacaacgac | ccacaagacg | aacgcatttc | caatctaccg | 240 |

```
actcatggtc cgctcgctgg tatgcggatt ccgattatca acgaacacgg agctgacgaa    300
ttacgacgcg aactggaact gttgatgtta gcttctgaag aagatgaaga ggtatcgtgt    360
ttaatcacgg atgctctttg gtacttcgcg caatctgttg ctgacagtct taacctccga    420
cggcttgttt tgatgacaag cagcttgttt aattttcatg cacatgtttc acttcctcag    480
tttgatgagc ttggttacct cgatcctgat gacaaaaccc gtttggaaga acaagcgagt    540
gggtttccta tgctaaaagt gaaagacatc aagtctgcgt attcgaactg gcaaatactc    600
aaagagatat tagggaagat gataaaacaa acaaaagcat cttcaggagt catctggaac    660
tcatttaagg aactcgaaga gtctgagctc gaaactgtta tccgtgagat cccggctcca    720
agtttcttga taccactccc caagcatttg acagcctctt ccagcagctt actagaccac    780
gatcgaaccg ttttccatg gttagaccaa caaccgtcac gttcggtact gtatgttagt    840
tttggtagtg gtactgaagt actggatgag aaagatttct tggaaatagc tcgtgggttg    900
gttgatagca agcagtcgtt tttatgggtg gttcgacctg ggtttgtcaa gggttcgacg    960
tgggtcgaac cgttgccaga tgggttcttg ggtgaaagag gacgtattgt gaaatgggtt    1020
ccacagcaag aagtgctagc tcatggagca ataggcgcat tctggactca tagcggatgg    1080
aactctacgt tggaaagcgt ttgtgaaggt gttcctatga tttttctcgga ttttgggctc    1140
gatcaaccgt tgaatgctag atacatgagt gatgttttga aggtagggt gtatttggaa    1200
aatgggtggg aaagaggaga gatagcaaat gcaataagaa gagttatggt ggatgaagaa    1260
ggagaataca ttagacagaa tgcaagagtt ttgaaacaaa aggcagatgt ttctttgatg    1320
aagggtggtt cgtcttacga atcattagag tctctagttt cttacatttc atcgttgtaa    1380
```

<210> SEQ ID NO 98
<211> LENGTH: 459
<212> TYPE: PRT
<213> ORGANISM: Stevia rebaudiana

<400> SEQUENCE: 98

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
            20                  25                  30

Ala Asn Val Leu Tyr Ser Lys Gly Phe Ser Ile Thr Ile Phe His Thr
        35                  40                  45

Asn Phe Asn Lys Pro Lys Thr Ser Asn Tyr Pro His Phe Thr Phe Arg
    50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
            100                 105                 110

Glu Glu Asp Glu Glu Val Ser Cys Leu Ile Thr Asp Ala Leu Trp Tyr
        115                 120                 125

Phe Ala Gln Ser Val Ala Asp Ser Leu Asn Leu Arg Arg Leu Val Leu
    130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175
```

Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
            245                 250                 255

Leu Leu Asp His Asp Arg Thr Val Phe Pro Trp Leu Asp Gln Gln Pro
        260                 265                 270

Ser Arg Ser Val Leu Tyr Val Ser Phe Gly Ser Gly Thr Glu Val Leu
    275                 280                 285

Asp Glu Lys Asp Phe Leu Glu Ile Ala Arg Gly Leu Val Asp Ser Lys
290                 295                 300

Gln Ser Phe Leu Trp Val Val Arg Pro Gly Phe Val Lys Gly Ser Thr
305                 310                 315                 320

Trp Val Glu Pro Leu Pro Asp Gly Phe Leu Gly Glu Arg Gly Arg Ile
            325                 330                 335

Val Lys Trp Val Pro Gln Gln Glu Val Leu Ala His Gly Ala Ile Gly
        340                 345                 350

Ala Phe Trp Thr His Ser Gly Trp Asn Ser Thr Leu Glu Ser Val Cys
    355                 360                 365

Glu Gly Val Pro Met Ile Phe Ser Asp Phe Gly Leu Asp Gln Pro Leu
370                 375                 380

Asn Ala Arg Tyr Met Ser Asp Val Leu Lys Val Gly Val Tyr Leu Glu
385                 390                 395                 400

Asn Gly Trp Glu Arg Gly Glu Ile Ala Asn Ala Ile Arg Arg Val Met
            405                 410                 415

Val Asp Glu Glu Gly Glu Tyr Ile Arg Gln Asn Ala Arg Val Leu Lys
        420                 425                 430

Gln Lys Ala Asp Val Ser Leu Met Lys Gly Gly Ser Ser Tyr Glu Ser
    435                 440                 445

Leu Glu Ser Leu Val Ser Tyr Ile Ser Ser Leu
450                 455

<210> SEQ ID NO 99
<211> LENGTH: 1380
<212> TYPE: DNA
<213> ORGANISM: Stevia rebaudiana
<220> FEATURE:
<221> NAME/KEY: modified_base
<222> LOCATION: (861)..(863)
<223> OTHER INFORMATION: a, c, t, g, unknown or other

<400> SEQUENCE: 99
atggaaaata aaacggagac caccgttcgc cggcgccgga gaataatatt attcccggta     60
ccatttcaag gccacattaa cccaattctt cagctagcca atgtgttgta ctctaaagga    120
ttcagtatca ccatctttca caccaacttc aacaaaccca aacatctaa ttaccctcac    180 ttcactttca gattcatcct cgacaacgac ccacaagacg aacgcatttc caatctaccg    240
actcatggtc cgctcgctgg tatgcggatt ccgattatca cgaacacgg agctgacgaa     300 ttacgacgcg aactggaact gttgatgtta gcttctgaag aagatgaaga ggtatcgtgt    360
ttaatcacgg atgctctttg gtacttcgcg caatctgttg ctgacagtct taacctccga    420

```
cggcttgttt tgatgacaag cagcttgttt aattttcatg cacatgtttc acttcctcag    480
tttgatgagc ttggttacct cgatcctgat gacaaaaccc gtttggaaga caagcgagt    540 gggtttccta tgctaaaagt gaaagacatc aagtctgcgt attcgaactg caaatactc    600 aaagagatat tagggaagat gataaaacaa acaaaagcat cttcaggagt catctggaac    660
tcatttaagg aactcgaaga gtctgagctc gaaactgtta tccgtgagat cccggctcca    720 agttcttga taccactccc caagcatttg acagcctctt ccagcagctt actagaccac    780
gatcgaaccg tttttcaatg ttagaccaa caaccgccaa gttcggtact gtatgttagt    840
tttggtagta ctagtgaagt nnnggatgag aaagatttct tggaaatagc tcgtgggttg    900
gttgatagca agcagtcgtt tttatgggtg gttcgacctg ggtttgtcaa gggttcgacg    960
tgggtcgaac cgttgccaga tgggttcgtg gccgaaagag ggcgtattgt gaaatgggtt   1020
ccgcaacagg aagtgatagc tcatggagca atcggtgcat tctggactca tagcggatgg   1080
aactctacat tggaaagcgt ttgtgaaggt gttcctatga ttttctcgga ttttgggctc   1140
gatcaaccgt tgaatgctag atacatgagt gatgttttga aggtaggggt gtatttggaa   1200
aatgggtggg aaagaggaga gatagcaaat gcaatacgaa gagttatggt ggatgaagaa   1260
ggagaataca ttagacagaa tgcaagagtt ttgaaacaaa aggcagatgt ttctttgatg   1320
aagggtggtt catcttacga atcattagag tctctagttt cttacatttc atcgttgtaa   1380
```

<210> SEQ ID NO 100
<211> LENGTH: 459
<212> TYPE: PRT
<213> ORGANISM: Stevia rebaudiana
<220> FEATURE:
<221> NAME/KEY: MOD_RES
<222> LOCATION: (288)..(288)
<223> OTHER INFORMATION: Any amino acid

<400> SEQUENCE: 100

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
                100                 105                 110

Glu Glu Asp Glu Glu Val Ser Cys Leu Ile Thr Asp Ala Leu Trp Tyr
            115                 120                 125

Phe Ala Gln Ser Val Ala Asp Ser Leu Asn Leu Arg Arg Leu Val Leu
        130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
```

```
            180                 185                 190
Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Xaa
        275                 280                 285

Asp Glu Lys Asp Phe Leu Glu Ile Ala Arg Gly Leu Val Asp Ser Lys
    290                 295                 300

Gln Ser Phe Leu Trp Val Val Arg Pro Gly Phe Val Lys Gly Ser Thr
305                 310                 315                 320

Trp Val Glu Pro Leu Pro Asp Gly Phe Val Ala Glu Arg Gly Arg Ile
                325                 330                 335

Val Lys Trp Val Pro Gln Gln Glu Val Ile Ala His Gly Ala Ile Gly
            340                 345                 350

Ala Phe Trp Thr His Ser Gly Trp Asn Ser Thr Leu Glu Ser Val Cys
        355                 360                 365

Glu Gly Val Pro Met Ile Phe Ser Asp Phe Gly Leu Asp Gln Pro Leu
    370                 375                 380

Asn Ala Arg Tyr Met Ser Asp Val Leu Lys Val Gly Val Tyr Leu Glu
385                 390                 395                 400

Asn Gly Trp Glu Arg Gly Glu Ile Ala Asn Ala Ile Arg Arg Val Met
                405                 410                 415

Val Asp Glu Glu Gly Glu Tyr Ile Arg Gln Asn Ala Arg Val Leu Lys
            420                 425                 430

Gln Lys Ala Asp Val Ser Leu Met Lys Gly Gly Ser Ser Tyr Glu Ser
        435                 440                 445

Leu Glu Ser Leu Val Ser Tyr Ile Ser Ser Leu
    450                 455

<210> SEQ ID NO 101
<211> LENGTH: 1380
<212> TYPE: DNA
<213> ORGANISM: Stevia rebaudiana
<220> FEATURE:
<221> NAME/KEY: modified_base
<222> LOCATION: (861)..(863)
<223> OTHER INFORMATION: a, c, t, g, unknown or other

<400> SEQUENCE: 101
atggaaaata aaacggagac caccgttcgc cggcgccgga gaataatatt attcccggta      60
ccatttcaag gccacattaa cccaattctt cagctagcca atgtgttgta ctctaaagga     120
ttcagtatca ccatctttca caccaacttc aacaaaccca aaacatctaa ttaccctcac     180
ttcactttca gattcatcct cgacaacgac ccacaagacg aacgcatttc caatctaccg     240
actcatggtc cgctcgctgg tatgcggatt ccgattatca cgaacacgg agctgacgaa       300 ttacgacgcg aactggaact gttgatgtta gcttctgaag aagatgaaga ggtatcgtgt     360
ttaatcacgg atgctctttg gtacttcgcg caatctgttg ctgacagtct taacctccga     420
```

-continued

```
cggcttgttt tgatgacaag cagcttgttt aattttcatg cacatgtttc acttcctcag    480
tttgatgagc ttggttacct cgatcctgat gacaaaaccc gtttggaaga caagcgagt    540
gggtttccta tgctaaaagt gaaagacatc aagtctgcgt attcgaactg gcaaatactc    600
aaagagatat tagggaagat gataaaacaa acaaaagcat cttcaggagt catctggaac    660
tcatttaagg aactcgaaga gtctgagctc gaaactgtta tccgtgagat cccggctcca    720
agtttcttga taccactccc caagcatttg acagcctctt ccagcagctt actagaccac    780
gatcgaaccg ttttttcaatg gttagaccaa caaccgccaa gttcggtact gtatgttagt    840
tttggtagta ctagtgaagt nnnggatgag aaagatttct tggaaatagc tcgtgggttg    900
gttgatagca agcagtcgtt tttatgggtg gttcgacctg ggtttgtcaa gggttcgacg    960
tgggtcgaac cgttgccaga tgggttcttg ggtgaaagag gacgtattgt gaaatgggtt   1020
ccacagcaag aagtgctagc tcatggagca ataggcgcat tctggactca tagcggatgg   1080
aactctacgt tggaaagcgt ttgtgaaggt gttcctatga ttttctcgga ttttgggctc   1140
gatcaaccgt tgaatgctag atacatgagt gatgttttga aggtaggggt gtatttggaa   1200
aatgggtggg aaagaggaga gatagcaaat gcaataagaa gagttatggt ggatgaagaa   1260
ggagaataca ttagacagaa tgcaagagtt ttgaaacaaa aggcagatgt ttctttgatg   1320
aagggtggtt cgtcttacga atcattagag tctctagttt cttacatttc atcgttgtaa   1380
```

<210> SEQ ID NO 102
<211> LENGTH: 459
<212> TYPE: PRT
<213> ORGANISM: Stevia rebaudiana
<220> FEATURE:
<221> NAME/KEY: MOD_RES
<222> LOCATION: (288)..(288)
<223> OTHER INFORMATION: Any amino acid

<400> SEQUENCE: 102

```
Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Met Leu Ala Ser
                100                 105                 110

Glu Glu Asp Glu Glu Val Ser Cys Leu Ile Thr Asp Ala Leu Trp Tyr
            115                 120                 125

Phe Ala Gln Ser Val Ala Asp Ser Leu Asn Leu Arg Arg Leu Val Leu
        130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175

Glu Gln Ala Ser Gly Phe Pro Met Leu Lys Val Lys Asp Ile Lys Ser
            180                 185                 190
```

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Xaa
        275                 280                 285

Asp Glu Lys Asp Phe Leu Glu Ile Ala Arg Gly Leu Val Asp Ser Lys
    290                 295                 300

Gln Ser Phe Leu Trp Val Val Arg Pro Gly Phe Val Lys Gly Ser Thr
305                 310                 315                 320

Trp Val Glu Pro Leu Pro Asp Gly Phe Leu Gly Glu Arg Gly Arg Ile
                325                 330                 335

Val Lys Trp Val Pro Gln Gln Val Leu Ala His Gly Ala Ile Gly
            340                 345                 350

Ala Phe Trp Thr His Ser Gly Trp Asn Ser Thr Leu Glu Ser Val Cys
        355                 360                 365

Glu Gly Val Pro Met Ile Phe Ser Asp Phe Gly Leu Asp Gln Pro Leu
    370                 375                 380

Asn Ala Arg Tyr Met Ser Asp Val Leu Lys Val Gly Val Tyr Leu Glu
385                 390                 395                 400

Asn Gly Trp Glu Arg Gly Glu Ile Ala Asn Ala Ile Arg Arg Val Met
                405                 410                 415

Val Asp Glu Glu Gly Glu Tyr Ile Arg Gln Asn Ala Arg Val Leu Lys
            420                 425                 430

Gln Lys Ala Asp Val Ser Leu Met Lys Gly Gly Ser Ser Tyr Glu Ser
        435                 440                 445

Leu Glu Ser Leu Val Ser Tyr Ile Ser Ser Leu
    450                 455

<210> SEQ ID NO 103
<211> LENGTH: 1323
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103
atgcattcta ccagacatat cttaagacaa agggccgtcc tagttacagg cgctagaaca      60
ccattcgtga atcatttggg ggctcttatg aaagcagata ccttggaatt ggcatcagca     120
tcagtcgctg ggttgctgaa caagacctca ctggacccta gagatatcga tcatatcgtt     180
tggggtaatg ttgtacttca aggatcagct cataactgcg ccagagaaat agttatcgac     240
cttaacatgc ctaaaaagat catcggtaat ttgacatcta tggcctgtgc ttcaggctta     300
tcttctttgt cacaagcctg tatgctaata gagggtggtc atgccgatgt cgtcattgct     360
ggcggttctg attcagtctc caacactgaa gtgccttttgc caagatccgt cacttacggt     420
ctaatgatgg cccaaaggaa gggtgttatg ggcttcttta aggaagcagg atacaaccca     480

```
ttcaaatggt tccaggcgg tattgcttta accgaacgta gtacaggaaa aactatgggt    540
tggcatggag acttaattgc tgagttaaac tctatatcta gagatgacca ggaagccctg    600
gctgtggctt ctcatgcaaa tgctgctaga gcagaaaaag ctgggtactt taaggaggaa    660
attgtacctg tgacaatcga caaaaagggc aaaaagactg aagtaacatg tgatgatgtt    720
atgcaaagag atacagaaaa gatgaaggcc aagatgccat cattgaagcc tgttttcaga    780
aaagagggag gtacaataac agcagccact tccagtactc tgactgatgg tggctctgca    840
atgttggtta tgtcagagga aaaggccaaa aagttgggtt atccaactga tgtctgcgtg    900
aagtcttggt atttcagtgg tatcgatcct tacccacaac ttttgttagc accagttcta    960
ggttggggtc cagctttgaa aaaggccgga ttaaccccta agatatcga tttgtacgaa   1020 attcacgaag catttgctgc acaagttcta gccacaatta agtgtttgaa gtctcaggaa   1080
ttcttcgata ggtacgctaa cggtgcaaag ccagtattaa ctgaggatat tgatctttct   1140
aaactaaatg ttaatggcgg ttccttagca cttggccacc cattcgccgc tacaggaggt   1200
agaatcgtaa tctctctagc aaatgagttg agaagatccg aaagagaca cgggctggtc   1260 agtatttgtg cagctggagg gttaggcgga gtagctatac ttgagcatac agcaagtaag   1320
taa                                                                 1323
```

<210> SEQ ID NO 104
<211> LENGTH: 440
<212> TYPE: PRT
<213> ORGANISM: Leishmania infantum

<400> SEQUENCE: 104

```
Met His Ser Thr Arg His Ile Leu Arg Gln Arg Ala Val Leu Val Thr
1               5                   10                  15

Gly Ala Arg Thr Pro Phe Val Lys Ser Phe Gly Ala Leu Met Lys Ala
                20                  25                  30

Asp Thr Leu Glu Leu Ala Ser Ala Ser Val Ala Gly Leu Leu Asn Lys
            35                  40                  45

Thr Ser Leu Asp Pro Arg Asp Ile Asp His Ile Val Trp Gly Asn Val
        50                  55                  60

Val Leu Gln Gly Ser Ala His Asn Cys Ala Arg Glu Ile Val Ile Asp
65                  70                  75                  80

Leu Asn Met Pro Lys Lys Ile Ile Gly Asn Leu Thr Ser Met Ala Cys
                85                  90                  95

Ala Ser Gly Leu Ser Ser Leu Ser Gln Ala Cys Met Leu Ile Glu Gly
            100                 105                 110

Gly His Ala Asp Val Val Ile Ala Gly Gly Ser Asp Ser Val Ser Asn
        115                 120                 125

Thr Glu Val Pro Leu Pro Arg Ser Val Thr Tyr Gly Leu Met Met Ala
    130                 135                 140

Gln Arg Lys Gly Val Met Gly Phe Phe Lys Glu Ala Gly Tyr Asn Pro
145                 150                 155                 160

Phe Lys Trp Phe Pro Gly Gly Ile Ala Leu Thr Glu Arg Ser Thr Gly
                165                 170                 175

Lys Thr Met Gly Trp His Gly Asp Leu Ile Ala Glu Leu Asn Ser Ile
            180                 185                 190

Ser Arg Asp Asp Gln Glu Ala Leu Ala Val Ala Ser His Ala Asn Ala
        195                 200                 205

Ala Arg Ala Glu Lys Ala Gly Tyr Phe Lys Glu Glu Ile Val Pro Val
    210                 215                 220
```

Thr Ile Asp Lys Lys Gly Lys Thr Glu Val Thr Cys Asp Asp Val
225                 230                 235                 240

Met Gln Arg Asp Thr Glu Lys Met Lys Ala Lys Met Pro Ser Leu Lys
            245                 250                 255

Pro Val Phe Arg Lys Glu Gly Gly Thr Ile Thr Ala Ala Thr Ser Ser
        260                 265                 270

Thr Leu Thr Asp Gly Gly Ser Ala Met Leu Val Met Ser Glu Glu Lys
    275                 280                 285

Ala Lys Lys Leu Gly Tyr Pro Thr Asp Val Cys Val Lys Ser Trp Tyr
290                 295                 300

Phe Ser Gly Ile Asp Pro Tyr Pro Gln Leu Leu Ala Pro Val Leu
305                 310                 315                 320

Gly Trp Gly Pro Ala Leu Lys Lys Ala Gly Leu Thr Pro Lys Asp Ile
                325                 330                 335

Asp Leu Tyr Glu Ile His Glu Ala Phe Ala Ala Gln Val Leu Ala Thr
            340                 345                 350

Ile Lys Cys Leu Lys Ser Gln Glu Phe Phe Asp Arg Tyr Ala Asn Gly
        355                 360                 365

Ala Lys Pro Val Leu Thr Glu Asp Ile Asp Leu Ser Lys Leu Asn Val
370                 375                 380

Asn Gly Gly Ser Leu Ala Leu Gly His Pro Phe Ala Ala Thr Gly Gly
385                 390                 395                 400

Arg Ile Val Ile Ser Leu Ala Asn Glu Leu Arg Arg Ser Gly Lys Arg
                405                 410                 415

His Gly Leu Val Ser Ile Cys Ala Ala Gly Gly Leu Gly Gly Val Ala
            420                 425                 430

Ile Leu Glu His Thr Ala Ser Lys
        435                 440

<210> SEQ ID NO 105
<211> LENGTH: 1584
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105
atggcagctg accaattggt gaaaactgaa gtcaccaaga agtcttttac tgctcctgta      60
caaaaggctt ctacaccagt tttaaccaat aaaacagtca tttctggatc gaaagtcaaa     120
agtttatcat ctgcgcaatc gagctcatca ggaccttcat catctagtga ggaagatgat     180
tcccgcgata ttgaaagctt ggataagaaa atacgtcctt tagaagaatt agaagcatta     240
ttaagtagtg aaatacaaa acaattgaag aacaaagagg tcgctgcctt ggttattcac      300
ggtaagttac ctttgtacgc tttggagaaa aaattaggtg atactacgag agcggttgcg     360
gtacgtagga aggctctttc aattttggca gaagctcctg tattagcatc tgatcgttta     420
ccatataaaa attatgacta cgaccgcgta tttggcgctt gttgtgaaaa tgttataggt     480
tacatgcctt tgcccgttgg tgttataggc cccttggtta tcgatggtac atcttatcat     540
ataccaatgg caactacaga gggttgtttg gtagcttctg ccatgcgtgg ctgtaaggca     600
atcaatgctg gcggtggtgc aacaactgtt taactaagg atggtatgac aagaggccca     660
gtagtccgtt tcccaacttt gaaagatct ggtgcctgta agatatggtt agactcagaa      720
gagggacaaa acgcaattaa aaaagctttt aactctacat caagatttgc acgtctgcaa     780

```
catattcaaa cttgtctagc aggagattta ctcttcatga gatttagaac aactactggt    840
gacgcaatgg gtatgaatat gatttctaaa ggtgtcgaat actcattaaa gcaaatggta    900
gaagagtatg gctgggaaga tatggaggtt gtctccgttt ctggtaacta ctgtaccgac    960
aaaaaaccag ctgccatcaa ctggatcgaa ggtcgtggta agagtgtcgt cgcagaagct   1020
actattcctg gtgatgttgt cagaaaagtg ttaaaaagtg atgtttccgc attggttgag   1080
ttgaacattg ctaagaattt ggttggatct gcaatggctg gtctgttgg tggatttaac   1140
gcacatgcag ctaatttagt gacagctgtt ttcttggcat taggacaaga tcctgcacaa   1200
aatgttgaaa gttccaactg tataacattg atgaaagaag tggacggtga tttgagaatt   1260
tccgtatcca tgccatccat cgaagtaggt accatcggtg gtggtactgt tctagaacca   1320
caaggtgcca tgttggactt attaggtgta agaggcccgc atgctaccgc tcctggtacc   1380
aacgcacgtc aattagcaag aatagttgcc tgtgccgtct ggcaggtga attatcctta   1440
tgtgctgccc tagcagccgg ccatttggtt caaagtcata tgacccacaa caggaaacct   1500
gctgaaccaa caaaacctaa caatttggac gccactgata taaatcgttt gaaagatggg   1560
tccgtcacct gcattaaatc ctaa                                          1584
```

<210> SEQ ID NO 106
<211> LENGTH: 527
<212> TYPE: PRT
<213> ORGANISM: Saccharomyces cerevisiae

<400> SEQUENCE: 106

```
Met Ala Ala Asp Gln Leu Val Lys Thr Glu Val Thr Lys Lys Ser Phe
1               5                   10                  15

Thr Ala Pro Val Gln Lys Ala Ser Thr Pro Val Leu Thr Asn Lys Thr
            20                  25                  30

Val Ile Ser Gly Ser Lys Val Lys Ser Leu Ser Ser Ala Gln Ser Ser
        35                  40                  45

Ser Ser Gly Pro Ser Ser Ser Ser Glu Glu Asp Asp Ser Arg Asp Ile
    50                  55                  60

Glu Ser Leu Asp Lys Lys Ile Arg Pro Leu Glu Glu Leu Glu Ala Leu
65                  70                  75                  80

Leu Ser Ser Gly Asn Thr Lys Gln Leu Lys Asn Lys Glu Val Ala Ala
                85                  90                  95

Leu Val Ile His Gly Lys Leu Pro Leu Tyr Ala Leu Glu Lys Lys Leu
            100                 105                 110

Gly Asp Thr Thr Arg Ala Val Ala Val Arg Arg Lys Ala Leu Ser Ile
        115                 120                 125

Leu Ala Glu Ala Pro Val Leu Ala Ser Asp Arg Leu Pro Tyr Lys Asn
    130                 135                 140

Tyr Asp Tyr Asp Arg Val Phe Gly Ala Cys Cys Glu Asn Val Ile Gly
145                 150                 155                 160

Tyr Met Pro Leu Pro Val Gly Val Ile Gly Pro Leu Val Ile Asp Gly
                165                 170                 175

Thr Ser Tyr His Ile Pro Met Ala Thr Thr Glu Gly Cys Leu Val Ala
            180                 185                 190

Ser Ala Met Arg Gly Cys Lys Ala Ile Asn Ala Gly Gly Gly Ala Thr
        195                 200                 205

Thr Val Leu Thr Lys Asp Gly Met Thr Arg Gly Pro Val Val Arg Phe
    210                 215                 220
```

```
Pro Thr Leu Lys Arg Ser Gly Ala Cys Lys Ile Trp Leu Asp Ser Glu
225                 230                 235                 240

Glu Gly Gln Asn Ala Ile Lys Lys Ala Phe Asn Ser Thr Ser Arg Phe
            245                 250                 255

Ala Arg Leu Gln His Ile Gln Thr Cys Leu Ala Gly Asp Leu Leu Phe
            260                 265                 270

Met Arg Phe Arg Thr Thr Thr Gly Asp Ala Met Gly Met Asn Met Ile
        275                 280                 285

Ser Lys Gly Val Glu Tyr Ser Leu Lys Gln Met Val Glu Glu Tyr Gly
        290                 295                 300

Trp Glu Asp Met Glu Val Val Ser Val Ser Gly Asn Tyr Cys Thr Asp
305                 310                 315                 320

Lys Lys Pro Ala Ala Ile Asn Trp Ile Glu Gly Arg Gly Lys Ser Val
                325                 330                 335

Val Ala Glu Ala Thr Ile Pro Gly Asp Val Val Arg Lys Val Leu Lys
                340                 345                 350

Ser Asp Val Ser Ala Leu Val Glu Leu Asn Ile Ala Lys Asn Leu Val
            355                 360                 365

Gly Ser Ala Met Ala Gly Ser Val Gly Gly Phe Asn Ala His Ala Ala
370                 375                 380

Asn Leu Val Thr Ala Val Phe Leu Ala Leu Gly Gln Asp Pro Ala Gln
385                 390                 395                 400

Asn Val Glu Ser Ser Asn Cys Ile Thr Leu Met Lys Glu Val Asp Gly
                405                 410                 415

Asp Leu Arg Ile Ser Val Ser Met Pro Ser Ile Glu Val Gly Thr Ile
            420                 425                 430

Gly Gly Gly Thr Val Leu Glu Pro Gln Gly Ala Met Leu Asp Leu Leu
        435                 440                 445

Gly Val Arg Gly Pro His Ala Thr Ala Pro Gly Thr Asn Ala Arg Gln
        450                 455                 460

Leu Ala Arg Ile Val Ala Cys Ala Val Leu Ala Gly Glu Leu Ser Leu
465                 470                 475                 480

Cys Ala Ala Leu Ala Ala Gly His Leu Val Gln Ser His Met Thr His
                485                 490                 495

Asn Arg Lys Pro Ala Glu Pro Thr Lys Pro Asn Asn Leu Asp Ala Thr
            500                 505                 510

Asp Ile Asn Arg Leu Lys Asp Gly Ser Val Thr Cys Ile Lys Ser
        515                 520                 525

<210> SEQ ID NO 107
<211> LENGTH: 3681
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
atgagagctg tccttagatt gttatcaaca catactgttt ctctcctat tgaaacaatt      60 gtatctgttt tcgtgttagc tacattagct tacttccaca tcttgtccgg aatcaagcac    120
tcaagtttct ttgcatcttc tcatcctcct gctatcagac tgcttttgc acatctgacc    180 aacggggaat gggttgccgt ctcccaacat gattggactg aagcatggaa gcatcctggc    240
ggttcacttg atgcattaga acttcaacaa gtagttttca ctttagatga caagactcaa    300
ccatctgctg tgctagatgc atccgcaatt agtcagcact agtttccaa tgttcctgca    360
```

```
ttatctggaa aagcctactc ttcattgtgc caccatccaa atgtatcagg caccctcctgt    420 tttacatcag tttctggtcc aggagcttca ccaatcttga cactgagttt taagcctgga    480
actagagacg attggttagg atcattaagg aaggagaaaa ctatcacact agatggggtt    540
aagtacgacg ttggagccgg aaaaagacaa gagtcaatcg gcgatatgga atcatctaag    600
tgggttgctt atgcattatc agctttggta cttagatttt gggaattaac aaaggcagat    660
tccttagata tactagtggt tctaactggg tacatcctaa tgcacgtaac attcatgaga    720
ttgttcttgg catccagagc acttggcagt aacttttggt tatcagctgg catattctcc    780
tccgcaacaa tttctttcct attcacttta ccaatgtgta gatctatgga tattccactt    840
gatccaattg ccttgacaga agccctgcca ttcttggtgt gtaccgtagg ttttgacaaa    900
ccacttagat tggcaagagc tgtgatggct catcctaata tccttaaacc tcaagatgat    960
ggtaggatga aagctgccgg agatgtcatt cttgaggcac tggacagagt tggtaacatg   1020
atattgagag attacgcttt agatcgcaga gttctattcg ttggcgttaa ctccagagtt   1080
ggcggtctta aggaattttg tgctgtagct gcagcattac ttgctatgga cagattaatg   1140
acattcacac tttatacagc agtgttaacc atcatggttg aggtaaggcg tatcaaaaag   1200
gtcagagata tgactaaggc tagatctaga agttcttcta ttaccgccgt tacagccaac   1260
ggcaccgcca taagaggcgt tttgagtaga aaatcttcaa aacaatctgt gacagaacca   1320
gagacaacta aaaacctaag acaaagagcc actgattcag ccatcggtgt taagggttca   1380
ttgctgaaag atggaggcag attgcaggaa gccgaggaga atccaatggc aagattaaag   1440
ctattgttaa tcgcttcctt cttaacacta cacatcttga acttttgtac tactttgact   1500
tcagccacag ctaacgcaag acatcaaaga catcctttta gaaccgttca agaggtagta   1560
ccaattccta gagttgacat tactaccccca gccatagcca atatcttgtc tcatctagct   1620
gtggctcagg aacctatgtt cactgttgtt ggcagtgaac ctatcgaact tcttgttaaa   1680
gtcgctgctc cagtctacgt ccatgctcta ccattggccc ctgctttaag agcttcaaac   1740
actaatactg gagaagctat tgaaaacttt atgagttcat ggtctagtct ggtaggtgac   1800
ccagttgtta gtaagtggat cgtagcattg ctagctgtct ctgttgcatt gaatggatac   1860
ttgttaaagg gtatagccgc aggttccggg ttggctgcca tgagagctgt tagatctcaa   1920
ggtgttcgtt tcagatctag agctagaagt atcgtaaaga tatctgatga acctgagcca   1980
gagccagaac actctatcga cccagcacca gtagtgttct tcgcttccgc agcaccagct   2040
gtagaggccc ctgctccagc tcctgcacct gaaccagaac caccagtcaa cagaccacca   2100
ccattgacta ttttctcaag accactgaac ttagaaacag tggacaaaaa gttacaagat   2160
gctctgccaa taagatcccc accacctgtt gaaccaatca ctccagaatc tagagaagtg   2220
gaaccaaccc aagtagaagt aagatctcta gctgaatgtg tggatgtgtt cgagaatggg   2280
ccaagaccag tctcagtggc tttaaagact ctgaatgatg aggaagttat cctgctttgc   2340
caaacaggta agatagctcc atatgcattg gttaagatgt tggctgattt cgatagggcc   2400
gtacgtgtca gaagagcact tattagtaga gcttcacgta caaaaacttt agaaaactca   2460
ctggttccta tgaaagatta tgattacgcc agagtcatgg gtgcctgttg tgaaaacgtt   2520
atcggataca tgccattacc actagggatt gcaggtccat tgaagattga tggcttgatg   2580
tatcctatac caatggcaac cgcagaaggt accttggttg catctacttc taggggctgt   2640
aaggccttaa atgctggtgg aggggtcaca actgtcttga cagcagatgg catgacaaga   2700
```

-continued

```
gggccagcta tagactttcc ttccatcgtc agagctgcag aggctaaggc cttcattgaa    2760
tcagaagatg gatacgctac aatcagggag gctttcgagt ctacttctag atttgccaag    2820
ttgcaaaaga tcaagtgtgc actagctggt cgtactcttt ttgtcagatt tgctactaga    2880
acaggagatg ccatgggtat gaacatgatt tctaaggcta ccgaaaaggc acttgatgtc    2940
ctgagtcacg agttccctga aatggtcgtc cttgctttgt ctggtaacta ctgcacagac    3000
aaaaagcctg cagctatttc atggatcgaa ggtaggggaa aatctattgt agcagaagca    3060
gttattcctg gtaaggtcgt taagtcagtc ctgaaaacaa cagtcgagtc tctttgcaat    3120
gtcaacacta agaaaaacct gattggttca gccatggcag ttctgttgg tggtttcaac     3180 gctcatgccg ccaacatcct aacagctgtg ttcctagcca caggtcagga tcctgctcaa    3240
aatgtcgaat cttctaattg catgacttta atggaaccaa caaacggcgg tgaggatttg    3300
ctaatgacaa tttcaatgcc atgtatagag gtaggaaccg ttggtggagg acaattctg    3360 gaaccacaag gtgcagtttt ggatttgttg ggcgttagag gggctcaccc tactaatcct    3420
ggtcaaaacg ctcaacagtt agccagaatt atcgcatcag ctgtaatggc aggcgaattg    3480
tctttgataa gtgccttagc cgcaggtcat ttggttagag ctcatcttgc ccacaatcgt    3540
tctcaattga atacaccaat gccatccaga ccacatactc ctggccctga ggatgtctca    3600
catgtgcagc agctacctac accatctgca tctgatgata aggtgttac agctcaaggt     3660 tacgttgtcg aagcaaaata a                                              3681
```

<210> SEQ ID NO 108
<211> LENGTH: 1226
<212> TYPE: PRT
<213> ORGANISM: Ganoderma lucidum

<400> SEQUENCE: 108

```
Met Arg Ala Val Leu Arg Leu Leu Ser Thr His Thr Val Phe Ser Pro
1               5                   10                  15

Ile Glu Thr Ile Val Ser Val Phe Val Leu Ala Thr Leu Ala Tyr Phe
            20                  25                  30

His Ile Leu Ser Gly Ile Lys His Ser Ser Phe Phe Ala Ser Ser His
        35                  40                  45

Pro Pro Ala Ile Arg Pro Ala Phe Ala His Leu Thr Asn Gly Glu Trp
    50                  55                  60

Val Ala Val Ser Gln His Asp Trp Thr Glu Ala Trp Lys His Pro Gly
65                  70                  75                  80

Gly Ser Leu Asp Ala Leu Glu Leu Gln Gln Val Val Phe Thr Leu Asp
                85                  90                  95

Asp Lys Thr Gln Pro Ser Ala Val Leu Asp Ala Ser Ala Ile Ser Gln
            100                 105                 110

His Leu Val Ser Asn Val Pro Ala Leu Ser Gly Lys Ala Tyr Ser Ser
        115                 120                 125

Leu Cys His His Pro Asn Val Ser Gly Thr Ser Cys Phe Thr Ser Val
    130                 135                 140

Ser Gly Pro Gly Ala Ser Pro Ile Leu Thr Leu Ser Phe Lys Pro Gly
145                 150                 155                 160

Thr Arg Asp Asp Trp Leu Gly Ser Leu Arg Lys Glu Lys Thr Ile Thr
                165                 170                 175

Leu Asp Gly Val Lys Tyr Asp Val Gly Ala Gly Lys Arg Gln Glu Ser
            180                 185                 190

Ile Gly Asp Met Glu Ser Ser Lys Trp Val Ala Tyr Ala Leu Ser Ala
```

```
            195                 200                 205
Leu Val Leu Arg Phe Trp Glu Leu Thr Lys Ala Asp Ser Leu Asp Ile
210                 215                 220

Leu Val Val Leu Thr Gly Tyr Ile Leu Met His Val Thr Phe Met Arg
225                 230                 235                 240

Leu Phe Leu Ala Ser Arg Ala Leu Gly Ser Asn Phe Trp Leu Ser Ala
                245                 250                 255

Gly Ile Phe Ser Ser Ala Thr Ile Ser Phe Leu Phe Thr Leu Pro Met
                260                 265                 270

Cys Arg Ser Met Asp Ile Pro Leu Asp Pro Ile Ala Leu Thr Glu Ala
                275                 280                 285

Leu Pro Phe Leu Val Cys Thr Val Gly Phe Asp Lys Pro Leu Arg Leu
290                 295                 300

Ala Arg Ala Val Met Ala His Pro Asn Ile Leu Lys Pro Gln Asp Asp
305                 310                 315                 320

Gly Arg Met Lys Ala Ala Gly Asp Val Ile Leu Glu Ala Leu Asp Arg
                325                 330                 335

Val Gly Asn Met Ile Leu Arg Asp Tyr Ala Leu Glu Ile Ala Val Leu
                340                 345                 350

Phe Val Gly Val Asn Ser Arg Val Gly Leu Lys Glu Phe Cys Ala
                355                 360                 365

Val Ala Ala Leu Leu Ala Met Asp Arg Leu Met Thr Phe Thr Leu
370                 375                 380

Tyr Thr Ala Val Leu Thr Ile Met Val Glu Val Arg Arg Ile Lys Lys
385                 390                 395                 400

Val Arg Asp Met Thr Lys Ala Arg Ser Arg Ser Ser Ile Thr Ala
                405                 410                 415

Val Thr Ala Asn Gly Thr Ala Ile Arg Gly Val Leu Ser Arg Lys Ser
                420                 425                 430

Ser Lys Gln Ser Val Thr Glu Pro Glu Thr Thr Lys Asn Leu Arg Gln
                435                 440                 445

Arg Ala Thr Asp Ser Ala Ile Gly Val Lys Gly Ser Leu Leu Lys Asp
450                 455                 460

Gly Gly Arg Leu Gln Glu Ala Glu Glu Asn Pro Met Ala Arg Leu Lys
465                 470                 475                 480

Leu Leu Leu Ile Ala Ser Phe Leu Thr Leu His Ile Leu Asn Phe Cys
                485                 490                 495

Thr Thr Leu Thr Ser Ala Thr Ala Asn Ala Arg His Gln Arg His Pro
                500                 505                 510

Phe Arg Thr Val Gln Glu Val Val Pro Ile Pro Arg Val Asp Ile Thr
                515                 520                 525

Thr Pro Ala Ile Ala Asn Ile Leu Ser His Leu Ala Val Ala Gln Glu
                530                 535                 540

Pro Met Phe Thr Val Val Gly Ser Glu Pro Ile Glu Leu Leu Val Lys
545                 550                 555                 560

Val Ala Ala Pro Val Tyr Val His Ala Leu Pro Leu Ala Pro Ala Leu
                565                 570                 575

Arg Ala Ser Asn Thr Asn Thr Gly Glu Ala Ile Glu Asn Phe Met Ser
                580                 585                 590

Ser Trp Ser Ser Leu Val Gly Asp Pro Val Val Ser Lys Trp Ile Val
                595                 600                 605

Ala Leu Leu Ala Val Ser Val Ala Leu Asn Gly Tyr Leu Leu Lys Gly
610                 615                 620
```

Ile Ala Ala Gly Ser Gly Leu Ala Ala Met Arg Ala Val Arg Ser Gln
625                 630                 635                 640

Gly Val Arg Phe Arg Ser Arg Ala Arg Ser Ile Val Lys Ile Ser Asp
            645                 650                 655

Glu Pro Glu Pro Glu Pro Glu His Ser Ile Asp Pro Ala Pro Val Val
                660                 665                 670

Phe Phe Ala Ser Ala Ala Pro Ala Val Glu Ala Pro Ala Pro Ala Pro
            675                 680                 685

Ala Pro Glu Pro Glu Pro Pro Val Asn Arg Pro Pro Leu Thr Ile
690                 695                 700

Phe Ser Arg Pro Leu Asn Leu Glu Thr Val Asp Lys Lys Leu Gln Asp
705                 710                 715                 720

Ala Leu Pro Ile Arg Ser Pro Pro Val Glu Pro Ile Thr Pro Glu
                725                 730                 735

Ser Arg Glu Val Glu Pro Thr Gln Val Glu Val Arg Ser Leu Ala Glu
            740                 745                 750

Cys Val Asp Val Phe Glu Asn Gly Pro Arg Pro Val Ser Val Ala Leu
            755                 760                 765

Lys Thr Leu Asn Asp Glu Glu Val Ile Leu Leu Cys Gln Thr Gly Lys
770                 775                 780

Ile Ala Pro Tyr Ala Leu Val Lys Met Leu Ala Asp Phe Asp Arg Ala
785                 790                 795                 800

Val Arg Val Arg Arg Ala Leu Ile Ser Arg Ala Ser Arg Thr Lys Thr
                805                 810                 815

Leu Glu Asn Ser Leu Val Pro Met Lys Asp Tyr Asp Tyr Ala Arg Val
            820                 825                 830

Met Gly Ala Cys Cys Glu Asn Val Ile Gly Tyr Met Pro Leu Pro Leu
            835                 840                 845

Gly Ile Ala Gly Pro Leu Lys Ile Asp Gly Leu Met Tyr Pro Ile Pro
850                 855                 860

Met Ala Thr Ala Glu Gly Thr Leu Val Ala Ser Thr Ser Arg Gly Cys
865                 870                 875                 880

Lys Ala Leu Asn Ala Gly Gly Val Thr Thr Val Leu Thr Ala Asp
                885                 890                 895

Gly Met Thr Arg Gly Pro Ala Ile Asp Phe Pro Ser Ile Val Arg Ala
            900                 905                 910

Ala Glu Ala Lys Ala Phe Ile Glu Ser Glu Asp Gly Tyr Ala Thr Ile
            915                 920                 925

Arg Glu Ala Phe Glu Ser Thr Ser Arg Phe Ala Lys Leu Gln Lys Ile
            930                 935                 940

Lys Cys Ala Leu Ala Gly Arg Thr Leu Phe Val Arg Phe Ala Thr Arg
945                 950                 955                 960

Thr Gly Asp Ala Met Gly Met Asn Met Ile Ser Lys Ala Thr Glu Lys
            965                 970                 975

Ala Leu Asp Val Leu Ser His Glu Phe Pro Glu Met Val Val Leu Ala
            980                 985                 990

Leu Ser Gly Asn Tyr Cys Thr Asp Lys Lys Pro Ala Ala Ile Ser Trp
            995                 1000                1005

Ile Glu Gly Arg Gly Lys Ser Ile Val Ala Glu Ala Val Ile Pro
      1010                1015                1020

Gly Lys Val Val Lys Ser Val Leu Lys Thr Thr Val Glu Ser Leu
      1025                1030                1035

```
Cys Asn Val Asn Thr Lys Lys Asn Leu Ile Gly Ser Ala Met Ala
    1040                1045                1050

Gly Ser Val Gly Gly Phe Asn Ala His Ala Ala Asn Ile Leu Thr
    1055                1060                1065

Ala Val Phe Leu Ala Thr Gly Gln Asp Pro Ala Gln Asn Val Glu
    1070                1075                1080

Ser Ser Asn Cys Met Thr Leu Met Glu Pro Thr Asn Gly Gly Glu
    1085                1090                1095

Asp Leu Leu Met Thr Ile Ser Met Pro Cys Ile Glu Val Gly Thr
    1100                1105                1110

Val Gly Gly Thr Ile Leu Glu Pro Gln Gly Ala Val Leu Asp
    1115                1120                1125

Leu Leu Gly Val Arg Gly Ala His Pro Thr Asn Pro Gly Gln Asn
    1130                1135                1140

Ala Gln Gln Leu Ala Arg Ile Ile Ala Ser Ala Val Met Ala Gly
    1145                1150                1155

Glu Leu Ser Leu Ile Ser Ala Leu Ala Ala Gly His Leu Val Arg
    1160                1165                1170

Ala His Leu Ala His Asn Arg Ser Gln Leu Asn Thr Pro Met Pro
    1175                1180                1185

Ser Arg Pro His Thr Pro Gly Pro Glu Asp Val Ser His Val Gln
    1190                1195                1200

Gln Leu Pro Thr Pro Ser Ala Ser Asp Asp Lys Gly Val Thr Ala
    1205                1210                1215

Gln Gly Tyr Val Val Glu Ala Lys
    1220                1225

<210> SEQ ID NO 109
<211> LENGTH: 2667
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 109
atgttatcaa gattgttcag aatgcatggt ctatttgttg cttctcaccc ttgggaagta      60
atagttggta ctgtaacatt aacgatctgt atgatgtcta tgaacatgtt taccggaaac    120
aacaagattt gtggttggaa ttatgagtgt cctaagctgg aagaggatgt gttgagttca    180
gacatcatca tacttactat aacaagatgc attgcaatat tgtatatcta cttccaattt    240
caaaacctta gacaattggg tagtaaatac atcctaggca tcgccggatt gttcactatt    300
ttctctagtt ttgttttctc aaccgtcgtt attcacttt tggacaaaga gttaactggt    360
ttgaacgaag ctctaccatt cttcttgctg ctggtagatt tgtccagagc ttccgcttta    420
gctaaattcg ctctgtcctc taattctcaa gatgaagtta gagagaatat agcaagggga    480
atggccatac ttggacctac tttcacactt gatgcccttg tcgaatgttt ggttattggg    540
gttggcacaa tgtccggcgt tagacagtta gaaatcatgt gttgttttgg ctgtatgagt    600
gtcttggcta actactttgt ctttatgaca ttctttccag cttgcgtttc tttggtattg    660
gagctgtcaa gagaatcaag agaaggcaga ccaatatggc aactatcaca tttcgccaga    720
gtgttagaag aggaggaaaa caaacctaat cctgtcacac agagagtgaa aatgatcatg    780
tctttgggtt tagtcctagt gcatgctcat tctagatgga tcgcagatcc atcccctcag    840
aattctacag ctgataactc taagttagt ttaggtttag atgaaaatgt aagtaagagg    900
```

```
attgaacctt ccgtgtcttt gtggcaattc tacttatcaa aaatgatttc catggatatt    960
gaacaagtga taacgttgtc tttggcttta ttgttagccg ttaagtacat tttcttttgag   1020 caagccgaaa cggaatctac attatcactg aaaaacccaa ttacatcccc agtcgttacc   1080
cagaaaaaga taactgatga ttgctgtaga agagatccag tgttggtcag gaatgatcaa   1140
aagttccacg ccatggagga ggaaactagg aaaaacagag aaaggaaagt tgaagttatc   1200
aagcctctat tagcagaaaa tgacacttca catagggcca ctttcgttgt cggcaattca   1260
tctcttttag gtacgtcatt ggagctggaa acacaggaac cagaaatgga actaccagtt   1320
gaaccaagac caaatgagga atgtttgcaa atactagaga acgctgaaaa gggagccaag   1380
ttcctatctg atgccgagat tatccagctg gtcaatgcca agcacattcc tgcctacaag   1440
ttggaaaccc ttatggagac acatgagaga ggtgtgtcta ttaggagaca attactatct   1500
aaaaagttac ctgaaccaag ttccctacaa tacctgcctt atagagatta caattactcc   1560
ttggtaatgg gagcttgttg tgaaaatgtc attgggtaca tgccaattcc agtgggtgtc   1620
gccggtccac tatgtttgga cggtaaggaa tttcaagtac ctatggcaac gactgaaggc   1680
tgcttagttg catctacaaa cagaggttgt agagccattg gattaggtgg cggtgcttct   1740
tcaagagtct ggctgacgg tatgactaga ggtcctgttg tgagatttcc tagggcctgt   1800
gactctgcag aagttaaggc ttggttggaa actccagaag gtttcaccgt aatcaaagag   1860
gcctttgatt ccacatcaag ggtggccaga ttacaaaaac tacacatgtc tgtcgctggg   1920
agaaatctgt atatcagatt tcaatccaga tccggcgacg caatgggtat gaatatgatt   1980 tcaaaggga cagaaaaggc tttgtcaaag ctgcaggagt atttcccaga gatgcaaatc   2040
ttggccgtat ctggcaacta ttgcacagac aaaaagcctg ccgccatcaa ctggattgaa   2100
ggaagaggca atctgtggt tgtgaagct gtaattccag ccaaagttgt tagagaagtg   2160
ttaaagacca caacgaagc tatgattgaa gtaaacataa acaaaaactt agtagggtct   2220
gccatggctg gttcaattgg aggatacaac gctcatgctg ccaatattgt aaccgctatc   2280
tacatcgcat gtggacaaga tgctgcccaa aatgtcggtt cctcaaattg catcacattg   2340
atggaagcat ctggccctac aaacgaggat ttgtatatca gttgcacaat gccatctata   2400
gaaatgggga ctgtgggagg aggaactaac ttacttccac agcaagcctg cttacaaatg   2460
ctgggtgtac aaggagcctg tagagataat ccagggaga acgctagaca acttgccaga   2520
attgtttgtg gacagttat ggctggtgaa cttagtctaa tggcagcttt ggctgctggg   2580
cacctggtga gatctcatat gattcataat agaagtaaga ttaaccttca agatttgcaa   2640
ggtacgtgta cgaaaaaggc tgcctaa                                        2667
```

<210> SEQ ID NO 110
<211> LENGTH: 888
<212> TYPE: PRT
<213> ORGANISM: Bos taurus

<400> SEQUENCE: 110

```
Met Leu Ser Arg Leu Phe Arg Met His Gly Leu Phe Val Ala Ser His
1               5                   10                  15

Pro Trp Glu Val Ile Val Gly Thr Val Thr Leu Thr Ile Cys Met Met
            20                  25                  30

Ser Met Asn Met Phe Thr Gly Asn Asn Lys Ile Cys Gly Trp Asn Tyr
        35                  40                  45

Glu Cys Pro Lys Leu Glu Glu Asp Val Leu Ser Ser Asp Ile Ile Ile
```

```
                50                  55                  60
Leu Thr Ile Thr Arg Cys Ile Ala Ile Leu Tyr Ile Tyr Phe Gln Phe
 65                      70                  75                  80

Gln Asn Leu Arg Gln Leu Gly Ser Lys Tyr Ile Leu Gly Ile Ala Gly
                     85                  90                  95

Leu Phe Thr Ile Phe Ser Ser Phe Val Phe Ser Thr Val Val Ile His
                    100                 105                 110

Phe Leu Asp Lys Glu Leu Thr Gly Leu Asn Glu Ala Leu Pro Phe Phe
                115                 120                 125

Leu Leu Leu Val Asp Leu Ser Arg Ala Ser Ala Leu Ala Lys Phe Ala
            130                 135                 140

Leu Ser Ser Asn Ser Gln Asp Glu Val Arg Glu Asn Ile Ala Arg Gly
145                 150                 155                 160

Met Ala Ile Leu Gly Pro Thr Phe Thr Leu Asp Ala Leu Val Glu Cys
                    165                 170                 175

Leu Val Ile Gly Val Gly Thr Met Ser Gly Val Arg Gln Leu Glu Ile
                180                 185                 190

Met Cys Cys Phe Gly Cys Met Ser Val Leu Ala Asn Tyr Phe Val Phe
                195                 200                 205

Met Thr Phe Phe Pro Ala Cys Val Ser Leu Val Leu Glu Leu Ser Arg
210                 215                 220

Glu Ser Arg Glu Gly Arg Pro Ile Trp Gln Leu Ser His Phe Ala Arg
225                 230                 235                 240

Val Leu Glu Glu Glu Glu Asn Lys Pro Asn Pro Val Thr Gln Arg Val
                245                 250                 255

Lys Met Ile Met Ser Leu Gly Leu Val Leu Val His Ala His Ser Arg
                260                 265                 270

Trp Ile Ala Asp Pro Ser Pro Gln Asn Ser Thr Ala Asp Asn Ser Lys
            275                 280                 285

Val Ser Leu Gly Leu Asp Glu Asn Val Ser Lys Arg Ile Glu Pro Ser
            290                 295                 300

Val Ser Leu Trp Gln Phe Tyr Leu Ser Lys Met Ile Ser Met Asp Ile
305                 310                 315                 320

Glu Gln Val Ile Thr Leu Ser Leu Ala Leu Leu Ala Val Lys Tyr
                    325                 330                 335

Ile Phe Phe Glu Gln Ala Glu Thr Glu Ser Thr Leu Ser Leu Lys Asn
                340                 345                 350

Pro Ile Thr Ser Pro Val Val Thr Gln Lys Lys Ile Thr Asp Asp Cys
                355                 360                 365

Cys Arg Arg Asp Pro Val Leu Val Arg Asn Asp Gln Lys Phe His Ala
            370                 375                 380

Met Glu Glu Glu Thr Arg Lys Asn Arg Glu Arg Lys Val Glu Val Ile
385                 390                 395                 400

Lys Pro Leu Leu Ala Glu Asn Asp Thr Ser His Arg Ala Thr Phe Val
                    405                 410                 415

Val Gly Asn Ser Ser Leu Leu Gly Thr Ser Leu Glu Leu Glu Thr Gln
                420                 425                 430

Glu Pro Glu Met Glu Leu Pro Val Glu Pro Arg Pro Asn Glu Glu Cys
            435                 440                 445

Leu Gln Ile Leu Glu Asn Ala Glu Lys Gly Ala Lys Phe Leu Ser Asp
            450                 455                 460

Ala Glu Ile Ile Gln Leu Val Asn Ala Lys His Ile Pro Ala Tyr Lys
465                 470                 475                 480
```

```
Leu Glu Thr Leu Met Glu Thr His Glu Arg Gly Val Ser Ile Arg Arg
                485                 490                 495

Gln Leu Leu Ser Lys Lys Leu Pro Glu Pro Ser Ser Leu Gln Tyr Leu
            500                 505                 510

Pro Tyr Arg Asp Tyr Asn Tyr Ser Leu Val Met Gly Ala Cys Cys Glu
            515                 520                 525

Asn Val Ile Gly Tyr Met Pro Ile Pro Val Gly Val Ala Gly Pro Leu
            530                 535                 540

Cys Leu Asp Gly Lys Glu Phe Gln Val Pro Met Ala Thr Thr Glu Gly
545                 550                 555                 560

Cys Leu Val Ala Ser Thr Asn Arg Gly Cys Arg Ala Ile Gly Leu Gly
            565                 570                 575

Gly Gly Ala Ser Ser Arg Val Leu Ala Asp Gly Met Thr Arg Gly Pro
            580                 585                 590

Val Val Arg Phe Pro Arg Ala Cys Asp Ser Ala Glu Val Lys Ala Trp
            595                 600                 605

Leu Glu Thr Pro Glu Gly Phe Thr Val Ile Lys Glu Ala Phe Asp Ser
            610                 615                 620

Thr Ser Arg Val Ala Arg Leu Gln Lys Leu His Met Ser Val Ala Gly
625                 630                 635                 640

Arg Asn Leu Tyr Ile Arg Phe Gln Ser Arg Ser Gly Asp Ala Met Gly
                645                 650                 655

Met Asn Met Ile Ser Lys Gly Thr Glu Lys Ala Leu Ser Lys Leu Gln
                660                 665                 670

Glu Tyr Phe Pro Glu Met Gln Ile Leu Ala Val Ser Gly Asn Tyr Cys
            675                 680                 685

Thr Asp Lys Lys Pro Ala Ala Ile Asn Trp Ile Glu Gly Arg Gly Lys
            690                 695                 700

Ser Val Val Cys Glu Ala Val Ile Pro Ala Lys Val Val Arg Glu Val
705                 710                 715                 720

Leu Lys Thr Thr Thr Glu Ala Met Ile Glu Val Asn Ile Asn Lys Asn
                725                 730                 735

Leu Val Gly Ser Ala Met Ala Gly Ser Ile Gly Gly Tyr Asn Ala His
            740                 745                 750

Ala Ala Asn Ile Val Thr Ala Ile Tyr Ile Ala Cys Gly Gln Asp Ala
            755                 760                 765

Ala Gln Asn Val Gly Ser Ser Asn Cys Ile Thr Leu Met Glu Ala Ser
            770                 775                 780

Gly Pro Thr Asn Glu Asp Leu Tyr Ile Ser Cys Thr Met Pro Ser Ile
785                 790                 795                 800

Glu Ile Gly Thr Val Gly Gly Gly Thr Asn Leu Leu Pro Gln Gln Ala
            805                 810                 815

Cys Leu Gln Met Leu Gly Val Gln Gly Ala Cys Arg Asp Asn Pro Gly
            820                 825                 830

Glu Asn Ala Arg Gln Leu Ala Arg Ile Val Cys Gly Thr Val Met Ala
            835                 840                 845

Gly Glu Leu Ser Leu Met Ala Ala Leu Ala Ala Gly His Leu Val Arg
            850                 855                 860

Ser His Met Ile His Asn Arg Ser Lys Ile Asn Leu Gln Asp Leu Gln
865                 870                 875                 880

Gly Thr Cys Thr Lys Lys Ala Ala
                885
```

<210> SEQ ID NO 111
<211> LENGTH: 1704
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 111

| | |
|---|---|
| atggatttga gaaggaaatt accacctaag cctccatctt caacaacaac aaaacagcca | 60 |
| agtcataggt cccattctcc tacgccaatt ccaaaggctt cagatgcatt gcctcttcca | 120 |
| ttgtacctga ccaatacgtt tttcttcact cttttctttt ccgtagcata ttacctgttg | 180 |
| cataggtgga gagacaagat tagatccgga acacctttac acgttgtgac actgactgaa | 240 |
| ctatccgcaa ttgtactgct gattgcttcc ttcatctatc ttttaggctt tttcggtatt | 300 |
| gattttgtgc aatctttcac atcaagagaa aatgagcaac taaacaacga tgatcacaac | 360 |
| gtcgtgtcaa caaacaatgt tttatctgat agaaggttag tttacgacta tggattcgat | 420 |
| gtgacaggag acaacgataa cgataatgat gacgatgtta ttgtgaaaag tgtcgtttct | 480 |
| ggggaagtta attcttatag tttggaggct tccctaggag attgttacag agccgcaaag | 540 |
| attagaaaga gagccgtcga gagaattgtc gggagagaag tattaggctt gggtttcgag | 600 |
| ggatttgatt atgaatctat cctggggcaa tgttgtgaaa tgcctatcgg gtacgtccaa | 660 |
| gtgccagtag gtgtcgctgg acctttattg ttaaatggtg gggaattcat ggttccaatg | 720 |
| gctacaactg aaggctgtct tgtagcttcc actaatagag gttgtaaagc catatgctta | 780 |
| tcaggtggtg ccactgccat attgctaaaa gatggtatga caagagcccc agtagtgaga | 840 |
| ttcgccacag ctgagagagc ttcacaacta aagtttttact tggaagatgg tgtcaatttc | 900 |
| gatacattgt ctgttgtctt taacaaaagt tcaagatttg ccagattgca aaacatccaa | 960 |
| tgctcaattg ccggtaaaaa cttgtacatt aggtttactt gctccacagg cgacgccatg | 1020 |
| ggtatgaaca tggtttcaaa aggagtacaa aatgtattag acttttttaca aaatgatttt | 1080 |
| cctgatatgg acgtaattgg gatctcttgg aagttctgct ctgacaaaaa gccaacagct | 1140 |
| gtcaactgga ttgagggcag aggaaagtct gtcgttttcc aggccgtaat taccaaaaag | 1200 |
| gtggttagaa agtctgcact gaaccctcaa acttgcacat gtagaacttt gacctgttta | 1260 |
| agaccattat tggttctgct acttctggtt ttgctagtgg acttaatgca tatgcttcat | 1320 |
| atcgtgtctg ccgtgttcat cgctaccggt caagatccag ctcagaatat cgaatctagt | 1380 |
| cactgtatca ctatgatgga ggctgtcaac aatggtaagg atttgcacgt taatgttacg | 1440 |
| atgccatcta tagaagttgg cacggtggga ggtggcactc agctagcctc tcaatcagcc | 1500 |
| tgtttgaact tgcttggtgt aaagggtgcc tgtatagaat ccccaggatc aaacgcccag | 1560 |
| ttgttagcta gaatcgttgc tggttctgtt ctggcaggcg aattaagttt gatgtcagct | 1620 |
| ataagtgctg ggcaactagt taaatctcat atgaaataca ataggtctag tagagatatg | 1680 |
| tcagcaatag cttctaaggt ctaa | 1704 |

<210> SEQ ID NO 112
<211> LENGTH: 567
<212> TYPE: PRT
<213> ORGANISM: Artemisia annua

<400> SEQUENCE: 112

Met Asp Leu Arg Arg Lys Leu Pro Pro Lys Pro Pro Ser Ser Thr Thr
1               5                   10                  15

```
Thr Lys Gln Pro Ser His Arg Ser His Ser Pro Thr Pro Ile Pro Lys
            20                  25                  30

Ala Ser Asp Ala Leu Pro Leu Pro Leu Tyr Leu Thr Asn Thr Phe Phe
        35                  40                  45

Phe Thr Leu Phe Phe Ser Val Ala Tyr Tyr Leu Leu His Arg Trp Arg
    50                  55                  60

Asp Lys Ile Arg Ser Gly Thr Pro Leu His Val Val Thr Leu Thr Glu
65                  70                  75                  80

Leu Ser Ala Ile Val Leu Leu Ile Ala Ser Phe Ile Tyr Leu Leu Gly
                85                  90                  95

Phe Phe Gly Ile Asp Phe Val Gln Ser Phe Thr Ser Arg Glu Asn Glu
            100                 105                 110

Gln Leu Asn Asn Asp Asp His Asn Val Val Ser Thr Asn Asn Val Leu
        115                 120                 125

Ser Asp Arg Arg Leu Val Tyr Asp Tyr Gly Phe Asp Val Thr Gly Asp
    130                 135                 140

Asn Asp Asn Asp Asn Asp Asp Val Ile Val Lys Ser Val Val Ser
145                 150                 155                 160

Gly Glu Val Asn Ser Tyr Ser Leu Glu Ala Ser Leu Gly Asp Cys Tyr
                165                 170                 175

Arg Ala Ala Lys Ile Arg Lys Arg Ala Val Glu Arg Ile Val Gly Arg
            180                 185                 190

Glu Val Leu Gly Leu Gly Phe Glu Gly Phe Asp Tyr Glu Ser Ile Leu
        195                 200                 205

Gly Gln Cys Cys Glu Met Pro Ile Gly Tyr Val Gln Val Pro Val Gly
    210                 215                 220

Val Ala Gly Pro Leu Leu Leu Asn Gly Gly Glu Phe Met Val Pro Met
225                 230                 235                 240

Ala Thr Thr Glu Gly Cys Leu Val Ala Ser Thr Asn Arg Gly Cys Lys
                245                 250                 255

Ala Ile Cys Leu Ser Gly Gly Ala Thr Ala Ile Leu Leu Lys Asp Gly
            260                 265                 270

Met Thr Arg Ala Pro Val Val Arg Phe Ala Thr Ala Glu Arg Ala Ser
        275                 280                 285

Gln Leu Lys Phe Tyr Leu Glu Asp Gly Val Asn Phe Asp Thr Leu Ser
    290                 295                 300

Val Val Phe Asn Lys Ser Ser Arg Phe Ala Arg Leu Gln Asn Ile Gln
305                 310                 315                 320

Cys Ser Ile Ala Gly Lys Asn Leu Tyr Ile Arg Phe Thr Cys Ser Thr
                325                 330                 335

Gly Asp Ala Met Gly Met Asn Met Val Ser Lys Gly Val Gln Asn Val
            340                 345                 350

Leu Asp Phe Leu Gln Asn Asp Phe Pro Asp Met Asp Val Ile Gly Ile
        355                 360                 365

Ser Trp Lys Phe Cys Ser Asp Lys Lys Pro Thr Ala Val Asn Trp Ile
    370                 375                 380

Glu Gly Arg Gly Lys Ser Val Val Phe Gln Ala Val Ile Thr Lys Lys
385                 390                 395                 400

Val Val Arg Lys Ser Ala Leu Asn Pro Gln Thr Cys Thr Cys Arg Thr
                405                 410                 415

Leu Thr Cys Leu Arg Pro Leu Leu Val Leu Leu Leu Val Leu Leu
            420                 425                 430
```

```
Val Asp Leu Met His Met Leu His Ile Val Ser Ala Val Phe Ile Ala
            435                 440                 445

Thr Gly Gln Asp Pro Ala Gln Asn Ile Glu Ser His Cys Ile Thr
    450                 455                 460

Met Met Glu Ala Val Asn Asn Gly Lys Asp Leu His Val Asn Val Thr
465                 470                 475                 480

Met Pro Ser Ile Glu Val Gly Thr Val Gly Gly Thr Gln Leu Ala
                485                 490                 495

Ser Gln Ser Ala Cys Leu Asn Leu Leu Gly Val Lys Gly Ala Cys Ile
                500                 505                 510

Glu Ser Pro Gly Ser Asn Ala Gln Leu Leu Ala Arg Ile Val Ala Gly
            515                 520                 525

Ser Val Leu Ala Gly Glu Leu Ser Leu Met Ser Ala Ile Ser Ala Gly
        530                 535                 540

Gln Leu Val Lys Ser His Met Lys Tyr Asn Arg Ser Ser Arg Asp Met
545                 550                 555                 560

Ser Ala Ile Ala Ser Lys Val
                565
```

<210> SEQ ID NO 113
<211> LENGTH: 1308
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113

```
atgtttagaa gagctatact gttaggatgc tctgctgcca agacaccatg gtctgagtgt      60
tctaacgctc aattagttga tgcagttaag tctagaaaga tctcattcta cggtcttgaa     120
caagccttgg aaccagatta tagaagggct atcgaagtaa ggagagaggt tgtctctgaa     180
atcgcctcac aacagccaga agcaaaaaag aagcaatccg cattgcacac aataccattt     240
gagaattatg attggaataa ggtcgttggc caaaactgtg aaaacattat tggatacgtc     300
ccaataccac tgggcgttgc tggccctatt ttgattgatg gtaaagagta cccaatacca     360
atggctacaa cagaaggcgc tttggtcgct agtactcata gaggtgctag agctattaca     420
agatccggag gttgtaagac attgttatta ggtgaaggta tgacaagagc accagtggtt     480
gaattgcctt cattagagga agctgggcgt tgcacaagt actgtaatga aacttctta      540 tctttaaagg aagcatttga atcaactacc aatatggaa acttaattc tttaaagtgc      600 gtactagctg gtagaaaagc ataccttaga ttcagagcca ctacaggcga tgctatgggc     660
atgaacatga taacaagggg tgtagacaaa gcactgtctg ttctacagca acatttccct     720
tcaatggaaa tcctagccct aagtggtaat tactgtaccg acaaaaagcc atctgctgta     780
aattggattg atggcagagg taaatcagtg gttgcagaag ccactttatt ggctgatgtt     840
gtcgaagata ctctgaaatg tacagtcgat tctttggtat ccttgaatat cgacaaaaac     900
cttgttgggt cagctatggc tggttctgtt ggaggtttta acgcccaggc tgcaaacgct     960
gtggcagcca ttttcattgc aaccggtcaa gatcctgctc aagtggtaga agttcaatg    1020 tgtatcacta caatgtccaa ggtaggtaac gatctattga tctctgtgac catgccttct    1080
atcgaggtcg gggtcgtggg aggagggact ggtcttgctg cccaagagg atgcttagag    1140 ttaataggggt gcggaggccc atctaaggag tctcctggta ctaatgccca acttctaagt    1200
agagttgttg cagctggcgt tttatcagcc gaactttcct tgatgtccgg actggcagca    1260
```
ggtcatctat tgtcagcaca tatgagattg aacagaaaga agaaataa          1308

<210> SEQ ID NO 114
<211> LENGTH: 435
<212> TYPE: PRT
<213> ORGANISM: Trypanosoma cruzi

<400> SEQUENCE: 114

```
Met Phe Arg Arg Ala Ile Leu Leu Gly Cys Ser Ala Ala Lys Thr Pro
1               5                   10                  15

Trp Ser Glu Cys Ser Asn Ala Gln Leu Val Asp Ala Val Lys Ser Arg
            20                  25                  30

Lys Ile Ser Phe Tyr Gly Leu Glu Gln Ala Leu Glu Pro Asp Tyr Arg
        35                  40                  45

Arg Ala Ile Glu Val Arg Arg Glu Val Val Ser Glu Ile Ala Ser Gln
    50                  55                  60

Gln Pro Glu Ala Lys Lys Lys Gln Ser Ala Leu His Thr Ile Pro Phe
65                  70                  75                  80

Glu Asn Tyr Asp Trp Asn Lys Val Val Gly Gln Asn Cys Glu Asn Ile
                85                  90                  95

Ile Gly Tyr Val Pro Ile Pro Leu Gly Val Ala Gly Pro Ile Leu Ile
            100                 105                 110

Asp Gly Lys Glu Tyr Pro Ile Pro Met Ala Thr Thr Glu Gly Ala Leu
        115                 120                 125

Val Ala Ser Thr His Arg Gly Ala Arg Ala Ile Thr Arg Ser Gly Gly
    130                 135                 140

Cys Lys Thr Leu Leu Leu Gly Glu Gly Met Thr Arg Ala Pro Val Val
145                 150                 155                 160

Glu Leu Pro Ser Leu Glu Glu Ala Gly Arg Leu His Lys Tyr Cys Asn
                165                 170                 175

Glu Asn Phe Leu Ser Leu Lys Glu Ala Phe Glu Ser Thr Thr Gln Tyr
            180                 185                 190

Gly Lys Leu Asn Ser Leu Lys Cys Val Leu Ala Gly Arg Lys Ala Tyr
        195                 200                 205

Leu Arg Phe Arg Ala Thr Thr Gly Asp Ala Met Gly Met Asn Met Ile
    210                 215                 220

Thr Lys Gly Val Asp Lys Ala Leu Ser Val Leu Gln Gln His Phe Pro
225                 230                 235                 240

Ser Met Glu Ile Leu Ala Leu Ser Gly Asn Tyr Cys Thr Asp Lys Lys
                245                 250                 255

Pro Ser Ala Val Asn Trp Ile Asp Gly Arg Gly Lys Ser Val Val Ala
            260                 265                 270

Glu Ala Thr Leu Leu Ala Asp Val Glu Asp Thr Leu Lys Cys Thr
        275                 280                 285

Val Asp Ser Leu Val Ser Leu Asn Ile Asp Lys Asn Leu Val Gly Ser
    290                 295                 300

Ala Met Ala Gly Ser Val Gly Gly Phe Asn Ala Gln Ala Ala Asn Ala
305                 310                 315                 320

Val Ala Ala Ile Phe Ile Ala Thr Gly Gln Asp Pro Ala Gln Val Val
                325                 330                 335

Glu Ser Ser Met Cys Ile Thr Thr Met Ser Lys Val Gly Asn Asp Leu
            340                 345                 350

Leu Ile Ser Val Thr Met Pro Ser Ile Glu Val Gly Val Val Gly Gly
        355                 360                 365
```

```
Gly Thr Gly Leu Ala Ala Gln Arg Gly Cys Leu Glu Leu Ile Gly Cys
        370                 375                 380

Gly Gly Pro Ser Lys Glu Ser Pro Gly Thr Asn Ala Gln Leu Leu Ser
385                 390                 395                 400

Arg Val Val Ala Ala Gly Val Leu Ser Ala Glu Leu Ser Leu Met Ser
                405                 410                 415

Gly Leu Ala Ala Gly His Leu Leu Ser Ala His Met Arg Leu Asn Arg
                420                 425                 430

Lys Lys Lys
        435

<210> SEQ ID NO 115
<211> LENGTH: 1281
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 115
atgcaatccc tggacaaaaa ctttagacac ttatcaagac aacagaagtt acaacagcta      60
gttgataaac aatggctatc agaggaacaa ttcaatattc tacttaacca cccacttatt     120
gatgaagagg tagcaaactc attgatgaaa aatgtcatcg cacagggcgc actgcctgtt     180
ggtttactac caaatatcat cgttgatgac aaagcatacg tcgtgcctat gatggtggaa     240
gagccatctg ttgttgccgc tgcttcatac ggcgctaaat tggtgaacca acaggtggt      300 ttcaaaaccg tgtcctcaga acgtatcatg ataggtcaaa tagtatttga tggagtcgat     360
gataccgaga actgtctgc agatatcaag gctcttgaaa acaaatcca tcagattgca      420 gatgaggctt acccttctat taaggccaga ggtggaggct atcaaaggat cgccatcgat     480
acattcccag aacaacagtt gctttcattg aaggttttcg ttgatactaa ggatgctatg     540
ggcgctaata tgttaaacac aatcctagaa gcaatcacag ccttttttgaa aaacgaattc    600 ccacaatctg atatcttgat gtctatcctt tccaaccacg caacagccag tgttgtcaag    660
gtccagggtg aaatagacgt taaggatttg caagaggag aacgtactgg agaagaggtc     720
gctaagagaa tggaaagagc atctgtgtta gctcaagtgg acattcatag agcagcaaca    780
cacaataagg gtgttatgaa tggcattcat gctgtagtct tggctacagg taatgatact    840
agaggtgcag aagcctctgc tcacgcttac gcttccaaag acggtcaata tagagggata    900
gctacatgga gatacgatca agagagacaa aggttaatag aactataga gttccaatg      960 actctggcca tgttggtgg cggtaccaag gtactgccta ttgctaaggc ctctttagaa    1020
ctgttaaacg tagaaagtgc ccaagagttg ggacatgttg tcgctgccgt tggactagct    1080
caaaacttcg ctgcatgtag agctttggtt tccgaaggta ttcaacaagg gcatatgtct    1140
ttgcaataca agtctttagc catcgtagtc ggggctaagg gcgatgaaat tgctcaggta    1200
gccgaagcac taaagcaaga gccaagagca aacactcaag ttgcagagag aattttgcaa    1260
gatttgagaa gtcaacaata a                                              1281

<210> SEQ ID NO 116
<211> LENGTH: 426
<212> TYPE: PRT
<213> ORGANISM: Staphylococcus aureus

<400> SEQUENCE: 116
```

```
Met Gln Ser Leu Asp Lys Asn Phe Arg His Leu Ser Arg Gln Gln Lys
1               5                   10                  15
Leu Gln Gln Leu Val Asp Lys Gln Trp Leu Ser Glu Glu Gln Phe Asn
            20                  25                  30
Ile Leu Leu Asn His Pro Leu Ile Asp Glu Glu Val Ala Asn Ser Leu
        35                  40                  45
Ile Glu Asn Val Ile Ala Gln Gly Ala Leu Pro Val Gly Leu Leu Pro
50                  55                  60
Asn Ile Ile Val Asp Asp Lys Ala Tyr Val Pro Met Met Val Glu
65                  70                  75                  80
Glu Pro Ser Val Val Ala Ala Ser Tyr Gly Ala Lys Leu Val Asn
                85                  90                  95
Gln Thr Gly Gly Phe Lys Thr Val Ser Ser Glu Arg Ile Met Ile Gly
                100                 105                 110
Gln Ile Val Phe Asp Gly Val Asp Asp Thr Glu Lys Leu Ser Ala Asp
            115                 120                 125
Ile Lys Ala Leu Glu Lys Gln Ile His Gln Ile Ala Asp Glu Ala Tyr
        130                 135                 140
Pro Ser Ile Lys Ala Arg Gly Gly Tyr Gln Arg Ile Ala Ile Asp
145                 150                 155                 160
Thr Phe Pro Glu Gln Gln Leu Leu Ser Leu Lys Val Phe Val Asp Thr
                165                 170                 175
Lys Asp Ala Met Gly Ala Asn Met Leu Asn Thr Ile Leu Glu Ala Ile
            180                 185                 190
Thr Ala Phe Leu Lys Asn Glu Phe Pro Gln Ser Asp Ile Leu Met Ser
        195                 200                 205
Ile Leu Ser Asn His Ala Thr Ala Ser Val Val Lys Val Gln Gly Glu
        210                 215                 220
Ile Asp Val Lys Asp Leu Ala Arg Gly Glu Arg Thr Gly Glu Glu Val
225                 230                 235                 240
Ala Lys Arg Met Glu Arg Ala Ser Val Leu Ala Gln Val Asp Ile His
                245                 250                 255
Arg Ala Ala Thr His Asn Lys Gly Val Met Asn Gly Ile His Ala Val
            260                 265                 270
Val Leu Ala Thr Gly Asn Asp Thr Arg Gly Ala Glu Ala Ser Ala His
        275                 280                 285
Ala Tyr Ala Ser Lys Asp Gly Gln Tyr Arg Gly Ile Ala Thr Trp Arg
        290                 295                 300
Tyr Asp Gln Glu Arg Gln Arg Leu Ile Gly Thr Ile Glu Val Pro Met
305                 310                 315                 320
Thr Leu Ala Ile Val Gly Gly Gly Thr Lys Val Leu Pro Ile Ala Lys
                325                 330                 335
Ala Ser Leu Glu Leu Leu Asn Val Glu Ser Ala Gln Glu Leu Gly His
            340                 345                 350
Val Val Ala Ala Val Gly Leu Ala Gln Asn Phe Ala Ala Cys Arg Ala
        355                 360                 365
Leu Val Ser Glu Gly Ile Gln Gln Gly His Met Ser Leu Gln Tyr Lys
        370                 375                 380
Ser Leu Ala Ile Val Val Gly Ala Lys Gly Asp Glu Ile Ala Gln Val
385                 390                 395                 400
Ala Glu Ala Leu Lys Gln Glu Pro Arg Ala Asn Thr Gln Val Ala Glu
                405                 410                 415
Arg Ile Leu Gln Asp Leu Arg Ser Gln Gln
```

<210> SEQ ID NO 117
<211> LENGTH: 1311
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 117

```
atgcaggtct taagattgga taggagacat tacaaaagtg caagattag aagagcaatg      60
agttctagaa ttcctggttt ctacaaattg tcagtcgagg aaagactgaa aaaggttgct    120
gaatttgcag ggttatctga tgaggaagtg aaagctgttt tgtcacaagg tttacctttg    180
gacgtagctg atagaatgat cgaaaatgtg atcggtacat ttgaattacc acttggtata    240
gcaaccaatt tccttattga tggcaaggat tatctaatcc ctatggctat agaggaacca    300
tcagtagttg cagctgcttc taacgcagct agaatggcca gagagtctgg cgggtttaca    360
actgattaca cagggtccct gatgattggt caaattcaag tcacaaaact gttgaatcca    420
aatgcagcta agttcgaagt tctacgtcaa aaagacgaaa tcatagaaag agcaaatgag    480
tgtgatccaa tgttggtgaa tttgggcggt ggatgtaaag atatagaagc aagggtgatc    540
gatacaatca tgggtaagat gctaattgtt catctgatcg ttgatgttaa agacgctatg    600
ggtgcaaatg ctgtcaacac tatgtgtgaa aaagttgctc ctttcatcga acgtattact    660
gggggaaagg tctatcttag aatcatttcc aacttggctg catatagact tgctagagca    720
aaggccgttt ttgacaaaga cgttattggc ggagaggagg ttgtagaagg gatcatgctt    780
gcatacgcct tcgctgccgc tgacccattt cgttgcgcca cccacaataa gggtatcatg    840
aatggcatat cagccttaat gatcgctaca ggaaacgact ttagagccat tgaagcagga    900
gctcattcct atgctgcaat aggtggatac aaaccactaa ctaccacga agttgataga    960
aaaggtaatc tagtaggcac aattgaaata cctatggcag taggcgtgat tggtggtgca   1020
accaaagtca acccactagc caagatctct cttaagatac taggagtgaa cactgctgaa   1080
gagttagcca gagtcgcagc cgctctaggt ttggctcaaa actttgctgc cttaagagcc   1140
ttggccacag aaggtatcca agaggtcac atggaattac atgccaggaa cttagcaatc   1200
atggctggag ctactggaga tgaggttgac agagttgtag agattatggt gagagatggc   1260
aaaatcagat tggactacgc taaggaagta ttggagagac tgcgttccta a            1311
```

<210> SEQ ID NO 118
<211> LENGTH: 436
<212> TYPE: PRT
<213> ORGANISM: Archaeoglobus fulgidus

<400> SEQUENCE: 118

Met Gln Val Leu Arg Leu Asp Arg Arg His Tyr Lys Ser Gly Lys Ile
1               5                   10                  15

Arg Arg Ala Met Ser Ser Arg Ile Pro Gly Phe Tyr Lys Leu Ser Val
            20                  25                  30

Glu Glu Arg Leu Lys Lys Val Ala Glu Phe Ala Gly Leu Ser Asp Glu
        35                  40                  45

Glu Val Lys Ala Val Leu Ser Gln Gly Leu Pro Leu Asp Val Ala Asp
    50                  55                  60

Arg Met Ile Glu Asn Val Ile Gly Thr Phe Glu Leu Pro Leu Gly Ile
65                  70                  75                  80

```
Ala Thr Asn Phe Leu Ile Asp Gly Lys Asp Tyr Leu Ile Pro Met Ala
                85                  90                  95

Ile Glu Glu Pro Ser Val Val Ala Ala Ser Asn Ala Ala Arg Met
            100                 105                 110

Ala Arg Glu Ser Gly Gly Phe Thr Thr Asp Tyr Thr Gly Ser Leu Met
        115                 120                 125

Ile Gly Gln Ile Gln Val Thr Lys Leu Leu Asn Pro Asn Ala Ala Lys
    130                 135                 140

Phe Glu Val Leu Arg Gln Lys Asp Glu Ile Ile Glu Arg Ala Asn Glu
145                 150                 155                 160

Cys Asp Pro Met Leu Val Asn Leu Gly Gly Cys Lys Asp Ile Glu
                165                 170                 175

Ala Arg Val Ile Asp Thr Ile Met Gly Lys Met Leu Ile Val His Leu
            180                 185                 190

Ile Val Asp Val Lys Asp Ala Met Gly Ala Asn Ala Val Asn Thr Met
    195                 200                 205

Cys Glu Lys Val Ala Pro Phe Ile Glu Arg Ile Thr Gly Gly Lys Val
    210                 215                 220

Tyr Leu Arg Ile Ile Ser Asn Leu Ala Ala Tyr Arg Leu Ala Arg Ala
225                 230                 235                 240

Lys Ala Val Phe Asp Lys Asp Val Ile Gly Gly Glu Val Val Glu
                245                 250                 255

Gly Ile Met Leu Ala Tyr Ala Phe Ala Ala Asp Pro Phe Arg Cys
                260                 265                 270

Ala Thr His Asn Lys Gly Ile Met Asn Gly Ile Ser Ala Leu Met Ile
        275                 280                 285

Ala Thr Gly Asn Asp Phe Arg Ala Ile Glu Ala Gly Ala His Ser Tyr
        290                 295                 300

Ala Ala Ile Gly Gly Tyr Lys Pro Leu Thr Thr Tyr Glu Val Asp Arg
305                 310                 315                 320

Lys Gly Asn Leu Val Gly Thr Ile Glu Ile Pro Met Ala Val Gly Val
                325                 330                 335

Ile Gly Gly Ala Thr Lys Val Asn Pro Leu Ala Lys Ile Ser Leu Lys
            340                 345                 350

Ile Leu Gly Val Asn Thr Ala Glu Glu Leu Ala Arg Val Ala Ala Ala
        355                 360                 365

Leu Gly Leu Ala Gln Asn Phe Ala Ala Leu Arg Ala Leu Ala Thr Glu
    370                 375                 380

Gly Ile Gln Arg Gly His Met Glu Leu His Ala Arg Asn Leu Ala Ile
385                 390                 395                 400

Met Ala Gly Ala Thr Gly Asp Glu Val Asp Arg Val Val Glu Ile Met
                405                 410                 415

Val Arg Asp Gly Lys Ile Arg Leu Asp Tyr Ala Lys Glu Val Leu Glu
            420                 425                 430

Arg Leu Arg Ser
        435

<210> SEQ ID NO 119
<211> LENGTH: 1287
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 119

```
atgtccttag attcaagact gccagctttc agaaatctgt ctccagctgc aagactagat        60
cacattggcc aacttttggg actaagtcat gacgacgttt cccttttagc aaacgccggt       120
gctttaccaa tggatatcgc taatggtatg attgaaaatg taatcgggac ctttgaactg       180
ccatatgcag tggccagtaa ctttcagatc aatggccgtg acgtcttagt accattagtt       240
gtggaggaac ctagtatcgt tgctgcagcc tcttacatgg caaagttagc tagagccaat       300
ggtgggttca ctacatcttc atctgctcca ctaatgcatg cacaagtaca aattgtcggc       360
attcaggatc cactaaacgc aagattgtct ttactgcgta gaaaggatga gatcatagaa       420
ttagccaata ggaaggacca acttctgaat tcattgggcg gtggttgcag agacatagag       480
gtgcatacat ttgccgatac tccaagagga ccaatgcttg tagcacacct tattgtcgat       540
gtgcgtgatg ccatgggagc taatactgtt aacactatgg ctgaagcagt agcacctctg       600
atggaagcca taacaggtgg ccaggtaaga ttgagaatcc tttccaattt ggctgatctt       660
agattggcca gagcccaagt gagaatcact cctcagcaat ggaaactgc cgaattctca        720
ggtgaggcag taattgaggg tatcttggac gcatatgctt ttgccgctgt ggacccttac       780
agagccgcta cccacaacaa aggcataatg aacggtatcg atccttttgat cgtcgctaca      840
ggaaatgatt ggagagctgt tgaggcagga gctcatgcat acgcttgtag atccggacat       900
tacggttcat taacaacatg ggaaaaagat aacaatggac acttggtcgg acattggaa        960
atgcctatgc cagttggttt agttgggggt gctacaaaaa cccatcctct tgctcaattg      1020
tctttgagga tacttggtgt caaaactgct caagcactag ccgaaattgc cgttgctgtt      1080
ggtttggcac aaaacttggg tgcaatgcgt gctttagcta cagaaggcat ccaaagagga      1140
catatggctc tacacgctag aaacattgca gttgttgcag gagccagagg tgatgaggtt      1200
gattgggtgg ctagacaact tgtcgaatat catgatgtca gagcagacag ggctgtggca      1260
ttactgaaac agaagagagg tcaataa                                          1287
```

<210> SEQ ID NO 120
<211> LENGTH: 428
<212> TYPE: PRT
<213> ORGANISM: Pseudomonas mevalonii

<400> SEQUENCE: 120

```
Met Ser Leu Asp Ser Arg Leu Pro Ala Phe Arg Asn Leu Ser Pro Ala
1               5                   10                  15

Ala Arg Leu Asp His Ile Gly Gln Leu Leu Gly Leu Ser His Asp Asp
                20                  25                  30

Val Ser Leu Leu Ala Asn Ala Gly Ala Leu Pro Met Asp Ile Ala Asn
            35                  40                  45

Gly Met Ile Glu Asn Val Ile Gly Thr Phe Glu Leu Pro Tyr Ala Val
        50                  55                  60

Ala Ser Asn Phe Gln Ile Asn Gly Arg Asp Val Leu Val Pro Leu Val
65                  70                  75                  80

Val Glu Glu Pro Ser Ile Val Ala Ala Ser Tyr Met Ala Lys Leu
                85                  90                  95

Ala Arg Ala Asn Gly Gly Phe Thr Thr Ser Ser Ala Pro Leu Met
                100                 105                 110

His Ala Gln Val Gln Ile Val Gly Ile Gln Asp Pro Leu Asn Ala Arg
            115                 120                 125

Leu Ser Leu Leu Arg Arg Lys Asp Glu Ile Ile Glu Leu Ala Asn Arg
```

```
                130                 135                 140
Lys Asp Gln Leu Leu Asn Ser Leu Gly Gly Gly Cys Arg Asp Ile Glu
145                 150                 155                 160

Val His Thr Phe Ala Asp Thr Pro Arg Gly Pro Met Leu Val Ala His
                165                 170                 175

Leu Ile Val Asp Val Arg Asp Ala Met Gly Ala Asn Thr Val Asn Thr
                180                 185                 190

Met Ala Glu Ala Val Ala Pro Leu Met Glu Ala Ile Thr Gly Gly Gln
                195                 200                 205

Val Arg Leu Arg Ile Leu Ser Asn Leu Ala Asp Leu Arg Leu Ala Arg
210                 215                 220

Ala Gln Val Arg Ile Thr Pro Gln Gln Leu Glu Thr Ala Glu Phe Ser
225                 230                 235                 240

Gly Glu Ala Val Ile Glu Gly Ile Leu Asp Ala Tyr Ala Phe Ala Ala
                245                 250                 255

Val Asp Pro Tyr Arg Ala Ala Thr His Asn Lys Gly Ile Met Asn Gly
                260                 265                 270

Ile Asp Pro Leu Ile Val Ala Thr Gly Asn Asp Trp Arg Ala Val Glu
                275                 280                 285

Ala Gly Ala His Ala Tyr Ala Cys Arg Ser Gly His Tyr Gly Ser Leu
                290                 295                 300

Thr Thr Trp Glu Lys Asp Asn Asn Gly His Leu Val Gly Thr Leu Glu
305                 310                 315                 320

Met Pro Met Pro Val Gly Leu Val Gly Gly Ala Thr Lys Thr His Pro
                325                 330                 335

Leu Ala Gln Leu Ser Leu Arg Ile Leu Gly Val Lys Thr Ala Gln Ala
                340                 345                 350

Leu Ala Glu Ile Ala Val Ala Val Gly Leu Ala Gln Asn Leu Gly Ala
                355                 360                 365

Met Arg Ala Leu Ala Thr Glu Gly Ile Gln Arg Gly His Met Ala Leu
                370                 375                 380

His Ala Arg Asn Ile Ala Val Val Ala Gly Ala Arg Gly Asp Glu Val
385                 390                 395                 400

Asp Trp Val Ala Arg Gln Leu Val Glu Tyr His Asp Val Arg Ala Asp
                405                 410                 415

Arg Ala Val Ala Leu Leu Lys Gln Lys Arg Gly Gln
                420                 425

<210> SEQ ID NO 121
<211> LENGTH: 361
<212> TYPE: PRT
<213> ORGANISM: Stevia rebaudiana

<400> SEQUENCE: 121

Met Ala Leu Val Asn Pro Thr Ala Leu Phe Tyr Gly Thr Ser Ile Arg
1                   5                   10                  15

Thr Arg Pro Thr Asn Leu Leu Asn Pro Thr Gln Lys Leu Arg Pro Val
                20                  25                  30

Ser Ser Ser Ser Leu Pro Ser Phe Ser Val Ser Ala Ile Leu Thr
                35                  40                  45

Glu Lys His Gln Ser Asn Pro Ser Glu Asn Asn Leu Gln Thr His
    50                  55                  60

Leu Glu Thr Pro Phe Asn Phe Asp Ser Tyr Met Leu Glu Lys Val Asn
65                  70                  75                  80
```

```
Met Val Asn Glu Ala Leu Asp Ala Ser Val Pro Leu Lys Asp Pro Ile
             85                  90                  95

Lys Ile His Glu Ser Met Arg Tyr Ser Leu Leu Ala Gly Gly Lys Arg
        100                 105                 110

Ile Arg Pro Met Met Cys Ile Ala Ala Cys Glu Ile Val Gly Gly Asn
        115                 120                 125

Ile Leu Asn Ala Met Pro Ala Ala Cys Ala Val Glu Met Ile His Thr
    130                 135                 140

Met Ser Leu Val His Asp Leu Pro Cys Met Asp Asn Asp Asp Phe
145                 150                 155                 160

Arg Arg Gly Lys Pro Ile Ser His Lys Val Tyr Gly Glu Met Ala
                165                 170                 175

Val Leu Thr Gly Asp Ala Leu Leu Ser Leu Ser Phe Glu His Ile Ala
            180                 185                 190

Thr Ala Thr Lys Gly Val Ser Lys Asp Arg Ile Val Arg Ala Ile Gly
        195                 200                 205

Glu Leu Ala Arg Ser Val Gly Ser Glu Gly Leu Val Ala Gly Gln Val
    210                 215                 220

Val Asp Ile Leu Ser Glu Gly Ala Asp Val Gly Leu Asp His Leu Glu
225                 230                 235                 240

Tyr Ile His Ile His Lys Thr Ala Met Leu Leu Glu Ser Ser Val Val
                245                 250                 255

Ile Gly Ala Ile Met Gly Gly Gly Ser Asp Gln Gln Ile Glu Lys Leu
            260                 265                 270

Arg Lys Phe Ala Arg Ser Ile Gly Leu Leu Phe Gln Val Val Asp Asp
        275                 280                 285

Ile Leu Asp Val Thr Lys Ser Thr Glu Glu Leu Gly Lys Thr Ala Gly
    290                 295                 300

Lys Asp Leu Leu Thr Asp Lys Thr Thr Tyr Pro Lys Leu Leu Gly Ile
305                 310                 315                 320

Glu Lys Ser Arg Glu Phe Ala Glu Lys Leu Asn Lys Glu Ala Gln Glu
                325                 330                 335

Gln Leu Ser Gly Phe Asp Arg Arg Lys Ala Ala Pro Leu Ile Ala Leu
            340                 345                 350

Ala Asn Tyr Asn Ala Tyr Arg Gln Asn
        355                 360

<210> SEQ ID NO 122
<211> LENGTH: 342
<212> TYPE: PRT
<213> ORGANISM: Gibberella fujikuroi

<400> SEQUENCE: 122

Met Ala Glu Gln Gln Ile Ser Asn Leu Leu Ser Met Phe Asp Ala Ser
1               5                   10                  15

His Ala Ser Gln Lys Leu Glu Ile Thr Val Gln Met Met Asp Thr Tyr
            20                  25                  30

His Tyr Arg Glu Thr Pro Pro Asp Ser Ser Ser Glu Gly Gly Ser
        35                  40                  45

Leu Ser Arg Tyr Asp Glu Arg Arg Val Ser Leu Pro Leu Ser His Asn
    50                  55                  60

Ala Ala Ser Pro Asp Ile Val Ser Gln Leu Cys Phe Ser Thr Ala Met
65                  70                  75                  80

Ser Ser Glu Leu Asn His Arg Trp Lys Ser Gln Arg Leu Lys Val Ala
                85                  90                  95
```

```
Asp Ser Pro Tyr Asn Tyr Ile Leu Thr Leu Pro Ser Lys Gly Ile Arg
                100                 105                 110

Gly Ala Phe Ile Asp Ser Leu Asn Val Trp Leu Glu Val Pro Glu Asp
            115                 120                 125

Glu Thr Ser Val Ile Lys Glu Val Ile Gly Met Leu His Asn Ser Ser
130                 135                 140

Leu Ile Ile Asp Asp Phe Gln Asp Asn Ser Pro Leu Arg Arg Gly Lys
145                 150                 155                 160

Pro Ser Thr His Thr Val Phe Gly Pro Ala Gln Ala Ile Asn Thr Ala
                165                 170                 175

Thr Tyr Val Ile Val Lys Ala Ile Glu Lys Ile Gln Asp Ile Val Gly
            180                 185                 190

His Asp Ala Leu Ala Asp Val Thr Gly Thr Ile Thr Thr Ile Phe Gln
        195                 200                 205

Gly Gln Ala Met Asp Leu Trp Trp Thr Ala Asn Ala Ile Val Pro Ser
210                 215                 220

Ile Gln Glu Tyr Leu Leu Met Val Asn Asp Lys Thr Gly Ala Leu Phe
225                 230                 235                 240

Arg Leu Ser Leu Glu Leu Leu Ala Leu Asn Ser Glu Ala Ser Ile Ser
                245                 250                 255

Asp Ser Ala Leu Glu Ser Leu Ser Ser Ala Val Ser Leu Leu Gly Gln
            260                 265                 270

Tyr Phe Gln Ile Arg Asp Asp Tyr Met Asn Leu Ile Asp Asn Lys Tyr
        275                 280                 285

Thr Asp Gln Lys Gly Phe Cys Glu Asp Leu Asp Glu Gly Lys Tyr Ser
290                 295                 300

Leu Thr Leu Ile His Ala Leu Gln Thr Asp Ser Ser Asp Leu Leu Thr
305                 310                 315                 320

Asn Ile Leu Ser Met Arg Arg Val Gln Gly Lys Leu Thr Ala Gln Lys
                325                 330                 335

Arg Cys Trp Phe Trp Lys
            340

<210> SEQ ID NO 123
<211> LENGTH: 300
<212> TYPE: PRT
<213> ORGANISM: Mus musculus

<400> SEQUENCE: 123

Met Glu Lys Thr Lys Glu Lys Ala Glu Arg Ile Leu Leu Glu Pro Tyr
1               5                   10                  15

Arg Tyr Leu Leu Gln Leu Pro Gly Lys Gln Val Arg Ser Lys Leu Ser
            20                  25                  30

Gln Ala Phe Asn His Trp Leu Lys Val Pro Glu Asp Lys Leu Gln Ile
        35                  40                  45

Ile Ile Glu Val Thr Glu Met Leu His Asn Ala Ser Leu Leu Ile Asp
    50                  55                  60

Asp Ile Glu Asp Ser Ser Lys Leu Arg Arg Gly Phe Pro Val Ala His
65                  70                  75                  80

Ser Ile Tyr Gly Val Pro Ser Val Ile Asn Ser Ala Asn Tyr Val Tyr
                85                  90                  95

Phe Leu Gly Leu Glu Lys Val Leu Thr Leu Asp His Pro Asp Ala Val
            100                 105                 110

Lys Leu Phe Thr Arg Gln Leu Leu Glu Leu His Gln Gly Gln Gly Leu
```

```
            115                 120                 125
Asp Ile Tyr Trp Arg Asp Thr Tyr Thr Cys Pro Thr Glu Glu Glu Tyr
130                 135                 140

Lys Ala Met Val Leu Gln Lys Thr Gly Gly Leu Phe Gly Leu Ala Val
145                 150                 155                 160

Gly Leu Met Gln Leu Phe Ser Asp Tyr Lys Glu Asp Leu Lys Pro Leu
                165                 170                 175

Leu Asp Thr Leu Gly Leu Phe Phe Gln Ile Arg Asp Asp Tyr Ala Asn
                180                 185                 190

Leu His Ser Lys Glu Tyr Ser Glu Asn Lys Ser Phe Cys Glu Asp Leu
                195                 200                 205

Thr Glu Gly Lys Phe Ser Phe Pro Thr Ile His Ala Ile Trp Ser Arg
                210                 215                 220

Pro Glu Ser Thr Gln Val Gln Asn Ile Leu Arg Gln Arg Thr Glu Asn
225                 230                 235                 240

Ile Asp Ile Lys Lys Tyr Cys Val Gln Tyr Leu Glu Asp Val Gly Ser
                245                 250                 255

Phe Ala Tyr Thr Arg His Thr Leu Arg Glu Leu Glu Ala Lys Ala Tyr
                260                 265                 270

Lys Gln Ile Glu Ala Cys Gly Gly Asn Pro Ser Leu Val Ala Leu Val
                275                 280                 285

Lys His Leu Ser Lys Met Phe Thr Glu Glu Asn Lys
                290                 295                 300

<210> SEQ ID NO 124
<211> LENGTH: 339
<212> TYPE: PRT
<213> ORGANISM: Thalassiosira pseudonana

<400> SEQUENCE: 124

Met Ala Arg Phe Tyr Phe Leu Asn Ala Leu Leu Met Val Ile Ser Leu
1               5                   10                  15

Gln Ser Thr Thr Ala Phe Thr Pro Ala Lys Leu Ala Tyr Pro Thr Thr
                20                  25                  30

Thr Thr Ala Leu Asn Val Ala Ser Ala Glu Thr Ser Phe Ser Leu Asp
                35                  40                  45

Glu Tyr Leu Ala Ser Lys Ile Gly Pro Ile Glu Ser Ala Leu Glu Ala
50                  55                  60

Ser Val Lys Ser Arg Ile Pro Gln Thr Asp Lys Ile Cys Glu Ser Met
65                  70                  75                  80

Ala Tyr Ser Leu Met Ala Gly Gly Lys Arg Ile Arg Pro Val Leu Cys
                85                  90                  95

Ile Ala Ala Cys Glu Met Phe Gly Gly Ser Gln Asp Val Ala Met Pro
                100                 105                 110

Thr Ala Val Ala Leu Glu Met Ile His Thr Met Ser Leu Ile His Asp
                115                 120                 125

Asp Leu Pro Ser Met Asp Asn Asp Leu Arg Arg Gly Lys Pro Thr
                130                 135                 140

Asn His Val Val Phe Gly Glu Asp Val Ala Ile Leu Ala Gly Asp Ser
145                 150                 155                 160

Leu Leu Ser Thr Ser Phe Glu His Val Ala Arg Glu Thr Lys Gly Val
                165                 170                 175

Ser Ala Glu Lys Ile Val Asp Val Ile Ala Arg Leu Gly Lys Ser Val
                180                 185                 190
```

```
Gly Ala Glu Gly Leu Ala Gly Gln Val Met Asp Leu Glu Cys Glu
            195                 200                 205

Ala Lys Pro Gly Thr Thr Leu Asp Asp Leu Lys Trp Ile His Ile His
    210                 215                 220

Lys Thr Ala Thr Leu Leu Gln Val Ala Val Ala Ser Gly Ala Val Leu
225                 230                 235                 240

Gly Gly Ala Thr Pro Glu Val Ala Ala Cys Glu Leu Phe Ala Met
            245                 250                 255

Asn Ile Gly Leu Ala Phe Gln Val Ala Asp Asp Ile Leu Asp Val Thr
            260                 265                 270

Ala Ser Ser Glu Asp Leu Gly Lys Thr Ala Gly Lys Asp Glu Ala Thr
        275                 280                 285

Asp Lys Thr Thr Tyr Pro Lys Leu Leu Gly Leu Glu Glu Ser Lys Ala
    290                 295                 300

Tyr Ala Arg Gln Leu Ile Asp Glu Ala Lys Glu Ser Leu Ala Pro Phe
305                 310                 315                 320

Gly Asp Arg Ala Ala Pro Leu Leu Ala Ile Ala Asp Phe Ile Ile Asp
            325                 330                 335

Arg Lys Asn

<210> SEQ ID NO 125
<211> LENGTH: 355
<212> TYPE: PRT
<213> ORGANISM: Streptomyces clavuligerus

<400> SEQUENCE: 125

Met His Leu Ala Pro Arg Arg Val Pro Arg Gly Arg Ser Pro Pro
1               5                   10                  15

Asp Arg Val Pro Glu Arg Gln Gly Ala Leu Gly Arg Arg Gly Ala
            20                  25                  30

Gly Ser Thr Gly Cys Ala Arg Ala Ala Gly Val His Arg Arg Arg
        35                  40                  45

Gly Gly Gly Glu Ala Asp Pro Ser Ala Ala Val His Arg Gly Trp Gln
    50                  55                  60

Ala Gly Gly Gly Thr Gly Leu Pro Asp Glu Val Val Ser Thr Ala Ala
65                  70                  75                  80

Ala Leu Glu Met Phe His Ala Phe Ala Leu Ile His Asp Asp Ile Met
                85                  90                  95

Asp Asp Ser Ala Thr Arg Arg Gly Ser Pro Thr Val His Arg Ala Leu
            100                 105                 110

Ala Asp Arg Leu Gly Ala Ala Leu Asp Pro Asp Gln Ala Gly Gln Leu
        115                 120                 125

Gly Val Ser Thr Ala Ile Leu Val Gly Asp Leu Ala Leu Thr Trp Ser
    130                 135                 140

Asp Glu Leu Leu Tyr Ala Pro Leu Thr Pro His Arg Leu Ala Ala Val
145                 150                 155                 160

Leu Pro Leu Val Thr Ala Met Arg Ala Glu Thr Val His Gly Gln Tyr
                165                 170                 175

Leu Asp Ile Thr Ser Ala Arg Arg Pro Gly Thr Asp Thr Ser Leu Ala
            180                 185                 190

Leu Arg Ile Ala Arg Tyr Lys Thr Ala Ala Tyr Thr Met Glu Arg Pro
        195                 200                 205

Leu His Ile Gly Ala Ala Leu Ala Gly Ala Arg Pro Glu Leu Leu Ala
    210                 215                 220
```

Gly Leu Ser Ala Tyr Ala Leu Pro Ala Gly Glu Ala Phe Gln Leu Ala
225                 230                 235                 240

Asp Asp Leu Leu Gly Val Phe Gly Asp Pro Arg Arg Thr Gly Lys Pro
            245                 250                 255

Asp Leu Asp Asp Leu Arg Gly Gly Lys His Thr Val Leu Val Ala Leu
            260                 265                 270

Ala Arg Glu His Ala Thr Pro Glu Gln Arg His Thr Leu Asp Thr Leu
            275                 280                 285

Leu Gly Thr Pro Gly Leu Asp Arg Gln Gly Ala Ser Arg Leu Arg Cys
            290                 295                 300

Val Leu Val Ala Thr Gly Ala Arg Ala Glu Ala Glu Arg Leu Ile Thr
305                 310                 315                 320

Glu Arg Arg Asp Gln Ala Leu Thr Ala Leu Asn Ala Leu Thr Leu Pro
            325                 330                 335

Pro Pro Leu Ala Glu Ala Leu Ala Arg Leu Thr Leu Gly Ser Thr Ala
            340                 345                 350

His Pro Ala
        355

<210> SEQ ID NO 126
<211> LENGTH: 330
<212> TYPE: PRT
<213> ORGANISM: Sulfulobus acidicaldarius

<400> SEQUENCE: 126

Met Ser Tyr Phe Asp Asn Tyr Phe Asn Glu Ile Val Asn Ser Val Asn
1               5                   10                  15

Asp Ile Ile Lys Ser Tyr Ile Ser Gly Asp Val Pro Lys Leu Tyr Glu
            20                  25                  30

Ala Ser Tyr His Leu Phe Thr Gly Gly Lys Arg Leu Arg Pro Leu
            35                  40                  45

Ile Leu Thr Ile Ser Ser Asp Leu Phe Gly Gly Gln Arg Glu Arg Ala
        50                  55                  60

Tyr Tyr Ala Gly Ala Ala Ile Glu Val Leu His Thr Phe Thr Leu Val
65                  70                  75                  80

His Asp Asp Ile Met Asp Gln Asp Asn Ile Arg Arg Gly Leu Pro Thr
            85                  90                  95

Val His Val Lys Tyr Gly Leu Pro Leu Ala Ile Leu Ala Gly Asp Leu
            100                 105                 110

Leu His Ala Lys Ala Phe Gln Leu Leu Thr Gln Ala Leu Arg Gly Leu
            115                 120                 125

Pro Ser Glu Thr Ile Ile Lys Ala Phe Asp Ile Phe Thr Arg Ser Ile
        130                 135                 140

Ile Ile Ser Glu Gly Gln Ala Val Asp Met Glu Phe Glu Asp Arg
145                 150                 155                 160

Ile Asp Ile Lys Glu Gln Glu Tyr Leu Asp Met Ile Ser Arg Lys Thr
            165                 170                 175

Ala Ala Leu Phe Ser Ala Ser Ser Ile Gly Ala Leu Ile Ala Gly
            180                 185                 190

Ala Asn Asp Asn Asp Val Arg Leu Met Ser Asp Phe Gly Thr Asn Leu
        195                 200                 205

Gly Ile Ala Phe Gln Ile Val Asp Asp Ile Leu Gly Leu Thr Ala Asp
    210                 215                 220

Glu Lys Glu Leu Gly Lys Pro Val Phe Ser Asp Ile Arg Glu Gly Lys
225                 230                 235                 240

```
Lys Thr Ile Leu Val Ile Lys Thr Leu Glu Leu Cys Lys Glu Asp Glu
                245                 250                 255

Lys Lys Ile Val Leu Lys Ala Leu Gly Asn Lys Ser Ala Ser Lys Glu
            260                 265                 270

Glu Leu Met Ser Ser Ala Asp Ile Ile Lys Lys Tyr Ser Leu Asp Tyr
        275                 280                 285

Ala Tyr Asn Leu Ala Glu Lys Tyr Tyr Lys Asn Ala Ile Asp Ser Leu
    290                 295                 300

Asn Gln Val Ser Ser Lys Ser Asp Ile Pro Gly Lys Ala Leu Lys Tyr
305                 310                 315                 320

Leu Ala Glu Phe Thr Ile Arg Arg Lys
                325                 330

<210> SEQ ID NO 127
<211> LENGTH: 297
<212> TYPE: PRT
<213> ORGANISM: Synechococcus sp.

<400> SEQUENCE: 127

Met Val Ala Gln Thr Phe Asn Leu Asp Thr Tyr Leu Ser Gln Arg Gln
1               5                   10                  15

Gln Gln Val Glu Glu Ala Leu Ser Ala Ala Leu Val Pro Ala Tyr Pro
            20                  25                  30

Glu Arg Ile Tyr Glu Ala Met Arg Tyr Ser Leu Leu Ala Gly Gly Lys
        35                  40                  45

Arg Leu Arg Pro Ile Leu Cys Leu Ala Ala Cys Glu Leu Ala Gly Gly
    50                  55                  60

Ser Val Glu Gln Ala Met Pro Thr Ala Cys Ala Leu Glu Met Ile His
65              70                  75                  80

Thr Met Ser Leu Ile His Asp Asp Leu Pro Ala Met Asp Asn Asp Asp
                85                  90                  95

Phe Arg Arg Gly Lys Pro Thr Asn His Lys Val Phe Gly Glu Asp Ile
            100                 105                 110

Ala Ile Leu Ala Gly Asp Ala Leu Leu Ala Tyr Ala Phe Glu His Ile
        115                 120                 125

Ala Ser Gln Thr Arg Gly Val Pro Pro Gln Leu Val Leu Gln Val Ile
    130                 135                 140

Ala Arg Ile Gly His Ala Val Ala Ala Thr Gly Leu Val Gly Gly Gln
145                 150                 155                 160

Val Val Asp Leu Glu Ser Glu Gly Lys Ala Ile Ser Leu Glu Thr Leu
                165                 170                 175

Glu Tyr Ile His Ser His Lys Thr Gly Ala Leu Leu Glu Ala Ser Val
            180                 185                 190

Val Ser Gly Gly Ile Leu Ala Gly Ala Asp Glu Glu Leu Leu Ala Arg
        195                 200                 205

Leu Ser His Tyr Ala Arg Asp Ile Gly Leu Ala Phe Gln Ile Val Asp
    210                 215                 220

Asp Ile Leu Asp Val Thr Ala Thr Ser Glu Gln Leu Gly Lys Thr Ala
225                 230                 235                 240

Gly Lys Asp Gln Ala Ala Ala Lys Ala Thr Tyr Pro Ser Leu Leu Gly
                245                 250                 255

Leu Glu Ala Ser Arg Gln Lys Ala Glu Glu Leu Ile Gln Ser Ala Lys
            260                 265                 270

Glu Ala Leu Arg Pro Tyr Gly Ser Gln Ala Glu Pro Leu Leu Ala Leu
```

Ala Asp Phe Ile Thr Arg Arg Gln His
            275                 280                 285
290                 295

<210> SEQ ID NO 128
<211> LENGTH: 371
<212> TYPE: PRT
<213> ORGANISM: Arabidopsis thaliana

<400> SEQUENCE: 128

Met Ala Ser Val Thr Leu Gly Ser Trp Ile Val His His Asn
1               5                   10                  15

His His His Pro Ser Ser Ile Leu Thr Lys Ser Arg Ser Cys
            20                  25                  30

Pro Ile Thr Leu Thr Lys Pro Ile Ser Phe Arg Ser Lys Arg Thr Val
            35                  40                  45

Ser Ser Ser Ser Ser Ile Val Ser Ser Val Val Thr Lys Glu Asp
            50                  55                  60

Asn Leu Arg Gln Ser Glu Pro Ser Ser Phe Asp Phe Met Ser Tyr Ile
65                  70                  75                  80

Ile Thr Lys Ala Glu Leu Val Asn Lys Ala Leu Asp Ser Ala Val Pro
                85                  90                  95

Leu Arg Glu Pro Leu Lys Ile His Glu Ala Met Arg Tyr Ser Leu Leu
            100                 105                 110

Ala Gly Gly Lys Arg Val Arg Pro Val Leu Cys Ile Ala Ala Cys Glu
            115                 120                 125

Leu Val Gly Gly Glu Glu Ser Thr Ala Met Pro Ala Ala Cys Ala Val
130                 135                 140

Glu Met Ile His Thr Met Ser Leu Ile His Asp Asp Leu Pro Cys Met
145                 150                 155                 160

Asp Asn Asp Asp Leu Arg Arg Gly Lys Pro Thr Asn His Lys Val Phe
                165                 170                 175

Gly Glu Asp Val Ala Val Leu Ala Gly Asp Ala Leu Leu Ser Phe Ala
            180                 185                 190

Phe Glu His Leu Ala Ser Ala Thr Ser Ser Asp Val Val Ser Pro Val
            195                 200                 205

Arg Val Val Arg Ala Val Gly Glu Leu Ala Lys Ala Ile Gly Thr Glu
            210                 215                 220

Gly Leu Val Ala Gly Gln Val Val Asp Ile Ser Ser Glu Gly Leu Asp
225                 230                 235                 240

Leu Asn Asp Val Gly Leu Glu His Leu Glu Phe Ile His Leu His Lys
                245                 250                 255

Thr Ala Ala Leu Leu Glu Ala Ser Ala Val Leu Gly Ala Ile Val Gly
            260                 265                 270

Gly Gly Ser Asp Asp Glu Ile Glu Arg Leu Arg Lys Phe Ala Arg Cys
            275                 280                 285

Ile Gly Leu Leu Phe Gln Val Val Asp Asp Ile Leu Asp Val Thr Lys
            290                 295                 300

Ser Ser Lys Glu Leu Gly Lys Thr Ala Gly Lys Asp Leu Ile Ala Asp
305                 310                 315                 320

Lys Leu Thr Tyr Pro Lys Ile Met Gly Leu Glu Lys Ser Arg Glu Phe
                325                 330                 335

Ala Glu Lys Leu Asn Arg Glu Ala Arg Asp Gln Leu Leu Gly Phe Asp
            340                 345                 350

```
Ser Asp Lys Val Ala Pro Leu Leu Ala Leu Ala Asn Tyr Ile Ala Tyr
        355                 360                 365
Arg Gln Asn
    370

<210> SEQ ID NO 129
<211> LENGTH: 787
<212> TYPE: PRT
<213> ORGANISM: Stevia rebaudiana

<400> SEQUENCE: 129

Met Lys Thr Gly Phe Ile Ser Pro Ala Thr Val Phe His His Arg Ile
1               5                   10                  15

Ser Pro Ala Thr Thr Phe Arg His His Leu Ser Pro Ala Thr Thr Asn
            20                  25                  30

Ser Thr Gly Ile Val Ala Leu Arg Asp Ile Asn Phe Arg Cys Lys Ala
        35                  40                  45

Val Ser Lys Glu Tyr Ser Asp Leu Leu Gln Lys Asp Glu Ala Ser Phe
    50                  55                  60

Thr Lys Trp Asp Asp Lys Val Lys Asp His Leu Asp Thr Asn Lys
65                  70                  75                  80

Asn Leu Tyr Pro Asn Asp Glu Ile Lys Glu Phe Val Glu Ser Val Lys
                85                  90                  95

Ala Met Phe Gly Ser Met Asn Asp Gly Glu Ile Asn Val Ser Ala Tyr
            100                 105                 110

Asp Thr Ala Trp Val Ala Leu Val Gln Asp Val Asp Gly Ser Gly Ser
        115                 120                 125

Pro Gln Phe Pro Ser Ser Leu Glu Trp Ile Ala Asn Asn Gln Leu Ser
    130                 135                 140

Asp Gly Ser Trp Gly Asp His Leu Leu Phe Ser Ala His Asp Arg Ile
145                 150                 155                 160

Ile Asn Thr Leu Ala Cys Val Ile Ala Leu Thr Ser Trp Asn Val His
                165                 170                 175

Pro Ser Lys Cys Glu Lys Gly Leu Asn Phe Leu Arg Glu Asn Ile Cys
            180                 185                 190

Lys Leu Glu Asp Glu Asn Ala Glu His Met Pro Ile Gly Phe Glu Val
        195                 200                 205

Thr Phe Pro Ser Leu Ile Asp Ile Ala Lys Lys Leu Asn Ile Glu Val
    210                 215                 220

Pro Glu Asp Thr Pro Ala Leu Lys Glu Ile Tyr Ala Arg Arg Asp Ile
225                 230                 235                 240

Lys Leu Thr Lys Ile Pro Met Glu Val Leu His Lys Val Pro Thr Thr
                245                 250                 255

Leu Leu His Ser Leu Glu Gly Met Pro Asp Leu Glu Trp Glu Lys Leu
            260                 265                 270

Leu Lys Leu Gln Cys Lys Asp Gly Ser Phe Leu Phe Ser Pro Ser Ser
        275                 280                 285

Thr Ala Phe Ala Leu Met Gln Thr Lys Asp Glu Lys Cys Leu Gln Tyr
    290                 295                 300

Leu Thr Asn Ile Val Thr Lys Phe Asn Gly Gly Val Pro Asn Val Tyr
305                 310                 315                 320

Pro Val Asp Leu Phe Glu His Ile Trp Val Val Asp Arg Leu Gln Arg
                325                 330                 335

Leu Gly Ile Ala Arg Tyr Phe Lys Ser Glu Ile Lys Asp Cys Val Glu
            340                 345                 350
```

Tyr Ile Asn Lys Tyr Trp Thr Lys Asn Gly Ile Cys Trp Ala Arg Asn
            355                 360                 365

Thr His Val Gln Asp Ile Asp Asp Thr Ala Met Gly Phe Arg Val Leu
            370                 375                 380

Arg Ala His Gly Tyr Asp Val Thr Pro Asp Val Phe Arg Gln Phe Glu
385                 390                 395                 400

Lys Asp Gly Lys Phe Val Cys Phe Ala Gly Gln Ser Thr Gln Ala Val
                    405                 410                 415

Thr Gly Met Phe Asn Val Tyr Arg Ala Ser Gln Met Leu Phe Pro Gly
                420                  425                430

Glu Arg Ile Leu Glu Asp Ala Lys Lys Phe Ser Tyr Asn Tyr Leu Lys
            435                 440                 445

Glu Lys Gln Ser Thr Asn Glu Leu Leu Asp Lys Trp Ile Ile Ala Lys
            450                 455                 460

Asp Leu Pro Gly Glu Val Gly Tyr Ala Leu Asp Ile Pro Trp Tyr Ala
465                 470                 475                 480

Ser Leu Pro Arg Leu Glu Thr Arg Tyr Tyr Leu Glu Gln Tyr Gly Gly
                    485                 490                 495

Glu Asp Asp Val Trp Ile Gly Lys Thr Leu Tyr Arg Met Gly Tyr Val
                500                 505                 510

Ser Asn Asn Thr Tyr Leu Glu Met Ala Lys Leu Asp Tyr Asn Asn Tyr
            515                 520                 525

Val Ala Val Leu Gln Leu Glu Trp Tyr Thr Ile Gln Gln Trp Tyr Val
            530                 535                 540

Asp Ile Gly Ile Glu Lys Phe Glu Ser Asp Asn Ile Lys Ser Val Leu
545                 550                 555                 560

Val Ser Tyr Tyr Leu Ala Ala Ser Ile Phe Glu Pro Glu Arg Ser
                    565                 570                 575

Lys Glu Arg Ile Ala Trp Ala Lys Thr Thr Ile Leu Val Asp Lys Ile
                580                 585                 590

Thr Ser Ile Phe Asp Ser Ser Gln Ser Ser Lys Glu Asp Ile Thr Ala
            595                 600                 605

Phe Ile Asp Lys Phe Arg Asn Lys Ser Ser Ser Lys Lys His Ser Ile
610                 615                 620

Asn Gly Glu Pro Trp His Glu Val Met Val Ala Leu Lys Lys Thr Leu
625                 630                 635                 640

His Gly Phe Ala Leu Asp Ala Leu Met Thr His Ser Gln Asp Ile His
                    645                 650                 655

Pro Gln Leu His Gln Ala Trp Glu Met Trp Leu Thr Lys Leu Gln Asp
                660                 665                 670

Gly Val Asp Val Thr Ala Glu Leu Met Val Gln Met Ile Asn Met Thr
            675                 680                 685

Ala Gly Arg Trp Val Ser Lys Glu Leu Leu Thr His Pro Gln Tyr Gln
            690                 695                 700

Arg Leu Ser Thr Val Thr Asn Ser Val Cys His Asp Ile Thr Lys Leu
705                 710                 715                 720

His Asn Phe Lys Glu Asn Ser Thr Thr Val Asp Ser Lys Val Gln Glu
                    725                 730                 735

Leu Val Gln Leu Val Phe Ser Asp Thr Pro Asp Asp Leu Asp Gln Asp
                740                 745                 750

Met Lys Gln Thr Phe Leu Thr Val Met Lys Thr Phe Tyr Tyr Lys Ala
            755                 760                 765

```
Trp Cys Asp Pro Asn Thr Ile Asn Asp His Ile Ser Lys Val Phe Glu
        770                 775                 780

Ile Val Ile
785

<210> SEQ ID NO 130
<211> LENGTH: 527
<212> TYPE: PRT
<213> ORGANISM: Streptomyces clavuligerus

<400> SEQUENCE: 130

Met Pro Asp Ala His Asp Ala Pro Pro Gln Ile Arg Gln Arg Thr
1               5                  10                  15

Leu Val Asp Glu Ala Thr Gln Leu Leu Thr Glu Ser Ala Glu Asp Ala
            20                  25                  30

Trp Gly Glu Val Ser Val Ser Glu Tyr Glu Thr Ala Arg Leu Val Ala
        35                  40                  45

His Ala Thr Trp Leu Gly Gly His Ala Thr Arg Val Ala Phe Leu Leu
    50                  55                  60

Glu Arg Gln His Glu Asp Gly Ser Trp Gly Pro Pro Gly Gly Tyr Arg
65              70                  75                  80

Leu Val Pro Thr Leu Ser Ala Val His Ala Leu Leu Thr Cys Leu Ala
            85                  90                  95

Ser Pro Ala Gln Asp His Gly Val Pro His Asp Arg Leu Leu Arg Ala
        100                 105                 110

Val Asp Ala Gly Leu Thr Ala Leu Arg Arg Leu Gly Thr Ser Asp Ser
    115                 120                 125

Pro Pro Asp Thr Ile Ala Val Glu Leu Val Ile Pro Ser Leu Leu Glu
130                 135                 140

Gly Ile Gln His Leu Leu Asp Pro Ala His Pro His Ser Arg Pro Ala
145                 150                 155                 160

Phe Ser Gln His Arg Gly Ser Leu Val Cys Pro Gly Gly Leu Asp Gly
            165                 170                 175

Arg Thr Leu Gly Ala Leu Arg Ser His Ala Ala Ala Gly Thr Pro Val
        180                 185                 190

Pro Gly Lys Val Trp His Ala Ser Glu Thr Leu Gly Leu Ser Thr Glu
    195                 200                 205

Ala Ala Ser His Leu Gln Pro Ala Gln Gly Ile Ile Gly Gly Ser Ala
210                 215                 220

Ala Ala Thr Ala Thr Trp Leu Thr Arg Val Ala Pro Ser Gln Gln Ser
225                 230                 235                 240

Asp Ser Ala Arg Arg Tyr Leu Glu Glu Leu Gln His Arg Tyr Ser Gly
            245                 250                 255

Pro Val Pro Ser Ile Thr Pro Ile Thr Tyr Phe Glu Arg Ala Trp Leu
        260                 265                 270

Leu Asn Asn Phe Ala Ala Gly Val Pro Cys Glu Ala Pro Ala Ala
    275                 280                 285

Leu Leu Asp Ser Leu Glu Ala Ala Leu Thr Pro Gln Gly Ala Pro Ala
290                 295                 300

Gly Ala Gly Leu Pro Pro Asp Ala Asp Thr Ala Val Leu Leu
305                 310                 315                 320

Ala Leu Ala Thr His Gly Arg Gly Arg Pro Glu Val Leu Met Asp
            325                 330                 335

Tyr Arg Thr Asp Gly Tyr Phe Gln Cys Phe Ile Gly Glu Arg Thr Pro
        340                 345                 350
```

```
Ser Ile Ser Thr Asn Ala His Val Leu Glu Thr Leu Gly His His Val
        355                 360                 365

Ala Gln His Pro Gln Asp Arg Ala Arg Tyr Gly Ser Ala Met Asp Thr
370                 375                 380

Ala Ser Ala Trp Leu Leu Ala Ala Gln Lys Gln Asp Gly Ser Trp Leu
385                 390                 395                 400

Asp Lys Trp His Ala Ser Pro Tyr Tyr Ala Thr Val Cys Cys Thr Gln
                405                 410                 415

Ala Leu Ala Ala His Ala Ser Pro Ala Thr Ala Pro Ala Arg Gln Arg
                420                 425                 430

Ala Val Arg Trp Val Leu Ala Thr Gln Arg Ser Asp Gly Gly Trp Gly
            435                 440                 445

Leu Trp His Ser Thr Val Glu Glu Thr Ala Tyr Ala Leu Gln Ile Leu
        450                 455                 460

Ala Pro Pro Ser Gly Gly Asn Ile Pro Val Gln Gln Ala Leu Thr
465                 470                 475                 480

Arg Gly Arg Ala Arg Leu Cys Gly Ala Leu Pro Leu Thr Pro Leu Trp
                485                 490                 495

His Asp Lys Asp Leu Tyr Thr Pro Val Arg Val Val Arg Val Ala Ala Arg
                500                 505                 510

Ala Ala Ala Leu Tyr Thr Thr Arg Asp Leu Leu Leu Pro Pro Leu
                515                 520                 525

<210> SEQ ID NO 131
<211> LENGTH: 516
<212> TYPE: PRT
<213> ORGANISM: Bradyrhizobium japonicum

<400> SEQUENCE: 131

Met Asn Ala Leu Ser Glu His Ile Leu Ser Glu Leu Arg Arg Leu Leu
1               5                   10                  15

Ser Glu Met Ser Asp Gly Gly Ser Val Gly Pro Ser Val Tyr Asp Thr
            20                  25                  30

Ala Gln Ala Leu Arg Phe His Gly Asn Val Thr Gly Arg Gln Asp Ala
        35                  40                  45

Tyr Ala Trp Leu Ile Ala Gln Gln Ala Asp Gly Gly Trp Gly Ser
    50                  55                  60

Ala Asp Phe Pro Leu Phe Arg His Ala Pro Thr Trp Ala Ala Leu Leu
65                  70                  75                  80

Ala Leu Gln Arg Ala Asp Pro Leu Pro Gly Ala Ala Asp Ala Val Gln
                85                  90                  95

Thr Ala Thr Arg Phe Leu Gln Arg Gln Pro Asp Pro Tyr Ala His Ala
            100                 105                 110

Val Pro Glu Asp Ala Pro Ile Gly Ala Glu Leu Ile Leu Pro Gln Phe
        115                 120                 125

Cys Gly Glu Ala Ala Trp Leu Leu Gly Gly Val Ala Phe Pro Arg His
    130                 135                 140

Pro Ala Leu Leu Pro Leu Arg Gln Ala Cys Leu Val Lys Leu Gly Ala
145                 150                 155                 160

Val Ala Met Leu Pro Ser Gly His Pro Leu His Ser Trp Glu Ala
                165                 170                 175

Trp Gly Thr Ser Pro Thr Thr Ala Cys Pro Asp Asp Gly Ser Ile
            180                 185                 190

Gly Ile Ser Pro Ala Ala Thr Ala Ala Trp Arg Ala Gln Ala Val Thr
```

```
                195                 200                 205
Arg Gly Ser Thr Pro Gln Val Gly Arg Ala Asp Ala Tyr Leu Gln Met
210                 215                 220

Ala Ser Arg Ala Thr Arg Ser Gly Ile Glu Gly Val Phe Pro Asn Val
225                 230                 235                 240

Trp Pro Ile Asn Val Phe Glu Pro Cys Trp Ser Leu Tyr Thr Leu His
                245                 250                 255

Leu Ala Gly Leu Phe Ala His Pro Ala Leu Ala Glu Ala Val Arg Val
            260                 265                 270

Ile Val Ala Gln Leu Glu Ala Arg Leu Gly Val His Gly Leu Gly Pro
        275                 280                 285

Ala Leu His Phe Ala Ala Asp Ala Asp Thr Ala Val Ala Leu Cys
    290                 295                 300

Val Leu His Leu Ala Gly Arg Asp Pro Ala Val Asp Ala Leu Arg His
305                 310                 315                 320

Phe Glu Ile Gly Glu Leu Phe Val Thr Phe Pro Gly Glu Arg Asn Ala
                325                 330                 335

Ser Val Ser Thr Asn Ile His Ala Leu His Ala Leu Arg Leu Leu Gly
            340                 345                 350

Lys Pro Ala Ala Gly Ala Ser Ala Tyr Val Glu Ala Asn Arg Asn Pro
        355                 360                 365

His Gly Leu Trp Asp Asn Glu Lys Trp His Val Ser Trp Leu Tyr Pro
    370                 375                 380

Thr Ala His Ala Val Ala Ala Leu Ala Gln Gly Lys Pro Gln Trp Arg
385                 390                 395                 400

Asp Glu Arg Ala Leu Ala Ala Leu Leu Gln Ala Gln Arg Asp Asp Gly
                405                 410                 415

Gly Trp Gly Ala Gly Arg Gly Ser Thr Phe Glu Glu Thr Ala Tyr Ala
            420                 425                 430

Leu Phe Ala Leu His Val Met Asp Gly Ser Glu Glu Ala Thr Gly Arg
        435                 440                 445

Arg Arg Ile Ala Gln Val Val Ala Arg Ala Leu Glu Trp Met Leu Ala
450                 455                 460

Arg His Ala Ala His Gly Leu Pro Gln Thr Pro Leu Trp Ile Gly Lys
465                 470                 475                 480

Glu Leu Tyr Cys Pro Thr Arg Val Val Arg Val Ala Glu Leu Ala Gly
                485                 490                 495

Leu Trp Leu Ala Leu Arg Trp Gly Arg Arg Val Leu Ala Glu Gly Ala
            500                 505                 510

Gly Ala Ala Pro
        515

<210> SEQ ID NO 132
<211> LENGTH: 784
<212> TYPE: PRT
<213> ORGANISM: Stevia rebaudiana

<400> SEQUENCE: 132

Met Asn Leu Ser Leu Cys Ile Ala Ser Pro Leu Leu Thr Lys Ser Asn
1               5                   10                  15

Arg Pro Ala Ala Leu Ser Ala Ile His Thr Ala Ser Thr Ser His Gly
                20                  25                  30

Gly Gln Thr Asn Pro Thr Asn Leu Ile Ile Asp Thr Thr Lys Glu Arg
            35                  40                  45
```

```
Ile Gln Lys Gln Phe Lys Asn Val Glu Ile Ser Val Ser Ser Tyr Asp
 50                  55                  60

Thr Ala Trp Val Ala Met Val Pro Ser Pro Asn Ser Pro Lys Ser Pro
 65                  70                  75                  80

Cys Phe Pro Glu Cys Leu Asn Trp Leu Ile Asn Asn Gln Leu Asn Asp
                 85                  90                  95

Gly Ser Trp Gly Leu Val Asn His Thr His Asn His Asn His Pro Leu
                100                 105                 110

Leu Lys Asp Ser Leu Ser Ser Thr Leu Ala Cys Ile Val Ala Leu Lys
                115                 120                 125

Arg Trp Asn Val Gly Glu Asp Gln Ile Asn Lys Gly Leu Ser Phe Ile
    130                 135                 140

Glu Ser Asn Leu Ala Ser Ala Thr Glu Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
                180                 185                 190

Lys Arg Glu Leu Glu Gln Lys Arg Cys His Ser Asn Glu Met Asp Gly
                195                 200                 205

Tyr Leu Ala Tyr Ile Ser Glu Gly Leu Gly Asn Leu Tyr Asp Trp Asn
    210                 215                 220

Met Val Lys Lys Tyr Gln Met Lys Asn Gly Ser Val Phe Asn Ser Pro
225                 230                 235                 240

Ser Ala Thr Ala Ala Ala Phe Ile Asn His Gln Asn Pro Gly Cys Leu
                245                 250                 255

Asn Tyr Leu Asn Ser Leu Leu Asp Lys Phe Gly Asn Ala Val Pro Thr
                260                 265                 270

Val Tyr Pro His Asp Leu Phe Ile Arg Leu Ser Met Val Asp Thr Ile
            275                 280                 285

Glu Arg Leu Gly Ile Ser His His Phe Arg Val Glu Ile Lys Asn Val
    290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile Asn
                325                 330                 335

Gly Tyr Glu Val Ser Pro Asp Pro Leu Ala Glu Ile Thr Asn Glu Leu
                340                 345                 350

Ala Leu Lys Asp Glu Tyr Ala Ala Leu Glu Thr Tyr His Ala Ser His
            355                 360                 365

Ile Leu Tyr Gln Glu Asp Leu Ser Ser Gly Lys Gln Ile Leu Lys Ser
    370                 375                 380

Ala Asp Phe Leu Lys Glu Ile Ile Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
                420                 425                 430

Val Asp Asn Thr Arg Ile Leu Lys Thr Thr Tyr His Ser Ser Asn Ile
            435                 440                 445

Ser Asn Thr Asp Tyr Leu Arg Leu Ala Val Glu Asp Phe Tyr Thr Cys
    450                 455                 460

Gln Ser Ile Tyr Arg Glu Glu Leu Lys Gly Leu Glu Arg Trp Val Val
```

```
                465                 470                 475                 480
Glu Asn Lys Leu Asp Gln Leu Lys Phe Ala Arg Gln Lys Thr Ala Tyr
                    485                 490                 495

Cys Tyr Phe Ser Val Ala Ala Thr Leu Ser Ser Pro Glu Leu Ser Asp
                500                 505                 510

Ala Arg Ile Ser Trp Ala Lys Asn Gly Ile Leu Thr Val Val Asp
            515                 520                 525

Asp Phe Phe Asp Ile Gly Gly Thr Ile Asp Glu Leu Thr Asn Leu Ile
            530                 535                 540

Gln Cys Val Glu Lys Trp Asn Val Asp Val Asp Lys Asp Cys Cys Ser
545                 550                 555                 560

Glu His Val Arg Ile Leu Phe Leu Ala Leu Lys Asp Ala Ile Cys Trp
                565                 570                 575

Ile Gly Asp Glu Ala Phe Lys Trp Gln Ala Arg Asp Val Thr Ser His
            580                 585                 590

Val Ile Gln Thr Trp Leu Glu Leu Met Asn Ser Met Leu Arg Glu Ala
            595                 600                 605

Ile Trp Thr Arg Asp Ala Tyr Val Pro Thr Leu Asn Glu Tyr Met Glu
        610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Glu Ile Val Glu Ser Ser Glu
                645                 650                 655

Tyr His Asn Leu Phe Lys Leu Met Ser Thr Gln Gly Arg Leu Leu Asn
            660                 665                 670

Asp Ile His Ser Phe Lys Arg Glu Phe Lys Glu Gly Lys Leu Asn Ala
            675                 680                 685

Val Ala Leu His Leu Ser Asn Gly Glu Ser Gly Lys Val Glu Glu Glu
            690                 695                 700

Val Val Glu Glu Met Met Met Met Ile Lys Asn Lys Arg Lys Glu Leu
705                 710                 715                 720

Met Lys Leu Ile Phe Glu Glu Asn Gly Ser Ile Val Pro Arg Ala Cys
                725                 730                 735

Lys Asp Ala Phe Trp Asn Met Cys His Val Leu Asn Phe Phe Tyr Ala
            740                 745                 750

Asn Asp Asp Gly Phe Thr Gly Asn Thr Ile Leu Asp Thr Val Lys Asp
            755                 760                 765

Ile Ile Tyr Asn Pro Leu Val Leu Val Asn Glu Asn Glu Glu Gln Arg
        770                 775                 780

<210> SEQ ID NO 133
<211> LENGTH: 784
<212> TYPE: PRT
<213> ORGANISM: Stevia rebaudiana

<400> SEQUENCE: 133

Met Asn Leu Ser Leu Cys Ile Ala Ser Pro Leu Leu Thr Lys Ser Ser
1               5                   10                  15

Arg Pro Thr Ala Leu Ser Ala Ile His Thr Ala Ser Thr Ser His Gly
                20                  25                  30

Gly Gln Thr Asn Pro Thr Asn Leu Ile Ile Asp Thr Thr Lys Glu Arg
            35                  40                  45

Ile Gln Lys Leu Phe Lys Asn Val Glu Ile Ser Val Ser Ser Tyr Asp
        50                  55                  60
```

```
Thr Ala Trp Val Ala Met Val Pro Ser Pro Asn Ser Pro Lys Ser Pro
65                  70                  75                  80

Cys Phe Pro Glu Cys Leu Asn Trp Leu Ile Asn Asn Gln Leu Asn Asp
                85                  90                  95

Gly Ser Trp Gly Leu Val Asn His Thr His Asn His Asn His Pro Leu
            100                 105                 110

Leu Lys Asp Ser Leu Ser Ser Thr Leu Ala Cys Ile Val Ala Leu Lys
        115                 120                 125

Arg Trp Asn Val Gly Glu Asp Gln Ile Asn Lys Gly Leu Ser Phe Ile
    130                 135                 140

Glu Ser Asn Leu Ala Ser Ala Thr Asp Lys Ser Gln Pro Ser Pro Ile
145                 150                 155                 160

Gly Phe Asp Ile Ile Phe Pro Gly Leu Leu Glu Tyr Ala Lys Asn Leu
                165                 170                 175

Asp Ile Asn Leu Leu Ser Lys Gln Thr Asp Phe Ser Leu Met Leu His
            180                 185                 190

Lys Arg Glu Leu Glu Gln Lys Arg Cys His Ser Asn Glu Ile Asp Gly
        195                 200                 205

Tyr Leu Ala Tyr Ile Ser Glu Gly Leu Gly Asn Leu Tyr Asp Trp Asn
    210                 215                 220

Met Val Lys Lys Tyr Gln Met Lys Asn Gly Ser Val Phe Asn Ser Pro
225                 230                 235                 240

Ser Ala Thr Ala Ala Phe Ile Asn His Gln Asn Pro Gly Cys Leu
                245                 250                 255

Asn Tyr Leu Asn Ser Leu Leu Asp Lys Phe Gly Asn Ala Val Pro Thr
        260                 265                 270

Val Tyr Pro Leu Asp Leu Tyr Ile Arg Leu Ser Met Val Asp Thr Ile
    275                 280                 285

Glu Arg Leu Gly Ile Ser His His Phe Arg Val Glu Ile Lys Asn Val
290                 295                 300

Leu Asp Glu Thr Tyr Arg Cys Trp Val Glu Arg Asp Glu Gln Ile Phe
305                 310                 315                 320

Met Asp Val Val Thr Cys Ala Leu Ala Phe Arg Leu Leu Arg Ile His
                325                 330                 335

Gly Tyr Lys Val Ser Pro Asp Gln Leu Ala Glu Ile Thr Asn Glu Leu
        340                 345                 350

Ala Phe Lys Asp Glu Tyr Ala Ala Leu Glu Thr Tyr His Ala Ser Gln
    355                 360                 365

Ile Leu Tyr Gln Glu Asp Leu Ser Ser Gly Lys Gln Ile Leu Lys Ser
    370                 375                 380

Ala Asp Phe Leu Lys Gly Ile Leu Ser Thr Asp Ser Asn Arg Leu Ser
385                 390                 395                 400

Lys Leu Ile His Lys Glu Val Glu Asn Ala Leu Lys Phe Pro Ile Asn
                405                 410                 415

Thr Gly Leu Glu Arg Ile Asn Thr Arg Arg Asn Ile Gln Leu Tyr Asn
        420                 425                 430

Val Asp Asn Thr Arg Ile Leu Lys Thr Thr Tyr His Ser Ser Asn Ile
    435                 440                 445

Ser Asn Thr Tyr Tyr Leu Arg Leu Ala Val Glu Asp Phe Tyr Thr Cys
    450                 455                 460

Gln Ser Ile Tyr Arg Glu Glu Leu Lys Gly Leu Glu Arg Trp Val Val
465                 470                 475                 480

Gln Asn Lys Leu Asp Gln Leu Lys Phe Ala Arg Gln Lys Thr Ala Tyr
```

```
                485                 490                 495
Cys Tyr Phe Ser Val Ala Ala Thr Leu Ser Ser Pro Glu Leu Ser Asp
            500                 505                 510

Ala Arg Ile Ser Trp Ala Lys Asn Gly Ile Leu Thr Thr Val Val Asp
            515                 520                 525

Asp Phe Asp Ile Gly Gly Thr Ile Asp Glu Leu Thr Asn Leu Ile
            530                 535                 540

Gln Cys Val Glu Lys Trp Asn Val Asp Val Asp Lys Asp Cys Cys Ser
545                 550                 555                 560

Glu His Val Arg Ile Leu Phe Leu Ala Leu Lys Asp Ala Ile Cys Trp
                565                 570                 575

Ile Gly Asp Glu Ala Phe Lys Trp Gln Ala Arg Asp Val Thr Ser His
            580                 585                 590

Val Ile Gln Thr Trp Leu Glu Leu Met Asn Ser Met Leu Arg Glu Ala
            595                 600                 605

Ile Trp Thr Arg Asp Ala Tyr Val Pro Thr Leu Asn Glu Tyr Met Glu
            610                 615                 620

Asn Ala Tyr Val Ser Phe Ala Leu Gly Pro Ile Val Lys Pro Ala Ile
625                 630                 635                 640

Tyr Phe Val Gly Pro Lys Leu Ser Glu Glu Ile Val Glu Ser Ser Glu
                645                 650                 655

Tyr His Asn Leu Phe Lys Leu Met Ser Thr Gln Gly Arg Leu Leu Asn
            660                 665                 670

Asp Ile His Ser Phe Lys Arg Glu Phe Lys Glu Gly Lys Leu Asn Ala
            675                 680                 685

Val Ala Leu His Leu Ser Asn Gly Glu Ser Gly Lys Val Glu Glu Glu
            690                 695                 700

Val Val Glu Glu Met Met Met Ile Lys Asn Lys Arg Lys Glu Leu
705                 710                 715                 720

Met Lys Leu Ile Phe Glu Glu Asn Gly Ser Ile Val Pro Arg Ala Cys
                725                 730                 735

Lys Asp Ala Phe Trp Asn Met Cys His Val Leu Asn Phe Phe Tyr Ala
            740                 745                 750

Asn Asp Asp Gly Phe Thr Gly Asn Thr Ile Leu Asp Thr Val Lys Asp
            755                 760                 765

Ile Ile Tyr Asn Pro Leu Val Leu Val Asn Glu Asn Glu Glu Gln Arg
            770                 775                 780

<210> SEQ ID NO 134
<211> LENGTH: 590
<212> TYPE: PRT
<213> ORGANISM: Zea mays

<400> SEQUENCE: 134

Met Ala Met Pro Val Lys Leu Thr Pro Ala Ser Leu Ser Leu Lys Ala
1               5                   10                  15

Val Cys Cys Arg Phe Ser Ser Gly Gly His Ala Leu Arg Phe Gly Ser
                20                  25                  30

Ser Leu Pro Cys Trp Arg Arg Thr Pro Thr Gln Arg Ser Thr Ser Ser
            35                  40                  45

Ser Thr Thr Arg Pro Ala Ala Glu Val Ser Ser Gly Lys Ser Lys Gln
        50                  55                  60

His Asp Gln Glu Ala Ser Glu Ala Thr Ile Arg Gln Gln Leu Gln Leu
65                  70                  75                  80
```

```
Val Asp Val Leu Glu Asn Met Gly Ile Ser Arg His Phe Ala Ala Glu
                 85                  90                  95

Ile Lys Cys Ile Leu Asp Arg Thr Tyr Arg Ser Trp Leu Gln Arg His
            100                 105                 110

Glu Glu Ile Met Leu Asp Thr Met Thr Cys Ala Met Ala Phe Arg Ile
            115                 120                 125

Leu Arg Leu Asn Gly Tyr Asn Val Ser Ser Asp Glu Leu Tyr His Val
        130                 135                 140

Val Glu Ala Ser Gly Leu His Asn Ser Leu Gly Gly Tyr Leu Asn Asp
145                 150                 155                 160

Thr Arg Thr Leu Leu Glu Leu His Lys Ala Ser Thr Val Ser Ile Ser
                165                 170                 175

Glu Asp Glu Ser Ile Leu Asp Ser Ile Gly Ser Arg Ser Arg Thr Leu
            180                 185                 190

Leu Arg Glu Gln Leu Glu Ser Gly Ala Leu Arg Lys Pro Ser Leu
        195                 200                 205

Phe Lys Glu Val Glu His Ala Leu Asp Gly Pro Phe Tyr Thr Thr Leu
    210                 215                 220

Asp Arg Leu His His Arg Trp Asn Ile Glu Asn Phe Asn Ile Ile Glu
225                 230                 235                 240

Gln His Met Leu Glu Thr Pro Tyr Leu Ser Asn Gln His Thr Ser Arg
                245                 250                 255

Asp Ile Leu Ala Leu Ser Ile Arg Asp Phe Ser Ser Gln Phe Thr
            260                 265                 270

Tyr Gln Gln Glu Leu Gln His Leu Glu Ser Trp Val Lys Glu Cys Arg
        275                 280                 285

Leu Asp Gln Leu Gln Phe Ala Arg Gln Lys Leu Ala Tyr Phe Tyr Leu
    290                 295                 300

Ser Ala Ala Gly Thr Met Phe Ser Pro Glu Leu Ser Asp Ala Arg Thr
305                 310                 315                 320

Leu Trp Ala Lys Asn Gly Val Leu Thr Thr Ile Val Asp Phe Phe
                325                 330                 335

Asp Val Ala Gly Ser Lys Glu Glu Leu Glu Asn Leu Val Met Leu Val
            340                 345                 350

Glu Met Trp Asp Glu His His Lys Val Glu Phe Tyr Ser Glu Gln Val
        355                 360                 365

Glu Ile Ile Phe Ser Ser Ile Tyr Asp Ser Val Asn Gln Leu Gly Glu
    370                 375                 380

Lys Ala Ser Leu Val Gln Asp Arg Ser Ile Thr Lys His Leu Val Glu
385                 390                 395                 400

Ile Trp Leu Asp Leu Leu Lys Ser Met Met Thr Glu Val Glu Trp Arg
                405                 410                 415

Leu Ser Lys Tyr Val Pro Thr Glu Lys Glu Tyr Met Ile Asn Ala Ser
            420                 425                 430

Leu Ile Phe Gly Leu Gly Pro Ile Val Leu Pro Ala Leu Tyr Phe Val
        435                 440                 445

Gly Pro Lys Ile Ser Glu Ser Ile Val Lys Asp Pro Glu Tyr Asp Glu
    450                 455                 460

Leu Phe Lys Leu Met Ser Thr Cys Gly Arg Leu Leu Asn Asp Val Gln
465                 470                 475                 480

Thr Phe Glu Arg Glu Tyr Asn Glu Gly Lys Leu Asn Ser Val Ser Leu
                485                 490                 495

Leu Val Leu His Gly Gly Pro Met Ser Ile Ser Asp Ala Lys Arg Lys
```

```
                  500                 505                 510
Leu Gln Lys Pro Ile Asp Thr Cys Arg Arg Asp Leu Leu Ser Leu Val
            515                 520                 525

Leu Arg Glu Glu Ser Val Val Pro Arg Pro Cys Lys Glu Leu Phe Trp
        530                 535                 540

Lys Met Cys Lys Val Cys Tyr Phe Tyr Ser Thr Thr Asp Gly Phe
545                 550                 555                 560

Ser Ser Gln Val Glu Arg Ala Lys Glu Val Asp Ala Val Ile Asn Glu
                565                 570                 575

Pro Leu Lys Leu Gln Gly Ser His Thr Leu Val Ser Asp Val
            580                 585                 590

<210> SEQ ID NO 135
<211> LENGTH: 743
<212> TYPE: PRT
<213> ORGANISM: Populus trichocarpa

<400> SEQUENCE: 135

Met Gln Asn Phe His Gly Thr Lys Glu Arg Ile Lys Lys Met Phe Asp
1               5                   10                  15

Lys Ile Glu Leu Ser Val Ser Ser Tyr Asp Thr Ala Trp Val Ala Met
            20                  25                  30

Val Pro Ser Pro Asp Cys Pro Glu Thr Pro Cys Phe Pro Glu Cys Thr
        35                  40                  45

Lys Trp Ile Leu Glu Asn Gln Leu Gly Asp Gly Ser Trp Ser Leu Pro
    50                  55                  60

His Gly Asn Pro Leu Leu Val Lys Asp Ala Leu Ser Ser Thr Leu Ala
65                  70                  75                  80

Cys Ile Leu Ala Leu Lys Arg Trp Gly Ile Gly Glu Glu Gln Ile Asn
                85                  90                  95

Lys Gly Leu Arg Phe Ile Glu Leu Asn Ser Ala Ser Val Thr Asp Asn
            100                 105                 110

Glu Gln His Lys Pro Ile Gly Phe Asp Ile Ile Phe Pro Gly Met Ile
        115                 120                 125

Glu Tyr Ala Ile Asp Leu Asp Leu Asn Leu Pro Leu Lys Pro Thr Asp
    130                 135                 140

Ile Asn Ser Met Leu His Arg Arg Ala Leu Glu Leu Thr Ser Gly Gly
145                 150                 155                 160

Gly Lys Asn Leu Glu Gly Arg Arg Ala Tyr Leu Ala Tyr Val Ser Glu
                165                 170                 175

Gly Ile Gly Lys Leu Gln Asp Trp Glu Met Ala Met Lys Tyr Gln Arg
            180                 185                 190

Lys Asn Gly Ser Leu Phe Asn Ser Pro Ser Thr Thr Ala Ala Ala Phe
        195                 200                 205

Ile His Ile Gln Asp Ala Glu Cys Leu His Tyr Ile Arg Ser Leu Leu
    210                 215                 220

Gln Lys Phe Gly Asn Ala Val Pro Thr Ile Tyr Pro Leu Asp Ile Tyr
225                 230                 235                 240

Ala Arg Leu Ser Met Val Asp Ala Leu Glu Arg Leu Gly Ile Asp Arg
                245                 250                 255

His Phe Arg Lys Glu Arg Lys Phe Val Leu Asp Glu Thr Tyr Arg Phe
            260                 265                 270

Trp Leu Gln Gly Glu Glu Glu Ile Phe Ser Asp Asn Ala Thr Cys Ala
        275                 280                 285
```

-continued

```
Leu Ala Phe Arg Ile Leu Arg Leu Asn Gly Tyr Asp Val Ser Leu Glu
        290                 295                 300
Asp His Phe Ser Asn Ser Leu Gly Gly Tyr Leu Lys Asp Ser Gly Ala
305                 310                 315                 320
Ala Leu Glu Leu Tyr Arg Ala Leu Gln Leu Ser Tyr Pro Asp Glu Ser
                325                 330                 335
Leu Leu Glu Lys Gln Asn Ser Arg Thr Ser Tyr Phe Leu Lys Gln Gly
            340                 345                 350
Leu Ser Asn Val Ser Leu Cys Gly Asp Arg Leu Arg Lys Asn Ile Ile
        355                 360                 365
Gly Glu Val His Asp Ala Leu Asn Phe Ser Asp His Ala Asn Leu Gln
370                 375                 380
Arg Leu Ala Ile Arg Arg Ile Lys His Tyr Ala Thr Asp Thr
385                 390                 395                 400
Arg Ile Leu Lys Thr Ser Tyr Arg Cys Ser Thr Ile Gly Asn Gln Asp
                405                 410                 415
Phe Leu Lys Leu Ala Val Glu Asp Phe Asn Ile Cys Gln Ser Ile Gln
            420                 425                 430
Arg Glu Glu Phe Lys His Ile Glu Arg Trp Val Val Glu Arg Arg Leu
        435                 440                 445
Asp Lys Leu Lys Phe Ala Arg Gln Lys Glu Ala Tyr Cys Tyr Phe Ser
450                 455                 460
Ala Ala Ala Thr Leu Phe Ala Pro Glu Leu Ser Asp Ala Arg Met Ser
465                 470                 475                 480
Trp Ala Lys Asn Gly Val Leu Thr Thr Val Val Asp Asp Phe Phe Asp
                485                 490                 495
Val Gly Gly Ser Glu Glu Leu Val Asn Leu Ile Glu Leu Ile Glu
            500                 505                 510
Arg Trp Asp Val Asn Gly Ser Ala Asp Phe Cys Ser Glu Glu Val Glu
        515                 520                 525
Ile Ile Tyr Ser Ala Ile His Ser Thr Ile Ser Glu Ile Gly Asp Lys
530                 535                 540
Ser Phe Gly Trp Gln Gly Arg Asp Val Lys Ser Gln Val Ile Lys Ile
545                 550                 555                 560
Trp Leu Asp Leu Leu Lys Ser Met Leu Thr Glu Ala Gln Trp Ser Ser
                565                 570                 575
Asn Lys Ser Val Pro Thr Leu Asp Glu Tyr Met Thr Thr Ala His Val
            580                 585                 590
Ser Phe Ala Leu Gly Pro Ile Val Leu Pro Ala Leu Tyr Phe Val Gly
        595                 600                 605
Pro Lys Leu Ser Glu Glu Val Ala Gly His Pro Glu Leu Leu Asn Leu
610                 615                 620
Tyr Lys Val Thr Ser Thr Cys Gly Arg Leu Leu Asn Asp Trp Arg Ser
625                 630                 635                 640
Phe Lys Arg Glu Ser Glu Glu Gly Lys Leu Asn Ala Ile Ser Leu Tyr
                645                 650                 655
Met Ile His Ser Gly Gly Ala Ser Thr Glu Glu Thr Ile Glu His
            660                 665                 670
Phe Lys Gly Leu Ile Asp Ser Gln Arg Arg Gln Leu Leu Gln Leu Val
        675                 680                 685
Leu Gln Glu Lys Asp Ser Ile Ile Pro Arg Pro Cys Lys Asp Leu Phe
690                 695                 700
Trp Asn Met Ile Lys Leu Leu His Thr Phe Tyr Met Lys Asp Asp Gly
```

```
                  705                 710                 715                 720
Phe Thr Ser Asn Glu Met Arg Asn Val Val Lys Ala Ile Ile Asn Glu
                      725                 730                 735

Pro Ile Ser Leu Asp Glu Leu
                740

<210> SEQ ID NO 136
<211> LENGTH: 983
<212> TYPE: PRT
<213> ORGANISM: Phomopsis amygdali

<400> SEQUENCE: 136

Met Glu Phe Asp Glu Pro Leu Val Asp Glu Ala Arg Ser Leu Val Gln
1               5                   10                  15

Arg Thr Leu Gln Asp Tyr Asp Asp Arg Tyr Gly Phe Gly Thr Met Ser
            20                  25                  30

Cys Ala Ala Tyr Asp Thr Ala Trp Val Ser Leu Val Thr Lys Thr Val
        35                  40                  45

Asp Gly Arg Lys Gln Trp Leu Phe Pro Glu Cys Phe Glu Phe Leu Leu
    50                  55                  60

Glu Thr Gln Ser Asp Ala Gly Gly Trp Glu Ile Gly Asn Ser Ala Pro
65                  70                  75                  80

Ile Asp Gly Ile Leu Asn Thr Ala Ala Ser Leu Leu Ala Leu Lys Arg
                85                  90                  95

His Val Gln Thr Glu Gln Ile Ile Gln Pro Gln His Asp His Lys Asp
            100                 105                 110

Leu Ala Gly Arg Ala Glu Arg Ala Ala Ala Ser Leu Arg Ala Gln Leu
        115                 120                 125

Ala Ala Leu Asp Val Ser Thr Thr Glu His Val Gly Phe Glu Ile Ile
    130                 135                 140

Val Pro Ala Met Leu Asp Pro Leu Glu Ala Glu Asp Pro Ser Leu Val
145                 150                 155                 160

Phe Asp Phe Pro Ala Arg Lys Pro Leu Met Lys Ile His Asp Ala Lys
                165                 170                 175

Met Ser Arg Phe Arg Pro Glu Tyr Leu Tyr Gly Lys Gln Pro Met Thr
            180                 185                 190

Ala Leu His Ser Leu Glu Ala Phe Ile Gly Lys Ile Asp Phe Asp Lys
        195                 200                 205

Val Arg His His Arg Thr His Gly Ser Met Met Gly Ser Pro Ser Ser
    210                 215                 220

Thr Ala Ala Tyr Leu Met His Ala Ser Gln Trp Asp Gly Asp Ser Glu
225                 230                 235                 240

Ala Tyr Leu Arg His Val Ile Lys His Ala Ala Gly Gln Gly Thr Gly
                245                 250                 255

Ala Val Pro Ser Ala Phe Pro Ser Thr His Phe Glu Ser Ser Trp Ile
            260                 265                 270

Leu Thr Thr Leu Phe Arg Ala Gly Phe Ser Ala Ser His Leu Ala Cys
        275                 280                 285

Asp Glu Leu Asn Lys Leu Val Glu Ile Leu Glu Gly Ser Phe Glu Lys
    290                 295                 300

Glu Gly Gly Ala Ile Gly Tyr Ala Pro Gly Phe Gln Ala Asp Val Asp
305                 310                 315                 320

Asp Thr Ala Lys Thr Ile Ser Leu Ala Val Leu Gly Arg Asp Ala
                325                 330                 335
```

```
Thr Pro Arg Gln Met Ile Lys Val Phe Glu Ala Asn Thr His Phe Arg
            340                 345                 350

Thr Tyr Pro Gly Glu Arg Asp Pro Ser Leu Thr Ala Asn Cys Asn Ala
        355                 360                 365

Leu Ser Ala Leu Leu His Gln Pro Asp Ala Ala Met Tyr Gly Ser Gln
    370                 375                 380

Ile Gln Lys Ile Thr Lys Phe Val Cys Asp Tyr Trp Trp Lys Ser Asp
385                 390                 395                 400

Gly Lys Ile Lys Asp Lys Trp Asn Thr Cys Tyr Leu Tyr Pro Ser Val
                405                 410                 415

Leu Leu Val Glu Val Leu Val Asp Leu Val Ser Leu Leu Glu Gln Gly
            420                 425                 430

Lys Leu Pro Asp Val Leu Asp Gln Glu Leu Gln Tyr Arg Val Ala Ile
        435                 440                 445

Thr Leu Phe Gln Ala Cys Leu Arg Pro Leu Leu Asp Gln Asp Ala Glu
    450                 455                 460

Gly Ser Trp Asn Lys Ser Ile Glu Ala Thr Ala Tyr Gly Ile Leu Ile
465                 470                 475                 480

Leu Thr Glu Ala Arg Arg Val Cys Phe Phe Asp Arg Leu Ser Glu Pro
                485                 490                 495

Leu Asn Glu Ala Ile Arg Arg Gly Ile Ala Phe Ala Asp Ser Met Ser
            500                 505                 510

Gly Thr Glu Ala Gln Leu Asn Tyr Ile Trp Ile Glu Lys Val Ser Tyr
        515                 520                 525

Ala Pro Ala Leu Leu Thr Lys Ser Tyr Leu Leu Ala Ala Arg Trp Ala
    530                 535                 540

Ala Lys Ser Pro Leu Gly Ala Ser Val Gly Ser Ser Leu Trp Thr Pro
545                 550                 555                 560

Pro Arg Glu Gly Leu Asp Lys His Val Arg Leu Phe His Gln Ala Glu
                565                 570                 575

Leu Phe Arg Ser Leu Pro Glu Trp Glu Leu Arg Ala Ser Met Ile Glu
            580                 585                 590

Ala Ala Leu Phe Thr Pro Leu Leu Arg Ala His Arg Leu Asp Val Phe
        595                 600                 605

Pro Arg Gln Asp Val Gly Glu Asp Lys Tyr Leu Asp Val Val Pro Phe
    610                 615                 620

Phe Trp Thr Ala Ala Asn Asn Arg Asp Arg Thr Tyr Ala Ser Thr Leu
625                 630                 635                 640

Phe Leu Tyr Asp Met Cys Phe Ile Ala Met Leu Asn Phe Gln Leu Asp
                645                 650                 655

Glu Phe Met Glu Ala Thr Ala Gly Ile Leu Phe Arg Asp His Met Asp
            660                 665                 670

Asp Leu Arg Gln Leu Ile His Asp Leu Leu Ala Glu Lys Thr Ser Pro
        675                 680                 685

Lys Ser Ser Gly Arg Ser Ser Gln Gly Thr Lys Asp Ala Asp Ser Gly
    690                 695                 700

Ile Glu Glu Asp Val Ser Met Ser Asp Ser Ala Ser Asp Ser Gln Asp
705                 710                 715                 720

Arg Ser Pro Glu Tyr Asp Leu Val Phe Ser Ala Leu Ser Thr Phe Thr
                725                 730                 735

Lys His Val Leu Gln His Pro Ser Ile Gln Ser Ala Ser Val Trp Asp
            740                 745                 750

Arg Lys Leu Leu Ala Arg Glu Met Lys Ala Tyr Leu Leu Ala His Ile
```

```
                755                 760                 765
Gln Gln Ala Glu Asp Ser Thr Pro Leu Ser Glu Leu Lys Asp Val Pro
    770                 775                 780

Gln Lys Thr Asp Val Thr Arg Val Ser Thr Ser Thr Thr Thr Phe Phe
785                 790                 795                 800

Asn Trp Val Arg Thr Thr Ser Ala Asp His Ile Ser Cys Pro Tyr Ser
                805                 810                 815

Phe His Phe Val Ala Cys His Leu Gly Ala Ala Leu Ser Pro Lys Gly
                820                 825                 830

Ser Asn Gly Asp Cys Tyr Pro Ser Ala Gly Glu Lys Phe Leu Ala Ala
            835                 840                 845

Ala Val Cys Arg His Leu Ala Thr Met Cys Arg Met Tyr Asn Asp Leu
        850                 855                 860

Gly Ser Ala Glu Arg Asp Ser Asp Glu Gly Asn Leu Asn Ser Leu Asp
865                 870                 875                 880

Phe Pro Glu Phe Ala Asp Ser Ala Gly Asn Gly Gly Ile Glu Ile Gln
                885                 890                 895

Lys Ala Ala Leu Leu Arg Leu Ala Glu Phe Glu Arg Asp Ser Tyr Leu
            900                 905                 910

Glu Ala Phe Arg Arg Leu Gln Asp Glu Ser Asn Arg Val His Gly Pro
        915                 920                 925

Ala Gly Gly Asp Glu Ala Arg Leu Ser Arg Arg Met Ala Ile Leu
        930                 935                 940

Glu Phe Phe Ala Gln Gln Val Asp Leu Tyr Gly Gln Val Tyr Val Ile
945                 950                 955                 960

Arg Asp Ile Ser Ala Arg Ile Pro Lys Asn Glu Val Glu Lys Lys Arg
                965                 970                 975

Lys Leu Asp Asp Ala Phe Asn
            980

<210> SEQ ID NO 137
<211> LENGTH: 881
<212> TYPE: PRT
<213> ORGANISM: Physcomitrella patens

<400> SEQUENCE: 137

Met Ala Ser Ser Thr Leu Ile Gln Asn Arg Ser Cys Gly Val Thr Ser
1               5                   10                  15

Ser Met Ser Ser Phe Gln Ile Phe Arg Gly Gln Pro Leu Arg Phe Pro
                20                  25                  30

Gly Thr Arg Thr Pro Ala Ala Val Gln Cys Leu Lys Lys Arg Arg Cys
            35                  40                  45

Leu Arg Pro Thr Glu Ser Val Leu Glu Ser Ser Pro Gly Ser Gly Ser
        50                  55                  60

Tyr Arg Ile Val Thr Gly Pro Ser Gly Ile Asn Pro Ser Ser Asn Gly
65                  70                  75                  80

His Leu Gln Glu Gly Ser Leu Thr His Arg Leu Pro Ile Pro Met Glu
                85                  90                  95

Lys Ser Ile Asp Asn Phe Gln Ser Thr Leu Tyr Val Ser Asp Ile Trp
            100                 105                 110

Ser Glu Thr Leu Gln Arg Thr Glu Cys Leu Leu Gln Val Thr Glu Asn
        115                 120                 125

Val Gln Met Asn Glu Trp Ile Glu Glu Ile Arg Met Tyr Phe Arg Asn
    130                 135                 140
```

```
Met Thr Leu Gly Glu Ile Ser Met Ser Pro Tyr Asp Thr Ala Trp Val
145                 150                 155                 160

Ala Arg Val Pro Ala Leu Asp Gly Ser His Gly Pro Gln Phe His Arg
            165                 170                 175

Ser Leu Gln Trp Ile Ile Asp Asn Gln Leu Pro Asp Gly Asp Trp Gly
        180                 185                 190

Glu Pro Ser Leu Phe Leu Gly Tyr Asp Arg Val Cys Asn Thr Leu Ala
    195                 200                 205

Cys Val Ile Ala Leu Lys Thr Trp Gly Val Gly Ala Gln Asn Val Glu
210                 215                 220

Arg Gly Ile Gln Phe Leu Gln Ser Asn Ile Tyr Lys Met Glu Glu Asp
225                 230                 235                 240

Asp Ala Asn His Met Pro Ile Gly Phe Glu Ile Val Phe Pro Ala Met
            245                 250                 255

Met Glu Asp Ala Lys Ala Leu Gly Leu Asp Leu Pro Tyr Asp Ala Thr
        260                 265                 270

Ile Leu Gln Gln Ile Ser Ala Glu Arg Glu Lys Lys Met Lys Lys Ile
    275                 280                 285

Pro Met Ala Met Val Tyr Lys Tyr Pro Thr Thr Leu Leu His Ser Leu
290                 295                 300

Glu Gly Leu His Arg Glu Val Asp Trp Asn Lys Leu Leu Gln Leu Gln
305                 310                 315                 320

Ser Glu Asn Gly Ser Phe Leu Tyr Ser Pro Ala Ser Thr Ala Cys Ala
            325                 330                 335

Leu Met Tyr Thr Lys Asp Val Lys Cys Phe Asp Tyr Leu Asn Gln Leu
        340                 345                 350

Leu Ile Lys Phe Asp His Ala Cys Pro Asn Val Tyr Pro Val Asp Leu
    355                 360                 365

Phe Glu Arg Leu Trp Met Val Asp Arg Leu Gln Arg Leu Gly Ile Ser
370                 375                 380

Arg Tyr Phe Glu Arg Glu Ile Arg Asp Cys Leu Gln Tyr Val Tyr Arg
385                 390                 395                 400

Tyr Trp Lys Asp Cys Gly Ile Gly Trp Ala Ser Asn Ser Ser Val Gln
            405                 410                 415

Asp Val Asp Asp Thr Ala Met Ala Phe Arg Leu Leu Arg Thr His Gly
        420                 425                 430

Phe Asp Val Lys Glu Asp Cys Phe Arg Gln Phe Lys Asp Gly Glu
    435                 440                 445

Phe Phe Cys Phe Ala Gly Gln Ser Ser Gln Ala Val Thr Gly Met Phe
450                 455                 460

Asn Leu Ser Arg Ala Ser Gln Thr Leu Phe Pro Gly Glu Ser Leu Leu
465                 470                 475                 480

Lys Lys Ala Arg Thr Phe Ser Arg Asn Phe Leu Arg Thr Lys His Glu
            485                 490                 495

Asn Asn Glu Cys Phe Asp Lys Trp Ile Ile Thr Lys Asp Leu Ala Gly
        500                 505                 510

Glu Val Glu Tyr Asn Leu Thr Phe Pro Trp Tyr Ala Ser Leu Pro Arg
    515                 520                 525

Leu Glu His Arg Thr Tyr Leu Asp Gln Tyr Gly Ile Asp Asp Ile Trp
530                 535                 540

Ile Gly Lys Ser Leu Tyr Lys Met Pro Ala Val Thr Asn Glu Val Phe
545                 550                 555                 560

Leu Lys Leu Ala Lys Ala Asp Phe Asn Met Cys Gln Ala Leu His Lys
```

```
                565                 570                 575
Lys Glu Leu Glu Gln Val Ile Lys Trp Asn Ala Ser Cys Gln Phe Arg
            580                 585                 590

Asp Leu Glu Phe Ala Arg Gln Lys Ser Val Glu Cys Tyr Phe Ala Gly
        595                 600                 605

Ala Ala Thr Met Phe Glu Pro Glu Met Val Gln Ala Arg Leu Val Trp
610                 615                 620

Ala Arg Cys Cys Val Leu Thr Thr Val Leu Asp Asp Tyr Phe Asp His
625                 630                 635                 640

Gly Thr Pro Val Glu Glu Leu Arg Val Phe Val Gln Ala Val Arg Thr
            645                 650                 655

Trp Asn Pro Glu Leu Ile Asn Gly Leu Pro Glu Gln Ala Lys Ile Leu
        660                 665                 670

Phe Met Gly Leu Tyr Lys Thr Val Asn Thr Ile Ala Glu Glu Ala Phe
    675                 680                 685

Met Ala Gln Lys Arg Asp Val His His His Leu Lys His Tyr Trp Asp
690                 695                 700

Lys Leu Ile Thr Ser Ala Leu Lys Glu Ala Glu Trp Ala Glu Ser Gly
705                 710                 715                 720

Tyr Val Pro Thr Phe Asp Glu Tyr Met Glu Val Ala Glu Ile Ser Val
            725                 730                 735

Ala Leu Glu Pro Ile Val Cys Ser Thr Leu Phe Phe Ala Gly His Arg
        740                 745                 750

Leu Asp Glu Asp Val Leu Asp Ser Tyr Asp Tyr His Leu Val Met His
    755                 760                 765

Leu Val Asn Arg Val Gly Arg Ile Leu Asn Asp Ile Gln Gly Met Lys
770                 775                 780

Arg Glu Ala Ser Gln Gly Lys Ile Ser Ser Val Gln Ile Tyr Met Glu
785                 790                 795                 800

Glu His Pro Ser Val Pro Ser Glu Ala Met Ala Ile Ala His Leu Gln
            805                 810                 815

Glu Leu Val Asp Asn Ser Met Gln Gln Leu Thr Tyr Glu Val Leu Arg
        820                 825                 830

Phe Thr Ala Val Pro Lys Ser Cys Lys Arg Ile His Leu Asn Met Ala
    835                 840                 845

Lys Ile Met His Ala Phe Tyr Lys Asp Thr Asp Gly Phe Ser Ser Leu
850                 855                 860

Thr Ala Met Thr Gly Phe Val Lys Lys Val Leu Phe Glu Pro Val Pro
865                 870                 875                 880

Glu

<210> SEQ ID NO 138
<211> LENGTH: 513
<212> TYPE: PRT
<213> ORGANISM: Stevia rebaudiana

<400> SEQUENCE: 138

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
```

-continued

```
            50                  55                  60
Leu Lys Glu Lys Lys Pro Tyr Met Thr Phe Thr Arg Trp Ala Ala Thr
 65                  70                  75                  80

Tyr Gly Pro Ile Tyr Ser Ile Lys Thr Gly Ala Thr Ser Met Val Val
                     85                  90                  95

Val Ser Ser Asn Glu Ile Ala Lys Glu Ala Leu Val Thr Arg Phe Gln
                    100                 105                 110

Ser Ile Ser Thr Arg Asn Leu Ser Lys Ala Leu Lys Val Leu Thr Ala
                115                 120                 125

Asp Lys Thr Met Val Ala Met Ser Asp Tyr Asp Tyr His Lys Thr
            130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                    165                 170                 175

Leu His Glu Phe Val Lys Asn Asn Pro Glu Gln Glu Glu Val Asp Leu
                180                 185                 190

Arg Lys Ile Phe Gln Ser Glu Leu Phe Gly Leu Ala Met Arg Gln Ala
                195                 200                 205

Leu Gly Lys Asp Val Glu Ser Leu Tyr Val Glu Asp Leu Lys Ile Thr
                210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                    245                 250                 255

Val Pro Asn Lys Lys Phe Glu Asn Thr Ile Gln Gln Met Tyr Ile Arg
                260                 265                 270

Arg Glu Ala Val Met Lys Ser Leu Ile Lys Glu His Lys Lys Arg Ile
                275                 280                 285

Ala Ser Gly Glu Lys Leu Asn Ser Tyr Ile Asp Tyr Leu Leu Ser Glu
                290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                    325                 330                 335

Tyr Glu Leu Ala Lys Asn Pro Lys Leu Gln Asp Arg Leu Tyr Arg Asp
                340                 345                 350

Ile Lys Ser Val Cys Gly Ser Glu Lys Ile Thr Glu Glu His Leu Ser
                355                 360                 365

Gln Leu Pro Tyr Ile Thr Ala Ile Phe His Glu Thr Leu Arg Arg His
370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                    405                 410                 415

Tyr Gly Cys Asn Met Asp Lys Asn Val Trp Glu Asn Pro Glu Glu Trp
                420                 425                 430

Asn Pro Glu Arg Phe Met Lys Glu Asn Glu Thr Ile Asp Phe Gln Lys
                435                 440                 445

Thr Met Ala Phe Gly Gly Gly Lys Arg Val Cys Ala Gly Ser Leu Gln
450                 455                 460

Ala Leu Leu Thr Ala Ser Ile Gly Ile Gly Arg Met Val Gln Glu Phe
465                 470                 475                 480
```

Glu Trp Lys Leu Lys Asp Met Thr Gln Glu Glu Val Asn Thr Ile Gly
            485                 490                 495

Leu Thr Thr Gln Met Leu Arg Pro Leu Arg Ala Ile Ile Lys Pro Arg
            500                 505                 510

Ile

<210> SEQ ID NO 139
<211> LENGTH: 509
<212> TYPE: PRT
<213> ORGANISM: Arabidopsis thaliana

<400> SEQUENCE: 139

Met Ala Phe Phe Ser Met Ile Ser Ile Leu Leu Gly Phe Val Ile Ser
1               5                   10                  15

Ser Phe Ile Phe Ile Phe Phe Lys Lys Leu Leu Ser Phe Ser Arg
            20                  25                  30

Lys Asn Met Ser Glu Val Ser Thr Leu Pro Ser Val Pro Val Val Pro
            35                  40                  45

Gly Phe Pro Val Ile Gly Asn Leu Leu Gln Leu Lys Glu Lys Lys Pro
        50                  55                  60

His Lys Thr Phe Thr Arg Trp Ser Glu Ile Tyr Gly Pro Ile Tyr Ser
65                  70                  75                  80

Ile Lys Met Gly Ser Ser Ser Leu Ile Val Leu Asn Ser Thr Glu Thr
                85                  90                  95

Ala Lys Glu Ala Met Val Thr Arg Phe Ser Ser Ile Ser Thr Arg Lys
            100                 105                 110

Leu Ser Asn Ala Leu Thr Val Leu Thr Cys Asp Lys Ser Met Val Ala
        115                 120                 125

Thr Ser Asp Tyr Asp Asp Phe His Lys Leu Val Lys Arg Cys Leu Leu
130                 135                 140

Asn Gly Leu Leu Gly Ala Asn Ala Gln Lys Arg Lys His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205

Ile Tyr Val Lys Glu Leu Gly Val Thr Leu Ser Lys Asp Glu Ile Phe
210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
                245                 250                 255

Ala Arg Ile Gln Gln Lys His Lys Arg Arg Leu Ala Val Met Asn Ala
            260                 265                 270

Leu Ile Gln Asp Arg Leu Lys Gln Asn Gly Ser Glu Ser Asp Asp Asp
        275                 280                 285

Cys Tyr Leu Asn Phe Leu Met Ser Glu Ala Lys Thr Leu Thr Lys Glu
290                 295                 300

Gln Ile Ala Ile Leu Val Trp Glu Thr Ile Ile Glu Thr Ala Asp Thr
305                 310                 315                 320

Thr Leu Val Thr Thr Glu Trp Ala Ile Tyr Glu Leu Ala Lys His Pro
                325                 330                 335

```
Ser Val Gln Asp Arg Leu Cys Lys Glu Ile Gln Asn Val Cys Gly Gly
            340                 345                 350

Glu Lys Phe Lys Glu Glu Gln Leu Ser Gln Val Pro Tyr Leu Asn Gly
            355                 360                 365

Val Phe His Glu Thr Leu Arg Lys Tyr Ser Pro Ala Pro Leu Val Pro
            370                 375                 380

Ile Arg Tyr Ala His Glu Asp Thr Gln Ile Gly Gly Tyr His Val Pro
385                 390                 395                 400

Ala Gly Ser Glu Ile Ala Ile Asn Ile Tyr Gly Cys Asn Met Asp Lys
            405                 410                 415

Lys Arg Trp Glu Arg Pro Glu Asp Trp Trp Pro Glu Arg Phe Leu Asp
            420                 425                 430

Asp Gly Lys Tyr Glu Thr Ser Asp Leu His Lys Thr Met Ala Phe Gly
            435                 440                 445

Ala Gly Lys Arg Val Cys Ala Gly Ala Leu Gln Ala Ser Leu Met Ala
            450                 455                 460

Gly Ile Ala Ile Gly Arg Leu Val Gln Glu Phe Glu Trp Lys Leu Arg
465                 470                 475                 480

Asp Gly Glu Glu Glu Asn Val Asp Thr Tyr Gly Leu Thr Ser Gln Lys
            485                 490                 495

Leu Tyr Pro Leu Met Ala Ile Ile Asn Pro Arg Arg Ser
            500                 505

<210> SEQ ID NO 140
<211> LENGTH: 525
<212> TYPE: PRT
<213> ORGANISM: Gibberella fujikoroi

<400> SEQUENCE: 140

Met Ser Lys Ser Asn Ser Met Asn Ser Thr Ser His Glu Thr Leu Phe
1               5                   10                  15

Gln Gln Leu Val Leu Gly Leu Asp Arg Met Pro Leu Met Asp Val His
            20                  25                  30

Trp Leu Ile Tyr Val Ala Phe Gly Ala Trp Leu Cys Ser Tyr Val Ile
            35                  40                  45

His Val Leu Ser Ser Ser Thr Val Lys Val Pro Val Val Gly Tyr
        50                  55                  60

Arg Ser Val Phe Glu Pro Thr Trp Leu Leu Arg Leu Arg Phe Val Trp
65                  70                  75                  80

Glu Gly Gly Ser Ile Ile Gly Gln Gly Tyr Asn Lys Phe Lys Asp Ser
            85                  90                  95

Ile Phe Gln Val Arg Lys Leu Gly Thr Asp Ile Val Ile Pro Pro
            100                 105                 110

Asn Tyr Ile Asp Glu Val Arg Lys Leu Ser Gln Asp Lys Thr Arg Ser
            115                 120                 125

Val Glu Pro Phe Ile Asn Asp Phe Ala Gly Gln Tyr Thr Arg Gly Met
            130                 135                 140

Val Phe Leu Gln Ser Asp Leu Gln Asn Arg Val Ile Gln Gln Arg Leu
145                 150                 155                 160

Thr Pro Lys Leu Val Ser Leu Thr Lys Val Met Lys Glu Glu Leu Asp
            165                 170                 175

Tyr Ala Leu Thr Lys Glu Met Pro Asp Met Lys Asn Asp Glu Trp Val
            180                 185                 190

Glu Val Asp Ile Ser Ser Ile Met Val Arg Leu Ile Ser Arg Ile Ser
```

```
                195                 200                 205
Ala Arg Val Phe Leu Gly Pro Glu His Cys Arg Asn Gln Glu Trp Leu
210                 215                 220

Thr Thr Thr Ala Glu Tyr Ser Glu Ser Leu Phe Ile Thr Gly Phe Ile
225                 230                 235                 240

Leu Arg Val Val Pro His Ile Leu Arg Pro Phe Ile Ala Pro Leu Leu
                245                 250                 255

Pro Ser Tyr Arg Thr Leu Leu Arg Asn Val Ser Ser Gly Arg Arg Val
                260                 265                 270

Ile Gly Asp Ile Ile Arg Ser Gln Gln Gly Asp Gly Asn Glu Asp Ile
                275                 280                 285

Leu Ser Trp Met Arg Asp Ala Ala Thr Gly Glu Glu Lys Gln Ile Asp
290                 295                 300

Asn Ile Ala Gln Arg Met Leu Ile Leu Ser Leu Ala Ser Ile His Thr
305                 310                 315                 320

Thr Ala Met Thr Met Thr His Ala Met Tyr Asp Leu Cys Ala Cys Pro
                325                 330                 335

Glu Tyr Ile Glu Pro Leu Arg Asp Glu Val Lys Ser Val Val Gly Ala
                340                 345                 350

Ser Gly Trp Asp Lys Thr Ala Leu Asn Arg Phe His Lys Leu Asp Ser
                355                 360                 365

Phe Leu Lys Glu Ser Gln Arg Phe Asn Pro Val Phe Leu Leu Thr Phe
370                 375                 380

Asn Arg Ile Tyr His Gln Ser Met Thr Leu Ser Asp Gly Thr Asn Ile
385                 390                 395                 400

Pro Ser Gly Thr Arg Ile Ala Val Pro Ser His Ala Met Leu Gln Asp
                405                 410                 415

Ser Ala His Val Pro Gly Pro Thr Pro Thr Glu Phe Asp Gly Phe
                420                 425                 430

Arg Tyr Ser Lys Ile Arg Ser Asp Ser Asn Tyr Ala Gln Lys Tyr Leu
                435                 440                 445

Phe Ser Met Thr Asp Ser Ser Asn Met Ala Phe Gly Tyr Gly Lys Tyr
450                 455                 460

Ala Cys Pro Gly Arg Phe Tyr Ala Ser Asn Glu Met Lys Leu Thr Leu
465                 470                 475                 480

Ala Ile Leu Leu Leu Gln Phe Glu Phe Lys Leu Pro Asp Gly Lys Gly
                485                 490                 495

Arg Pro Arg Asn Ile Thr Ile Asp Ser Asp Met Ile Pro Asp Pro Arg
                500                 505                 510

Ala Arg Leu Cys Val Arg Lys Arg Ser Leu Arg Asp Glu
                515                 520                 525

<210> SEQ ID NO 141
<211> LENGTH: 499
<212> TYPE: PRT
<213> ORGANISM: Trametes versicolor

<400> SEQUENCE: 141

Met Glu Asp Pro Thr Val Leu Tyr Ala Cys Leu Ala Ile Ala Val Ala
1               5                   10                  15

Thr Phe Val Val Arg Trp Tyr Arg Asp Pro Leu Arg Ser Ile Pro Thr
                20                  25                  30

Val Gly Gly Ser Asp Leu Pro Ile Leu Ser Tyr Ile Gly Ala Leu Arg
                35                  40                  45
```

-continued

Trp Thr Arg Arg Gly Arg Glu Ile Leu Gln Glu Gly Tyr Asp Gly Tyr
    50              55                  60

Arg Gly Ser Thr Phe Lys Ile Ala Met Leu Asp Arg Trp Ile Val Ile
65              70              75                  80

Ala Asn Gly Pro Lys Leu Ala Asp Glu Val Arg Arg Pro Asp Glu
            85              90              95

Glu Leu Asn Phe Met Asp Gly Leu Gly Ala Phe Val Gln Thr Lys Tyr
            100             105             110

Thr Leu Gly Glu Ala Ile His Asn Asp Pro Tyr His Val Asp Ile Ile
        115             120             125

Arg Glu Lys Leu Thr Arg Gly Leu Pro Ala Val Leu Pro Asp Val Ile
    130             135             140

Glu Glu Leu Thr Leu Ala Val Arg Gln Tyr Ile Pro Thr Glu Gly Asp
145             150             155             160

Glu Trp Val Ser Val Asn Cys Ser Lys Ala Ala Arg Asp Ile Val Ala
            165             170             175

Arg Ala Ser Asn Arg Val Phe Val Gly Leu Pro Ala Cys Arg Asn Gln
            180             185             190

Gly Tyr Leu Asp Leu Ala Ile Asp Phe Thr Leu Ser Val Val Lys Asp
        195             200             205

Arg Ala Ile Ile Asn Met Phe Pro Glu Leu Leu Lys Pro Ile Val Gly
    210             215             220

Arg Val Val Gly Asn Ala Thr Arg Asn Val Arg Ala Val Pro Phe
225             230             235             240

Val Ala Pro Leu Val Glu Glu Arg Arg Leu Met Glu Glu Tyr Gly
            245             250             255

Glu Asp Trp Ser Glu Lys Pro Asn Asp Met Leu Gln Trp Ile Met Asp
            260             265             270

Glu Ala Ala Ser Arg Asp Ser Ser Val Lys Ala Ile Ala Glu Arg Leu
        275             280             285

Leu Met Val Asn Phe Ala Ala Ile His Thr Ser Ser Asn Thr Ile Thr
    290             295             300

His Ala Leu Tyr His Leu Ala Glu Met Pro Glu Thr Leu Gln Pro Leu
305             310             315             320

Arg Glu Glu Ile Glu Pro Leu Val Lys Glu Glu Gly Trp Thr Lys Ala
            325             330             335

Ala Met Gly Lys Met Trp Trp Leu Asp Ser Phe Leu Arg Glu Ser Gln
            340             345             350

Arg Tyr Asn Gly Ile Asn Ile Val Ser Leu Thr Arg Met Ala Asp Lys
        355             360             365

Asp Ile Thr Leu Ser Asp Gly Thr Phe Leu Pro Lys Gly Thr Leu Val
    370             375             380

Ala Val Pro Ala Tyr Ser Thr His Arg Asp Asp Ala Val Tyr Ala Asp
385             390             395             400

Ala Leu Val Phe Asp Pro Phe Arg Phe Ser Arg Met Arg Ala Arg Glu
            405             410             415

Gly Glu Gly Thr Lys His Gln Phe Val Asn Thr Ser Val Glu Tyr Val
            420             425             430

Pro Phe Gly His Gly Lys His Ala Cys Pro Gly Arg Phe Phe Ala Ala
        435             440             445

Asn Glu Leu Lys Ala Met Leu Ala Tyr Ile Val Leu Asn Tyr Asp Val
    450             455             460

Lys Leu Pro Gly Asp Gly Lys Arg Pro Leu Asn Met Tyr Trp Gly Pro

```
                465                 470                 475                 480
Thr Val Leu Pro Ala Pro Ala Gly Gln Val Leu Phe Arg Lys Arg Gln
                    485                 490                 495
Val Ser Leu

<210> SEQ ID NO 142
<211> LENGTH: 525
<212> TYPE: PRT
<213> ORGANISM: Stevia rebaudiana

<400> SEQUENCE: 142

Met Gly Leu Phe Pro Leu Glu Asp Ser Tyr Ala Leu Val Phe Glu Gly
1               5                   10                  15

Leu Ala Ile Thr Leu Ala Leu Tyr Tyr Leu Leu Ser Phe Ile Tyr Lys
                20                  25                  30

Thr Ser Lys Lys Thr Cys Thr Pro Lys Ala Ser Gly Glu Ile Ile
            35                  40                  45

Pro Ile Thr Gly Ile Ile Leu Asn Leu Leu Ser Gly Ser Gly Leu
    50                  55                  60

Pro Ile Ile Leu Ala Leu Ala Ser Leu Ala Asp Arg Cys Gly Pro Ile
65                  70                  75                  80

Phe Thr Ile Arg Leu Gly Ile Arg Arg Val Leu Val Val Ser Asn Trp
                85                  90                  95

Glu Ile Ala Lys Glu Ile Phe Thr Thr His Asp Leu Ile Val Ser Asn
                100                 105                 110

Arg Pro Lys Tyr Leu Ala Ala Lys Ile Leu Gly Phe Asn Tyr Val Ser
            115                 120                 125

Phe Ser Phe Ala Pro Tyr Gly Pro Tyr Trp Val Gly Ile Arg Lys Ile
    130                 135                 140

Ile Ala Thr Lys Leu Met Ser Ser Ser Arg Leu Gln Lys Leu Gln Phe
145                 150                 155                 160

Val Arg Val Phe Glu Leu Glu Asn Ser Met Lys Ser Ile Arg Glu Ser
                165                 170                 175

Trp Lys Glu Lys Lys Asp Glu Glu Gly Lys Val Leu Val Glu Met Lys
            180                 185                 190

Lys Trp Phe Trp Glu Leu Asn Met Asn Ile Val Leu Arg Thr Val Ala
    195                 200                 205

Gly Lys Gln Tyr Thr Gly Thr Val Asp Asp Ala Asp Ala Lys Arg Ile
210                 215                 220

Ser Glu Leu Phe Arg Glu Trp Phe His Tyr Thr Gly Arg Phe Val Val
225                 230                 235                 240

Gly Asp Ala Phe Pro Phe Leu Gly Trp Leu Asp Leu Gly Gly Tyr Lys
                245                 250                 255

Lys Thr Met Glu Leu Val Ala Ser Arg Leu Asp Ser Met Val Ser Lys
            260                 265                 270

Trp Leu Asp Glu His Arg Lys Lys Gln Ala Asn Asp Asp Lys Lys Glu
    275                 280                 285

Asp Met Asp Phe Met Asp Ile Met Ile Ser Met Thr Glu Ala Asn Ser
290                 295                 300

Pro Leu Glu Gly Tyr Gly Thr Asp Thr Ile Ile Lys Thr Thr Cys Met
305                 310                 315                 320

Thr Leu Ile Val Ser Gly Val Asp Thr Thr Ser Ile Val Leu Thr Trp
                325                 330                 335

Ala Leu Ser Leu Leu Leu Asn Asn Arg Asp Thr Leu Lys Lys Ala Gln
```

```
                340             345             350
Glu Glu Leu Asp Met Cys Val Gly Lys Gly Arg Gln Val Asn Glu Ser
            355                 360             365
Asp Leu Val Asn Leu Ile Tyr Leu Glu Ala Val Leu Lys Glu Ala Leu
        370                 375             380
Arg Leu Tyr Pro Ala Ala Phe Leu Gly Gly Pro Arg Ala Phe Leu Glu
385                 390             395                 400
Asp Cys Thr Val Ala Gly Tyr Arg Ile Pro Lys Gly Thr Cys Leu Leu
                405             410             415
Ile Asn Met Trp Lys Leu His Arg Asp Pro Asn Ile Trp Ser Asp Pro
            420             425             430
Cys Glu Phe Lys Pro Glu Arg Phe Leu Thr Pro Asn Gln Lys Asp Val
        435             440             445
Asp Val Ile Gly Met Asp Phe Glu Leu Ile Pro Phe Gly Ala Gly Arg
        450             455             460
Arg Tyr Cys Pro Gly Thr Arg Leu Ala Leu Gln Met Leu His Ile Val
465             470             475             480
Leu Ala Thr Leu Leu Gln Asn Phe Glu Met Ser Thr Pro Asn Asp Ala
            485             490             495
Pro Val Asp Met Thr Ala Ser Val Gly Met Thr Asn Ala Lys Ala Ser
            500             505             510
Pro Leu Glu Val Leu Leu Ser Pro Arg Val Lys Trp Ser
            515             520             525

<210> SEQ ID NO 143
<211> LENGTH: 476
<212> TYPE: PRT
<213> ORGANISM: Stevia rebaudiana

<400> SEQUENCE: 143

Met Ile Gln Val Leu Thr Pro Ile Leu Leu Phe Leu Ile Phe Phe Val
1               5                   10                  15
Phe Trp Lys Val Tyr Lys His Gln Lys Thr Lys Ile Asn Leu Pro Pro
            20                  25                  30
Gly Ser Phe Gly Trp Pro Phe Leu Gly Glu Thr Leu Ala Leu Leu Arg
        35                  40                  45
Ala Gly Trp Asp Ser Glu Pro Glu Arg Phe Val Arg Glu Arg Ile Lys
    50                  55                  60
Lys His Gly Ser Pro Leu Val Phe Lys Thr Ser Leu Phe Gly Asp Arg
65                  70                  75                  80
Phe Ala Val Leu Cys Gly Pro Ala Gly Asn Lys Phe Leu Phe Cys Asn
                85                  90                  95
Glu Asn Lys Leu Val Ala Ser Trp Trp Pro Val Pro Val Arg Lys Leu
            100                 105                 110
Phe Gly Lys Ser Leu Leu Thr Ile Arg Gly Asp Glu Ala Lys Trp Met
        115                 120                 125
Arg Lys Met Leu Leu Ser Tyr Leu Gly Pro Asp Ala Phe Ala Thr His
    130                 135                 140
Tyr Ala Val Thr Met Asp Val Val Thr Arg Arg His Ile Asp Val His
145                 150                 155                 160
Trp Arg Gly Lys Glu Glu Val Asn Val Phe Gln Thr Val Lys Leu Tyr
                165                 170                 175
Ala Phe Glu Leu Ala Cys Arg Leu Phe Met Asn Leu Asp Asp Pro Asn
            180                 185                 190
```

-continued

His Ile Ala Lys Leu Gly Ser Leu Phe Asn Ile Phe Leu Lys Gly Ile
            195                 200                 205

Ile Glu Leu Pro Ile Asp Val Pro Gly Thr Arg Phe Tyr Ser Ser Lys
    210                 215                 220

Lys Ala Ala Ala Ile Arg Ile Glu Leu Lys Lys Leu Ile Lys Ala
225                 230                 235                 240

Arg Lys Leu Glu Leu Lys Glu Gly Lys Ala Ser Ser Gln Asp Leu
                245                 250                 255

Leu Ser His Leu Leu Thr Ser Pro Asp Glu Asn Gly Met Phe Leu Thr
            260                 265                 270

Glu Glu Glu Ile Val Asp Asn Ile Leu Leu Leu Phe Ala Gly His
            275                 280                 285

Asp Thr Ser Ala Leu Ser Ile Thr Leu Leu Met Lys Thr Leu Gly Glu
    290                 295                 300

His Ser Asp Val Tyr Asp Lys Val Leu Lys Glu Gln Leu Glu Ile Ser
305                 310                 315                 320

Lys Thr Lys Glu Ala Trp Glu Ser Leu Lys Trp Glu Asp Ile Gln Lys
                325                 330                 335

Met Lys Tyr Ser Trp Ser Val Ile Cys Glu Val Met Arg Leu Asn Pro
            340                 345                 350

Pro Val Ile Gly Thr Tyr Arg Glu Ala Leu Val Asp Ile Asp Tyr Ala
        355                 360                 365

Gly Tyr Thr Ile Pro Lys Gly Trp Lys Leu His Trp Ser Ala Val Ser
        370                 375                 380

Thr Gln Arg Asp Glu Ala Asn Phe Glu Asp Val Thr Arg Phe Asp Pro
385                 390                 395                 400

Ser Arg Phe Glu Gly Ala Gly Pro Thr Pro Phe Thr Phe Val Pro Phe
                405                 410                 415

Gly Gly Gly Pro Arg Met Cys Leu Gly Lys Glu Phe Ala Arg Leu Glu
            420                 425                 430

Val Leu Ala Phe Leu His Asn Ile Val Thr Asn Phe Lys Trp Asp Leu
            435                 440                 445

Leu Ile Pro Asp Glu Lys Ile Glu Tyr Asp Pro Met Ala Thr Pro Ala
    450                 455                 460

Lys Gly Leu Pro Ile Arg Leu His Pro His Gln Val
465                 470                 475

<210> SEQ ID NO 144
<211> LENGTH: 525
<212> TYPE: PRT
<213> ORGANISM: Arabidopsis thaliana

<400> SEQUENCE: 144

Met Glu Ser Leu Val Val His Thr Val Asn Ala Ile Trp Cys Ile Val
1               5                   10                  15

Ile Val Gly Ile Phe Ser Val Gly Tyr His Val Tyr Gly Arg Ala Val
                20                  25                  30

Val Glu Gln Trp Arg Met Arg Arg Ser Leu Lys Leu Gln Gly Val Lys
            35                  40                  45

Gly Pro Pro Pro Ser Ile Phe Asn Gly Asn Val Ser Glu Met Gln Arg
        50                  55                  60

Ile Gln Ser Glu Ala Lys His Cys Ser Gly Asp Asn Ile Ile Ser His
65                  70                  75                  80

Asp Tyr Ser Ser Ser Leu Phe Pro His Phe Asp His Trp Arg Lys Gln
                85                  90                  95

```
Tyr Gly Arg Ile Tyr Thr Tyr Ser Thr Gly Leu Lys Gln His Leu Tyr
            100                 105                 110

Ile Asn His Pro Glu Met Val Lys Glu Leu Ser Gln Thr Asn Thr Leu
            115                 120                 125

Asn Leu Gly Arg Ile Thr His Ile Thr Lys Arg Leu Asn Pro Ile Leu
            130                 135                 140

Gly Asn Gly Ile Ile Thr Ser Asn Gly Pro His Trp Ala His Gln Arg
145                 150                 155                 160

Arg Ile Ile Ala Tyr Glu Phe Thr His Asp Lys Ile Lys Gly Met Val
                165                 170                 175

Gly Leu Met Val Glu Ser Ala Met Pro Met Leu Asn Lys Trp Glu Glu
            180                 185                 190

Met Val Lys Arg Gly Gly Glu Met Gly Cys Asp Ile Arg Val Asp Glu
                195                 200                 205

Asp Leu Lys Asp Val Ser Ala Asp Val Ile Ala Lys Ala Cys Phe Gly
            210                 215                 220

Ser Ser Phe Ser Lys Gly Lys Ala Ile Phe Ser Met Ile Arg Asp Leu
225                 230                 235                 240

Leu Thr Ala Ile Thr Lys Arg Ser Val Leu Phe Arg Phe Asn Gly Phe
                245                 250                 255

Thr Asp Met Val Phe Gly Ser Lys Lys His Gly Asp Val Asp Ile Asp
            260                 265                 270

Ala Leu Glu Met Glu Leu Glu Ser Ser Ile Trp Glu Thr Val Lys Glu
            275                 280                 285

Arg Glu Ile Glu Cys Lys Asp Thr His Lys Lys Asp Leu Met Gln Leu
            290                 295                 300

Ile Leu Glu Gly Ala Met Arg Ser Cys Asp Gly Asn Leu Trp Asp Lys
305                 310                 315                 320

Ser Ala Tyr Arg Arg Phe Val Val Asp Asn Cys Lys Ser Ile Tyr Phe
                325                 330                 335

Ala Gly His Asp Ser Thr Ala Val Ser Val Ser Trp Cys Leu Met Leu
            340                 345                 350

Leu Ala Leu Asn Pro Ser Trp Gln Val Lys Ile Arg Asp Glu Ile Leu
            355                 360                 365

Ser Ser Cys Lys Asn Gly Ile Pro Asp Ala Glu Ser Ile Pro Asn Leu
            370                 375                 380

Lys Thr Val Thr Met Val Ile Gln Glu Thr Met Arg Leu Tyr Pro Pro
385                 390                 395                 400

Ala Pro Ile Val Gly Arg Glu Ala Ser Lys Asp Ile Arg Leu Gly Asp
                405                 410                 415

Leu Val Val Pro Lys Gly Val Cys Ile Trp Thr Leu Ile Pro Ala Leu
            420                 425                 430

His Arg Asp Pro Glu Ile Trp Gly Pro Asp Ala Asn Asp Phe Lys Pro
            435                 440                 445

Glu Arg Phe Ser Glu Gly Ile Ser Lys Ala Cys Lys Tyr Pro Gln Ser
            450                 455                 460

Tyr Ile Pro Phe Gly Leu Gly Pro Arg Thr Cys Val Gly Lys Asn Phe
465                 470                 475                 480

Gly Met Met Glu Val Lys Val Leu Val Ser Leu Ile Val Ser Lys Phe
                485                 490                 495

Ser Phe Thr Leu Ser Pro Thr Tyr Gln His Ser Pro Ser His Lys Leu
            500                 505                 510
```

```
Leu Val Glu Pro Gln His Gly Val Ile Arg Val Val
            515                 520                 525

<210> SEQ ID NO 145
<211> LENGTH: 529
<212> TYPE: PRT
<213> ORGANISM: Vitis vinifera

<400> SEQUENCE: 145

Met Tyr Phe Leu Leu Gln Tyr Leu Asn Ile Thr Thr Val Gly Val Phe
  1               5                  10                  15

Ala Thr Leu Phe Leu Ser Tyr Cys Leu Leu Trp Arg Ser Arg Ala
             20                  25                  30

Gly Asn Lys Lys Ile Ala Pro Glu Ala Ala Ala Trp Pro Ile Ile
             35                  40                  45

Gly His Leu His Leu Leu Ala Gly Gly Ser His Gln Leu Pro His Ile
         50                  55                  60

Thr Leu Gly Asn Met Ala Asp Lys Tyr Gly Pro Val Phe Thr Ile Arg
 65                  70                  75                  80

Ile Gly Leu His Arg Ala Val Val Ser Ser Trp Glu Met Ala Lys
             85                  90                  95

Glu Cys Ser Thr Ala Asn Asp Gln Val Ser Ser Arg Pro Glu Leu
                100                 105                 110

Leu Ala Ser Lys Leu Leu Gly Tyr Asn Tyr Ala Met Phe Gly Phe Ser
            115                 120                 125

Pro Tyr Gly Ser Tyr Trp Arg Glu Met Arg Lys Ile Ile Ser Leu Glu
    130                 135                 140

Leu Leu Ser Asn Ser Arg Leu Glu Leu Leu Lys Asp Val Arg Ala Ser
145                 150                 155                 160

Glu Val Val Thr Ser Ile Lys Glu Leu Tyr Lys Leu Trp Ala Glu Lys
                165                 170                 175

Lys Asn Glu Ser Gly Leu Val Ser Val Glu Met Lys Gln Trp Phe Gly
            180                 185                 190

Asp Leu Thr Leu Asn Val Ile Leu Arg Met Val Ala Gly Lys Arg Tyr
        195                 200                 205

Phe Ser Ala Ser Asp Ala Ser Glu Asn Lys Gln Ala Gln Arg Cys Arg
    210                 215                 220

Arg Val Phe Arg Glu Phe Phe His Leu Ser Gly Leu Phe Val Val Ala
225                 230                 235                 240

Asp Ala Ile Pro Phe Leu Gly Trp Leu Asp Trp Gly Arg His Glu Lys
                245                 250                 255

Thr Leu Lys Lys Thr Ala Ile Glu Met Asp Ser Ile Ala Gln Glu Trp
            260                 265                 270

Leu Glu Glu His Arg Arg Arg Lys Asp Ser Gly Asp Asp Asn Ser Thr
        275                 280                 285

Gln Asp Phe Met Asp Val Met Gln Ser Val Leu Asp Gly Lys Asn Leu
    290                 295                 300

Gly Gly Tyr Asp Ala Asp Thr Ile Asn Lys Ala Thr Cys Leu Thr Leu
305                 310                 315                 320

Ile Ser Gly Gly Ser Asp Thr Thr Val Val Ser Leu Thr Trp Ala Leu
                325                 330                 335

Ser Leu Val Leu Asn Asn Arg Asp Thr Leu Lys Lys Ala Gln Glu Glu
            340                 345                 350

Leu Asp Ile Gln Val Gly Lys Glu Arg Leu Val Asn Glu Gln Asp Ile
        355                 360                 365
```

```
Ser Lys Leu Val Tyr Leu Gln Ala Ile Val Lys Glu Thr Leu Arg Leu
    370                 375                 380
Tyr Pro Pro Gly Pro Leu Gly Gly Leu Arg Gln Phe Thr Glu Asp Cys
385                 390                 395                 400
Thr Leu Gly Gly Tyr His Val Ser Lys Gly Thr Arg Leu Ile Met Asn
                405                 410                 415
Leu Ser Lys Ile Gln Lys Asp Pro Arg Ile Trp Ser Asp Pro Thr Glu
            420                 425                 430
Phe Gln Pro Glu Arg Phe Leu Thr Thr His Lys Asp Val Asp Pro Arg
        435                 440                 445
Gly Lys His Phe Glu Phe Ile Pro Phe Gly Ala Gly Arg Arg Ala Cys
    450                 455                 460
Pro Gly Ile Thr Phe Gly Leu Gln Val Leu His Leu Thr Leu Ala Ser
465                 470                 475                 480
Phe Leu His Ala Phe Glu Phe Ser Thr Pro Ser Asn Glu Gln Val Asn
                485                 490                 495
Met Arg Glu Ser Leu Gly Leu Thr Asn Met Lys Ser Thr Pro Leu Glu
            500                 505                 510
Val Leu Ile Ser Pro Arg Leu Ser Leu Asn Cys Phe Asn Leu Met Lys
        515                 520                 525
Ile

<210> SEQ ID NO 146
<211> LENGTH: 479
<212> TYPE: PRT
<213> ORGANISM: Medicago trunculata

<400> SEQUENCE: 146

Met Glu Pro Asn Phe Tyr Leu Ser Leu Leu Leu Phe Val Thr Phe
1               5                   10                  15
Ile Ser Leu Ser Leu Phe Phe Ile Phe Tyr Lys Gln Lys Ser Pro Leu
            20                  25                  30
Asn Leu Pro Pro Gly Lys Met Gly Tyr Pro Ile Ile Gly Glu Ser Leu
        35                  40                  45
Glu Phe Leu Ser Thr Gly Trp Lys Gly His Pro Glu Lys Phe Ile Phe
    50                  55                  60
Asp Arg Met Arg Lys Tyr Ser Ser Glu Leu Phe Lys Thr Ser Ile Val
65                  70                  75                  80
Gly Glu Ser Thr Val Val Cys Cys Gly Ala Ala Ser Asn Lys Phe Leu
                85                  90                  95
Phe Ser Asn Glu Asn Lys Leu Val Thr Ala Trp Trp Pro Asp Ser Val
            100                 105                 110
Asn Lys Ile Phe Pro Thr Thr Ser Leu Asp Ser Asn Leu Lys Glu Glu
        115                 120                 125
Ser Ile Lys Met Arg Lys Leu Leu Pro Gln Phe Phe Lys Pro Glu Ala
    130                 135                 140
Leu Gln Arg Tyr Val Gly Val Met Asp Val Ile Ala Gln Arg His Phe
145                 150                 155                 160
Val Thr His Trp Asp Asn Lys Asn Glu Ile Thr Val Tyr Pro Leu Ala
                165                 170                 175
Lys Arg Tyr Thr Phe Leu Leu Ala Cys Arg Leu Phe Met Ser Val Glu
            180                 185                 190
Asp Glu Asn His Val Ala Lys Phe Ser Asp Pro Phe Gln Leu Ile Ala
        195                 200                 205
```

```
Ala Gly Ile Ile Ser Leu Pro Ile Asp Leu Pro Gly Thr Pro Phe Asn
            210                 215                 220

Lys Ala Ile Lys Ala Ser Asn Phe Ile Arg Lys Glu Leu Ile Lys Ile
225                 230                 235                 240

Ile Lys Gln Arg Arg Val Asp Leu Ala Glu Gly Thr Ala Ser Pro Thr
                245                 250                 255

Gln Asp Ile Leu Ser His Met Leu Leu Thr Ser Asp Glu Asn Gly Lys
            260                 265                 270

Ser Met Asn Glu Leu Asn Ile Ala Asp Lys Ile Leu Gly Leu Leu Ile
        275                 280                 285

Gly Gly His Asp Thr Ala Ser Val Ala Cys Thr Phe Leu Val Lys Tyr
    290                 295                 300

Leu Gly Glu Leu Pro His Ile Tyr Asp Lys Val Tyr Gln Glu Gln Met
305                 310                 315                 320

Glu Ile Ala Lys Ser Lys Pro Ala Gly Glu Leu Leu Asn Trp Asp Asp
                325                 330                 335

Leu Lys Lys Met Lys Tyr Ser Trp Asn Val Ala Cys Glu Val Met Arg
            340                 345                 350

Leu Ser Pro Pro Leu Gln Gly Gly Phe Arg Glu Ala Ile Thr Asp Phe
        355                 360                 365

Met Phe Asn Gly Phe Ser Ile Pro Lys Gly Trp Lys Leu Tyr Trp Ser
    370                 375                 380

Ala Asn Ser Thr His Lys Asn Ala Glu Cys Phe Pro Met Pro Glu Lys
385                 390                 395                 400

Phe Asp Pro Thr Arg Phe Glu Gly Asn Gly Pro Ala Pro Tyr Thr Phe
                405                 410                 415

Val Pro Phe Gly Gly Gly Pro Arg Met Cys Pro Gly Lys Glu Tyr Ala
            420                 425                 430

Arg Leu Glu Ile Leu Val Phe Met His Asn Leu Val Lys Arg Phe Lys
        435                 440                 445

Trp Glu Lys Val Ile Pro Asp Glu Lys Ile Ile Val Asp Pro Phe Pro
    450                 455                 460

Ile Pro Ala Lys Asp Leu Pro Ile Arg Leu Tyr Pro His Lys Ala
465                 470                 475

<210> SEQ ID NO 147
<211> LENGTH: 710
<212> TYPE: PRT
<213> ORGANISM: Stevia rebaudiana

<400> SEQUENCE: 147

Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
            20                  25                  30

Asp Pro Thr Thr Leu Pro Ala Leu Lys Met Leu Val Glu Asn Arg Glu
        35                  40                  45

Leu Leu Thr Leu Phe Thr Thr Ser Phe Ala Val Leu Ile Gly Cys Leu
    50                  55                  60

Val Phe Leu Met Trp Arg Arg Ser Ser Lys Lys Leu Val Gln Asp
65                  70                  75                  80

Pro Val Pro Gln Val Ile Val Lys Lys Glu Lys Glu Ser Glu
                85                  90                  95

Val Asp Asp Gly Lys Lys Lys Val Ser Ile Phe Tyr Gly Thr Gln Thr
```

-continued

```
                100                 105                 110
Gly Thr Ala Glu Gly Phe Ala Lys Ala Leu Val Glu Glu Ala Lys Val
                115                 120                 125
Arg Tyr Glu Lys Thr Ser Phe Lys Val Ile Asp Leu Asp Tyr Ala
        130                 135                 140
Ala Asp Asp Glu Tyr Glu Glu Lys Leu Lys Lys Glu Ser Leu Ala
145                 150                 155                 160
Phe Phe Phe Leu Ala Thr Tyr Gly Asp Gly Glu Pro Thr Asp Asn Ala
                165                 170                 175
Ala Asn Phe Tyr Lys Trp Phe Thr Glu Gly Asp Lys Gly Glu Trp
        180                 185                 190
Leu Lys Lys Leu Gln Tyr Gly Val Phe Gly Leu Gly Asn Arg Gln Tyr
                195                 200                 205
Glu His Phe Asn Lys Ile Ala Ile Val Val Asp Asp Lys Leu Thr Glu
                210                 215                 220
Met Gly Ala Lys Arg Leu Val Pro Val Gly Leu Gly Asp Asp Gln
225                 230                 235                 240
Cys Ile Glu Asp Asp Phe Thr Ala Trp Lys Glu Leu Val Trp Pro Glu
                245                 250                 255
Leu Asp Gln Leu Leu Arg Asp Glu Asp Asp Thr Ser Val Thr Thr Pro
                260                 265                 270
Tyr Thr Ala Ala Val Leu Glu Tyr Arg Val Val Tyr His Asp Lys Pro
        275                 280                 285
Ala Asp Ser Tyr Ala Glu Asp Gln Thr His Thr Asn Gly His Val Val
        290                 295                 300
His Asp Ala Gln His Pro Ser Arg Ser Asn Val Ala Phe Lys Lys Glu
305                 310                 315                 320
Leu His Thr Ser Gln Ser Asp Arg Ser Cys Thr His Leu Glu Phe Asp
                325                 330                 335
Ile Ser His Thr Gly Leu Ser Tyr Glu Thr Gly Asp His Val Gly Val
                340                 345                 350
Tyr Ser Glu Asn Leu Ser Glu Val Val Asp Glu Ala Leu Lys Leu Leu
                355                 360                 365
Gly Leu Ser Pro Asp Thr Tyr Phe Ser Val His Ala Asp Lys Glu Asp
        370                 375                 380
Gly Thr Pro Ile Gly Gly Ala Ser Leu Pro Pro Phe Pro Pro Cys
385                 390                 395                 400
Thr Leu Arg Asp Ala Leu Thr Arg Tyr Ala Asp Val Leu Ser Ser Pro
                405                 410                 415
Lys Lys Val Ala Leu Leu Ala Leu Ala Ala His Ala Ser Asp Pro Ser
                420                 425                 430
Glu Ala Asp Arg Leu Lys Phe Leu Ala Ser Pro Ala Gly Lys Asp Glu
        435                 440                 445
Tyr Ala Gln Trp Ile Val Ala Asn Gln Arg Ser Leu Leu Glu Val Met
        450                 455                 460
Gln Ser Phe Pro Ser Ala Lys Pro Pro Leu Gly Val Phe Phe Ala Ala
465                 470                 475                 480
Val Ala Pro Arg Leu Gln Pro Arg Tyr Tyr Ser Ile Ser Ser Ser Pro
                485                 490                 495
Lys Met Ser Pro Asn Arg Ile His Val Thr Cys Ala Leu Val Tyr Glu
                500                 505                 510
Thr Thr Pro Ala Gly Arg Ile His Arg Gly Leu Cys Ser Thr Trp Met
        515                 520                 525
```

```
Lys Asn Ala Val Pro Leu Thr Glu Ser Pro Asp Cys Ser Gln Ala Ser
            530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
            580                 585                 590

Ser Ser Ile Phe Phe Gly Cys Arg Asn Arg Lys Val Asp Phe Ile
            595                 600                 605

Tyr Glu Asp Glu Leu Asn Asn Phe Val Glu Thr Gly Ala Leu Ser Glu
610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
                660                 665                 670

Val His Arg Thr Leu His Thr Ile Val Gln Glu Gln Gly Ser Leu Asp
            675                 680                 685

Ser Ser Lys Ala Glu Leu Tyr Val Lys Asn Leu Gln Met Ser Gly Arg
690                 695                 700

Tyr Leu Arg Asp Val Trp
705             710

<210> SEQ ID NO 148
<211> LENGTH: 692
<212> TYPE: PRT
<213> ORGANISM: Arabidopsis thaliana

<400> SEQUENCE: 148

Met Thr Ser Ala Leu Tyr Ala Ser Asp Leu Phe Lys Gln Leu Lys Ser
1               5                   10                  15

Ile Met Gly Thr Asp Ser Leu Ser Asp Asp Val Val Leu Val Ile Ala
                20                  25                  30

Thr Thr Ser Leu Ala Leu Val Ala Gly Phe Val Val Leu Leu Trp Lys
            35                  40                  45

Lys Thr Thr Ala Asp Arg Ser Gly Glu Leu Lys Pro Leu Met Ile Pro
50                  55                  60

Lys Ser Leu Met Ala Lys Asp Glu Asp Asp Leu Asp Leu Gly Ser
65                  70                  75                  80

Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
                100                 105                 110

Lys Ala Ala Val Lys Val Ile Asp Leu Asp Asp Tyr Ala Ala Asp Asp
            115                 120                 125

Asp Gln Tyr Glu Glu Lys Leu Lys Lys Glu Thr Leu Ala Phe Phe Cys
130                 135                 140

Val Ala Thr Tyr Gly Asp Gly Glu Pro Thr Asp Asn Ala Ala Arg Phe
145                 150                 155                 160

Tyr Lys Trp Phe Thr Glu Glu Asn Glu Arg Asp Ile Lys Leu Gln Gln
                165                 170                 175

Leu Ala Tyr Gly Val Phe Ala Leu Gly Asn Arg Gln Tyr Glu His Phe
```

-continued

```
                180                 185                 190
Asn Lys Ile Gly Ile Val Leu Asp Glu Glu Leu Cys Lys Lys Gly Ala
            195                 200                 205

Lys Arg Leu Ile Glu Val Gly Leu Gly Asp Asp Gln Ser Ile Glu
        210                 215                 220

Asp Asp Phe Asn Ala Trp Lys Glu Ser Leu Trp Ser Glu Leu Asp Lys
225                 230                 235                 240

Leu Leu Lys Asp Glu Asp Lys Ser Val Ala Thr Pro Tyr Thr Ala
            245                 250                 255

Val Ile Pro Glu Tyr Arg Val Val Thr His Asp Pro Arg Phe Thr Thr
            260                 265                 270

Gln Lys Ser Met Glu Ser Asn Val Ala Asn Gly Asn Thr Thr Ile Asp
            275                 280                 285

Ile His His Pro Cys Arg Val Asp Val Ala Val Gln Lys Glu Leu His
            290                 295                 300

Thr His Glu Ser Asp Arg Ser Cys Ile His Leu Glu Phe Asp Ile Ser
305                 310                 315                 320

Arg Thr Gly Ile Thr Tyr Glu Thr Gly Asp His Val Gly Val Tyr Ala
                325                 330                 335

Glu Asn His Val Glu Ile Val Glu Glu Ala Gly Lys Leu Leu Gly His
                340                 345                 350

Ser Leu Asp Leu Val Phe Ser Ile His Ala Asp Lys Glu Asp Gly Ser
            355                 360                 365

Pro Leu Glu Ser Ala Val Pro Pro Pro Phe Pro Gly Pro Cys Thr Leu
        370                 375                 380

Gly Thr Gly Leu Ala Arg Tyr Ala Asp Leu Leu Asn Pro Pro Arg Lys
385                 390                 395                 400

Ser Ala Leu Val Ala Leu Ala Ala Tyr Ala Thr Glu Pro Ser Glu Ala
                405                 410                 415

Glu Lys Leu Lys His Leu Thr Ser Pro Asp Gly Lys Asp Glu Tyr Ser
            420                 425                 430

Gln Trp Ile Val Ala Ser Gln Arg Ser Leu Leu Glu Val Met Ala Ala
            435                 440                 445

Phe Pro Ser Ala Lys Pro Pro Leu Gly Val Phe Phe Ala Ala Ile Ala
450                 455                 460

Pro Arg Leu Gln Pro Arg Tyr Tyr Ser Ile Ser Ser Ser Pro Arg Leu
465                 470                 475                 480

Ala Pro Ser Arg Val His Val Thr Ser Ala Leu Val Tyr Gly Pro Thr
                485                 490                 495

Pro Thr Gly Arg Ile His Lys Gly Val Cys Ser Thr Trp Met Lys Asn
            500                 505                 510

Ala Val Pro Ala Glu Lys Ser His Glu Cys Ser Gly Ala Pro Ile Phe
            515                 520                 525

Ile Arg Ala Ser Asn Phe Lys Leu Pro Ser Asn Pro Ser Thr Pro Ile
            530                 535                 540

Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Glu Leu Gly Ser Ser
                565                 570                 575

Leu Leu Phe Phe Gly Cys Arg Asn Arg Gln Met Asp Phe Ile Tyr Glu
            580                 585                 590

Asp Glu Leu Asn Asn Phe Val Asp Gln Gly Val Ile Ser Glu Leu Ile
            595                 600                 605
```

```
Met Ala Phe Ser Arg Glu Gly Ala Gln Lys Glu Tyr Val Gln His Lys
    610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
                645                 650                 655

Arg Thr Leu His Thr Ile Val Gln Gln Glu Gly Val Ser Ser Ser
            660                 665                 670

Glu Ala Glu Ala Ile Val Lys Lys Leu Gln Thr Glu Gly Arg Tyr Leu
        675                 680                 685

Arg Asp Val Trp
    690

<210> SEQ ID NO 149
<211> LENGTH: 713
<212> TYPE: PRT
<213> ORGANISM: Giberella fujikuroi

<400> SEQUENCE: 149

Met Ala Glu Leu Asp Thr Leu Asp Ile Val Val Leu Gly Val Ile Phe
1               5                   10                  15

Leu Gly Thr Val Ala Tyr Phe Thr Lys Gly Lys Leu Trp Gly Val Thr
            20                  25                  30

Lys Asp Pro Tyr Ala Asn Gly Phe Ala Gly Gly Ala Ser Lys Pro
        35                  40                  45

Gly Arg Thr Arg Asn Ile Val Glu Ala Met Glu Glu Ser Gly Lys Asn
    50                  55                  60

Cys Val Val Phe Tyr Gly Ser Gln Thr Gly Thr Ala Glu Asp Tyr Ala
65                  70                  75                  80

Ser Arg Leu Ala Lys Glu Gly Lys Ser Arg Phe Gly Leu Asn Thr Met
                85                  90                  95

Ile Ala Asp Leu Glu Asp Tyr Asp Phe Asp Asn Leu Asp Thr Val Pro
            100                 105                 110

Ser Asp Asn Ile Val Met Phe Val Leu Ala Thr Tyr Gly Glu Gly Glu
        115                 120                 125

Pro Thr Asp Asn Ala Val Asp Phe Tyr Glu Phe Ile Thr Gly Glu Asp
    130                 135                 140

Ala Ser Phe Asn Glu Gly Asn Asp Pro Pro Leu Gly Asn Leu Asn Tyr
145                 150                 155                 160

Val Ala Phe Gly Leu Gly Asn Asn Thr Tyr Glu His Tyr Asn Ser Met
                165                 170                 175

Val Arg Asn Val Asn Lys Ala Leu Glu Lys Leu Gly Ala His Arg Ile
            180                 185                 190

Gly Glu Ala Gly Glu Gly Asp Asp Gly Ala Gly Thr Met Glu Glu Asp
        195                 200                 205

Phe Leu Ala Trp Lys Asp Pro Met Trp Glu Ala Leu Ala Lys Lys Met
    210                 215                 220

Gly Leu Glu Glu Arg Glu Ala Val Tyr Glu Pro Ile Phe Ala Ile Asn
225                 230                 235                 240

Glu Arg Asp Asp Leu Thr Pro Glu Ala Asn Val Tyr Leu Gly Glu
                245                 250                 255

Pro Asn Lys Leu His Leu Glu Gly Thr Ala Lys Gly Pro Phe Asn Ser
            260                 265                 270

His Asn Pro Tyr Ile Ala Pro Ile Ala Glu Ser Tyr Glu Leu Phe Ser
```

```
                275                 280                 285
Ala Lys Asp Arg Asn Cys Leu His Met Glu Ile Asp Ile Ser Gly Ser
290                 295                 300
Asn Leu Lys Tyr Glu Thr Gly Asp His Ile Ala Ile Trp Pro Thr Asn
305                 310                 315                 320
Pro Gly Glu Glu Val Asn Lys Phe Leu Asp Ile Leu Asp Leu Ser Gly
                325                 330                 335
Lys Gln His Ser Val Val Thr Val Lys Ala Leu Glu Pro Thr Ala Lys
                340                 345                 350
Val Pro Phe Pro Asn Pro Thr Thr Tyr Asp Ala Ile Leu Arg Tyr His
                355                 360                 365
Leu Glu Ile Cys Ala Pro Val Ser Arg Gln Phe Val Ser Thr Leu Ala
                370                 375                 380
Ala Phe Ala Pro Asn Asp Asp Ile Lys Ala Glu Met Asn Arg Leu Gly
385                 390                 395                 400
Ser Asp Lys Asp Tyr Phe His Glu Lys Thr Gly Pro His Tyr Tyr Asn
                405                 410                 415
Ile Ala Arg Phe Leu Ala Ser Val Ser Lys Gly Glu Lys Trp Thr Lys
                420                 425                 430
Ile Pro Phe Ser Ala Phe Ile Glu Gly Leu Thr Lys Leu Gln Pro Arg
                435                 440                 445
Tyr Tyr Ser Ile Ser Ser Ser Leu Val Gln Pro Lys Lys Ile Ser
450                 455                 460
Ile Thr Ala Val Val Glu Ser Gln Gln Ile Pro Gly Arg Asp Asp Pro
465                 470                 475                 480
Phe Arg Gly Val Ala Thr Asn Tyr Leu Phe Ala Leu Lys Gln Lys Gln
                485                 490                 495
Asn Gly Asp Pro Asn Pro Ala Pro Phe Gly Gln Ser Tyr Glu Leu Thr
                500                 505                 510
Gly Pro Arg Asn Lys Tyr Asp Gly Ile His Val Pro Val His Val Arg
                515                 520                 525
His Ser Asn Phe Lys Leu Pro Ser Asp Pro Gly Lys Pro Ile Ile Met
                530                 535                 540
Ile Gly Pro Gly Thr Gly Val Ala Pro Phe Arg Gly Phe Val Gln Glu
545                 550                 555                 560
Arg Ala Lys Gln Ala Arg Asp Gly Val Glu Val Gly Lys Thr Leu Leu
                565                 570                 575
Phe Phe Gly Cys Arg Lys Ser Thr Glu Asp Phe Met Tyr Gln Lys Glu
                580                 585                 590
Trp Gln Glu Tyr Lys Glu Ala Leu Gly Asp Lys Phe Glu Met Ile Thr
                595                 600                 605
Ala Phe Ser Arg Glu Gly Ser Lys Lys Val Tyr Val Gln His Arg Leu
610                 615                 620
Lys Glu Arg Ser Lys Glu Val Ser Asp Leu Leu Ser Gln Lys Ala Tyr
625                 630                 635                 640
Phe Tyr Val Cys Gly Asp Ala Ala His Met Ala Arg Glu Val Asn Thr
                645                 650                 655
Val Leu Ala Gln Ile Ile Ala Glu Gly Arg Gly Val Ser Glu Ala Lys
                660                 665                 670
Gly Glu Glu Ile Val Lys Asn Met Arg Ser Ala Asn Gln Tyr Gln Val
                675                 680                 685
Cys Ser Asp Phe Val Thr Leu His Cys Lys Glu Thr Thr Tyr Ala Asn
690                 695                 700
```

```
Ser Glu Leu Gln Glu Asp Val Trp Ser
705                 710
```

\<210\> SEQ ID NO 150
\<211\> LENGTH: 453
\<212\> TYPE: PRT
\<213\> ORGANISM: Arabidopsis thaliana

\<400\> SEQUENCE: 150

```
Met Gly Gly Leu Lys Phe His Val Leu Met Tyr Pro Trp Phe Ala Thr
1               5                   10                  15

Gly His Met Thr Pro Phe Leu Phe Leu Ala Asn Lys Leu Ala Glu Lys
            20                  25                  30

Gly His Thr Val Thr Phe Leu Leu Pro Lys Lys Ser Leu Lys Gln Leu
        35                  40                  45

Glu His Phe Asn Leu Phe Pro His Asn Ile Val Phe Arg Ser Val Thr
    50                  55                  60

Val Pro His Val Asp Gly Leu Pro Val Gly Thr Glu Thr Ala Ser Glu
65                  70                  75                  80

Ile Pro Val Thr Ser Thr Asp Leu Leu Met Ser Ala Met Asp Leu Thr
                85                  90                  95

Arg Asp Gln Val Glu Ala Val Val Arg Ala Val Glu Pro Asp Leu Ile
            100                 105                 110

Phe Phe Asp Phe Ala His Trp Ile Pro Glu Val Ala Arg Asp Phe Gly
        115                 120                 125

Leu Lys Thr Val Lys Tyr Val Val Ser Ala Ser Thr Ile Ala Ser
130                 135                 140

Met Leu Val Pro Gly Gly Glu Leu Gly Val Pro Pro Gly Tyr Pro
145                 150                 155                 160

Ser Ser Lys Val Leu Leu Arg Lys Gln Asp Ala Tyr Thr Met Lys Lys
                165                 170                 175

Leu Glu Pro Thr Asn Thr Ile Asp Val Gly Pro Asn Leu Leu Glu Arg
            180                 185                 190

Val Thr Thr Ser Leu Met Asn Ser Asp Val Ile Ala Ile Arg Thr Ala
        195                 200                 205

Arg Glu Ile Glu Gly Asn Phe Cys Asp Tyr Ile Glu Lys His Cys Arg
    210                 215                 220

Lys Lys Val Leu Leu Thr Gly Pro Val Phe Pro Glu Pro Asp Lys Thr
225                 230                 235                 240

Arg Glu Leu Glu Glu Arg Trp Val Lys Trp Leu Ser Gly Tyr Glu Pro
                245                 250                 255

Asp Ser Val Val Phe Cys Ala Leu Gly Ser Gln Val Ile Leu Glu Lys
            260                 265                 270

Asp Gln Phe Gln Glu Leu Cys Leu Gly Met Glu Leu Thr Gly Ser Pro
        275                 280                 285

Phe Leu Val Ala Val Lys Pro Pro Arg Gly Ser Ser Thr Ile Gln Glu
    290                 295                 300

Ala Leu Pro Glu Gly Phe Glu Glu Arg Val Lys Gly Arg Gly Leu Val
305                 310                 315                 320

Trp Gly Gly Trp Val Gln Gln Pro Leu Ile Leu Ser His Pro Ser Val
                325                 330                 335

Gly Cys Phe Val Ser His Cys Gly Phe Gly Ser Met Trp Glu Ser Leu
            340                 345                 350

Leu Ser Asp Cys Gln Ile Val Leu Val Pro Gln Leu Gly Asp Gln Val
```

```
                355              360              365
Leu Asn Thr Arg Leu Leu Ser Asp Glu Leu Lys Val Ser Val Glu Val
       370              375              380

Ala Arg Glu Glu Thr Gly Trp Phe Ser Lys Glu Ser Leu Cys Asp Ala
385              390              395              400

Val Asn Ser Val Met Lys Arg Asp Ser Glu Leu Gly Asn Leu Val Arg
               405              410              415

Lys Asn His Thr Lys Trp Arg Glu Thr Val Ala Ser Pro Gly Leu Met
           420              425              430

Thr Gly Tyr Val Asp Ala Phe Val Glu Ser Leu Gln Asp Leu Val Ser
       435              440              445

Gly Thr Thr His Asp
    450
```

<210> SEQ ID NO 151
<211> LENGTH: 1362
<212> TYPE: DNA
<213> ORGANISM: Arabidopsis thaliana

<400> SEQUENCE: 151

```
atgggtggtt tgaagtttca tgtacttatg tatccatggt tcgcaacagg ccatatgacc        60
ccgttccttt ttcttgccaa caaattggct gagaaaggtc atacggtcac tttcttgctt       120
cccaagaaat ctctgaaaca gttggaacat tcaatctgt ttccacacaa cattgtcttt        180
cgctctgtca ccgtccctca tgtggatggt ctccccgttg cacagagac agcctctgag        240
atccctgtga catcaactga tctcttgatg tctgctatgg atctcacacg tgatcaagtt       300
gaagctgtgg tccgagccgt tgaaccggac ctgatcttct ttgactttgc tcattggatt      360
ccagaagtag ctagggactt cggccttaag actgtaaagt acgtcgtggt gtctgcatcg      420
actatagcta gtatgcttgt cccaggtggt gagttaggtg ttcctccacc gggatatcca      480
tcatcaaagg tgctgcttcg taaacaagat gcttacacta tgaagaaact ggagcctaca      540
aatacaatcg atgtcggacc aaacctcttg gaacgagtca ctacaagtct tatgaactct      600
gatgtcattg cgataaggac agccagagaa atcgaaggaa acttttgcga ctatatagaa      660
aaacattgca ggaaaaaggt tctcttgaca ggtccggtgt tccctgagcc agacaagact      720
agagagctag aggaacgatg ggttaagtgg ctaagtgggt atgaaccaga ctcagtggtg      780
ttttgtgcac tgggctcaca agtcatttta gagaaagatc aattccaaga actctgctta      840
ggaatggagc taacaggttc accgtttctt gtagcggtta agcccctag aggctcatca      900
acgattcaag aagcacttcc tgaaggattc gaagagcggg ttaaaggaag aggccttgtt      960
tggggaggat gggttcaaca accattgata ttgtctcatc catcagtcgg gtgctttgtg     1020
agccattgtg ggtttggatc aatgtgggag tctttgctga gtgattgtca gatagtctta     1080
gtaccacagt tgggtgatca agtcctgaac acaagattgc tgagtgacga actcaaggtt     1140
tcggttgaag tggcaagaga ggaaacagga tggttctcga agagagctt gtgcgatgct     1200
gtcaatagtg tgatgaaaag ggacagcgag ctcgggaacc tggtgaggaa gaatcacacc     1260
aagtggaggg agacagtagc tagtcctgga ctaatgactg ttatgtcga tgctttcgta      1320
gagtcattgc aggatcttgt ctctgggacc acccatgact ga                         1362
```